United States Patent
Boustany et al.

(10) Patent No.: US 11,472,889 B2
(45) Date of Patent: Oct. 18, 2022

(54) ANTIBODIES, ACTIVATABLE ANTIBODIES, BISPECIFIC ANTIBODIES, AND BISPECIFIC ACTIVATABLE ANTIBODIES AND METHODS OF USE THEREOF

(71) Applicant: CytomX Therapeutics, Inc., South San Francisco, CA (US)

(72) Inventors: Leila Marie Boustany, Redwood City, CA (US); Sherry L. La Porte, San Francisco, CA (US); Bryan A. Irving, Woodside, CA (US); Jeanne Grace Flandez, Oakland, CA (US)

(73) Assignee: CYTOMX THERAPEUTICS, INC., Redwood City, CA (US)

( * ) Notice: Subject to any disclaimer, the term of this patent is extended or adjusted under 35 U.S.C. 154(b) by 938 days.

(21) Appl. No.: 16/159,451

(22) Filed: Oct. 12, 2018

(65) Prior Publication Data
US 2019/0135943 A1    May 9, 2019

Related U.S. Application Data

(60) Provisional application No. 62/572,468, filed on Oct. 14, 2017, provisional application No. 62/577,140, filed on Oct. 25, 2017, provisional application No. 62/613,358, filed on Jan. 3, 2018, provisional application No. 62/666,065, filed on May 2, 2018, provisional application No. 62/731,622, filed on Sep. 14, 2018.

(51) Int. Cl.
| | |
|---|---|
| *G01N 31/00* | (2006.01) |
| *G01N 33/53* | (2006.01) |
| *C07K 16/40* | (2006.01) |
| *C07K 16/28* | (2006.01) |
| *A61P 35/00* | (2006.01) |
| *C12N 15/62* | (2006.01) |
| *A61K 39/00* | (2006.01) |

(52) U.S. Cl.
CPC .............. *C07K 16/40* (2013.01); *A61P 35/00* (2018.01); *C07K 16/2809* (2013.01); *C07K 16/2863* (2013.01); *C12N 15/62* (2013.01); *A61K 2039/505* (2013.01); *C07K 2317/24* (2013.01); *C07K 2317/31* (2013.01); *C07K 2317/52* (2013.01); *C07K 2317/622* (2013.01); *C07K 2317/64* (2013.01); *C07K 2317/71* (2013.01); *C07K 2317/73* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,522,811 A | 6/1985 | Eppstein et al. |
| 4,544,545 A | 10/1985 | Ryan et al. |
| 5,013,556 A | 5/1991 | Woodle et al. |
| 5,030,719 A | 7/1991 | Umemoto et al. |
| 5,151,510 A | 9/1992 | Stec et al. |
| 5,624,821 A | 4/1997 | Winter et al. |
| 5,733,743 A | 3/1998 | Johnson et al. |
| 6,538,124 B1 | 3/2003 | Idusogie et al. |
| 6,737,056 B1 | 5/2004 | Presta |
| 7,465,790 B2 | 12/2008 | Waldmann et al. |
| 7,563,441 B2 | 7/2009 | Graus et al. |
| 7,728,114 B2 | 6/2010 | Mach et al. |
| 7,951,918 B2 | 5/2011 | Glaser et al. |
| 8,513,390 B2 | 8/2013 | Stagliano et al. |
| 8,518,404 B2 | 8/2013 | Daugherty et al. |
| 8,529,898 B2 | 9/2013 | Daugherty et al. |
| 8,541,203 B2 | 9/2013 | Daugherty et al. |
| 8,563,269 B2 | 10/2013 | Stagliano et al. |
| 8,809,504 B2 | 8/2014 | Lauermann |
| 8,846,042 B2 | 9/2014 | Zhou |
| 8,969,526 B2 | 3/2015 | Baehner et al. |
| 9,079,965 B2 * | 7/2015 | Zhou .................... C07K 16/468 |
| 9,120,853 B2 | 9/2015 | Lowman et al. |
| 9,169,321 B2 | 10/2015 | Daugherty et al. |
| 9,212,225 B1 | 12/2015 | Ellwanger et al. |
| 9,453,078 B2 | 9/2016 | Stagliano et al. |
| 9,540,440 B2 | 1/2017 | Lowman et al. |
| 9,545,442 B2 | 1/2017 | Lowman et al. |
| 9,562,073 B2 | 2/2017 | Moore et al. |
| 9,889,211 B2 | 2/2018 | Lowman et al. |
| 10,059,762 B2 | 8/2018 | Stagliano et al. |
| 10,077,300 B2 | 9/2018 | Daugherty et al. |

(Continued)

FOREIGN PATENT DOCUMENTS

| | | |
|---|---|---|
| EP | 1 523 503 B1 | 4/2009 |
| EP | 1 324 771 B1 | 6/2011 |

(Continued)

OTHER PUBLICATIONS

Luo et al. (Moleuclar Pharmaceutics, 2014, vol. 11, pp. 1750-1761) (Year: 2014).*
Costa et al. (European Journal of Pharmaceutics and Biopharmaceutics 74 (2010) 127-138) (Year: 2010).*
*Amgen, Inc. et al.* vs *Sanofi and Regeneron.* U.S. Court of Appeals For the Federal Circuit, Case: 17-1480, Document 176, Filed: Feb. 6, 2018.
Baeuerle, P.A. and Reinhardt, C. (Jun. 15, 2009) "Bispecific T-cell engaging antibodies for cancer therapy" *Cancer Res*, 69(12):4941-4944.

(Continued)

*Primary Examiner* — Lisa V Cook
(74) *Attorney, Agent, or Firm* — Rothwell, Figg, Ernst & Manbeck, P.C.

(57) ABSTRACT

Provided herein antibodies, activatable antibodies (AAs), bispecific antibodies, and bispecific activatable antibodies (BAAs). Also provided herein are methods of making and methods of use of these antibodies, AAs, bispecific antibodies, and BAAs.

18 Claims, 25 Drawing Sheets

Specification includes a Sequence Listing.

(56) References Cited

U.S. PATENT DOCUMENTS

| | | | |
|---|---|---|---|
| 10,118,961 B2 | 11/2018 | Stagliano et al. | |
| 10,138,272 B2 | 11/2018 | Moore et al. | |
| 10,179,817 B2 | 1/2019 | Sagert et al. | |
| 10,533,053 B2 | 1/2020 | Lowman et al. | |
| 10,669,337 B2* | 6/2020 | Irving | A61K 47/6851 |
| 10,709,799 B2 | 7/2020 | Lowman et al. | |
| 10,875,913 B2 | 12/2020 | Stagliano et al. | |
| 11,161,906 B2* | 11/2021 | Lowman | C07K 16/2896 |
| 2003/0150294 A1 | 6/2003 | Gillies et al. | |
| 2004/0109855 A1 | 6/2004 | Waldmann et al. | |
| 2005/0226876 A1 | 10/2005 | Graus et al. | |
| 2009/0304719 A1 | 12/2009 | Daugherty et al. | |
| 2010/0189651 A1 | 6/2010 | Stagliano et al. | |
| 2010/0189727 A1 | 7/2010 | Rodeck et al. | |
| 2011/0059078 A1 | 3/2011 | Coyle et al. | |
| 2012/0149061 A1 | 6/2012 | Stagliano et al. | |
| 2012/0207756 A1 | 8/2012 | Stagliano et al. | |
| 2012/0237512 A1 | 9/2012 | Daugherty et al. | |
| 2012/0237977 A1 | 9/2012 | Daugherty et al. | |
| 2012/0244154 A1 | 9/2012 | Daugherty et al. | |
| 2013/0060011 A1 | 3/2013 | Bruenker et al. | |
| 2013/0129730 A1 | 5/2013 | Kufer et al. | |
| 2013/0150558 A1 | 6/2013 | Williams et al. | |
| 2013/0195881 A1 | 8/2013 | Singh et al. | |
| 2013/0309230 A1 | 11/2013 | Stagliano et al. | |
| 2013/0315906 A1 | 11/2013 | Lowman et al. | |
| 2014/0010810 A1 | 1/2014 | West et al. | |
| 2014/0024810 A1 | 1/2014 | Stagliano et al. | |
| 2014/0045195 A1 | 2/2014 | Daugherty et al. | |
| 2014/0154253 A1 | 6/2014 | Ng et al. | |
| 2014/0212436 A1 | 7/2014 | Moore et al. | |
| 2014/0255313 A1 | 9/2014 | Vasiljeva et al. | |
| 2014/0363430 A1 | 12/2014 | West et al. | |
| 2015/0005477 A1 | 1/2015 | Lowman et al. | |
| 2015/0079088 A1 | 3/2015 | Lowman et al. | |
| 2015/0118254 A1 | 4/2015 | Lowman et al. | |
| 2015/0376271 A1 | 12/2015 | Perlroth et al. | |
| 2016/0122425 A1 | 5/2016 | Daugherty et al. | |
| 2016/0193332 A1 | 7/2016 | Lowman et al. | |
| 2016/0194399 A1 | 7/2016 | Irving et al. | |
| 2016/0200826 A1 | 7/2016 | West et al. | |
| 2016/0220537 A1 | 8/2016 | Garner et al. | |
| 2016/0228546 A1 | 8/2016 | Stagliano et al. | |
| 2017/0081397 A1 | 3/2017 | Stagliano et al. | |
| 2017/0096489 A1 | 4/2017 | Lowman et al. | |
| 2017/0196996 A1 | 7/2017 | Lowman et al. | |
| 2018/0333507 A1 | 11/2018 | Lowman et al. | |
| 2019/0119370 A1 | 4/2019 | Stagliano et al. | |
| 2019/0211089 A1 | 7/2019 | Daugherty et al. | |
| 2020/0270350 A1 | 8/2020 | Lowman et al. | |
| 2021/0023243 A1 | 1/2021 | Lowman et al. | |
| 2021/0047406 A1 | 2/2021 | Irving et al. | |

FOREIGN PATENT DOCUMENTS

| | | |
|---|---|---|
| EP | 2155788 B1 | 6/2012 |
| EP | 2155783 B1 | 7/2013 |
| WO | WO 1994/11026 A2 | 5/1994 |
| WO | WO 1995/16037 A1 | 6/1995 |
| WO | 1999/043713 | 9/1999 |
| WO | 2000/042072 | 7/2000 |
| WO | 2001/058957 | 8/2001 |
| WO | WO 2001/91798 A2 | 12/2001 |
| WO | WO 2002/30460 A2 | 4/2002 |
| WO | WO 2004/003019 A2 | 1/2004 |
| WO | WO 2004/009638 A1 | 1/2004 |
| WO | WO 2005/047461 A2 | 5/2005 |
| WO | 2005/100402 | 10/2005 |
| WO | 2005/118635 | 12/2005 |
| WO | WO 2007/027935 A2 | 3/2007 |
| WO | WO 2007/042261 A2 | 4/2007 |
| WO | 2007/109254 | 9/2007 |
| WO | WO 2007/105027 A1 | 9/2007 |
| WO | 2007/147001 | 12/2007 |
| WO | WO 2008/119566 A2 | 10/2008 |
| WO | WO 2008/119567 A2 | 10/2008 |
| WO | 2008/134046 | 11/2008 |
| WO | WO 2009/014726 A1 | 1/2009 |
| WO | WO 2009/018386 A1 | 2/2009 |
| WO | WO 2009/025846 A2 | 2/2009 |
| WO | 2009/100309 | 8/2009 |
| WO | 2010/042904 | 4/2010 |
| WO | WO 2010/037836 A2 | 4/2010 |
| WO | WO 2010/037838 A2 | 4/2010 |
| WO | WO 2010/081173 A2 | 7/2010 |
| WO | WO 2010/096838 A2 | 8/2010 |
| WO | WO 2010/129609 A2 | 11/2010 |
| WO | WO 2011/109789 A2 | 9/2011 |
| WO | WO 2012/025525 A1 | 3/2012 |
| WO | 2012/088247 | 6/2012 |
| WO | 2012/130831 | 10/2012 |
| WO | WO 2012/158818 A2 | 11/2012 |
| WO | WO 2012/162067 A2 | 11/2012 |
| WO | 2013/026835 | 2/2013 |
| WO | 2013/026839 | 2/2013 |
| WO | 2013/092001 | 6/2013 |
| WO | 2013/136078 | 9/2013 |
| WO | WO 2013/128194 A1 | 9/2013 |
| WO | WO 2013/163631 A2 | 10/2013 |
| WO | WO 2013/192546 A1 | 12/2013 |
| WO | WO 2013/192550 A2 | 12/2013 |
| WO | 2014/022592 | 2/2014 |
| WO | WO 2014/047231 A1 | 3/2014 |
| WO | 2014/100139 | 6/2014 |
| WO | 2014/108483 | 7/2014 |
| WO | 2014/113510 | 7/2014 |
| WO | WO 2014/107599 A2 | 7/2014 |
| WO | 2014/186842 | 11/2014 |
| WO | 2015/001085 | 1/2015 |
| WO | WO 2015/013671 A1 | 1/2015 |
| WO | WO 2016/014974 A2 | 1/2016 |
| WO | 2016/071355 | 5/2016 |
| WO | 2016/086189 | 6/2016 |
| WO | 2016/116626 | 7/2016 |
| WO | WO 2016/118629 A1 | 7/2016 |
| WO | 2017/162587 | 9/2017 |
| WO | WO 2017/157305 A1 | 9/2017 |
| WO | 2019/213444 | 11/2019 |

OTHER PUBLICATIONS

Bagshawe, K.D. (2006) "Antibody-directed enzyme prodrug therapy (ADEPT) for cancer" *Expert Rev Anticancer Ther*, 6(10):1421-1431.

Bahr, Robert W., Deputy Commissioner for Patent Examination Policy, U.S. Patent and Trademark Office. Memorandum of Feb. 22, 2018, 2 pages.

Bluemel, C. et al. (2010) "Epitope distance to the target cell membrane and antigen size determine the potency of T cell-mediated lysis by BiTE anibodies specific for a large melanoma surface antigen" *Cancer Immunol Immunother*, 59:1197-1209.

Boersma, Y.L. et al. (Dec. 2, 2011) "Bispecific Designed Ankyrin Repeat Proteins (DARPins) Targeting Epidermal Growth Factor Receptor Inhibit A431 Cell Proliferation and Receptor Recycling" *J. Biol. Chem.* 286(48):41273-41285.

Bostrom, J. et al. (Mar. 20, 2009) "Variants of the antibody herceptin that interact with HER2 and VEGF at the antigen binding" *Science*, 323:1610-1614.

Brorson, K. et al. (1999) "Mutational Analysis of Avidity and Fine Specificity of Anti-Levan Antibodies" *J Immunol*, vol. 163, p. 6694-6701.

Brummell et al. "Probing the combining site of an anti-carbohydrate antibody by saturation-mutagenesis: role of the heavy-chain CDR3 residues", *Biochemistry*, vol. 32, p. 1180-1187 (1993).

Burks, E. A. et al. (Jan. 1997) "In vitro scanning satmation mutagenesis of an antibody binding pocket" *Proc Natl Acad Sci USA*, vol. 94, p. 412-417.

Caron et al. "Engineered Humanized Dimeric Forms of IgG Are More Effective Antibodies" *J. Exp Med.*, vol. 176, p. 1191-1195 (1992).

Chan, A.C. and Carter, P.J. (2010) "Therapeutic antibodies for autoimmunity and inflammation" *Nature Reviews Immunol*, 10:301-316.

(56) References Cited

OTHER PUBLICATIONS

Chatenoud, L. (2005) "CD3-specific antibodies restore self-tolerance: mechamsms and clinical applications" *Curr Opin Immunol*, 17:632-637.
Chichili, G.R. et al. (May 27, 2015) "A CD3×CD123 bispecific DART for redirecting host T cells to myelogenous leukemia: Preclinical activity and safety in nonhuman primates" *Sci Transl Med*, 7(289):289ra82, 14 pages.
Cochlovius, B. et al. (2000) "Cure of Burkitt's lymphoma in severe combined immunodeficiency mice by T cells, tetravalent CD3 × CD19 tandem diabody, and CD28 costimulation" *Cancer Res*, 60:4336-4341.
Colman, P.M. (1994) "Effects of amino acid sequence changes on antibody-antigen interactions" *Research in Immunology*, vol. 145, p. 33-36.
Conrad, M.L. et al. (2007) "TCR and CD3 Antibody Cross-Reactivity in 44 Species" *Cytometry Part A*, 71A:925-933.
Deng, R. et al., "Subcutaneous bioavailability of therapeutic antibodies as a function of FcRn binding affinity in mice" *mAbs*, 4:101-109 (2012).
Desnoyers, L.R. et al. (2013) "Tumor-Specific Activation of an EGFR-Targeting Probody Enhances Therapeutic Index" *Science Translational Medicine*, 5(207):207ra144, 10 pages.
Dimasi, N. et al. (2009) "The Design and Characterization of Oligospecific Antibodies for Simultaneous Targeting of Multiple Disease Mediators" *J Mol Biol*, 393:672-692.
Donaldson, J. et al. (Nov. 2009) "Design and development of masked therapeutic antibodies to limit off-target effects: Application to anti-EGFR antibodies" *Cancer Biol Ther*, 8(22):2147-2152. NIH Public Access Author Manuscript; available in PMC Jan. 16, 2013, 12 pages.
Dong, J. et al. (2011) "A stable IgG-like bispecific antibody targeting the epidermal growth factor receptor and the type I insulin-like growth factor receptor demonstrates superior anti-tumor activity" *MAbs*, 3(3):273-288.
Epstein, D.A. et al. "Biological activity of liposome-encapsulated murine interferon gamma is mediated by a cell membrane receptor" *Proc. Natl. Acad. Sci. USA*, vol. 82, p. 3688-3692 (1985).
European Patent No. 2 155 783, Notice of Opposition by Affimed Therapeutics, Apr. 29, 2014, 10 pages.
European Patent No. 2 155 783, "D4" Submission filed with Notice of Opposition by Affimed Therapeutics, Apr. 29, 2014, p. 1-5.
European Patent No. 2 155 783, Notice of Opposition by Chugai Seiyaku, Apr. 29, 2014, 19 pages.
European Patent No. 2 155 783, "D05" Submission filed with Notice of Opposition by Chugai Seiyaku, Apr. 29, 2014, 6 pages.
European Patent No. 2 155 788, Notice of Opposition by F. Hoffmann-La Roche Ag, Mar. 22, 2013, 39 pages.
European Patent No. 2 155 788, "D17" Summary: Methods used for the sequencing of SP34, filed dated Mar. 22, 2013, by F. Hoffmann-La Roche Ag, p. 1-4.
Fitzgerald, J. and A. Lugovsky (2011) "Rational engineering of antibody therapeutics targeting multiple oncogene pathways" *MAbs*, 3(3):299-309.
Grosschedl, R. and D. Baltimore (1985) "Cell-type specificity of immunoglobulin gene expression is regulated by at least three DNA sequence elements" *Cell*, 41:885-897.
Guilmeau, S. et al. (2010) "Heterogeneity of Jagged1 expression in human and mouse intestinal tumors: implications for targeting Notch signaling" *Oncogene*, 29:992-1002.
Ibragimova, G.T. et al. "Stability of the β-Sheet of the WW Domain: A Molecular Dynamics Simulation Study" *Biophysical Journal*, vol. 77, pp. 2191-2198 (1999).
Irving, B.A. (Feb. 2015) "Probodies Empower a New Generation of Antibody Immunotherapies," CytomX Therapeutics Inc. presentation at Keystone Symposia™ on Molecular and Cellular Biology, Feb. 8-13, 2015; 25 pages.

Jackman. J. et al. "Development of a two-part strategy to identify a therapeutic human bispecific antibody that inhibits IgE receptor signaling" *J. Biol. Chem.*, 285:20850-20859 (2010) Epub May 5, 2010.
Jang, Y-L. et al. "The structural basis for DNA binding by an anti-DNA Autoantibody", *Molecular Immunology*, vol. 35, p. 1207-1217 (1998).
Junttila, T.T. et al. (Oct. 2014) "Antitumor efficacy of a bispecific antibody that targets HER2 and activates T cells" *Cancer Res*, 74(19):5561-5571. Epub Sep. 16, 2014.
Kiewe, P. (2008) "Ertumaxomab: a trifimctional antibody for breast cancer treatment" *Expert Opinion on Investigational Drugs*, 17:1553-1558.
Kobayashi, H et al. (1999) "Tryptophan H33 plays an important role in pyrimidine (6-4) pyrimidine photoproduct binding by a high-affinity antibody" *Protein Engineering*, vol. 12, No. 10, p. 879-844.
Kroesen, B.J. et al. (1998) "Bispecific antibodies for treatment of cancer in experimental animal models and man" *Adv. Drug Delivery Rev*, 31:105-129.
Kumar, S. et al. "Molecular Cloning and Expression of the Fabs of Human Autoantibodies in *Escherichia coli*", *Journal of Biological Chemistry*, vol. 275, p. 35129-35136 (2000).
La Rocca, G. et al. "Zymographic detection and clinical correlations of MMP-2 and MMP-9 in breast cancer sera" *British Journal of Cancer*, vol. 90, p. 1414-1421 (2004).
Linke, R. et al. "Catumaxomab: clinical development and future directions" *mAbs*, 2:129-136 (2010).
Liu, M.A. et al. (1985) "Heteroantibody duplexes target cells for lysis by cytotoxic T lymphocytes" *Proc. Natl. Acad. Sci. USA*, 82:8648-8652.
Lund, J. et al. "Multiple binding sites on the CH2 domain of IgG for mouse FcgammaR11" *Mol. Immunol*. 29:53-39 (1992).
Lutterbuese, R. et al. (Jul. 13, 2010) "T cell-engaging BiTE antibodies specific for EGFR potently eliminate KRAS- and BRAF-mutated colorectal cancer cells" *Proc Natl Acad Sci USA*, 107(28): 12605-12610. Epub Jun. 28, 2010.
Malcolm, S.L. et al. (2012) "A humanised mouse model of cytokine release: Comparison of CD3-specific antibody fragments" *J Immunol Meth*, 384:33-42.
Malmqvist, M. (Jan. 14, 1993) "Biospecific interaction analysis using biosensor technology" *Nature*, 361:186-187.
Marvin, J.S. and Z. Zhu "Recombinant approaches to IgG-like bispecific antibodies" *Acta Pharm. Sinica*, 26:649-658 (2005).
Nisonoff, A. and W.J. Mandy, "Quantitative estimation of the hybridization of rabbit antibodies" *Nature*, 194:355-359 (1962).
Okayama, H. and P. Berg, "A cDNA cloning vector that permits expression of cDNA inserts in mammalian cells" *Mol. Cell. Biol.*, 3:280-289 (1983).
Olafsen, T. "Fc engineering: serum half-life modulation through FcRn binding" in *Antibody Engineering: Methods and Protocols, Second Edition.Methods Mol. Biol.*, vol. 907, pp. 537-556 (2012).
Orcutt, K.D. et al., "A modular IgG-scFv bispecific antibody topology" *Prot. Eng. Design Select.*, 23:221-228 (2010).
Pace, C.S. et al. (Aug. 13, 2013) "Bispecific antibodies directed to CD4 domain 2 and HIV envelope exhibit exceptional breadth and picomolar potency against HIV-1" *PNAS*, 110(33): 13540-13545.
Petkova, S.B et al., "Enhanced half-life of genetically engineered human IgG1 antibodies in a humanized FcRn mouse model: potential application in humorally mediated autoimmune disease" *Intl. Immunol.*, 18:1759-1769 (2006).
Polu, K.R. and H.B. Lowman (2014) "Probody therapeutics for targeting antibodies to diseased tissue" *Expert Opin Biol Ther*, 14(8):1049-1053.
Reusch, U. et al. (Jan. 1, 20016) "Anti-CD3 x anti-epidermal growth factor receptor (EGFR) bispecific antibody redirects T-cell cytolytic activity to EGFR-positive cancers in vitro and in an animal model" *Clinical Cancer Research*, vol. 12, No. 1, p. 183-190.
Riethmuller, G. "Symmetry breaking: bispecific antibodies, the beginnings, and 50 years on" *Cancer Immunity*, 12:12-18 (2012).
Sebastian, M. et al. (2007) "Treatment of non-small cell lung cancer patients with the trifimctional monoclonal antibody catumaxomab (anti-EpCAM x anti-CD3): a phase I study" *Cancer Immunol. Immunother*, 56:1637-1644.

(56) References Cited

OTHER PUBLICATIONS

Shopes, B. (1992) "A Genetically Engineered Human IgG Mutant with Enhanced Cytolytic Activity" *Journal of Immunology*, vol. 148, No. 1, p. 2918-2922.
Smith-Gill, S.J. et al. "Contributions of Immunoglobin Heavy and Light Chains to Antoibody Specificty for Lysozome and Two Haptens" *J Immunol*, vol. 139, p. 4135-4144 (1987).
Song, M-K. et al. "Light chain of. Natural Antibody Plays a Dominant Role in Protein Antigen Binding" *Biochemical and Biophysical Research Communications*, vol. 268, p. 390-394 (2000).
Stevenson, G.T. et al., "A chimeric antibody with dual Fc regions (bisFabFc) prepared by manipulations at the IgG hinge" *Anti-Cancer Drug Design*, vol. 3, p. 219-230 (1989).
Sun, L.L. et al. (May 13, 2015) "Anti-CD20/CD3 T cell-dependent bispecific antibody for the treatment of B cell malignancies" *Sci Transl Med.*, 7(287):287ra70, 11 pages.
Ward, E.S. et al. "Binding activities of a repertoire of single immunoglobin variable domains secreted from *Escherichia coli*" *Nature*, vol. 341, p. 544-546 (1989).
Watanabe, Y. et al. (2011) "In vitro and in vivo antitumor effects of recombinant bispecific antibodies based on humanized anti-EGFR antibody", *Oncology Reports*, 26:949-955.
Wu, C. et al. (Nov. 2007) "Simultaneous targeting of multiple disease mediators by a dual-variable-domain immunoglobulin" *Nature Biotechnol.*, 25:1290-1297.
Bedouelle et al., "Diversity and junction residues as hotspots of binding energy in an antibody neutralizing the dengue virus", FEBS J. (2006) 273(1):34-46.
Canfield and Morrison, "The Binding Affinity of Human Igg for its High Affinity Fc Receptor is Determined by Multiple Amino Acids in the CH2 Domain and is Modulated by the Hinge Region", J. Exp. Med. (1991) 173(6):1483-1491.
Chappel et al., "Identification of a secondary Fc gamma RI binding site within a genetically engineered human IgG antibody", J. Biol. Chem. (1993) 268(33):25124-25131.
Dong et al., "Stable IgG-like Bispecific Antibodies Directed toward the Type I Insulin-like Growth Factor Receptor Demonstrate Enhanced Ligand Blockade and Anti-tumor Activity", JBC (2011) 286(6):4703-4717. (Supplemental pp. 1-6).
Dufner et al., "Harnessing phage and ribosome display for antibody optimization", Trends Biotechnol. (2006) 24 (11):523-529.
Erster et al., "Site-specific targeting of antibody activity in vivo mediated by disease-associated proteases", J. Control Release (2012) 161(3):804-812.
Geiger et al., "Protease-Activation Using Anti-Idiotypic Masks Enables Tumor Specificity of a Folate Receptor 1-T Cell Bispecific Antibody", Nat. Commun. (2020) 11:3196.
Han et al., "Masked Chimeric Antigen Receptor for Tumor-Specific Activation", Mol. Ther. (2017) 25(1):274-284.
Metz et al., "Bispecific Antibody Derivatives with Restricted Binding Functionalities that are Activated by Proteolytic Processing" Prot. Eng. Des. & Sel. (2012) 25(10): 571-580.
Vajdos et al., "Comprehensive Functional Maps of the Antigen-binding Site of an Anti-Erb82 Antibody Obtained with Shotgun Scanning Mutagenesis", J. Mol Biol (2002) 320(2):415-428.
Viricel et al., "Monodisperse Polysarcosine-Based Highly-Loaded Antibody-Drug Conjugates", Chem, Sci. (2019) 10 (14):4048-4053.

\* cited by examiner

FIGS. 3A-B
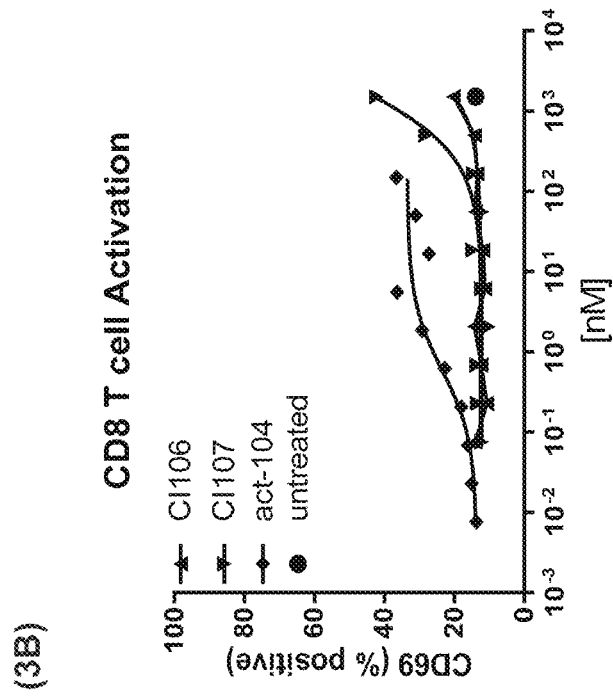
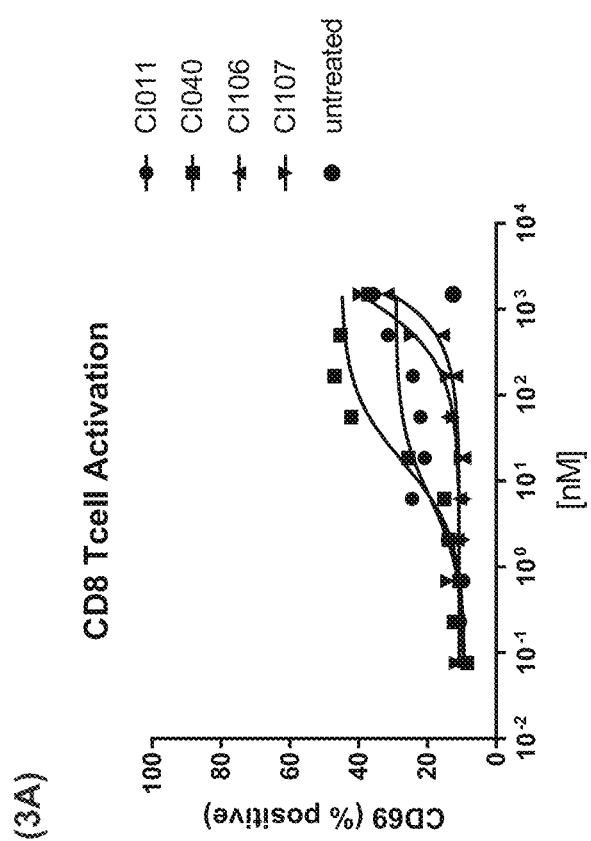

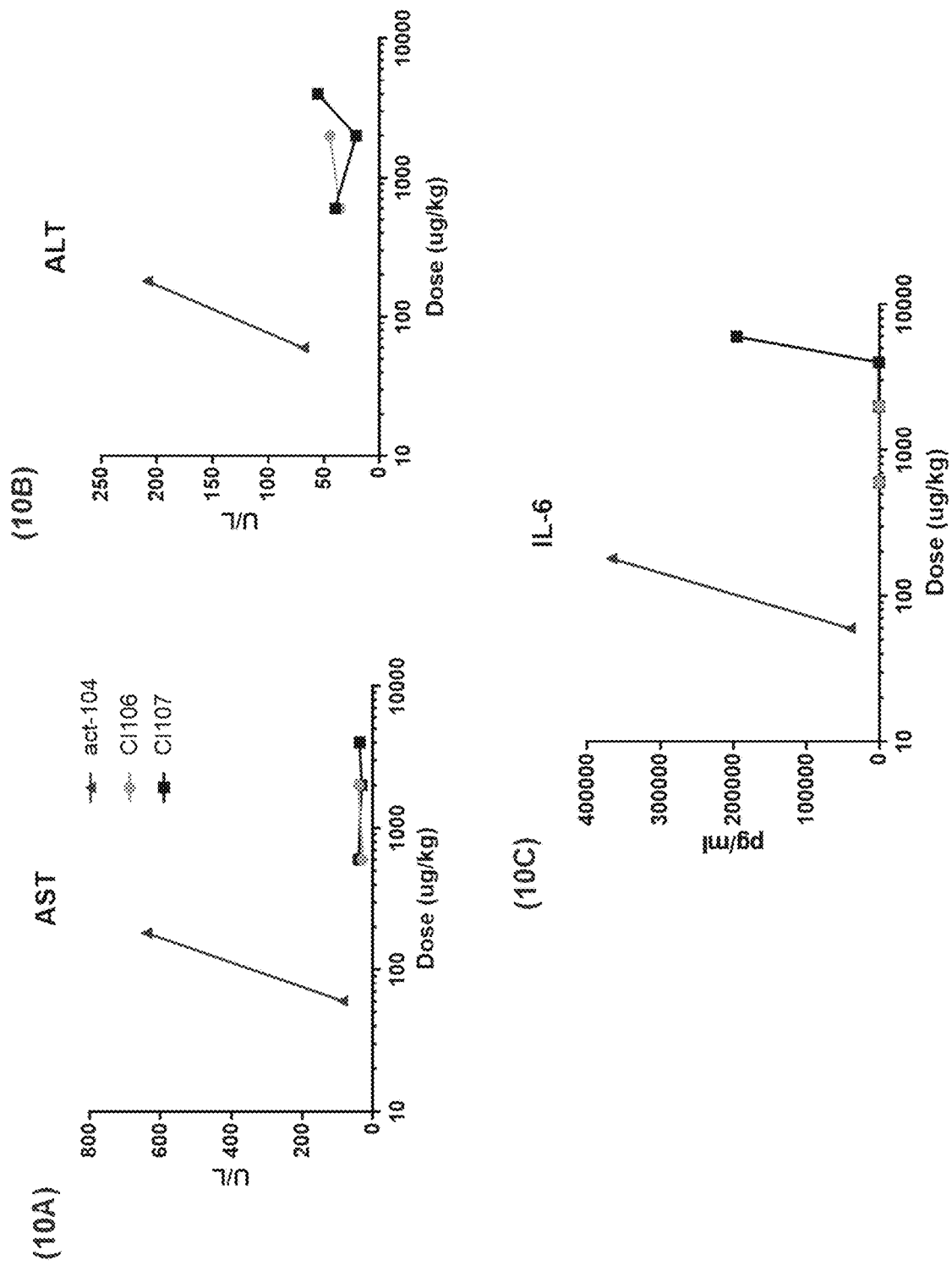
FIGS. 10A-C

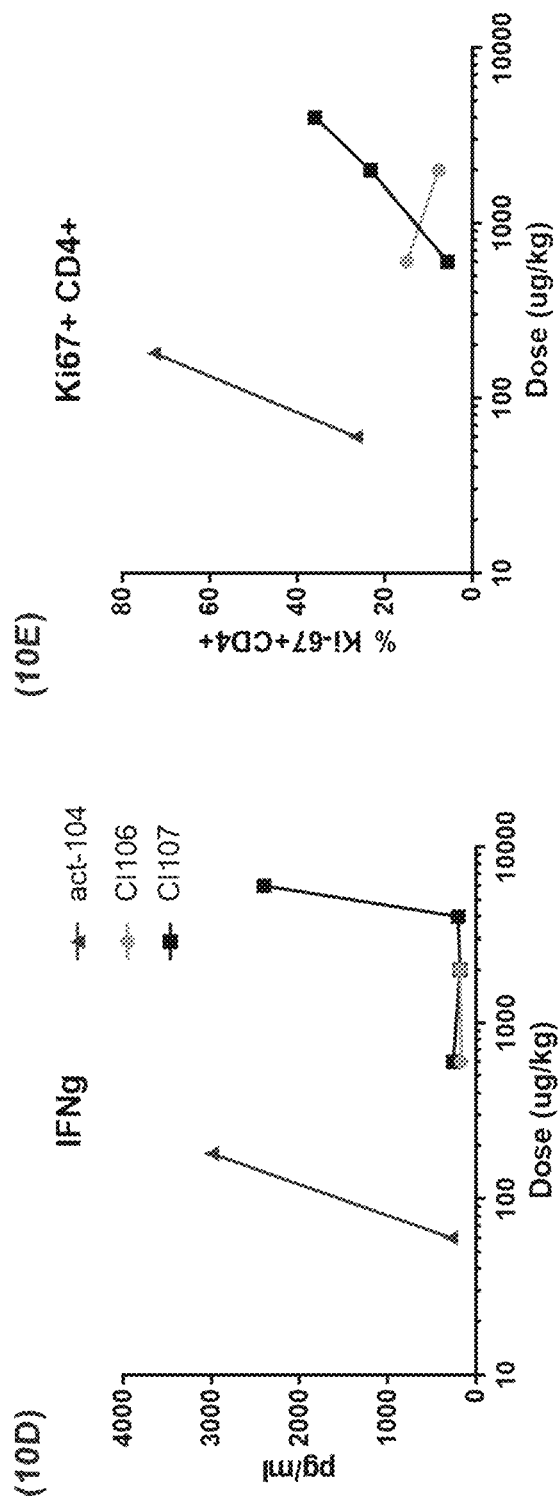
FIGS. 10D-E (14A)

(14B)

US 11,472,889 B2

```
                          SEQUENCE LISTING

<160> NUMBER OF SEQ ID NOS: 216

<210> SEQ ID NO 1
<211> LENGTH: 109
<212> TYPE: PRT
<213> ORGANISM: Artificial Sequence
<220> FEATURE:
<223> OTHER INFORMATION: synthetic

<400> SEQUENCE: 1

Gln Thr Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Pro Arg Gly
        35                  40                  45

Leu Ile Gly Gly Thr Asn Lys Arg Ala Pro Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 2
<211> LENGTH: 125
<212> TYPE: PRT
<213> ORGANISM: Artificial Sequence
<220> FEATURE:
<223> OTHER INFORMATION: synthetic

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80
```

```
Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 3
<211> LENGTH: 125
<212> TYPE: PRT
<213> ORGANISM: Artificial Sequence
<220> FEATURE:
<223> OTHER INFORMATION: synthetic

<400> SEQUENCE: 3

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
                20                  25                  30

Ala Met Asn Trp Val Arg Gln Ala Ser Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 4
<211> LENGTH: 109
<212> TYPE: PRT
<213> ORGANISM: Artificial Sequence
<220> FEATURE:
<223> OTHER INFORMATION: synthetic

<400> SEQUENCE: 4

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Gly Thr Pro Ala Arg Phe
        50                  55                  60

Ser Gly Ser Leu Ile Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 5
<211> LENGTH: 7
<212> TYPE: PRT
<213> ORGANISM: Artificial Sequence
```

```
<220> FEATURE:
<223> OTHER INFORMATION: synthetic

<400> SEQUENCE: 5

Gly Thr Asn Lys Arg Ala Pro
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic

<400> SEQUENCE: 6

Ala Leu Trp Tyr Ser Asn Leu Trp Val
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic

<400> SEQUENCE: 7

Thr Tyr Ala Met Asn
1               5

<210> SEQ ID NO 8
<211> LENGTH: 19
<212> TYPE: PRT
<213> ORGANISM: Artificial Sequence
<220> FEATURE:
<223> OTHER INFORMATION: synthetic

<400> SEQUENCE: 8

Arg Ile Arg Ser Lys Tyr Asn Asn Tyr Ala Thr Tyr Tyr Ala Asp Ser
1               5                   10                  15

Val Lys Asp

<210> SEQ ID NO 9
<211> LENGTH: 14
<212> TYPE: PRT
<213> ORGANISM: Artificial Sequence
<220> FEATURE:
<223> OTHER INFORMATION: synthetic

<400> SEQUENCE: 9

His Gly Asn Phe Gly Asn Ser Tyr Val Ser Trp Phe Ala Tyr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: synthetic

<400> SEQUENCE: 10

Met Met Tyr Cys Gly Gly Asn Glu Val Leu Cys Gly Pro Arg Val
1               5                   10                  15

<210> SEQ ID NO 11
<211> LENGTH: 15
<212> TYPE: PRT
```

```
<213> ORGANISM: Artificial Sequence
<220> FEATURE:
<223> OTHER INFORMATION: synthetic

<400> SEQUENCE: 11

Gly Tyr Arg Trp Gly Cys Glu Trp Asn Cys Gly Gly Ile Thr Thr
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic

<400> SEQUENCE: 12

Gly Tyr Leu Trp Gly Cys Glu Trp Asn Cys Gly Gly Ile Thr Thr
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: synthetic

<400> SEQUENCE: 13

Leu Ser Gly Arg Ser Asp Asn His
1               5

<210> SEQ ID NO 14
<211> LENGTH: 8
<212> TYPE: PRT
<213> ORGANISM: Artificial Sequence
<220> FEATURE:
<223> OTHER INFORMATION: synthetic

<400> SEQUENCE: 14

Leu Ser Gly Arg Ser Asp Asp His
1               5

<210> SEQ ID NO 15
<211> LENGTH: 13
<212> TYPE: PRT
<213> ORGANISM: Artificial Sequence
<220> FEATURE:
<223> OTHER INFORMATION: synthetic

<400> SEQUENCE: 15

Ile Ser Ser Gly Leu Leu Ser Gly Arg Ser Asp Asn His
1               5                   10

<210> SEQ ID NO 16
<211> LENGTH: 13
<212> TYPE: PRT
<213> ORGANISM: Artificial Sequence
<220> FEATURE:
<223> OTHER INFORMATION: synthetic

<400> SEQUENCE: 16

Ile Ser Ser Gly Leu Leu Ser Gly Arg Ser Asp Gln His
1               5                   10

<210> SEQ ID NO 17
<211> LENGTH: 13
<212> TYPE: PRT
<213> ORGANISM: Artificial Sequence
```

```
<220> FEATURE:
<223> OTHER INFORMATION: synthetic

<400> SEQUENCE: 17

Ile Ser Ser Gly Leu Leu Ser Gly Arg Ser Asp Asp His
1               5                   10

<210> SEQ ID NO 18
<211> LENGTH: 8
<212> TYPE: PRT
<213> ORGANISM: Artificial Sequence
<220> FEATURE:
<223> OTHER INFORMATION: synthetic

<400> SEQUENCE: 18

Leu Ser Gly Arg Ser Asp Asn His
1               5

<210> SEQ ID NO 19
<211> LENGTH: 8
<212> TYPE: PRT
<213> ORGANISM: Artificial Sequence
<220> FEATURE:
<223> OTHER INFORMATION: synthetic

<400> SEQUENCE: 19

Leu Ser Gly Arg Ser Gly Asn His
1               5

<210> SEQ ID NO 20
<211> LENGTH: 12
<212> TYPE: PRT
<213> ORGANISM: Artificial Sequence
<220> FEATURE:
<223> OTHER INFORMATION: synthetic

<400> SEQUENCE: 20

Thr Ser Thr Ser Gly Arg Ser Ala Asn Pro Arg Gly
1               5                   10

<210> SEQ ID NO 21
<211> LENGTH: 8
<212> TYPE: PRT
<213> ORGANISM: Artificial Sequence
<220> FEATURE:
<223> OTHER INFORMATION: synthetic

<400> SEQUENCE: 21

Ile Ser Ser Gly Leu Leu Ser Ser
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Gln Asn Gln Ala Leu Arg Met Ala
1               5

<210> SEQ ID NO 23
<211> LENGTH: 10
<212> TYPE: PRT
<213> ORGANISM: Artificial Sequence
<220> FEATURE:
```

<223> OTHER INFORMATION: synthetic

<400> SEQUENCE: 23

Val His Met Pro Leu Gly Phe Leu Gly Pro
1               5                   10

<210> SEQ ID NO 24
<211> LENGTH: 8
<212> TYPE: PRT
<213> ORGANISM: Artificial Sequence
<220> FEATURE:
<223> OTHER INFORMATION: synthetic

<400> SEQUENCE: 24

Ala Val Gly Leu Leu Ala Pro Pro
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic

<400> SEQUENCE: 25

Leu Ser Gly Arg Ser Asp Asp His
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic

<400> SEQUENCE: 26

Leu Ser Gly Arg Ser Asp Ile His
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic

<400> SEQUENCE: 27

Leu Ser Gly Arg Ser Asp Gln His
1               5

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

Leu Ser Gly Arg Ser Asp Thr His
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic

```
<400> SEQUENCE: 29

Leu Ser Gly Arg Ser Asp Tyr His
1               5

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Leu Ser Gly Arg Ser Asp Asn Pro
1               5

<210> SEQ ID NO 31
<211> LENGTH: 8
<212> TYPE: PRT
<213> ORGANISM: Artificial Sequence
<220> FEATURE:
<223> OTHER INFORMATION: synthetic

<400> SEQUENCE: 31

Leu Ser Gly Arg Ser Ala Asn Pro
1               5

<210> SEQ ID NO 32
<211> LENGTH: 8
<212> TYPE: PRT
<213> ORGANISM: Artificial Sequence
<220> FEATURE:
<223> OTHER INFORMATION: synthetic

<400> SEQUENCE: 32

Leu Ser Gly Arg Ser Ala Asn Ile
1               5

<210> SEQ ID NO 33
<211> LENGTH: 8
<212> TYPE: PRT
<213> ORGANISM: Artificial Sequence
<220> FEATURE:
<223> OTHER INFORMATION: synthetic

<400> SEQUENCE: 33

Leu Ser Gly Arg Ser Asp Asn Ile
1               5

<210> SEQ ID NO 34
<211> LENGTH: 13
<212> TYPE: PRT
<213> ORGANISM: Artificial Sequence
<220> FEATURE:
<223> OTHER INFORMATION: synthetic

<400> SEQUENCE: 34

Ile Ser Ser Gly Leu Leu Ser Gly Arg Ser Asp Asn His
1               5                   10

<210> SEQ ID NO 35
<211> LENGTH: 13
<212> TYPE: PRT
<213> ORGANISM: Artificial Sequence
<220> FEATURE:
<223> OTHER INFORMATION: synthetic
```

```
<400> SEQUENCE: 35

Ile Ser Ser Gly Leu Leu Ser Gly Arg Ser Gly Asn His
1               5                   10

<210> SEQ ID NO 36
<211> LENGTH: 15
<212> TYPE: PRT
<213> ORGANISM: Artificial Sequence
<220> FEATURE:
<223> OTHER INFORMATION: synthetic

<400> SEQUENCE: 36

Ile Ser Ser Gly Leu Leu Ser Gly Arg Ser Ala Asn Pro Arg Gly
1               5                   10                  15

<210> SEQ ID NO 37
<211> LENGTH: 17
<212> TYPE: PRT
<213> ORGANISM: Artificial Sequence
<220> FEATURE:
<223> OTHER INFORMATION: synthetic

<400> SEQUENCE: 37

Ala Val Gly Leu Leu Ala Pro Pro Ser Gly Arg Ser Ala Asn Pro Arg
1               5                   10                  15

Gly

<210> SEQ ID NO 38
<211> LENGTH: 13
<212> TYPE: PRT
<213> ORGANISM: Artificial Sequence
<220> FEATURE:
<223> OTHER INFORMATION: synthetic

<400> SEQUENCE: 38

Ile Ser Ser Gly Leu Leu Ser Gly Arg Ser Asp Asp His
1               5                   10

<210> SEQ ID NO 39
<211> LENGTH: 13
<212> TYPE: PRT
<213> ORGANISM: Artificial Sequence
<220> FEATURE:
<223> OTHER INFORMATION: synthetic

<400> SEQUENCE: 39

Ile Ser Ser Gly Leu Leu Ser Gly Arg Ser Asp Ile His
1               5                   10

<210> SEQ ID NO 40
<211> LENGTH: 13
<212> TYPE: PRT
<213> ORGANISM: Artificial Sequence
<220> FEATURE:
<223> OTHER INFORMATION: synthetic

<400> SEQUENCE: 40

Ile Ser Ser Gly Leu Leu Ser Gly Arg Ser Asp Gln His
1               5                   10

<210> SEQ ID NO 41
<211> LENGTH: 13
<212> TYPE: PRT
<213> ORGANISM: Artificial Sequence
<220> FEATURE:
<223> OTHER INFORMATION: synthetic
```

<400> SEQUENCE: 41

Ile Ser Ser Gly Leu Leu Ser Gly Arg Ser Asp Thr His
1               5                   10

<210> SEQ ID NO 42
<211> LENGTH: 13
<212> TYPE: PRT
<213> ORGANISM: Artificial Sequence
<220> FEATURE:
<223> OTHER INFORMATION: synthetic

<400> SEQUENCE: 42

Ile Ser Ser Gly Leu Leu Ser Gly Arg Ser Asp Tyr His
1               5                   10

<210> SEQ ID NO 43
<211> LENGTH: 13
<212> TYPE: PRT
<213> ORGANISM: Artificial Sequence
<220> FEATURE:
<223> OTHER INFORMATION: synthetic

<400> SEQUENCE: 43

Ile Ser Ser Gly Leu Leu Ser Gly Arg Ser Asp Asn Pro
1               5                   10

<210> SEQ ID NO 44
<211> LENGTH: 13
<212> TYPE: PRT
<213> ORGANISM: Artificial Sequence
<220> FEATURE:
<223> OTHER INFORMATION: synthetic

<400> SEQUENCE: 44

Ile Ser Ser Gly Leu Leu Ser Gly Arg Ser Ala Asn Pro
1               5                   10

<210> SEQ ID NO 45
<211> LENGTH: 13
<212> TYPE: PRT
<213> ORGANISM: Artificial Sequence
<220> FEATURE:
<223> OTHER INFORMATION: synthetic

<400> SEQUENCE: 45

Ile Ser Ser Gly Leu Leu Ser Gly Arg Ser Ala Asn Ile
1               5                   10

<210> SEQ ID NO 46
<211> LENGTH: 13
<212> TYPE: PRT
<213> ORGANISM: Artificial Sequence
<220> FEATURE:
<223> OTHER INFORMATION: synthetic

<400> SEQUENCE: 46

Ile Ser Ser Gly Leu Leu Ser Gly Arg Ser Asp Asn Ile
1               5                   10

<210> SEQ ID NO 47
<211> LENGTH: 18
<212> TYPE: PRT
<213> ORGANISM: Artificial Sequence
<220> FEATURE:
<223> OTHER INFORMATION: synthetic

```
<400> SEQUENCE: 47

Ala Val Gly Leu Leu Ala Pro Pro Gly Gly Leu Ser Gly Arg Ser Asp
1               5                   10                  15

Asn His

<210> SEQ ID NO 48
<211> LENGTH: 18
<212> TYPE: PRT
<213> ORGANISM: Artificial Sequence
<220> FEATURE:
<223> OTHER INFORMATION: synthetic

<400> SEQUENCE: 48

Ala Val Gly Leu Leu Ala Pro Pro Gly Gly Leu Ser Gly Arg Ser Asp
1               5                   10                  15

Asp His

<210> SEQ ID NO 49
<211> LENGTH: 18
<212> TYPE: PRT
<213> ORGANISM: Artificial Sequence
<220> FEATURE:
<223> OTHER INFORMATION: synthetic

<400> SEQUENCE: 49

Ala Val Gly Leu Leu Ala Pro Pro Gly Gly Leu Ser Gly Arg Ser Asp
1               5                   10                  15

Ile His

<210> SEQ ID NO 50
<211> LENGTH: 18
<212> TYPE: PRT
<213> ORGANISM: Artificial Sequence
<220> FEATURE:
<223> OTHER INFORMATION: synthetic

<400> SEQUENCE: 50

Ala Val Gly Leu Leu Ala Pro Pro Gly Gly Leu Ser Gly Arg Ser Asp
1               5                   10                  15

Gln His

<210> SEQ ID NO 51
<211> LENGTH: 18
<212> TYPE: PRT
<213> ORGANISM: Artificial Sequence
<220> FEATURE:
<223> OTHER INFORMATION: synthetic

<400> SEQUENCE: 51

Ala Val Gly Leu Leu Ala Pro Pro Gly Gly Leu Ser Gly Arg Ser Asp
1               5                   10                  15

Thr His

<210> SEQ ID NO 52
<211> LENGTH: 18
<212> TYPE: PRT
<213> ORGANISM: Artificial Sequence
<220> FEATURE:
<223> OTHER INFORMATION: synthetic

<400> SEQUENCE: 52

Ala Val Gly Leu Leu Ala Pro Pro Gly Gly Leu Ser Gly Arg Ser Asp
1               5                   10                  15
```

<210> SEQ ID NO 53
<211> LENGTH: 18
<212> TYPE: PRT
<213> ORGANISM: Artificial Sequence
<220> FEATURE:
<223> OTHER INFORMATION: synthetic

<400> SEQUENCE: 53

Ala Val Gly Leu Leu Ala Pro Pro Gly Gly Leu Ser Gly Arg Ser Asp
1               5                   10                  15

Asn Pro

<210> SEQ ID NO 54
<211> LENGTH: 18
<212> TYPE: PRT
<213> ORGANISM: Artificial Sequence
<220> FEATURE:
<223> OTHER INFORMATION: synthetic

<400> SEQUENCE: 54

Ala Val Gly Leu Leu Ala Pro Pro Gly Gly Leu Ser Gly Arg Ser Ala
1               5                   10                  15

Asn Pro

<210> SEQ ID NO 55
<211> LENGTH: 18
<212> TYPE: PRT
<213> ORGANISM: Artificial Sequence
<220> FEATURE:
<223> OTHER INFORMATION: synthetic

<400> SEQUENCE: 55

Ala Val Gly Leu Leu Ala Pro Pro Gly Gly Leu Ser Gly Arg Ser Ala
1               5                   10                  15

Asn Ile

<210> SEQ ID NO 56
<211> LENGTH: 18
<212> TYPE: PRT
<213> ORGANISM: Artificial Sequence
<220> FEATURE:
<223> OTHER INFORMATION: synthetic

<400> SEQUENCE: 56

Ala Val Gly Leu Leu Ala Pro Pro Gly Gly Leu Ser Gly Arg Ser Asp
1               5                   10                  15

Asn Ile

<210> SEQ ID NO 57
<211> LENGTH: 11
<212> TYPE: PRT
<213> ORGANISM: Artificial Sequence
<220> FEATURE:
<223> OTHER INFORMATION: synthetic

<400> SEQUENCE: 57

Arg Ala Ser Gln Ser Ile Gly Thr Asn Ile His
1               5                   10

<210> SEQ ID NO 58
<211> LENGTH: 7

```
<212> TYPE: PRT
<213> ORGANISM: Artificial Sequence
<220> FEATURE:
<223> OTHER INFORMATION: synthetic

<400> SEQUENCE: 58

Tyr Ala Ser Glu Ser Ile Ser
1               5

<210> SEQ ID NO 59
<211> LENGTH: 9
<212> TYPE: PRT
<213> ORGANISM: Artificial Sequence
<220> FEATURE:
<223> OTHER INFORMATION: synthetic

<400> SEQUENCE: 59

Gln Gln Asn Asn Asn Trp Pro Thr Thr
1               5

<210> SEQ ID NO 60
<211> LENGTH: 5
<212> TYPE: PRT
<213> ORGANISM: Artificial Sequence
<220> FEATURE:
<223> OTHER INFORMATION: synthetic

<400> SEQUENCE: 60

Asn Tyr Gly Val His
1               5

<210> SEQ ID NO 61
<211> LENGTH: 16
<212> TYPE: PRT
<213> ORGANISM: Artificial Sequence
<220> FEATURE:
<223> OTHER INFORMATION: synthetic

<400> SEQUENCE: 61

Val Ile Trp Ser Gly Gly Asn Thr Asp Tyr Asn Thr Pro Phe Thr Ser
1               5                   10                  15

<210> SEQ ID NO 62
<211> LENGTH: 11
<212> TYPE: PRT
<213> ORGANISM: Artificial Sequence
<220> FEATURE:
<223> OTHER INFORMATION: synthetic

<400> SEQUENCE: 62

Ala Leu Thr Tyr Tyr Asp Tyr Glu Phe Ala Tyr
1               5                   10

<210> SEQ ID NO 63
<211> LENGTH: 107
<212> TYPE: PRT
<213> ORGANISM: Artificial Sequence
<220> FEATURE:
<223> OTHER INFORMATION: synthetic

<400> SEQUENCE: 63

Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
```

35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys
            100                 105

<210> SEQ ID NO 64
<211> LENGTH: 119
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala

<400> SEQUENCE: 64

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
     50                  55                  60

Ser Arg Leu Ser Ile Asn Lys Asp Asn Ser Lys Ser Gln Val Phe Phe
 65                  70                  75                  80

Lys Met Asn Ser Leu Gln Ser Gln Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa
        115

<210> SEQ ID NO 65
<211> LENGTH: 214
<212> TYPE: PRT
<213> ORGANISM: Artificial Sequence
<220> FEATURE:
<223> OTHER INFORMATION: synthetic

<400> SEQUENCE: 65

Gln Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

```
Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 66
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala

<400> SEQUENCE: 66

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 67
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa  may be Ser or Ala
<220> FEATURE:
<221> NAME/KEY: misc_feature
<222> LOCATION: (299)..(299)
<223> OTHER INFORMATION: Xaa can be any amino acid

<400> SEQUENCE: 67

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

```
Lys Met Asn Ser Leu Gln Ser Gln Asp Thr Ala Ile Tyr Tyr Cys Ala
                 85                  90                  95
Arg Ala Leu Thr Tyr Tyr Asp Tyr Glu Phe Ala Tyr Trp Gly Gln Gly
            100                 105                 110
Thr Leu Val Thr Val Ser Xaa Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Xaa Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

<210> SEQ ID NO 68
<211> LENGTH: 449
<212> TYPE: PRT
<213> ORGANISM: Artificial Sequence
<220> FEATURE:
<223> OTHER INFORMATION: synthetic
<220> FEATURE:

```
<221> NAME/KEY: MISC_FEATURE
<222> LOCATION: (119)..(119)
<223> OTHER INFORMATION: Xaa may be Ser or Ala

<400> SEQUENCE: 68
```

| | | | | | | | | | | | | | | | |
|---|---|---|---|---|---|---|---|---|---|---|---|---|---|---|---|
| Gln | Val | Gln | Leu | Lys | Gln | Ser | Gly | Pro | Gly | Leu | Val | Gln | Pro | Ser | Gln |
| 1 | | | | 5 | | | | | 10 | | | | | 15 | |
| Ser | Leu | Ser | Ile | Thr | Cys | Thr | Val | Ser | Gly | Phe | Ser | Leu | Thr | Asn | Tyr |
| | | | 20 | | | | | 25 | | | | | 30 | | |
| Gly | Val | His | Trp | Val | Arg | Gln | Ser | Pro | Gly | Lys | Gly | Leu | Glu | Trp | Leu |
| | | 35 | | | | | 40 | | | | | 45 | | | |
| Gly | Val | Ile | Trp | Ser | Gly | Gly | Asn | Thr | Asp | Tyr | Asn | Thr | Pro | Phe | Thr |
| | 50 | | | | | 55 | | | | | 60 | | | | |
| Ser | Arg | Leu | Ser | Ile | Asn | Lys | Asp | Asn | Ser | Lys | Ser | Gln | Val | Phe | Phe |
| 65 | | | | | 70 | | | | | 75 | | | | | 80 |
| Lys | Met | Asn | Ser | Leu | Gln | Ser | Gln | Asp | Thr | Ala | Ile | Tyr | Tyr | Cys | Ala |
| | | | | 85 | | | | | 90 | | | | | 95 | |
| Arg | Ala | Leu | Thr | Tyr | Tyr | Asp | Tyr | Glu | Phe | Ala | Tyr | Trp | Gly | Gln | Gly |
| | | | 100 | | | | | 105 | | | | | 110 | | |
| Thr | Leu | Val | Thr | Val | Ser | Xaa | Ala | Ser | Thr | Lys | Gly | Pro | Ser | Val | Phe |
| | | | 115 | | | | | 120 | | | | | 125 | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | | 180 | | | | | 185 | | | | | 190 | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | | 260 | | | | | 265 | | | | | 270 | |
| Pro | Glu | Val | Lys | Phe | Asn | Trp | Tyr | Val | Asp | Gly | Val | Glu | Val | His | Asn |
| | | | 275 | | | | | 280 | | | | | 285 | | |
| Ala | Lys | Thr | Lys | Pro | Arg | Glu | Glu | Gln | Tyr | Gln | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Glu | Glu | Met | Thr | Lys | Asn | Gln | Val | Ser | Leu | Thr |
| | | | 355 | | | | | 360 | | | | | 365 | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |
| Ser | Asn | Gly | Gln | Pro | Glu | Asn | Asn | Tyr | Lys | Thr | Thr | Pro | Pro | Val | Leu |

```
385                 390                 395                 400
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 69
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala
<220> FEATURE:
<221> NAME/KEY: misc_feature
<222> LOCATION: (236)..(236)
<223> OTHER INFORMATION: Xaa can be any amino acid

<400> SEQUENCE: 69

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Xaa Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 70
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala

<400> SEQUENCE: 70

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
            85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 71
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala
<220> FEATURE:
<221> NAME/KEY: misc_feature
<222> LOCATION: (237)..(237)
<223> OTHER INFORMATION: Xaa can be any amino acid

<400> SEQUENCE: 71

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Xaa Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 72
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala

<400> SEQUENCE: 72

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 73
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala
<220> FEATURE:
<221> NAME/KEY: misc_feature
<222> LOCATION: (333)..(333)
<223> OTHER INFORMATION: Xaa can be any amino acid

<400> SEQUENCE: 73

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Xaa Ile Glu Lys
                325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 74
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala

<400> SEQUENCE: 74

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

```
Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 75
<211> LENGTH: 449
<212> TYPE: PRT
<213> ORGANISM: Artificial Sequence
<220> FEATURE:
<223> OTHER INFORMATION: synthetic
```

<220> FEATURE:
<221> NAME/KEY: MISC_FEATURE
<222> LOCATION: (119)..(119)
<223> OTHER INFORMATION: Xaa may be Ser or Ala

<400> SEQUENCE: 75

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 76
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala

<400> SEQUENCE: 76

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 77
<211> LENGTH: 401
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (120)..(120)
<223> OTHER INFORMATION: Xaa may be Ser  or Ala

<400> SEQUENCE: 77

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Xaa Val His Thr Phe Pro Ala Val Leu
            115                 120                 125

Gln Ser Ser Gly Leu Tyr Ser Leu Ser Val Val Thr Val Pro Ser
            130                 135                 140

Ser Ser Leu Gly Thr Gln Thr Tyr Ile Cys Asn Val Asn His Lys Pro
145                 150                 155                 160
```

```
Ser Asn Thr Lys Val Asp Lys Lys Val Glu Pro Lys Ser Cys Asp Lys
            165                 170                 175

Thr His Thr Cys Pro Pro Cys Pro Ala Pro Glu Phe Glu Gly Gly Pro
            180                 185                 190

Ser Val Phe Leu Phe Pro Pro Lys Pro Lys Asp Thr Leu Met Ile Ser
            195                 200                 205

Arg Thr Pro Glu Val Thr Cys Val Val Val Asp Val Ser His Glu Asp
            210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Gln Ser Thr Tyr Arg Val
            245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Ser Ile Glu Lys
            275                 280                 285

Thr Ile Ser Lys Ala Lys Gly Gln Pro Arg Glu Pro Gln Val Tyr Thr
            290                 295                 300

Leu Pro Pro Ser Arg Glu Glu Met Thr Lys Asn Gln Val Ser Leu Thr
305                 310                 315                 320

Cys Leu Val Lys Gly Phe Tyr Pro Ser Asp Ile Ala Val Glu Trp Glu
            325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
            355                 360                 365

Ser Arg Trp Gln Gln Gly Asn Val Phe Ser Cys Ser Val Met His Glu
            370                 375                 380

Ala Leu His Asn His Tyr Thr Gln Lys Ser Leu Ser Leu Ser Pro Gly
385                 390                 395                 400

Lys

<210> SEQ ID NO 78
<211> LENGTH: 15
<212> TYPE: PRT
<213> ORGANISM: Artificial Sequence
<220> FEATURE:
<223> OTHER INFORMATION: synthetic

<400> SEQUENCE: 78

Leu Ser Cys Glu Gly Trp Ala Met Asn Arg Gln Cys Arg Ala
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: synthetic

<400> SEQUENCE: 79

Pro Pro Leu Glu Cys Asn Thr Lys Ser Met Cys Ser Lys His Asp
1               5                   10                  15

<210> SEQ ID NO 80
<211> LENGTH: 15
<212> TYPE: PRT
<213> ORGANISM: Artificial Sequence
<220> FEATURE:
```

```
<223> OTHER INFORMATION: synthetic

<400> SEQUENCE: 80

Asp Arg Asp Cys Arg Gly Arg Arg Ala Arg Cys Gln Gln Glu Gly
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: synthetic

<400> SEQUENCE: 81

Phe Thr Cys Glu Gly Trp Ala Met Asn Arg Glu Gln Cys Arg Thr
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: synthetic

<400> SEQUENCE: 82

Gly Arg Cys Pro Pro Ser Arg Asp Ile Arg Phe Cys Thr Tyr Met
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: synthetic

<400> SEQUENCE: 83

Phe Ser Cys Glu Gly Trp Ala Met Asn Arg Ser Gln Cys Arg Thr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: synthetic

<400> SEQUENCE: 84

Phe Thr Cys Glu Gly Trp Ala Met Asn Arg Asp Gln Cys Arg Thr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: synthetic

<400> SEQUENCE: 85

Cys Ile Ser Pro Arg Gly Cys Pro Asp Gly Pro Tyr Val Met Tyr
1               5                   10                  15

<210> SEQ ID NO 86
<211> LENGTH: 14
<212> TYPE: PRT
<213> ORGANISM: Artificial Sequence
<220> FEATURE:
<223> OTHER INFORMATION: synthetic
```

<400> SEQUENCE: 86

Cys Ile Ser Pro Arg Gly Cys Pro Asp Gly Pro Tyr Val Met
1               5                   10

<210> SEQ ID NO 87
<211> LENGTH: 7
<212> TYPE: PRT
<213> ORGANISM: Artificial Sequence
<220> FEATURE:
<223> OTHER INFORMATION: synthetic

<400> SEQUENCE: 87

Cys Ile Ser Pro Arg Gly Cys
1               5

<210> SEQ ID NO 88
<211> LENGTH: 5
<212> TYPE: PRT
<213> ORGANISM: Artificial Sequence
<220> FEATURE:
<223> OTHER INFORMATION: synthetic

<400> SEQUENCE: 88

Gly Ser Gly Gly Ser
1               5

<210> SEQ ID NO 89
<211> LENGTH: 4
<212> TYPE: PRT
<213> ORGANISM: Artificial Sequence
<220> FEATURE:
<223> OTHER INFORMATION: synthetic

<400> SEQUENCE: 89

Gly Gly Gly Ser
1

<210> SEQ ID NO 90
<211> LENGTH: 4
<212> TYPE: PRT
<213> ORGANISM: Artificial Sequence
<220> FEATURE:
<223> OTHER INFORMATION: synthetic

<400> SEQUENCE: 90

Gly Gly Ser Gly
1

<210> SEQ ID NO 91
<211> LENGTH: 5
<212> TYPE: PRT
<213> ORGANISM: Artificial Sequence
<220> FEATURE:
<223> OTHER INFORMATION: synthetic

<400> SEQUENCE: 91

Gly Gly Ser Gly Gly
1               5

<210> SEQ ID NO 92
<211> LENGTH: 5
<212> TYPE: PRT
<213> ORGANISM: Artificial Sequence
<220> FEATURE:
<223> OTHER INFORMATION: synthetic

```
<400> SEQUENCE: 92

Gly Ser Gly Ser Gly
1               5

<210> SEQ ID NO 93
<211> LENGTH: 5
<212> TYPE: PRT
<213> ORGANISM: Artificial Sequence
<220> FEATURE:
<223> OTHER INFORMATION: synthetic

<400> SEQUENCE: 93

Gly Ser Gly Gly Gly
1               5

<210> SEQ ID NO 94
<211> LENGTH: 5
<212> TYPE: PRT
<213> ORGANISM: Artificial Sequence
<220> FEATURE:
<223> OTHER INFORMATION: synthetic

<400> SEQUENCE: 94

Gly Gly Gly Ser Gly
1               5

<210> SEQ ID NO 95
<211> LENGTH: 5
<212> TYPE: PRT
<213> ORGANISM: Artificial Sequence
<220> FEATURE:
<223> OTHER INFORMATION: synthetic

<400> SEQUENCE: 95

Gly Ser Ser Ser Gly
1               5

<210> SEQ ID NO 96
<211> LENGTH: 11
<212> TYPE: PRT
<213> ORGANISM: Artificial Sequence
<220> FEATURE:
<223> OTHER INFORMATION: synthetic

<400> SEQUENCE: 96

Gly Ser Ser Gly Gly Ser Gly Gly Ser Gly Gly
1               5                   10

<210> SEQ ID NO 97
<211> LENGTH: 4
<212> TYPE: PRT
<213> ORGANISM: Artificial Sequence
<220> FEATURE:
<223> OTHER INFORMATION: synthetic

<400> SEQUENCE: 97

Gly Gly Gly Ser
1

<210> SEQ ID NO 98
<211> LENGTH: 15
<212> TYPE: PRT
<213> ORGANISM: Artificial Sequence
<220> FEATURE:
<223> OTHER INFORMATION: synthetic

<400> SEQUENCE: 98
```

```
Gly Gly Gly Gly Ser Gly Gly Gly Ser Gly Gly Gly Ser
1               5                   10                  15

<210> SEQ ID NO 99
<211> LENGTH: 5
<212> TYPE: PRT
<213> ORGANISM: Artificial Sequence
<220> FEATURE:
<223> OTHER INFORMATION: synthetic

<400> SEQUENCE: 99

Gly Gly Gly Gly Ser
1               5

<210> SEQ ID NO 100
<211> LENGTH: 13
<212> TYPE: PRT
<213> ORGANISM: Artificial Sequence
<220> FEATURE:
<223> OTHER INFORMATION: synthetic

<400> SEQUENCE: 100

Gly Ser Ser Gly Gly Ser Gly Gly Ser Gly Gly Ser Gly
1               5                   10

<210> SEQ ID NO 101
<211> LENGTH: 23
<212> TYPE: PRT
<213> ORGANISM: Artificial Sequence
<220> FEATURE:
<223> OTHER INFORMATION: synthetic

<400> SEQUENCE: 101

Gly Ser Ser Gly Gly Ser Gly Gly Ser Gly Gly Gly Gly Ser Gly
1               5                   10                  15

Gly Gly Ser Gly Gly Gly Ser
            20

<210> SEQ ID NO 102
<211> LENGTH: 23
<212> TYPE: PRT
<213> ORGANISM: Artificial Sequence
<220> FEATURE:
<223> OTHER INFORMATION: synthetic

<400> SEQUENCE: 102

Gly Ser Ser Gly Gly Ser Gly Gly Ser Gly Ser Gly Gly Gly Ser
1               5                   10                  15

Gly Gly Gly Ser Gly Gly Ser
            20

<210> SEQ ID NO 103
<211> LENGTH: 5
<212> TYPE: PRT
<213> ORGANISM: Artificial Sequence
<220> FEATURE:
<223> OTHER INFORMATION: synthetic

<400> SEQUENCE: 103

Gly Ser Ser Gly Thr
1               5

<210> SEQ ID NO 104
<211> LENGTH: 8
<212> TYPE: PRT
```

<213> ORGANISM: Artificial Sequence
<220> FEATURE:
<223> OTHER INFORMATION: synthetic

<400> SEQUENCE: 104

Gly Gly Gly Ser Ser Gly Gly Ser
1               5

<210> SEQ ID NO 105
<211> LENGTH: 2241
<212> TYPE: DNA
<213> ORGANISM: Artificial Sequence
<220> FEATURE:
<223> OTHER INFORMATION: synthetic

<400> SEQUENCE: 105

| | | | | | |
|---|---|---|---|---|---|
| caaggccagt | ctggccaaat | gatgtattgc | ggtgggaatg | aggtgttgtg | cgggccgcgg | 60 |
| gttggctcga | gcggtggcag | cggtggctct | ggtggtctga | gcggccgttc | cgataatcat | 120 |
| ggcggcggtt | ctcagaccgt | ggtcacacag | gagccctcac | tgacagtgag | ccctggcggg | 180 |
| accgtcacac | tgacttgtcg | cagttcaact | ggcgccgtga | ctaccagcaa | ttacgctaac | 240 |
| tgggtccagc | agaaaccagg | acaggcacca | cgaggactga | tcggaggaac | taataagaga | 300 |
| gcaccaggaa | cccctgcaag | gttctccgga | tctctgctgg | ggggaaaagc | cgctctgaca | 360 |
| ctgagcggcg | tgcagcctga | ggacgaagct | gagtactatt | gcgcactgtg | gtactccaac | 420 |
| ctgtgggtgt | ttggcggggg | aactaagctg | accgtcctgg | gaggaggagg | aagcggagga | 480 |
| ggagggagcg | gaggaggagg | atccgaagtg | cagctggtcg | agagcggagg | aggactggtg | 540 |
| cagccaggag | gatccctgaa | gctgtcttgt | gcagccagtg | gcttcacctt | caacacttac | 600 |
| gcaatgaact | gggtgcggca | ggcacctggg | aagggactgg | aatgggtcgc | ccggatcaga | 660 |
| tctaaataca | taactatgc | cacctactat | gctgacagtg | tgaaggatag | gttcaccatt | 720 |
| tcacgcgacg | atagcaaaaa | cacagcttat | ctgcagatga | ataacctgaa | gaccgaggat | 780 |
| acagcagtgt | actattgcgt | cagacacggc | aatttcggga | actcttacgt | gagttggttt | 840 |
| gcctattggg | gacaggggac | actggtcacc | gtctcctcag | gaggtggtgg | atcccaggtg | 900 |
| cagctgaaac | agagcggccc | gggcctggtg | cagccgagcc | agagcctgag | cattacctgc | 960 |
| accgtgagcg | gctttagcct | gaccaactat | ggcgtgcatt | gggtgcgcca | gagcccgggc | 1020 |
| aaaggcctgg | aatggctggg | cgtgatttgg | agcggcggca | acaccgatta | taacaccccg | 1080 |
| tttaccagcc | gcctgagcat | taacaaagat | aacagcaaaa | gccaggtgtt | ttttaaaatg | 1140 |
| aacagcctgc | aaagccagga | taccgcgatt | tattattgcg | cgcgcgcgct | gacctattat | 1200 |
| gattatgaat | ttgcgtattg | gggccagggc | accctggtga | ccgtgagcgc | ggctagcacc | 1260 |
| aagggcccat | cggtcttccc | cctggcaccc | tcctccaaga | gcacctctgg | gggcacagcg | 1320 |
| gccctgggct | gcctggtcaa | ggactacttc | cccgaaccgg | tgacggtgtc | gtggaactca | 1380 |
| ggcgccctga | ccagcggcgt | gcacaccttc | ccggctgtcc | tacagtcctc | aggactctac | 1440 |
| tccctcagca | gcgtggtgac | cgtgccctcc | agcagcttgg | gcacccagac | ctacatctgc | 1500 |
| aacgtgaatc | acaagcccag | caacaccaag | gtggacaaga | aagttgagcc | caaatcttgt | 1560 |
| gacaaaactc | acacatgccc | accgtgccca | gcacctgaac | tcctgggggg | accgtcagtc | 1620 |
| ttcctcttcc | ccccaaaacc | caaggacacc | ctcatgatct | cccggacccc | tgaggtcaca | 1680 |
| tgcgtggtgg | tggacgtgag | ccacgaagac | cctgaggtca | agttcaactg | gtacgtggac | 1740 |
| ggcgtggagg | tgcataatgc | caagacaaag | ccgcgggagg | agcagtacca | gagcacgtac | 1800 |

```
cgtgtggtca gcgtcctcac cgtcctgcac caggactggc tgaatggcaa ggagtacaag   1860
tgcaaggtct ccaacaaagc cctcccagcc cccatcgaga aaaccatctc caaagccaaa   1920
gggcagcccc gagaaccaca ggtgtacacc ctgcccccat cccgggagga gatgaccaag   1980
aaccaggtca gcctgacctg cctggtcaaa ggcttctatc ccagcgacat cgccgtggag   2040
tgggagagca atgggcagcc ggagaacaac tacaagacca cgcctcccgt gctggactcc   2100
gacggctcct tcttcctcta cagcaagctc accgtggaca agagcaggtg gcagcagggg   2160
aacgtcttct catgctccgt gatgcatgag gctctgcaca accactacac gcagaagagc   2220
ctctccctgt ctccgggtaa a                                            2241

<210> SEQ ID NO 106
<211> LENGTH: 747
<212> TYPE: PRT
<213> ORGANISM: Artificial Sequence
<220> FEATURE:
<223> OTHER INFORMATION: synthetic

<400> SEQUENCE: 106

Gln Gly Gln Ser Gly Gln Met Met Tyr Cys Gly Gly Asn Glu Val Leu
1               5                   10                  15

Cys Gly Pro Arg Val Gly Ser Ser Gly Ser Gly Ser Gly Gly
            20                  25                  30

Leu Ser Gly Arg Ser Asp Asn His Gly Gly Ser Gln Thr Val Val
            35                  40                  45

Thr Gln Glu Pro Ser Leu Thr Val Ser Pro Gly Gly Thr Val Thr Leu
    50                  55                  60

Thr Cys Arg Ser Ser Thr Gly Ala Val Thr Thr Ser Asn Tyr Ala Asn
65                  70                  75                  80

Trp Val Gln Gln Lys Pro Gly Gln Ala Pro Arg Gly Leu Ile Gly Gly
                85                  90                  95

Thr Asn Lys Arg Ala Pro Gly Thr Pro Ala Arg Phe Ser Gly Ser Leu
            100                 105                 110

Leu Gly Gly Lys Ala Ala Leu Thr Leu Ser Gly Val Gln Pro Glu Asp
        115                 120                 125

Glu Ala Glu Tyr Tyr Cys Ala Leu Trp Tyr Ser Asn Leu Trp Val Phe
    130                 135                 140

Gly Gly Gly Thr Lys Leu Thr Val Leu Gly Gly Gly Ser Gly Gly
145                 150                 155                 160

Gly Gly Ser Gly Gly Gly Ser Glu Val Gln Leu Val Glu Ser Gly
                165                 170                 175

Gly Gly Leu Val Gln Pro Gly Gly Ser Leu Lys Leu Ser Cys Ala Ala
            180                 185                 190

Ser Gly Phe Thr Phe Asn Thr Tyr Ala Met Asn Trp Val Arg Gln Ala
        195                 200                 205

Pro Gly Lys Gly Leu Glu Trp Val Ala Arg Ile Arg Ser Lys Tyr Asn
    210                 215                 220

Asn Tyr Ala Thr Tyr Tyr Ala Asp Ser Val Lys Asp Arg Phe Thr Ile
225                 230                 235                 240

Ser Arg Asp Asp Ser Lys Asn Thr Ala Tyr Leu Gln Met Asn Asn Leu
                245                 250                 255

Lys Thr Glu Asp Thr Ala Val Tyr Tyr Cys Val Arg His Gly Asn Phe
            260                 265                 270

Gly Asn Ser Tyr Val Ser Trp Phe Ala Tyr Trp Gly Gln Gly Thr Leu
        275                 280                 285
```

```
Val Thr Val Ser Ser Gly Gly Gly Ser Gln Val Gln Leu Lys Gln
    290                 295                 300

Ser Gly Pro Gly Leu Val Gln Pro Ser Gln Ser Leu Ser Ile Thr Cys
305                 310                 315                 320

Thr Val Ser Gly Phe Ser Leu Thr Asn Tyr Gly Val His Trp Val Arg
                325                 330                 335

Gln Ser Pro Gly Lys Gly Leu Glu Trp Leu Gly Val Ile Trp Ser Gly
                340                 345                 350

Gly Asn Thr Asp Tyr Asn Thr Pro Phe Thr Ser Arg Leu Ser Ile Asn
        355                 360                 365

Lys Asp Asn Ser Lys Ser Gln Val Phe Phe Lys Met Asn Ser Leu Gln
    370                 375                 380

Ser Gln Asp Thr Ala Ile Tyr Tyr Cys Ala Arg Ala Leu Thr Tyr Tyr
385                 390                 395                 400

Asp Tyr Glu Phe Ala Tyr Trp Gly Gln Gly Thr Leu Val Thr Val Ser
                405                 410                 415

Ala Ala Ser Thr Lys Gly Pro Ser Val Phe Pro Leu Ala Pro Ser Ser
                420                 425                 430

Lys Ser Thr Ser Gly Gly Thr Ala Ala Leu Gly Cys Leu Val Lys Asp
                435                 440                 445

Tyr Phe Pro Glu Pro Val Thr Val Ser Trp Asn Ser Gly Ala Leu Thr
    450                 455                 460

Ser Gly Val His Thr Phe Pro Ala Val Leu Gln Ser Ser Gly Leu Tyr
465                 470                 475                 480

Ser Leu Ser Ser Val Val Thr Val Pro Ser Ser Ser Leu Gly Thr Gln
                485                 490                 495

Thr Tyr Ile Cys Asn Val Asn His Lys Pro Ser Asn Thr Lys Val Asp
            500                 505                 510

Lys Lys Val Glu Pro Lys Ser Cys Asp Lys Thr His Thr Cys Pro Pro
        515                 520                 525

Cys Pro Ala Pro Glu Leu Leu Gly Gly Pro Ser Val Phe Leu Phe Pro
    530                 535                 540

Pro Lys Pro Lys Asp Thr Leu Met Ile Ser Arg Thr Pro Glu Val Thr
545                 550                 555                 560

Cys Val Val Val Asp Val Ser His Glu Asp Pro Glu Val Lys Phe Asn
                565                 570                 575

Trp Tyr Val Asp Gly Val Glu Val His Asn Ala Lys Thr Lys Pro Arg
            580                 585                 590

Glu Glu Gln Tyr Gln Ser Thr Tyr Arg Val Val Ser Val Leu Thr Val
        595                 600                 605

Leu His Gln Asp Trp Leu Asn Gly Lys Glu Tyr Lys Cys Lys Val Ser
    610                 615                 620

Asn Lys Ala Leu Pro Ala Pro Ile Glu Lys Thr Ile Ser Lys Ala Lys
625                 630                 635                 640

Gly Gln Pro Arg Glu Pro Gln Val Tyr Thr Leu Pro Pro Ser Arg Glu
                645                 650                 655

Glu Met Thr Lys Asn Gln Val Ser Leu Thr Cys Leu Val Lys Gly Phe
            660                 665                 670

Tyr Pro Ser Asp Ile Ala Val Glu Trp Glu Ser Asn Gly Gln Pro Glu
        675                 680                 685

Asn Asn Tyr Lys Thr Thr Pro Pro Val Leu Asp Ser Asp Gly Ser Phe
    690                 695                 700
```

```
Phe Leu Tyr Ser Lys Leu Thr Val Asp Lys Ser Arg Trp Gln Gln Gly
705                 710                 715                 720

Asn Val Phe Ser Cys Ser Val Met His Glu Ala Leu His Asn His Tyr
            725                 730                 735

Thr Gln Lys Ser Leu Ser Leu Ser Pro Gly Lys
            740                 745
```

<210> SEQ ID NO 107
<211> LENGTH: 783
<212> TYPE: DNA
<213> ORGANISM: Artificial Sequence
<220> FEATURE:
<223> OTHER INFORMATION: synthetic

<400> SEQUENCE: 107

```
caaggccagt ctggccagtg catctcacct cgtggttgtc cggacggccc atacgtcatg    60
tacggctcga gcggtggcag cggtggctct ggtggatccg gtctgagcgg ccgttccgat   120
aatcatggca gtagcggtac ccagatcttg ctgacccaga gcccggtgat tctgagcgtg   180
agcccgggcg aacgtgtgag ctttagctgc cgcgcgagcc agagcattgg caccaacatt   240
cattggtatc agcagcgcac caacggcagc ccgcgcctgc tgattaaata tgcgagcgaa   300
agcattagcg gcattccgag ccgctttagc ggcagcggca gcggcaccga ttttacccct g   360 agcattaaca gcgtggaaag cgaagatatt gcggattatt attgccagca gaacaacaac   420
tggccgacca cctttggcgc gggcaccaaa ctggaactga acgtacggt ggctgcacca    480 tctgtcttca tcttcccgcc atctgatgag cagttgaaat ctggaactgc ctctgttgtg   540
tgcctgctga taacttcta tcccagagag gccaaagtac agtggaaggt ggataacgcc    600
ctccaatcgg gtaactccca ggagagtgtc acagagcagg acagcaagga cagcacctac   660
agcctcagca gcaccctgac gctgagcaaa gcagactacg agaaacacaa agtctacgcc   720
tgcgaagtca cccatcaggg cctgagctcg cccgtcacaa agagcttcaa caggggagag   780
tgt                                                                783
```

<210> SEQ ID NO 108
<211> LENGTH: 261
<212> TYPE: PRT
<213> ORGANISM: Artificial Sequence
<220> FEATURE:
<223> OTHER INFORMATION: synthetic

<400> SEQUENCE: 108

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Leu Ser Gly Arg Ser Asp Asn His Gly Ser Ser Gly Thr Gln
            35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
```

```
            115                 120                 125
Asp Ile Ala Asp Tyr Tyr Cys Gln Gln Asn Asn Asn Trp Pro Thr Thr
        130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 109
<211> LENGTH: 2241
<212> TYPE: DNA
<213> ORGANISM: Artificial Sequence
<220> FEATURE:
<223> OTHER INFORMATION: synthetic

<400> SEQUENCE: 109
caaggccagt ctggccaaat gatgtattgc ggtgggaatg aggtgttgtg cgggccgcgg      60
gttggctcga gcggtggcag cggtggctct ggtggtggtg gaggctcggg cggtgggagc     120
ggcggcggtt ctcagaccgt ggtcacacag gagccctcac tgacagtgag ccctggcggg     180
accgtcacac tgacttgtcg cagttcaact ggcgccgtga ctaccagcaa ttacgctaac     240
tgggtccagc agaaaccagg acaggcacca cgaggactga tcggaggaac taataagaga     300
gcaccaggaa cccctgcaag gttctccgga tctctgctgg ggggaaaagc cgctctgaca     360
ctgagcggcg tgcagcctga ggacgaagct gagtactatt gcgcactgtg gtactccaac     420
ctgtgggtgt ttggcggggg aactaagctg accgtcctgg gaggaggagg aagcggagga     480
ggagggagcg gaggaggagg atccgaagtg cagctggtcg agagcggagg aggactggtg     540
cagccaggag gatccctgaa gctgtcttgt gcagccagtg gcttcacctt caacacttac     600
gcaatgaact gggtgcggca ggcacctggg aagggactgg aatgggtcgc ccggatcaga     660
tctaaataca taactatgc cacctactat gctgacagtg tgaaggatag gttcaccatt     720
tcacgcgacg atagcaaaaa cacagcttat ctgcagatga taacctgaa gaccgaggat     780 acagcagtgt actattgcgt cagacacggc aatttcggga actcttacgt gagttggttt     840
gcctattggg gacaggggac actggtcacc gtctcctcag aggtggtgg atcccaggtg     900 cagctgaaac agagcggccc gggcctggtg cagccgagcc agagcctgag cattacctgc     960
accgtgagcg gctttagcct gaccaactat ggcgtgcatt gggtgcgcca gagcccgggc    1020
aaaggcctgg aatggctggg cgtgatttgg agcggcggca acaccgatta taacaccccg    1080
tttaccagcc gcctgagcat taacaaagat aacagcaaaa gccaggtgtt ttttaaaatg    1140
aacagcctgc aaagccagga taccgcgatt tattattgcg cgcgcgcgct gacctattat    1200
```

```
gattatgaat ttgcgtattg gggccagggc accctggtga ccgtgagcgc ggctagcacc    1260
aagggcccat cggtcttccc cctggcaccc tcctccaaga gcacctctgg gggcacagcg    1320
gccctgggct gcctggtcaa ggactacttc cccgaaccgg tgacggtgtc gtggaactca    1380
ggcgccctga ccagcggcgt gcacaccttc ccggctgtcc tacagtcctc aggactctac    1440
tccctcagca gcgtggtgac cgtgccctcc agcagcttgg gcacccagac ctacatctgc    1500
aacgtgaatc acaagcccag caacaccaag gtggacaaga agttgagcc caaatcttgt     1560 gacaaaactc acacatgccc accgtgccca gcacctgaac tcctgggggg accgtcagtc    1620
ttcctcttcc ccccaaaacc caaggacacc ctcatgatct cccggacccc tgaggtcaca    1680
tgcgtggtgg tggacgtgag ccacgaagac cctgaggtca agttcaactg gtacgtggac    1740
ggcgtggagg tgcataatgc caagacaaag ccgcgggagg agcagtacca gagcacgtac    1800
cgtgtggtca gcgtcctcac cgtcctgcac caggactggc tgaatggcaa ggagtacaag    1860
tgcaaggtct ccaacaaagc cctcccagcc cccatcgaga aaaccatctc caaagccaaa    1920
gggcagcccc gagaaccaca ggtgtacacc ctgcccccat cccgggagga gatgaccaag    1980
aaccaggtca gcctgacctg cctggtcaaa ggcttctatc ccagcgacat cgccgtggag    2040
tgggagagca atgggcagcc ggagaacaac tacaagacca cgcctcccgt gctggactcc    2100
gacggctcct tcttcctcta cagcaagctc accgtggaca gagcaggtg gcagcagggg     2160 aacgtcttct catgctccgt gatgcatgag gctctgcaca accactacac gcagaagagc    2220
ctctccctgt ctccgggtaa a                                              2241
```

<210> SEQ ID NO 110  
<211> LENGTH: 747  
<212> TYPE: PRT  
<213> ORGANISM: Artificial Sequence  
<220> FEATURE:  
<223> OTHER INFORMATION: synthetic

<400> SEQUENCE: 110

```
Gln Gly Gln Ser Gly Gln Met Met Tyr Cys Gly Gly Asn Glu Val Leu
1               5                   10                  15

Cys Gly Pro Arg Val Gly Ser Ser Gly Ser Gly Gly Ser Gly Gly
                20                  25                  30

Gly Gly Gly Ser Gly Gly Gly Ser Gly Gly Gly Ser Gln Thr Val Val
            35                  40                  45

Thr Gln Glu Pro Ser Leu Thr Val Ser Pro Gly Gly Thr Val Thr Leu
        50                  55                  60

Thr Cys Arg Ser Ser Thr Gly Ala Val Thr Thr Ser Asn Tyr Ala Asn
65                  70                  75                  80

Trp Val Gln Gln Lys Pro Gly Gln Ala Pro Arg Gly Leu Ile Gly Gly
                85                  90                  95

Thr Asn Lys Arg Ala Pro Gly Thr Pro Ala Arg Phe Ser Gly Ser Leu
            100                 105                 110

Leu Gly Gly Lys Ala Ala Leu Thr Leu Ser Gly Val Gln Pro Glu Asp
        115                 120                 125

Glu Ala Glu Tyr Tyr Cys Ala Leu Trp Tyr Ser Asn Leu Trp Val Phe
    130                 135                 140

Gly Gly Gly Thr Lys Leu Thr Val Leu Gly Gly Gly Ser Gly Gly
145                 150                 155                 160

Gly Gly Ser Gly Gly Gly Ser Glu Val Gln Leu Val Glu Ser Gly
                165                 170                 175
```

```
Gly Gly Leu Val Gln Pro Gly Gly Ser Leu Lys Leu Ser Cys Ala Ala
            180                 185                 190

Ser Gly Phe Thr Phe Asn Thr Tyr Ala Met Asn Trp Val Arg Gln Ala
        195                 200                 205

Pro Gly Lys Gly Leu Glu Trp Val Ala Arg Ile Arg Ser Lys Tyr Asn
    210                 215                 220

Asn Tyr Ala Thr Tyr Tyr Ala Asp Ser Val Lys Asp Arg Phe Thr Ile
225                 230                 235                 240

Ser Arg Asp Asp Ser Lys Asn Thr Ala Tyr Leu Gln Met Asn Asn Leu
                245                 250                 255

Lys Thr Glu Asp Thr Ala Val Tyr Tyr Cys Val Arg His Gly Asn Phe
            260                 265                 270

Gly Asn Ser Tyr Val Ser Trp Phe Ala Tyr Trp Gly Gln Gly Thr Leu
        275                 280                 285

Val Thr Val Ser Ser Gly Gly Gly Ser Gln Val Gln Leu Lys Gln
    290                 295                 300

Ser Gly Pro Gly Leu Val Gln Pro Ser Gln Ser Leu Ser Ile Thr Cys
305                 310                 315                 320

Thr Val Ser Gly Phe Ser Leu Thr Asn Tyr Gly Val His Trp Val Arg
                325                 330                 335

Gln Ser Pro Gly Lys Gly Leu Glu Trp Leu Gly Val Ile Trp Ser Gly
            340                 345                 350

Gly Asn Thr Asp Tyr Asn Thr Pro Phe Thr Ser Arg Leu Ser Ile Asn
        355                 360                 365

Lys Asp Asn Ser Lys Ser Gln Val Phe Phe Lys Met Asn Ser Leu Gln
    370                 375                 380

Ser Gln Asp Thr Ala Ile Tyr Tyr Cys Ala Arg Ala Leu Thr Tyr Tyr
385                 390                 395                 400

Asp Tyr Glu Phe Ala Tyr Trp Gly Gln Gly Thr Leu Val Thr Val Ser
                405                 410                 415

Ala Ala Ser Thr Lys Gly Pro Ser Val Phe Pro Leu Ala Pro Ser Ser
            420                 425                 430

Lys Ser Thr Ser Gly Gly Thr Ala Ala Leu Gly Cys Leu Val Lys Asp
        435                 440                 445

Tyr Phe Pro Glu Pro Val Thr Val Ser Trp Asn Ser Gly Ala Leu Thr
    450                 455                 460

Ser Gly Val His Thr Phe Pro Ala Val Leu Gln Ser Ser Gly Leu Tyr
465                 470                 475                 480

Ser Leu Ser Ser Val Val Thr Val Pro Ser Ser Ser Leu Gly Thr Gln
                485                 490                 495

Thr Tyr Ile Cys Asn Val Asn His Lys Pro Ser Asn Thr Lys Val Asp
            500                 505                 510

Lys Lys Val Glu Pro Lys Ser Cys Asp Lys Thr His Thr Cys Pro Pro
        515                 520                 525

Cys Pro Ala Pro Glu Leu Leu Gly Gly Pro Ser Val Phe Leu Phe Pro
    530                 535                 540

Pro Lys Pro Lys Asp Thr Leu Met Ile Ser Arg Thr Pro Glu Val Thr
545                 550                 555                 560

Cys Val Val Val Asp Val Ser His Glu Asp Pro Glu Val Lys Phe Asn
                565                 570                 575

Trp Tyr Val Asp Gly Val Glu Val His Asn Ala Lys Thr Lys Pro Arg
            580                 585                 590

Glu Glu Gln Tyr Gln Ser Thr Tyr Arg Val Val Ser Val Leu Thr Val
```

```
                595                 600                 605
Leu His Gln Asp Trp Leu Asn Gly Lys Glu Tyr Lys Cys Lys Val Ser
    610                 615                 620

Asn Lys Ala Leu Pro Ala Pro Ile Glu Lys Thr Ile Ser Lys Ala Lys
625                 630                 635                 640

Gly Gln Pro Arg Glu Pro Gln Val Tyr Thr Leu Pro Pro Ser Arg Glu
                645                 650                 655

Glu Met Thr Lys Asn Gln Val Ser Leu Thr Cys Leu Val Lys Gly Phe
                660                 665                 670

Tyr Pro Ser Asp Ile Ala Val Glu Trp Glu Ser Asn Gly Gln Pro Glu
                675                 680                 685

Asn Asn Tyr Lys Thr Thr Pro Pro Val Leu Asp Ser Asp Gly Ser Phe
690                 695                 700

Phe Leu Tyr Ser Lys Leu Thr Val Asp Lys Ser Arg Trp Gln Gln Gly
705                 710                 715                 720

Asn Val Phe Ser Cys Ser Val Met His Glu Ala Leu His Asn His Tyr
                725                 730                 735

Thr Gln Lys Ser Leu Ser Leu Ser Pro Gly Lys
                740                 745
```

<210> SEQ ID NO 111
<211> LENGTH: 774
<212> TYPE: DNA
<213> ORGANISM: Artificial Sequence
<220> FEATURE:
<223> OTHER INFORMATION: synthetic

<400> SEQUENCE: 111

```
caaggccagt ctggccagtg catctcacct cgtggttgtc cggacggccc atacgtcatg    60
tacggctcga gcggtggcag cggtggctct ggtggctcag gtggaggctc gggcggtggg   120
agcggcggtt ctgatatctt gctgacccag agcccggtga ttctgagcgt gagcccgggc   180
gaacgtgtga gctttagctg ccgcgcgagc cagagcattg caccaacat tcattggtat     240
cagcagcgca ccaacggcag cccgcgcctg ctgattaaat atgcgagcga aagcattagc   300
ggcattccga gccgctttag cggcagcggc agcggcaccg attttaccct gagcattaac   360
agcgtggaaa gcgaagatat tgcggattat tattgccagc agaacaacaa ctggccgacc   420
acctttggcg cgggcaccaa actggaactg aaacgtacgg tggctgcacc atctgtcttc   480
atcttcccgc catctgatga gcagttgaaa tctggaactg cctctgttgt gtgcctgctg   540
aataacttct atcccagaga ggccaaagta cagtggaagg tggataacgc cctccaatcg   600
ggtaactccc aggagagtgt cacagagcag gacagcaagg acagcaccta cagcctcagc   660
agcaccctga cgctgagcaa agcagactac gagaaacaca agtctacgc ctgcgaagtc    720
acccatcagg gcctgagctc gcccgtcaca aagagcttca caggggaga gtgt           774
```

<210> SEQ ID NO 112
<211> LENGTH: 258
<212> TYPE: PRT
<213> ORGANISM: Artificial Sequence
<220> FEATURE:
<223> OTHER INFORMATION: synthetic

<400> SEQUENCE: 112

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
```

20                  25                  30
Ser Gly Gly Gly Ser Gly Gly Ser Gly Gly Ser Asp Ile Leu Leu
            35                  40                  45
Thr Gln Ser Pro Val Ile Leu Ser Val Ser Pro Gly Glu Arg Val Ser
 50                  55                  60
Phe Ser Cys Arg Ala Ser Gln Ser Ile Gly Thr Asn Ile His Trp Tyr
 65                  70                  75                  80
Gln Gln Arg Thr Asn Gly Ser Pro Arg Leu Leu Ile Lys Tyr Ala Ser
                85                  90                  95
Glu Ser Ile Ser Gly Ile Pro Ser Arg Phe Ser Gly Ser Gly Ser Gly
               100                 105                 110
Thr Asp Phe Thr Leu Ser Ile Asn Ser Val Glu Ser Glu Asp Ile Ala
           115                 120                 125
Asp Tyr Tyr Cys Gln Gln Asn Asn Asn Trp Pro Thr Thr Phe Gly Ala
       130                 135                 140
Gly Thr Lys Leu Glu Leu Lys Arg Thr Val Ala Ala Pro Ser Val Phe
145                 150                 155                 160
Ile Phe Pro Pro Ser Asp Glu Gln Leu Lys Ser Gly Thr Ala Ser Val
                165                 170                 175
Val Cys Leu Leu Asn Asn Phe Tyr Pro Arg Glu Ala Lys Val Gln Trp
            180                 185                 190
Lys Val Asp Asn Ala Leu Gln Ser Gly Asn Ser Gln Glu Ser Val Thr
        195                 200                 205
Glu Gln Asp Ser Lys Asp Ser Thr Tyr Ser Leu Ser Ser Thr Leu Thr
    210                 215                 220
Leu Ser Lys Ala Asp Tyr Glu Lys His Lys Val Tyr Ala Cys Glu Val
225                 230                 235                 240
Thr His Gln Gly Leu Ser Ser Pro Val Thr Lys Ser Phe Asn Arg Gly
                245                 250                 255
Glu Cys

<210> SEQ ID NO 113
<211> LENGTH: 2256
<212> TYPE: DNA
<213> ORGANISM: Artificial Sequence
<220> FEATURE:
<223> OTHER INFORMATION: synthetic

<400> SEQUENCE: 113
caaggccagt ctggccaaat gatgtattgc ggtgggaatg aggtgttgtg cgggccgcgg      60
gttggctcga gcggtggcag cggtggctct ggtggtatct cttccggact gctgtccggc     120
agatccgaca tcacggcgg cggttctcag accgtggtca cacaggagcc ctcactgaca     180
gtgagccctg gcgggaccgt cacactgact tgtcgcagtt caactggcgc cgtgactacc     240
agcaattacg ctaactgggt ccagcagaaa ccaggacagg caccgagg actgatcgga     300
ggaactaata agagcacc aggaaccccct gcaaggttct ccggatctct gctgggggga     360
aaagccgctc tgacactgag cggcgtgcag cctgaggacg aagctgagta ctattgcgca     420
ctgtggtact ccaacctgtg ggtgtttggc gggaacta agctgaccgt cctgggagga     480
ggaggaagcg gaggaggagg gagcggagga ggaggatccg aagtgcagct ggtcgagagc     540
ggaggaggac tggtgcagcc aggaggatcc ctgaagctgt cttgtgcagc cagtggcttc     600
accttcaaca cttacgcaat gaactgggtg cggcaggcac tgggaagggg actggaatgg     660
gtcgcccgga tcagatctaa atacaataac tatgccacct actatgctga cagtgtgaag     720

```
gataggttca ccatttcacg cgacgatagc aaaaacacag cttatctgca gatgaataac      780
ctgaagaccg aggatacagc agtgtactat tgcgtcagac acggcaattt cgggaactct      840
tacgtgagtt ggtttgccta ttggggacag gggacactgg tcaccgtctc ctcaggaggt      900
ggtggatccc aggtgcagct gaaacagagc ggcccgggcc tggtgcagcc gagccagagc      960
ctgagcatta cctgcaccgt gagcggcttt agcctgacca actatggcgt gcattgggtg     1020
cgccagagcc cgggcaaagg cctggaatgg ctgggcgtga tttggagcgg cggcaacacc     1080
gattataaca ccccgtttac cagccgcctg agcattaaca agataaacag caaaagccag     1140
gtgtttttta aaatgaacag cctgcaaagc caggataccg cgatttatta ttgcgcgcgc     1200
gcgctgacct attatgatta tgaatttgcg tattgggccc agggcaccct ggtgaccgtg     1260
agcgcggcta gcaccaaggg cccatcggtc ttccccctgg caccctcctc caagagcacc     1320
tctgggggca gcggccctgg gctgcctgt caaggact cttccccga accggtgacg     1380
gtgtcgtgga actcaggcgc cctgaccagc ggcgtgcaca ccttcccggc tgtcctacag     1440
tcctcaggac tctactccct cagcagcgtg gtgaccgtgc cctccagcag cttgggcacc     1500
cagacctaca tctgcaacgt gaatcacaag cccagcaaca ccaaggtgga caagaaagtt     1560
gagcccaaat cttgtgacaa aactcacaca tgcccaccgt gcccagcacc tgaactcctg     1620
gggggaccgt cagtcttcct cttccccca aacccaagg acaccctcat gatctcccgg     1680
acccctgagg tcacatgcgt ggtggtggac gtgagccacg aagaccctga ggtcaagttc     1740
aactggtacg tggacggcgt ggaggtgcat aatgccaaga caaagccgcg ggaggagcag     1800
taccagagca cgtaccgtgt ggtcagcgtc ctcaccgtcc tgcaccagga ctggctgaat     1860
ggcaaggagt acaagtgcaa ggtctccaac aaagccctcc cagcccccat cgagaaaacc     1920
atctccaaag ccaagggca gccccgagaa ccacaggtgt acaccctgcc cccatcccgg     1980
gaggagatga ccaagaacca ggtcagcctg acctgcctgg tcaaaggctt ctatcccagc     2040
gacatcgccg tggagtggga gagcaatggg cagccggaga caactacaa gaccacgcct     2100
cccgtgctgg actccgacgg ctccttcttc ctctacagca agctcaccgt ggacaagagc     2160
aggtggcagc aggggaacgt cttctcatgc tccgtgatgc atgaggctct gcacaaccac     2220
tacacgcaga agagcctctc cctgtctccg ggtaaa                              2256
```

<210> SEQ ID NO 114
<211> LENGTH: 752
<212> TYPE: PRT
<213> ORGANISM: Artificial Sequence
<220> FEATURE:
<223> OTHER INFORMATION: synthetic

<400> SEQUENCE: 114

Gln Gly Gln Ser Gly Gln Met Met Tyr Cys Gly Gly Asn Glu Val Leu
1               5                   10                  15

Cys Gly Pro Arg Val Gly Ser Ser Gly Gly Ser Gly Gly Ser Gly Gly
            20                  25                  30

Ile Ser Ser Gly Leu Leu Ser Gly Arg Ser Asp Asn His Gly Gly Gly
        35                  40                  45

Ser Gln Thr Val Val Thr Gln Glu Pro Ser Leu Thr Val Ser Pro Gly
    50                  55                  60

Gly Thr Val Thr Leu Thr Cys Arg Ser Ser Thr Gly Ala Val Thr Thr
65                  70                  75                  80

Ser Asn Tyr Ala Asn Trp Val Gln Gln Lys Pro Gly Gln Ala Pro Arg

-continued

```
                85                  90                  95
Gly Leu Ile Gly Gly Thr Asn Lys Arg Ala Pro Gly Thr Pro Ala Arg
            100                 105                 110

Phe Ser Gly Ser Leu Leu Gly Gly Lys Ala Ala Leu Thr Leu Ser Gly
            115                 120                 125

Val Gln Pro Glu Asp Glu Ala Glu Tyr Tyr Cys Ala Leu Trp Tyr Ser
            130                 135                 140

Asn Leu Trp Val Phe Gly Gly Gly Thr Lys Leu Thr Val Leu Gly Gly
145                 150                 155                 160

Gly Gly Ser Gly Gly Gly Gly Ser Gly Gly Gly Gly Ser Glu Val Gln
            165                 170                 175

Leu Val Glu Ser Gly Gly Gly Leu Val Gln Pro Gly Gly Ser Leu Lys
            180                 185                 190

Leu Ser Cys Ala Ala Ser Gly Phe Thr Phe Asn Thr Tyr Ala Met Asn
            195                 200                 205

Trp Val Arg Gln Ala Pro Gly Lys Gly Leu Glu Trp Val Ala Arg Ile
            210                 215                 220

Arg Ser Lys Tyr Asn Asn Tyr Ala Thr Tyr Tyr Ala Asp Ser Val Lys
225                 230                 235                 240

Asp Arg Phe Thr Ile Ser Arg Asp Asp Ser Lys Asn Thr Ala Tyr Leu
                245                 250                 255

Gln Met Asn Asn Leu Lys Thr Glu Asp Thr Ala Val Tyr Tyr Cys Val
            260                 265                 270

Arg His Gly Asn Phe Gly Asn Ser Tyr Val Ser Trp Phe Ala Tyr Trp
            275                 280                 285

Gly Gln Gly Thr Leu Val Thr Val Ser Ser Gly Gly Gly Gly Ser Gln
            290                 295                 300

Val Gln Leu Lys Gln Ser Gly Pro Gly Leu Val Gln Pro Ser Gln Ser
305                 310                 315                 320

Leu Ser Ile Thr Cys Thr Val Ser Gly Phe Ser Leu Thr Asn Tyr Gly
                325                 330                 335

Val His Trp Val Arg Gln Ser Pro Gly Lys Gly Leu Glu Trp Leu Gly
            340                 345                 350

Val Ile Trp Ser Gly Gly Asn Thr Asp Tyr Asn Thr Pro Phe Thr Ser
            355                 360                 365

Arg Leu Ser Ile Asn Lys Asp Asn Ser Lys Ser Gln Val Phe Phe Lys
            370                 375                 380

Met Asn Ser Leu Gln Ser Gln Asp Thr Ala Ile Tyr Tyr Cys Ala Arg
385                 390                 395                 400

Ala Leu Thr Tyr Tyr Asp Tyr Glu Phe Ala Tyr Trp Gly Gln Gly Thr
                405                 410                 415

Leu Val Thr Val Ser Ala Ala Ser Thr Lys Gly Pro Ser Val Phe Pro
            420                 425                 430

Leu Ala Pro Ser Ser Lys Ser Thr Ser Gly Gly Thr Ala Ala Leu Gly
            435                 440                 445

Cys Leu Val Lys Asp Tyr Phe Pro Glu Pro Val Thr Val Ser Trp Asn
            450                 455                 460

Ser Gly Ala Leu Thr Ser Gly Val His Thr Phe Pro Ala Val Leu Gln
465                 470                 475                 480

Ser Ser Gly Leu Tyr Ser Leu Ser Ser Val Val Thr Val Pro Ser Ser
                485                 490                 495

Ser Leu Gly Thr Gln Thr Tyr Ile Cys Asn Val Asn His Lys Pro Ser
            500                 505                 510
```

```
Asn Thr Lys Val Asp Lys Lys Val Glu Pro Lys Ser Cys Asp Lys Thr
            515                 520                 525
His Thr Cys Pro Pro Cys Pro Ala Pro Glu Leu Leu Gly Gly Pro Ser
        530                 535                 540
Val Phe Leu Phe Pro Pro Lys Pro Lys Asp Thr Leu Met Ile Ser Arg
545                 550                 555                 560
Thr Pro Glu Val Thr Cys Val Val Val Asp Val Ser His Glu Asp Pro
                565                 570                 575
Glu Val Lys Phe Asn Trp Tyr Val Asp Gly Val Glu Val His Asn Ala
            580                 585                 590
Lys Thr Lys Pro Arg Glu Glu Gln Tyr Gln Ser Thr Tyr Arg Val Val
        595                 600                 605
Ser Val Leu Thr Val Leu His Gln Asp Trp Leu Asn Gly Lys Glu Tyr
    610                 615                 620
Lys Cys Lys Val Ser Asn Lys Ala Leu Pro Ala Pro Ile Glu Lys Thr
625                 630                 635                 640
Ile Ser Lys Ala Lys Gly Gln Pro Arg Glu Pro Gln Val Tyr Thr Leu
                645                 650                 655
Pro Pro Ser Arg Glu Glu Met Thr Lys Asn Gln Val Ser Leu Thr Cys
            660                 665                 670
Leu Val Lys Gly Phe Tyr Pro Ser Asp Ile Ala Val Glu Trp Glu Ser
        675                 680                 685
Asn Gly Gln Pro Glu Asn Asn Tyr Lys Thr Thr Pro Pro Val Leu Asp
    690                 695                 700
Ser Asp Gly Ser Phe Phe Leu Tyr Ser Lys Leu Thr Val Asp Lys Ser
705                 710                 715                 720
Arg Trp Gln Gln Gly Asn Val Phe Ser Cys Ser Val Met His Glu Ala
                725                 730                 735
Leu His Asn His Tyr Thr Gln Lys Ser Leu Ser Leu Ser Pro Gly Lys
            740                 745                 750

<210> SEQ ID NO 115
<211> LENGTH: 798
<212> TYPE: DNA
<213> ORGANISM: Artificial Sequence
<220> FEATURE:
<223> OTHER INFORMATION: synthetic

<400> SEQUENCE: 115
caaggccagt ctggccagtg catctcacct cgtggttgtc cggacggccc atacgtcatg      60
tacggctcga gcggtggcag cggtggctct ggtggatccg gtattagcag tggtctgtta     120
agcggtcgta gcgataatca tgcagtagc ggtacccaga tcttgctgac ccagagcccg      180
gtgattctga gcgtgagccc gggcgaacgt gtgagcttta gctccgcgc gagccagagc      240 attggcacca acattcattg gtatcagcag cgcaccaacg gcagcccgcg cctgctgatt      300
aaatatgcga gcgaaagcat tagcggcatt ccgagccgct ttagcggcag cggcagcggc     360 accgattta ccctgagcat taacagcgtg aaagcgaag atattgcgga ttattattgc       420
cagcagaaca caactggcc gaccaccttt ggcgcgggca ccaaactgga actgaaacgt      480
acggtggctg caccatctgt cttcatcttc ccgccatctg atgagcagtt gaaatctgga     540
actgcctctg ttgtgtgcct gctgaataac ttctatccca gagaggccaa agtacagtgg     600
aaggtggata acgccctcca atcgggtaac tcccaggaga gtgtcacaga gcaggacagc     660
aaggacagca cctacagcct cagcagcacc ctgacgctga gcaaagcaga ctacgagaaa     720
```
cacaaagtct acgcctgcga agtcacccat cagggcctga gctcgcccgt cacaaagagc     780
ttcaacaggg gagagtgt                                                   798

<210> SEQ ID NO 116
<211> LENGTH: 266
<212> TYPE: PRT
<213> ORGANISM: Artificial Sequence
<220> FEATURE:
<223> OTHER INFORMATION: synthetic

<400> SEQUENCE: 116

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly
            20                  25                  30

Ser Gly Ile Ser Ser Gly Leu Leu Ser Gly Arg Ser Asp Asn His Gly
            35                  40                  45

Ser Ser Gly Thr Gln Ile Leu Leu Thr Gln Ser Pro Val Ile Leu Ser
        50                  55                  60

Val Ser Pro Gly Glu Arg Val Ser Phe Ser Cys Arg Ala Ser Gln Ser
65                  70                  75                  80

Ile Gly Thr Asn Ile His Trp Tyr Gln Gln Arg Thr Asn Gly Ser Pro
                85                  90                  95

Arg Leu Leu Ile Lys Tyr Ala Ser Glu Ser Ile Ser Gly Ile Pro Ser
            100                 105                 110

Arg Phe Ser Gly Ser Gly Ser Gly Thr Asp Phe Thr Leu Ser Ile Asn
        115                 120                 125

Ser Val Glu Ser Glu Asp Ile Ala Asp Tyr Tyr Cys Gln Gln Asn Asn
    130                 135                 140

Asn Trp Pro Thr Thr Phe Gly Ala Gly Thr Lys Leu Glu Leu Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 117
<211> LENGTH: 2133
<212> TYPE: DNA
<213> ORGANISM: Artificial Sequence
<220> FEATURE:
<223> OTHER INFORMATION: synthetic

<400> SEQUENCE: 117
tccgataatc atggcggcgg ttctcagacc gtggtcacac aggagccctc actgacagtg     60
agccctggcg ggaccgtcac actgacttgt cgcagttcaa ctggcgccgt gactaccagc    120

```
aattacgcta actgggtcca gcagaaacca ggacaggcac cacgaggact gatcggagga    180
actaataaga gagcaccagg aacccctgca aggttctccg gatctctgct gggggggaaaa   240 gccgctctga cactgagcgg cgtgcagcct gaggacgaag ctgagtacta ttgcgcactg    300
tggtactcca acctgtgggt gtttggcggg ggaactaagc tgaccgtcct gggaggagga    360
ggaagcggag gaggagggag cggaggagga ggatccgaag tgcagctggt cgagagcgga    420
ggaggactgg tgcagccagg aggatccctg aagctgtctt gtgcagccag tggcttcacc    480
ttcaacactt acgcaatgaa ctgggtgcgg caggcacctg ggaagggact ggaatgggtc    540
gcccggatca gatctaaata caataactat gccacctact atgctgacag tgtgaaggat    600
aggttcacca tttcacgcga cgatagcaaa aacacagctt atctgcagat gaataacctg    660
aagaccgagg atacagcagt gtactattgc gtcagacacg gcaatttcgg gaactcttac    720
gtgagttggt ttgcctattg gggacagggg acactggtca ccgtctcctc aggaggtggt    780
ggatcccagg tgcagctgaa acagagcggc ccgggcctgg tgcagccgag ccagagcctg    840
agcattacct gcaccgtgag cggctttagc ctgaccaact atggcgtgca ttgggtgcgc    900
cagagcccgg gcaaaggcct ggaatggctg ggcgtgattt ggagcggcgg caacaccgat    960
tataacaccc cgtttaccag ccgcctgagc attaacaaag ataacagcaa agccaggtg   1020 ttttttaaaa tgaacagcct gcaaagccag gataccgcga tttattattg cgcgcgcgcg   1080
ctgacctatt atgattatga atttgcgtat tggggccagg gcaccctggt gaccgtgagc   1140
gcggctagca ccaagggccc atcggtcttc cccctggcac cctcctccaa gagcacctct   1200
gggggcacag cggccctggg ctgcctggtc aaggactact tccccgaacc ggtgacggtg   1260
tcgtggaact caggcgccct gaccagcggc gtgcacacct tcccggctgt cctacagtcc   1320
tcaggactct actccctcag cagcgtggtg accgtgccct ccagcagctt gggcacccag   1380
acctacatct gcaacgtgaa tcacaagccc agcaacacca aggtggacaa gaaagttgag   1440
cccaaatctt gtgacaaaac tcacacatgc ccaccgtgcc cagcacctga actcctgggg   1500
ggaccgtcag tcttcctctt ccccccaaaa cccaaggaca cctcatgat ctcccggacc    1560 cctgaggtca catgcgtggt ggtggacgtg agccacgaag accctgaggt caagttcaac   1620
tggtacgtgg acggcgtgga ggtgcataat gccaagacaa agccgcggga ggagcagtac   1680
cagagcacgt accgtgtggt cagcgtcctc accgtcctgc accaggactg gctgaatggc   1740
aaggagtaca agtgcaaggt ctccaacaaa gccctcccag cccccatcga aaaaccatc    1800 tccaaagcca aagggcagcc ccgagaacca caggtgtaca ccctgccccc atcccgggag   1860
gagatgacca agaaccaggt cagcctgacc tgcctggtca aaggcttcta tcccagcgac   1920
atcgccgtgg agtgggagag caatgggcag ccggagaaca actacaagac cacgcctccc   1980
gtgctggact ccgacggctc cttcttcctc tacagcaagc tcaccgtgga caagagcagg   2040
tggcagcagg ggaacgtctt ctcatgctcc gtgatgcatg aggctctgca caaccactac   2100
acgcagaaga gcctctccct gtctccgggt aaa                                2133
```

<210> SEQ ID NO 118
<211> LENGTH: 711
<212> TYPE: PRT
<213> ORGANISM: Artificial Sequence
<220> FEATURE:
<223> OTHER INFORMATION: synthetic

<400> SEQUENCE: 118

```
Ser Asp Asn His Gly Gly Ser Gln Thr Val Thr Gln Glu Pro
1               5                   10                  15

Ser Leu Thr Val Ser Pro Gly Gly Thr Val Thr Leu Thr Cys Arg Ser
            20                  25                  30

Ser Thr Gly Ala Val Thr Thr Ser Asn Tyr Ala Asn Trp Val Gln Gln
        35                  40                  45

Lys Pro Gly Gln Ala Pro Arg Gly Leu Ile Gly Gly Thr Asn Lys Arg
50                      55                  60

Ala Pro Gly Thr Pro Ala Arg Phe Ser Gly Ser Leu Leu Gly Gly Lys
65                  70                  75                  80

Ala Ala Leu Thr Leu Ser Gly Val Gln Pro Glu Asp Glu Ala Glu Tyr
                85                  90                  95

Tyr Cys Ala Leu Trp Tyr Ser Asn Leu Trp Val Phe Gly Gly Gly Thr
            100                 105                 110

Lys Leu Thr Val Leu Gly Gly Gly Ser Gly Gly Gly Gly Ser Gly
        115                 120                 125

Gly Gly Gly Ser Glu Val Gln Leu Val Glu Ser Gly Gly Gly Leu Val
        130                 135                 140

Gln Pro Gly Gly Ser Leu Lys Leu Ser Cys Ala Ala Ser Gly Phe Thr
145                 150                 155                 160

Phe Asn Thr Tyr Ala Met Asn Trp Val Arg Gln Ala Pro Gly Lys Gly
            165                 170                 175

Leu Glu Trp Val Ala Arg Ile Arg Ser Lys Tyr Asn Asn Tyr Ala Thr
            180                 185                 190

Tyr Tyr Ala Asp Ser Val Lys Asp Arg Phe Thr Ile Ser Arg Asp Asp
        195                 200                 205

Ser Lys Asn Thr Ala Tyr Leu Gln Met Asn Asn Leu Lys Thr Glu Asp
        210                 215                 220

Thr Ala Val Tyr Tyr Cys Val Arg His Gly Asn Phe Gly Asn Ser Tyr
225                 230                 235                 240

Val Ser Trp Phe Ala Tyr Trp Gly Gln Gly Thr Leu Val Thr Val Ser
            245                 250                 255

Ser Gly Gly Gly Gly Ser Gln Val Gln Leu Lys Gln Ser Gly Pro Gly
        260                 265                 270

Leu Val Gln Pro Ser Gln Ser Leu Ser Ile Thr Cys Thr Val Ser Gly
        275                 280                 285

Phe Ser Leu Thr Asn Tyr Gly Val His Trp Val Arg Gln Ser Pro Gly
        290                 295                 300

Lys Gly Leu Glu Trp Leu Gly Val Ile Trp Ser Gly Gly Asn Thr Asp
305                 310                 315                 320

Tyr Asn Thr Pro Phe Thr Ser Arg Leu Ser Ile Asn Lys Asp Asn Ser
            325                 330                 335

Lys Ser Gln Val Phe Phe Lys Met Asn Ser Leu Gln Ser Gln Asp Thr
            340                 345                 350

Ala Ile Tyr Tyr Cys Ala Arg Ala Leu Thr Tyr Tyr Asp Tyr Glu Phe
        355                 360                 365

Ala Tyr Trp Gly Gln Gly Thr Leu Val Thr Val Ser Ala Ala Ser Thr
        370                 375                 380

Lys Gly Pro Ser Val Phe Pro Leu Ala Pro Ser Ser Lys Ser Thr Ser
385                 390                 395                 400

Gly Gly Thr Ala Ala Leu Gly Cys Leu Val Lys Asp Tyr Phe Pro Glu
            405                 410                 415

Pro Val Thr Val Ser Trp Asn Ser Gly Ala Leu Thr Ser Gly Val His
```

```
            420              425               430
Thr Phe Pro Ala Val Leu Gln Ser Ser Gly Leu Tyr Ser Leu Ser Ser
            435                  440                 445
Val Val Thr Val Pro Ser Ser Ser Leu Gly Thr Gln Thr Tyr Ile Cys
            450                  455                 460
Asn Val Asn His Lys Pro Ser Asn Thr Lys Val Asp Lys Lys Val Glu
465                 470                  475                 480
Pro Lys Ser Cys Asp Lys Thr His Thr Cys Pro Pro Cys Pro Ala Pro
                485                  490                 495
Glu Leu Leu Gly Gly Pro Ser Val Phe Leu Phe Pro Pro Lys Pro Lys
            500                  505                 510
Asp Thr Leu Met Ile Ser Arg Thr Pro Glu Val Thr Cys Val Val Val
            515                  520                 525
Asp Val Ser His Glu Asp Pro Glu Val Lys Phe Asn Trp Tyr Val Asp
            530                  535                 540
Gly Val Glu Val His Asn Ala Lys Thr Lys Pro Arg Glu Glu Gln Tyr
545                 550                  555                 560
Gln Ser Thr Tyr Arg Val Val Ser Val Leu Thr Val Leu His Gln Asp
                565                  570                 575
Trp Leu Asn Gly Lys Glu Tyr Lys Cys Lys Val Ser Asn Lys Ala Leu
            580                  585                 590
Pro Ala Pro Ile Glu Lys Thr Ile Ser Lys Ala Lys Gly Gln Pro Arg
            595                  600                 605
Glu Pro Gln Val Tyr Thr Leu Pro Pro Ser Arg Glu Glu Met Thr Lys
            610                  615                 620
Asn Gln Val Ser Leu Thr Cys Leu Val Lys Gly Phe Tyr Pro Ser Asp
625                 630                  635                 640
Ile Ala Val Glu Trp Glu Ser Asn Gly Gln Pro Glu Asn Asn Tyr Lys
                645                  650                 655
Thr Thr Pro Pro Val Leu Asp Ser Asp Gly Ser Phe Phe Leu Tyr Ser
            660                  665                 670
Lys Leu Thr Val Asp Lys Ser Arg Trp Gln Gln Gly Asn Val Phe Ser
            675                  680                 685
Cys Ser Val Met His Glu Ala Leu His Asn His Tyr Thr Gln Lys Ser
            690                  695                 700
Leu Ser Leu Ser Pro Gly Lys
705                 710

<210> SEQ ID NO 119
<211> LENGTH: 669
<212> TYPE: DNA
<213> ORGANISM: Artificial Sequence
<220> FEATURE:
<223> OTHER INFORMATION: synthetic

<400> SEQUENCE: 119
tccgataatc atggcagtag cggtacccag atcttgctga cccagagccc ggtgattctg      60
agcgtgagcc cgggcgaacg tgtgagcttt agctgccgcg cgagccagag cattggcacc     120
aacattcatt ggtatcagca gcgcaccaac ggcagcccgc gcctgctgat taaatatgcg     180
agcgaaagca ttagcggcat tccgagccgc tttagcggca gcggcagcgg caccgatttt     240
accctgagca ttaacagcgt ggaaagcgaa gatattgcgg attattattg ccagcagaac     300
aacaactggc cgaccacctt tggcgcgggc accaaactgg aactgaaacg tacggtggct     360
gcaccatctg tcttcatctt cccgccatct gatgagcagt tgaaatctgg aactgcctct     420
```

```
gttgtgtgcc tgctgaataa cttctatccc agagaggcca aagtacagtg gaaggtggat    480
aacgccctcc aatcgggtaa ctcccaggag agtgtcacag agcaggacag caaggacagc    540
acctacagcc tcagcagcac cctgacgctg agcaaagcag actacgagaa acacaaagtc    600
tacgcctgcg aagtcaccca tcagggcctg agctcgcccg tcacaaagag cttcaacagg    660
ggagagtgt                                                             669
```

<210> SEQ ID NO 120
<211> LENGTH: 223
<212> TYPE: PRT
<213> ORGANISM: Artificial Sequence
<220> FEATURE:
<223> OTHER INFORMATION: synthetic

<400> SEQUENCE: 120

```
Ser Asp Asn His Gly Ser Ser Gly Thr Gln Ile Leu Leu Thr Gln Ser
1               5                  10                  15

Pro Val Ile Leu Ser Val Ser Pro Gly Glu Arg Val Ser Phe Ser Cys
            20                  25                  30

Arg Ala Ser Gln Ser Ile Gly Thr Asn Ile His Trp Tyr Gln Gln Arg
        35                  40                  45

Thr Asn Gly Ser Pro Arg Leu Leu Ile Lys Tyr Ala Ser Glu Ser Ile
    50                  55                  60

Ser Gly Ile Pro Ser Arg Phe Ser Gly Ser Gly Ser Gly Thr Asp Phe
65                  70                  75                  80

Thr Leu Ser Ile Asn Ser Val Glu Ser Glu Asp Ile Ala Asp Tyr Tyr
                85                  90                  95

Cys Gln Gln Asn Asn Asn Trp Pro Thr Thr Phe Gly Ala Gly Thr Lys
            100                 105                 110

Leu Glu Leu Lys Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220
```

<210> SEQ ID NO 121
<211> LENGTH: 2244
<212> TYPE: DNA
<213> ORGANISM: Artificial Sequence
<220> FEATURE:
<223> OTHER INFORMATION: synthetic

<400> SEQUENCE: 121

```
caaggccagt ctggatccgg ttatctgtgg ggttgcgagt ggaattgcgg agggatcact     60
acaggctcga gcgtggcag cggtggctct ggtggtctga gcggccgttc cgataatcat    120
ggcggcggtt ctcaaactgt agtaactcaa gaaccaagct ctccgtctc ccctggggga    180
```

| | |
|---|---|
| acagtcacac ttacctgccg aagtagtaca ggtgctgtta cgaccagtaa ctatgccaat | 240 |
| tgggtacaac aaacgcctgg tcaggctccg cgcggattga taggaggcac gaataaacgg | 300 |
| gcacccggtg tcccggacag attcagcgga agcatactcg gtaataaggc agctcttact | 360 |
| atcactgggg cccaagctga tgatgaaagt gattattatt gtgcgctctg gtacagcaac | 420 |
| ctctgggtgt ttgggggtgg cacgaaactt actgtcttgg gcggcggcgg atcaggggga | 480 |
| ggtggctctg gaggaggagg ctcagaagtc caactggtcg aatccggggg agggctcgta | 540 |
| cagccgggtg ggtccctcaa actctcttgt gcggcctcag ggtttacctt cagtacatac | 600 |
| gcgatgaatt gggtccggca ggccagtggg aaagggctcg aatgggtagg acgaatccga | 660 |
| tcaaaataca acaactacgc tacttattac gctgattccg tgaaggacag attcacaata | 720 |
| tcccgcgacg atagcaagaa tacggcatat cttcagatga attctcttaa aactgaggat | 780 |
| accgctgtgt attactgcac aagacatggt aattttggaa actcatatgt ctcttggttc | 840 |
| gcttattggg gacagggcac gttggttacc gtgtctagcg gaggtggtgg atcccaggtg | 900 |
| cagctgaaac agagcggccc gggcctggtg cagccgagcc agagcctgag cattacctgc | 960 |
| accgtgagcg gctttagcct gaccaactat ggcgtgcatt gggtgcgcca gagcccgggc | 1020 |
| aaaggcctgg aatggctggg cgtgatttgg agcggcggca acaccgatta taacaccccg | 1080 |
| tttaccagcc gcctgagcat taacaaagat aacagcaaaa gccaggtgtt ttttaaaatg | 1140 |
| aacagcctgc aaagccagga taccgcgatt tattattgcg cgcgcgcgct gacctattat | 1200 |
| gattatgaat ttgcgtattg gggccagggc accctggtga ccgtgagcgc ggctagcacc | 1260 |
| aagggcccat cggtcttccc cctggcaccc tcctccaaga gcacctctgg ggcacagcg | 1320 |
| gccctgggct gcctggtcaa ggactacttc cccgaaccgg tgacggtgtc gtggaactca | 1380 |
| ggcgccctga ccagcggcgt gcacaccttc ccggctgtcc tacagtcctc aggactctac | 1440 |
| tccctcagca gcgtggtgac cgtgccctcc agcagcttgg gcacccagac ctacatctgc | 1500 |
| aacgtgaatc acaagcccag caacaccaag gtggacaaga agttgagcc caaatcttgt | 1560 |
| gacaaaactc acacatgccc accgtgccca gcacctgaat ttgaaggggg accgtcagtc | 1620 |
| ttcctcttcc cccaaaaacc caaggacacc ctcatgatct cccggacccc tgaggtcaca | 1680 |
| tgcgtggtgg tggacgtgag ccacgaagac cctgaggtca agttcaactg gtacgtggac | 1740 |
| ggcgtggagg tgcataatgc caagacaaag ccgcggagg agcagtacaa tagcacgtac | 1800 |
| cgtgtggtca gcgtcctcac cgtcctgcac caggactggc tgaatggcaa ggagtacaag | 1860 |
| tgcaaggtct ccaacaaagc cctcccagcc tcaatcgaga aaaccatctc caaagccaaa | 1920 |
| gggcagcccc gagaaccaca ggtgtacacc ctgcccccat cccgggagga gatgaccaag | 1980 |
| aaccaggtca gcctgacctg cctggtcaaa ggcttctatc ccagcgacat cgccgtggag | 2040 |
| tgggagagca atgggcagcc ggagaacaac tacaagacca cgcctcccgt gctggactcc | 2100 |
| gacggctcct tcttcctcta cagcaagctc accgtggaca agagcaggtg gcagcagggg | 2160 |
| aacgtcttct catgctccgt gatgcatgag gctctgcaca accactacac gcagaagagc | 2220 |
| ctctccctgt ctccgggtaa atga | 2244 |

<210> SEQ ID NO 122
<211> LENGTH: 747
<212> TYPE: PRT
<213> ORGANISM: Artificial Sequence
<220> FEATURE:
<223> OTHER INFORMATION: synthetic

<400> SEQUENCE: 122

```
Gln Gly Gln Ser Gly Ser Gly Tyr Leu Trp Gly Cys Glu Trp Asn Cys
1               5                   10                  15

Gly Gly Ile Thr Thr Gly Ser Ser Gly Ser Gly Ser Gly Gly
            20              25              30

Leu Ser Gly Arg Ser Asp Asn His Gly Gly Ser Gln Thr Val Val
        35              40              45

Thr Gln Glu Pro Ser Phe Ser Val Ser Pro Gly Gly Thr Val Thr Leu
    50              55                  60

Thr Cys Arg Ser Ser Thr Gly Ala Val Thr Thr Ser Asn Tyr Ala Asn
65              70              75                  80

Trp Val Gln Gln Thr Pro Gly Gln Ala Pro Arg Gly Leu Ile Gly Gly
                85              90                  95

Thr Asn Lys Arg Ala Pro Gly Val Pro Asp Arg Phe Ser Gly Ser Ile
            100             105             110

Leu Gly Asn Lys Ala Ala Leu Thr Ile Thr Gly Ala Gln Ala Asp Asp
        115             120             125

Glu Ser Asp Tyr Tyr Cys Ala Leu Trp Tyr Ser Asn Leu Trp Val Phe
    130             135             140

Gly Gly Gly Thr Lys Leu Thr Val Leu Gly Gly Gly Ser Gly Gly
145             150             155             160

Gly Gly Ser Gly Gly Gly Ser Glu Val Gln Leu Val Glu Ser Gly
            165             170             175

Gly Gly Leu Val Gln Pro Gly Gly Ser Leu Lys Leu Ser Cys Ala Ala
            180             185             190

Ser Gly Phe Thr Phe Ser Thr Tyr Ala Met Asn Trp Val Arg Gln Ala
    195             200             205

Ser Gly Lys Gly Leu Glu Trp Val Gly Arg Ile Arg Ser Lys Tyr Asn
    210             215             220

Asn Tyr Ala Thr Tyr Tyr Ala Asp Ser Val Lys Asp Arg Phe Thr Ile
225             230             235             240

Ser Arg Asp Asp Ser Lys Asn Thr Ala Tyr Leu Gln Met Asn Ser Leu
            245             250             255

Lys Thr Glu Asp Thr Ala Val Tyr Tyr Cys Thr Arg His Gly Asn Phe
            260             265             270

Gly Asn Ser Tyr Val Ser Trp Phe Ala Tyr Trp Gly Gln Gly Thr Leu
        275             280             285

Val Thr Val Ser Ser Gly Gly Gly Ser Gln Val Gln Leu Lys Gln
    290             295             300

Ser Gly Pro Gly Leu Val Gln Pro Ser Gln Ser Leu Ser Ile Thr Cys
305             310             315             320

Thr Val Ser Gly Phe Ser Leu Thr Asn Tyr Gly Val His Trp Val Arg
            325             330             335

Gln Ser Pro Gly Lys Gly Leu Glu Trp Leu Gly Val Ile Trp Ser Gly
            340             345             350

Gly Asn Thr Asp Tyr Asn Thr Pro Phe Thr Ser Arg Leu Ser Ile Asn
            355             360             365

Lys Asp Asn Ser Lys Ser Gln Val Phe Phe Lys Met Asn Ser Leu Gln
            370             375             380

Ser Gln Asp Thr Ala Ile Tyr Tyr Cys Ala Arg Ala Leu Thr Tyr Tyr
385             390             395             400

Asp Tyr Glu Phe Ala Tyr Trp Gly Gln Gly Thr Leu Val Thr Val Ser
                405             410             415
```

```
Ala Ala Ser Thr Lys Gly Pro Ser Val Phe Pro Leu Ala Pro Ser Ser
            420                 425                 430

Lys Ser Thr Ser Gly Gly Thr Ala Ala Leu Gly Cys Leu Val Lys Asp
        435                 440                 445

Tyr Phe Pro Glu Pro Val Thr Val Ser Trp Asn Ser Gly Ala Leu Thr
450                 455                 460

Ser Gly Val His Thr Phe Pro Ala Val Leu Gln Ser Ser Gly Leu Tyr
465                 470                 475                 480

Ser Leu Ser Ser Val Val Thr Val Pro Ser Ser Leu Gly Thr Gln
                485                 490                 495

Thr Tyr Ile Cys Asn Val Asn His Lys Pro Ser Asn Thr Lys Val Asp
            500                 505                 510

Lys Lys Val Glu Pro Lys Ser Cys Asp Lys Thr His Thr Cys Pro Pro
        515                 520                 525

Cys Pro Ala Pro Glu Phe Glu Gly Gly Pro Ser Val Phe Leu Phe Pro
530                 535                 540

Pro Lys Pro Lys Asp Thr Leu Met Ile Ser Arg Thr Pro Glu Val Thr
545                 550                 555                 560

Cys Val Val Val Asp Val Ser His Glu Asp Pro Glu Val Lys Phe Asn
                565                 570                 575

Trp Tyr Val Asp Gly Val Glu Val His Asn Ala Lys Thr Lys Pro Arg
            580                 585                 590

Glu Glu Gln Tyr Asn Ser Thr Tyr Arg Val Val Ser Val Leu Thr Val
        595                 600                 605

Leu His Gln Asp Trp Leu Asn Gly Lys Glu Tyr Lys Cys Lys Val Ser
610                 615                 620

Asn Lys Ala Leu Pro Ala Ser Ile Glu Lys Thr Ile Ser Lys Ala Lys
625                 630                 635                 640

Gly Gln Pro Arg Glu Pro Gln Val Tyr Thr Leu Pro Pro Ser Arg Glu
                645                 650                 655

Glu Met Thr Lys Asn Gln Val Ser Leu Thr Cys Leu Val Lys Gly Phe
            660                 665                 670

Tyr Pro Ser Asp Ile Ala Val Glu Trp Glu Ser Asn Gly Gln Pro Glu
        675                 680                 685

Asn Asn Tyr Lys Thr Thr Pro Pro Val Leu Asp Ser Asp Gly Ser Phe
690                 695                 700

Phe Leu Tyr Ser Lys Leu Thr Val Asp Lys Ser Arg Trp Gln Gln Gly
705                 710                 715                 720

Asn Val Phe Ser Cys Ser Val Met His Glu Ala Leu His Asn His Tyr
                725                 730                 735

Thr Gln Lys Ser Leu Ser Leu Ser Pro Gly Lys
            740                 745
```

<210> SEQ ID NO 123
<211> LENGTH: 2244
<212> TYPE: DNA
<213> ORGANISM: Artificial Sequence
<220> FEATURE:
<223> OTHER INFORMATION: synthetic

<400> SEQUENCE: 123
caaggccagt ctggatccgg ttatctgtgg ggttgcgagt ggaattgcgg agggatcact    60
acaggctcga gcgtggcag cggtggctct ggtggtctga gcggccgttc cgataatcat   120
ggcggcggtt ctcaaactgt agtaactcaa gaaccaagct tctccgtctc ccctggggga   180

| acagtcacac ttacctgccg aagtagtaca ggtgctgtta cgaccagtaa ctatgccaat | 240 |
| tgggtacaac aaacgcctgg tcaggctccg cgcggattga taggaggcac gaataaacgg | 300 |
| gcacccggtg tcccggacag attcagcgga agcatactcg gtaataaggc agctcttact | 360 |
| atcactgggg cccaagctga tgatgaaagt gattattatt gtgcgctctg gtacagcaac | 420 |
| ctctgggtgt ttgggggtgg cacgaaactt actgtcttgg gcggcggcgg atcagggga | 480 |
| ggtggctctg gaggaggagg ctcagaagtc caactggtcg aatccggggg agggctcgta | 540 |
| cagccgggtg ggtccctcaa actctcttgt gcggcctcag ggtttacctt cagtacatac | 600 |
| gcgatgaatt gggtccggca ggccagtggg aaagggctcg aatgggtagg acgaatccga | 660 |
| tcaaaataca acaactacgc tacttattac gctgattccg tgaaggacag attcacaata | 720 |
| tcccgcgacg atagcaagaa tacggcatat cttcagatga attctcttaa aactgaggat | 780 |
| accgctgtgt attactgcac aagacatggt aattttggaa actcatatgt ctcttggttc | 840 |
| gcttattggg gacagggcac gttggttacc gtgtctagcg gaggtggtgg atcccaggtg | 900 |
| cagctgaaac agagcggccc gggcctggtg cagccgagcc agagcctgag cattacctgc | 960 |
| accgtgagcg gctttagcct gaccaactat ggcgtgcatt gggtgcgcca gagcccgggc | 1020 |
| aaaggcctgg aatggctggg cgtgatttgg agcggcggca acaccgatta taacaccccg | 1080 |
| tttaccagcc gcctgagcat taacaaagat aacagcaaaa gccaggtgtt ttttaaaatg | 1140 |
| aacagcctgc aaagccagga taccgcgatt tattattgcg cgcgcgcgct gacctattat | 1200 |
| gattatgaat ttgcgtattg gggccagggc accctggtga ccgtgagcgc ggctagcacc | 1260 |
| aagggcccat cggtcttccc cctggcaccc tcctccaaga gcacctctgg gggcacagcg | 1320 |
| gccctgggct gcctggtcaa ggactacttc cccgaaccgg tgacggtgtc gtggaactca | 1380 |
| ggcgccctga ccagcggcgt gcacaccttc ccggctgtcc tacagtcctc aggactctac | 1440 |
| tccctcagca gcgtggtgac cgtgccctcc agcagcttgg gcacccagac ctacatctgc | 1500 |
| aacgtgaatc acaagcccag caacaccaag gtggacaaga agttgagccc aaatcttgt | 1560 |
| gacaaaactc acacatgccc accgtgccca gcacctgaat ttgaaggggg accgtcagtc | 1620 |
| ttcctcttcc ccccaaaacc caaggacacc ctcatgatct cccggacccc tgaggtcaca | 1680 |
| tgcgtggtgg tggacgtgag ccacgaagac cctgaggtca agttcaactg gtacgtggac | 1740 |
| ggcgtggagg tgcataatgc caagacaaag ccgcgggagg agcagtacca gagcacgtac | 1800 |
| cgtgtggtca gcgtcctcac cgtcctgcac caggactggc tgaatggcaa ggagtacaag | 1860 |
| tgcaaggtct ccaacaaagc cctcccagcc tcaatcgaga aaaccatctc caaagccaaa | 1920 |
| gggcagcccc gagaaccaca ggtgtacacc ctgcccccat cccgggagga gatgaccaag | 1980 |
| aaccaggtca gcctgacctg cctggtcaaa ggcttctatc ccagcgacat cgccgtggag | 2040 |
| tgggagagca atgggcagcc ggagaacaac tacaagacca cgcctcccgt gctggactcc | 2100 |
| gacggctcct tcttcctcta cagcaagctc accgtggaca gagcaggtg gcagcagggg | 2160 |
| aacgtcttct catgctccgt gatgcatgag gctctgcaca accactacac gcagaagagc | 2220 |
| ctctccctgt ctccgggtaa atga | 2244 |

<210> SEQ ID NO 124
<211> LENGTH: 747
<212> TYPE: PRT
<213> ORGANISM: Artificial Sequence
<220> FEATURE:
<223> OTHER INFORMATION: synthetic

<400> SEQUENCE: 124

-continued

```
Gln Gly Gln Ser Gly Ser Gly Tyr Leu Trp Gly Cys Glu Trp Asn Cys
1               5                   10                  15
Gly Gly Ile Thr Thr Gly Ser Ser Gly Ser Gly Gly Ser Gly Gly
            20                  25                  30
Leu Ser Gly Arg Ser Asp Asn His Gly Gly Ser Gln Thr Val Val
        35                  40                  45
Thr Gln Glu Pro Ser Phe Ser Val Ser Pro Gly Gly Thr Val Thr Leu
    50                  55                  60
Thr Cys Arg Ser Ser Thr Gly Ala Val Thr Thr Ser Asn Tyr Ala Asn
65                  70                  75                  80
Trp Val Gln Gln Thr Pro Gly Gln Ala Pro Arg Gly Leu Ile Gly Gly
                85                  90                  95
Thr Asn Lys Arg Ala Pro Gly Val Pro Asp Arg Phe Ser Gly Ser Ile
            100                 105                 110
Leu Gly Asn Lys Ala Ala Leu Thr Ile Thr Gly Ala Gln Ala Asp Asp
        115                 120                 125
Glu Ser Asp Tyr Tyr Cys Ala Leu Trp Tyr Ser Asn Leu Trp Val Phe
    130                 135                 140
Gly Gly Gly Thr Lys Leu Thr Val Leu Gly Gly Gly Ser Gly Gly
145                 150                 155                 160
Gly Gly Ser Gly Gly Gly Gly Ser Glu Val Gln Leu Val Glu Ser Gly
            165                 170                 175
Gly Gly Leu Val Gln Pro Gly Gly Ser Leu Lys Leu Ser Cys Ala Ala
        180                 185                 190
Ser Gly Phe Thr Phe Ser Thr Tyr Ala Met Asn Trp Val Arg Gln Ala
    195                 200                 205
Ser Gly Lys Gly Leu Glu Trp Val Gly Arg Ile Arg Ser Lys Tyr Asn
210                 215                 220
Asn Tyr Ala Thr Tyr Tyr Ala Asp Ser Val Lys Asp Arg Phe Thr Ile
225                 230                 235                 240
Ser Arg Asp Asp Ser Lys Asn Thr Ala Tyr Leu Gln Met Asn Ser Leu
            245                 250                 255
Lys Thr Glu Asp Thr Ala Val Tyr Tyr Cys Thr Arg His Gly Asn Phe
        260                 265                 270
Gly Asn Ser Tyr Val Ser Trp Phe Ala Tyr Trp Gly Gln Gly Thr Leu
    275                 280                 285
Val Thr Val Ser Ser Gly Gly Gly Ser Gln Val Gln Leu Lys Gln
    290                 295                 300
Ser Gly Pro Gly Leu Val Gln Pro Ser Gln Ser Leu Ser Ile Thr Cys
305                 310                 315                 320
Thr Val Ser Gly Phe Ser Leu Thr Asn Tyr Gly Val His Trp Val Arg
            325                 330                 335
Gln Ser Pro Gly Lys Gly Leu Glu Trp Leu Gly Val Ile Trp Ser Gly
        340                 345                 350
Gly Asn Thr Asp Tyr Asn Thr Pro Phe Thr Ser Arg Leu Ser Ile Asn
    355                 360                 365
Lys Asp Asn Ser Lys Ser Gln Val Phe Phe Lys Met Asn Ser Leu Gln
370                 375                 380
Ser Gln Asp Thr Ala Ile Tyr Tyr Cys Ala Arg Ala Leu Thr Tyr Tyr
385                 390                 395                 400
Asp Tyr Glu Phe Ala Tyr Trp Gly Gln Gly Thr Leu Val Thr Val Ser
            405                 410                 415
```

| | | | | | | | | | | | |
|---|---|---|---|---|---|---|---|---|---|---|---|
|Ala|Ala|Ser|Thr|Lys|Gly|Pro|Ser|Val|Phe|Pro|Leu|Ala|Pro|Ser|Ser|
| | | |420| | | |425| | | |430| | | | |

Ala Ala Ser Thr Lys Gly Pro Ser Val Phe Pro Leu Ala Pro Ser Ser
            420                 425                 430

Lys Ser Thr Ser Gly Gly Thr Ala Ala Leu Gly Cys Leu Val Lys Asp
        435                 440                 445

Tyr Phe Pro Glu Pro Val Thr Val Ser Trp Asn Ser Gly Ala Leu Thr
450                 455                 460

Ser Gly Val His Thr Phe Pro Ala Val Leu Gln Ser Ser Gly Leu Tyr
465                 470                 475                 480

Ser Leu Ser Ser Val Val Thr Val Pro Ser Ser Leu Gly Thr Gln
                485                 490                 495

Thr Tyr Ile Cys Asn Val Asn His Lys Pro Ser Asn Thr Lys Val Asp
            500                 505                 510

Lys Lys Val Glu Pro Lys Ser Cys Asp Lys Thr His Thr Cys Pro Pro
        515                 520                 525

Cys Pro Ala Pro Glu Phe Glu Gly Gly Pro Ser Val Phe Leu Phe Pro
            530                 535                 540

Pro Lys Pro Lys Asp Thr Leu Met Ile Ser Arg Thr Pro Glu Val Thr
545                 550                 555                 560

Cys Val Val Val Asp Val Ser His Glu Asp Pro Glu Val Lys Phe Asn
                565                 570                 575

Trp Tyr Val Asp Gly Val Glu Val His Asn Ala Lys Thr Lys Pro Arg
            580                 585                 590

Glu Glu Gln Tyr Gln Ser Thr Tyr Arg Val Val Ser Val Leu Thr Val
        595                 600                 605

Leu His Gln Asp Trp Leu Asn Gly Lys Glu Tyr Lys Cys Lys Val Ser
    610                 615                 620

Asn Lys Ala Leu Pro Ala Ser Ile Glu Lys Thr Ile Ser Lys Ala Lys
625                 630                 635                 640

Gly Gln Pro Arg Glu Pro Gln Val Tyr Thr Leu Pro Pro Ser Arg Glu
            645                 650                 655

Glu Met Thr Lys Asn Gln Val Ser Leu Thr Cys Leu Val Lys Gly Phe
        660                 665                 670

Tyr Pro Ser Asp Ile Ala Val Glu Trp Glu Ser Asn Gly Gln Pro Glu
    675                 680                 685

Asn Asn Tyr Lys Thr Thr Pro Pro Val Leu Asp Ser Asp Gly Ser Phe
690                 695                 700

Phe Leu Tyr Ser Lys Leu Thr Val Asp Lys Ser Arg Trp Gln Gln Gly
705                 710                 715                 720

Asn Val Phe Ser Cys Ser Val Met His Glu Ala Leu His Asn His Tyr
                725                 730                 735

Thr Gln Lys Ser Leu Ser Leu Ser Pro Gly Lys
        740                 745

<210> SEQ ID NO 125
<211> LENGTH: 2133
<212> TYPE: DNA
<213> ORGANISM: Artificial Sequence
<220> FEATURE:
<223> OTHER INFORMATION: synthetic

<400> SEQUENCE: 125
tccgatgatc atggcggcgg ttctcaaact gtagtaactc aagaaccaag cttctccgtc    60 tccccctgggg gaacagtcac acttacctgc cgaagtagta caggtgctgt tacgaccagt   120
aactatgcca attgggtaca acaaacgcct ggtcaggctc cgcgcggatt gataggaggc   180

| | |
|---|---|
| acgaataaac gggcacccgg tgtcccggac agattcagcg aagcatact cggtaataag | 240 |
| gcagctctta ctatcactgg ggcccaagct gatgatgaaa gtgattatta ttgtgcgctc | 300 |
| tggtacagca acctctgggt gtttgggggt ggcacgaaac ttactgtctt gggcggcggc | 360 |
| ggatcagggg gaggtggctc tgaggagga ggctcagaag tccaactggt cgaatccggg | 420 |
| ggagggctcg tacagccggg tgggtccctc aaactctctt gtgcggcctc agggtttacc | 480 |
| ttcagtacat acgcgatgaa ttgggtccgg caggccagtg ggaaagggct cgaatgggta | 540 |
| ggacgaatcc gatcaaaata caacaactac gctacttatt acgctgattc cgtgaaggac | 600 |
| agattcacaa tatcccgcga cgatagcaag aatacggcat atcttcagat gaattctctt | 660 |
| aaaactgagg ataccgctgt gtattactgc acaagacatg gtaattttgg aaactcatat | 720 |
| gtctcttggt tcgcttattg gggacagggc acgttggtta ccgtgtctag cggaggtggt | 780 |
| ggatcccagg tgcagctgaa acagagcggc ccgggcctgg tgcagccgag ccagagcctg | 840 |
| agcattacct gcaccgtgag cggctttagc ctgaccaact atggcgtgca ttgggtgcgc | 900 |
| cagagcccgg gcaaaggcct ggaatggctg ggcgtgattt ggagcggcgg caacaccgat | 960 |
| tataacaccc cgtttaccag ccgcctgagc attaacaaag ataacagcaa aagccaggtg | 1020 |
| tttttttaaaa tgaacagcct gcaaagccag gataccgcga tttattattg cgcgcgcgcg | 1080 |
| ctgacctatt atgattatga atttgcgtat tggggccagg gcaccctggt gaccgtgagc | 1140 |
| gcggctagca ccaagggccc atcggtcttc cccctggcac cctcctccaa gagcacctct | 1200 |
| ggggggcacag cggccctggg ctgcctggtc aaggactact ccccgaacc ggtgacggtg | 1260 |
| tcgtggaact caggcgccct gaccagcggc gtgcacacct tcccggctgt cctacagtcc | 1320 |
| tcaggactct actccctcag cagcgtggtg accgtgccct ccagcagctt gggcacccag | 1380 |
| acctacatct gcaacgtgaa tcacaagccc agcaacacca aggtggacaa gaaagttgag | 1440 |
| cccaaatctt gtgacaaaac tcacacatgc ccaccgtgcc cagcacctga atttgaaggg | 1500 |
| ggaccgtcag tcttcctctt ccccccaaaa cccaaggaca ccctcatgat ctcccggacc | 1560 |
| cctgaggtca catgcgtggt ggtggacgtg agccacgaag accctgaggt caagttcaac | 1620 |
| tggtacgtgg acggcgtgga ggtgcataat gccaagacaa agccgcggga ggagcagtac | 1680 |
| cagagcacgt accgtgtggt cagcgtcctc accgtcctgc accaggactg gctgaatggc | 1740 |
| aaggagtaca agtgcaaggt ctccaacaaa gccctcccag cctcaatcga gaaaaccatc | 1800 |
| tccaaagcca aagggcagcc ccgagaacca caggtgtaca ccctgccccc atcccgggag | 1860 |
| gagatgacca agaaccaggt cagcctgacc tgcctggtca aaggcttcta tcccagcgac | 1920 |
| atcgccgtgg agtgggagag caatgggcag ccggagaaca actacaagac cacgcctccc | 1980 |
| gtgctggact ccgacggctc cttcttcctc tacagcaagc tcaccgtgga caagagcagg | 2040 |
| tggcagcagg ggaacgtctt ctcatgctcc gtgatgcatg aggctctgca caaccactac | 2100 |
| acgcagaaga gcctctccct gtctccgggt aaa | 2133 |

<210> SEQ ID NO 126
<211> LENGTH: 711
<212> TYPE: PRT
<213> ORGANISM: Artificial Sequence
<220> FEATURE:
<223> OTHER INFORMATION: synthetic

<400> SEQUENCE: 126

Ser Asp Asp His Gly Gly Gly Ser Gln Thr Val Val Thr Gln Glu Pro
1               5                   10                  15

```
Ser Phe Ser Val Ser Pro Gly Gly Thr Val Thr Leu Thr Cys Arg Ser
                20                  25                  30

Ser Thr Gly Ala Val Thr Thr Ser Asn Tyr Ala Asn Trp Val Gln Gln
        35                  40                  45

Thr Pro Gly Gln Ala Pro Arg Gly Leu Ile Gly Gly Thr Asn Lys Arg
 50                  55                  60

Ala Pro Gly Val Pro Asp Arg Phe Ser Gly Ser Ile Leu Gly Asn Lys
 65                  70                  75                  80

Ala Ala Leu Thr Ile Thr Gly Ala Gln Ala Asp Asp Glu Ser Asp Tyr
                85                  90                  95

Tyr Cys Ala Leu Trp Tyr Ser Asn Leu Trp Val Phe Gly Gly Gly Thr
            100                 105                 110

Lys Leu Thr Val Leu Gly Gly Gly Ser Gly Gly Gly Gly Ser Gly
            115                 120                 125

Gly Gly Gly Ser Glu Val Gln Leu Val Glu Ser Gly Gly Gly Leu Val
            130                 135                 140

Gln Pro Gly Gly Ser Leu Lys Leu Ser Cys Ala Ala Ser Gly Phe Thr
145                 150                 155                 160

Phe Ser Thr Tyr Ala Met Asn Trp Val Arg Gln Ala Ser Gly Lys Gly
                165                 170                 175

Leu Glu Trp Val Gly Arg Ile Arg Ser Lys Tyr Asn Asn Tyr Ala Thr
            180                 185                 190

Tyr Tyr Ala Asp Ser Val Lys Asp Arg Phe Thr Ile Ser Arg Asp Asp
            195                 200                 205

Ser Lys Asn Thr Ala Tyr Leu Gln Met Asn Ser Leu Lys Thr Glu Asp
210                 215                 220

Thr Ala Val Tyr Tyr Cys Thr Arg His Gly Asn Phe Gly Asn Ser Tyr
225                 230                 235                 240

Val Ser Trp Phe Ala Tyr Trp Gly Gln Gly Thr Leu Val Thr Val Ser
                245                 250                 255

Ser Gly Gly Gly Gly Ser Gln Val Gln Leu Lys Gln Ser Gly Pro Gly
            260                 265                 270

Leu Val Gln Pro Ser Gln Ser Leu Ser Ile Thr Cys Thr Val Ser Gly
        275                 280                 285

Phe Ser Leu Thr Asn Tyr Gly Val His Trp Val Arg Gln Ser Pro Gly
290                 295                 300

Lys Gly Leu Glu Trp Leu Gly Val Ile Trp Ser Gly Gly Asn Thr Asp
305                 310                 315                 320

Tyr Asn Thr Pro Phe Thr Ser Arg Leu Ser Ile Asn Lys Asp Asn Ser
                325                 330                 335

Lys Ser Gln Val Phe Phe Lys Met Asn Ser Leu Gln Ser Gln Asp Thr
            340                 345                 350

Ala Ile Tyr Tyr Cys Ala Arg Ala Leu Thr Tyr Tyr Asp Tyr Glu Phe
        355                 360                 365

Ala Tyr Trp Gly Gln Gly Thr Leu Val Thr Val Ser Ala Ala Ser Thr
370                 375                 380

Lys Gly Pro Ser Val Phe Pro Leu Ala Pro Ser Ser Lys Ser Thr Ser
385                 390                 395                 400

Gly Gly Thr Ala Ala Leu Gly Cys Leu Val Lys Asp Tyr Phe Pro Glu
                405                 410                 415

Pro Val Thr Val Ser Trp Asn Ser Gly Ala Leu Thr Ser Gly Val His
            420                 425                 430

Thr Phe Pro Ala Val Leu Gln Ser Ser Gly Leu Tyr Ser Leu Ser Ser
```

-continued

```
                435                 440                 445
    Val Val Thr Val Pro Ser Ser Leu Gly Thr Gln Thr Tyr Ile Cys
    450                 455                 460
Asn Val Asn His Lys Pro Ser Asn Thr Lys Val Asp Lys Lys Val Glu
465                 470                 475                 480
Pro Lys Ser Cys Asp Lys Thr His Thr Cys Pro Pro Cys Pro Ala Pro
                485                 490                 495
Glu Phe Glu Gly Gly Pro Ser Val Phe Leu Phe Pro Pro Lys Pro Lys
                500                 505                 510
Asp Thr Leu Met Ile Ser Arg Thr Pro Glu Val Thr Cys Val Val Val
                515                 520                 525
Asp Val Ser His Glu Asp Pro Glu Val Lys Phe Asn Trp Tyr Val Asp
            530                 535                 540
Gly Val Glu Val His Asn Ala Lys Thr Lys Pro Arg Glu Glu Gln Tyr
545                 550                 555                 560
Gln Ser Thr Tyr Arg Val Val Ser Val Leu Thr Val Leu His Gln Asp
                565                 570                 575
Trp Leu Asn Gly Lys Glu Tyr Lys Cys Lys Val Ser Asn Lys Ala Leu
            580                 585                 590
Pro Ala Ser Ile Glu Lys Thr Ile Ser Lys Ala Lys Gly Gln Pro Arg
            595                 600                 605
Glu Pro Gln Val Tyr Thr Leu Pro Pro Ser Arg Glu Glu Met Thr Lys
610                 615                 620
Asn Gln Val Ser Leu Thr Cys Leu Val Lys Gly Phe Tyr Pro Ser Asp
625                 630                 635                 640
Ile Ala Val Glu Trp Glu Ser Asn Gly Gln Pro Glu Asn Asn Tyr Lys
                645                 650                 655
Thr Thr Pro Pro Val Leu Asp Ser Asp Gly Ser Phe Phe Leu Tyr Ser
                660                 665                 670
Lys Leu Thr Val Asp Lys Ser Arg Trp Gln Gln Gly Asn Val Phe Ser
            675                 680                 685
Cys Ser Val Met His Glu Ala Leu His Asn His Tyr Thr Gln Lys Ser
        690                 695                 700
Leu Ser Leu Ser Pro Gly Lys
705                 710
```

<210> SEQ ID NO 127
<211> LENGTH: 669
<212> TYPE: DNA
<213> ORGANISM: Artificial Sequence
<220> FEATURE:
<223> OTHER INFORMATION: synthetic

<400> SEQUENCE: 127

```
tccgatgatc atggcagtag cggtacccag atcttgctga cccagagccc ggtgattctg    60
agcgtgagcc cgggcgaacg tgtgagcttt agctgccgcg cgagccagag cattggcacc   120
aacattcatt ggtatcagca gcgcaccaac ggcagcccgc gcctgctgat taaatatgcg   180
agcgaaagca ttagcggcat tccgagccgc tttagcggca gcggcagcgg caccgatttt   240
accctgagca ttaacagcgt ggaaagcgaa gatattgcgg attattattg ccagcagaac   300
aacaactggc cgaccacctt ggcgcgggc accaaactgg aactgaaacg tacggtggct   360
gcaccatctg tcttcatctt cccgccatct gatgagcagt tgaaatctgg aactgcctct   420
gttgtgtgcc tgctgaataa cttctatccc agagaggcca agtacagtg gaaggtggat   480
```

| | |
|---|---:|
| aacgccctcc aatcgggtaa ctcccaggag agtgtcacag agcaggacag caaggacagc | 540 |
| acctacagcc tcagcagcac cctgacgctg agcaaagcag actacgagaa acacaaagtc | 600 |
| tacgcctgcg aagtcaccca tcagggcctg agctcgcccg tcacaaagag cttcaacagg | 660 |
| ggagagtgt | 669 |

<210> SEQ ID NO 128
<211> LENGTH: 223
<212> TYPE: PRT
<213> ORGANISM: Artificial Sequence
<220> FEATURE:
<223> OTHER INFORMATION: synthetic

<400> SEQUENCE: 128

```
Ser Asp Asp His Gly Ser Ser Gly Thr Gln Ile Leu Leu Thr Gln Ser
1               5                   10                  15

Pro Val Ile Leu Ser Val Ser Pro Gly Glu Arg Val Ser Phe Ser Cys
            20                  25                  30

Arg Ala Ser Gln Ser Ile Gly Thr Asn Ile His Trp Tyr Gln Gln Arg
        35                  40                  45

Thr Asn Gly Ser Pro Arg Leu Leu Ile Lys Tyr Ala Ser Glu Ser Ile
    50                  55                  60

Ser Gly Ile Pro Ser Arg Phe Ser Gly Ser Gly Ser Gly Thr Asp Phe
65                  70                  75                  80

Thr Leu Ser Ile Asn Ser Val Glu Ser Glu Asp Ile Ala Asp Tyr Tyr
                85                  90                  95

Cys Gln Gln Asn Asn Asn Trp Pro Thr Thr Phe Gly Ala Gly Thr Lys
            100                 105                 110

Leu Glu Leu Lys Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220
```

<210> SEQ ID NO 129
<211> LENGTH: 2241
<212> TYPE: DNA
<213> ORGANISM: Artificial Sequence
<220> FEATURE:
<223> OTHER INFORMATION: synthetic

<400> SEQUENCE: 129

| | |
|---|---:|
| caaggccagt ctggatccgg ttatctgtgg ggttgcgagt ggaattgcgg agggatcact | 60 |
| acaggctcga gcggtggcag cggtggctct ggtggtctga gcggccgttc cgatgatcat | 120 |
| ggcggcggtt ctcaaactgt agtaactcaa gaaccaagct ctccgtctc ccctggggga | 180 |
| acagtcacac ttacctgccg aagtagtaca ggtgctgtta cgaccagtaa ctatgccaat | 240 |
| tgggtacaac aaacgcctgg tcaggctccg cgcggattga taggaggcac gaataaacgg | 300 |

```
gcacccggtg tcccggacag attcagcgga agcatactcg gtaataaggc agctcttact    360
atcactgggg cccaagctga tgatgaaagt gattattatt gtgcgctctg gtacagcaac    420
ctctgggtgt ttgggggtgg cacgaaactt actgtcttgg gcggcggcgg atcaggggga    480
ggtggctctg gaggaggagg ctcagaagtc caactggtcg aatccggggg agggctcgta    540
cagccgggtg ggtccctcaa actctcttgt gcggcctcag ggtttacctt cagtacatac    600
gcgatgaatt gggtccggca ggccagtggg aaagggctcg aatgggtagg acgaatccga    660
tcaaaataca caactacgc tacttattac gctgattccg tgaaggacag attcacaata    720
tcccgcgacg atagcaagaa tacggcatat cttcagatga attctcttaa aactgaggat    780
accgctgtgt attactgcac aagacatggt aattttggaa actcatatgt ctcttggttc    840
gcttattggg acagggcac gttggttacc gtgtctagcg gaggtggtgg atcccaggtg    900
cagctgaaac agagcggccc gggcctggtg cagccgagcc agagcctgag cattacctgc    960
accgtgagcg gctttagcct gaccaactat ggcgtgcatt gggtgcgcca gagcccgggc   1020
aaaggcctgg aatggctggg cgtgatttgg agcggcggca caccgattaa taccccg      1080
tttaccagcc gcctgagcat taacaaagat aacagcaaaa gccaggtgtt ttttaaaatg   1140
aacagcctgc aaagccagga taccgcgatt tattattgcg cgcgcgcgct gacctattat   1200
gattatgaat ttgcgtattg gggccagggc accctggtga ccgtgagcgc ggctagcacc   1260
aagggcccat cggtcttccc cctggcaccc tcctccaaga gcacctctgg gggcacagcg   1320
gccctgggct gcctggtcaa ggactacttc cccgaaccgg tgacggtgtc gtggaactca   1380
ggcgccctga ccagcggcgt gcacaccttc ccggctgtcc tacagtcctc aggactctac   1440
tccctcagca gcgtggtgac cgtgccctcc agcagcttgg gcacccagac ctacatctgc   1500
aacgtgaatc acaagcccag caacaccaag gtggacaaga agttgagcc caaatcttgt   1560
gacaaaactc acacatgccc accgtgccca gcacctgaat tgaaggggg accgtcagtc   1620
ttcctcttcc ccccaaaacc caaggacacc ctcatgatct cccggacccc tgaggtcaca   1680
tgcgtggtgg tggacgtgag ccacgaagac cctgaggtca agttcaactg gtacgtggac   1740
ggcgtggagg tgcataatgc caagacaaag ccgcgggagg agcagtacca gagcacgtac   1800
cgtgtggtca gcgtcctcac cgtcctgcac caggactggc tgaatggcaa ggagtacaag   1860
tgcaaggtct ccaacaaagc cctcccagcc tcaatcgaga aaaccatctc caaagccaaa   1920
gggcagcccc gagaaccaca ggtgtacacc ctgcccccat cccgggagga tgaccaag    1980
aaccaggtca gcctgacctg cctggtcaaa ggcttctatc ccagcgacat cgccgtggag   2040
tgggagagca atgggcagcc ggagaacaac tacaagacca cgcctcccgt gctggactcc   2100
gacggctcct tcttcctcta cagcaagctc accgtggaca gagcaggtg gcagcagggg   2160
aacgtcttct catgctccgt gatgcatgag gctctgcaca accactacac gcagaagagc   2220
ctctccctgt ctccgggtaa a                                             2241
```

<210> SEQ ID NO 130
<211> LENGTH: 747
<212> TYPE: PRT
<213> ORGANISM: Artificial Sequence
<220> FEATURE:
<223> OTHER INFORMATION: synthetic

<400> SEQUENCE: 130

```
Gln Gly Gln Ser Gly Ser Gly Tyr Leu Trp Gly Cys Glu Trp Asn Cys
1               5                   10                  15
```

```
Gly Gly Ile Thr Thr Gly Ser Ser Gly Gly Ser Gly Gly
            20              25              30

Leu Ser Gly Arg Ser Asp Asp His Gly Gly Gly Ser Gln Thr Val Val
            35              40              45

Thr Gln Glu Pro Ser Phe Ser Val Ser Pro Gly Gly Thr Val Thr Leu
 50              55              60

Thr Cys Arg Ser Ser Thr Gly Ala Val Thr Thr Ser Asn Tyr Ala Asn
 65              70              75              80

Trp Val Gln Gln Thr Pro Gly Gln Ala Pro Arg Gly Leu Ile Gly Gly
                85              90              95

Thr Asn Lys Arg Ala Pro Gly Val Pro Asp Arg Phe Ser Gly Ser Ile
            100             105             110

Leu Gly Asn Lys Ala Ala Leu Thr Ile Thr Gly Ala Gln Ala Asp Asp
            115             120             125

Glu Ser Asp Tyr Tyr Cys Ala Leu Trp Tyr Ser Asn Leu Trp Val Phe
130             135             140

Gly Gly Gly Thr Lys Leu Thr Val Leu Gly Gly Gly Gly Ser Gly Gly
145             150             155             160

Gly Gly Ser Gly Gly Gly Gly Ser Glu Val Gln Leu Val Glu Ser Gly
            165             170             175

Gly Gly Leu Val Gln Pro Gly Gly Ser Leu Lys Leu Ser Cys Ala Ala
            180             185             190

Ser Gly Phe Thr Phe Ser Thr Tyr Ala Met Asn Trp Val Arg Gln Ala
            195             200             205

Ser Gly Lys Gly Leu Glu Trp Val Gly Arg Ile Arg Ser Lys Tyr Asn
            210             215             220

Asn Tyr Ala Thr Tyr Tyr Ala Asp Ser Val Lys Asp Arg Phe Thr Ile
225             230             235             240

Ser Arg Asp Asp Ser Lys Asn Thr Ala Tyr Leu Gln Met Asn Ser Leu
            245             250             255

Lys Thr Glu Asp Thr Ala Val Tyr Tyr Cys Thr Arg His Gly Asn Phe
            260             265             270

Gly Asn Ser Tyr Val Ser Trp Phe Ala Tyr Trp Gly Gln Gly Thr Leu
            275             280             285

Val Thr Val Ser Ser Gly Gly Gly Gly Ser Gln Val Gln Leu Lys Gln
            290             295             300

Ser Gly Pro Gly Leu Val Gln Pro Ser Gln Ser Leu Ser Ile Thr Cys
305             310             315             320

Thr Val Ser Gly Phe Ser Leu Thr Asn Tyr Gly Val His Trp Val Arg
                325             330             335

Gln Ser Pro Gly Lys Gly Leu Glu Trp Leu Gly Val Ile Trp Ser Gly
            340             345             350

Gly Asn Thr Asp Tyr Asn Thr Pro Phe Thr Ser Arg Leu Ser Ile Asn
            355             360             365

Lys Asp Asn Ser Lys Ser Gln Val Phe Phe Lys Met Asn Ser Leu Gln
            370             375             380

Ser Gln Asp Thr Ala Ile Tyr Tyr Cys Ala Arg Ala Leu Thr Tyr Tyr
385             390             395             400

Asp Tyr Glu Phe Ala Tyr Trp Gly Gln Gly Thr Leu Val Thr Val Ser
                405             410             415

Ala Ala Ser Thr Lys Gly Pro Ser Val Phe Pro Leu Ala Pro Ser Ser
            420             425             430
```

```
Lys Ser Thr Ser Gly Gly Thr Ala Ala Leu Gly Cys Leu Val Lys Asp
            435                 440                 445

Tyr Phe Pro Glu Pro Val Thr Val Ser Trp Asn Ser Gly Ala Leu Thr
450                 455                 460

Ser Gly Val His Thr Phe Pro Ala Val Leu Gln Ser Ser Gly Leu Tyr
465                 470                 475                 480

Ser Leu Ser Ser Val Val Thr Val Pro Ser Ser Ser Leu Gly Thr Gln
                485                 490                 495

Thr Tyr Ile Cys Asn Val Asn His Lys Pro Ser Asn Thr Lys Val Asp
            500                 505                 510

Lys Lys Val Glu Pro Lys Ser Cys Asp Lys Thr His Thr Cys Pro Pro
        515                 520                 525

Cys Pro Ala Pro Glu Phe Glu Gly Gly Pro Ser Val Phe Leu Phe Pro
    530                 535                 540

Pro Lys Pro Lys Asp Thr Leu Met Ile Ser Arg Thr Pro Glu Val Thr
545                 550                 555                 560

Cys Val Val Val Asp Val Ser His Glu Asp Pro Glu Val Lys Phe Asn
                565                 570                 575

Trp Tyr Val Asp Gly Val Glu Val His Asn Ala Lys Thr Lys Pro Arg
            580                 585                 590

Glu Glu Gln Tyr Gln Ser Thr Tyr Arg Val Val Ser Val Leu Thr Val
        595                 600                 605

Leu His Gln Asp Trp Leu Asn Gly Lys Glu Tyr Lys Cys Lys Val Ser
    610                 615                 620

Asn Lys Ala Leu Pro Ala Ser Ile Glu Lys Thr Ile Ser Lys Ala Lys
625                 630                 635                 640

Gly Gln Pro Arg Glu Pro Gln Val Tyr Thr Leu Pro Pro Ser Arg Glu
                645                 650                 655

Glu Met Thr Lys Asn Gln Val Ser Leu Thr Cys Leu Val Lys Gly Phe
            660                 665                 670

Tyr Pro Ser Asp Ile Ala Val Glu Trp Glu Ser Asn Gly Gln Pro Glu
        675                 680                 685

Asn Asn Tyr Lys Thr Thr Pro Pro Val Leu Asp Ser Asp Gly Ser Phe
    690                 695                 700

Phe Leu Tyr Ser Lys Leu Thr Val Asp Lys Ser Arg Trp Gln Gln Gly
705                 710                 715                 720

Asn Val Phe Ser Cys Ser Val Met His Glu Ala Leu His Asn His Tyr
                725                 730                 735

Thr Gln Lys Ser Leu Ser Leu Ser Pro Gly Lys
            740                 745
```

<210> SEQ ID NO 131
<211> LENGTH: 783
<212> TYPE: DNA
<213> ORGANISM: Artificial Sequence
<220> FEATURE:
<223> OTHER INFORMATION: synthetic

<400> SEQUENCE: 131

```
caaggccagt ctggccaagg tcttagttgt gaaggttggg cgatgaatag agaacaatgt    60
cgagccggag gtggctcgag cggcggctct atctcttccg gactgctgtc cggcagatcc   120
gaccagcacg gcggaggatc ccaaatcctg ctgacacagt ctcctgtcat actgagtgtc   180
tcccccggcg agagagtctc tttctcatgt cgggccagtc agtctattgg gactaacata   240
cactggtacc agcaacgcac caacggaagc ccgcgcctgc tgattaaata tgcgagcgaa   300
```

```
agcattagcg gcattccgag ccgctttagc ggcagcggca gcggcaccga ttttaccctg    360
agcattaaca gcgtggaaag cgaagatatt gcggattatt attgccagca gaacaacaac    420
tggccgacca cctttggcgc gggcaccaaa ctggaactga aacgtacggt ggctgcacca    480
tctgtcttca tcttcccgcc atctgatgag cagttgaaat ctggaactgc ctctgttgtg    540
tgcctgctga ataacttcta tcccagagag gccaaagtac agtggaaggt ggataacgcc    600
ctccaatcgg gtaactccca ggagagtgtc acagagcagg acagcaagga cagcacctac    660
agcctcagca gcaccctgac gctgagcaaa gcagactacg agaaacacaa agtctacgcc    720
tgcgaagtca cccatcaggg cctgagctcg cccgtcacaa agagcttcaa caggggagag    780
tgt                                                                  783
```

<210> SEQ ID NO 132
<211> LENGTH: 261
<212> TYPE: PRT
<213> ORGANISM: Artificial Sequence
<220> FEATURE:
<223> OTHER INFORMATION: synthetic

<400> SEQUENCE: 132

```
Gln Gly Gln Ser Gly Gln Gly Leu Ser Cys Glu Gly Trp Ala Met Asn
1               5                   10                  15

Arg Glu Gln Cys Arg Ala Gly Gly Ser Ser Gly Gly Ser Ile Ser
            20                  25                  30

Ser Gly Leu Leu Ser Gly Arg Ser Asp Gln His Gly Gly Ser Gln
        35                  40                  45

Ile Leu Leu Thr Gln Ser Pro Val Ile Leu Ser Val Ser Pro Gly Glu
50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260
```

<210> SEQ ID NO 133
<211> LENGTH: 2256
<212> TYPE: DNA
<213> ORGANISM: Artificial Sequence
<220> FEATURE:
<223> OTHER INFORMATION: synthetic

<400> SEQUENCE: 133

```
caaggccagt ctggatccgg ttatctgtgg ggttgcgagt ggaattgcgg agggatcact      60
acaggctcga gcggtggcag cggtggctct ggtggtatat cgagtggatt gctgtctggc     120
agatctgacg atcacggcgg cggttctcaa actgtagtaa ctcaagaacc aagcttctcc     180
gtctcccctg ggggaacagt cacacttacc tgccgaagta gtacaggtgc tgttacgacc     240
agtaactatg ccaattgggt acaacaaacg cctggtcagg ctccgcgcgg attgatagga     300
ggcacgaata aacgggcacc cggtgtcccg gacagattca gcggaagcat actcggtaat     360
aaggcagctc ttactatcac tggggcccaa gctgatgatg aaagtgatta ttattgtgcg     420
ctctggtaca gcaacctctg ggtgtttggg ggtggcacga acttactgt cttgggcggc      480
ggcggatcag ggggaggtgg ctctggagga ggaggctcag aagtccaact ggtcgaatcc     540
gggggagggc tcgtacagcc gggtgggtcc ctcaaactct cttgtgcggc ctcagggttt     600
accttcagta catacgcgat gaattgggtc cggcaggcca gtgggaaagg gctcgaatgg     660
gtaggacgaa tccgatcaaa atacaacaac tacgctactt attacgctga ttccgtgaag     720
gacagattca caatatcccg cgacgatagc aagaatacgg catatcttca gatgaattct     780
cttaaaactg aggataccgc tgtgtattac tgcacaagac atggtaattt tggaaactca     840
tatgtctctt ggttcgctta ttggggacag ggcacgttgg ttaccgtgtc tagcggaggt     900
ggtggatccc aggtgcagct gaaacagagc ggcccgggcc tggtgcagcc gagccagagc     960
ctgagcatta cctgcaccgt gagcggcttt agcctgacca actatggcgt gcattgggtg    1020
cgccagagcc cgggcaaagg cctggaatgg ctgggcgtga tttggagcgg cggcaacacc    1080
gattataaca ccccgtttac cagccgcctg agcattaaca agataacag caaaagccag    1140
gtgttttta aaatgaacag cctgcaaagc caggataccg cgatttatta ttgcgcgcgc    1200
gcgctgacct attatgatta tgaatttgcg tattggggcc agggcacccc tggtgaccgtg   1260
agcgcggcta gcaccaaggg cccatcggtc ttccccctgg cacctcctc caagagcacc    1320
tctgggggca gcgcggccct gggctgcctg gtcaaggact acttccccga accggtgacg    1380
gtgtcgtgga actcaggcgc cctgaccagc ggcgtgcaca ccttcccggc tgtcctacag    1440
tcctcaggac tctactccct cagcagcgtg gtgaccgtgc cctccagcag cttgggcacc    1500
cagacctaca tctgcaacgt gaatcacaag cccagcaaca ccaaggtgga caagaaagtt    1560
gagcccaaat cttgtgacaa aactcacaca tgcccaccgt gcccagcacc tgaatttgaa    1620
gggggaccgt cagtcttcct cttccccca aaacccaagg acaccctcat gatctcccgg    1680
acccctgagg tcacatgcgt ggtggtggac gtgagccacg aagaccctga ggtcaagttc    1740
aactggtacg tggacggcgt ggaggtgcat aatgccaaga caaagccgcg ggaggagcag    1800
taccagagca cgtaccgtgt ggtcagcgtc ctcaccgtcc tgcaccagga ctggctgaat    1860
ggcaaggagt acaagtgcaa ggtctccaac aaagccctcc cagcctcaat cgagaaaacc    1920
atctccaaag ccaagggca gccccgagaa ccacaggtgt acaccctgcc cccatcccgg    1980
gaggagatga ccaagaacca ggtcagcctg acctgcctgg tcaaaggctt ctatcccagc    2040
```

-continued

```
gacatcgccg tggagtggga gagcaatggg cagccggaga caactacaa gaccacgcct    2100 cccgtgctgg actccgacgg ctccttcttc ctctacagca agctcaccgt ggacaagagc    2160
aggtggcagc aggggaacgt cttctcatgc tccgtgatgc atgaggctct gcacaaccac    2220
tacacgcaga agagcctctc cctgtctccg ggtaaa                              2256
```

<210> SEQ ID NO 134
<211> LENGTH: 752
<212> TYPE: PRT
<213> ORGANISM: Artificial Sequence
<220> FEATURE:
<223> OTHER INFORMATION: synthetic

<400> SEQUENCE: 134

```
Gln Gly Gln Ser Gly Ser Gly Tyr Leu Trp Gly Cys Glu Trp Asn Cys
1               5                   10                  15
Gly Gly Ile Thr Thr Gly Ser Ser Gly Ser Gly Gly Ser Gly Gly
            20                  25                  30
Ile Ser Ser Gly Leu Leu Ser Gly Arg Ser Asp Asp His Gly Gly Gly
        35                  40                  45
Ser Gln Thr Val Val Thr Gln Glu Pro Ser Phe Ser Val Ser Pro Gly
    50                  55                  60
Gly Thr Val Thr Leu Thr Cys Arg Ser Ser Thr Gly Ala Val Thr Thr
65                  70                  75                  80
Ser Asn Tyr Ala Asn Trp Val Gln Gln Thr Pro Gly Gln Ala Pro Arg
                85                  90                  95
Gly Leu Ile Gly Gly Thr Asn Lys Arg Ala Pro Gly Val Pro Asp Arg
            100                 105                 110
Phe Ser Gly Ser Ile Leu Gly Asn Lys Ala Ala Leu Thr Ile Thr Gly
        115                 120                 125
Ala Gln Ala Asp Asp Glu Ser Asp Tyr Tyr Cys Ala Leu Trp Tyr Ser
    130                 135                 140
Asn Leu Trp Val Phe Gly Gly Gly Thr Lys Leu Thr Val Leu Gly Gly
145                 150                 155                 160
Gly Gly Ser Gly Gly Gly Ser Gly Gly Gly Ser Glu Val Gln
                165                 170                 175
Leu Val Glu Ser Gly Gly Gly Leu Val Gln Pro Gly Gly Ser Leu Lys
            180                 185                 190
Leu Ser Cys Ala Ala Ser Gly Phe Thr Phe Ser Thr Tyr Ala Met Asn
        195                 200                 205
Trp Val Arg Gln Ala Ser Gly Lys Gly Leu Glu Trp Val Gly Arg Ile
    210                 215                 220
Arg Ser Lys Tyr Asn Asn Tyr Ala Thr Tyr Tyr Ala Asp Ser Val Lys
225                 230                 235                 240
Asp Arg Phe Thr Ile Ser Arg Asp Asp Ser Lys Asn Thr Ala Tyr Leu
                245                 250                 255
Gln Met Asn Ser Leu Lys Thr Glu Asp Thr Ala Val Tyr Tyr Cys Thr
            260                 265                 270
Arg His Gly Asn Phe Gly Asn Ser Tyr Val Ser Trp Phe Ala Tyr Trp
        275                 280                 285
Gly Gln Gly Thr Leu Val Thr Val Ser Ser Gly Gly Gly Gly Ser Gln
    290                 295                 300
Val Gln Leu Lys Gln Ser Gly Pro Gly Leu Val Gln Pro Ser Gln Ser
305                 310                 315                 320
Leu Ser Ile Thr Cys Thr Val Ser Gly Phe Ser Leu Thr Asn Tyr Gly
```

```
                    325                 330                 335
Val His Trp Val Arg Gln Ser Pro Gly Lys Gly Leu Glu Trp Leu Gly
            340                 345                 350
Val Ile Trp Ser Gly Gly Asn Thr Asp Tyr Asn Thr Pro Phe Thr Ser
            355                 360                 365
Arg Leu Ser Ile Asn Lys Asp Asn Ser Lys Ser Gln Val Phe Phe Lys
            370                 375                 380
Met Asn Ser Leu Gln Ser Gln Asp Thr Ala Ile Tyr Tyr Cys Ala Arg
385                 390                 395                 400
Ala Leu Thr Tyr Tyr Asp Tyr Glu Phe Ala Tyr Trp Gly Gln Gly Thr
                405                 410                 415
Leu Val Thr Val Ser Ala Ala Ser Thr Lys Gly Pro Ser Val Phe Pro
            420                 425                 430
Leu Ala Pro Ser Ser Lys Ser Thr Ser Gly Gly Thr Ala Ala Leu Gly
            435                 440                 445
Cys Leu Val Lys Asp Tyr Phe Pro Glu Pro Val Thr Val Ser Trp Asn
450                 455                 460
Ser Gly Ala Leu Thr Ser Gly Val His Thr Phe Pro Ala Val Leu Gln
465                 470                 475                 480
Ser Ser Gly Leu Tyr Ser Leu Ser Ser Val Val Thr Val Pro Ser Ser
                485                 490                 495
Ser Leu Gly Thr Gln Thr Tyr Ile Cys Asn Val Asn His Lys Pro Ser
            500                 505                 510
Asn Thr Lys Val Asp Lys Lys Val Glu Pro Lys Ser Cys Asp Lys Thr
            515                 520                 525
His Thr Cys Pro Pro Cys Pro Ala Pro Glu Phe Glu Gly Gly Pro Ser
            530                 535                 540
Val Phe Leu Phe Pro Pro Lys Pro Lys Asp Thr Leu Met Ile Ser Arg
545                 550                 555                 560
Thr Pro Glu Val Thr Cys Val Val Val Asp Val Ser His Glu Asp Pro
                565                 570                 575
Glu Val Lys Phe Asn Trp Tyr Val Asp Gly Val Glu Val His Asn Ala
            580                 585                 590
Lys Thr Lys Pro Arg Glu Glu Gln Tyr Gln Ser Thr Tyr Arg Val Val
            595                 600                 605
Ser Val Leu Thr Val Leu His Gln Asp Trp Leu Asn Gly Lys Glu Tyr
            610                 615                 620
Lys Cys Lys Val Ser Asn Lys Ala Leu Pro Ala Ser Ile Glu Lys Thr
625                 630                 635                 640
Ile Ser Lys Ala Lys Gly Gln Pro Arg Glu Pro Gln Val Tyr Thr Leu
                645                 650                 655
Pro Pro Ser Arg Glu Glu Met Thr Lys Asn Gln Val Ser Leu Thr Cys
            660                 665                 670
Leu Val Lys Gly Phe Tyr Pro Ser Asp Ile Ala Val Glu Trp Glu Ser
            675                 680                 685
Asn Gly Gln Pro Glu Asn Asn Tyr Lys Thr Thr Pro Pro Val Leu Asp
            690                 695                 700
Ser Asp Gly Ser Phe Phe Leu Tyr Ser Lys Leu Thr Val Asp Lys Ser
705                 710                 715                 720
Arg Trp Gln Gln Gly Asn Val Phe Ser Cys Ser Val Met His Glu Ala
                725                 730                 735
Leu His Asn His Tyr Thr Gln Lys Ser Leu Ser Leu Ser Pro Gly Lys
            740                 745                 750
```

<210> SEQ ID NO 135
<211> LENGTH: 783
<212> TYPE: DNA
<213> ORGANISM: Artificial Sequence
<220> FEATURE:
<223> OTHER INFORMATION: synthetic

<400> SEQUENCE: 135

```
caaggccagt ctggccagtg catctcacct cgtggttgtc cggacggccc atacgtcatg      60
tacggctcga gcggtggcag cggtggctct ggtggatccg gtctgagcgg ccgttccgat     120
gatcatggca gtagcggtac ccagatcttg ctgacccaga gcccggtgat tctgagcgtg     180
agcccgggcg aacgtgtgag ctttagctgc cgcgcgagcc agagcattgg caccaacatt     240
cattggtatc agcagcgcac caacggcagc ccgcgcctgc tgattaaata tgcgagcgaa     300
agcattagcg gcattccgag ccgctttagc ggcagcggca gcggcaccga ttttaccctg     360
agcattaaca gcgtggaaag cgaagatatt gcggattatt attgccagca gaacaacaac     420
tggccgacca cctttggcgc gggcaccaaa ctggaactga acgtacggt ggctgcacca      480 tctgtcttca tcttcccgcc atctgatgag cagttgaaat ctggaactgc ctctgttgtg     540
tgcctgctga ataacttcta tcccagagag gccaaagtac agtggaaggt ggataacgcc     600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgt                                                                   783
```

<210> SEQ ID NO 136
<211> LENGTH: 261
<212> TYPE: PRT
<213> ORGANISM: Artificial Sequence
<220> FEATURE:
<223> OTHER INFORMATION: synthetic

<400> SEQUENCE: 136

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Leu Ser Gly Arg Ser Asp Asp His Gly Ser Ser Gly Thr Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160
```

Ser Val Phe Ile Phe Pro Pro Ser Asp Glu Gln Leu Lys Ser Gly Thr
            165                 170                 175

Ala Ser Val Val Cys Leu Leu Asn Asn Phe Tyr Pro Arg Glu Ala Lys
        180                 185                 190

Val Gln Trp Lys Val Asp Asn Ala Leu Gln Ser Gly Asn Ser Gln Glu
    195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
            245                 250                 255

Asn Arg Gly Glu Cys
            260

<210> SEQ ID NO 137
<211> LENGTH: 2244
<212> TYPE: DNA
<213> ORGANISM: Artificial Sequence
<220> FEATURE:
<223> OTHER INFORMATION: synthetic

<400> SEQUENCE: 137

```
caaggccagt ctggatccgg ttatctgtgg ggttgcgagt ggaattgcgg agggatcact      60
acaggctcga gcggtggcag cggtggctct ggtggtctga gcggccgttc cgatgatcat     120
ggcggcggtt ctcaaactgt agtaactcaa gaaccaagct tctccgtctc ccctggggga     180
acagtcacac ttacctgccg aagtagtaca ggtgctgtta cgaccagtaa ctatgccaat     240
tgggtacaac aaacgcctgg tcaggctccg cgcggattga taggaggcac gaataaacgg     300
gcacccggtg tcccggacag attcagcgga agcatactcg gtaataaggc agctcttact     360
atcactgggg cccaagctga tgatgaaagt gattattatt gtgcgctctg gtacagcaac     420
ctctgggtgt ttgggggtgg cacgaaactt actgtcttgg gcggcggcgg atcaggggga     480
ggtggctctg gaggaggagg ctcagaagtc caactggtcg aatccggggg agggctcgta     540
cagccgggtg ggtccctcaa actctcttgt gcggcctcag ggtttacctt cagtacatac     600
gcgatgaatt gggtccggca ggccagtggg aaagggctcg aatgggtagg acgaatccga     660
tcaaaataca caaactacgc tactattac gctgattccg tgaaggacag attcacaata     720
tcccgcgacg atagcaagaa tacggcatat cttcagatga attctcttaa aactgaggat     780
accgctgtgt attactgcac aagacatggt aattttggaa actcatatgt ctcttggttc     840
gcttattggg gacagggcac gttggttacc gtgtctagcg gaggtggtgg atcccaagtg     900
accctgagag agtctggccc tgccctcgtg aagcctaccc agaccctgac actgacctgc     960
accttcagcg gcttcagcct gagcaccagc ggcatgtctg tgggctggat cagacagcct    1020
cctggcaagg ccctggaatg gctggccgac atttggtggg acgacaagaa ggactacaac    1080
cccagcctga agtcccggct gaccatcagc aaggacacca gcaagaacca ggtggtgctg    1140
aaagtgacca acatggaccc cgccgacacc gccacctact actgcgccag atccatgatc    1200
accaactggt acttcgacgt gtggggagcc ggcaccaccg tgacagtgtc atctgctagc    1260
accaagggcc catcggtctt ccccctggca ccctcctcca agagcacctc tgggggcaca    1320
gcggccctgg gctgcctggt caaggactac ttccccgaac cggtgacggt gtcgtggaac    1380
tcaggcgccc tgaccagcgg cgtgcacacc ttcccggctg tcctacagtc ctcaggactc    1440
```

```
tactccctca gcagcgtggt gaccgtgccc tccagcagct tgggcaccca gacctacatc    1500
tgcaacgtga atcacaagcc cagcaacacc aaggtggaca gaaaagttga gcccaaatct    1560
tgtgacaaaa ctcacacatg cccaccgtgc ccagcacctg aatttgaagg gggaccgtca    1620
gtcttcctct ccccccaaa acccaaggac accctcatga tctcccggac ccctgaggtc    1680
acatgcgtgg tggtggacgt gagccacgaa gaccctgagg tcaagttcaa ctggtacgtg    1740
gacggcgtgg aggtgcataa tgccaagaca aagccgcggg aggagcagta ccagagcacg    1800
taccgtgtgg tcagcgtcct caccgtcctg caccaggact ggctgaatgg caaggagtac    1860
aagtgcaagg tctccaacaa agccctccca gcctcaatcg agaaaaccat ctccaaagcc    1920
aaagggcagc ccgagaacc acaggtgtac accctgcccc catcccggga ggagatgacc    1980
aagaaccagg tcagcctgac ctgcctggtc aaaggcttct atcccagcga catcgccgtg    2040
gagtgggaga gcaatgggca gccggagaac aactacaaga ccacgcctcc cgtgctggac    2100
tccgacggct ccttcttcct ctacagcaag ctcaccgtgg acaagagcag gtggcagcag    2160
gggaacgtct tctcatgctc cgtgatgcat gaggctctgc acaaccacta cacgcagaag    2220
agcctctccc tgtctccggg taaa                                           2244
```

<210> SEQ ID NO 138
<211> LENGTH: 748
<212> TYPE: PRT
<213> ORGANISM: Artificial Sequence
<220> FEATURE:
<223> OTHER INFORMATION: synthetic

<400> SEQUENCE: 138

```
Gln Gly Gln Ser Gly Ser Gly Tyr Leu Trp Gly Cys Glu Trp Asn Cys
1               5                   10                  15

Gly Gly Ile Thr Thr Gly Ser Ser Gly Ser Gly Ser Gly Gly
            20                  25                  30

Leu Ser Gly Arg Ser Asp Asp His Gly Gly Gly Ser Gln Thr Val Val
        35                  40                  45

Thr Gln Glu Pro Ser Phe Ser Val Ser Pro Gly Gly Thr Val Thr Leu
    50                  55                  60

Thr Cys Arg Ser Ser Thr Gly Ala Val Thr Thr Ser Asn Tyr Ala Asn
65                  70                  75                  80

Trp Val Gln Gln Thr Pro Gly Gln Ala Pro Arg Gly Leu Ile Gly Gly
                85                  90                  95

Thr Asn Lys Arg Ala Pro Gly Val Pro Asp Arg Phe Ser Gly Ser Ile
            100                 105                 110

Leu Gly Asn Lys Ala Ala Leu Thr Ile Thr Gly Ala Gln Ala Asp Asp
        115                 120                 125

Glu Ser Asp Tyr Tyr Cys Ala Leu Trp Tyr Ser Asn Leu Trp Val Phe
    130                 135                 140

Gly Gly Gly Thr Lys Leu Thr Val Leu Gly Gly Gly Ser Gly Gly
145                 150                 155                 160

Gly Gly Ser Gly Gly Gly Ser Glu Val Gln Leu Val Glu Ser Gly
                165                 170                 175

Gly Gly Leu Val Gln Pro Gly Gly Ser Leu Lys Leu Ser Cys Ala Ala
            180                 185                 190

Ser Gly Phe Thr Phe Ser Thr Tyr Ala Met Asn Trp Val Arg Gln Ala
        195                 200                 205

Ser Gly Lys Gly Leu Glu Trp Val Gly Arg Ile Arg Ser Lys Tyr Asn
    210                 215                 220
```

```
Asn Tyr Ala Thr Tyr Tyr Ala Asp Ser Val Lys Asp Arg Phe Thr Ile
225                 230                 235                 240

Ser Arg Asp Asp Ser Lys Asn Thr Ala Tyr Leu Gln Met Asn Ser Leu
            245                 250                 255

Lys Thr Glu Asp Thr Ala Val Tyr Tyr Cys Thr Arg His Gly Asn Phe
        260                 265                 270

Gly Asn Ser Tyr Val Ser Trp Phe Ala Tyr Trp Gly Gln Gly Thr Leu
    275                 280                 285

Val Thr Val Ser Ser Gly Gly Gly Ser Gln Val Thr Leu Arg Glu
290                 295                 300

Ser Gly Pro Ala Leu Val Lys Pro Thr Gln Thr Leu Thr Leu Thr Cys
305                 310                 315                 320

Thr Phe Ser Gly Phe Ser Leu Ser Thr Ser Gly Met Ser Val Gly Trp
                325                 330                 335

Ile Arg Gln Pro Pro Gly Lys Ala Leu Glu Trp Leu Ala Asp Ile Trp
            340                 345                 350

Trp Asp Asp Lys Lys Asp Tyr Asn Pro Ser Leu Lys Ser Arg Leu Thr
        355                 360                 365

Ile Ser Lys Asp Thr Ser Lys Asn Gln Val Val Leu Lys Val Thr Asn
370                 375                 380

Met Asp Pro Ala Asp Thr Ala Thr Tyr Tyr Cys Ala Arg Ser Met Ile
385                 390                 395                 400

Thr Asn Trp Tyr Phe Asp Val Trp Gly Ala Gly Thr Thr Val Thr Val
                405                 410                 415

Ser Ser Ala Ser Thr Lys Gly Pro Ser Val Phe Pro Leu Ala Pro Ser
            420                 425                 430

Ser Lys Ser Thr Ser Gly Gly Thr Ala Ala Leu Gly Cys Leu Val Lys
        435                 440                 445

Asp Tyr Phe Pro Glu Pro Val Thr Val Ser Trp Asn Ser Gly Ala Leu
450                 455                 460

Thr Ser Gly Val His Thr Phe Pro Ala Val Leu Gln Ser Ser Gly Leu
465                 470                 475                 480

Tyr Ser Leu Ser Ser Val Val Thr Val Pro Ser Ser Ser Leu Gly Thr
                485                 490                 495

Gln Thr Tyr Ile Cys Asn Val Asn His Lys Pro Ser Asn Thr Lys Val
            500                 505                 510

Asp Lys Lys Val Glu Pro Lys Ser Cys Asp Lys Thr His Thr Cys Pro
        515                 520                 525

Pro Cys Pro Ala Pro Glu Phe Glu Gly Gly Pro Ser Val Phe Leu Phe
530                 535                 540

Pro Pro Lys Pro Lys Asp Thr Leu Met Ile Ser Arg Thr Pro Glu Val
545                 550                 555                 560

Thr Cys Val Val Val Asp Val Ser His Glu Asp Pro Glu Val Lys Phe
                565                 570                 575

Asn Trp Tyr Val Asp Gly Val Glu Val His Asn Ala Lys Thr Lys Pro
            580                 585                 590

Arg Glu Glu Gln Tyr Gln Ser Thr Tyr Arg Val Val Ser Val Leu Thr
        595                 600                 605

Val Leu His Gln Asp Trp Leu Asn Gly Lys Glu Tyr Lys Cys Lys Val
610                 615                 620

Ser Asn Lys Ala Leu Pro Ala Ser Ile Glu Lys Thr Ile Ser Lys Ala
625                 630                 635                 640
```

Lys Gly Gln Pro Arg Glu Pro Gln Val Tyr Thr Leu Pro Pro Ser Arg
            645                 650                 655

Glu Glu Met Thr Lys Asn Gln Val Ser Leu Thr Cys Leu Val Lys Gly
        660                 665                 670

Phe Tyr Pro Ser Asp Ile Ala Val Glu Trp Glu Ser Asn Gly Gln Pro
            675                 680                 685

Glu Asn Asn Tyr Lys Thr Thr Pro Pro Val Leu Asp Ser Asp Gly Ser
        690                 695                 700

Phe Phe Leu Tyr Ser Lys Leu Thr Val Asp Lys Ser Arg Trp Gln Gln
705                 710                 715                 720

Gly Asn Val Phe Ser Cys Ser Val Met His Glu Ala Leu His Asn His
            725                 730                 735

Tyr Thr Gln Lys Ser Leu Ser Leu Ser Pro Gly Lys
            740                 745

<210> SEQ ID NO 139
<211> LENGTH: 639
<212> TYPE: DNA
<213> ORGANISM: Artificial Sequence
<220> FEATURE:
<223> OTHER INFORMATION: synthetic

<400> SEQUENCE: 139
gacatccaga tgacccagag ccccagcaca ctgagcgcca gcgtgggcga cagagtgacc        60
atcacatgca agtgccagct gagcgtgggc tacatgcact ggtatcagca gaagcccggc       120
aaggccccca agctgctgat ctacgacacc agcaagctgg cctccggcgt gcccagcaga       180 tttttctggca gcggctccgg caccgagttc accctgacaa tcagcagcct gcagcccgac       240
gacttcgcca cctactactg ttttcaaggc tccggctacc ccttcacctt cggcggaggc       300
accaagctgg aaatcaagcg gacggtggct gcaccatctg tcttcatctt cccgccatct       360
gatgagcagt tgaaatctgg aactgcctct gttgtgtgcc tgctgaataa cttctatccc       420
agagaggcca agtacagtg gaaggtggat aacgccctcc aatcgggtaa ctcccaggag       480
agtgtcacag agcaggacag caaggacagc acctacagcc tcagcagcac cctgacgctg       540
agcaaagcag actacgagaa acacaaagtc tacgcctgcg aagtcaccca tcagggcctg       600
agctcgcccg tcacaaagag cttcaacagg ggagagtgt                              639

<210> SEQ ID NO 140
<211> LENGTH: 213
<212> TYPE: PRT
<213> ORGANISM: Artificial Sequence
<220> FEATURE:
<223> OTHER INFORMATION: synthetic

<400> SEQUENCE: 140

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr

```
            85                  90                  95
Phe Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210
```

<210> SEQ ID NO 141
<211> LENGTH: 2259
<212> TYPE: DNA
<213> ORGANISM: Artificial Sequence
<220> FEATURE:
<223> OTHER INFORMATION: synthetic

<400> SEQUENCE: 141

```
caaggccagt ctggatccgg ttatctgtgg ggttgcgagt ggaattgcgg agggatcact    60
acaggctcga gcggtggcag cggtggctct ggtggtatat cgagtggatt gctgtctggc   120
agatctgacg atcacggcgg cggttctcaa actgtagtaa ctcaagaacc aagcttctcc   180
gtctcccctg ggggaacagt cacacttacc tgccgaagta gtacaggtgc tgttacgacc   240
agtaactatg ccaattgggt acaacaaacg cctggtcagg ctccgcgcgg attgatagga   300
ggcacgaata acgggcaccc ggtgtcccg acagattca gcggaagcat actcggtaat     360
aaggcagctc ttactatcac tggggcccaa gctgatgatg aaagtgatta ttattgtgcg   420
ctctggtaca gcaacctctg ggtgtttggg ggtggcacga acttactgt cttgggcggc   480
ggcggatcag ggggaggtgg ctctggagga ggaggctcag aagtccaact ggtcgaatcc   540
gggggagggc tcgtacagcc gggtgggtcc ctcaaactct cttgtgcggc ctcagggttt   600
accttcagta catacgcgat gaattgggtc cggcaggcca gtgggaaagg ctcgaatgg    660
gtaggacgaa tccgatcaaa atacaacaac tacgctactt attacgctga ttccgtgaag   720
gacagattca caatatcccg cgacgatagc aagaatacgg catatcttca gatgaattct   780
cttaaaactg aggataccgc tgtgtattac tgcacaagac atggtaattt tggaaactca   840
tatgtctctt ggttcgctta ttggggacag ggcacgttgg ttaccgtgtc tagcggaggt   900
ggtggatccc aagtgaccct gagagagtct ggccctgccc tcgtgaagcc tacccagacc   960
ctgacactga cctgcacctt cagcggcttc agcctgagca ccagcggcat gtctgtgggc  1020
tggatcagac agcctcctgg caaggccctg gaatggctgg ccgacatttg tgggacgac   1080
aagaaggact acaaccccag cctgaagtcc cggctgacca tcagcaagga caccagcaag  1140
aaccaggtgg tgctgaaagt gaccaacatg gaccccgccg acaccgccac ctactactgc  1200
gccagatcca tgatcaccaa ctggtacttc gacgtgtggg gagccggcac caccgtgaca  1260
gtgtcatctg ctagcaccaa gggcccatcg gtcttccccc tggcaccctc ctccaagagc  1320
```

```
acctctgggg gcacagcggc cctgggctgc ctggtcaagg actacttccc cgaaccggtg   1380
acggtgtcgt ggaactcagg cgccctgacc agcggcgtgc acaccttccc ggctgtccta   1440
cagtcctcag gactctactc cctcagcagc gtggtgaccg tgccctccag cagcttgggc   1500
acccagacct acatctgcaa cgtgaatcac aagcccagca caccaaggt ggacaagaaa    1560 gttgagccca atcttgtga caaaactcac acatgcccac cgtgcccagc acctgaattt    1620 gaaggggac cgtcagtctt cctcttcccc ccaaaaccca aggacaccct catgatctcc    1680
cggacccctg aggtcacatg cgtggtggtg gacgtgagcc acgaagaccc tgaggtcaag   1740
ttcaactggt acgtggacgg cgtggaggtg cataatgcca agacaaagcc gcgggaggag   1800
cagtaccaga gcacgtaccg tgtggtcagc gtcctcaccg tcctgcacca ggactggctg   1860
aatggcaagg agtacaagtg caaggtctcc aacaaagccc tcccagcctc aatcgagaaa   1920
accatctcca aagccaaagg gcagccccga gaaccacagg tgtacaccct gcccccatcc   1980
cgggaggaga tgaccaagaa ccaggtcagc ctgacctgcc tggtcaaagg cttctatccc   2040
agcgacatcg ccgtggagtg ggagagcaat gggcagccgg agaacaacta caagaccacg   2100
cctcccgtgc tggactccga cggctccttc ttcctctaca gcaagctcac cgtggacaag   2160
agcaggtggc agcaggggaa cgtcttctca tgctccgtga tgcatgaggc tctgcacaac   2220
cactacacgc agaagagcct ctccctgtct ccgggtaaa                         2259
```

<210> SEQ ID NO 142
<211> LENGTH: 753
<212> TYPE: PRT
<213> ORGANISM: Artificial Sequence
<220> FEATURE:
<223> OTHER INFORMATION: synthetic

<400> SEQUENCE: 142

```
Gln Gly Gln Ser Gly Ser Gly Tyr Leu Trp Gly Cys Glu Trp Asn Cys
1               5                   10                  15

Gly Gly Ile Thr Thr Gly Ser Ser Gly Gly Ser Gly Gly Ser Gly Gly
            20                  25                  30

Ile Ser Ser Gly Leu Leu Ser Gly Arg Ser Asp Asp His Gly Gly Gly
        35                  40                  45

Ser Gln Thr Val Val Thr Gln Glu Pro Ser Phe Ser Val Ser Pro Gly
    50                  55                  60

Gly Thr Val Thr Leu Thr Cys Arg Ser Ser Thr Gly Ala Val Thr Thr
65                  70                  75                  80

Ser Asn Tyr Ala Asn Trp Val Gln Gln Thr Pro Gly Gln Ala Pro Arg
                85                  90                  95

Gly Leu Ile Gly Gly Thr Asn Lys Arg Ala Pro Gly Val Pro Asp Arg
            100                 105                 110

Phe Ser Gly Ser Ile Leu Gly Asn Lys Ala Ala Leu Thr Ile Thr Gly
        115                 120                 125

Ala Gln Ala Asp Asp Glu Ser Asp Tyr Tyr Cys Ala Leu Trp Tyr Ser
    130                 135                 140

Asn Leu Trp Val Phe Gly Gly Gly Thr Lys Leu Thr Val Leu Gly Gly
145                 150                 155                 160

Gly Gly Ser Gly Gly Gly Gly Ser Gly Gly Gly Gly Ser Glu Val Gln
                165                 170                 175

Leu Val Glu Ser Gly Gly Gly Leu Val Gln Pro Gly Gly Ser Leu Lys
            180                 185                 190
```

```
Leu Ser Cys Ala Ala Ser Gly Phe Thr Phe Ser Thr Tyr Ala Met Asn
        195                 200                 205
Trp Val Arg Gln Ala Ser Gly Lys Gly Leu Glu Trp Val Gly Arg Ile
    210                 215                 220
Arg Ser Lys Tyr Asn Asn Tyr Ala Thr Tyr Tyr Ala Asp Ser Val Lys
225                 230                 235                 240
Asp Arg Phe Thr Ile Ser Arg Asp Ser Lys Asn Thr Ala Tyr Leu
                245                 250                 255
Gln Met Asn Ser Leu Lys Thr Glu Asp Thr Ala Val Tyr Tyr Cys Thr
            260                 265                 270
Arg His Gly Asn Phe Gly Asn Ser Tyr Val Ser Trp Phe Ala Tyr Trp
        275                 280                 285
Gly Gln Gly Thr Leu Val Thr Val Ser Ser Gly Gly Gly Gly Ser Gln
    290                 295                 300
Val Thr Leu Arg Glu Ser Gly Pro Ala Leu Val Lys Pro Thr Gln Thr
305                 310                 315                 320
Leu Thr Leu Thr Cys Thr Phe Ser Gly Phe Ser Leu Ser Thr Ser Gly
                325                 330                 335
Met Ser Val Gly Trp Ile Arg Gln Pro Pro Gly Lys Ala Leu Glu Trp
            340                 345                 350
Leu Ala Asp Ile Trp Trp Asp Asp Lys Lys Asp Tyr Asn Pro Ser Leu
        355                 360                 365
Lys Ser Arg Leu Thr Ile Ser Lys Asp Thr Ser Lys Asn Gln Val Val
    370                 375                 380
Leu Lys Val Thr Asn Met Asp Pro Ala Asp Thr Ala Thr Tyr Tyr Cys
385                 390                 395                 400
Ala Arg Ser Met Ile Thr Asn Trp Tyr Phe Asp Val Trp Gly Ala Gly
                405                 410                 415
Thr Thr Val Thr Val Ser Ser Ala Ser Thr Lys Gly Pro Ser Val Phe
            420                 425                 430
Pro Leu Ala Pro Ser Ser Lys Ser Thr Ser Gly Gly Thr Ala Ala Leu
        435                 440                 445
Gly Cys Leu Val Lys Asp Tyr Phe Pro Glu Pro Val Thr Val Ser Trp
    450                 455                 460
Asn Ser Gly Ala Leu Thr Ser Gly Val His Thr Phe Pro Ala Val Leu
465                 470                 475                 480
Gln Ser Ser Gly Leu Tyr Ser Leu Ser Ser Val Val Thr Val Pro Ser
                485                 490                 495
Ser Ser Leu Gly Thr Gln Thr Tyr Ile Cys Asn Val Asn His Lys Pro
            500                 505                 510
Ser Asn Thr Lys Val Asp Lys Lys Val Glu Pro Lys Ser Cys Asp Lys
        515                 520                 525
Thr His Thr Cys Pro Pro Cys Pro Ala Pro Glu Phe Glu Gly Gly Pro
    530                 535                 540
Ser Val Phe Leu Phe Pro Pro Lys Pro Lys Asp Thr Leu Met Ile Ser
545                 550                 555                 560
Arg Thr Pro Glu Val Thr Cys Val Val Val Asp Val Ser His Glu Asp
                565                 570                 575
Pro Glu Val Lys Phe Asn Trp Tyr Val Asp Gly Val Glu Val His Asn
            580                 585                 590
Ala Lys Thr Lys Pro Arg Glu Glu Gln Tyr Gln Ser Thr Tyr Arg Val
        595                 600                 605
Val Ser Val Leu Thr Val Leu His Gln Asp Trp Leu Asn Gly Lys Glu
```

```
                610                 615                 620
Tyr Lys Cys Lys Val Ser Asn Lys Ala Leu Pro Ala Ser Ile Glu Lys
625                 630                 635                 640

Thr Ile Ser Lys Ala Lys Gly Gln Pro Arg Glu Pro Gln Val Tyr Thr
                645                 650                 655

Leu Pro Pro Ser Arg Glu Glu Met Thr Lys Asn Gln Val Ser Leu Thr
                660                 665                 670

Cys Leu Val Lys Gly Phe Tyr Pro Ser Asp Ile Ala Val Glu Trp Glu
                675                 680                 685

Ser Asn Gly Gln Pro Glu Asn Asn Tyr Lys Thr Thr Pro Pro Val Leu
690                 695                 700

Asp Ser Asp Gly Ser Phe Phe Leu Tyr Ser Lys Leu Thr Val Asp Lys
705                 710                 715                 720

Ser Arg Trp Gln Gln Gly Asn Val Phe Ser Cys Ser Val Met His Glu
                725                 730                 735

Ala Leu His Asn His Tyr Thr Gln Lys Ser Leu Ser Leu Ser Pro Gly
                740                 745                 750

Lys

<210> SEQ ID NO 143
<211> LENGTH: 249
<212> TYPE: PRT
<213> ORGANISM: Artificial Sequence
<220> FEATURE:
<223> OTHER INFORMATION: synthetic

<400> SEQUENCE: 143

Gln Thr Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Pro Arg Gly
            35                  40                  45

Leu Ile Gly Gly Thr Asn Lys Arg Ala Pro Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
                100                 105                 110

Gly Ser Gly Gly Gly Gly Ser Gly Gly Gly Ser Glu Val Gln Leu
            115                 120                 125

Val Glu Ser Gly Gly Gly Leu Val Gln Pro Gly Gly Ser Leu Arg Leu
            130                 135                 140

Ser Cys Ala Ala Ser Gly Phe Thr Phe Ser Thr Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Lys Asn Ser Leu Tyr Leu Gln
            195                 200                 205

Met Asn Ser Leu Lys Thr Glu Asp Thr Ala Val Tyr Tyr Cys Val Arg
        210                 215                 220
```

His Gly Asn Phe Gly Asn Ser Tyr Val Ser Trp Phe Ala Tyr Trp Gly
225                 230                 235                 240

Gln Gly Thr Leu Val Thr Val Ser Ser
                245

<210> SEQ ID NO 144
<211> LENGTH: 249
<212> TYPE: PRT
<213> ORGANISM: Artificial Sequence
<220> FEATURE:
<223> OTHER INFORMATION: synthetic

<400> SEQUENCE: 144

Gln Thr Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Pro Arg Gly
        35                  40                  45

Leu Ile Gly Gly Thr Asn Lys Arg Ala Pro Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Ser Thr Tyr Ala Met Asn Trp
145                 150                 155                 160

Val Arg Gln Ala Ser Gly Lys Gly Leu Glu Trp Val Gly Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Thr Ala Tyr Leu Gln
        195                 200                 205

Met Asn Ser Leu Lys Thr Glu Asp Thr Ala Val Tyr Tyr Cys Thr Arg
    210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser
                245

<210> SEQ ID NO 145
<211> LENGTH: 249
<212> TYPE: PRT
<213> ORGANISM: Artificial Sequence
<220> FEATURE:
<223> OTHER INFORMATION: synthetic

<400> SEQUENCE: 145

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser

```
            20                  25                  30
Asn Tyr Ala Asn Trp Val Gln Gln Lys Pro Gly Gln Ala Pro Arg Gly
         35                  40                  45

Leu Ile Gly Gly Thr Asn Lys Arg Ala Pro Gly Thr Pro Ala Arg Phe
 50                  55                  60

Ser Gly Ser Leu Ile Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Gln Leu
         115                 120                 125

Val Glu Ser Gly Gly Gly Leu Val Gln Pro Gly Gly Ser Leu Lys Leu
        130                 135                 140

Ser Cys Ala Ala Ser Gly Phe Thr Phe Ser Thr Tyr Ala Met Asn Trp
145                 150                 155                 160

Val Arg Gln Ala Ser Gly Lys Gly Leu Glu Trp Val Gly Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Lys Asn Thr Ala Tyr Leu Gln
            195                 200                 205

Met Asn Ser Leu Lys Thr Glu Asp Thr Ala Val Tyr Tyr Cys Thr Arg
    210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser
                245

<210> SEQ ID NO 146
<211> LENGTH: 747
<212> TYPE: PRT
<213> ORGANISM: Artificial Sequence
<220> FEATURE:
<223> OTHER INFORMATION: synthetic

<400> SEQUENCE: 146

Gln Gly Gln Ser Gly Ser Gly Tyr Leu Trp Gly Cys Glu Trp Asn Cys
1               5                   10                  15

Gly Gly Ile Thr Thr Gly Ser Ser Gly Gly Ser Gly Gly Ser Gly Gly
             20                  25                  30

Leu Ser Gly Arg Ser Asp Asp His Gly Gly Gly Ser Gln Thr Val Val
         35                  40                  45

Thr Gln Glu Pro Ser Phe Ser Val Ser Pro Gly Gly Thr Val Thr Leu
 50                  55                  60

Thr Cys Arg Ser Ser Thr Gly Ala Val Thr Thr Ser Asn Tyr Ala Asn
 65                  70                  75                  80

Trp Val Gln Gln Thr Pro Gly Gln Ala Pro Arg Gly Leu Ile Gly Gly
                 85                  90                  95

Thr Asn Lys Arg Ala Pro Gly Val Pro Asp Arg Phe Ser Gly Ser Ile
            100                 105                 110

Leu Gly Asn Lys Ala Ala Leu Thr Ile Thr Gly Ala Gln Ala Asp Asp
        115                 120                 125

Glu Ser Asp Tyr Tyr Cys Ala Leu Trp Tyr Ser Asn Leu Trp Val Phe
```

```
                 130                 135                 140
Gly Gly Gly Thr Lys Leu Thr Val Leu Gly Gly Gly Ser Gly Gly
145                 150                 155                 160
Gly Gly Ser Gly Gly Gly Ser Glu Val Gln Leu Val Glu Ser Gly
                165                 170                 175
Gly Gly Leu Val Gln Pro Gly Gly Ser Leu Arg Leu Ser Cys Ala Ala
                180                 185                 190
Ser Gly Phe Thr Phe Ser Thr Tyr Ala Met Asn Trp Val Arg Gln Ala
                195                 200                 205
Pro Gly Lys Gly Leu Glu Trp Val Ala Arg Ile Arg Ser Lys Tyr Asn
                210                 215                 220
Asn Tyr Ala Thr Tyr Tyr Ala Asp Ser Val Lys Asp Arg Phe Thr Ile
225                 230                 235                 240
Ser Arg Asp Asp Ser Lys Asn Ser Leu Tyr Leu Gln Met Asn Ser Leu
                245                 250                 255
Lys Thr Glu Asp Thr Ala Val Tyr Tyr Cys Val Arg His Gly Asn Phe
                260                 265                 270
Gly Asn Ser Tyr Val Ser Trp Phe Ala Tyr Trp Gly Gln Gly Thr Leu
                275                 280                 285
Val Thr Val Ser Ser Gly Gly Gly Gly Ser Gln Val Gln Leu Lys Gln
290                 295                 300
Ser Gly Pro Gly Leu Val Gln Pro Ser Gln Ser Leu Ser Ile Thr Cys
305                 310                 315                 320
Thr Val Ser Gly Phe Ser Leu Thr Asn Tyr Gly Val His Trp Val Arg
                325                 330                 335
Gln Ser Pro Gly Lys Gly Leu Glu Trp Leu Gly Val Ile Trp Ser Gly
                340                 345                 350
Gly Asn Thr Asp Tyr Asn Thr Pro Phe Thr Ser Arg Leu Ser Ile Asn
                355                 360                 365
Lys Asp Asn Ser Lys Ser Gln Val Phe Phe Lys Met Asn Ser Leu Gln
                370                 375                 380
Ser Gln Asp Thr Ala Ile Tyr Tyr Cys Ala Arg Ala Leu Thr Tyr Tyr
385                 390                 395                 400
Asp Tyr Glu Phe Ala Tyr Trp Gly Gln Gly Thr Leu Val Thr Val Ser
                405                 410                 415
Ala Ala Ser Thr Lys Gly Pro Ser Val Phe Pro Leu Ala Pro Ser Ser
                420                 425                 430
Lys Ser Thr Ser Gly Gly Thr Ala Ala Leu Gly Cys Leu Val Lys Asp
                435                 440                 445
Tyr Phe Pro Glu Pro Val Thr Val Ser Trp Asn Ser Gly Ala Leu Thr
450                 455                 460
Ser Gly Val His Thr Phe Pro Ala Val Leu Gln Ser Ser Gly Leu Tyr
465                 470                 475                 480
Ser Leu Ser Ser Val Val Thr Val Pro Ser Ser Ser Leu Gly Thr Gln
                485                 490                 495
Thr Tyr Ile Cys Asn Val Asn His Lys Pro Ser Asn Thr Lys Val Asp
                500                 505                 510
Lys Lys Val Glu Pro Lys Ser Cys Asp Lys Thr His Thr Cys Pro Pro
                515                 520                 525
Cys Pro Ala Pro Glu Phe Glu Gly Gly Pro Ser Val Phe Leu Phe Pro
530                 535                 540
Pro Lys Pro Lys Asp Thr Leu Met Ile Ser Arg Thr Pro Glu Val Thr
545                 550                 555                 560
```

```
Cys Val Val Val Asp Val Ser His Glu Asp Pro Glu Val Lys Phe Asn
                565                 570                 575

Trp Tyr Val Asp Gly Val Glu Val His Asn Ala Lys Thr Lys Pro Arg
            580                 585                 590

Glu Glu Gln Tyr Gln Ser Thr Tyr Arg Val Val Ser Val Leu Thr Val
        595                 600                 605

Leu His Gln Asp Trp Leu Asn Gly Lys Glu Tyr Lys Cys Lys Val Ser
    610                 615                 620

Asn Lys Ala Leu Pro Ala Ser Ile Glu Lys Thr Ile Ser Lys Ala Lys
625                 630                 635                 640

Gly Gln Pro Arg Glu Pro Gln Val Tyr Thr Leu Pro Pro Ser Arg Glu
                645                 650                 655

Glu Met Thr Lys Asn Gln Val Ser Leu Thr Cys Leu Val Lys Gly Phe
            660                 665                 670

Tyr Pro Ser Asp Ile Ala Val Glu Trp Glu Ser Asn Gly Gln Pro Glu
        675                 680                 685

Asn Asn Tyr Lys Thr Thr Pro Pro Val Leu Asp Ser Asp Gly Ser Phe
    690                 695                 700

Phe Leu Tyr Ser Lys Leu Thr Val Asp Lys Ser Arg Trp Gln Gln Gly
705                 710                 715                 720

Asn Val Phe Ser Cys Ser Val Met His Glu Ala Leu His Asn His Tyr
                725                 730                 735

Thr Gln Lys Ser Leu Ser Leu Ser Pro Gly Lys
            740                 745
```

<210> SEQ ID NO 147
<211> LENGTH: 2244
<212> TYPE: DNA
<213> ORGANISM: Artificial Sequence
<220> FEATURE:
<223> OTHER INFORMATION: synthetic

<400> SEQUENCE: 147

```
caaggccagt ctggccaaat gatgtattgc ggtgggaatg aggtgttgtg cgggccgcgg      60
gttggctcga gcggtggcag cggtggctct ggtggtctga gcggccgttc cgataatcat     120
ggcggcggtt ctcagaccgt ggtcacacag agccctcac tgacagtgag ccctggcggg      180
accgtcacac tgacttgtcg cagttcaact ggcgccgtga ctaccagcaa ttacgctaac     240
tgggtccagc agaaaccagg acaggcacca cgaggactga tcggaggaac taataagaga     300
gcaccaggaa cccctgcaag gttctccgga tctctgctgg ggggaaaagc cgctctgaca     360
ctgagcggcg tgcagcctga ggacgaagct gagtactatt gcgcactgtg gtactccaac     420
ctgtgggtgt ttggcggggg aactaagctg accgtcctgg gaggaggagg aagcggagga     480
ggagggagcg gaggaggagg atccgaagtg cagctggtcg agagcggagg aggactggtg     540
cagccaggag gatccctgaa gctgtcttgt gcagccagtg gcttcacctt caacacttac     600
gcaatgaact gggtgcggca ggcacctggg aagggactgg aatgggtcgc ccggatcaga     660
tctaaataca ataactatgc cacctactat gctgacagtg tgaaggatag gttcaccatt     720
tcacgcgacg atagcaaaaa cacagcttat ctgcagatga ataacctgaa gaccgaggat     780
acagcagtgt actattgcgt cagacacggc aatttcggga actcttacgt gagttggttt     840
gcctattggg gacaggggac actggtcacc gtctcctcag gaggtggtgg atcccaagtg     900
accctgagag agtctggccc tgccctcgtg aagcctacc agaccctgac actgacctgc     960
```

-continued

```
accttcagcg gcttcagcct gagcaccagc ggcatgtctg tgggctggat cagacagcct    1020
cctggcaagg ccctggaatg gctggccgac atttggtggg acgacaagaa ggactacaac    1080
cccagcctga agtcccggct gaccatcagc aaggacacca gcaagaacca ggtggtgctg    1140
aaagtgacca acatggaccc cgccgacacc gccacctact actgcgccag atccatgatc    1200
accaactggt acttcgacgt gtggggagcc ggcaccaccg tgacagtgtc atctgctagc    1260
accaagggcc catcggtctt ccccctggca ccctcctcca agagcacctc tgggggcaca    1320
gcggccctgg gctgcctggt caaggactac ttccccgaac cggtgacggt gtcgtggaac    1380
tcaggcgccc tgaccagcgg cgtgcacacc ttcccggctg tcctacagtc ctcaggactc    1440
tactccctca gcagcgtggt gaccgtgccc tccagcagct gggcaccca gacctacatc    1500 tgcaacgtga atcacaagcc cagcaacacc aaggtggaca gaaagttga gcccaaatct    1560 tgtgacaaaa ctcacacatg cccaccgtgc ccagcacctg aactcctggg gggaccgtca    1620
gtcttcctct tccccccaaa acccaaggac accctcatga tctcccggac ccctgaggtc    1680
acatgcgtgg tggtggacgt gagccacgaa gaccctgagg tcaagttcaa ctggtacgtg    1740
gacggcgtgg aggtgcataa tgccaagaca aagccgcggg aggagcagta ccagagcacg    1800
taccgtgtgg tcagcgtcct caccgtcctg caccaggact ggctgaatgg caaggagtac    1860
aagtgcaagg tctccaacaa agccctccca gcccccatcg agaaaaccat ctccaaagcc    1920
aaagggcagc cccgagaacc acaggtgtac accctgcccc catcccggga ggagatgacc    1980
aagaaccagg tcagcctgac ctgcctggtc aaaggcttct atcccagcga catcgccgtg    2040
gagtgggaga gcaatgggca gccggagaac aactacaaga ccacgcctcc cgtgctggac    2100
tccgacggct ccttcttcct ctacagcaag ctcaccgtgg acaagagcag gtggcagcag    2160
gggaacgtct tctcatgctc cgtgatgcat gaggctctgc acaaccacta cacgcagaag    2220
agcctctccc tgtctccggg taaa                                          2244
```

<210> SEQ ID NO 148
<211> LENGTH: 747
<212> TYPE: PRT
<213> ORGANISM: Artificial Sequence
<220> FEATURE:
<223> OTHER INFORMATION: synthetic

<400> SEQUENCE: 148

```
Gln Gly Gln Ser Gly Ser Gly Tyr Leu Trp Gly Cys Glu Trp Asn Cys
1               5                   10                  15

Gly Gly Ile Thr Thr Gly Ser Ser Gly Gly Ser Gly Gly Ser Gly Gly
            20                  25                  30

Leu Ser Gly Arg Ser Asp Asp His Gly Gly Gly Ser Gln Ala Val Val
        35                  40                  45

Thr Gln Glu Pro Ser Leu Thr Val Ser Pro Gly Gly Thr Val Thr Leu
    50                  55                  60

Thr Cys Arg Ser Ser Thr Gly Ala Val Thr Thr Ser Asn Tyr Ala Asn
65                  70                  75                  80

Trp Val Gln Gln Lys Pro Gly Gln Ala Pro Arg Gly Leu Ile Gly Gly
                85                  90                  95

Thr Asn Lys Arg Ala Pro Gly Thr Pro Ala Arg Phe Ser Gly Ser Leu
            100                 105                 110

Ile Gly Gly Lys Ala Ala Leu Thr Leu Ser Gly Ala Gln Pro Glu Asp
        115                 120                 125

Glu Ala Glu Tyr Tyr Cys Ala Leu Trp Tyr Ser Asn Leu Trp Val Phe
```

```
                130                 135                 140
Gly Gly Gly Thr Lys Leu Thr Val Leu Gly Gly Gly Ser Gly Gly
145                 150                 155                 160

Gly Gly Ser Gly Gly Gly Ser Glu Val Gln Leu Val Glu Ser Gly
                165                 170                 175

Gly Gly Leu Val Gln Pro Gly Gly Ser Leu Lys Leu Ser Cys Ala Ala
                180                 185                 190

Ser Gly Phe Thr Phe Ser Thr Tyr Ala Met Asn Trp Val Arg Gln Ala
                195                 200                 205

Ser Gly Lys Gly Leu Glu Trp Val Gly Arg Ile Arg Ser Lys Tyr Asn
210                 215                 220

Asn Tyr Ala Thr Tyr Tyr Ala Asp Ser Val Lys Asp Arg Phe Thr Ile
225                 230                 235                 240

Ser Arg Asp Asp Ser Lys Asn Thr Ala Tyr Leu Gln Met Asn Ser Leu
                245                 250                 255

Lys Thr Glu Asp Thr Ala Val Tyr Tyr Cys Thr Arg His Gly Asn Phe
                260                 265                 270

Gly Asn Ser Tyr Val Ser Trp Phe Ala Tyr Trp Gly Gln Gly Thr Leu
                275                 280                 285

Val Thr Val Ser Ser Gly Gly Gly Ser Gln Val Gln Leu Lys Gln
290                 295                 300

Ser Gly Pro Gly Leu Val Gln Pro Ser Gln Ser Leu Ser Ile Thr Cys
305                 310                 315                 320

Thr Val Ser Gly Phe Ser Leu Thr Asn Tyr Gly Val His Trp Val Arg
                325                 330                 335

Gln Ser Pro Gly Lys Gly Leu Glu Trp Leu Gly Val Ile Trp Ser Gly
                340                 345                 350

Gly Asn Thr Asp Tyr Asn Thr Pro Phe Thr Ser Arg Leu Ser Ile Asn
                355                 360                 365

Lys Asp Asn Ser Lys Ser Gln Val Phe Phe Lys Met Asn Ser Leu Gln
370                 375                 380

Ser Gln Asp Thr Ala Ile Tyr Tyr Cys Ala Arg Ala Leu Thr Tyr Tyr
385                 390                 395                 400

Asp Tyr Glu Phe Ala Tyr Trp Gly Gln Gly Thr Leu Val Thr Val Ser
                405                 410                 415

Ala Ala Ser Thr Lys Gly Pro Ser Val Phe Pro Leu Ala Pro Ser Ser
                420                 425                 430

Lys Ser Thr Ser Gly Gly Thr Ala Ala Leu Gly Cys Leu Val Lys Asp
                435                 440                 445

Tyr Phe Pro Glu Pro Val Thr Val Ser Trp Asn Ser Gly Ala Leu Thr
                450                 455                 460

Ser Gly Val His Thr Phe Pro Ala Val Leu Gln Ser Ser Gly Leu Tyr
465                 470                 475                 480

Ser Leu Ser Ser Val Val Thr Val Pro Ser Ser Ser Leu Gly Thr Gln
                485                 490                 495

Thr Tyr Ile Cys Asn Val Asn His Lys Pro Ser Asn Thr Lys Val Asp
                500                 505                 510

Lys Lys Val Glu Pro Lys Ser Cys Asp Lys Thr His Thr Cys Pro Pro
                515                 520                 525

Cys Pro Ala Pro Glu Phe Glu Gly Gly Pro Ser Val Phe Leu Phe Pro
                530                 535                 540

Pro Lys Pro Lys Asp Thr Leu Met Ile Ser Arg Thr Pro Glu Val Thr
545                 550                 555                 560
```

```
Cys Val Val Asp Val Ser His Glu Asp Pro Glu Val Lys Phe Asn
            565                 570                 575

Trp Tyr Val Asp Gly Val Glu Val His Asn Ala Lys Thr Lys Pro Arg
            580                 585                 590

Glu Glu Gln Tyr Gln Ser Thr Tyr Arg Val Val Ser Val Leu Thr Val
            595                 600                 605

Leu His Gln Asp Trp Leu Asn Gly Lys Glu Tyr Lys Cys Lys Val Ser
            610                 615                 620

Asn Lys Ala Leu Pro Ala Ser Ile Glu Lys Thr Ile Ser Lys Ala Lys
625                 630                 635                 640

Gly Gln Pro Arg Glu Pro Gln Val Tyr Thr Leu Pro Pro Ser Arg Glu
            645                 650                 655

Glu Met Thr Lys Asn Gln Val Ser Leu Thr Cys Leu Val Lys Gly Phe
            660                 665                 670

Tyr Pro Ser Asp Ile Ala Val Glu Trp Glu Ser Asn Gly Gln Pro Glu
            675                 680                 685

Asn Asn Tyr Lys Thr Thr Pro Pro Val Leu Asp Ser Asp Gly Ser Phe
690                 695                 700

Phe Leu Tyr Ser Lys Leu Thr Val Asp Lys Ser Arg Trp Gln Gln Gly
705                 710                 715                 720

Asn Val Phe Ser Cys Ser Val Met His Glu Ala Leu His Asn His Tyr
            725                 730                 735

Thr Gln Lys Ser Leu Ser Leu Ser Pro Gly Lys
            740                 745

<210> SEQ ID NO 149
<211> LENGTH: 14
<212> TYPE: PRT
<213> ORGANISM: Artificial Sequence
<220> FEATURE:
<223> OTHER INFORMATION: synthetic

<400> SEQUENCE: 149

Arg Ser Ser Thr Gly Ala Val Thr Thr Ser Asn Tyr Ala Asn
1               5                   10

<210> SEQ ID NO 150
<211> LENGTH: 249
<212> TYPE: PRT
<213> ORGANISM: Artificial Sequence
<220> FEATURE:
<223> OTHER INFORMATION: synthetic

<400> SEQUENCE: 150

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Gly Thr Pro Ala Arg Phe
        50                  55                  60

Ser Gly Ser Leu Ile Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
            85                  90                  95

Leu Trp Val Phe Gly Gly Gly Thr Lys Leu Thr Val Leu Gly Gly Gly
```

```
                    100                 105                 110
Gly Ser Gly Gly Gly Ser Gly Gly Gly Ser Glu Val Gln Leu
            115                 120                 125
Val Glu Ser Gly Gly Gly Leu Val Gln Pro Gly Gly Ser Leu Arg Leu
        130                 135                 140
Ser Cys Ala Ala Ser Gly Phe Thr Phe Ser Thr Tyr Ala Met Asn Trp
145                 150                 155                 160
Val Arg Gln Ala Pro Gly Lys Gly Leu Glu Trp Val Ala Arg Ile Arg
                165                 170                 175
Ser Lys Tyr Asn Asn Tyr Ala Thr Tyr Tyr Ala Asp Ser Val Lys Asp
            180                 185                 190
Arg Phe Thr Ile Ser Arg Asp Asp Ser Lys Asn Ser Leu Tyr Leu Gln
                195                 200                 205
Met Asn Ser Leu Lys Thr Glu Asp Thr Ala Val Tyr Tyr Cys Val Arg
            210                 215                 220
His Gly Asn Phe Gly Asn Ser Tyr Val Ser Trp Phe Ala Tyr Trp Gly
225                 230                 235                 240
Gln Gly Thr Leu Val Thr Val Ser Ser
                245

<210> SEQ ID NO 151
<211> LENGTH: 2241
<212> TYPE: DNA
<213> ORGANISM: Artificial Sequence
<220> FEATURE:
<223> OTHER INFORMATION: synthetic

<400> SEQUENCE: 151
caaggccagt ctggttctgg ttatctgtgg ggttgcgagt ggaattgcgg agggatcact      60
acaggctcga gcggtggcag cggtggctct ggtggtctga gcggccgttc cgatgatcat     120
ggcggcggat cccagacggt agtgactcag gagccatcat tttctgtctc tcctggaggt     180
actgtgacac tcacatgtag aagctcaact ggtgcagtca ccacttcaaa ttacgcgaat     240
tgggtccagc agaccctgg gcaggctccg agagggttga ttggaggtac taacaaacgg      300
gcaccgggag tgcctgatag gttttccggt tctattctcg gaaacaaggc ggctctcacg     360
atcacgggtg cgcaggccga cgatgaatca gactattact gcgctttgtg gtactcaaac     420
ctgtgggtat tcggaggggg caccaagctg acggtgttgg gtggggggg ctctggggga      480
gggggaagcg gaggtggggg cagcgaggtt cagcttgttg aaagtggtgg cggactcgta     540
caaccgggtg gaagtcttag actctcatgt gcagcatctg gatttacttt ttctacttat     600
gctatgaact gggtaagaca ggcaccgggg aaagggctgg aatgggttgc acgcattcga     660
tctaaataca ataactatgc tacatactac gccgatagtg ttaaggatcg attcactata     720
tctcgggacg acagtaagaa ctcactttac ctgcagatga attccttgaa aactgaggac     780
acggccgttt attattgtgt acggcacggg aatttcggca attcttacgt ttcctggttc     840
gcctattggg ggcaaggtac gctggtcacg gtgtctagcg gaggtggtgg atcccaggtg     900
cagctgaaac agagcggccc gggcctggtg cagccgagcc agagcctgag cattacctgc     960
accgtgagcg gctttagcct gaccaactat ggcgtgcatt gggtgcgcca gagcccgggc    1020
aaaggcctgg aatggctggg cgtgatttgg agcggcggca acaccgatta taacacccg     1080
tttaccagcc gcctgagcat taacaaagat aacagcaaaa gccaggtgtt ttttaaaatg    1140
aacagcctgc aaagccagga taccgcgatt tattattgcg cgcgcgcgct gacctattat    1200
```

```
gattatgaat ttgcgtattg gggccagggc accctggtga ccgtgagcgc ggctagcacc   1260
aagggcccat cggtcttccc cctggcaccc tcctccaaga gcacctctgg ggcacagcg    1320 gccctgggct gcctggtcaa ggactacttc cccgaaccgg tgacggtgtc gtggaactca   1380
ggcgccctga ccagcggcgt gcacaccttc ccggctgtcc tacagtcctc aggactctac   1440
tccctcagca gcgtggtgac cgtgccctcc agcagcttgg gcacccagac ctacatctgc   1500
aacgtgaatc acaagcccag caacaccaag gtggacaaga agttgagcc caaatcttgt    1560 gacaaaactc acacatgccc accgtgccca gcacctgaat ttgaagggg accgtcagtc    1620 ttcctcttcc ccccaaaacc caaggacacc ctcatgatct cccggacccc tgaggtcaca   1680
tgcgtggtgg tggacgtgag ccacgaagac cctgaggtca agttcaactg gtacgtggac   1740
ggcgtggagg tgcataatgc caagacaaag ccgcgggagg agcagtacca gagcacgtac   1800
cgtgtggtca gcgtcctcac cgtcctgcac caggactggc tgaatggcaa ggagtacaag   1860
tgcaaggtct ccaacaaagc cctcccagcc tcaatcgaga aaaccatctc caaagccaaa   1920
gggcagcccc gagaaccaca ggtgtacacc ctgcccccat cccgggagga tgaccaag     1980 aaccaggtca gcctgacctg cctggtcaaa ggcttctatc ccagcgacat cgccgtggag   2040
tgggagagca atgggcagcc ggagaacaac tacaagacca cgcctcccgt gctggactcc   2100
gacggctcct tcttcctcta cagcaagctc accgtggaca gagcaggtg gcagcagggg    2160 aacgtcttct catgctccgt gatgcatgag gctctgcaca accactacac gcagaagagc   2220
ctctccctgt ctccgggtaa a                                              2241

<210> SEQ ID NO 152
<211> LENGTH: 2241
<212> TYPE: DNA
<213> ORGANISM: Artificial Sequence
<220> FEATURE:
<223> OTHER INFORMATION: synthetic

<400> SEQUENCE: 152
caaggccagt ctggatccgg ttatctgtgg ggttgcgagt ggaattgcgg agggatcact     60
acaggctcga gcgtggcag cggtggctct ggtggtctga gcggccgttc cgatgatcat    120
ggcggcggtt ctcaggccgt tgttacacaa gagccttcac ttactgtgtc tccaggaggc   180
actgtgacac ttacgtgccg atcctctacg ggtgccgtga ccacaagcaa ctatgccaac   240
tgggtccagc agaagccagg tcaagcgcct cgaggtctga tcggggcac gaataaacga    300 gctcctggaa ctccggccag attttctggg agtcttattg gtggcaaggc ggcgttgacc   360
ctgagtggag cccaaccgga agacgaggcc gagtactact gcgccttgtg gtattccaat   420
ttgtgggtct tcggaggcgg aacaaagctc acagtactgg gaggtggagg tagcgggggc   480
ggaggctccg ggggaggtgg ttccgaagtc cagcttgttg aatcaggtgg ggcttggta    540 caaccaggtg gttcactgaa gttgtcctgt gcagcgtccg gatttacatt tagtacgtat   600
gctatgaact gggtcaggca ggccagtggt aaaggtctcg aatgggttgg ccggataagg   660
tcaaagtaca ataattacgc aacctactac gcggattccg tgaaagacag gttcactatt   720
tcacgagatg atagcaaaaa tactgcgtat ctccaaatga atagtcttaa aactgaagac   780
actgccgtat attattgcac taggcacggc aactttggta actcttatgt ttcttggttc   840
gcatactggg gacaaggaac tttggtcact gtctcatctg gaggtggtgg atcccaggtg   900
cagctgaaac agagcggccc gggcctggtg cagccgagcc agagcctgag cattacctgc    960
accgtgagcg gctttagcct gaccaactat ggcgtgcatt gggtgcgcca gagcccgggc   1020
```

-continued

```
aaaggcctgg aatggctggg cgtgatttgg agcggcggca acaccgatta taacaccccg    1080
tttaccagcc gcctgagcat taacaaagat aacagcaaaa gccaggtgtt ttttaaaatg    1140
aacagcctgc aaagccagga taccgcgatt tattattgcg cgcgcgcgct gacctattat    1200
gattatgaat ttgcgtattg gggccagggc accctggtga ccgtgagcgc ggctagcacc    1260
aagggcccat cggtcttccc cctggcaccc tcctccaaga gcacctctgg gggcacagcg    1320
gccctgggct gcctggtcaa ggactacttc cccgaaccgg tgacggtgtc gtggaactca    1380
ggcgccctga ccagcggcgt gcacaccttc ccggctgtcc tacagtcctc aggactctac    1440
tccctcagca gcgtggtgac cgtgccctcc agcagcttgg gcacccagac ctacatctgc    1500
aacgtgaatc acaagcccag caacaccaag gtggacaaga agttgagccc aaatcttgt    1560 gacaaaactc acacatgccc accgtgccca gcacctgaat tgaaggggg accgtcagtc    1620 ttcctcttcc ccccaaaacc caaggacacc ctcatgatct cccggacccc tgaggtcaca    1680
tgcgtggtgg tggacgtgag ccacgaagac cctgaggtca agttcaactg gtacgtggac    1740
ggcgtggagg tgcataatgc caagacaaag ccgcgggagg agcagtacca gagcacgtac    1800
cgtgtggtca gcgtcctcac cgtcctgcac caggactggc tgaatggcaa ggagtacaag    1860
tgcaaggtct ccaacaaagc cctcccagcc tcaatcgaga aaaccatctc caaagccaaa    1920
gggcagcccc gagaaccaca ggtgtacacc ctgcccccat cccgggagga gatgaccaag    1980
aaccaggtca gcctgacctg cctggtcaaa ggcttctatc ccagcgacat cgccgtggag    2040
tgggagagca atgggcagcc ggagaacaac tacaagacca cgcctcccgt gctggactcc    2100
gacggctcct tcttcctcta cagcaagctc accgtggaca agagcaggtg gcagcagggg    2160
aacgtcttct catgctccgt gatgcatgag gctctgcaca accactacac gcagaagagc    2220
ctctccctgt ctccgggtaa a                                              2241
```

<210> SEQ ID NO 153
<211> LENGTH: 742
<212> TYPE: PRT
<213> ORGANISM: Artificial Sequence
<220> FEATURE:
<223> OTHER INFORMATION: synthetic

<400> SEQUENCE: 153

```
Met Met Tyr Cys Gly Gly Asn Glu Val Leu Cys Gly Pro Arg Val Gly
1               5                   10                  15

Ser Ser Gly Gly Ser Gly Gly Ser Gly Gly Leu Ser Gly Arg Ser Asp
            20                  25                  30

Asn His Gly Gly Gly Ser Gln Thr Val Val Thr Gln Glu Pro Ser Leu
        35                  40                  45

Thr Val Ser Pro Gly Gly Thr Val Thr Leu Thr Cys Arg Ser Ser Thr
    50                  55                  60

Gly Ala Val Thr Thr Ser Asn Tyr Ala Asn Trp Val Gln Gln Lys Pro
65                  70                  75                  80

Gly Gln Ala Pro Arg Gly Leu Ile Gly Gly Thr Asn Lys Arg Ala Pro
                85                  90                  95

Gly Thr Pro Ala Arg Phe Ser Gly Ser Leu Leu Gly Gly Lys Ala Ala
            100                 105                 110

Leu Thr Leu Ser Gly Val Gln Pro Glu Asp Glu Ala Glu Tyr Tyr Cys
        115                 120                 125

Ala Leu Trp Tyr Ser Asn Leu Trp Val Phe Gly Gly Gly Thr Lys Leu
    130                 135                 140
```

```
Thr Val Leu Gly Gly Gly Ser Gly Gly Gly Ser Gly Gly
145                 150                 155             160

Gly Ser Glu Val Gln Leu Val Glu Ser Gly Gly Leu Val Gln Pro
            165                 170                 175

Gly Gly Ser Leu Lys Leu Ser Cys Ala Ala Ser Gly Phe Thr Phe Asn
        180                 185                 190

Thr Tyr Ala Met Asn Trp Val Arg Gln Ala Pro Gly Lys Gly Leu Glu
        195                 200                 205

Trp Val Ala Arg Ile Arg Ser Lys Tyr Asn Asn Tyr Ala Thr Tyr Tyr
210                 215                 220

Ala Asp Ser Val Lys Asp Arg Phe Thr Ile Ser Arg Asp Asp Ser Lys
225                 230                 235                 240

Asn Thr Ala Tyr Leu Gln Met Asn Asn Leu Lys Thr Glu Asp Thr Ala
            245                 250                 255

Val Tyr Tyr Cys Val Arg His Gly Asn Phe Gly Asn Ser Tyr Val Ser
            260                 265                 270

Trp Phe Ala Tyr Trp Gly Gln Gly Thr Leu Val Thr Val Ser Ser Gly
        275                 280                 285

Gly Gly Gly Ser Gln Val Thr Leu Arg Glu Ser Gly Pro Ala Leu Val
        290                 295                 300

Lys Pro Thr Gln Thr Leu Thr Leu Thr Cys Thr Phe Ser Gly Phe Ser
305                 310                 315                 320

Leu Ser Thr Ser Gly Met Ser Val Gly Trp Ile Arg Gln Pro Pro Gly
            325                 330                 335

Lys Ala Leu Glu Trp Leu Ala Asp Ile Trp Trp Asp Asp Lys Lys Asp
            340                 345                 350

Tyr Asn Pro Ser Leu Lys Ser Arg Leu Thr Ile Ser Lys Asp Thr Ser
        355                 360                 365

Lys Asn Gln Val Val Leu Lys Val Thr Asn Met Asp Pro Ala Asp Thr
        370                 375                 380

Ala Thr Tyr Tyr Cys Ala Arg Ser Met Ile Thr Asn Trp Tyr Phe Asp
385                 390                 395                 400

Val Trp Gly Ala Gly Thr Thr Val Thr Val Ser Ser Ala Ser Thr Lys
            405                 410                 415

Gly Pro Ser Val Phe Pro Leu Ala Pro Ser Ser Lys Ser Thr Ser Gly
            420                 425                 430

Gly Thr Ala Ala Leu Gly Cys Leu Val Lys Asp Tyr Phe Pro Glu Pro
        435                 440                 445

Val Thr Val Ser Trp Asn Ser Gly Ala Leu Thr Ser Gly Val His Thr
        450                 455                 460

Phe Pro Ala Val Leu Gln Ser Ser Gly Leu Tyr Ser Leu Ser Ser Val
465                 470                 475                 480

Val Thr Val Pro Ser Ser Ser Leu Gly Thr Gln Thr Tyr Ile Cys Asn
            485                 490                 495

Val Asn His Lys Pro Ser Asn Thr Lys Val Asp Lys Lys Val Glu Pro
            500                 505                 510

Lys Ser Cys Asp Lys Thr His Thr Cys Pro Pro Cys Pro Ala Pro Glu
        515                 520                 525

Leu Leu Gly Gly Pro Ser Val Phe Leu Phe Pro Pro Lys Pro Lys Asp
        530                 535                 540

Thr Leu Met Ile Ser Arg Thr Pro Glu Val Thr Cys Val Val Val Asp
545                 550                 555                 560
```

```
Val Ser His Glu Asp Pro Glu Val Lys Phe Asn Trp Tyr Val Asp Gly
            565                 570                 575

Val Glu Val His Asn Ala Lys Thr Lys Pro Arg Glu Glu Gln Tyr Gln
        580                 585                 590

Ser Thr Tyr Arg Val Val Ser Val Leu Thr Val Leu His Gln Asp Trp
            595                 600                 605

Leu Asn Gly Lys Glu Tyr Lys Cys Lys Val Ser Asn Lys Ala Leu Pro
        610                 615                 620

Ala Pro Ile Glu Lys Thr Ile Ser Lys Ala Lys Gly Gln Pro Arg Glu
625                 630                 635                 640

Pro Gln Val Tyr Thr Leu Pro Pro Ser Arg Glu Glu Met Thr Lys Asn
            645                 650                 655

Gln Val Ser Leu Thr Cys Leu Val Lys Gly Phe Tyr Pro Ser Asp Ile
            660                 665                 670

Ala Val Glu Trp Glu Ser Asn Gly Gln Pro Glu Asn Asn Tyr Lys Thr
            675                 680                 685

Thr Pro Pro Val Leu Asp Ser Asp Gly Ser Phe Phe Leu Tyr Ser Lys
            690                 695                 700

Leu Thr Val Asp Lys Ser Arg Trp Gln Gln Gly Asn Val Phe Ser Cys
705                 710                 715                 720

Ser Val Met His Glu Ala Leu His Asn His Tyr Thr Gln Lys Ser Leu
            725                 730                 735

Ser Leu Ser Pro Gly Lys
            740

<210> SEQ ID NO 154
<211> LENGTH: 330
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (180)..(180)
<223> OTHER INFORMATION: Xaa may be any amino acid

<400> SEQUENCE: 154

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Xaa Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 155
<211> LENGTH: 330
<212> TYPE: PRT
<213> ORGANISM: Artificial Sequence
<220> FEATURE:
<223> OTHER INFORMATION: synthetic

<400> SEQUENCE: 155

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 156
<211> LENGTH: 330
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (117)..(117)
<223> OTHER INFORMATION: Xaa can be any amino acid

<400> SEQUENCE: 156

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Xaa Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
```

```
                195                 200                 205
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 157
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala

<400> SEQUENCE: 157

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 158
<211> LENGTH: 449
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (119)..(119)
<223> OTHER INFORMATION: Xaa may be Ser or Ala
<220> FEATURE:
<221> NAME/KEY: MISC_FEATURE
<222> LOCATION: (237)..(237)
<223> OTHER INFORMATION: Xaa may be any amino acid

<400> SEQUENCE: 158

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80
```

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Xaa Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Xaa Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 159
<211> LENGTH: 330
<212> TYPE: PRT
<213> ORGANISM: Artificial Sequence
<220> FEATURE:
<223> OTHER INFORMATION: synthetic

<400> SEQUENCE: 159

| Ala | Ser | Thr | Lys | Gly | Pro | Ser | Val | Phe | Pro | Leu | Ala | Pro | Ser | Ser | Lys |
|---|---|---|---|---|---|---|---|---|---|---|---|---|---|---|---|
| 1 | | | | 5 | | | | | 10 | | | | | 15 | |

| Ser | Thr | Ser | Gly | Gly | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | 35 | | | | | 40 | | | | | 45 | | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| | 50 | | | | | 55 | | | | | 60 | | | | |

| Leu | Ser | Ser | Val | Val | Thr | Val | Pro | Ser | Ser | Ser | Leu | Gly | Thr | Gln | Thr |
|---|---|---|---|---|---|---|---|---|---|---|---|---|---|---|---|
| 65 | | | | | 70 | | | | | 75 | | | | | 80 |

| Tyr | Ile | Cys | Asn | Val | Asn | His | Lys | Pro | Ser | Asn | Thr | Lys | Val | Asp | Lys |
|---|---|---|---|---|---|---|---|---|---|---|---|---|---|---|---|
| | | | | 85 | | | | | 90 | | | | | 95 | |

| Lys | Val | Glu | Pro | Lys | Ser | Cys | Asp | Lys | Thr | His | Thr | Cys | Pro | Pro | Cys |
|---|---|---|---|---|---|---|---|---|---|---|---|---|---|---|---|
| | | | 100 | | | | | 105 | | | | | 110 | | |

| Pro | Ala | Pro | Glu | Leu | Glu | Gly | Gly | Pro | Ser | Val | Phe | Leu | Phe | Pro | Pro |
|---|---|---|---|---|---|---|---|---|---|---|---|---|---|---|---|
| | | 115 | | | | | 120 | | | | | 125 | | | |

| Lys | Pro | Lys | Asp | Thr | Leu | Met | Ile | Ser | Arg | Thr | Pro | Glu | Val | Thr | Cys |
|---|---|---|---|---|---|---|---|---|---|---|---|---|---|---|---|
| 130 | | | | | 135 | | | | | 140 | | | | | |

| Val | Val | Val | Asp | Val | Ser | His | Glu | Asp | Pro | Glu | Val | Lys | Phe | Asn | Trp |
|---|---|---|---|---|---|---|---|---|---|---|---|---|---|---|---|
| 145 | | | | | 150 | | | | | 155 | | | | | 160 |

| Tyr | Val | Asp | Gly | Val | Glu | Val | His | Asn | Ala | Lys | Thr | Lys | Pro | Arg | Glu |
|---|---|---|---|---|---|---|---|---|---|---|---|---|---|---|---|
| | | | | 165 | | | | | 170 | | | | | 175 | |

| Glu | Gln | Tyr | Asn | Ser | Thr | Tyr | Arg | Val | Val | Ser | Val | Leu | Thr | Val | Leu |
|---|---|---|---|---|---|---|---|---|---|---|---|---|---|---|---|
| | | | 180 | | | | | 185 | | | | | 190 | | |

| His | Gln | Asp | Trp | Leu | Asn | Gly | Lys | Glu | Tyr | Lys | Cys | Lys | Val | Ser | Asn |
|---|---|---|---|---|---|---|---|---|---|---|---|---|---|---|---|
| | | 195 | | | | | 200 | | | | | 205 | | | |

| Lys | Ala | Leu | Pro | Ala | Pro | Ile | Glu | Lys | Thr | Ile | Ser | Lys | Ala | Lys | Gly |
|---|---|---|---|---|---|---|---|---|---|---|---|---|---|---|---|
| | 210 | | | | | 215 | | | | | 220 | | | | |

| Gln | Pro | Arg | Glu | Pro | Gln | Val | Tyr | Thr | Leu | Pro | Pro | Ser | Arg | Glu | Glu |
|---|---|---|---|---|---|---|---|---|---|---|---|---|---|---|---|
| 225 | | | | | 230 | | | | | 235 | | | | | 240 |

| Met | Thr | Lys | Asn | Gln | Val | Ser | Leu | Thr | Cys | Leu | Val | Lys | Gly | Phe | Tyr |
|---|---|---|---|---|---|---|---|---|---|---|---|---|---|---|---|
| | | | | 245 | | | | | 250 | | | | | 255 | |

| Pro | Ser | Asp | Ile | Ala | Val | Glu | Trp | Glu | Ser | Asn | Gly | Gln | Pro | Glu | Asn |
|---|---|---|---|---|---|---|---|---|---|---|---|---|---|---|---|
| | | | 260 | | | | | 265 | | | | | 270 | | |

| Asn | Tyr | Lys | Thr | Thr | Pro | Pro | Val | Leu | Asp | Ser | Asp | Gly | Ser | Phe | Phe |
|---|---|---|---|---|---|---|---|---|---|---|---|---|---|---|---|
| | | 275 | | | | | 280 | | | | | 285 | | | |

| Leu | Tyr | Ser | Lys | Leu | Thr | Val | Asp | Lys | Ser | Arg | Trp | Gln | Gln | Gly | Asn |
|---|---|---|---|---|---|---|---|---|---|---|---|---|---|---|---|
| | 290 | | | | | 295 | | | | | 300 | | | | |

| Val | Phe | Ser | Cys | Ser | Val | Met | His | Glu | Ala | Leu | His | Asn | His | Tyr | Thr |
|---|---|---|---|---|---|---|---|---|---|---|---|---|---|---|---|
| 305 | | | | | 310 | | | | | 315 | | | | | 320 |

| Gln | Lys | Ser | Leu | Ser | Leu | Ser | Pro | Gly | Lys |
|---|---|---|---|---|---|---|---|---|---|
| | | | | 325 | | | | | 330 |

<210> SEQ ID NO 160
<211> LENGTH: 330
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (214)..(214)
<223> OTHER INFORMATION: Xaa can be any amino acid

<400> SEQUENCE: 160

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Xaa Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 161
<211> LENGTH: 330
<212> TYPE: PRT
<213> ORGANISM: Artificial Sequence
<220> FEATURE:
<223> OTHER INFORMATION: synthetic

<400> SEQUENCE: 161

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Ser Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 162
<211> LENGTH: 330
<212> TYPE: PRT
<213> ORGANISM: Artificial Sequence
<220> FEATURE:
<223> OTHER INFORMATION: synthetic

<400> SEQUENCE: 162

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Ser Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 163
<211> LENGTH: 330
<212> TYPE: PRT
<213> ORGANISM: Artificial Sequence
<220> FEATURE:
<223> OTHER INFORMATION: synthetic

<400> SEQUENCE: 163

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 164
<211> LENGTH: 2133
<212> TYPE: DNA
<213> ORGANISM: Artificial Sequence
<220> FEATURE:
<223> OTHER INFORMATION: synthetic

<400> SEQUENCE: 164
tccgataatc atggcggcgg ttctcaaact gtagtaactc aagaaccaag cttctccgtc    60
tcccctgggg gaacagtcac acttacctgc cgaagtagta caggtgctgt tacgaccagt   120
aactatgcca attgggtaca acaaacgcct ggtcaggctc cgcgcggatt gataggaggc   180
acgaataaac gggcacccgg tgtcccggac agattcagcg gaagcatact cggtaataag   240
gcagctctta ctatcactgg ggcccaagct gatgatgaaa gtgattatta ttgtgcgctc   300
tggtacagca acctctgggt gtttggggt ggcacgaaac ttactgtctt gggcggcggc    360
ggatcagggg gaggtggctc tggaggagga ggctcagaag tccaactggt cgaatccggg   420
ggagggctcg tacagccggg tgggtccctc aaactctctt gtgcggcctc agggtttacc   480
ttcagtacat acgcgatgaa ttgggtccgg caggccagtg ggaaagggct cgaatgggta   540
ggacgaatcc gatcaaaata caacaactac gctacttatt acgctgattc cgtgaaggac   600
agattccaca tatcccgcga cgatagcaag aatacggcat atcttcagat gaattctctt   660
aaaactgagg ataccgctgt gtattactgc acaagacatg gtaatttggg aaactcatat   720

```
gtctcttggt tcgcttattg gggacagggc acgttggtta ccgtgtctag cggaggtggt    780
ggatcccagg tgcagctgaa acagagcggc ccgggcctgg tgcagccgag ccagagcctg    840
agcattacct gcaccgtgag cggctttagc ctgaccaact atggcgtgca ttgggtgcgc    900
cagagcccgg gcaaaggcct ggaatggctg gcgtgatttt ggagcggcgg caacaccgat    960
tataacaccc cgtttaccag ccgcctgagc attaacaaag ataacagcaa agccaggtg    1020
ttttttaaaa tgaacagcct gcaaagccag gataccgcga tttattattg cgcgcgcgcg   1080
ctgacctatt atgattatga atttgcgtat tggggccagg gcaccctggt gaccgtgagc   1140
gcggctagca ccaaggggcc catcggtctt ccccctggca cctcctccaa gagcacctct   1200
gggggcacag cggccctggg ctgcctggtc aaggactact cccccgaacc ggtgacggtg   1260
tcgtggaact caggcgccct gaccagcggc gtgcacacct tcccggctgt cctacagtcc   1320
tcaggactct actccctcag cagcgtggtg accgtgccct ccagcagctt gggcacccag   1380
acctacatct gcaacgtgaa tcacaagccc agcaacacca aggtggacaa gaaagttgag   1440
cccaaatctt gtgacaaaac tcacacatgc ccaccgtgcc cagcacctga atttgaaggg   1500
ggaccgtcag tcttcctctt ccccccaaaa cccaaggaca ccctcatgat ctcccggacc   1560
cctgaggtca catgcgtggt ggtggacgtg agccacgaag accctgaggt caagttcaac   1620
tggtacgtgg acggcgtgga ggtgcataat gccaagacaa agccgcggga ggagcagtac   1680
cagagcacgt accgtgtggt cagcgtcctc accgtcctgc accaggactg gctgaatggc   1740
aaggagtaca agtgcaaggt ctccaacaaa gccctcccag cctcaatcga gaaaaccatc   1800
tccaaagcca agggcagccc cgagaaccca ggtgtaca ccctgccccc atcccgggag   1860
gagatgacca agaaccaggt cagcctgacc tgcctggtca aaggcttcta tcccagcgac   1920
atcgccgtgg agtgggagag caatgggcag ccggagaaca actacaagac cacgcctccc   1980
gtgctggact ccgacggctc cttcttcctc tacagcaagc tcaccgtgga caagagcagg   2040
tggcagcagg ggaacgtctt ctcatgctcc gtgatgcatg aggctctgca caaccactac   2100
acgcagaaga gcctctccct gtctccgggt aaa                                2133
```

<210> SEQ ID NO 165
<211> LENGTH: 711
<212> TYPE: PRT
<213> ORGANISM: Artificial Sequence
<220> FEATURE:
<223> OTHER INFORMATION: synthetic

<400> SEQUENCE: 165

Ser Asp Asn His Gly Gly Gly Ser Gln Thr Val Val Thr Gln Glu Pro
1               5                   10                  15

Ser Phe Ser Val Ser Pro Gly Gly Thr Val Thr Leu Thr Cys Arg Ser
            20                  25                  30

Ser Thr Gly Ala Val Thr Thr Ser Asn Tyr Ala Asn Trp Val Gln Gln
        35                  40                  45

Thr Pro Gly Gln Ala Pro Arg Gly Leu Ile Gly Gly Thr Asn Lys Arg
    50                  55                  60

Ala Pro Gly Val Pro Asp Arg Phe Ser Gly Ser Ile Leu Gly Asn Lys
65                  70                  75                  80

Ala Ala Leu Thr Ile Thr Gly Ala Gln Ala Asp Asp Glu Ser Asp Tyr
                85                  90                  95

Tyr Cys Ala Leu Trp Tyr Ser Asn Leu Trp Val Phe Gly Gly Gly Thr
            100                 105                 110

-continued

```
Lys Leu Thr Val Leu Gly Gly Gly Ser Gly Gly Gly Ser Gly
            115                 120                 125
Gly Gly Gly Ser Glu Val Gln Leu Val Glu Ser Gly Gly Leu Val
        130                 135                 140
Gln Pro Gly Gly Ser Leu Lys Leu Ser Cys Ala Ala Ser Gly Phe Thr
145                 150                 155                 160
Phe Ser Thr Tyr Ala Met Asn Trp Val Arg Gln Ala Ser Gly Lys Gly
                165                 170                 175
Leu Glu Trp Val Gly Arg Ile Arg Ser Lys Tyr Asn Asn Tyr Ala Thr
            180                 185                 190
Tyr Tyr Ala Asp Ser Val Lys Asp Arg Phe Thr Ile Ser Arg Asp Asp
        195                 200                 205
Ser Lys Asn Thr Ala Tyr Leu Gln Met Asn Ser Leu Lys Thr Glu Asp
210                 215                 220
Thr Ala Val Tyr Tyr Cys Thr Arg His Gly Asn Phe Gly Asn Ser Tyr
225                 230                 235                 240
Val Ser Trp Phe Ala Tyr Trp Gly Gln Gly Thr Leu Val Thr Val Ser
                245                 250                 255
Ser Gly Gly Gly Gly Ser Gln Val Gln Leu Lys Gln Ser Gly Pro Gly
            260                 265                 270
Leu Val Gln Pro Ser Gln Ser Leu Ser Ile Thr Cys Thr Val Ser Gly
        275                 280                 285
Phe Ser Leu Thr Asn Tyr Gly Val His Trp Val Arg Gln Ser Pro Gly
290                 295                 300
Lys Gly Leu Glu Trp Leu Gly Val Ile Trp Ser Gly Gly Asn Thr Asp
305                 310                 315                 320
Tyr Asn Thr Pro Phe Thr Ser Arg Leu Ser Ile Asn Lys Asp Asn Ser
                325                 330                 335
Lys Ser Gln Val Phe Phe Lys Met Asn Ser Leu Gln Ser Gln Asp Thr
            340                 345                 350
Ala Ile Tyr Tyr Cys Ala Arg Ala Leu Thr Tyr Tyr Asp Tyr Glu Phe
        355                 360                 365
Ala Tyr Trp Gly Gln Gly Thr Leu Val Thr Val Ser Ala Ala Ser Thr
370                 375                 380
Lys Gly Pro Ser Val Phe Pro Leu Ala Pro Ser Ser Lys Ser Thr Ser
385                 390                 395                 400
Gly Gly Thr Ala Ala Leu Gly Cys Leu Val Lys Asp Tyr Phe Pro Glu
                405                 410                 415
Pro Val Thr Val Ser Trp Asn Ser Gly Ala Leu Thr Ser Gly Val His
            420                 425                 430
Thr Phe Pro Ala Val Leu Gln Ser Ser Gly Leu Tyr Ser Leu Ser Ser
        435                 440                 445
Val Val Thr Val Pro Ser Ser Ser Leu Gly Thr Gln Thr Tyr Ile Cys
450                 455                 460
Asn Val Asn His Lys Pro Ser Asn Thr Lys Val Asp Lys Lys Val Glu
465                 470                 475                 480
Pro Lys Ser Cys Asp Lys Thr His Thr Cys Pro Pro Cys Pro Ala Pro
                485                 490                 495
Glu Phe Glu Gly Gly Pro Ser Val Phe Leu Phe Pro Pro Lys Pro Lys
            500                 505                 510
Asp Thr Leu Met Ile Ser Arg Thr Pro Glu Val Thr Cys Val Val Val
        515                 520                 525
```

Asp Val Ser His Glu Asp Pro Glu Val Lys Phe Asn Trp Tyr Val Asp
                530                 535                 540

Gly Val Glu Val His Asn Ala Lys Thr Lys Pro Arg Glu Glu Gln Tyr
545                 550                 555                 560

Gln Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
                580                 585                 590

Pro Ala Ser Ile Glu Lys Thr Ile Ser Lys Ala Lys Gly Gln Pro Arg
                595                 600                 605

Glu Pro Gln Val Tyr Thr Leu Pro Pro Ser Arg Glu Glu Met Thr Lys
610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
                660                 665                 670

Lys Leu Thr Val Asp Lys Ser Arg Trp Gln Gln Gly Asn Val Phe Ser
                675                 680                 685

Cys Ser Val Met His Glu Ala Leu His Asn His Tyr Thr Gln Lys Ser
690                 695                 700

Leu Ser Leu Ser Pro Gly Lys
705                 710

<210> SEQ ID NO 166
<211> LENGTH: 669
<212> TYPE: DNA
<213> ORGANISM: Artificial Sequence
<220> FEATURE:
<223> OTHER INFORMATION: synthetic

<400> SEQUENCE: 166
tccgataatc atggcagtag cggtacccag atcttgctga cccagagccc ggtgattctg      60
agcgtgagcc cgggcgaacg tgtgagcttt agctgccgcg cgagccagag cattggcacc     120
aacattcatt ggtatcagca gcgcaccaac ggcagcccgc gcctgctgat taaatatgcg     180
agcgaaagca ttagcggcat tccgagccgc tttagcggca gcggcagcgg caccgatttt     240
accctgagca ttaacagcgt ggaaagcgaa gatattgcgg attattattg ccagcagaac     300
aacaactggc cgaccacctt tggcgcgggc accaaactgg aactgaaacg tacggtggct     360
gcaccatctg tcttcatctt cccgccatct gatgagcagt tgaaatctgg aactgcctct     420
gttgtgtgcc tgctgaataa cttctatccc agagaggcca agtacagtg gaaggtggat      480 aacgccctcc aatcgggtaa ctcccaggag agtgtcacag agcaggacag caaggacagc     540
acctacagcc tcagcagcac cctgacgctg agcaaagcag actacgagaa acacaaagtc     600
tacgcctgcg aagtcaccca tcagggcctg agctcgcccg tcacaaagag cttcaacagg     660
ggagagtgt                                                             669

<210> SEQ ID NO 167
<211> LENGTH: 223
<212> TYPE: PRT
<213> ORGANISM: Artificial Sequence
<220> FEATURE:
<223> OTHER INFORMATION: synthetic

<400> SEQUENCE: 167

```
Ser Asp Asn His Gly Ser Ser Gly Thr Gln Ile Leu Leu Thr Gln Ser
1               5                   10                  15

Pro Val Ile Leu Ser Val Ser Pro Gly Glu Arg Val Ser Phe Ser Cys
            20                  25                  30

Arg Ala Ser Gln Ser Ile Gly Thr Asn Ile His Trp Tyr Gln Gln Arg
        35                  40                  45

Thr Asn Gly Ser Pro Arg Leu Leu Ile Lys Tyr Ala Ser Glu Ser Ile
    50                  55                  60

Ser Gly Ile Pro Ser Arg Phe Ser Gly Ser Gly Ser Gly Thr Asp Phe
65                  70                  75                  80

Thr Leu Ser Ile Asn Ser Val Glu Ser Glu Asp Ile Ala Asp Tyr Tyr
                85                  90                  95

Cys Gln Gln Asn Asn Asn Trp Pro Thr Thr Phe Gly Ala Gly Thr Lys
            100                 105                 110

Leu Glu Leu Lys Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
210                 215                 220
```

<210> SEQ ID NO 168
<211> LENGTH: 2256
<212> TYPE: DNA
<213> ORGANISM: Artificial Sequence
<220> FEATURE:
<223> OTHER INFORMATION: synthetic

<400> SEQUENCE: 168

```
caaggccagt ctggatccgg ttatctgtgg ggttgcgagt ggaattgcgg agggatcact      60
acaggctcga gcggtggcag cggtggctct ggtggtatat cgagtggatt gctgtctggc     120
agatctgacc aacacggcgg cggttctcaa actgtagtaa ctcaagaacc aagcttctcc     180
gtctcccctg ggggaacagt cacacttacc tgccgaagta gtacaggtgc tgttacgacc     240
agtaactatg ccaattgggt acaacaaacg cctggtcagg ctccgcgcgg attgatagga     300
ggcacgaata acgggcaccc cggtgtcccg gacagattca gcggaagcat actcggtaat     360
aaggcagctc ttactatcac tggggcccaa gctgatgatg aaagtgatta ttattgtgcg     420
ctctggtaca gcaacctctg ggtgtttggg ggtggcacga acttactgtc ttgggcggc     480 ggcggatcag ggggaggtgg ctctggagga ggaggctcag aagtccaact ggtcgaatcc     540
gggggagggc tcgtacagcc gggtgggtcc ctcaaactct cttgtgcggc ctcagggttt     600
accttcagta catacgcgat gaattgggtc cggcaggcca gtgggaaagg ctcgaatgg     660 gtaggacgaa tccgatcaaa atacaacaac tacgctactt attacgctga ttccgtgaag     720
gacagattca caatatcccg cgacgatagc aagaatacgg catatcttca gatgaattct     780
```

```
cttaaaactg aggataccgc tgtgtattac tgcacaagac atggtaattt tggaaactca    840
tatgtctctt ggttcgctta ttggggacag ggcacgttgg ttaccgtgtc tagcggaggt    900
ggtggatccc aggtgcagct gaaacagagc ggcccgggcc tggtgcagcc gagccagagc    960
ctgagcatta cctgcaccgt gagcggcttt agcctgacca actatggcgt gcattgggtg   1020
cgccagagcc cgggcaaagg cctggaatgg ctgggcgtga tttggagcgg cggcaacacc   1080
gattataaca ccccgtttac cagccgcctg agcattaaca agataacag caaaagccag    1140
gtgttttta aaatgaacag cctgcaaagc caggataccg cgatttatta ttgcgcgcgc   1200
gcgctgacct attatgatta tgaatttgcg tattggggcc agggcaccct ggtgaccgtg   1260
agcgcggcta gcaccaaggg cccatcggtc ttccccctgg cacctcctc caagagcacc   1320
tctgggggca gcgcggccct gggctgcctg gtcaaggact acttccccga accggtgacg   1380
gtgtcgtgga actcaggcgc cctgaccagc ggcgtgcaca ccttcccggc tgtcctacag   1440
tcctcaggac tctactccct cagcagcgtg gtgaccgtgc cctccagcag cttgggcacc   1500
cagacctaca tctgcaacgt gaatcacaag cccagcaaca ccaaggtgga caagaaagtt   1560
gagcccaaat cttgtgacaa aactcacaca tgcccaccgt gcccagcacc tgaatttgaa   1620
gggggaccgt cagtcttcct cttccccca aacccaagg acaccctcat gatctcccgg    1680
accctgagg tcacatgcgt ggtggtggac gtgagccacg aagaccctga ggtcaagttc    1740
aactggtacg tggacggcgt ggaggtgcat aatgccaaga caaagccgcg ggaggagcag   1800
taccagagca cgtaccgtgt ggtcagcgtc ctcaccgtcc tgcaccagga ctggctgaat   1860
ggcaaggagt acaagtgcaa ggtctccaac aaagccctcc cagcctcaat cgagaaaacc   1920
atctccaaag ccaaagggca gccccgagaa ccacaggtgt acaccctgcc cccatcccgg   1980
gaggagatga ccaagaacca ggtcagcctg acctgcctgg tcaaaggctt ctatcccagc   2040
gacatcgccg tggagtggga gagcaatggg cagccggaga caactacaa gaccacgcct    2100
cccgtgctgg actccgacgg ctccttcttc ctctacagca agctcaccgt ggacaagagc   2160
aggtggcagc aggggaacgt cttctcatgc tccgtgatgc atgaggctct gcacaaccac   2220
tacacgcaga agagcctctc cctgtctccg ggtaaa                              2256
```

<210> SEQ ID NO 169
<211> LENGTH: 752
<212> TYPE: PRT
<213> ORGANISM: Artificial Sequence
<220> FEATURE:
<223> OTHER INFORMATION: synthetic

<400> SEQUENCE: 169

Gln Gly Gln Ser Gly Ser Gly Tyr Leu Trp Gly Cys Glu Trp Asn Cys
1               5                   10                  15

Gly Gly Ile Thr Thr Gly Ser Ser Gly Gly Ser Gly Gly Ser Gly Gly
                20                  25                  30

Ile Ser Ser Gly Leu Leu Ser Gly Arg Ser Asp Gln His Gly Gly Gly
            35                  40                  45

Ser Gln Thr Val Val Thr Gln Glu Pro Ser Phe Ser Val Ser Pro Gly
        50                  55                  60

Gly Thr Val Thr Leu Thr Cys Arg Ser Ser Thr Gly Ala Val Thr Thr
65                  70                  75                  80

Ser Asn Tyr Ala Asn Trp Val Gln Gln Thr Pro Gly Gln Ala Pro Arg
                85                  90                  95

Gly Leu Ile Gly Gly Thr Asn Lys Arg Ala Pro Gly Val Pro Asp Arg

```
                100                 105                 110
Phe Ser Gly Ser Ile Leu Gly Asn Lys Ala Ala Leu Thr Ile Thr Gly
            115                 120                 125
Ala Gln Ala Asp Asp Glu Ser Asp Tyr Tyr Cys Ala Leu Trp Tyr Ser
        130                 135                 140
Asn Leu Trp Val Phe Gly Gly Gly Thr Lys Leu Thr Val Leu Gly Gly
145                 150                 155                 160
Gly Gly Ser Gly Gly Gly Gly Ser Gly Gly Gly Gly Ser Glu Val Gln
                165                 170                 175
Leu Val Glu Ser Gly Gly Gly Leu Val Gln Pro Gly Gly Ser Leu Lys
            180                 185                 190
Leu Ser Cys Ala Ala Ser Gly Phe Thr Phe Ser Thr Tyr Ala Met Asn
        195                 200                 205
Trp Val Arg Gln Ala Ser Gly Lys Gly Leu Glu Trp Val Gly Arg Ile
    210                 215                 220
Arg Ser Lys Tyr Asn Asn Tyr Ala Thr Tyr Tyr Ala Asp Ser Val Lys
225                 230                 235                 240
Asp Arg Phe Thr Ile Ser Arg Asp Asp Ser Lys Asn Thr Ala Tyr Leu
                245                 250                 255
Gln Met Asn Ser Leu Lys Thr Glu Asp Thr Ala Val Tyr Tyr Cys Thr
            260                 265                 270
Arg His Gly Asn Phe Gly Asn Ser Tyr Val Ser Trp Phe Ala Tyr Trp
        275                 280                 285
Gly Gln Gly Thr Leu Val Thr Val Ser Ser Gly Gly Gly Gly Ser Gln
    290                 295                 300
Val Gln Leu Lys Gln Ser Gly Pro Gly Leu Val Gln Pro Ser Gln Ser
305                 310                 315                 320
Leu Ser Ile Thr Cys Thr Val Ser Gly Phe Ser Leu Thr Asn Tyr Gly
                325                 330                 335
Val His Trp Val Arg Gln Ser Pro Gly Lys Gly Leu Glu Trp Leu Gly
            340                 345                 350
Val Ile Trp Ser Gly Gly Asn Thr Asp Tyr Asn Thr Pro Phe Thr Ser
        355                 360                 365
Arg Leu Ser Ile Asn Lys Asp Asn Ser Lys Ser Gln Val Phe Phe Lys
    370                 375                 380
Met Asn Ser Leu Gln Ser Gln Asp Thr Ala Ile Tyr Tyr Cys Ala Arg
385                 390                 395                 400
Ala Leu Thr Tyr Tyr Asp Tyr Glu Phe Ala Tyr Trp Gly Gln Gly Thr
                405                 410                 415
Leu Val Thr Val Ser Ala Ala Ser Thr Lys Gly Pro Ser Val Phe Pro
            420                 425                 430
Leu Ala Pro Ser Ser Lys Ser Thr Ser Gly Gly Thr Ala Ala Leu Gly
        435                 440                 445
Cys Leu Val Lys Asp Tyr Phe Pro Glu Pro Val Thr Val Ser Trp Asn
    450                 455                 460
Ser Gly Ala Leu Thr Ser Gly Val His Thr Phe Pro Ala Val Leu Gln
465                 470                 475                 480
Ser Ser Gly Leu Tyr Ser Leu Ser Val Val Thr Val Pro Ser Ser
                485                 490                 495
Ser Leu Gly Thr Gln Thr Tyr Ile Cys Asn Val Asn His Lys Pro Ser
            500                 505                 510
Asn Thr Lys Val Asp Lys Lys Val Glu Pro Lys Ser Cys Asp Lys Thr
        515                 520                 525
```

```
His Thr Cys Pro Pro Cys Pro Ala Pro Glu Phe Glu Gly Gly Pro Ser
        530                 535                 540

Val Phe Leu Phe Pro Pro Lys Pro Lys Asp Thr Leu Met Ile Ser Arg
545                 550                 555                 560

Thr Pro Glu Val Thr Cys Val Val Val Asp Val Ser His Glu Asp Pro
                565                 570                 575

Glu Val Lys Phe Asn Trp Tyr Val Asp Gly Val Glu Val His Asn Ala
            580                 585                 590

Lys Thr Lys Pro Arg Glu Glu Gln Tyr Gln Ser Thr Tyr Arg Val Val
        595                 600                 605

Ser Val Leu Thr Val Leu His Gln Asp Trp Leu Asn Gly Lys Glu Tyr
    610                 615                 620

Lys Cys Lys Val Ser Asn Lys Ala Leu Pro Ala Ser Ile Glu Lys Thr
625                 630                 635                 640

Ile Ser Lys Ala Lys Gly Gln Pro Arg Glu Pro Gln Val Tyr Thr Leu
                645                 650                 655

Pro Pro Ser Arg Glu Glu Met Thr Lys Asn Gln Val Ser Leu Thr Cys
            660                 665                 670

Leu Val Lys Gly Phe Tyr Pro Ser Asp Ile Ala Val Glu Trp Glu Ser
        675                 680                 685

Asn Gly Gln Pro Glu Asn Asn Tyr Lys Thr Thr Pro Pro Val Leu Asp
    690                 695                 700

Ser Asp Gly Ser Phe Phe Leu Tyr Ser Lys Leu Thr Val Asp Lys Ser
705                 710                 715                 720

Arg Trp Gln Gln Gly Asn Val Phe Ser Cys Ser Val Met His Glu Ala
                725                 730                 735

Leu His Asn His Tyr Thr Gln Lys Ser Leu Ser Leu Ser Pro Gly Lys
            740                 745                 750
```

<210> SEQ ID NO 170
<211> LENGTH: 798
<212> TYPE: DNA
<213> ORGANISM: Artificial Sequence
<220> FEATURE:
<223> OTHER INFORMATION: synthetic

<400> SEQUENCE: 170

```
caaggccagt ctggccagtg catctcacct cgtggttgtc cggacggccc atacgtcatg    60
tacggctcga gcggtggcag cggtggctct ggtggatccg gtatatcgag tggattgctg   120
tctggcagat ctgaccaaca cggcagtagc ggtacccaga tcttgctgac ccagagcccg   180
gtgattctga gcgtgagccc gggcgaacgt gtgagcttta gctgccgcgc gagccagagc   240
attggcacca acattcattg gtatcagcag cgcaccaacg gcagcccgcg cctgctgatt   300
aaatatgcga gcgaaagcat tagcggcatt ccgagccgct ttagcggcag cggcagcggc   360
accgatttta ccctgagcat taacagcgtg gaaagcgaag atattgcgga ttattattgc   420
cagcagaaca caactggcc gaccaccttt ggcgcgggca ccaaactgga actgaaacgt   480
acggtggctg caccatctgt cttcatcttc ccgccatctg atgagcagtt gaaatctgga   540
actgcctctg ttgtgtgcct gctgaataac ttctatccca gagaggccaa agtacagtgg   600
aaggtggata acgccctcca atcgggtaac tcccaggaga gtgtcacaga gcaggacagc   660
aaggacagca cctacagcct cagcagcacc ctgacgctga gcaaagcaga ctacgagaaa   720
cacaaagtct acgcctgcga agtcacccat cagggcctga gctcgcccgt cacaaagagc   780
```
ttcaacaggg gagagtgt 798

<210> SEQ ID NO 171
<211> LENGTH: 266
<212> TYPE: PRT
<213> ORGANISM: Artificial Sequence
<220> FEATURE:
<223> OTHER INFORMATION: synthetic

<400> SEQUENCE: 171

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly
            20                  25                  30

Ser Gly Ile Ser Ser Gly Leu Leu Ser Gly Arg Ser Asp Gln His Gly
        35                  40                  45

Ser Ser Gly Thr Gln Ile Leu Leu Thr Gln Ser Pro Val Ile Leu Ser
    50                  55                  60

Val Ser Pro Gly Glu Arg Val Ser Phe Ser Cys Arg Ala Ser Gln Ser
65                  70                  75                  80

Ile Gly Thr Asn Ile His Trp Tyr Gln Gln Arg Thr Asn Gly Ser Pro
                85                  90                  95

Arg Leu Leu Ile Lys Tyr Ala Ser Glu Ser Ile Ser Gly Ile Pro Ser
            100                 105                 110

Arg Phe Ser Gly Ser Gly Ser Gly Thr Asp Phe Thr Leu Ser Ile Asn
        115                 120                 125

Ser Val Glu Ser Glu Asp Ile Ala Asp Tyr Tyr Cys Gln Gln Asn Asn
    130                 135                 140

Asn Trp Pro Thr Thr Phe Gly Ala Gly Thr Lys Leu Glu Leu Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 172
<211> LENGTH: 2244
<212> TYPE: DNA
<213> ORGANISM: Artificial Sequence
<220> FEATURE:
<223> OTHER INFORMATION: synthetic

<400> SEQUENCE: 172
caaggccagt ctggccaaat gatgtattgc ggtgggaatg aggtgttgtg cgggccgcgg      60
gttggctcga gcgtggcag cggtggctct ggtggtctga gcggccgttc cgataatcat     120
ggcggcggtt ctcagaccgt ggtcacacag gagccctcac tgacagtgag ccctggcggg     180

```
accgtcacac tgacttgtcg cagttcaact ggcgccgtga ctaccagcaa ttacgctaac    240
tgggtccagc agaaaccagg acaggcacca cgaggactga tcggaggaac taataagaga    300
gcaccaggaa cccctgcaag gttctccgga tctctgctgg ggggaaaagc cgctctgaca    360
ctgagcggcg tgcagcctga ggacgaagct gagtactatt gcgcactgtg gtactccaac    420
ctgtgggtgt ttggcggggg aactaagctg accgtcctgg gaggaggagg aagcggagga    480
ggagggagcg gaggaggagg atccgaagtg cagctggtcg agagcggagg aggactggtg    540
cagccaggag gatccctgaa gctgtcttgt gcagccagtg gcttcacctt caacacttac    600
gcaatgaact gggtgcggca ggcacctggg aagggactgg aatgggtcgc ccggatcaga    660
tctaaataca ataactatgc cacctactat gctgacagtg tgaaggatag gttcaccatt    720
tcacgcgacg atagcaaaaa cacagcttat ctgcagatga ataacctgaa gaccgaggat    780
acagcagtgt actattgcgt cagacacggc aatttcggga actcttacgt gagttggttt    840
gcctattggg gacaggggac actggtcacc gtctcctcag gaggtggtgg atcccaagtg    900
accctgagag agtctggccc tgccctcgtg aagcctaccc agaccctgac actgacctgc    960
accttcagcg gcttcagcct gagcaccagc ggcatgtctg tgggctggat cagacagcct   1020
cctggcaagg ccctggaatg gctggccgac atttggtggg acgacaagaa ggactacaac   1080
cccagcctga gtcccggct gaccatcagc aaggacacca gcaagaacca ggtggtgctg   1140
aaagtgacca catgagccc cgccgacacc gccacctact actgcgccag atccatgatc   1200
accaactggt acttcgacgt gtggggagcc ggcaccaccg tgacagtgtc atctgctagc   1260
accaagggcc catcggtctt ccccctggca cccctcctcca agagcacctc tgggggcaca   1320
gcggccctgg gctgcctggt caaggactac ttccccgaac cggtgacggt gtcgtggaac   1380
tcaggcgccc tgaccagcgg cgtgcacacc ttccgcgctg tcctacagtc ctcaggactc   1440
tactccctca gcagcgtggt gaccgtgccc tccagcagct gggcaccca gacctacatc   1500
tgcaacgtga atcacaagcc cagcaacacc aaggtggaca gaaagttga gcccaaatct   1560
tgtgacaaaa ctcacacatg cccaccgtgc ccagcacctg aactcctggg gggaccgtca   1620
gtcttcctct tccccccaaa acccaaggac accctcatga tctcccggac ccctgaggtc   1680
acatgcgtgg tggtggacgt gagccacgaa gaccctgagg tcaagttcaa ctggtacgtg   1740
gacggcgtgg aggtgcataa tgccaagaca aagccgcggg aggagcagta ccagagcacg   1800
taccgtgtgg tcagcgtcct caccgtcctg caccaggact ggctgaatgg caaggagtac   1860
aagtgcaagg tctccaacaa agccctccca gcccccatcg agaaaaccat ctccaaagcc   1920
aaagggcagc ccgagaacc acaggtgtac accctgcccc catcccggga ggagatgacc   1980
aagaaccagg tcagcctgac ctgcctggtc aaaggcttct atcccagcga catcgccgtg   2040
gagtgggaga gcaatgggca gccggagaac aactacaaga ccacgcctcc cgtgctggac   2100
tccgacggct ccttcttcct ctacagcaag ctcaccgtgg acaagagcag gtggcagcag   2160
gggaacgtct tctcatgctc cgtgatgcat gaggctctgc acaaccacta cacgcagaag   2220
agcctctccc tgtctccggg taaa                                          2244
```

<210> SEQ ID NO 173
<211> LENGTH: 748
<212> TYPE: PRT
<213> ORGANISM: Artificial Sequence
<220> FEATURE:
<223> OTHER INFORMATION: synthetic

<400> SEQUENCE: 173

```
Gln Gly Gln Ser Gly Gln Met Met Tyr Cys Gly Gly Asn Glu Val Leu
1               5                   10                  15

Cys Gly Pro Arg Val Gly Ser Ser Gly Ser Gly Gly Ser Gly Gly Gly
            20                  25                  30

Leu Ser Gly Arg Ser Asp Asn His Gly Gly Ser Gln Thr Val Val
        35                  40                  45

Thr Gln Glu Pro Ser Leu Thr Val Ser Pro Gly Gly Thr Val Thr Leu
    50                  55                  60

Thr Cys Arg Ser Ser Thr Gly Ala Val Thr Thr Ser Asn Tyr Ala Asn
65              70                  75                  80

Trp Val Gln Gln Lys Pro Gly Gln Ala Pro Arg Gly Leu Ile Gly Gly
                85                  90                  95

Thr Asn Lys Arg Ala Pro Gly Thr Pro Ala Arg Phe Ser Gly Ser Leu
            100                 105                 110

Leu Gly Gly Lys Ala Ala Leu Thr Leu Ser Gly Val Gln Pro Glu Asp
        115                 120                 125

Glu Ala Glu Tyr Tyr Cys Ala Leu Trp Tyr Ser Asn Leu Trp Val Phe
    130                 135                 140

Gly Gly Gly Thr Lys Leu Thr Val Leu Gly Gly Gly Ser Gly Gly
145                 150                 155                 160

Gly Gly Ser Gly Gly Gly Ser Glu Val Gln Leu Val Glu Ser Gly
            165                 170                 175

Gly Gly Leu Val Gln Pro Gly Gly Ser Leu Lys Leu Ser Cys Ala Ala
        180                 185                 190

Ser Gly Phe Thr Phe Asn Thr Tyr Ala Met Asn Trp Val Arg Gln Ala
        195                 200                 205

Pro Gly Lys Gly Leu Glu Trp Val Ala Arg Ile Arg Ser Lys Tyr Asn
    210                 215                 220

Asn Tyr Ala Thr Tyr Tyr Ala Asp Ser Val Lys Asp Arg Phe Thr Ile
225                 230                 235                 240

Ser Arg Asp Asp Ser Lys Asn Thr Ala Tyr Leu Gln Met Asn Asn Leu
            245                 250                 255

Lys Thr Glu Asp Thr Ala Val Tyr Tyr Cys Val Arg His Gly Asn Phe
        260                 265                 270

Gly Asn Ser Tyr Val Ser Trp Phe Ala Tyr Trp Gly Gln Gly Thr Leu
        275                 280                 285

Val Thr Val Ser Ser Gly Gly Gly Ser Gln Val Thr Leu Arg Glu
    290                 295                 300

Ser Gly Pro Ala Leu Val Lys Pro Thr Gln Thr Leu Thr Leu Thr Cys
305                 310                 315                 320

Thr Phe Ser Gly Phe Ser Leu Ser Thr Ser Gly Met Ser Val Gly Trp
            325                 330                 335

Ile Arg Gln Pro Pro Gly Lys Ala Leu Glu Trp Leu Ala Asp Ile Trp
        340                 345                 350

Trp Asp Asp Lys Lys Asp Tyr Asn Pro Ser Leu Lys Ser Arg Leu Thr
        355                 360                 365

Ile Ser Lys Asp Thr Ser Lys Asn Gln Val Val Leu Lys Val Thr Asn
    370                 375                 380

Met Asp Pro Ala Asp Thr Ala Thr Tyr Tyr Cys Ala Arg Ser Met Ile
385                 390                 395                 400

Thr Asn Trp Tyr Phe Asp Val Trp Gly Ala Gly Thr Thr Val Thr Val
                405                 410                 415
```

Ser Ser Ala Ser Thr Lys Gly Pro Ser Val Phe Pro Leu Ala Pro Ser
            420                 425                 430

Ser Lys Ser Thr Ser Gly Gly Thr Ala Ala Leu Gly Cys Leu Val Lys
        435                 440                 445

Asp Tyr Phe Pro Glu Pro Val Thr Val Ser Trp Asn Ser Gly Ala Leu
    450                 455                 460

Thr Ser Gly Val His Thr Phe Pro Ala Val Leu Gln Ser Ser Gly Leu
465                 470                 475                 480

Tyr Ser Leu Ser Ser Val Val Thr Val Pro Ser Ser Ser Leu Gly Thr
                485                 490                 495

Gln Thr Tyr Ile Cys Asn Val Asn His Lys Pro Ser Asn Thr Lys Val
            500                 505                 510

Asp Lys Lys Val Glu Pro Lys Ser Cys Asp Lys Thr His Thr Cys Pro
        515                 520                 525

Pro Cys Pro Ala Pro Glu Leu Leu Gly Gly Pro Ser Val Phe Leu Phe
    530                 535                 540

Pro Pro Lys Pro Lys Asp Thr Leu Met Ile Ser Arg Thr Pro Glu Val
545                 550                 555                 560

Thr Cys Val Val Val Asp Val Ser His Glu Asp Pro Glu Val Lys Phe
                565                 570                 575

Asn Trp Tyr Val Asp Gly Val Glu Val His Asn Ala Lys Thr Lys Pro
            580                 585                 590

Arg Glu Glu Gln Tyr Gln Ser Thr Tyr Arg Val Val Ser Val Leu Thr
        595                 600                 605

Val Leu His Gln Asp Trp Leu Asn Gly Lys Glu Tyr Lys Cys Lys Val
    610                 615                 620

Ser Asn Lys Ala Leu Pro Ala Pro Ile Glu Lys Thr Ile Ser Lys Ala
625                 630                 635                 640

Lys Gly Gln Pro Arg Glu Pro Gln Val Tyr Thr Leu Pro Pro Ser Arg
                645                 650                 655

Glu Glu Met Thr Lys Asn Gln Val Ser Leu Thr Cys Leu Val Lys Gly
            660                 665                 670

Phe Tyr Pro Ser Asp Ile Ala Val Glu Trp Glu Ser Asn Gly Gln Pro
        675                 680                 685

Glu Asn Asn Tyr Lys Thr Thr Pro Pro Val Leu Asp Ser Asp Gly Ser
    690                 695                 700

Phe Phe Leu Tyr Ser Lys Leu Thr Val Asp Lys Ser Arg Trp Gln Gln
705                 710                 715                 720

Gly Asn Val Phe Ser Cys Ser Val Met His Glu Ala Leu His Asn His
                725                 730                 735

Tyr Thr Gln Lys Ser Leu Ser Leu Ser Pro Gly Lys
            740                 745

<210> SEQ ID NO 174
<211> LENGTH: 639
<212> TYPE: DNA
<213> ORGANISM: Artificial Sequence
<220> FEATURE:
<223> OTHER INFORMATION: synthetic

<400> SEQUENCE: 174
gacatccaga tgacccagag ccccagcaca ctgagcgcca gcgtgggcga cagagtgacc    60
atcacatgca agtgccagct gagcgtgggc tacatgcact ggtatcagca gaagcccggc   120
aaggccccca agctgctgat ctacgacacc agcaagctgg cctccggcgt gcccagcaga   180

```
tttctggca gcggctccgg caccgagttc accctgacaa tcagcagcct gcagcccgac    240
gacttcgcca cctactactg ttttcaaggc tccggctacc ccttcacctt cggcggaggc    300
accaagctgg aaatcaagcg gacggtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                          639
```

<210> SEQ ID NO 175
<211> LENGTH: 213
<212> TYPE: PRT
<213> ORGANISM: Artificial Sequence
<220> FEATURE:
<223> OTHER INFORMATION: synthetic

<400> SEQUENCE: 175

```
Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 176
<211> LENGTH: 18
<212> TYPE: DNA
<213> ORGANISM: Artificial Sequence
<220> FEATURE:
<223> OTHER INFORMATION: synthetic

<400> SEQUENCE: 176

```
caaggccagt ctggccaa                                                 18
```

<210> SEQ ID NO 177
<211> LENGTH: 2223
<212> TYPE: DNA
<213> ORGANISM: Artificial Sequence
<220> FEATURE:
<223> OTHER INFORMATION: synthetic

<400> SEQUENCE: 177

```
atgatgtatt gcggtgggaa tgaggtgttg tgcgggccgc gggttggctc gagcggtggc      60
agcggtggct ctggtggtct gagcggccgt tccgataatc atggcggcgg ttctcagacc     120
gtggtcacac aggagccctc actgacagtg agccctggcg ggaccgtcac actgacttgt     180
cgcagttcaa ctggcgccgt gactaccagc aattacgcta actgggtcca gcagaaacca     240
ggacaggcac cacgaggact gatcggagga actaataaga gcaccagg aaccctgca       300
aggttctccg gatctctgct gggggaaaa gccgctctga cactgagcgg cgtgcagcct      360
gaggacgaag ctgagtacta ttgcgcactg tggtactcca acctgtgggt gtttggcggg     420
ggaactaagc tgaccgtcct gggaggagga ggaagcggag gaggagggag cggaggagga     480
ggatccgaag tgcagctggt cgagagcgga ggaggactgg tgcagccagg aggatccctg     540
aagctgtctt gtgcagccag tggcttcacc ttcaacactt acgcaatgaa ctgggtgcgg     600
caggcacctg gaagggact ggaatgggtc gccggatca gatctaaata caataactat      660
gccacctact atgctgacag tgtgaaggat aggttcacca tttcacgcga cgatagcaaa     720
aacacagctt atctgcagat gaataacctg aagaccgagg atacagcagt gtactattgc     780
gtcagacacg gcaatttcgg gaactcttac gtgagttggt ttgcctattg gggacagggg     840
acactggtca ccgtctcctc aggaggtggt ggatcccagg tgcagctgaa acagagcggc     900
ccgggcctgg tgcagccgag ccagagcctg agcattacct gcaccgtgag cggctttagc     960
ctgaccaact atggcgtgca ttgggtgcgc cagagcccgg caaaggcct ggaatggctg     1020
ggcgtgattt ggagcggcgg caacaccgat tataacaccc cgtttaccag ccgcctgagc    1080
attaacaaag ataacagcaa agccaggtg ttttttaaaa tgaacagcct gcaaagccag     1140
gataccgcga tttattattg cgcgcgcgcg ctgacctatt atgattatga atttgcgtat    1200
tggggccagg gcaccctggt gaccgtgagc gcggctagca ccaagggccc atcggtcttc    1260
cccctggcac cctcctccaa gagcacctct ggggcacag cggccctggg ctgcctggtc     1320
aaggactact ccccgaacc ggtgacggtg tcgtggaact caggcgccct gaccagcggc    1380
gtgcacacct tcccggctgt cctacagtcc tcaggactct actccctcag cagcgtggtg    1440
accgtgccct ccagcagctt gggcacccag acctacatct gcaacgtgaa tcacaagccc    1500
agcaacacca aggtggacaa gaaagttgag cccaaatctt gtgacaaaac tcacacatgc    1560
ccaccgtgcc cagcacctga actcctgggg ggaccgtcag tcttcctctt ccccccaaaa    1620
cccaaggaca ccctcatgat ctcccggacc cctgaggtca catgcgtggt ggtggacgtg    1680
agccacgaag accctgaggt caagttcaac tggtacgtgg acggcgtgga ggtgcataat    1740
gccaagacaa agccgcggga ggagcagtac cagagcacgt accgtgtggt cagcgtcctc    1800
accgtcctgc accaggactg gctgaatggc aaggagtaca agtgcaaggt ctccaacaaa    1860
gccctcccag cccccatcga gaaaaccatc tccaaagcca agggcagcc ccgagaacca    1920
caggtgtaca ccctgccccc atcccgggag gagatgacca agaaccaggt cagcctgacc    1980
tgcctggtca aaggcttcta tcccagcgac atcgccgtgg agtgggagag caatgggcag    2040
```

```
ccggagaaca actacaagac cacgcctccc gtgctggact ccgacggctc cttcttcctc    2100
tacagcaagc tcaccgtgga caagagcagg tggcagcagg ggaacgtctt ctcatgctcc    2160
gtgatgcatg aggctctgca caaccactac acgcagaaga gcctctccct gtctccgggt    2220
aaa                                                                  2223
```

```
<210> SEQ ID NO 178
<211> LENGTH: 6
<212> TYPE: PRT
<213> ORGANISM: Artificial Sequence
<220> FEATURE:
<223> OTHER INFORMATION: synthetic

<400> SEQUENCE: 178

Gln Gly Gln Ser Gly Gln
1               5

<210> SEQ ID NO 179
<211> LENGTH: 741
<212> TYPE: PRT
<213> ORGANISM: Artificial Sequence
<220> FEATURE:
<223> OTHER INFORMATION: synthetic

<400> SEQUENCE: 179

Met Met Tyr Cys Gly Gly Asn Glu Val Leu Cys Gly Pro Arg Val Gly
1               5                   10                  15

Ser Ser Gly Gly Ser Gly Gly Ser Gly Gly Leu Ser Gly Arg Ser Asp
                20                  25                  30

Asn His Gly Gly Gly Ser Gln Thr Val Val Thr Gln Glu Pro Ser Leu
            35                  40                  45

Thr Val Ser Pro Gly Gly Thr Val Thr Leu Thr Cys Arg Ser Ser Thr
        50                  55                  60

Gly Ala Val Thr Thr Ser Asn Tyr Ala Asn Trp Val Gln Gln Lys Pro
65                  70                  75                  80

Gly Gln Ala Pro Arg Gly Leu Ile Gly Gly Thr Asn Lys Arg Ala Pro
                85                  90                  95

Gly Thr Pro Ala Arg Phe Ser Gly Ser Leu Leu Gly Lys Ala Ala
            100                 105                 110

Leu Thr Leu Ser Gly Val Gln Pro Glu Asp Glu Ala Glu Tyr Tyr Cys
        115                 120                 125

Ala Leu Trp Tyr Ser Asn Leu Trp Val Phe Gly Gly Thr Lys Leu
130                 135                 140

Thr Val Leu Gly Gly Gly Gly Ser Gly Gly Gly Gly Ser Gly Gly Gly
145                 150                 155                 160

Gly Ser Glu Val Gln Leu Val Glu Ser Gly Gly Gly Leu Val Gln Pro
                165                 170                 175

Gly Gly Ser Leu Lys Leu Ser Cys Ala Ala Ser Gly Phe Thr Phe Asn
            180                 185                 190

Thr Tyr Ala Met Asn Trp Val Arg Gln Ala Pro Gly Lys Gly Leu Glu
        195                 200                 205

Trp Val Ala Arg Ile Arg Ser Lys Tyr Asn Asn Tyr Ala Thr Tyr Tyr
    210                 215                 220

Ala Asp Ser Val Lys Asp Arg Phe Thr Ile Ser Arg Asp Asp Ser Lys
225                 230                 235                 240

Asn Thr Ala Tyr Leu Gln Met Asn Asn Leu Lys Thr Glu Asp Thr Ala
                245                 250                 255
```

```
Val Tyr Tyr Cys Val Arg His Gly Asn Phe Gly Asn Ser Tyr Val Ser
            260                 265                 270

Trp Phe Ala Tyr Trp Gly Gln Gly Thr Leu Val Thr Val Ser Ser Gly
            275                 280                 285

Gly Gly Gly Ser Gln Val Gln Leu Lys Gln Ser Gly Pro Gly Leu Val
        290                 295                 300

Gln Pro Ser Gln Ser Leu Ser Ile Thr Cys Thr Val Ser Gly Phe Ser
305                 310                 315                 320

Leu Thr Asn Tyr Gly Val His Trp Val Arg Gln Ser Pro Gly Lys Gly
                325                 330                 335

Leu Glu Trp Leu Gly Val Ile Trp Ser Gly Gly Asn Thr Asp Tyr Asn
            340                 345                 350

Thr Pro Phe Thr Ser Arg Leu Ser Ile Asn Lys Asp Asn Ser Lys Ser
            355                 360                 365

Gln Val Phe Phe Lys Met Asn Ser Leu Gln Ser Gln Asp Thr Ala Ile
        370                 375                 380

Tyr Tyr Cys Ala Arg Ala Leu Thr Tyr Tyr Asp Tyr Glu Phe Ala Tyr
385                 390                 395                 400

Trp Gly Gln Gly Thr Leu Val Thr Val Ser Ala Ala Ser Thr Lys Gly
                405                 410                 415

Pro Ser Val Phe Pro Leu Ala Pro Ser Ser Lys Ser Thr Ser Gly Gly
            420                 425                 430

Thr Ala Ala Leu Gly Cys Leu Val Lys Asp Tyr Phe Pro Glu Pro Val
            435                 440                 445

Thr Val Ser Trp Asn Ser Gly Ala Leu Thr Ser Gly Val His Thr Phe
        450                 455                 460

Pro Ala Val Leu Gln Ser Ser Gly Leu Tyr Ser Leu Ser Ser Val Val
465                 470                 475                 480

Thr Val Pro Ser Ser Ser Leu Gly Thr Gln Thr Tyr Ile Cys Asn Val
                485                 490                 495

Asn His Lys Pro Ser Asn Thr Lys Val Asp Lys Lys Val Glu Pro Lys
            500                 505                 510

Ser Cys Asp Lys Thr His Thr Cys Pro Pro Cys Pro Ala Pro Glu Leu
        515                 520                 525

Leu Gly Gly Pro Ser Val Phe Leu Phe Pro Pro Lys Pro Lys Asp Thr
            530                 535                 540

Leu Met Ile Ser Arg Thr Pro Glu Val Thr Cys Val Val Val Asp Val
545                 550                 555                 560

Ser His Glu Asp Pro Glu Val Lys Phe Asn Trp Tyr Val Asp Gly Val
                565                 570                 575

Glu Val His Asn Ala Lys Thr Lys Pro Arg Glu Glu Gln Tyr Gln Ser
            580                 585                 590

Thr Tyr Arg Val Val Ser Val Leu Thr Val Leu His Gln Asp Trp Leu
        595                 600                 605

Asn Gly Lys Glu Tyr Lys Cys Lys Val Ser Asn Lys Ala Leu Pro Ala
            610                 615                 620

Pro Ile Glu Lys Thr Ile Ser Lys Ala Lys Gly Gln Pro Arg Glu Pro
625                 630                 635                 640

Gln Val Tyr Thr Leu Pro Pro Ser Arg Glu Glu Met Thr Lys Asn Gln
                645                 650                 655

Val Ser Leu Thr Cys Leu Val Lys Gly Phe Tyr Pro Ser Asp Ile Ala
            660                 665                 670

Val Glu Trp Glu Ser Asn Gly Gln Pro Glu Asn Asn Tyr Lys Thr Thr
```

```
                675                 680                 685
Pro Pro Val Leu Asp Ser Asp Gly Ser Phe Phe Leu Tyr Ser Lys Leu
    690                 695                 700

Thr Val Asp Lys Ser Arg Trp Gln Gln Gly Asn Val Phe Ser Cys Ser
705                 710                 715                 720

Val Met His Glu Ala Leu His Asn His Tyr Thr Gln Lys Ser Leu Ser
                725                 730                 735

Leu Ser Pro Gly Lys
            740
```

<210> SEQ ID NO 180
<211> LENGTH: 18
<212> TYPE: DNA
<213> ORGANISM: Artificial Sequence
<220> FEATURE:
<223> OTHER INFORMATION: synthetic

<400> SEQUENCE: 180
caaggccagt ctggccag                                                     18

<210> SEQ ID NO 181
<211> LENGTH: 765
<212> TYPE: DNA
<213> ORGANISM: Artificial Sequence
<220> FEATURE:
<223> OTHER INFORMATION: synthetic

<400> SEQUENCE: 181
tgcatctcac ctcgtggttg tccggacggc ccatacgtca tgtacggctc gagcggtggc      60
agcggtggct ctggtggatc cggtctgagc ggccgttccg ataatcatgg cagtagcggt     120
acccagatct tgctgaccca gagcccggtg attctgagcg tgagcccggg cgaacgtgtg     180
agctttagct gccgcgcgag ccagagcatt ggcaccaaca ttcattggta tcagcagcgc     240
accaacggca gcccgcgcct gctgattaaa tatgcgagcg aaagcattag cggcattccg     300
agccgcttta gcggcagcgg cagcggcacc gattttaccc tgagcattaa cagcgtggaa     360
agcgaagata ttgcggatta ttattgccag cagaacaaca ctggccgac cacctttggc     420 gcgggcacca aactggaact gaaacgtacg gtggctgcac catctgtctt catcttcccg     480
ccatctgatg agcagttgaa atctggaact gcctctgttg tgtgcctgct gaataacttc     540
tatcccagag aggccaaagt acagtggaag gtggataacg ccctccaatc gggtaactcc     600
caggagagtg tcacagagca ggacagcaag gacagcacct acagcctcag cagcaccctg     660
acgctgagca agcagactac gagaaacac aaagtctacg cctgcgaagt cacccatcag     720
ggcctgagct cgcccgtcac aaagagcttc aacaggggag agtgt                     765

<210> SEQ ID NO 182
<211> LENGTH: 255
<212> TYPE: PRT
<213> ORGANISM: Artificial Sequence
<220> FEATURE:
<223> OTHER INFORMATION: synthetic

<400> SEQUENCE: 182

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Leu Ser Gly Arg
            20                  25                  30

Ser Asp Asn His Gly Ser Ser Gly Thr Gln Ile Leu Leu Thr Gln Ser

```
              35                  40                  45
Pro Val Ile Leu Ser Val Ser Pro Gly Glu Arg Val Ser Phe Ser Cys
 50                  55                  60
Arg Ala Ser Gln Ser Ile Gly Thr Asn Ile His Trp Tyr Gln Gln Arg
 65                  70                  75                  80
Thr Asn Gly Ser Pro Arg Leu Leu Ile Lys Tyr Ala Ser Glu Ser Ile
                 85                  90                  95
Ser Gly Ile Pro Ser Arg Phe Ser Gly Ser Gly Ser Thr Asp Phe
                100                 105                 110
Thr Leu Ser Ile Asn Ser Val Glu Ser Glu Asp Ile Ala Asp Tyr Tyr
                115                 120                 125
Cys Gln Gln Asn Asn Asn Trp Pro Thr Thr Phe Gly Ala Gly Thr Lys
130                 135                 140
Leu Glu Leu Lys Arg Thr Val Ala Ala Pro Ser Val Phe Ile Phe Pro
145                 150                 155                 160
Pro Ser Asp Glu Gln Leu Lys Ser Gly Thr Ala Ser Val Val Cys Leu
                165                 170                 175
Leu Asn Asn Phe Tyr Pro Arg Glu Ala Lys Val Gln Trp Lys Val Asp
                180                 185                 190
Asn Ala Leu Gln Ser Gly Asn Ser Gln Glu Ser Val Thr Glu Gln Asp
                195                 200                 205
Ser Lys Asp Ser Thr Tyr Ser Leu Ser Ser Thr Leu Thr Leu Ser Lys
210                 215                 220
Ala Asp Tyr Glu Lys His Lys Val Tyr Ala Cys Glu Val Thr His Gln
225                 230                 235                 240
Gly Leu Ser Ser Pro Val Thr Lys Ser Phe Asn Arg Gly Glu Cys
                245                 250                 255

<210> SEQ ID NO 183
<211> LENGTH: 2223
<212> TYPE: DNA
<213> ORGANISM: Artificial Sequence
<220> FEATURE:
<223> OTHER INFORMATION: synthetic

<400> SEQUENCE: 183
atgatgtatt gcggtgggaa tgaggtgttg tgcgggccgc gggttggctc gagcggtggc        60
agcggtggct ctggtggtgg tggaggctcg ggcggtggga gcggcggcgg ttctcagacc       120
gtggtcacac aggagccctc actgacagtg agccctggcg ggaccgtcac actgacttgt       180
cgcagttcaa ctggcgccgt gactaccagc aattacgcta actgggtcca gcagaaacca       240
ggacaggcac cacgaggact gatcggagga actaataaga gagcaccagg aaccccctgca      300 aggttctccg gatctctgct gggggggaaaa gccgctctga cactgagcgg cgtgcagcct      360
gaggacgaag ctgagtacta ttgcgcactg tggtactcca acctgtgggt gtttggcggg       420
ggaactaagc tgaccgtcct gggaggagga ggaagcggag gaggagggag cggaggagga       480
ggatccgaag tgcagctggt cgagagcgga ggaggactgg tgcagccagg aggatccctg       540
aagctgtctt gtgcagccag tggcttcacc ttcaacactt acgcaatgaa ctgggtgcgg       600
caggcacctg gaagggact ggaatgggtc gcccggatca gatctaaata caataactat       660 gccaccctact atgctgacag tgtgaaggat aggttcacca tttcacgcga cgatagcaaa      720
aacacagctt atctgcagat gaataacctg aagaccgagg atacagcagt gtactattgc       780
gtcagacacg gcaatttcgg gaactcttac gtgagttggt ttgcctattg gggacagggg       840
```

```
acactggtca ccgtctcctc aggaggtggt ggatcccagg tgcagctgaa acagagcggc    900
ccgggcctgg tgcagccgag ccagagcctg agcattacct gcaccgtgag cggctttagc    960
ctgaccaact atggcgtgca ttgggtgcgc cagagcccgg gcaaaggcct ggaatggctg   1020
ggcgtgattt ggagcggcgg caacaccgat tataacaccc cgtttaccag ccgcctgagc   1080
attaacaaag ataacagcaa aagccaggtg ttttttaaaa tgaacagcct gcaaagccag   1140
gataccgcga tttattattg cgcgcgcgcg ctgacctatt atgattatga atttgcgtat   1200
tggggccagg gcaccctggt gaccgtgagc gcggctagca ccaagggccc atcggtcttc   1260
cccctggcac cctcctccaa gagcacctct gggggcacag cggccctggg ctgcctggtc   1320
aaggactact cccccgaacc ggtgacggtg tcgtggaact caggcgccct gaccagcggc   1380
gtgcacacct tcccggctgt cctacagtcc tcaggactct actccctcag cagcgtggtg   1440
accgtgccct ccagcagctt gggcacccag acctacatct gcaacgtgaa tcacaagccc   1500
agcaacacca aggtggacaa gaaagttgag cccaaatctt gtgacaaaac tcacacatgc   1560
ccaccgtgcc cagcacctga actcctgggg ggaccgtcag tcttcctctt ccccccaaaa   1620
cccaaggaca ccctcatgat ctcccggacc cctgaggtca catgcgtggt ggtggacgtg   1680
agccacgaag accctgaggt caagttcaac tggtacgtgg acggcgtgga ggtgcataat   1740
gccaagacaa agccgcggga ggagcagtac cagagcacgt accgtgtggt cagcgtcctc   1800
accgtcctgc accaggactg gctgaatggc aaggagtaca agtgcaaggt ctccaacaaa   1860
gccctcccag cccccatcga gaaaaccatc tccaaagcca agggcagccc cgagaaccac   1920
caggtgtaca ccctgccccc atcccgggag gagatgacca agaaccaggt cagcctgacc   1980
tgcctggtca aaggcttcta tcccagcgac atcgccgtgg agtgggagag caatgggcag   2040
ccggagaaca actacaagac cacgcctccc gtgctggact ccgacggctc cttcttcctc   2100
tacagcaagc tcaccgtgga caagagcagg tggcagcagg ggaacgtctt ctcatgctcc   2160
gtgatgcatg aggctctgca caaccactac acgcagaaga gcctctccct gtctccgggt   2220
aaa                                                                 2223
```

<210> SEQ ID NO 184
<211> LENGTH: 741
<212> TYPE: PRT
<213> ORGANISM: Artificial Sequence
<220> FEATURE:
<223> OTHER INFORMATION: synthetic

<400> SEQUENCE: 184

```
Met Met Tyr Cys Gly Gly Asn Glu Val Leu Cys Gly Pro Arg Val Gly
1               5                   10                  15
Ser Ser Gly Gly Ser Gly Gly Ser Gly Gly Gly Gly Ser Gly Gly
            20                  25                  30
Gly Ser Gly Gly Gly Ser Gln Thr Val Thr Gln Glu Pro Ser Leu
        35                  40                  45
Thr Val Ser Pro Gly Gly Thr Val Thr Leu Thr Cys Arg Ser Ser Thr
    50                  55                  60
Gly Ala Val Thr Thr Ser Asn Tyr Ala Asn Trp Val Gln Gln Lys Pro
65                  70                  75                  80
Gly Gln Ala Pro Arg Gly Leu Ile Gly Gly Thr Asn Lys Arg Ala Pro
                85                  90                  95
Gly Thr Pro Ala Arg Phe Ser Gly Ser Leu Leu Gly Gly Lys Ala Ala
            100                 105                 110
```

Leu Thr Leu Ser Gly Val Gln Pro Glu Asp Glu Ala Glu Tyr Tyr Cys
            115                 120                 125

Ala Leu Trp Tyr Ser Asn Leu Trp Val Phe Gly Gly Gly Thr Lys Leu
130                 135                 140

Thr Val Leu Gly Gly Gly Gly Ser Gly Gly Gly Gly Ser Gly Gly Gly
145                 150                 155                 160

Gly Ser Glu Val Gln Leu Val Glu Ser Gly Gly Gly Leu Val Gln Pro
            165                 170                 175

Gly Gly Ser Leu Lys Leu Ser Cys Ala Ala Ser Gly Phe Thr Phe Asn
            180                 185                 190

Thr Tyr Ala Met Asn Trp Val Arg Gln Ala Pro Gly Lys Gly Leu Glu
            195                 200                 205

Trp Val Ala Arg Ile Arg Ser Lys Tyr Asn Asn Tyr Ala Thr Tyr Tyr
210                 215                 220

Ala Asp Ser Val Lys Asp Arg Phe Thr Ile Ser Arg Asp Asp Ser Lys
225                 230                 235                 240

Asn Thr Ala Tyr Leu Gln Met Asn Asn Leu Lys Thr Glu Asp Thr Ala
            245                 250                 255

Val Tyr Tyr Cys Val Arg His Gly Asn Phe Gly Asn Ser Tyr Val Ser
            260                 265                 270

Trp Phe Ala Tyr Trp Gly Gln Gly Thr Leu Val Thr Val Ser Ser Gly
            275                 280                 285

Gly Gly Gly Ser Gln Val Gln Leu Lys Gln Ser Gly Pro Gly Leu Val
            290                 295                 300

Gln Pro Ser Gln Ser Leu Ser Ile Thr Cys Thr Val Ser Gly Phe Ser
305                 310                 315                 320

Leu Thr Asn Tyr Gly Val His Trp Val Arg Gln Ser Pro Gly Lys Gly
            325                 330                 335

Leu Glu Trp Leu Gly Val Ile Trp Ser Gly Gly Asn Thr Asp Tyr Asn
            340                 345                 350

Thr Pro Phe Thr Ser Arg Leu Ser Ile Asn Lys Asp Asn Ser Lys Ser
            355                 360                 365

Gln Val Phe Phe Lys Met Asn Ser Leu Gln Ser Gln Asp Thr Ala Ile
            370                 375                 380

Tyr Tyr Cys Ala Arg Ala Leu Thr Tyr Tyr Asp Tyr Glu Phe Ala Tyr
385                 390                 395                 400

Trp Gly Gln Gly Thr Leu Val Thr Val Ser Ala Ala Ser Thr Lys Gly
                405                 410                 415

Pro Ser Val Phe Pro Leu Ala Pro Ser Ser Lys Ser Thr Ser Gly Gly
            420                 425                 430

Thr Ala Ala Leu Gly Cys Leu Val Lys Asp Tyr Phe Pro Glu Pro Val
            435                 440                 445

Thr Val Ser Trp Asn Ser Gly Ala Leu Thr Ser Gly Val His Thr Phe
450                 455                 460

Pro Ala Val Leu Gln Ser Ser Gly Leu Tyr Ser Leu Ser Ser Val Val
465                 470                 475                 480

Thr Val Pro Ser Ser Ser Leu Gly Thr Gln Thr Tyr Ile Cys Asn Val
            485                 490                 495

Asn His Lys Pro Ser Asn Thr Lys Val Asp Lys Lys Val Glu Pro Lys
            500                 505                 510

Ser Cys Asp Lys Thr His Thr Cys Pro Pro Cys Pro Ala Pro Glu Leu
            515                 520                 525

Leu Gly Gly Pro Ser Val Phe Leu Phe Pro Pro Lys Pro Lys Asp Thr

```
                530             535             540
Leu Met Ile Ser Arg Thr Pro Glu Val Thr Cys Val Val Asp Val
545                 550                 555                 560

Ser His Glu Asp Pro Glu Val Lys Phe Asn Trp Tyr Val Asp Gly Val
                565                 570                 575

Glu Val His Asn Ala Lys Thr Lys Pro Arg Glu Glu Gln Tyr Gln Ser
            580                 585                 590

Thr Tyr Arg Val Val Ser Val Leu Thr Val Leu His Gln Asp Trp Leu
        595                 600                 605

Asn Gly Lys Glu Tyr Lys Cys Lys Val Ser Asn Lys Ala Leu Pro Ala
    610                 615                 620

Pro Ile Glu Lys Thr Ile Ser Lys Ala Lys Gly Gln Pro Arg Glu Pro
625                 630                 635                 640

Gln Val Tyr Thr Leu Pro Pro Ser Arg Glu Glu Met Thr Lys Asn Gln
                645                 650                 655

Val Ser Leu Thr Cys Leu Val Lys Gly Phe Tyr Pro Ser Asp Ile Ala
            660                 665                 670

Val Glu Trp Glu Ser Asn Gly Gln Pro Glu Asn Asn Tyr Lys Thr Thr
        675                 680                 685

Pro Pro Val Leu Asp Ser Asp Gly Ser Phe Phe Leu Tyr Ser Lys Leu
    690                 695                 700

Thr Val Asp Lys Ser Arg Trp Gln Gln Gly Asn Val Phe Ser Cys Ser
705                 710                 715                 720

Val Met His Glu Ala Leu His Asn His Tyr Thr Gln Lys Ser Leu Ser
                725                 730                 735

Leu Ser Pro Gly Lys
            740

<210> SEQ ID NO 185
<211> LENGTH: 756
<212> TYPE: DNA
<213> ORGANISM: Artificial Sequence
<220> FEATURE:
<223> OTHER INFORMATION: synthetic

<400> SEQUENCE: 185
tgcatctcac ctcgtggttg tccggacggc ccatacgtca gtacggctc gagcggtggc      60 agcggtggct ctggtggctc aggtggaggc tcgggcggtg ggagcggcgg ttctgatatc     120
ttgctgaccc agagcccggt gattctgagc gtgagcccgg gcgaacgtgt gagctttagc     180
tgccgcgcga gccagagcat tggcaccaac attcattggt atcagcagcg caccaacggc     240
agcccgcgcc tgctgattaa atatgcgagc gaaagcatta gcggcattcc gagccgcttt     300
agcggcagcg gcagcggcac cgattttacc ctgagcatta cagcgtgga aagcgaagat      360 attgcggatt attattgcca gcagaacaac aactggccga ccacctttgg cgcgggcacc     420
aaactggaac tgaaacgtac ggtggctgca ccatctgtct tcatcttccc gccatctgat     480
gagcagttga aatctggaac tgcctctgtt gtgtgcctgc tgaataactt ctatcccaga     540
gaggccaaag tacagtggaa ggtggataac gccctccaat cgggtaactc ccaggagagt     600
gtcacagagc aggacagcaa ggacagcacc tacagcctca gcagcaccct gacgctgagc     660
aaagcagact acgagaaaca caaagtctac gcctgcgaag tcacccatca gggcctgagc     720
tcgcccgtca caaagagctt caacagggga gagtgt                              756

<210> SEQ ID NO 186
```

<211> LENGTH: 252
<212> TYPE: PRT
<213> ORGANISM: Artificial Sequence
<220> FEATURE:
<223> OTHER INFORMATION: synthetic

<400> SEQUENCE: 186

```
Cys Ile Ser Pro Arg Gly Cys Pro Asp Gly Pro Tyr Val Met Tyr Gly
1               5                   10                  15
Ser Ser Gly Gly Ser Gly Ser Gly Gly Ser Gly Gly Gly Ser Gly
            20                  25                  30
Gly Gly Ser Gly Gly Ser Asp Ile Leu Leu Thr Gln Ser Pro Val Ile
        35                  40                  45
Leu Ser Val Ser Pro Gly Glu Arg Val Ser Phe Ser Cys Arg Ala Ser
    50                  55                  60
Gln Ser Ile Gly Thr Asn Ile His Trp Tyr Gln Arg Thr Asn Gly
65                  70                  75                  80
Ser Pro Arg Leu Leu Ile Lys Tyr Ala Ser Glu Ser Ile Ser Gly Ile
                85                  90                  95
Pro Ser Arg Phe Ser Gly Ser Gly Ser Gly Thr Asp Phe Thr Leu Ser
            100                 105                 110
Ile Asn Ser Val Glu Ser Glu Asp Ile Ala Asp Tyr Tyr Cys Gln Gln
        115                 120                 125
Asn Asn Asn Trp Pro Thr Thr Phe Gly Ala Gly Thr Lys Leu Glu Leu
130                 135                 140
Lys Arg Thr Val Ala Ala Pro Ser Val Phe Ile Phe Pro Pro Ser Asp
145                 150                 155                 160
Glu Gln Leu Lys Ser Gly Thr Ala Ser Val Val Cys Leu Leu Asn Asn
                165                 170                 175
Phe Tyr Pro Arg Glu Ala Lys Val Gln Trp Lys Val Asp Asn Ala Leu
            180                 185                 190
Gln Ser Gly Asn Ser Gln Glu Ser Val Thr Glu Gln Asp Ser Lys Asp
        195                 200                 205
Ser Thr Tyr Ser Leu Ser Ser Thr Leu Thr Leu Ser Lys Ala Asp Tyr
    210                 215                 220
Glu Lys His Lys Val Tyr Ala Cys Glu Val Thr His Gln Gly Leu Ser
225                 230                 235                 240
Ser Pro Val Thr Lys Ser Phe Asn Arg Gly Glu Cys
                245                 250
```

<210> SEQ ID NO 187
<211> LENGTH: 2238
<212> TYPE: DNA
<213> ORGANISM: Artificial Sequence
<220> FEATURE:
<223> OTHER INFORMATION: synthetic

<400> SEQUENCE: 187

```
atgatgtatt gcggtgggaa tgaggtgttg tgcgggccgc gggttggctc gagcggtggc      60
agcggtggct ctggtggtat ctcttccgga ctgctgtccg gcagatccga caatcacggc     120
ggcggttctc agaccgtggt cacacaggag ccctcactga cagtgagccc tggcgggacc     180
gtcacactga cttgtcgcag ttcaactggc gccgtgacta ccagcaatta cgctaactgg     240
gtccagcaga aaccaggaca ggcaccacga ggactgatcg gaggaactaa taagagagca     300
ccaggaaccc ctgcaaggtt ctccggatct ctgctggggg gaaaagccgc tctgacactg     360
agcggcgtgc agcctgagga cgaagctgag tactattgcg cactgtggta ctccaacctg     420
```

```
tgggtgtttg gcggggggaac taagctgacc gtcctgggag gaggaggaag cggaggagga      480
gggagcggag gaggaggatc cgaagtgcag ctggtcgaga gcggaggagg actggtgcag      540
ccaggaggat ccctgaagct gtcttgtgca gccagtggct tcaccttcaa cacttacgca      600
atgaactggg tgcggcaggc acctgggaag ggactggaat gggtcgcccg gatcagatct      660
aaatacaata actatgccac ctactatgct gacagtgtga aggataggtt caccatttca      720
cgcgacgata gcaaaaacac agcttatctg cagatgaata acctgaagac cgaggataca      780
gcagtgtact attgcgtcag acacggcaat tcgggaact cttacgtgag ttggtttgcc       840
tattggggac aggggacact ggtcaccgtc tcctcaggag gtggtggatc ccaggtgcag      900
ctgaaacaga gcggcccggg cctggtgcag ccgagccaga gcctgagcat acctgcacc       960 gtgagcggct ttagcctgac caactatggc gtgcattggg tgcgccagag cccgggcaaa     1020
ggcctggaat ggctgggcgt gatttggagc ggcggcaaca ccgattataa caccccgttt     1080
accagccgcc tgagcattaa caaagataac agcaaaagcc aggtgttttt taaaatgaac     1140
agcctgcaaa gccaggatac cgcgatttat tattgcgcgc gcgcgctgac ctattatgat     1200
tatgaatttg cgtattgggg ccagggcacc ctggtgaccg tgagcgcggc tagcaccaag     1260
ggcccatcgg tcttccccct ggcaccctcc tccaagagca cctctggggg cacagcggcc     1320
ctgggctgcc tggtcaagga ctacttcccc gaaccggtga cggtgtcgtg gaactcaggc     1380
gccctgacca gcggcgtgca caccttcccg gctgtcctac agtcctcagg actctactcc     1440
ctcagcagcg tggtgaccgt gccctccagc agcttgggca cccagaccta catctgcaac     1500
gtgaatcaca agcccagcaa caccaaggtg gacaagaaag ttgagcccaa atcttgtgac     1560
aaaactcaca catgcccacc gtgcccagca cctgaactcc tggggggacc gtcagtcttc     1620
ctcttccccc caaaacccaa ggacaccctc atgatctccc ggacccctga ggtcacatgc     1680
gtggtggtgg acgtgagcca cgaagaccct gaggtcaagt tcaactggta cgtggacggc     1740
gtggaggtgc ataatgccaa gacaaagccg cgggaggagc agtaccagag cacgtaccgt     1800
gtggtcagcg tcctcaccgt cctgcaccag gactggctga atggcaagga gtacaagtgc     1860
aaggtctcca acaaagccct cccagccccc atcgagaaaa ccatctccaa agccaaaggg     1920
cagccccgag aaccacaggt gtacaccctg cccccatccc gggaggagat gaccaagaac     1980
caggtcagcc tgacctgcct ggtcaaaggc ttctatccca gcgacatcgc cgtggagtgg     2040
gagagcaatg ggcagccgga gaacaactac aagaccacgc ctcccgtgct ggactccgac     2100 ggctcctttct tcctctacag caagctcacc gtggacaaga gcaggtggca gcaggggaac     2160
gtcttctcat gctccgtgat gcatgaggct ctgcacaacc actacacgca agagagcctc     2220
tccctgtctc cgggtaaa                                                   2238
```

<210> SEQ ID NO 188
<211> LENGTH: 746
<212> TYPE: PRT
<213> ORGANISM: Artificial Sequence
<220> FEATURE:
<223> OTHER INFORMATION: synthetic

<400> SEQUENCE: 188

```
Met Met Tyr Cys Gly Gly Asn Glu Val Leu Cys Gly Pro Arg Val Gly
1               5                   10                  15

Ser Ser Gly Gly Ser Gly Gly Ser Gly Gly Ile Ser Ser Gly Leu Leu
            20                  25                  30
```

-continued

```
Ser Gly Arg Ser Asp Asn His Gly Gly Ser Gln Thr Val Val Thr
         35                  40                  45
Gln Glu Pro Ser Leu Thr Val Ser Pro Gly Gly Thr Val Thr Leu Thr
 50                  55                  60
Cys Arg Ser Ser Thr Gly Ala Val Thr Thr Ser Asn Tyr Ala Asn Trp
 65                  70                  75                  80
Val Gln Gln Lys Pro Gly Gln Ala Pro Arg Gly Leu Ile Gly Gly Thr
                 85                  90                  95
Asn Lys Arg Ala Pro Gly Thr Pro Ala Arg Phe Ser Gly Ser Leu Leu
             100                 105                 110
Gly Gly Lys Ala Ala Leu Thr Leu Ser Gly Val Gln Pro Glu Asp Glu
         115                 120                 125
Ala Glu Tyr Tyr Cys Ala Leu Trp Tyr Ser Asn Leu Trp Val Phe Gly
 130                 135                 140
Gly Gly Thr Lys Leu Thr Val Leu Gly Gly Gly Ser Gly Gly Gly
145                 150                 155                 160
Gly Ser Gly Gly Gly Ser Glu Val Gln Leu Val Glu Ser Gly Gly
                 165                 170                 175
Gly Leu Val Gln Pro Gly Gly Ser Leu Lys Leu Ser Cys Ala Ala Ser
             180                 185                 190
Gly Phe Thr Phe Asn Thr Tyr Ala Met Asn Trp Val Arg Gln Ala Pro
         195                 200                 205
Gly Lys Gly Leu Glu Trp Val Ala Arg Ile Arg Ser Lys Tyr Asn Asn
 210                 215                 220
Tyr Ala Thr Tyr Tyr Ala Asp Ser Val Lys Asp Arg Phe Thr Ile Ser
225                 230                 235                 240
Arg Asp Asp Ser Lys Asn Thr Ala Tyr Leu Gln Met Asn Asn Leu Lys
                 245                 250                 255
Thr Glu Asp Thr Ala Val Tyr Tyr Cys Val Arg His Gly Asn Phe Gly
             260                 265                 270
Asn Ser Tyr Val Ser Trp Phe Ala Tyr Trp Gly Gln Gly Thr Leu Val
         275                 280                 285
Thr Val Ser Ser Gly Gly Gly Gly Ser Gln Val Gln Leu Lys Gln Ser
 290                 295                 300
Gly Pro Gly Leu Val Gln Pro Ser Gln Ser Leu Ser Ile Thr Cys Thr
305                 310                 315                 320
Val Ser Gly Phe Ser Leu Thr Asn Tyr Gly Val His Trp Val Arg Gln
                 325                 330                 335
Ser Pro Gly Lys Gly Leu Glu Trp Leu Gly Val Ile Trp Ser Gly Gly
             340                 345                 350
Asn Thr Asp Tyr Asn Thr Pro Phe Thr Ser Arg Leu Ser Ile Asn Lys
         355                 360                 365
Asp Asn Ser Lys Ser Gln Val Phe Phe Lys Met Asn Ser Leu Gln Ser
 370                 375                 380
Gln Asp Thr Ala Ile Tyr Tyr Cys Ala Arg Ala Leu Thr Tyr Tyr Asp
385                 390                 395                 400
Tyr Glu Phe Ala Tyr Trp Gly Gln Gly Thr Leu Val Thr Val Ser Ala
                 405                 410                 415
Ala Ser Thr Lys Gly Pro Ser Val Phe Pro Leu Ala Pro Ser Ser Lys
             420                 425                 430
Ser Thr Ser Gly Gly Thr Ala Ala Leu Gly Cys Leu Val Lys Asp Tyr
         435                 440                 445
Phe Pro Glu Pro Val Thr Val Ser Trp Asn Ser Gly Ala Leu Thr Ser
```

Gly Val His Thr Phe Pro Ala Val Leu Gln Ser Ser Gly Leu Tyr Ser
465                 470                 475                 480

Leu Ser Ser Val Val Thr Val Pro Ser Ser Ser Leu Gly Thr Gln Thr
                485                 490                 495

Tyr Ile Cys Asn Val Asn His Lys Pro Ser Asn Thr Lys Val Asp Lys
            500                 505                 510

Lys Val Glu Pro Lys Ser Cys Asp Lys Thr His Thr Cys Pro Pro Cys
        515                 520                 525

Pro Ala Pro Glu Leu Leu Gly Gly Pro Ser Val Phe Leu Phe Pro Pro
530                 535                 540

Lys Pro Lys Asp Thr Leu Met Ile Ser Arg Thr Pro Glu Val Thr Cys
545                 550                 555                 560

Val Val Val Asp Val Ser His Glu Asp Pro Glu Val Lys Phe Asn Trp
                565                 570                 575

Tyr Val Asp Gly Val Glu Val His Asn Ala Lys Thr Lys Pro Arg Glu
            580                 585                 590

Glu Gln Tyr Gln Ser Thr Tyr Arg Val Val Ser Val Leu Thr Val Leu
        595                 600                 605

His Gln Asp Trp Leu Asn Gly Lys Glu Tyr Lys Cys Lys Val Ser Asn
610                 615                 620

Lys Ala Leu Pro Ala Pro Ile Glu Lys Thr Ile Ser Lys Ala Lys Gly
625                 630                 635                 640

Gln Pro Arg Glu Pro Gln Val Tyr Thr Leu Pro Pro Ser Arg Glu Glu
                645                 650                 655

Met Thr Lys Asn Gln Val Ser Leu Thr Cys Leu Val Lys Gly Phe Tyr
            660                 665                 670

Pro Ser Asp Ile Ala Val Glu Trp Glu Ser Asn Gly Gln Pro Glu Asn
        675                 680                 685

Asn Tyr Lys Thr Thr Pro Pro Val Leu Asp Ser Asp Gly Ser Phe Phe
690                 695                 700

Leu Tyr Ser Lys Leu Thr Val Asp Lys Ser Arg Trp Gln Gln Gly Asn
705                 710                 715                 720

Val Phe Ser Cys Ser Val Met His Glu Ala Leu His Asn His Tyr Thr
                725                 730                 735

Gln Lys Ser Leu Ser Leu Ser Pro Gly Lys
            740                 745

<210> SEQ ID NO 189
<211> LENGTH: 780
<212> TYPE: DNA
<213> ORGANISM: Artificial Sequence
<220> FEATURE:
<223> OTHER INFORMATION: synthetic

<400> SEQUENCE: 189
tgcatctcac ctcgtggttg tccggacggc ccatacgtca tgtacggctc gagcggtggc      60
agcggtggct ctggtggatc cggtattagc agtggtctgt taagcggtcg tagcgataat     120
catggcagta gcgtacccca gatcttgctg acccagagcc cggtgattct gagcgtgagc     180
ccgggcgaac gtgtgagctt tagctgccgc gcgagccaga gcattggcac caacattcat     240
tggtatcagc agcgcaccaa cggcagcccg cgcctgctga ttaaatatgc gagcgaaagc     300
attagcggca ttccgagccg ctttagcggc agcggcagcg gcaccgattt taccctgagc     360
attaacagcg tggaaagcga agatattgcg gattattatt gccagcagaa caacaactgg     420

```
ccgaccacct tggcgcggg caccaaactg gaactgaaac gtacggtggc tgcaccatct    480
gtcttcatct tcccgccatc tgatgagcag ttgaaatctg gaactgcctc tgttgtgtgc    540
ctgctgaata acttctatcc cagagaggcc aaagtacagt ggaaggtgga taacgccctc    600
caatcgggta actcccagga gagtgtcaca gagcaggaca gcaaggacag cacctacagc    660
ctcagcagca ccctgacgct gagcaaagca gactacgaga acacaaagt ctacgcctgc    720 gaagtcaccc atcagggcct gagctcgccc gtcacaaaga gcttcaacag gggagagtgt    780
```

<210> SEQ ID NO 190
<211> LENGTH: 260
<212> TYPE: PRT
<213> ORGANISM: Artificial Sequence
<220> FEATURE:
<223> OTHER INFORMATION: synthetic

<400> SEQUENCE: 190

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Ser Gly Ile Ser Ser Gly
            20                  25                  30

Leu Leu Ser Gly Arg Ser Asp Asn His Gly Ser Ser Gly Thr Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260
```

<210> SEQ ID NO 191
<211> LENGTH: 18
<212> TYPE: DNA
<213> ORGANISM: Artificial Sequence

```
<220> FEATURE:
<223> OTHER INFORMATION: synthetic

<400> SEQUENCE: 191
caaggccagt ctggatcc                                                     18

<210> SEQ ID NO 192
<211> LENGTH: 2226
<212> TYPE: DNA
<213> ORGANISM: Artificial Sequence
<220> FEATURE:
<223> OTHER INFORMATION: synthetic

<400> SEQUENCE: 192
ggttatctgt ggggttgcga gtggaattgc ggagggatca ctacaggctc gagcggtggc        60
agcggtggct ctggtggtct gagcggccgt ccgataatc atggcggcgg ttctcaaact        120
gtagtaactc aagaaccaag cttctccgtc tcccctgggg aacagtcac acttacctgc        180 cgaagtagta caggtgctgt tacgaccagt aactatgcca attgggtaca acaaacgcct       240
ggtcaggctc cgcgcggatt gataggaggc acgaataaac gggcacccgg tgtcccggac       300
agattcagcg gaagcatact cggtaataag gcagctctta ctatcactgg ggcccaagct       360
gatgatgaaa gtgattatta ttgtgcgctc tggtacagca acctctgggt gtttggggt        420 ggcacgaaac ttactgtctt gggcggcggc ggatcagggg gaggtggctc tggaggagga       480
ggctcagaag tccaactggt cgaatccggg ggagggctcg tacagccggg tgggtccctc       540
aaactctctt gtgcggcctc agggtttacc ttcagtacat acgcgatgaa ttgggtccgg       600
caggccagtg ggaaagggct cgaatgggta ggacgaatcc gatcaaaata caacaactac       660
gctacttatt acgctgattc cgtgaaggac agattcacaa tatcccgcga cgatagcaag       720
aatacggcat atcttcagat gaattctctt aaaactgagg ataccgctgt gtattactgc       780
acaagacatg gtaattttgg aaactcatat gtctcttggt tcgcttattg gggacagggc       840
acgttggtta ccgtgtctag cggaggtggt ggatcccagg tgcagctgaa acagagcggc       900
ccgggcctgg tgcagccgag ccagagcctg agcattacct gcaccgtgag cggctttagc       960
ctgaccaact atggcgtgca ttgggtgcgc cagagcccgg gcaaaggcct ggaatggctg      1020
ggcgtgattt ggagcggcgg caacaccgat tataacaccc cgtttaccag ccgcctgagc      1080
attaacaaag ataacagcaa aagccaggtg tttttaaaa tgaacagcct gcaaagccag      1140
gataccgcga tttattattg cgcgcgcgcg ctgacctatt atgattatga atttgcgtat      1200
tggggccagg gcaccctggt gaccgtgagc gcggctagca ccaagggccc atcggtcttc      1260
cccctggcac cctcctccaa gagcacctct gggggcacag cggccctggg ctgcctggtc      1320
aaggactact ccccgaacc ggtgacggtg tcgtggaact caggcgccct gaccagcggc       1380
gtgcacacct tcccggctgt cctacagtcc tcaggactct actccctcag cagcgtggtg      1440
accgtgccct ccagcagctt gggcacccag acctacatct gcaacgtgaa tcacaagccc      1500
agcaacacca aggtggacaa gaaagttgag cccaaatctt gtgacaaaac tcacacatgc      1560
ccaccgtgcc cagcacctga atttgaaggg gaccgtcag tcttcctctt ccccccaaaa      1620
cccaaggaca cctcatgat ctcccggacc cctgaggtca catgcgtggt ggtggacgtg       1680
agccacgaag accctgaggt caagttcaac tggtacgtgg acggcgtgga ggtgcataat      1740
gccaagacaa agccgcggga ggagcagtac aatagcacgt accgtgtggt cagcgtcctc      1800
accgtcctgc accaggactg gctgaatggc aaggagtaca agtgcaaggt ctccaacaaa      1860
```

```
gccctcccag cctcaatcga gaaaaccatc tccaaagcca aagggcagcc ccgagaacca    1920
caggtgtaca ccctgccccc atcccgggag gagatgacca agaaccaggt cagcctgacc    1980
tgcctggtca aaggcttcta tcccagcgac atcgccgtgg agtgggagag caatgggcag    2040
ccggagaaca actacaagac cacgcctccc gtgctggact ccgacggctc cttcttcctc    2100
tacagcaagc tcaccgtgga caagagcagg tggcagcagg ggaacgtctt ctcatgctcc    2160
gtgatgcatg aggctctgca caaccactac acgcagaaga gcctctccct gtctccgggt    2220
aaatga                                                               2226
```

<210> SEQ ID NO 193
<211> LENGTH: 741
<212> TYPE: PRT
<213> ORGANISM: Artificial Sequence
<220> FEATURE:
<223> OTHER INFORMATION: synthetic

<400> SEQUENCE: 193

```
Gly Tyr Leu Trp Gly Cys Glu Trp Asn Cys Gly Gly Ile Thr Thr Gly
1               5                   10                  15

Ser Ser Gly Gly Ser Gly Gly Ser Gly Gly Leu Ser Gly Arg Ser Asp
            20                  25                  30

Asn His Gly Gly Gly Ser Gln Thr Val Val Thr Gln Glu Pro Ser Phe
        35                  40                  45

Ser Val Ser Pro Gly Gly Thr Val Thr Leu Thr Cys Arg Ser Ser Thr
    50                  55                  60

Gly Ala Val Thr Thr Ser Asn Tyr Ala Asn Trp Val Gln Gln Thr Pro
65                  70                  75                  80

Gly Gln Ala Pro Arg Gly Leu Ile Gly Gly Thr Asn Lys Arg Ala Pro
                85                  90                  95

Gly Val Pro Asp Arg Phe Ser Gly Ser Ile Leu Gly Asn Lys Ala Ala
            100                 105                 110

Leu Thr Ile Thr Gly Ala Gln Ala Asp Asp Glu Ser Asp Tyr Tyr Cys
        115                 120                 125

Ala Leu Trp Tyr Ser Asn Leu Trp Val Phe Gly Gly Gly Thr Lys Leu
    130                 135                 140

Thr Val Leu Gly Gly Gly Gly Ser Gly Gly Gly Gly Ser Gly Gly Gly
145                 150                 155                 160

Gly Ser Glu Val Gln Leu Val Glu Ser Gly Gly Gly Leu Val Gln Pro
                165                 170                 175

Gly Gly Ser Leu Lys Leu Ser Cys Ala Ala Ser Gly Phe Thr Phe Ser
            180                 185                 190

Thr Tyr Ala Met Asn Trp Val Arg Gln Ala Ser Gly Lys Gly Leu Glu
        195                 200                 205

Trp Val Gly Arg Ile Arg Ser Lys Tyr Asn Asn Tyr Ala Thr Tyr Tyr
    210                 215                 220

Ala Asp Ser Val Lys Asp Arg Phe Thr Ile Ser Arg Asp Asp Ser Lys
225                 230                 235                 240

Asn Thr Ala Tyr Leu Gln Met Asn Ser Leu Lys Thr Glu Asp Thr Ala
                245                 250                 255

Val Tyr Tyr Cys Thr Arg His Gly Asn Phe Gly Asn Ser Tyr Val Ser
            260                 265                 270

Trp Phe Ala Tyr Trp Gly Gln Gly Thr Leu Val Thr Val Ser Ser Gly
        275                 280                 285

Gly Gly Gly Ser Gln Val Gln Leu Lys Gln Ser Gly Pro Gly Leu Val
```

```
              290                 295                 300
Gln Pro Ser Gln Ser Leu Ser Ile Thr Cys Thr Val Ser Gly Phe Ser
305                 310                 315                 320

Leu Thr Asn Tyr Gly Val His Trp Val Arg Gln Ser Pro Lys Gly
            325                 330                 335

Leu Glu Trp Leu Gly Val Ile Trp Ser Gly Gly Asn Thr Asp Tyr Asn
            340                 345                 350

Thr Pro Phe Thr Ser Arg Leu Ser Ile Asn Lys Asp Asn Ser Lys Ser
            355                 360                 365

Gln Val Phe Phe Lys Met Asn Ser Leu Gln Ser Gln Asp Thr Ala Ile
            370                 375                 380

Tyr Tyr Cys Ala Arg Ala Leu Thr Tyr Tyr Asp Tyr Glu Phe Ala Tyr
385                 390                 395                 400

Trp Gly Gln Gly Thr Leu Val Thr Val Ser Ala Ser Thr Lys Gly
            405                 410                 415

Pro Ser Val Phe Pro Leu Ala Pro Ser Ser Lys Ser Thr Ser Gly Gly
            420                 425                 430

Thr Ala Ala Leu Gly Cys Leu Val Lys Asp Tyr Phe Pro Glu Pro Val
            435                 440                 445

Thr Val Ser Trp Asn Ser Gly Ala Leu Thr Ser Gly Val His Thr Phe
            450                 455                 460

Pro Ala Val Leu Gln Ser Ser Gly Leu Tyr Ser Leu Ser Ser Val Val
465                 470                 475                 480

Thr Val Pro Ser Ser Ser Leu Gly Thr Gln Thr Tyr Ile Cys Asn Val
            485                 490                 495

Asn His Lys Pro Ser Asn Thr Lys Val Asp Lys Lys Val Glu Pro Lys
            500                 505                 510

Ser Cys Asp Lys Thr His Thr Cys Pro Pro Cys Pro Ala Pro Glu Phe
            515                 520                 525

Glu Gly Gly Pro Ser Val Phe Leu Phe Pro Pro Lys Pro Lys Asp Thr
            530                 535                 540

Leu Met Ile Ser Arg Thr Pro Glu Val Thr Cys Val Val Val Asp Val
545                 550                 555                 560

Ser His Glu Asp Pro Glu Val Lys Phe Asn Trp Tyr Val Asp Gly Val
            565                 570                 575

Glu Val His Asn Ala Lys Thr Lys Pro Arg Glu Glu Gln Tyr Asn Ser
            580                 585                 590

Thr Tyr Arg Val Val Ser Val Leu Thr Val Leu His Gln Asp Trp Leu
            595                 600                 605

Asn Gly Lys Glu Tyr Lys Cys Lys Val Ser Asn Lys Ala Leu Pro Ala
            610                 615                 620

Ser Ile Glu Lys Thr Ile Ser Lys Ala Lys Gly Gln Pro Arg Glu Pro
625                 630                 635                 640

Gln Val Tyr Thr Leu Pro Pro Ser Arg Glu Glu Met Thr Lys Asn Gln
            645                 650                 655

Val Ser Leu Thr Cys Leu Val Lys Gly Phe Tyr Pro Ser Asp Ile Ala
            660                 665                 670

Val Glu Trp Glu Ser Asn Gly Gln Pro Glu Asn Asn Tyr Lys Thr Thr
            675                 680                 685

Pro Pro Val Leu Asp Ser Asp Gly Ser Phe Phe Leu Tyr Ser Lys Leu
            690                 695                 700

Thr Val Asp Lys Ser Arg Trp Gln Gln Gly Asn Val Phe Ser Cys Ser
705                 710                 715                 720
```

Val Met His Glu Ala Leu His Asn His Tyr Thr Gln Lys Ser Leu Ser
            725                 730                 735

Leu Ser Pro Gly Lys
        740

<210> SEQ ID NO 194
<211> LENGTH: 2226
<212> TYPE: DNA
<213> ORGANISM: Artificial Sequence
<220> FEATURE:
<223> OTHER INFORMATION: synthetic

<400> SEQUENCE: 194

```
ggttatctgt ggggttgcga gtggaattgc ggagggatca ctacaggctc gagcggtggc      60
agcggtggct ctggtggtct gagcggccgt tccgataatc atggcggcgg ttctcaaact     120
gtagtaactc aagaaccaag cttctccgtc tcccctgggg aacagtcac acttacctgc      180
cgaagtagta caggtgctgt tacgaccagt aactatgcca attgggtaca acaaacgcct     240
ggtcaggctc cgcgcggatt gataggaggc acgaataaac gggcacccgg tgtcccggac     300
agattcagcg gaagcatact cggtaataag gcagctctta ctatcactgg ggcccaagct     360
gatgatgaaa gtgattatta ttgtgcgctc tggtacagca acctctgggt gtttggggt      420
ggcacgaaac ttactgtctt ggcggcggc ggatcagggg gaggtggctc tggaggagga     480
ggctcagaag tccaactggt cgaatccggg ggagggctcg tacagccggg tgggtccctc     540
aaactctctt gtgcggcctc agggtttacc ttcagtacat acgcgatgaa ttgggtccgg     600
caggccagtg ggaagggct cgaatgggta ggacgaatcc gatcaaaata caacaactac     660
gctacttatt acgctgattc cgtgaaggac agattcacaa tatcccgcga cgatagcaag     720
aatacggcat atcttcagat gaattctctt aaaactgagg ataccgctgt gtattactgc     780
acaagacatg gtaattttgg aaactcatat gtctcttggt tcgcttattg gggacagggc     840
acgttggtta ccgtgtctag cggaggtggt ggatcccagg tgcagctgaa acagagcggc     900
ccgggcctgg tgcagccgag ccagagcctg agcattacct gcaccgtgag cggctttagc     960
ctgaccaact atggcgtgca ttgggtgcgc cagagcccgg gcaaaggcct ggaatggctg    1020
ggcgtgattt ggagcggcgg caacaccgat tataacaccc cgtttaccag ccgcctgagc    1080
attaacaaag ataacagcaa aagccaggtg ttttttaaaa tgaacagcct gcaaagccag    1140
gataccgcga tttattattg cgcgcgcgcg ctgacctatt atgattatga atttgcgtat    1200
tggggccagg gcaccctggt gaccgtgagc gcggctagca ccaagggccc atcggtcttc    1260
cccctggcac cctcctccaa gagcacctct ggggggcacag cggccctggg ctgcctggtc    1320
aaggactact ccccgaacc ggtgacggtg tcgtggaact caggcgccct gaccagcggc    1380
gtgcacacct tcccggctgt cctacagtcc tcaggactct actccctcag cagcgtggtg    1440
accgtgccct ccagcagctt gggcacccag acctacatct gcaacgtgaa tcacaagccc    1500
agcaacacca aggtggacaa gaaagttgag cccaaatctt gtgacaaaac tcacacatgc    1560
ccaccgtgcc cagcacctga atttgaaggg gaccgtcag tcttcctctt ccccccaaaa    1620
cccaaggaca cctcatgat  ctcccggacc cctgaggtca catgcgtggt ggtgacgtg    1680
agccacgaag accctgaggt caagttcaac tggtacgtgg acggcgtgga ggtgcataat    1740
gccaagacaa agccgcggga ggagcagtac cagagcacgt accgtgtggt cagcgtcctc    1800
accgtcctgc accaggactg gctgaatggc aaggagtaca agtgcaaggt ctccaacaaa    1860
```

-continued

```
gccctcccag cctcaatcga gaaaaccatc tccaaagcca aagggcagcc ccgagaacca   1920
caggtgtaca ccctgccccc atcccgggag gagatgacca agaaccaggt cagcctgacc   1980
tgcctggtca aaggcttcta tcccagcgac atcgccgtgg agtgggagag caatgggcag   2040
ccggagaaca actacaagac cacgcctccc gtgctggact ccgacggctc cttcttcctc   2100
tacagcaagc tcaccgtgga caagagcagg tggcagcagg ggaacgtctt ctcatgctcc   2160
gtgatgcatg aggctctgca caaccactac acgcagaaga gcctctccct gtctccgggt   2220
aaatga                                                              2226
```

<210> SEQ ID NO 195
<211> LENGTH: 741
<212> TYPE: PRT
<213> ORGANISM: Artificial Sequence
<220> FEATURE:
<223> OTHER INFORMATION: synthetic

<400> SEQUENCE: 195

```
Gly Tyr Leu Trp Gly Cys Glu Trp Asn Cys Gly Gly Ile Thr Thr Gly
1               5                   10                  15

Ser Ser Gly Gly Ser Gly Gly Ser Gly Gly Leu Ser Gly Arg Ser Asp
                20                  25                  30

Asn His Gly Gly Gly Ser Gln Thr Val Val Thr Gln Glu Pro Ser Phe
            35                  40                  45

Ser Val Ser Pro Gly Gly Thr Val Thr Leu Thr Cys Arg Ser Ser Thr
        50                  55                  60

Gly Ala Val Thr Thr Ser Asn Tyr Ala Asn Trp Val Gln Gln Thr Pro
65                  70                  75                  80

Gly Gln Ala Pro Arg Gly Leu Ile Gly Gly Thr Asn Lys Arg Ala Pro
                85                  90                  95

Gly Val Pro Asp Arg Phe Ser Gly Ser Ile Leu Gly Asn Lys Ala Ala
            100                 105                 110

Leu Thr Ile Thr Gly Ala Gln Ala Asp Asp Glu Ser Asp Tyr Tyr Cys
        115                 120                 125

Ala Leu Trp Tyr Ser Asn Leu Trp Val Phe Gly Gly Gly Thr Lys Leu
    130                 135                 140

Thr Val Leu Gly Gly Gly Gly Ser Gly Gly Gly Gly Ser Gly Gly Gly
145                 150                 155                 160

Gly Ser Glu Val Gln Leu Val Glu Ser Gly Gly Leu Val Gln Pro
                165                 170                 175

Gly Gly Ser Leu Lys Leu Ser Cys Ala Ala Ser Gly Phe Thr Phe Ser
            180                 185                 190

Thr Tyr Ala Met Asn Trp Val Arg Gln Ala Ser Gly Lys Gly Leu Glu
        195                 200                 205

Trp Val Gly Arg Ile Arg Ser Lys Tyr Asn Asn Tyr Ala Thr Tyr Tyr
    210                 215                 220

Ala Asp Ser Val Lys Asp Arg Phe Thr Ile Ser Arg Asp Asp Ser Lys
225                 230                 235                 240

Asn Thr Ala Tyr Leu Gln Met Asn Ser Leu Lys Thr Glu Asp Thr Ala
                245                 250                 255

Val Tyr Tyr Cys Thr Arg His Gly Asn Phe Gly Asn Ser Tyr Val Ser
            260                 265                 270

Trp Phe Ala Tyr Trp Gly Gln Gly Thr Leu Val Thr Val Ser Ser Gly
        275                 280                 285

Gly Gly Gly Ser Gln Val Gln Leu Lys Gln Ser Gly Pro Gly Leu Val
```

```
            290                 295                 300
Gln Pro Ser Gln Ser Leu Ser Ile Thr Cys Thr Val Ser Gly Phe Ser
305                 310                 315                 320

Leu Thr Asn Tyr Gly Val His Trp Val Arg Gln Ser Pro Lys Gly
                325                 330                 335

Leu Glu Trp Leu Gly Val Ile Trp Ser Gly Gly Asn Thr Asp Tyr Asn
                340                 345                 350

Thr Pro Phe Thr Ser Arg Leu Ser Ile Asn Lys Asp Asn Ser Lys Ser
                355                 360                 365

Gln Val Phe Phe Lys Met Asn Ser Leu Gln Ser Gln Asp Thr Ala Ile
370                 375                 380

Tyr Tyr Cys Ala Arg Ala Leu Thr Tyr Tyr Asp Tyr Glu Phe Ala Tyr
385                 390                 395                 400

Trp Gly Gln Gly Thr Leu Val Thr Val Ser Ala Ala Ser Thr Lys Gly
                405                 410                 415

Pro Ser Val Phe Pro Leu Ala Pro Ser Ser Lys Ser Thr Ser Gly Gly
                420                 425                 430

Thr Ala Ala Leu Gly Cys Leu Val Lys Asp Tyr Phe Pro Glu Pro Val
                435                 440                 445

Thr Val Ser Trp Asn Ser Gly Ala Leu Thr Ser Gly Val His Thr Phe
                450                 455                 460

Pro Ala Val Leu Gln Ser Ser Gly Leu Tyr Ser Leu Ser Ser Val Val
465                 470                 475                 480

Thr Val Pro Ser Ser Ser Leu Gly Thr Gln Thr Tyr Ile Cys Asn Val
                485                 490                 495

Asn His Lys Pro Ser Asn Thr Lys Val Asp Lys Lys Val Glu Pro Lys
                500                 505                 510

Ser Cys Asp Lys Thr His Thr Cys Pro Pro Cys Pro Ala Pro Glu Phe
                515                 520                 525

Glu Gly Gly Pro Ser Val Phe Leu Phe Pro Pro Lys Pro Lys Asp Thr
                530                 535                 540

Leu Met Ile Ser Arg Thr Pro Glu Val Thr Cys Val Val Val Asp Val
545                 550                 555                 560

Ser His Glu Asp Pro Glu Val Lys Phe Asn Trp Tyr Val Asp Gly Val
                565                 570                 575

Glu Val His Asn Ala Lys Thr Lys Pro Arg Glu Glu Gln Tyr Gln Ser
                580                 585                 590

Thr Tyr Arg Val Val Ser Val Leu Thr Val Leu His Gln Asp Trp Leu
                595                 600                 605

Asn Gly Lys Glu Tyr Lys Cys Lys Val Ser Asn Lys Ala Leu Pro Ala
                610                 615                 620

Ser Ile Glu Lys Thr Ile Ser Lys Ala Lys Gly Gln Pro Arg Glu Pro
625                 630                 635                 640

Gln Val Tyr Thr Leu Pro Pro Ser Arg Glu Glu Met Thr Lys Asn Gln
                645                 650                 655

Val Ser Leu Thr Cys Leu Val Lys Gly Phe Tyr Pro Ser Asp Ile Ala
                660                 665                 670

Val Glu Trp Glu Ser Asn Gly Gln Pro Glu Asn Asn Tyr Lys Thr Thr
                675                 680                 685

Pro Pro Val Leu Asp Ser Asp Gly Ser Phe Phe Leu Tyr Ser Lys Leu
                690                 695                 700

Thr Val Asp Lys Ser Arg Trp Gln Gln Gly Asn Val Phe Ser Cys Ser
705                 710                 715                 720
```

Val Met His Glu Ala Leu His Asn His Tyr Thr Gln Lys Ser Leu Ser
            725                 730                 735

Leu Ser Pro Gly Lys
            740

<210> SEQ ID NO 196
<211> LENGTH: 2223
<212> TYPE: DNA
<213> ORGANISM: Artificial Sequence
<220> FEATURE:
<223> OTHER INFORMATION: synthetic

<400> SEQUENCE: 196

| | | | | | |
|---|---|---|---|---|---|
| ggttatctgt | ggggttgcga | gtggaattgc | ggagggatca | ctacaggctc | gagcggtggc | 60 |
| agcggtggct | ctggtggtct | gagcggccgt | tccgatgatc | atggcggcgg | ttctcaaact | 120 |
| gtagtaactc | aagaaccaag | cttctccgtc | tcccctgggg | aacagtcac | acttacctgc | 180 |
| cgaagtagta | caggtgctgt | tacgaccagt | aactatgcca | attgggtaca | acaaacgcct | 240 |
| ggtcaggctc | cgcgcggatt | gataggaggc | acgaataaac | gggcacccgg | tgtcccggac | 300 |
| agattcagcg | gaagcatact | cggtaataag | gcagctctta | ctatcactgg | ggcccaagct | 360 |
| gatgatgaaa | gtgattatta | ttgtgcgctc | tggtacagca | acctctgggt | gtttggggt | 420 |
| ggcacgaaac | ttactgtctt | gggcggcggc | ggatcagggg | gaggtggctc | tggaggagga | 480 |
| ggctcagaag | tccaactggt | cgaatccggg | ggagggctcg | tacagccggg | tgggtccctc | 540 |
| aaactctctt | gtgcggcctc | agggtttacc | ttcagtacat | acgcgatgaa | ttgggtccgg | 600 |
| caggccagtg | ggaaagggct | cgaatgggta | ggacgaatcc | gatcaaaata | caacaactac | 660 |
| gctacttatt | acgctgattc | cgtgaaggac | agattcacaa | tatcccgcga | cgatagcaag | 720 |
| aatacggcat | atcttcagat | gaattctctt | aaaactgagg | ataccgctgt | gtattactgc | 780 |
| acaagacatg | gtaattttgg | aaactcatat | gtctcttggt | tcgcttattg | gggacagggc | 840 |
| acgttggtta | ccgtgtctag | cggaggtggt | ggatcccagt | gcagctgaa | acagagcggc | 900 |
| ccgggcctgg | tgcagccgag | ccagagcctg | agcattacct | gcaccgtgag | cggctttagc | 960 |
| ctgaccaact | atggcgtgca | ttgggtgcgc | cagagcccgg | gcaaaggcct | ggaatggctg | 1020 |
| ggcgtgattt | ggagcggcgg | caacaccgat | tataacaccc | cgtttaccag | ccgcctgagc | 1080 |
| attaacaaag | ataacagcaa | aagccaggtg | ttttttaaaa | tgaacagcct | gcaaagccag | 1140 |
| gataccgcga | tttattattg | cgcgcgcgcg | ctgacctatt | atgattatga | atttgcgtat | 1200 |
| tggggccagg | gcacccctggt | gaccgtgagc | gcggctagca | ccaagggccc | atcggtcttc | 1260 |
| cccctggcac | cctcctccaa | gagcacctct | gggggcacag | cggccctggg | ctgcctggtc | 1320 |
| aaggactact | tccccgaacc | ggtgacggtg | tcgtggaact | caggcgccct | gaccagcggc | 1380 |
| gtgcacacct | tcccggctgt | cctacagtcc | tcaggactct | actccctcag | cagcgtggtg | 1440 |
| accgtgccct | ccagcagctt | gggcacccag | acctacatct | gcaacgtgaa | tcacaagccc | 1500 |
| agcaacacca | aggtggacaa | gaaagttgag | cccaaatctt | gtgacaaaac | tcacacatgc | 1560 |
| ccaccgtgcc | cagcacctga | atttgaaggg | ggaccgtcag | tcttcctctt | ccccccaaaa | 1620 |
| cccaaggaca | cctcatgat | ctcccggacc | cctgaggtca | catgcgtggt | ggtggacgtg | 1680 |
| agccacgaag | accctgaggt | caagttcaac | tggtacgtgg | acggcgtgga | ggtgcataat | 1740 |
| gccaagacaa | agccgcggga | ggagcagtac | cagagcacgt | accgtgtggt | cagcgtcctc | 1800 |
| accgtcctgc | accaggactg | gctgaatggc | aaggagtaca | agtgcaaggt | ctccaacaaa | 1860 |

```
gccctcccag cctcaatcga gaaaaccatc tccaaagcca agggcagcc ccgagaacca   1920 caggtgtaca ccctgccccc atcccgggag gagatgacca gaaccaggt cagcctgacc   1980 tgcctggtca aaggcttcta tcccagcgac atcgccgtgg agtgggagag caatgggcag   2040
ccggagaaca actacaagac cacgcctccc gtgctggact ccgacggctc cttcttcctc   2100
tacagcaagc tcaccgtgga caagagcagg tggcagcagg ggaacgtctt ctcatgctcc   2160
gtgatgcatg aggctctgca caaccactac acgcagaaga gcctctcccct gtctccgggt   2220 aaa                                                                 2223
```

<210> SEQ ID NO 197
<211> LENGTH: 741
<212> TYPE: PRT
<213> ORGANISM: Artificial Sequence
<220> FEATURE:
<223> OTHER INFORMATION: synthetic

<400> SEQUENCE: 197

```
Gly Tyr Leu Trp Gly Cys Glu Trp Asn Cys Gly Gly Ile Thr Thr Gly
1               5                   10                  15

Ser Ser Gly Gly Ser Gly Gly Ser Gly Gly Leu Ser Gly Arg Ser Asp
                20                  25                  30

Asp His Gly Gly Gly Ser Gln Thr Val Val Thr Gln Glu Pro Ser Phe
            35                  40                  45

Ser Val Ser Pro Gly Gly Thr Val Thr Leu Thr Cys Arg Ser Ser Thr
        50                  55                  60

Gly Ala Val Thr Thr Ser Asn Tyr Ala Asn Trp Val Gln Gln Thr Pro
65                  70                  75                  80

Gly Gln Ala Pro Arg Gly Leu Ile Gly Gly Thr Asn Lys Arg Ala Pro
                85                  90                  95

Gly Val Pro Asp Arg Phe Ser Gly Ser Ile Leu Gly Asn Lys Ala Ala
            100                 105                 110

Leu Thr Ile Thr Gly Ala Gln Ala Asp Asp Glu Ser Asp Tyr Tyr Cys
        115                 120                 125

Ala Leu Trp Tyr Ser Asn Leu Trp Val Phe Gly Gly Gly Thr Lys Leu
    130                 135                 140

Thr Val Leu Gly Gly Gly Gly Ser Gly Gly Gly Gly Ser Gly Gly Gly
145                 150                 155                 160

Gly Ser Glu Val Gln Leu Val Glu Ser Gly Gly Gly Leu Val Gln Pro
                165                 170                 175

Gly Gly Ser Leu Lys Leu Ser Cys Ala Ala Ser Gly Phe Thr Phe Ser
            180                 185                 190

Thr Tyr Ala Met Asn Trp Val Arg Gln Ala Ser Gly Lys Gly Leu Glu
        195                 200                 205

Trp Val Gly Arg Ile Arg Ser Lys Tyr Asn Asn Tyr Ala Thr Tyr Tyr
    210                 215                 220

Ala Asp Ser Val Lys Asp Arg Phe Thr Ile Ser Arg Asp Asp Ser Lys
225                 230                 235                 240

Asn Thr Ala Tyr Leu Gln Met Asn Ser Leu Lys Thr Glu Asp Thr Ala
                245                 250                 255

Val Tyr Tyr Cys Thr Arg His Gly Asn Phe Gly Asn Ser Tyr Val Ser
            260                 265                 270

Trp Phe Ala Tyr Trp Gly Gln Gly Thr Leu Val Thr Val Ser Ser Gly
        275                 280                 285

Gly Gly Gly Ser Gln Val Gln Leu Lys Gln Ser Gly Pro Gly Leu Val
```

-continued

```
            290                 295                 300
Gln Pro Ser Gln Ser Leu Ser Ile Thr Cys Thr Val Ser Gly Phe Ser
305                 310                 315                 320
Leu Thr Asn Tyr Gly Val His Trp Val Arg Gln Ser Pro Lys Gly
                325                 330                 335
Leu Glu Trp Leu Gly Val Ile Trp Ser Gly Gly Asn Thr Asp Tyr Asn
                340                 345                 350
Thr Pro Phe Thr Ser Arg Leu Ser Ile Asn Lys Asp Asn Ser Lys Ser
                355                 360                 365
Gln Val Phe Phe Lys Met Asn Ser Leu Gln Ser Gln Asp Thr Ala Ile
370                 375                 380
Tyr Tyr Cys Ala Arg Ala Leu Thr Tyr Tyr Asp Tyr Glu Phe Ala Tyr
385                 390                 395                 400
Trp Gly Gln Gly Thr Leu Val Thr Val Ser Ala Ala Ser Thr Lys Gly
                405                 410                 415
Pro Ser Val Phe Pro Leu Ala Pro Ser Ser Lys Ser Thr Ser Gly Gly
                420                 425                 430
Thr Ala Ala Leu Gly Cys Leu Val Lys Asp Tyr Phe Pro Glu Pro Val
                435                 440                 445
Thr Val Ser Trp Asn Ser Gly Ala Leu Thr Ser Gly Val His Thr Phe
                450                 455                 460
Pro Ala Val Leu Gln Ser Ser Gly Leu Tyr Ser Leu Ser Ser Val Val
465                 470                 475                 480
Thr Val Pro Ser Ser Ser Leu Gly Thr Gln Thr Tyr Ile Cys Asn Val
                485                 490                 495
Asn His Lys Pro Ser Asn Thr Lys Val Asp Lys Lys Val Glu Pro Lys
                500                 505                 510
Ser Cys Asp Lys Thr His Thr Cys Pro Pro Cys Pro Ala Pro Glu Phe
                515                 520                 525
Glu Gly Gly Pro Ser Val Phe Leu Phe Pro Pro Lys Pro Lys Asp Thr
                530                 535                 540
Leu Met Ile Ser Arg Thr Pro Glu Val Thr Cys Val Val Val Asp Val
545                 550                 555                 560
Ser His Glu Asp Pro Glu Val Lys Phe Asn Trp Tyr Val Asp Gly Val
                565                 570                 575
Glu Val His Asn Ala Lys Thr Lys Pro Arg Glu Glu Gln Tyr Gln Ser
                580                 585                 590
Thr Tyr Arg Val Val Ser Val Leu Thr Val Leu His Gln Asp Trp Leu
                595                 600                 605
Asn Gly Lys Glu Tyr Lys Cys Lys Val Ser Asn Lys Ala Leu Pro Ala
                610                 615                 620
Ser Ile Glu Lys Thr Ile Ser Lys Ala Lys Gly Gln Pro Arg Glu Pro
625                 630                 635                 640
Gln Val Tyr Thr Leu Pro Pro Ser Arg Glu Glu Met Thr Lys Asn Gln
                645                 650                 655
Val Ser Leu Thr Cys Leu Val Lys Gly Phe Tyr Pro Ser Asp Ile Ala
                660                 665                 670
Val Glu Trp Glu Ser Asn Gly Gln Pro Glu Asn Asn Tyr Lys Thr Thr
                675                 680                 685
Pro Pro Val Leu Asp Ser Asp Gly Ser Phe Phe Leu Tyr Ser Lys Leu
                690                 695                 700
Thr Val Asp Lys Ser Arg Trp Gln Gln Gly Asn Val Phe Ser Cys Ser
705                 710                 715                 720
```

Val Met His Glu Ala Leu His Asn His Tyr Thr Gln Lys Ser Leu Ser
            725                 730                 735

Leu Ser Pro Gly Lys
            740

<210> SEQ ID NO 198
<211> LENGTH: 768
<212> TYPE: DNA
<213> ORGANISM: Artificial Sequence
<220> FEATURE:
<223> OTHER INFORMATION: Synthetic

<400> SEQUENCE: 198
caaggtctta gttgtgaagg ttgggcgatg aatagagaac aatgtcgagc cggaggtggc      60
tcgagcggcg gctctatctc ttccggactg ctgtccggca gatccgacca gcacggcgga     120
ggatcccaaa tcctgctgac acagtctcct gtcatactga gtgtctcccc cggcgagaga     180
gtctctttct catgtcgggc cagtcagtct attgggacta acatacactg gtaccagcaa     240
cgcaccaacg gaagcccgcg cctgctgatt aaatatgcga gcgaaagcat tagcggcatt     300
ccgagccgct ttagcggcag cggcagcggc accgattta ccctgagcat taacagcgtg     360
gaaagcgaag atattgcgga ttattattgc cagcagaaca caactggcc gaccaccttt     420
ggcgcgggca ccaaactgga actgaaacgt acggtggctg caccatctgt cttcatcttc     480
ccgccatctg atgagcagtt gaaatctgga actgcctctg ttgtgtgcct gctgaataac     540
ttctatccca gagaggccaa agtacagtgg aaggtggata acgccctcca atcgggtaac     600
tcccaggaga gtgtcacaga gcaggacagc aaggacagca cctacagcct cagcagcacc     660
ctgacgctga gcaaagcaga ctacgagaaa cacaaagtct acgcctgcga agtcacccat     720
cagggcctga gctcgcccgt cacaaagagc ttcaacaggg gagagtgt                   768

<210> SEQ ID NO 199
<211> LENGTH: 254
<212> TYPE: PRT
<213> ORGANISM: Artificial Sequence
<220> FEATURE:
<223> OTHER INFORMATION: synthetic

<400> SEQUENCE: 199

Leu Ser Cys Glu Gly Trp Ala Met Asn Arg Glu Gln Cys Arg Ala Gly
1               5                   10                  15

Gly Gly Ser Ser Gly Gly Ser Ile Ser Ser Gly Leu Leu Ser Gly Arg
            20                  25                  30

Ser Asp Gln His Gly Gly Gly Ser Gln Ile Leu Leu Thr Gln Ser Pro
        35                  40                  45

Val Ile Leu Ser Val Ser Pro Gly Glu Arg Val Ser Phe Ser Cys Arg
    50                  55                  60

Ala Ser Gln Ser Ile Gly Thr Asn Ile His Trp Tyr Gln Gln Arg Thr
65                  70                  75                  80

Asn Gly Ser Pro Arg Leu Leu Ile Lys Tyr Ala Ser Glu Ser Ile Ser
                85                  90                  95

Gly Ile Pro Ser Arg Phe Ser Gly Ser Gly Ser Gly Thr Asp Phe Thr
            100                 105                 110

Leu Ser Ile Asn Ser Val Glu Ser Glu Asp Ile Ala Asp Tyr Tyr Cys
        115                 120                 125

Gln Gln Asn Asn Asn Trp Pro Thr Thr Phe Gly Ala Gly Thr Lys Leu
    130                 135                 140

```
Glu Leu Lys Arg Thr Val Ala Ala Pro Ser Val Phe Ile Phe Pro Pro
145                 150                 155                 160
Ser Asp Glu Gln Leu Lys Ser Gly Thr Ala Ser Val Val Cys Leu Leu
            165                 170                 175
Asn Asn Phe Tyr Pro Arg Glu Ala Lys Val Gln Trp Lys Val Asp Asn
        180                 185                 190
Ala Leu Gln Ser Gly Asn Ser Gln Glu Ser Val Thr Glu Gln Asp Ser
            195                 200                 205
Lys Asp Ser Thr Tyr Ser Leu Ser Ser Thr Leu Thr Leu Ser Lys Ala
    210                 215                 220
Asp Tyr Glu Lys His Lys Val Tyr Ala Cys Glu Val Thr His Gln Gly
225                 230                 235                 240
Leu Ser Ser Pro Val Thr Lys Ser Phe Asn Arg Gly Glu Cys
                245                 250
```

<210> SEQ ID NO 200
<211> LENGTH: 2238
<212> TYPE: DNA
<213> ORGANISM: Artificial Sequence
<220> FEATURE:
<223> OTHER INFORMATION: synthetic

<400> SEQUENCE: 200

```
ggttatctgt ggggttgcga gtggaattgc ggagggatca ctacaggctc gagcggtggc    60
agcggtggct ctggtggtat atcgagtgga ttgctgtctg gcagatctga cgatcacggc   120
ggcggttctc aaactgtagt aactcaagaa ccaagcttct ccgtctcccc tgggggaaca   180
gtcacactta cctgccgaag tagtacaggt gctgttacga ccagtaacta tgccaattgg   240
gtacaacaaa cgcctggtca ggctccgcgc ggattgatag gaggcacgaa taaacgggca   300
cccggtgtcc cggacagatt cagcggaagc atactcggta ataaggcagc tcttactatc   360
actgggccc aagctgatga tgaaagtgat tattattgtg cgctctggta cagcaacctc   420
tgggtgtttg ggggtggcac gaaacttact gtcttgggcg gcggcggatc agggggaggt   480
ggctctggag gaggaggctc agaagtccaa ctggtcgaat ccggggagg gctcgtacag   540
ccgggtgggt ccctcaaact ctcttgtgcg gcctcagggt ttaccttcag tacatacgcg   600
atgaattggg tccggcaggc cagtgggaaa gggctcgaat gggtaggacg aatccgatca   660
aaatacaaca actacgctac ttattacgct gattccgtga aggacagatt cacaatatcc   720
cgcgacgata gcaagaatac ggcatatctt cagatgaatt ctcttaaaac tgaggatacc   780
gctgtgtatt actgcacaag acatggtaat tttggaaact catatgtctc ttggttcgct   840
tattggggac agggcacgtt ggttaccgtg tctagcggag gtggtggatc ccaggtgcag   900
ctgaaacaga gcggcccggg cctggtgcag ccgagccaga gcctgagcat tacctgcacc   960
gtgagcggct ttagcctgac caactatggc gtgcattggg tgcgccagag cccgggcaaa  1020
ggcctggaat ggctgggcgt gatttggagc ggcggcaaca ccgattataa caccccgttt  1080
accagccgcc tgagcattaa caaagataac agcaaaagcc aggtgttttt taaaatgaac  1140
agcctgcaaa gccaggatac cgcgatttat tattgcgcgc gcgcgctgac ctattatgat  1200
tatgaatttg cgtattgggg ccagggcacc ctggtgaccg tgagcgcggc tagcaccaag  1260
ggcccatcgg tcttcccct ggcaccctc tccaagagca cctctggggg cacagcggcc  1320
ctgggctgcc tggtcaagga ctacttcccc gaaccggtga cggtgtcgtg gaactcaggc  1380
gccctgacca gcggcgtgca caccttcccg gctgtcctac agtcctcagg actctactcc  1440
```

```
ctcagcagcg tggtgaccgt gccctccagc agcttgggca cccagaccta catctgcaac    1500
gtgaatcaca agcccagcaa caccaaggtg gacaagaaag ttgagcccaa atcttgtgac    1560
aaaactcaca catgcccacc gtgcccagca cctgaatttg aaggggggacc gtcagtcttc   1620 ctcttccccc caaaacccaa ggacaccctc atgatctccc ggacccctga ggtcacatgc    1680
gtggtggtgg acgtgagcca cgaagaccct gaggtcaagt tcaactggta cgtggacggc    1740
gtggaggtgc ataatgccaa gacaaagccg cgggaggagc agtaccagag cacgtaccgt    1800
gtggtcagcg tcctcaccgt cctgcaccag gactggctga atggcaagga gtacaagtgc    1860
aaggtctcca acaaagccct cccagcctca atcgagaaaa ccatctccaa agccaaaggg    1920
cagccccgag aaccacaggt gtacaccctg cccccatccc gggaggagat gaccaagaac    1980
caggtcagcc tgacctgcct ggtcaaaggc ttctatccca gcgacatcgc cgtggagtgg    2040
gagagcaatg ggcagccgga gaacaactac aagaccacgc ctcccgtgct ggactccgac    2100
ggctccttct tcctctacag caagctcacc gtggacaaga gcaggtggca gcaggggaac    2160
gtcttctcat gctccgtgat gcatgaggct ctgcacaacc actacacgca gaagagcctc    2220
tccctgtctc cgggtaaa                                                 2238
```

<210> SEQ ID NO 201
<211> LENGTH: 746
<212> TYPE: PRT
<213> ORGANISM: Artificial Sequence
<220> FEATURE:
<223> OTHER INFORMATION: synthetic

<400> SEQUENCE: 201

```
Gly Tyr Leu Trp Gly Cys Glu Trp Asn Cys Gly Gly Ile Thr Thr Gly
1               5                   10                  15

Ser Ser Gly Gly Ser Gly Gly Ser Gly Gly Ile Ser Ser Gly Leu Leu
            20                  25                  30

Ser Gly Arg Ser Asp Asp His Gly Gly Gly Ser Gln Thr Val Val Thr
        35                  40                  45

Gln Glu Pro Ser Phe Ser Val Ser Pro Gly Gly Thr Val Thr Leu Thr
    50                  55                  60

Cys Arg Ser Ser Thr Gly Ala Val Thr Thr Ser Asn Tyr Ala Asn Trp
65                  70                  75                  80

Val Gln Gln Thr Pro Gly Gln Ala Pro Arg Gly Leu Ile Gly Gly Thr
                85                  90                  95

Asn Lys Arg Ala Pro Gly Val Pro Asp Arg Phe Ser Gly Ser Ile Leu
            100                 105                 110

Gly Asn Lys Ala Ala Leu Thr Ile Thr Gly Ala Gln Ala Asp Asp Glu
        115                 120                 125

Ser Asp Tyr Tyr Cys Ala Leu Trp Tyr Ser Asn Leu Trp Val Phe Gly
    130                 135                 140

Gly Gly Thr Lys Leu Thr Val Leu Gly Gly Gly Ser Gly Gly Gly
145                 150                 155                 160

Gly Ser Gly Gly Gly Gly Ser Glu Val Gln Leu Val Glu Ser Gly Gly
                165                 170                 175

Gly Leu Val Gln Pro Gly Gly Ser Leu Lys Leu Ser Cys Ala Ala Ser
            180                 185                 190

Gly Phe Thr Phe Ser Thr Tyr Ala Met Asn Trp Val Arg Gln Ala Ser
        195                 200                 205

Gly Lys Gly Leu Glu Trp Val Gly Arg Ile Arg Ser Lys Tyr Asn Asn
```

-continued

```
            210                 215                 220
Tyr Ala Thr Tyr Tyr Ala Asp Ser Val Lys Asp Arg Phe Thr Ile Ser
225                 230                 235                 240

Arg Asp Asp Ser Lys Asn Thr Ala Tyr Leu Gln Met Asn Ser Leu Lys
                245                 250                 255

Thr Glu Asp Thr Ala Val Tyr Tyr Cys Thr Arg His Gly Asn Phe Gly
            260                 265                 270

Asn Ser Tyr Val Ser Trp Phe Ala Tyr Trp Gly Gln Gly Thr Leu Val
        275                 280                 285

Thr Val Ser Ser Gly Gly Gly Ser Gln Val Gln Leu Lys Gln Ser
290                 295                 300

Gly Pro Gly Leu Val Gln Pro Ser Gln Ser Leu Ser Ile Thr Cys Thr
305                 310                 315                 320

Val Ser Gly Phe Ser Leu Thr Asn Tyr Gly Val His Trp Val Arg Gln
                325                 330                 335

Ser Pro Gly Lys Gly Leu Glu Trp Leu Gly Val Ile Trp Ser Gly Gly
            340                 345                 350

Asn Thr Asp Tyr Asn Thr Pro Phe Thr Ser Arg Leu Ser Ile Asn Lys
        355                 360                 365

Asp Asn Ser Lys Ser Gln Val Phe Phe Lys Met Asn Ser Leu Gln Ser
370                 375                 380

Gln Asp Thr Ala Ile Tyr Tyr Cys Ala Arg Ala Leu Thr Tyr Tyr Asp
385                 390                 395                 400

Tyr Glu Phe Ala Tyr Trp Gly Gln Gly Thr Leu Val Thr Val Ser Ala
                405                 410                 415

Ala Ser Thr Lys Gly Pro Ser Val Phe Pro Leu Ala Pro Ser Ser Lys
            420                 425                 430

Ser Thr Ser Gly Gly Thr Ala Ala Leu Gly Cys Leu Val Lys Asp Tyr
        435                 440                 445

Phe Pro Glu Pro Val Thr Val Ser Trp Asn Ser Gly Ala Leu Thr Ser
450                 455                 460

Gly Val His Thr Phe Pro Ala Val Leu Gln Ser Ser Gly Leu Tyr Ser
465                 470                 475                 480

Leu Ser Ser Val Val Thr Val Pro Ser Ser Ser Leu Gly Thr Gln Thr
                485                 490                 495

Tyr Ile Cys Asn Val Asn His Lys Pro Ser Asn Thr Lys Val Asp Lys
            500                 505                 510

Lys Val Glu Pro Lys Ser Cys Asp Lys Thr His Thr Cys Pro Pro Cys
        515                 520                 525

Pro Ala Pro Glu Phe Glu Gly Gly Pro Ser Val Phe Leu Phe Pro Pro
530                 535                 540

Lys Pro Lys Asp Thr Leu Met Ile Ser Arg Thr Pro Glu Val Thr Cys
545                 550                 555                 560

Val Val Val Asp Val Ser His Glu Asp Pro Glu Val Lys Phe Asn Trp
                565                 570                 575

Tyr Val Asp Gly Val Glu Val His Asn Ala Lys Thr Lys Pro Arg Glu
            580                 585                 590

Glu Gln Tyr Gln Ser Thr Tyr Arg Val Val Ser Val Leu Thr Val Leu
        595                 600                 605

His Gln Asp Trp Leu Asn Gly Lys Glu Tyr Lys Cys Lys Val Ser Asn
610                 615                 620

Lys Ala Leu Pro Ala Ser Ile Glu Lys Thr Ile Ser Lys Ala Lys Gly
625                 630                 635                 640
```

```
Gln Pro Arg Glu Pro Gln Val Tyr Thr Leu Pro Pro Ser Arg Glu Glu
            645                 650                 655
Met Thr Lys Asn Gln Val Ser Leu Thr Cys Leu Val Lys Gly Phe Tyr
        660                 665                 670
Pro Ser Asp Ile Ala Val Glu Trp Glu Ser Asn Gly Gln Pro Glu Asn
    675                 680                 685
Asn Tyr Lys Thr Thr Pro Pro Val Leu Asp Ser Asp Gly Ser Phe Phe
690                 695                 700
Leu Tyr Ser Lys Leu Thr Val Asp Lys Ser Arg Trp Gln Gln Gly Asn
705                 710                 715                 720
Val Phe Ser Cys Ser Val Met His Glu Ala Leu His Asn His Tyr Thr
                725                 730                 735
Gln Lys Ser Leu Ser Leu Ser Pro Gly Lys
            740                 745

<210> SEQ ID NO 202
<211> LENGTH: 765
<212> TYPE: DNA
<213> ORGANISM: Artificial Sequence
<220> FEATURE:
<223> OTHER INFORMATION: synthetic

<400> SEQUENCE: 202
tgcatctcac ctcgtggttg tccggacggc ccatacgtca tgtacggctc gagcggtggc      60
agcggtggct ctggtggatc cggtctgagc ggccgttccg atgatcatgg cagtagcggt     120
acccagatct tgctgaccca gagcccggtg attctgagcg tgagcccggg cgaacgtgtg     180
agctttagct gccgcgcgag ccagagcatt ggcaccaaca ttcattggta tcagcagcgc     240
accaacggca gcccgcgcct gctgattaaa tatgcgagcg aaagcattag cggcattccg     300
agccgcttta gcggcagcgg cagcggcacc gattttaccc tgagcattaa cagcgtggaa     360
agcgaagata ttgcggatta ttattgccag cagaacaaca ctggccgaca cacctttggc     420
gcgggcacca aactggaact gaaacgtacg gtggctgcac catctgtctt catcttcccg     480
ccatctgatg agcagttgaa atctggaact gcctctgttg tgtgcctgct gaataacttc     540
tatcccagag aggccaaagt acagtggaag gtggataacg ccctccaatc gggtaactcc     600
caggagagtg tcacagagca ggacagcaag gacagcacct acagcctcag cagcaccctg     660
acgctgagca agcagactac gagaaacac aaagtctacg cctgcgaagt cacccatcag     720
ggcctgagct cgcccgtcac aaagagcttc aacaggggag agtgt                     765

<210> SEQ ID NO 203
<211> LENGTH: 255
<212> TYPE: PRT
<213> ORGANISM: Artificial Sequence
<220> FEATURE:
<223> OTHER INFORMATION: synthetic

<400> SEQUENCE: 203

Cys Ile Ser Pro Arg Gly Cys Pro Asp Gly Pro Tyr Val Met Tyr Gly
1               5                   10                  15
Ser Ser Gly Gly Ser Gly Gly Ser Gly Gly Ser Gly Leu Ser Gly Arg
            20                  25                  30
Ser Asp Asp His Gly Ser Ser Gly Thr Gln Ile Leu Leu Thr Gln Ser
        35                  40                  45
Pro Val Ile Leu Ser Val Ser Pro Gly Glu Arg Val Ser Phe Ser Cys
    50                  55                  60
```

```
Arg Ala Ser Gln Ser Ile Gly Thr Asn Ile His Trp Tyr Gln Gln Arg
 65                  70                  75                  80

Thr Asn Gly Ser Pro Arg Leu Leu Ile Lys Tyr Ala Ser Glu Ser Ile
                 85                  90                  95

Ser Gly Ile Pro Ser Arg Phe Ser Gly Ser Gly Ser Thr Asp Phe
            100                 105                 110

Thr Leu Ser Ile Asn Ser Val Glu Ser Glu Asp Ile Ala Asp Tyr Tyr
            115                 120                 125

Cys Gln Gln Asn Asn Asn Trp Pro Thr Thr Phe Gly Ala Gly Thr Lys
            130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
            195                 200                 205

Ser Lys Asp Ser Thr Tyr Ser Leu Ser Ser Thr Leu Thr Leu Ser Lys
210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255

<210> SEQ ID NO 204
<211> LENGTH: 2226
<212> TYPE: DNA
<213> ORGANISM: Artificial Sequence
<220> FEATURE:
<223> OTHER INFORMATION: synthetic

<400> SEQUENCE: 204
ggttatctgt ggggttgcga gtggaattgc ggagggatca ctacaggctc gagcggtggc      60
agcggtggct ctggtggtct gagcggccgt tccgatgatc atggcggcgg ttctcaaact     120
gtagtaactc aagaaccaag cttctccgtc tcccctgggg aacagtcac acttacctgc     180
cgaagtagta caggtgctgt tacgaccagt aactatgcca attgggtaca caaacgcct     240
ggtcaggctc cgcgcggatt gataggaggc acgaataaac gggcacccgg tgtcccggac     300
agattcagcg gaagcatact cggtaataag gcagctctta ctatcactgg gcccaagct     360
gatgatgaaa gtgattatta ttgtgcgctc tggtacagca acctctgggt gtttggggt     420
ggcacgaaac ttactgtctt gggcggcggc ggatcagggg gaggtggctc tgaggagga     480
ggctcagaag tccaactggt cgaatccggg ggagggctcg tacagccggg tgggtccctc     540
aaactctctt gtgcggcctc agggtttacc ttcagtacat acgcgatgaa ttgggtccgg     600
caggccagtg ggaaagggct cgaatgggta ggacgaatcc gatcaaaata caacaactac     660
gctacttatt acgctgattc cgtgaaggac agattcacaa tatcccgcga cgatagcaag     720
aatacggcat atcttcagat gaattctctt aaaactgagg ataccgctgt gtattactgc     780
acaagacatg gtaattttgg aaactcatat gtctcttggt tcgcttattg gggacagggc     840
acgttggtta ccgtgtctag cggaggtggt ggatcccaag tgaccctgag agagtctggc     900
cctgccctcg tgaagcctac ccagaccctg acactgacct gcaccttcag cggcttcagc     960
```

-continued

```
ctgagcacca gcggcatgtc tgtgggctgg atcagacagc ctcctggcaa ggccctggaa    1020
tggctggccg acatttggtg ggacgacaag aaggactaca accccagcct gaagtcccgg    1080
ctgaccatca gcaaggacac cagcaagaac caggtggtgc tgaaagtgac caacatggac    1140
cccgccgaca ccgccaccta ctactgcgcc agatccatga tcaccaactg gtacttcgac    1200
gtgtggggag ccggcaccac cgtgacagtg tcatctgcta gcaccaaggg cccatcggtc    1260
ttccccctgg cacctcctc caagagcacc tctggggca cagcggccct gggctgcctg    1320
gtcaaggact acttccccga accggtgacg gtgtcgtgga actcaggcgc cctgaccagc    1380
ggcgtgcaca ccttcccggc tgtcctacag tcctcaggac tctactccct cagcagcgtg    1440
gtgaccgtgc cctccagcag cttgggcacc cagacctaca tctgcaacgt gaatcacaag    1500
cccagcaaca ccaaggtgga caagaaagtt gagcccaaat cttgtgacaa aactcacaca    1560
tgcccaccgt gcccagcacc tgaatttgaa gggggaccgt cagtcttcct cttccccca    1620 aaacccaagg acaccctcat gatctcccgg acccctgagg tcacatgcgt ggtggtggac    1680
gtgagccacg aagaccctga ggtcaagttc aactggtacg tggacggcgt ggaggtgcat    1740
aatgccaaga caaagccgcg ggaggagcag taccagagca cgtaccgtgt ggtcagcgtc    1800
ctcaccgtcc tgcaccagga ctggctgaat ggcaaggagt acaagtgcaa ggtctccaac    1860
aaagccctcc cagcctcaat cgagaaaacc atctccaaag ccaaagggca gccccgagaa    1920
ccacaggtgt acaccctgcc cccatcccgg gaggagatga ccaagaacca ggtcagcctg    1980
acctgcctgg tcaaaggctt ctatcccagc gacatcgccg tggagtggga gagcaatggg    2040
cagccggaga caactacaa gaccacgcct cccgtgctgg actccgacgg ctccttcttc    2100
ctctacagca agctcaccgt ggacaagagc aggtggcagc aggggaacgt cttctcatgc    2160
tccgtgatgc atgaggctct gcacaaccac tacacgcaga gagcctctc cctgtctccg    2220 ggtaaa                                                                2226
```

<210> SEQ ID NO 205
<211> LENGTH: 742
<212> TYPE: PRT
<213> ORGANISM: Artificial Sequence
<220> FEATURE:
<223> OTHER INFORMATION: synthetic

<400> SEQUENCE: 205

```
Gly Tyr Leu Trp Gly Cys Glu Trp Asn Cys Gly Gly Ile Thr Thr Gly
1               5                   10                  15

Ser Ser Gly Gly Ser Gly Gly Ser Gly Gly Leu Ser Gly Arg Ser Asp
            20                  25                  30

Asp His Gly Gly Gly Ser Gln Thr Val Val Thr Gln Glu Pro Ser Phe
        35                  40                  45

Ser Val Ser Pro Gly Gly Thr Val Thr Leu Thr Cys Arg Ser Ser Thr
    50                  55                  60

Gly Ala Val Thr Thr Ser Asn Tyr Ala Asn Trp Val Gln Gln Thr Pro
65                  70                  75                  80

Gly Gln Ala Pro Arg Gly Leu Ile Gly Gly Thr Asn Lys Arg Ala Pro
                85                  90                  95

Gly Val Pro Asp Arg Phe Ser Gly Ser Ile Leu Gly Asn Lys Ala Ala
            100                 105                 110

Leu Thr Ile Thr Gly Ala Gln Ala Asp Asp Glu Ser Asp Tyr Tyr Cys
        115                 120                 125

Ala Leu Trp Tyr Ser Asn Leu Trp Val Phe Gly Gly Gly Thr Lys Leu
```

-continued

```
                130                 135                 140
Thr Val Leu Gly Gly Gly Ser Gly Gly Gly Ser Gly Gly
145                 150                 155                 160

Gly Ser Glu Val Gln Leu Val Glu Ser Gly Gly Leu Val Gln Pro
                165                 170                 175

Gly Gly Ser Leu Lys Leu Ser Cys Ala Ala Ser Gly Phe Thr Phe Ser
                180                 185                 190

Thr Tyr Ala Met Asn Trp Val Arg Gln Ala Ser Gly Lys Gly Leu Glu
                195                 200                 205

Trp Val Gly Arg Ile Arg Ser Lys Tyr Asn Asn Tyr Ala Thr Tyr Tyr
                210                 215                 220

Ala Asp Ser Val Lys Asp Arg Phe Thr Ile Ser Arg Asp Asp Ser Lys
225                 230                 235                 240

Asn Thr Ala Tyr Leu Gln Met Asn Ser Leu Lys Thr Glu Asp Thr Ala
                245                 250                 255

Val Tyr Tyr Cys Thr Arg His Gly Asn Phe Gly Asn Ser Tyr Val Ser
                260                 265                 270

Trp Phe Ala Tyr Trp Gly Gln Gly Thr Leu Val Thr Val Ser Ser Gly
                275                 280                 285

Gly Gly Gly Ser Gln Val Thr Leu Arg Glu Ser Gly Pro Ala Leu Val
                290                 295                 300

Lys Pro Thr Gln Thr Leu Thr Leu Thr Cys Thr Phe Ser Gly Phe Ser
305                 310                 315                 320

Leu Ser Thr Ser Gly Met Ser Val Gly Trp Ile Arg Gln Pro Pro Gly
                325                 330                 335

Lys Ala Leu Glu Trp Leu Ala Asp Ile Trp Trp Asp Asp Lys Lys Asp
                340                 345                 350

Tyr Asn Pro Ser Leu Lys Ser Arg Leu Thr Ile Ser Lys Asp Thr Ser
                355                 360                 365

Lys Asn Gln Val Val Leu Lys Val Thr Asn Met Asp Pro Ala Asp Thr
                370                 375                 380

Ala Thr Tyr Tyr Cys Ala Arg Ser Met Ile Thr Asn Trp Tyr Phe Asp
385                 390                 395                 400

Val Trp Gly Ala Gly Thr Thr Val Thr Val Ser Ser Ala Ser Thr Lys
                405                 410                 415

Gly Pro Ser Val Phe Pro Leu Ala Pro Ser Ser Lys Ser Thr Ser Gly
                420                 425                 430

Gly Thr Ala Ala Leu Gly Cys Leu Val Lys Asp Tyr Phe Pro Glu Pro
                435                 440                 445

Val Thr Val Ser Trp Asn Ser Gly Ala Leu Thr Ser Gly Val His Thr
                450                 455                 460

Phe Pro Ala Val Leu Gln Ser Ser Gly Leu Tyr Ser Leu Ser Ser Val
465                 470                 475                 480

Val Thr Val Pro Ser Ser Ser Leu Gly Thr Gln Thr Tyr Ile Cys Asn
                485                 490                 495

Val Asn His Lys Pro Ser Asn Thr Lys Val Asp Lys Lys Val Glu Pro
                500                 505                 510

Lys Ser Cys Asp Lys Thr His Thr Cys Pro Pro Cys Pro Ala Pro Glu
                515                 520                 525

Phe Glu Gly Gly Pro Ser Val Phe Leu Phe Pro Pro Lys Pro Lys Asp
                530                 535                 540

Thr Leu Met Ile Ser Arg Thr Pro Glu Val Thr Cys Val Val Val Asp
545                 550                 555                 560
```

Val Ser His Glu Asp Pro Glu Val Lys Phe Asn Trp Tyr Val Asp Gly
            565                 570                 575

Val Glu Val His Asn Ala Lys Thr Lys Pro Arg Glu Gln Tyr Gln
        580                 585                 590

Ser Thr Tyr Arg Val Val Ser Val Leu Thr Val Leu His Gln Asp Trp
        595                 600                 605

Leu Asn Gly Lys Glu Tyr Lys Cys Lys Val Ser Asn Lys Ala Leu Pro
        610                 615                 620

Ala Ser Ile Glu Lys Thr Ile Ser Lys Ala Lys Gly Gln Pro Arg Glu
625                 630                 635                 640

Pro Gln Val Tyr Thr Leu Pro Pro Ser Arg Glu Glu Met Thr Lys Asn
            645                 650                 655

Gln Val Ser Leu Thr Cys Leu Val Lys Gly Phe Tyr Pro Ser Asp Ile
        660                 665                 670

Ala Val Glu Trp Glu Ser Asn Gly Gln Pro Glu Asn Asn Tyr Lys Thr
        675                 680                 685

Thr Pro Pro Val Leu Asp Ser Asp Gly Ser Phe Phe Leu Tyr Ser Lys
    690                 695                 700

Leu Thr Val Asp Lys Ser Arg Trp Gln Gln Gly Asn Val Phe Ser Cys
705                 710                 715                 720

Ser Val Met His Glu Ala Leu His Asn His Tyr Thr Gln Lys Ser Leu
            725                 730                 735

Ser Leu Ser Pro Gly Lys
            740

<210> SEQ ID NO 206
<211> LENGTH: 2241
<212> TYPE: DNA
<213> ORGANISM: Artificial Sequence
<220> FEATURE:
<223> OTHER INFORMATION: synthetic

<400> SEQUENCE: 206

```
ggttatctgt ggggttgcga gtggaattgc ggagggatca ctacaggctc gagcggtggc      60
agcggtggct ctggtggtat atcgagtgga ttgctgtctg gcagatctga cgatcacggc     120
ggcggttctc aaactgtagt aactcaagaa ccaagcttct ccgtctcccc tggggggaaca    180 gtcacactta cctgccgaag tagtacaggt gctgttacga ccagtaacta tgccaattgg    240
gtacaacaaa cgcctggtca ggctccgcgc ggattgatag gaggcacgaa taaacgggca    300
cccggtgtcc cggacagatt cagcggaagc atactcggta ataaggcagc tcttactatc    360
actggggccc aagctgatga tgaaagtgat tattattgtg cgctctggta cagcaacctc    420
tgggtgtttg ggggtggcac gaaacttact gtcttgggcg gcggcggatc aggggaggt    480 ggctctggag gaggaggctc agaagtccaa ctggtcgaat ccggggagg gctcgtacag    540 ccgggtgggt ccctcaaact ctcttgtgcg gcctcagggt ttaccttcag tacatacgcg    600
atgaattggg tccggcaggc cagtgggaaa gggctcgaat gggtaggacg aatccgatca    660
aaatacaaca actacgctac ttattacgct gattccgtga aggacagatt cacaatatcc    720
cgcgacgata gcaagaatac ggcatatctt cagatgaatt ctcttaaaac tgaggatacc    780
gctgtgtatt actgcacaag acatggtaat tttggaaact catatgtctc ttggttcgct    840
tattggggac agggcacgtt ggttaccgtg tctagcggag gtggtggatc ccaagtgacc    900
ctgagagagt ctggccctgc cctcgtgaag cctacccaga ccctgacact gacctgcacc    960
```

```
ttcagcggct tcagcctgag caccagcggc atgtctgtgg gctggatcag acagcctcct    1020
ggcaaggccc tggaatggct ggccgacatt tggtgggacg acaagaagga ctacaacccc    1080
agcctgaagt cccggctgac catcagcaag gacaccagca agaaccaggt ggtgctgaaa    1140
gtgaccaaca tggaccccgc cgacaccgcc acctactact gcgccagatc catgatcacc    1200
aactggtact cgacgtgtg gggagccggc accaccgtga cagtgtcatc tgctagcacc    1260
aagggcccat cggtcttccc cctggcaccc tcctccaaga gcacctctgg ggcacagcg     1320
gccctgggct gcctggtcaa ggactacttc cccgaaccgg tgacggtgtc gtggaactca    1380
ggcgccctga ccagcggcgt gcacaccttc ccggctgtcc tacagtcctc aggactctac    1440
tccctcagca gcgtggtgac cgtgccctcc agcagcttgg gcacccagac ctacatctgc    1500
aacgtgaatc acaagcccag caacaccaag gtggacaaga agttgagcc caaatcttgt     1560
gacaaaactc acacatgccc accgtgccca gcacctgaat ttgaaggggg accgtcagtc    1620
ttcctcttcc ccccaaaacc caaggacacc ctcatgatct cccggacccc tgaggtcaca    1680
tgcgtggtgg tggacgtgag ccacgaagac cctgaggtca agttcaactg gtacgtggac    1740
ggcgtggagg tgcataatgc caagacaaag ccgcgggagg agcagtacca gagcacgtac    1800
cgtgtggtca gcgtcctcac cgtcctgcac caggactggc tgaatggcaa ggagtacaag    1860
tgcaaggtct ccaacaaagc cctcccagcc tcaatcgaga aaaccatctc caaagccaaa    1920
gggcagcccc gagaaccaca ggtgtacacc ctgcccccat cccgggagga tgaccaag      1980
aaccaggtca gcctgacctg cctggtcaaa ggcttctatc ccagcgacat cgccgtggag    2040
tgggagagca atgggcagcc ggagaacaac tacaagacca cgcctcccgt gctggactcc    2100
gacggctcct tcttcctcta cagcaagctc accgtggaca agagcaggtg gcagcagggg    2160
aacgtcttct catgctccgt gatgcatgag gctctgcaca accactacac gcagaagagc    2220
ctctccctgt ctccgggtaa a                                              2241
```

<210> SEQ ID NO 207
<211> LENGTH: 747
<212> TYPE: PRT
<213> ORGANISM: Artificial Sequence
<220> FEATURE:
<223> OTHER INFORMATION: synthetic

<400> SEQUENCE: 207

```
Gly Tyr Leu Trp Gly Cys Glu Trp Asn Cys Gly Gly Ile Thr Thr Gly
1               5                   10                  15

Ser Ser Gly Gly Ser Gly Gly Ser Gly Gly Ile Ser Ser Gly Leu Leu
            20                  25                  30

Ser Gly Arg Ser Asp Asp His Gly Gly Gly Ser Gln Thr Val Val Thr
        35                  40                  45

Gln Glu Pro Ser Phe Ser Val Ser Pro Gly Gly Thr Val Thr Leu Thr
    50                  55                  60

Cys Arg Ser Ser Thr Gly Ala Val Thr Thr Ser Asn Tyr Ala Asn Trp
65                  70                  75                  80

Val Gln Gln Thr Pro Gly Gln Ala Pro Arg Gly Leu Ile Gly Gly Thr
                85                  90                  95

Asn Lys Arg Ala Pro Gly Val Pro Asp Arg Phe Ser Gly Ser Ile Leu
            100                 105                 110

Gly Asn Lys Ala Ala Leu Thr Ile Thr Gly Ala Gln Ala Asp Asp Glu
        115                 120                 125

Ser Asp Tyr Tyr Cys Ala Leu Trp Tyr Ser Asn Leu Trp Val Phe Gly
```

```
            130                 135                 140
Gly Gly Thr Lys Leu Thr Val Leu Gly Gly Gly Ser Gly Gly
145                 150                 155                 160

Gly Ser Gly Gly Gly Ser Glu Val Gln Leu Val Glu Ser Gly Gly
                165                 170                 175

Gly Leu Val Gln Pro Gly Gly Ser Leu Lys Leu Ser Cys Ala Ser
                180                 185                 190

Gly Phe Thr Phe Ser Thr Tyr Ala Met Asn Trp Val Arg Gln Ala Ser
            195                 200                 205

Gly Lys Gly Leu Glu Trp Val Gly Arg Ile Arg Ser Lys Tyr Asn Asn
210                 215                 220

Tyr Ala Thr Tyr Tyr Ala Asp Ser Val Lys Asp Arg Phe Thr Ile Ser
225                 230                 235                 240

Arg Asp Asp Ser Lys Asn Thr Ala Tyr Leu Gln Met Asn Ser Leu Lys
                245                 250                 255

Thr Glu Asp Thr Ala Val Tyr Tyr Cys Thr Arg His Gly Asn Phe Gly
                260                 265                 270

Asn Ser Tyr Val Ser Trp Phe Ala Tyr Trp Gly Gln Gly Thr Leu Val
            275                 280                 285

Thr Val Ser Ser Gly Gly Gly Gly Ser Gln Val Thr Leu Arg Glu Ser
290                 295                 300

Gly Pro Ala Leu Val Lys Pro Thr Gln Thr Leu Thr Leu Thr Cys Thr
305                 310                 315                 320

Phe Ser Gly Phe Ser Leu Ser Thr Ser Gly Met Ser Val Gly Trp Ile
                325                 330                 335

Arg Gln Pro Pro Gly Lys Ala Leu Glu Trp Leu Ala Asp Ile Trp Trp
                340                 345                 350

Asp Asp Lys Lys Asp Tyr Asn Pro Ser Leu Lys Ser Arg Leu Thr Ile
            355                 360                 365

Ser Lys Asp Thr Ser Lys Asn Gln Val Val Leu Lys Val Thr Asn Met
370                 375                 380

Asp Pro Ala Asp Thr Ala Thr Tyr Tyr Cys Ala Arg Ser Met Ile Thr
385                 390                 395                 400

Asn Trp Tyr Phe Asp Val Trp Gly Ala Gly Thr Thr Val Thr Val Ser
                405                 410                 415

Ser Ala Ser Thr Lys Gly Pro Ser Val Phe Pro Leu Ala Pro Ser Ser
                420                 425                 430

Lys Ser Thr Ser Gly Gly Thr Ala Ala Leu Gly Cys Leu Val Lys Asp
            435                 440                 445

Tyr Phe Pro Glu Pro Val Thr Val Ser Trp Asn Ser Gly Ala Leu Thr
450                 455                 460

Ser Gly Val His Thr Phe Pro Ala Val Leu Gln Ser Ser Gly Leu Tyr
465                 470                 475                 480

Ser Leu Ser Ser Val Val Thr Val Pro Ser Ser Ser Leu Gly Thr Gln
                485                 490                 495

Thr Tyr Ile Cys Asn Val Asn His Lys Pro Ser Asn Thr Lys Val Asp
                500                 505                 510

Lys Lys Val Glu Pro Lys Ser Cys Asp Lys Thr His Thr Cys Pro Pro
            515                 520                 525

Cys Pro Ala Pro Glu Phe Glu Gly Gly Pro Ser Val Phe Leu Phe Pro
530                 535                 540

Pro Lys Pro Lys Asp Thr Leu Met Ile Ser Arg Thr Pro Glu Val Thr
545                 550                 555                 560
```

```
Cys Val Val Val Asp Val Ser His Glu Asp Pro Glu Val Lys Phe Asn
                565                 570                 575
Trp Tyr Val Asp Gly Val Glu Val His Asn Ala Lys Thr Lys Pro Arg
            580                 585                 590
Glu Glu Gln Tyr Gln Ser Thr Tyr Arg Val Val Ser Val Leu Thr Val
        595                 600                 605
Leu His Gln Asp Trp Leu Asn Gly Lys Glu Tyr Lys Cys Lys Val Ser
    610                 615                 620
Asn Lys Ala Leu Pro Ala Ser Ile Glu Lys Thr Ile Ser Lys Ala Lys
625                 630                 635                 640
Gly Gln Pro Arg Glu Pro Gln Val Tyr Thr Leu Pro Pro Ser Arg Glu
                645                 650                 655
Glu Met Thr Lys Asn Gln Val Ser Leu Thr Cys Leu Val Lys Gly Phe
            660                 665                 670
Tyr Pro Ser Asp Ile Ala Val Glu Trp Glu Ser Asn Gly Gln Pro Glu
        675                 680                 685
Asn Asn Tyr Lys Thr Thr Pro Pro Val Leu Asp Ser Asp Gly Ser Phe
    690                 695                 700
Phe Leu Tyr Ser Lys Leu Thr Val Asp Lys Ser Arg Trp Gln Gln Gly
705                 710                 715                 720
Asn Val Phe Ser Cys Ser Val Met His Glu Ala Leu His Asn His Tyr
                725                 730                 735
Thr Gln Lys Ser Leu Ser Leu Ser Pro Gly Lys
            740                 745
```

```
<210> SEQ ID NO 208
<211> LENGTH: 18
<212> TYPE: DNA
<213> ORGANISM: Artificial Sequence
<220> FEATURE:
<223> OTHER INFORMATION: synthetic

<400> SEQUENCE: 208
caaggccagt ctggttct                                                    18

<210> SEQ ID NO 209
<211> LENGTH: 2223
<212> TYPE: DNA
<213> ORGANISM: Artificial Sequence
<220> FEATURE:
<223> OTHER INFORMATION: synthetic

<400> SEQUENCE: 209
ggttatctgt ggggttgcga gtggaattgc ggagggatca ctacaggctc gagcggtggc      60
agcggtggct ctggtggtct gagcggccgt tccgatgatc atggcggcgg atcccagacg     120
gtagtgactc aggagccatc attttctgtc tctcctggag gtactgtgac actcacatgt     180
agaagctcaa ctggtgcagt caccacttca aattacgcga attgggtcca gcagacccct     240
gggcaggctc cgagagggtt gattggaggt actaacaaac gggcaccggg agtgcctgat     300
aggttttccg gttctattct cggaaacaag gcggctctca cgatcacggg tgcgcaggcc     360
gacgatgaat cagactatta ctgcgctttg tggtactcaa acctgtgggt attcggaggg     420
ggcaccaagc tgacggtgtt gggtgggggg ggctctgggg agggggaag cggaggtggg      480 ggcagcgagg ttcagcttgt tgaaagtggt ggcggactcg tacaaccggg tggaagtctt     540
agactctcat gtgcagcatc tggatttact ttttctactt atgctatgaa ctgggtaaga     600
```

```
caggcaccgg ggaaagggct ggaatgggtt gcacgcattc gatctaaata caataactat    660
gctacatact acgccgatag tgttaaggat cgattcacta tatctcggga cgacagtaag    720
aactcacttt acctgcagat gaattccttg aaaactgagg acacggccgt ttattattgt    780
gtacggcacg ggaatttcgg caattcttac gtttcctggt tcgcctattg ggggcaaggt    840
acgctggtca cggtgtctag cggaggtggt ggatcccagg tgcagctgaa acagagcggc    900
ccgggcctgg tgcagccgag ccagagcctg agcattacct gcaccgtgag cggctttagc    960
ctgaccaact atggcgtgca ttgggtgcgc cagagcccgg gcaaaggcct ggaatggctg   1020
ggcgtgattt ggagcggcgg caacaccgat tataacaccc cgtttaccag ccgcctgagc   1080
attaacaaag ataacagcaa aagccaggtg ttttttaaaa tgaacagcct gcaaagccag   1140
gataccgcga tttattattg cgcgcgcgcg ctgacctatt atgattatga atttgcgtat   1200
tggggccagg gcaccctggt gaccgtgagc gcggctagca ccaagggccc atcggtcttc   1260
cccctggcac cctcctccaa gagcacctct ggggcacag cggccctggg ctgcctggtc   1320
aaggactact ccccgaacc ggtgacggtg tcgtggaact caggcgccct gaccagcggc   1380
gtgcacacct tcccggctgt cctacagtcc tcaggactct actccctcag cagcgtggtg   1440
accgtgccct ccagcagctt gggcacccag acctacatct gcaacgtgaa tcacaagccc   1500
agcaacacca aggtggacaa gaaagttgag cccaaatctt gtgacaaaac tcacacatgc   1560
ccaccgtgcc cagcacctga atttgaaggg ggaccgtcag tcttcctctt ccccccaaaa   1620
cccaaggaca ccctcatgat ctcccggacc cctgaggtca catgcgtggt ggtggacgtg   1680
agccacgaag accctgaggt caagttcaac tggtacgtgg acggcgtgga ggtgcataat   1740
gccaagacaa agccgcggga ggagcagtac cagagcacgt accgtgtggt cagcgtcctc   1800
accgtcctgc accaggactg gctgaatggc aaggagtaca agtgcaaggt ctccaacaaa   1860
gccctcccag cctcaatcga gaaaaccatc tccaaagcca agggcagccc cgagaaacca   1920
caggtgtaca ccctgccccc atcccgggag gagatgacca agaaccaggt cagcctgacc   1980
tgcctggtca aaggcttcta tcccagcgac atcgccgtgg agtgggagag caatgggcag   2040
ccggagaaca actacaagac cacgcctccc gtgctggact ccgacggctc cttcttcctc   2100
tacagcaagc tcaccgtgga caagagcagg tggcagcagg ggaacgtctt ctcatgctcc   2160
gtgatgcatg aggctctgca caaccactac acgcagaaga gcctctccct gtctccgggt   2220
aaa                                                                 2223
```

<210> SEQ ID NO 210
<211> LENGTH: 741
<212> TYPE: PRT
<213> ORGANISM: Artificial Sequence
<220> FEATURE:
<223> OTHER INFORMATION: synthetic

<400> SEQUENCE: 210

```
Gly Tyr Leu Trp Gly Cys Glu Trp Asn Cys Gly Ile Thr Thr Gly
1               5                   10                  15

Ser Ser Gly Gly Ser Gly Gly Ser Gly Gly Leu Ser Gly Arg Ser Asp
            20                  25                  30

Asp His Gly Gly Gly Ser Gln Thr Val Val Thr Gln Glu Pro Ser Phe
        35                  40                  45

Ser Val Ser Pro Gly Gly Thr Val Thr Leu Thr Cys Arg Ser Ser Thr
    50                  55                  60

Gly Ala Val Thr Thr Ser Asn Tyr Ala Asn Trp Val Gln Gln Thr Pro
```

```
                65                  70                  75                  80
Gly Gln Ala Pro Arg Gly Leu Ile Gly Gly Thr Asn Lys Arg Ala Pro
                        85                  90                  95
Gly Val Pro Asp Arg Phe Ser Gly Ser Ile Leu Gly Asn Lys Ala Ala
                100                 105                 110
Leu Thr Ile Thr Gly Ala Gln Ala Asp Asp Glu Ser Asp Tyr Tyr Cys
            115                 120                 125
Ala Leu Trp Tyr Ser Asn Leu Trp Val Phe Gly Gly Thr Lys Leu
        130                 135                 140
Thr Val Leu Gly Gly Gly Ser Gly Gly Gly Ser Gly Gly Gly
145                 150                 155                 160
Gly Ser Glu Val Gln Leu Val Glu Ser Gly Gly Leu Val Gln Pro
                165                 170                 175
Gly Gly Ser Leu Arg Leu Ser Cys Ala Ala Ser Gly Phe Thr Phe Ser
            180                 185                 190
Thr Tyr Ala Met Asn Trp Val Arg Gln Ala Pro Gly Lys Gly Leu Glu
        195                 200                 205
Trp Val Ala Arg Ile Arg Ser Lys Tyr Asn Asn Tyr Ala Thr Tyr Tyr
    210                 215                 220
Ala Asp Ser Val Lys Asp Arg Phe Thr Ile Ser Arg Asp Asp Ser Lys
225                 230                 235                 240
Asn Ser Leu Tyr Leu Gln Met Asn Ser Leu Lys Thr Glu Asp Thr Ala
                245                 250                 255
Val Tyr Tyr Cys Val Arg His Gly Asn Phe Gly Asn Ser Tyr Val Ser
            260                 265                 270
Trp Phe Ala Tyr Trp Gly Gln Gly Thr Leu Val Thr Val Ser Ser Gly
        275                 280                 285
Gly Gly Gly Ser Gln Val Gln Leu Lys Gln Ser Gly Pro Gly Leu Val
    290                 295                 300
Gln Pro Ser Gln Ser Leu Ser Ile Thr Cys Thr Val Ser Gly Phe Ser
305                 310                 315                 320
Leu Thr Asn Tyr Gly Val His Trp Val Arg Gln Ser Pro Gly Lys Gly
                325                 330                 335
Leu Glu Trp Leu Gly Val Ile Trp Ser Gly Gly Asn Thr Asp Tyr Asn
            340                 345                 350
Thr Pro Phe Thr Ser Arg Leu Ser Ile Asn Lys Asp Asn Ser Lys Ser
        355                 360                 365
Gln Val Phe Phe Lys Met Asn Ser Leu Gln Ser Gln Asp Thr Ala Ile
    370                 375                 380
Tyr Tyr Cys Ala Arg Ala Leu Thr Tyr Tyr Asp Tyr Glu Phe Ala Tyr
385                 390                 395                 400
Trp Gly Gln Gly Thr Leu Val Thr Val Ser Ala Ala Ser Thr Lys Gly
                405                 410                 415
Pro Ser Val Phe Pro Leu Ala Pro Ser Ser Lys Ser Thr Ser Gly Gly
            420                 425                 430
Thr Ala Ala Leu Gly Cys Leu Val Lys Asp Tyr Phe Pro Glu Pro Val
        435                 440                 445
Thr Val Ser Trp Asn Ser Gly Ala Leu Thr Ser Gly Val His Thr Phe
    450                 455                 460
Pro Ala Val Leu Gln Ser Ser Gly Leu Tyr Ser Leu Ser Ser Val Val
465                 470                 475                 480
Thr Val Pro Ser Ser Ser Leu Gly Thr Gln Thr Tyr Ile Cys Asn Val
                485                 490                 495
```

Asn His Lys Pro Ser Asn Thr Lys Val Asp Lys Val Glu Pro Lys
             500                 505                 510

Ser Cys Asp Lys Thr His Thr Cys Pro Pro Cys Pro Ala Pro Glu Phe
             515                 520                 525

Glu Gly Gly Pro Ser Val Phe Leu Phe Pro Pro Lys Pro Lys Asp Thr
             530                 535                 540

Leu Met Ile Ser Arg Thr Pro Glu Val Thr Cys Val Val Val Asp Val
545                 550                 555                 560

Ser His Glu Asp Pro Glu Val Lys Phe Asn Trp Tyr Val Asp Gly Val
                 565                 570                 575

Glu Val His Asn Ala Lys Thr Lys Pro Arg Glu Glu Gln Tyr Gln Ser
             580                 585                 590

Thr Tyr Arg Val Val Ser Val Leu Thr Val Leu His Gln Asp Trp Leu
         595                 600                 605

Asn Gly Lys Glu Tyr Lys Cys Lys Val Ser Asn Lys Ala Leu Pro Ala
     610                 615                 620

Ser Ile Glu Lys Thr Ile Ser Lys Ala Lys Gly Gln Pro Arg Glu Pro
625                 630                 635                 640

Gln Val Tyr Thr Leu Pro Pro Ser Arg Glu Glu Met Thr Lys Asn Gln
                 645                 650                 655

Val Ser Leu Thr Cys Leu Val Lys Gly Phe Tyr Pro Ser Asp Ile Ala
             660                 665                 670

Val Glu Trp Glu Ser Asn Gly Gln Pro Glu Asn Asn Tyr Lys Thr Thr
         675                 680                 685

Pro Pro Val Leu Asp Ser Asp Gly Ser Phe Phe Leu Tyr Ser Lys Leu
     690                 695                 700

Thr Val Asp Lys Ser Arg Trp Gln Gln Gly Asn Val Phe Ser Cys Ser
705                 710                 715                 720

Val Met His Glu Ala Leu His Asn His Tyr Thr Gln Lys Ser Leu Ser
                 725                 730                 735

Leu Ser Pro Gly Lys
             740

<210> SEQ ID NO 211
<211> LENGTH: 2223
<212> TYPE: DNA
<213> ORGANISM: Artificial Sequence
<220> FEATURE:
<223> OTHER INFORMATION: synthetic

<400> SEQUENCE: 211
ggttatctgt ggggttgcga gtggaattgc ggagggatca ctacaggctc gagcggtggc      60
agcggtggct ctggtggtct gagcggccgt tccgatgatc atggcggcgg ttctcaggcc     120
gttgttacac aagagccttc acttactgtg tctccaggag gcactgtgac acttacgtgc     180
cgatcctcta cgggtgccgt gaccacaagc aactatgcca actgggtcca gcagaagcca     240
ggtcaagcgc ctcgaggtct gatcggggc acgaataaac gagctcctgg aactccggcc      300
agattttctg ggagtcttat tggtggcaag gcggcgttga ccctgagtgg agcccaaccg     360
gaagacgagg ccgagtacta ctgcgccttg tggtattcca atttgtgggt cttcggaggc     420
ggaacaaagc tcacagtact gggaggtgga ggtagcgggg cggaggctc cggggaggt      480 ggttccgaag tccagcttgt tgaatcaggt gggggcttgg tacaaccagg tggttcactg     540
aagttgtcct gtgcagcgtc cggatttaca tttagtacgt atgctatgaa ctgggtcagg     600

```
caggccagtg gtaaaggtct cgaatgggtt ggccggataa ggtcaaagta caataattac    660
gcaacctact acgcggattc cgtgaaagac aggttcacta tttcacgaga tgatagcaaa    720
atactgcgt  atctccaaat gaatagtctt aaaactgaag acactgccgt atattattgc    780
actaggcacg gcaactttgg taactcttat gtttcttggt tcgcatactg gggacaagga    840
actttggtca ctgtctcatc tggaggtggt ggatcccagg tgcagctgaa acagagcggc    900
ccgggcctgg tgcagccgag ccagagcctg agcattacct gcaccgtgag cggctttagc    960
ctgaccaact atggcgtgca ttgggtgcgc cagagcccgg gcaaaggcct ggaatggctg   1020
ggcgtgattt ggagcggcgg caacaccgat tataacaccc cgtttaccag ccgcctgagc   1080
attaacaaag ataacagcaa aagccaggtg ttttttaaaa tgaacagcct gcaaagccag   1140
gataccgcga tttattattg cgcgcgcgcg ctgacctatt atgattatga atttgcgtat   1200
tggggccagg gcaccctggt gaccgtgagc gcggctagca ccaagggccc atcggtcttc   1260
cccctggcac cctcctccaa gagcacctct gggggcacag cggccctggg ctgcctggtc   1320
aaggactact tccccgaacc ggtgacggtg tcgtggaact caggcgccct gaccagcggc   1380
gtgcacacct tcccggctgt cctacagtcc tcaggactct actccctcag cagcgtggtg   1440
accgtgccct ccagcagctt gggcacccag acctacatct gcaacgtgaa tcacaagccc   1500
agcaacacca aggtggacaa gaaagttgag cccaaatctt gtgacaaaac tcacacatgc   1560
ccaccgtgcc cagcacctga atttgaaggg ggaccgtcag tcttcctctt ccccccaaaa   1620
cccaaggaca ccctcatgat ctcccggacc cctgaggtca catgcgtggt ggtggacgtg   1680
agccacgaag accctgaggt caagttcaac tggtacgtgg acggcgtgga ggtgcataat   1740
gccaagacaa agccgcggga ggagcagtac cagagcacgt accgtgtggt cagcgtcctc   1800
accgtcctgc accaggactg gctgaatggc aaggagtaca agtgcaaggt ctccaacaaa   1860
gccctcccag cctcaatcga gaaaaccatc tccaaagcca agggcagccc cgagaaccca   1920
caggtgtaca ccctgccccc atcccgggag gagatgacca agaaccaggt cagcctgacc   1980
tgcctggtca aaggcttcta tcccagcgac atcgccgtgg agtgggagag caatgggcag   2040
ccggagaaca actacaagac cacgcctccc gtgctggact ccgacggctc cttcttcctc   2100
tacagcaagc tcaccgtgga caagagcagg tggcagcagg ggaacgtctt ctcatgctcc   2160
gtgatgcatg aggctctgca caaccactac acgcagaaga gcctctccct gtctccgggt   2220
aaa                                                                 2223
```

<210> SEQ ID NO 212
<211> LENGTH: 741
<212> TYPE: PRT
<213> ORGANISM: Artificial Sequence
<220> FEATURE:
<223> OTHER INFORMATION: synthetic

<400> SEQUENCE: 212

Gly Tyr Leu Trp Gly Cys Glu Trp Asn Cys Gly Ile Thr Thr Gly
1               5                   10                  15

Ser Ser Gly Gly Ser Gly Gly Ser Gly Gly Leu Ser Gly Arg Ser Asp
            20                  25                  30

Asp His Gly Gly Gly Ser Gln Ala Val Val Thr Gln Glu Pro Ser Leu
        35                  40                  45

Thr Val Ser Pro Gly Gly Thr Val Thr Leu Thr Cys Arg Ser Ser Thr
    50                  55                  60

Gly Ala Val Thr Thr Ser Asn Tyr Ala Asn Trp Val Gln Gln Lys Pro

```
                65                  70                  75                  80
Gly Gln Ala Pro Arg Gly Leu Ile Gly Gly Thr Asn Lys Arg Ala Pro
                    85                  90                  95
Gly Thr Pro Ala Arg Phe Ser Gly Ser Leu Ile Gly Gly Lys Ala Ala
                    100                 105                 110
Leu Thr Leu Ser Gly Ala Gln Pro Glu Asp Glu Ala Glu Tyr Tyr Cys
                    115                 120                 125
Ala Leu Trp Tyr Ser Asn Leu Trp Val Phe Gly Gly Thr Lys Leu
                130                 135                 140
Thr Val Leu Gly Gly Gly Gly Ser Gly Gly Gly Gly Ser Gly Gly Gly
145                 150                 155                 160
Gly Ser Glu Val Gln Leu Val Glu Ser Gly Gly Leu Val Gln Pro
                    165                 170                 175
Gly Gly Ser Leu Lys Leu Ser Cys Ala Ala Ser Gly Phe Thr Phe Ser
                    180                 185                 190
Thr Tyr Ala Met Asn Trp Val Arg Gln Ala Ser Gly Lys Gly Leu Glu
                    195                 200                 205
Trp Val Gly Arg Ile Arg Ser Lys Tyr Asn Asn Tyr Ala Thr Tyr Tyr
    210                 215                 220
Ala Asp Ser Val Lys Asp Arg Phe Thr Ile Ser Arg Asp Asp Ser Lys
225                 230                 235                 240
Asn Thr Ala Tyr Leu Gln Met Asn Ser Leu Lys Thr Glu Asp Thr Ala
                    245                 250                 255
Val Tyr Tyr Cys Thr Arg His Gly Asn Phe Gly Asn Ser Tyr Val Ser
                    260                 265                 270
Trp Phe Ala Tyr Trp Gly Gln Gly Thr Leu Val Thr Val Ser Ser Gly
                    275                 280                 285
Gly Gly Gly Ser Gln Val Gln Leu Lys Gln Ser Gly Pro Gly Leu Val
                    290                 295                 300
Gln Pro Ser Gln Ser Leu Ser Ile Thr Cys Thr Val Ser Gly Phe Ser
305                 310                 315                 320
Leu Thr Asn Tyr Gly Val His Trp Val Arg Gln Ser Pro Gly Lys Gly
                    325                 330                 335
Leu Glu Trp Leu Gly Val Ile Trp Ser Gly Gly Asn Thr Asp Tyr Asn
                    340                 345                 350
Thr Pro Phe Thr Ser Arg Leu Ser Ile Asn Lys Asp Asn Ser Lys Ser
                    355                 360                 365
Gln Val Phe Phe Lys Met Asn Ser Leu Gln Ser Gln Asp Thr Ala Ile
                    370                 375                 380
Tyr Tyr Cys Ala Arg Ala Leu Thr Tyr Tyr Asp Tyr Glu Phe Ala Tyr
385                 390                 395                 400
Trp Gly Gln Gly Thr Leu Val Thr Val Ser Ala Ala Ser Thr Lys Gly
                    405                 410                 415
Pro Ser Val Phe Pro Leu Ala Pro Ser Ser Lys Ser Thr Ser Gly Gly
                    420                 425                 430
Thr Ala Ala Leu Gly Cys Leu Val Lys Asp Tyr Phe Pro Glu Pro Val
                    435                 440                 445
Thr Val Ser Trp Asn Ser Gly Ala Leu Thr Ser Gly Val His Thr Phe
                    450                 455                 460
Pro Ala Val Leu Gln Ser Ser Gly Leu Tyr Ser Leu Ser Ser Val Val
465                 470                 475                 480
Thr Val Pro Ser Ser Ser Leu Gly Thr Gln Thr Tyr Ile Cys Asn Val
                    485                 490                 495
```

Asn His Lys Pro Ser Asn Thr Lys Val Asp Lys Val Glu Pro Lys
            500                 505                 510

Ser Cys Asp Lys Thr His Thr Cys Pro Pro Cys Pro Ala Pro Glu Phe
            515                 520                 525

Glu Gly Gly Pro Ser Val Phe Leu Phe Pro Pro Lys Pro Lys Asp Thr
            530                 535                 540

Leu Met Ile Ser Arg Thr Pro Glu Val Thr Cys Val Val Val Asp Val
545                 550                 555                 560

Ser His Glu Asp Pro Glu Val Lys Phe Asn Trp Tyr Val Asp Gly Val
                565                 570                 575

Glu Val His Asn Ala Lys Thr Lys Pro Arg Glu Glu Gln Tyr Gln Ser
            580                 585                 590

Thr Tyr Arg Val Val Ser Val Leu Thr Val Leu His Gln Asp Trp Leu
            595                 600                 605

Asn Gly Lys Glu Tyr Lys Cys Lys Val Ser Asn Lys Ala Leu Pro Ala
            610                 615                 620

Ser Ile Glu Lys Thr Ile Ser Lys Ala Lys Gly Gln Pro Arg Glu Pro
625                 630                 635                 640

Gln Val Tyr Thr Leu Pro Pro Ser Arg Glu Glu Met Thr Lys Asn Gln
            645                 650                 655

Val Ser Leu Thr Cys Leu Val Lys Gly Phe Tyr Pro Ser Asp Ile Ala
            660                 665                 670

Val Glu Trp Glu Ser Asn Gly Gln Pro Glu Asn Asn Tyr Lys Thr Thr
            675                 680                 685

Pro Pro Val Leu Asp Ser Asp Gly Ser Phe Phe Leu Tyr Ser Lys Leu
            690                 695                 700

Thr Val Asp Lys Ser Arg Trp Gln Gln Gly Asn Val Phe Ser Cys Ser
705                 710                 715                 720

Val Met His Glu Ala Leu His Asn His Tyr Thr Gln Lys Ser Leu Ser
            725                 730                 735

Leu Ser Pro Gly Lys
            740

<210> SEQ ID NO 213
<211> LENGTH: 2256
<212> TYPE: DNA
<213> ORGANISM: Artificial Sequence
<220> FEATURE:
<223> OTHER INFORMATION: synthetic

<400> SEQUENCE: 213
caaggccagt ctggatccgg ttatctgtgg ggttgcgagt ggaattgcgg agggatcact      60
acaggctcga gcggtggcag cggtggctct ggtggtatat cgagtggatt gctgtctggc     120
agatctgacc aacacggcgg cggttctcaa actgtagtaa ctcaagaacc aagcttctcc     180
gtctcccctg ggggaacagt cacacttacc tgccgaagta gtacaggtgc tgttacgacc     240
agtaactatg ccaattgggt acaacaaacg cctggtcagg ctccgcgcgg attgatagga     300
ggcacgaata aacgggcacc cggtgtcccg gacagattca gcggaagcat actcggtaat     360
aaggcagctc ttactatcac tggggcccaa gctgatgatg aaagtgatta ttattgtgcg     420
ctctggtaca gcaacctctg ggtgtttggg ggtggcacga aacttactgt cttgggcggc     480
ggcggatcag ggggaggtgg ctctggagga ggaggctcag aagtccaact ggtcgaatcc     540
gggggagggc tcgtacagcc gggtgggtcc ctcaaactct cttgtgcggc ctcagggttt     600

```
accttcagta catacgcgat gaattgggtc cggcaggcca gtgggaaagg gctcgaatgg    660
gtaggacgaa tccgatcaaa atacaacaac tacgctactt attacgctga ttccgtgaag    720
gacagattca caatatcccg cgacgatagc aagaatacgg catatcttca gatgaattct    780
cttaaaactg aggataccgc tgtgtattac tgcacaagac atggtaattt tggaaactca    840
tatgtctctt ggttcgctta ttggggacag ggcacgttgg ttaccgtgtc tagcggaggt    900
ggtggatccc aggtgcagct gaaacagagc ggcccgggcc tggtgcagcc gagccagagc    960
ctgagcatta cctgcaccgt gagcggcttt agcctgacca ctatggcgt gcattgggtg    1020
cgccagagcc cgggcaaagg cctggaatgg ctgggcgtga tttggagcgg cggcaacacc    1080
gattataaca ccccgtttac cagccgcctg agcattaaca agataacag caaaagccag    1140
gtgtttttta aaatgaacag cctgcaaagc caggataccg cgatttatta ttgcgcgcgc    1200
gcgctgacct attatgatta tgaatttgcg tattggggcc agggcaccct ggtgaccgtg    1260
agcgcggcta gcaccaaggg cccatcggtc ttccccctgg cacccctcct caagagcacc    1320
tctgggggca gcggccct gggctgcctg gtcaaggact acttccccga accggtgacg    1380
gtgtcgtgga actcaggcgc cctgaccagc ggcgtgcaca ccttcccggc tgtcctacag    1440
tcctcaggac tctactccct cagcagcgtg gtgaccgtgc cctccagcag cttgggcacc    1500
cagacctaca tctgcaacgt gaatcacaag cccagcaaca ccaaggtgga caagaaagtt    1560
gagcccaaat cttgtgacaa aactcacaca tgcccaccgt gcccagcacc tgaatttgaa    1620
gggggaccgt cagtcttcct cttcccccca aaacccaagg acaccctcat gatctcccgg    1680
acccctgagg tcacatgcgt ggtggtggac gtgagccacg aagaccctga ggtcaagttc    1740
aactggtacg tggacggcgt ggaggtgcat aatgccaaga caaagccgcg ggaggagcag    1800
taccagagca cgtaccgtgt ggtcagcgtc ctcaccgtcc tgcaccagga ctggctgaat    1860
ggcaaggagt acaagtgcaa ggtctccaac aaagccctcc cagcctcaat cgagaaaacc    1920
atctccaaag ccaaagggca gccccgagaa ccacaggtgt acaccctgcc cccatcccgg    1980
gaggagatga ccaagaacca ggtcagcctg acctgcctgg tcaaaggctt ctatcccagc    2040
gacatcgccg tggagtggga gagcaatggg cagccggaga caactacaa gaccacgcct    2100
cccgtgctgg actccgacgg ctccttcttc ctctacagca agctcaccgt ggacaagagc    2160
aggtggcagc aggggaacgt cttctcatgc tccgtgatgc atgaggctct gcacaaccac    2220
tacacgcaga agagcctctc cctgtctccg ggtaaa    2256

<210> SEQ ID NO 214
<211> LENGTH: 746
<212> TYPE: PRT
<213> ORGANISM: Artificial Sequence
<220> FEATURE:
<223> OTHER INFORMATION: synthetic

<400> SEQUENCE: 214

Gly Tyr Leu Trp Gly Cys Glu Trp Asn Cys Gly Ile Thr Thr Gly
1               5                   10                  15

Ser Ser Gly Gly Ser Gly Gly Ser Gly Gly Ile Ser Ser Gly Leu Leu
            20                  25                  30

Ser Gly Arg Ser Asp Gln His Gly Gly Gly Ser Gln Thr Val Val Thr
        35                  40                  45

Gln Glu Pro Ser Phe Ser Val Ser Pro Gly Gly Thr Val Thr Leu Thr
    50                  55                  60

Cys Arg Ser Ser Thr Gly Ala Val Thr Thr Ser Asn Tyr Ala Asn Trp
```

-continued

```
                 65                  70                  75                  80
Val Gln Gln Thr Pro Gly Gln Ala Pro Arg Gly Leu Ile Gly Thr
                 85                  90                  95
Asn Lys Arg Ala Pro Gly Val Pro Asp Arg Phe Ser Gly Ser Ile Leu
                100                 105                 110
Gly Asn Lys Ala Ala Leu Thr Ile Thr Gly Ala Gln Ala Asp Asp Glu
                115                 120                 125
Ser Asp Tyr Tyr Cys Ala Leu Trp Tyr Ser Asn Leu Trp Val Phe Gly
                130                 135                 140
Gly Gly Thr Lys Leu Thr Val Leu Gly Gly Gly Ser Gly Gly Gly
145                 150                 155                 160
Gly Ser Gly Gly Gly Ser Glu Val Gln Leu Val Glu Ser Gly Gly
                165                 170                 175
Gly Leu Val Gln Pro Gly Gly Ser Leu Lys Leu Ser Cys Ala Ala Ser
                180                 185                 190
Gly Phe Thr Phe Ser Thr Tyr Ala Met Asn Trp Val Arg Gln Ala Ser
                195                 200                 205
Gly Lys Gly Leu Glu Trp Val Gly Arg Ile Arg Ser Lys Tyr Asn Asn
                210                 215                 220
Tyr Ala Thr Tyr Tyr Ala Asp Ser Val Lys Asp Arg Phe Thr Ile Ser
225                 230                 235                 240
Arg Asp Asp Ser Lys Asn Thr Ala Tyr Leu Gln Met Asn Ser Leu Lys
                245                 250                 255
Thr Glu Asp Thr Ala Val Tyr Tyr Cys Thr Arg His Gly Asn Phe Gly
                260                 265                 270
Asn Ser Tyr Val Ser Trp Phe Ala Tyr Trp Gly Gln Gly Thr Leu Val
                275                 280                 285
Thr Val Ser Ser Gly Gly Gly Gly Ser Gln Val Gln Leu Lys Gln Ser
                290                 295                 300
Gly Pro Gly Leu Val Gln Pro Ser Gln Ser Leu Ser Ile Thr Cys Thr
305                 310                 315                 320
Val Ser Gly Phe Ser Leu Thr Asn Tyr Gly Val His Trp Val Arg Gln
                325                 330                 335
Ser Pro Gly Lys Gly Leu Glu Trp Leu Gly Val Ile Trp Ser Gly Gly
                340                 345                 350
Asn Thr Asp Tyr Asn Thr Pro Phe Thr Ser Arg Leu Ser Ile Asn Lys
                355                 360                 365
Asp Asn Ser Lys Ser Gln Val Phe Phe Lys Met Asn Ser Leu Gln Ser
                370                 375                 380
Gln Asp Thr Ala Ile Tyr Tyr Cys Ala Arg Ala Leu Thr Tyr Tyr Asp
385                 390                 395                 400
Tyr Glu Phe Ala Tyr Trp Gly Gln Gly Thr Leu Val Thr Val Ser Ala
                405                 410                 415
Ala Ser Thr Lys Gly Pro Ser Val Phe Pro Leu Ala Pro Ser Ser Lys
                420                 425                 430
Ser Thr Ser Gly Gly Thr Ala Ala Leu Gly Cys Leu Val Lys Asp Tyr
                435                 440                 445
Phe Pro Glu Pro Val Thr Val Ser Trp Asn Ser Gly Ala Leu Thr Ser
                450                 455                 460
Gly Val His Thr Phe Pro Ala Val Leu Gln Ser Ser Gly Leu Tyr Ser
465                 470                 475                 480
Leu Ser Ser Val Val Thr Val Pro Ser Ser Ser Leu Gly Thr Gln Thr
                485                 490                 495
```

```
Tyr Ile Cys Asn Val Asn His Lys Pro Ser Asn Thr Lys Val Asp Lys
            500                 505                 510

Lys Val Glu Pro Lys Ser Cys Asp Lys Thr His Thr Cys Pro Pro Cys
        515                 520                 525

Pro Ala Pro Glu Phe Glu Gly Gly Pro Ser Val Phe Leu Phe Pro Pro
    530                 535                 540

Lys Pro Lys Asp Thr Leu Met Ile Ser Arg Thr Pro Glu Val Thr Cys
545                 550                 555                 560

Val Val Val Asp Val Ser His Glu Asp Pro Glu Val Lys Phe Asn Trp
                565                 570                 575

Tyr Val Asp Gly Val Glu Val His Asn Ala Lys Thr Lys Pro Arg Glu
            580                 585                 590

Glu Gln Tyr Gln Ser Thr Tyr Arg Val Val Ser Val Leu Thr Val Leu
        595                 600                 605

His Gln Asp Trp Leu Asn Gly Lys Glu Tyr Lys Cys Lys Val Ser Asn
    610                 615                 620

Lys Ala Leu Pro Ala Ser Ile Glu Lys Thr Ile Ser Lys Ala Lys Gly
625                 630                 635                 640

Gln Pro Arg Glu Pro Gln Val Tyr Thr Leu Pro Pro Ser Arg Glu Glu
                645                 650                 655

Met Thr Lys Asn Gln Val Ser Leu Thr Cys Leu Val Lys Gly Phe Tyr
            660                 665                 670

Pro Ser Asp Ile Ala Val Glu Trp Glu Ser Asn Gly Gln Pro Glu Asn
        675                 680                 685

Asn Tyr Lys Thr Thr Pro Pro Val Leu Asp Ser Asp Gly Ser Phe Phe
    690                 695                 700

Leu Tyr Ser Lys Leu Thr Val Asp Lys Ser Arg Trp Gln Gln Gly Asn
705                 710                 715                 720

Val Phe Ser Cys Ser Val Met His Glu Ala Leu His Asn His Tyr Thr
                725                 730                 735

Gln Lys Ser Leu Ser Leu Ser Pro Gly Lys
            740                 745

<210> SEQ ID NO 215
<211> LENGTH: 780
<212> TYPE: DNA
<213> ORGANISM: Artificial Sequence
<220> FEATURE:
<223> OTHER INFORMATION: synthetic

<400> SEQUENCE: 215
tgcatctcac ctcgtggttg tccggacggc ccatacgtca tgtacggctc gagcggtggc      60
agcggtggct ctggtggatc cggtatatcg agtggattgc tgtctggcag atctgaccaa     120
cacggcagta gcggtaccca gatcttgctg acccagagcc cggtgattct gagcgtgagc     180
ccgggcgaac gtgtgagctt tagctgccgc gcgagccaga gcattggcac caacattcat     240
tggtatcagc agcgcaccaa cggcagcccg cgcctgctga ttaaatatgc gagcgaaagc     300
attagcggca ttccgagccg ctttagcggc agcggcagcg gcaccgattt taccctgagc     360
attaacagcg tggaaagcga agatattgcg gattattatt gccagcagaa caacaactgg     420
ccgaccacct ttggcgcggg caccaaactg gaactgaaac gtacggtggc tgcaccatct     480
gtcttcatct tcccgccatc tgatgagcag ttgaaatctg gaactgcctc tgttgtgtgc     540
ctgctgaata acttctatcc cagagaggcc aaagtacagt ggaaggtgga taacgccctc     600
```

-continued

```
caatcgggta actcccagga gagtgtcaca gagcaggaca gcaaggacag cacctacagc    660
ctcagcagca ccctgacgct gagcaaagca gactacgaga acacaaagt ctacgcctgc    720 gaagtcaccc atcagggcct gagctcgccc gtcacaaaga gcttcaacag gggagagtgt   780

<210> SEQ ID NO 216
<211> LENGTH: 260
<212> TYPE: PRT
<213> ORGANISM: Artificial Sequence
<220> FEATURE:
<223> OTHER INFORMATION: synthetic

<400> SEQUENCE: 216

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
                20                  25                  30

Leu Leu Ser Gly Arg Ser Asp Gln His Gly Ser Ser Gly Thr Gln Ile
            35                  40                  45

Leu Leu Thr Gln Ser Pro Val Ile Leu Ser Val Ser Pro Gly Glu Arg
        50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
                260
```

ANTIBODIES, ACTIVATABLE ANTIBODIES, BISPECIFIC ANTIBODIES, AND BISPECIFIC ACTIVATABLE ANTIBODIES AND METHODS OF USE THEREOF

CROSS-REFERENCE TO RELATED APPLICATIONS

This application claims the benefit of U.S. Provisional Application No. 62/572,468, filed Oct. 14, 2017; U.S. Provisional Application No. 62/577,140, filed Oct. 25, 2017; U.S. Provisional Application No. 62/613,358, filed Jan. 3, 2018; U.S. Provisional Application No. 62/666,065, filed May 2, 2018; and U.S. Provisional Application No. 62/731,622, filed Sep. 14, 2018, the contents of each of which are incorporated herein by reference in their entirety.

FIELD OF THE INVENTION

Provided herein antibodies, activatable antibodies (AAs), bispecific antibodies, and bispecific activatable antibodies (BAAs). Also provided herein are methods of making and methods of use of these antibodies, AAs, bispecific antibodies, and BAAs.

REFERENCE TO SEQUENCE LISTING

The "Sequence Listing" submitted electronically concurrently herewith pursuant 37 C.F.R. § 1.821 in computer readable form (CRF) via EFS-Web as file name CYTX-045-US_SEQLIST_10-12-18_ST25.txt is incorporated herein by reference. The electronic copy of the Sequence Listing was created on 10-12-18, and the size on disk is 440 kilobytes.

BACKGROUND

Antibody-based therapies have proven effective treatments for several diseases but in some cases, toxicities due to broad target expression have limited their therapeutic effectiveness. In addition, antibody-based therapeutics have exhibited other limitations such as rapid clearance from the circulation following administration.

In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

Accordingly, there is a continued need in the field of antibody-based therapeutics for antibodies that mimic the desirable characteristics of the small molecule prodrug.

SUMMARY OF THE INVENTION

Provided herein are antibodies, bispecific antibodies, activatable antibodies, and bispecific activatable antibodies, methods of making, and methods of use thereof. These find use in therapeutics and diagnostics. The activatable antibodies and bispecific activatable antibodies of the present disclosure may be used to reduce damage to healthy tissue generally caused by an antibody binding to its target on healthy tissue as well as on diseased tissue.

Accordingly in one aspect, provided herein are bispecific activatable antibodies (BAA), wherein said BAA, when activated, specifically binds to two targets and comprises the following structure:

a) an IgG antibody (AB1) that specifically binds to a first target wherein the AB1 comprises:
   a. two heavy chains (AB1 HCs) and two light chains (AB1 LCs); and
   b. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein
   c. the MM1 inhibits the binding of the AB1 to its target; and
   d. the CM1 is a polypeptide that functions as a substrate for a first protease,
b) two scFvs (AB2) that each specifically binds to a second target wherein each AB2 comprises:
   a. a light chain variable region linked to a heavy chain variable region, wherein the carboxyl terminus of each AB2 is linked to the amino terminus each of the AB1 heavy chains; and
   b. a second masking moiety (MM2) linked to a second cleavable moiety (CM2) to form a MM2-CM2 construct, wherein the carboxyl terminus of a MM2-CM2 construct is linked to the amino terminus of each AB2 wherein
   c. the MM2 inhibits the binding of the AB2 to its target; and
   d. the CM2 is a polypeptide that functions as a substrate for a second protease,
c) and wherein the BAA has at least one of the following characteristics:
   a. MM2 comprises amino acid sequence SEQ ID NO: 12;
   b. MM1 comprises an amino acid sequence selected from the group consisting of sequences presented in Table 7;
   c. AB2 comprises a heavy chain variable domain as set forth in SEQ ID NO: 2 or SEQ ID NO: 3 or a light chain variable domain as set forth in SEQ ID NO: 1 or SEQ ID NO: 4; and
   d. AB1 comprises an Fc region comprising an amino acid substitution in at least one of amino acid positions L234, L235, N297, and P331, as numbered by the EU index as set forth in Kabat, such that the BAA has reduced effector function.

In some embodiments, the BAAs provided herein comprise: A bispecific activatable antibody (BAA), wherein said BAA, when activated, specifically binds to two targets and comprises the following structure:

a. an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, b. two scFvs (each an AB2) that each specifically binds to a second target wherein each AB2 comprises a light chain variable region linked to a heavy chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and the CM2 is a polypeptide that functions as a substrate for a second protease, and wherein the BAA has at least one of the following characteristics:
i. MM2 comprises amino acid sequence SEQ ID NO: 12;

ii. MM1 comprises an amino acid sequence selected from the group consisting of sequences presented in Table 7;

iii. AB2 comprises a heavy chain variable domain as set forth in SEQ ID NO: 2 or SEQ ID NO: 3 or a light chain variable domain as set forth in SEQ ID NO: 1 or SEQ ID NO: 4; and iv. AB1 comprises an Fc region comprising an amino acid substitution in at least one of amino acid positions L234, L235, N297, and P331, as numbered by the EU index as set forth in Kabat, such that the BAA has reduced effector function.

In some embodiments, the BAA comprises a heavy chain variable domain as set forth in SEQ ID NO: 2 or SEQ ID NO: 3 and a light chain variable domain as set forth in SEQ ID NO: 1 or SEQ ID NO: 4. In some embodiments, the AB1 binds a tumor target and the AB2 binds an immune effector target. In some embodiments, the BAA is a T cell-engaging bispecific (TCB) AA (TCBAA). In some embodiments, the AB1 binds EGFR and the AB2 binds CD3. In some embodiments, the MM1 comprises an amino acid sequence selected from the group consisting of sequences presented in Table 7. In some embodiments, the MM1 comprises an amino acid sequence selected from the group consisting of SEQ ID NO: 85 and SEQ ID NO: 78. In some embodiments, the MM1 comprises SEQ ID NO: 78. In some embodiments, the MM2 comprises the amino acid sequence SEQ ID NO: 12. In some embodiments, the CM comprises the amino acid sequence of SEQ ID NO: 14. In some embodiments, the CM comprises the amino acid sequence of SEQ ID NO: 17. In some embodiments, the CMs the CM comprises the amino acid sequence of SEQ ID NO: 16. In some embodiments, the CM1 comprises an amino acid sequence selected from the group comprising SEQ ID NO: 14 and SEQ ID NO: 16. In some embodiments, the CM2 comprises an amino acid sequence selected from the group comprising SEQ ID NO: 14 and SEQ ID NO: 17. In some embodiments, provided herein is BAA CI106, comprising the layout and sequence as provided in Table 11 and Example 1. In some embodiments, provided herein is BAA CI107, comprising the layout and sequence as provided in Table 11 and Example 1. In some embodiments, provided herein is BAA CI079, comprising the layout and sequence as provided in Table 11 and Example 1. In some embodiments, provided herein is BAA CI090, comprising the layout and sequence as provided in Table 11 and Example 1. In some embodiments, provided herein is BAA CI135, comprising the layout and sequence as provided in Table 11 and Example 1. In some embodiments, provided herein is BAA CI136, comprising the layout and sequence as provided in Table 11 and Example 1. In some embodiments, the AB1 comprises amino acid substitutions in at least two of amino acid positions L234, L235, and P331. In some embodiments, the AB1 comprises amino acid substitutions at amino acid positions L234, L235, and P331. In some embodiments, the AB1 comprises L234F, L235E, and P331S amino acid substitutions. In some embodiments, the AB1 comprises an Fc region comprising an amino acid substitution at N297. In some embodiments, the AB1 comprises L234F, L235E, P331S, and N297Q amino acid substitutions. In some embodiments, the heavy chain of the AB1 comprises any one of SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76, as set forth in Table 6.

In another aspect, provided herein is a bispecific activatable antibody (BAA) comprising:

a) an IgG antibody (AB1) that specifically binds to a first target wherein the AB1 comprises:

i. two heavy chains (AB1 HCs) and two light chains (AB1 LCs); and ii. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, b) two scFvs (AB2) that each specifically binds to a second target wherein each AB2 comprises:

i. a heavy chain variable region linked to a light chain variable region, wherein the carboxyl terminus of each AB2 is linked to the amino terminus each of the AB1 heavy chains; and ii. a second masking moiety (MM2) linked to a second cleavable moiety (CM2) to form a MM2-CM2 construct, wherein the carboxyl terminus of a MM2-CM2 construct is linked to the amino terminus of each AB2 wherein the MM2 inhibits the binding of the AB2 to its target; and the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function. In some embodiments, the Fc region comprises amino acid substitutions in at least amino acid positions L234, L235, N297 and P331, as numbered by the EU index as set forth in Kabat, such that the BAA has reduced effector function. In some embodiments, the Fc region comprises amino acid substitutions in at least amino acid positions L234, L235, and P331, as numbered by the EU index as set forth in Kabat, such that the BAA has reduced effector function. In some embodiments, the first target is selected from the group consisting of the targets presented in Table 9 and the second target is selected from the group consisting of the targets presented in Table 9.

In some embodiments, the BAAs provided herein comprise:

a) A bispecific activatable antibody (BAA) comprising:

i) an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, ii) two scFvs (each an AB2) that each specifically binds to a second target wherein each AB2 comprises a heavy chain variable region linked to a light chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function. In some embodiments, the Fc region comprises amino acid substitutions in at least amino acid positions L234, L235, N297 and P331, as numbered by the EU index as set forth in Kabat, such that the BAA has reduced effector function. In some embodiments, the Fc region comprises amino acid substitutions in at least amino acid positions L234, L235, and P331, as numbered by the EU index as set forth in Kabat, such that the BAA has reduced effector function. In some embodiments, the first target is selected from the group consisting of the targets presented in Table 9 and the second target is selected from the group consisting of the targets presented in Table 9.

In another aspect, provided herein is an activatable antibody (AA) comprising: (a) an antibody (AB) that specifically binds to Epidermal Growth Factor Receptor (EGFR), wherein the AB is an IgG1 antibody, and wherein the Fc region of the AB comprises an amino acid substitution in at least one of amino acid positions L234, L235, and P331, as numbered by the EU index as set forth in Kabat, such that the AA has reduced effector function; (b) a masking moiety (MM) coupled to the AB, wherein the MM reduces or inhibits the binding of the AB to the EGFR when the AA is in an uncleaved state; and (c) a cleavable moiety (CM) coupled to the AB, wherein the CM is a polypeptide that functions as a substrate for a protease. In some embodiments, the amino acid substitution is any one or more of L234F, L235E, and P331S. In some embodiments, the AB comprises amino acid substitutions in at least two of amino acid positions L234, L235, and P331. In some embodiments, the AB comprises amino acid substitutions at amino acid positions L234, L235, and P331. In some embodiments, the AB comprises L234F, L235E, and P331S amino acid substitutions. In some embodiments, the AB comprises an Fc region comprising an amino acid substitution at N297. In some embodiments, the Fc region comprises an N297Q mutation. In some embodiments, the AB comprises L234F, L235E, P331S, and N297Q amino acid substitutions. In some embodiments, the MM comprises an amino acid sequence selected from the group consisting of sequences presented in Table 7. In some embodiments, the MM comprises the amino acid sequence of SEQ ID NO: 78. In some embodiments, the MM comprises the amino acid sequence of SEQ ID NO: 85. In some embodiments, the CM comprises an amino acid sequence selected from the group consisting of sequences presented in Table 4. In some embodiments, the CM comprises the amino acid sequence of SEQ ID NO: 14. In some embodiments, the CM comprises the amino acid sequence of SEQ ID NO: 16. In some embodiments, the AA is part of a BAA.

In another aspect, provided herein is an activatable antibody (AA) comprising: (a) an antibody or an antigen binding fragment thereof (AB) that specifically binds to Epidermal Growth Factor Receptor (EGFR); (b) a masking moiety (MM) coupled to the AB, wherein the MM reduces or inhibits the binding of the AB to the EGFR when the AA is in an uncleaved state, and wherein the MM comprises an amino acid sequence selected from the group consisting of sequences presented in Table 7; and (c) a cleavable moiety (CM) coupled to the AB, wherein the CM is a polypeptide that functions as a substrate for a protease. In some embodiments, the MM comprises the amino acid sequence of SEQ ID NO: 78. In some embodiments, the CM comprises a substrate cleavable by a serine protease or an MMP. In some embodiments, the CM comprises an amino acid sequence selected from the group consisting of SEQ ID NO: 18-56. In some embodiments, the CM comprises the amino acid sequence of SEQ ID NO: 14. In some embodiments, the CM comprises the amino acid sequence of SEQ ID NO: 16. In some embodiments, the AA is part of a BAA.

In another aspect, provided herein is an activatable antibody (AA) comprising:

(a) an antibody or antigen binding fragment thereof (AB) that specifically binds to the epsilon chain of CD3, wherein the antibody comprises a heavy chain variable domain as set forth in SEQ ID NO: 2 or SEQ ID NO: 3 or comprises a light chain variable domain as set forth in SEQ ID NO: 1 or SEQ ID NO: 4; (b) a masking moiety (MM) coupled to the AB, wherein the MM reduces or inhibits the binding of the AB to the CD3 when the AA is in an uncleaved state; and (c) a cleavable moiety (CM) coupled to the AB, wherein the CM is a polypeptide that functions as a substrate for a protease. In some embodiments, the AB comprises a heavy chain variable domain as set forth in SEQ ID NO: 2. In some embodiments, the AB comprises a heavy chain variable domain as set forth in SEQ ID NO: 3. In some embodiments, the AB comprises a light chain variable domain as set forth in SEQ ID NO: 1. In some embodiments, the AB comprises a light chain variable domain as set forth in SEQ ID NO: 4. In some embodiments, the AB comprises a heavy chain variable domain as set forth in SEQ ID NO: 2 and a light chain variable domain as set forth in SEQ ID NO: 1. In some embodiments, the AB comprises a heavy chain variable domain as set forth in SEQ ID NO: 3 and a light chain variable domain as set forth in SEQ ID NO: 1. In some embodiments, the AB comprises a heavy chain variable domain as set forth in SEQ ID NO: 2 and a light chain variable domain as set forth in SEQ ID NO: 4. In some embodiments, the AB comprises a heavy chain variable domain as set forth in SEQ ID NO: 3 and a light chain variable domain as set forth in SEQ ID NO: 4. In some embodiments, the MM comprises any one of the sequences set forth in Table 3. In some embodiments, the CM comprises any one of the sequences set forth in Table 4. In some embodiments, the AA is part of a BAA.

In another aspect, provided herein is an activatable antibody (AA) comprising: (a) an antibody or antigen binding fragment thereof (AB) that specifically binds to the epsilon chain of CD3; (b) a masking moiety (MM) coupled to the AB, wherein the MM reduces or inhibits the binding of the AB to the CD3 when the AA is in an uncleaved state, wherein the MM comprises amino acid sequence SEQ ID NO: 12; and (b) a cleavable moiety (CM) coupled to the AB, wherein the CM is a polypeptide that functions as a substrate for a protease. In some embodiments, the CM comprises any one of the sequences set forth in Table 4. In some embodiments, the CM comprises a substrate cleavable by a serine protease or an MMP. In some embodiments, the CM comprises an amino acid sequence selected from the group consisting of SEQ ID NO: 18-56. In some embodiments, the protease is an MMP. In some embodiments, protease is a serine protease. In some embodiments, the AA is part of a BAA.

In another aspect, provided herein is an activatable antibody (AA) comprising: (a) an antibody (AB) that specifically binds a target, wherein the antibody is an IgG1 antibody, and wherein the Fc region of the antibody comprises an amino acid substitution in at least one of amino acid positions L234, L235, and P331, as numbered by the EU index as set forth in Kabat, such that the AA has reduced effector function; (b) a masking moiety (MM) coupled to the AB, wherein the MM reduces or inhibits the binding of the AB to the target when the AA is in an uncleaved state; and (c) a cleavable moiety (CM) coupled to the AB, wherein the CM is a polypeptide that functions as a substrate for a protease. In some embodiments, the Fc region comprises amino acid substitutions in at least amino acid positions L234, L235, N297 and P331, as numbered by the EU index as set forth in Kabat, such that the AA has reduced effector function. In some embodiments, the target is selected from the group consisting of the targets presented in Table 9. In some embodiments, the AA is part of a BAA.

In another aspect, provided herein is an antibody or antigen binding fragment thereof (AB) that specifically binds to the epsilon chain of CD3, wherein the antibody comprises a heavy chain variable domain as set forth in SEQ ID NO: 2 or SEQ ID NO: 3 or a light chain variable domain as set forth in SEQ ID NO: 1 or SEQ ID NO: 4. In some embodiments the antibody comprises a heavy chain variable domain as set forth in SEQ ID NO: 2 or SEQ ID NO: 3 and a light chain variable domain as set forth in SEQ ID NO: 1 or SEQ ID NO: 4. In some embodiments the AB comprises a heavy chain variable domain as set forth in SEQ ID NO: 2. In some embodiments the AB comprises a heavy chain variable domain as set forth in SEQ ID NO: 3. In some embodiments the AB comprises a light chain variable domain as set forth in SEQ ID NO: 1. In some embodiments the AB comprises a light chain variable domain as set forth in SEQ ID NO: 4. In some embodiments the AB comprises a heavy chain variable domain as set forth in SEQ ID NO: 2 and a light chain variable domain as set forth in SEQ ID NO: 1. In some embodiments the AB comprises a heavy chain variable domain as set forth in SEQ ID NO: 3 and a light chain variable domain as set forth in SEQ ID NO: 1. In some embodiments the AB comprises a heavy chain variable domain as set forth in SEQ ID NO: 3 and a light chain variable domain as set forth in SEQ ID NO: 4. In some embodiments the AB comprises a heavy chain variable domain as set forth in SEQ ID NO: 2 and a light chain variable domain as set forth in SEQ ID NO: 4. In some embodiments, the antibody is a bispecific AB. In some embodiments the antibody is a scFv. In some embodiments the antibody is an IgG1 antibody. In some embodiments, the antibody is part of an AA or is part of a BAA.

In another aspect, provided herein is an antibody that specifically binds to EGFR or CD3 (AB), wherein the antibody is an IgG1 antibody or a scFv linked to an Fc domain, wherein the antibody comprises an Fc region comprising an amino acid substitution in at least one of amino acid positions L234, L235, and P331, as numbered by the EU index as set forth in Kabat, such that the antibody has reduced effector function. In some embodiments, the amino acid substitution is any one or more of L234F, L235E, and P331S. In some embodiments, the antibody comprises amino acid substitutions in at least two of amino acid positions L234, L235, and P331. In some embodiments, the antibody comprises amino acid substitutions at amino acid positions L234, L235, and P331. In some embodiments, the antibody comprises L234F, L235E, and P331S amino acid substitutions. In some embodiments, the antibody comprises an Fc region comprising an amino acid substitution at N297. In some embodiments, the Fc region comprises an N297Q mutation. In some embodiments, the antibody comprises L234F, L235E, P331S, and N297Q amino acid substitutions. In some embodiments, the heavy chain of the antibody comprises any one of SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76, as set forth in Table 6. In some embodiments, the heavy chain variable domain of the antibody comprises any one of SEQ ID NO: 2 or SEQ ID NO: 3 or wherein the light chain variable domain of the AB comprises any one of SEQ ID NO: 1 or SEQ ID NO: 4. In some embodiments, the antibody is part of an AA or is part of a BAA.

In another aspect, also provided herein are pharmaceutical composition comprising any one of the BAAs, AAs, and antibodies described above, and optionally a carrier. In another aspect, also provided herein are pharmaceutical composition comprising any one of the BAAs, AAs, and antibodies described above and a carrier. In some embodiments, the composition comprises an additional agent, for example the additional agent can be a therapeutic agent.

In another aspect, also provided herein are isolated nucleic acid molecules encoding any one of the BAAs, AAs, and antibodies described above. Also provided are vectors comprising the nucleic acid is provided. In some embodiments, the vector comprises the nucleic acid sequence of pLW289. In some embodiments, the vector comprises the nucleic acid sequence of pLW246. In some embodiments, the vector comprises the nucleic acid sequence of pLW307. In some embodiments, the vector comprises the nucleic acid sequence of pLW291. In some embodiments, the vector comprises the nucleic acid sequence of pLW352. In some embodiments, the vector comprises the nucleic acid sequence of pLW246. In some embodiments, the vector comprises the nucleic acid sequence of pLW353.

In another aspect, also provided herein is a cell comprising any one of the vectors described above. In some embodiments, provided herein is a cell comprising pLW289 and pLW246. In some embodiments, provided herein is a cell comprising pLW307 and pLW291. In some embodiments, provided herein is a cell comprising pLW352 and pLW246. In some embodiments, provided herein is a cell comprising pLW353 and pLW246.

In another aspect, provided herein are methods of producing the antibody, AA, or BAA provided above, by culturing a cell under conditions that lead to expression of the antibody, AA, or BAA, wherein the cell comprises the relevant nucleic acid molecule or vectors provided herein.

In another aspect, provided herein is a method of treating, alleviating a symptom of, or delaying the progression of a disorder or disease comprising administering a therapeutically effective amount of the antibodies/AAs/BAAs/pharmaceutical compositions described above to a subject in need thereof. In some embodiments, the disorder or disease comprises disease cells expressing EGFR. In some embodiments, the disorder or disease is cancer. In some embodiments, the cancer is anal cancer, basal cell carcinoma, brain cancer, bladder cancer, bone cancer, breast cancer, cervical cancer, cholangiocarcinoma, colorectal cancer, endometrial cancer, esophageal cancer, gall bladder cancer, gastric cancer, glioblastoma, head and neck cancer, liver cancer, lung cancer, ovarian cancer, pancreatic cancer, prostate cancer, renal cancer, sarcoma, small bowel carcinoma, skin cancer, testicular cancer, thyroid cancer or uterine cancer. In some embodiments, the disorder is lymphoma, e.g. Epstein-Barr virus associated lymphoma, B-cell lymphoma, T-cell lymphoma Hodgkins and non-Hodgkins lymphoma. In some embodiments, the cancer is a squamous cell cancer. In some embodiments, the cancer is a head and neck squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

In another aspect, provided herein is a method of inhibiting angiogenesis in a subject comprising administering a therapeutically effective amount of the antibodies/AAs/BAAs/pharmaceutical compositions described above to a subject in need thereof. In some embodiments, the method comprises administering an additional agent. In some embodiments, the additional agent is a therapeutic agent.

In another aspect, provided herein is a method to reduce damage to healthy tissue caused by an antibody binding to its target on healthy tissue as well as on diseased tissue (e.g. cancerous tissue), the method comprising administering to a subject in need thereof an AA or BAA or a pharmaceutical composition comprising an AA or BAA, wherein said AA or BAA is an AA or BAA of any one of the embodiments provided herein.

In another aspect, provided herein is a method to improve tolerability of an antibody treatment comprising administering to a subject in need thereof (e.g. a subject suffering from cancer) an AA or BAA or a pharmaceutical composition comprising an AA or BAA, wherein said AA or BAA is an AA or BAA of any one of the embodiments provided herein.

In another aspect provided herein is a method to recruit T cells to tumor tissue comprising administering to a subject in need thereof an AA or BAA or a pharmaceutical composition comprising an AA or BAA, wherein said AA or BAA is an AA or BAA of any one of the embodiments provided herein.

In another aspect provided herein is an antibody, AA, BAA, or pharmaceutical composition, of any one of the embodiments provided herein, for use as a medicament. The medicament may be for use in a method of reducing damage to healthy tissue caused by an antibody binding to its target on healthy tissue as well as on diseased tissue. The medicament may be for use in improving the tolerability of an antibody treatment.

In another aspect, provided herein is an antibody, AA, BAA, or pharmaceutical composition, of any one of the embodiments provided herein, for use in a method of treating, alleviating a symptom of, or delaying the progression of a disorder or disease, wherein the disorder or disease comprises disease cells expressing EGFR.

In another aspect provided herein is an antibody, AA, BAA, or pharmaceutical composition, of any one of the embodiments provided herein, for use in a method of treating cancer; optionally wherein the cancer is anal cancer, basal cell carcinoma, brain cancer, bladder cancer, breast cancer, bone cancer, cervical cancer, cholangiocarcinoma, colorectal cancer, endometrial cancer, esophageal cancer, gall bladder cancer, gastric cancer, glioblastoma, head and neck cancer, liver cancer, lung cancer, ovarian cancer, pancreatic cancer, prostate cancer, renal cancer, sarcoma, small bowel carcinoma, squamous cell cancer, skin cancer testicular cancer, thyroid cancer or uterine cancer. The use may comprise the recruitment of T cells to tumor tissue.

In another aspect provided herein is an antibody, AA, BAA, or pharmaceutical composition, of any one of the embodiments provided herein, for use in a method comprising inhibiting angiogenesis.

The antibody, AA, BAA, or pharmaceutical composition, of any one of the embodiments provided herein, may be for use in a method of treatment comprising administering an additional agent; optionally wherein the additional agent is a therapeutic agent.

BRIEF DESCRIPTION OF THE DRAWINGS

FIG. 2B also depicts a more than 300,000 fold EC50 shift of the dually masked antibodies (i.e., BAAs masked at both the EGFR and CD3 target binding domains) CI106 and CI107 relative to the protease activated bispecific antibody (i.e., BAA activated by protease treatment) act-104 (interchangeably referred to as CI104).

FIG. 3A demonstrates that activation of primary CD8+ T cells was attenuated by CI106 and CI107, relative to CI011 and CI040. FIG. 3B demonstrates that dually masked antibodies display a shifted dose response curve for T cell activation relative to protease activated bispecific antibody act-104 indicating that masking attenuates T cell activation.

FIGS. 6A-6B demonstrate that the EC50s of the tested dually masked and protease activated bispecific antibodies are similar when either human (6A) or cyno (6B) effector cells are used. FIGS. 6C-6D demonstrate that binding of the protease-activated and dually masked antibodies to human (6C) and cyno (6D) T cells is similar.

FIGS. 10A-E plot dose dependent increases in AST at 48 h post dose (10A), ALT at 48 h post dose (10B), L-6 at 8 h post dose (10C), IFNg at 8 h post dose (10D), and Ki67 at 72 h post dose (10E) in cynomolgus monkeys treated with act-104, CI106 or CI107. The dose response curve for all parameters was shifted for the dually masked antibodies indicating improved tolerability and decreased pharmacodynamics effects relative to the protease activated bispecific antibody.

DETAILED DESCRIPTION OF THE INVENTION

Figure 1A:
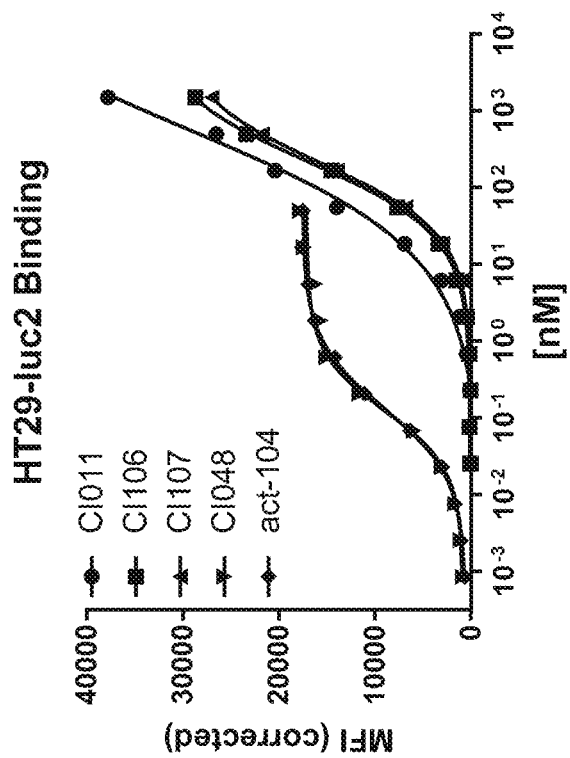
FIG. 1A demonstrates that incorporation of the h20GG CD3ε masking peptide into the EGFR masked BAAs CI106 and CI107 significantly reduced binding to Jurkat cells relative to CI011. A reduction in binding to EGFR+HT29-luc2 cells was also evident for CI106 and CI107 relative to CI011 (FIG. 1B).

Provided herein are antibodies, activatable antibodies (AAs), bispecific antibodies, and bispecific activatable antibodies (BAAs).

In some embodiments, provided herein are humanized antibodies that specifically bind to the epsilon chain of CD3 (CD3ε; referred to herein interchangeably as CD3).

In some embodiments, provided herein are IgG1 antibodies that specifically bind to Epidermal Growth Factor Receptor (EGFR), wherein the antibodies comprise point mutations in the Fc region, such that the antibody has reduced effector function.

In some embodiments provided herein are AAs, for example AAs that specifically bind to EGFR or CD3. These AAs are optimized for affinity, effector function, masking, and cleavability.

In some embodiments, provided herein are BAAs, for example BAAs that bind to a target antigen (e.g. tumor antigen, such as a target presented in Table 9) and a second antigen (e.g. immune effector antigen on an immune effector cell). In some embodiments, the immune effector cell is a leukocyte cell. In some embodiments, the immune effector cell is a T cell. In some embodiments, the immune effector cell is a natural killer (NK) cell. In some embodiments, the immune effector cell is a macrophage. In some embodiments, the immune effector cell is a mononuclear cell, such as a myeloid mononuclear cell. In some embodiments, the BAAs are immune effector cell-engaging BAAs. In some embodiments, the BAAs are leukocyte cell-engaging BAAs. In some embodiments, the BAAs are T cell engaging bispecific (TCB) AAs, also referred to herein as TCBAAs. In some embodiments, the BAAs are NK cell-engaging BAAs. In some embodiments, the BAAs are macrophage cell-engaging BAAs. In some embodiments, the BAAs are mononuclear cell-engaging BAAs, such as myeloid mononuclear cell-engaging BAAs. In some embodiments, the bispecific antibodies bind EGFR and CD3. These BAAs are optimized for affinity, effector function, masking, and cleavability.

Also provided herein are methods of making and methods of use of these antibodies, AAs, and BAAs. AAs, including general production thereof and identification of masking moieties (MMs) and cleavable moieties (CMs) is described in International Publication Numbers WO 2009/025846 by Daugherty et al., published 26 Feb. 2009, and WO 2010/081173 by Stagliano et al., published 15 Jul. 2010, both of which are incorporated by reference in their entirety. BAAs, including general production thereof and identification of masking moieties (MMs) and cleavable moieties (CMs) is described in International Publication Numbers WO2015/013671 by Lowman et al., published 29 Jan. 2015 and WO2016/014974 by Irving et al., published 28 Jan. 2016, both of which are incorporated by reference in their entirety. Also incorporated by reference are International Publication WO2016/014974 by Irving et al., published 28 Jan. 2016, and International Publication WO2016/118629 by Moore et al., published 28 Jul. 2016 which provide AAs, general production, MMs, and CMs.

As used herein, unless specified otherwise, the term "antibody" includes an antibody or antigen-binding fragment thereof that specifically binds its target and is a monoclonal antibody, domain antibody, single chain, Fab fragment, a F(ab')2 fragment, a scFv, a scAb, a dAb, a single domain heavy chain antibody, and a single domain light chain antibody. In some embodiments, the antibody is an IgG antibody. In some embodiments, the antibody is an IgG1 antibody. In some embodiments, the antibody is an IgG4 antibody. In some embodiments, the antibody is a scFv antibody. In some embodiments, such an antibody or immunologically active fragment thereof that binds its target is a mouse, chimeric, humanized or fully human monoclonal antibody.

1. CD3 Antibodies

Provided herein is an antibody or antigen binding fragment thereof (AB) that specifically binds to the epsilon chain of CD3 (CD3ε, referred to herein throughout as CD3).

Exemplary amino acid sequences of CD3-binding antibodies of the disclosure (variable domains) are provided in Table 1. (Predicted CDR sequences are underlined). As provided below, L3 is a linker, linking the light and heavy chain variable domains, in the exemplary CD3-binding antibodies.

TABLE 1

```
Anti-CD3 variant v12
Light Chain Variable Domain LV12
                                     (SEQ ID NO: 1)
QTVVTQEPSFSVSPGGTVTLTCRSSTGAVTTSNYANWVQQTPGQAP

RGLIGGTNKRAPGVPDRFSGSILGNKAALTITGAQADDESDYYCAL

WYSNLWVFGGGTKLTVL

Heavy Chain Variable Domain HV12, wherein L3
is SEQ ID NO: 98
                                     (SEQ ID NO: 2)
EVQLVESGGGLVQPGSLRLSCAASGFTFSTYAMNWVRQAPGKGLE

WVARIRSKYNNYATYYADSVKDRFTISRDDSKNSLYLQMNSLKTED

TAVYYCVRHGNFGNSYVSWFAYWGQGTLVTVSS

LV12-L3-HV12
                                   (SEQ ID NO: 143)
QTVVTQEPSFSVSPGGTVTLTCRSSTGAVTTSNYANWVQQTPGQAP

RGLIGGTNKRAPGVPDRFSGSILGNKAALTITGAQADDESDYYCAL

WYSNLWVFGGGTKLTVL[GGGGSGGGGSGGGGS]EVQLVESGGGLV

QPGGSLRLSCAASGFTFSTYAMNWVRQAPGKGLEWVARIRSKYNNY

ATYYADSVKDRFTISRDDSKNSLYLQMNSLKTEDTAVYYCVRHGNF

GNSYVSWFAYWGQGTLVTVSS

Anti-CD3 variant v16
Light Chain Variable Domain LV12
Sequence provided above

Heavy Chain Variable Domain HV20
                                     (SEQ ID NO: 3)
EVQLVESGGGLVQPGGSLKLSCAASGFTFSTYAMNWVRQASGKGLE

WVGRIRSKYNNYATYYADSVKDRFTISRDDSKNTAYLQMNSLKTED

TAVYYCTRHGNFGNSYVSWFAYWGQGTLVTVSS

LV12-L3-HV20, wherein L3 is SEQ ID NO: 98
                                   (SEQ ID NO: 144)
QTVVTQEPSFSVSPGGTVTLTCRSSTGAVTTSNYANWVQQTPGQAP

RGLIGGTNKRAPGVPDRFSGSILGNKAALTITGAQADDESDYYCAL

WYSNLWVFGGGTKLTVL[GGGGSGGGGSGGGGS]EVQLVESGGGLV

QPGGSLKLSCAASGFTFSTYAMNWVRQASGKGLEWVGRIRSKYNNY

ATYYADSVKDRFTISRDDSKNTAYLQMNSLKTEDTAVYYCTRHGNF

GNSYVSWFAYWGQGTLVTVSS

Anti-CD3 variant v19
Light Chain Variable Domain LV19
                                     (SEQ ID NO: 4)
QAVVTQEPSLTVSPGGTVTLTCRSSTGAVTTSNYANWVQQKPGQAP

RGLIGGTNKRAPGTPARFSGSLIGGKAALTLSGAQPEDEAEYYCAL

WYSNLWVFGGGTKLTVL
```

TABLE 1-continued

```
Heavy Chain Variable Domain HV20
Sequence provided above

LV19-L3-HV20, wherein L3 is SEQ ID NO: 98
                                   (SEQ ID NO: 145)
QAVVTQEPSLTVSPGGTVTLTCRSSTGAVTTSNYANWVQQKPGQAP

RGLIGGTNKRAPGTPARFSGSLIGGKAALTLSGAQPEDEAEYYCAL

WYSNLWVFGGGTKLTVL[GGGGSGGGGSGGGGS]EVQLVESGGGLV

QPGGSLKLSCAASGFTFSTYAMNWVRQASGKGLEWVGRIRSKYNNY

ATYYADSVKDRFTISRDDSKNTAYLQMNSLKTEDTAVYYCTRHGNF

GNSYVSWFAYWGQGTLVTVSS

Anti-CD3 variant v26
Light Chain Variable Domain LV19
Sequence provided above

Heavy Chain Variable Domain HV12
Sequence provided above

LV19-L3-HV12, wherein L3 is SEQ ID NO: 98
                                   (SEQ ID NO: 150)
QAVVTQEPSLTVSPGGTVTLTCRSSTGAVTTSNYANWVQQKPGQAP

RGLIGGTNKRAPGTPARFSGSLIGGKAALTLSGAQPEDEAEYYCAL

WYSNLWVFGGGTKLTVL[GGGGSGGGGSGGGGS]EVQLVESGGGLV

QPGGSLRLSCAASGFTFSTYAMNWVRQAPGKGLEWVARIRSKYNNY

ATYYADSVKDRFTISRDDSKNSLYLQMNSLKTEDTAVYYCVRHGNF

GNSYVSWFAYWGQGTLVTVSS
```

Exemplary scFv linkers (referred to herein as "L3" linking a VH and VL) are provided in Table 1-1.

TABLE 1-1

| SEQ ID NO: | Linker Amino Acid Sequence |
|---|---|
| 98 | GGGGSGGGGSGGGGS |

Exemplary CDR sequences of CD3-binding antibodies are provided in Table 2.

TABLE 2

| Name | CD3 Ab CDR Sequences | SEQ ID NO: |
|---|---|---|
| SP34L1 | RSSTGAVTTSNYAN | SEQ ID NO: 149 |
| SP34L2 | GTNKRAP | SEQ ID NO: 5 |
| SP34L3 | ALWYSNLWV | SEQ ID NO: 6 |
| SP34H1 | TYAMN | SEQ ID NO: 7 |
| SP34H2 | RIRSKYNNYATYYADSVKD | SEQ ID NO: 8 |
| SP34H3 | HGNFGNSYVSWFAY | SEQ ID NO: 9 |

As provided herein, the CD3 antibody comprises at least one of the CDR sequences provided in Table 2.

In some embodiments, the CD3 antibody comprises heavy chain variable domain as set forth in SEQ ID NO: 2.

In some embodiments, the CD3 antibody comprises a heavy chain variable domain as set forth in SEQ ID NO: 3.

In some embodiments, the CD3 antibody comprises a light chain variable domain as set forth in SEQ ID NO: 1.

In some embodiments, the CD3 antibody comprises a light chain variable domain as set forth in SEQ ID NO: 4.

In some embodiments, the CD3 antibody comprises a heavy chain variable domain as set forth in SEQ ID NO: 2 and a light chain variable domain as set forth in SEQ ID NO: 1.

In some embodiments, the CD3 antibody comprises a heavy chain variable domain as set forth in SEQ ID NO: 3 and a light chain variable domain as set forth in SEQ ID NO: 1.

In some embodiments, the CD3 antibody comprises a heavy chain variable domain as set forth in SEQ ID NO: 3 and a light chain variable domain as set forth in SEQ ID NO: 4.

In some embodiments, the CD3 antibody comprises a heavy chain variable domain as set forth in SEQ ID NO: 2 and a light chain variable domain as set forth in SEQ ID NO: 4.

In some embodiments, the CD3 antibody comprises a heavy chain variable domain as set forth in SEQ ID NO: 2 or SEQ ID NO: 3 or comprises a light chain variable domain as set forth in SEQ ID NO: 1 or SEQ ID NO: 4.

In some embodiments, the CD3 antibody comprises a heavy chain variable domain as set forth in SEQ ID NO: 2 or SEQ ID NO: 3 and comprises a light chain variable domain as set forth in SEQ ID NO: 1 or SEQ ID NO: 4.

In some embodiments, the CD3 antibody is a scFv antibody. In some embodiments, the variable domains comprise the following structure from N terminus to C terminus: LV-HV. In some embodiments, the variable domains comprise the following structure from N terminus to C terminus: HV-LV.

In some embodiments, the CD3 antibody is a scFv antibody comprising a heavy chain variable region (VH) linked to a light chain variable region (VL), wherein the VH is linked to the VL by a linker comprising amino acid sequence SEQ ID NO: 98. Exemplary sequences with such a linker are provided in Table 1.

In exemplary embodiments, provided herein is an antibody that specifically binds to CD3 (AB), wherein the antibody is an IgG1 antibody or a scFv linked to an Fc domain, wherein the antibody comprises an Fc region comprising an amino acid substitution in at least one of amino acid positions L234, L235, and P331, as numbered by the EU index as set forth in Kabat, such that the antibody has reduced effector function. In some embodiments, the amino acid substitution is any one or more of L234F, L235E, and P331S. In some embodiments, the antibody comprises amino acid substitutions in at least two of amino acid positions L234, L235, and P331. In some embodiments, the antibody comprises amino acid substitutions at amino acid positions L234, L235, and P331. In some embodiments, the antibody comprises L234F, L235E, and P331S amino acid substitutions. In some embodiments, the antibody comprises an Fc region comprising an amino acid substitution at N297. In some embodiments, the Fc region comprises an N297Q mutation. In some embodiments, the antibody comprises L234F, L235E, P331S, and N297Q amino acid substitutions. In some embodiments, the heavy chain variable domain of the antibody comprises any one of SEQ ID NO: 2 or SEQ ID NO: 3 or wherein the light chain variable domain of the AB comprises any one of SEQ ID NO: 1 or SEQ ID NO: 4.

2. Activatable CD3 Antibodies

In some embodiments, any one of the CD3 antibodies provided herein is in an activatable antibody (AA) format.

As generally provided herein, the AAs of the invention comprise MM-CM constructs, also referred to herein as a prodomain. Accordingly, as used herein, the term "prodomain" refers to a polypeptide comprising a masking moiety (MM) and a cleavable moiety (CM). In some embodiments, the MM and the CM are separated by a linker, referred to herein as L1. In some embodiments, the prodomain comprises a linker at the carboxyl terminus of the CM; this linker, referred to herein as L2, links the CM of the prodomain to the AB. In some embodiments, the prodomain comprises a linker between MM and CM and a linker after CM. In some embodiments, the MM and the CM are not separated by a linker. In certain embodiments a prodomain comprises one of the following formulae (where the formula below represents an amino acid sequence in either N- to C-terminal direction or C- to N-terminal direction): (MM)-L1-(CM), (MM)-(CM)-L2, (MM)-L1-(CM)-L2, or (MM)-(CM). In exemplary embodiments, a prodomain comprises an EGFR MM and a CM cleavable by a matriptase or MMP; or a CD3ε MM and a CM cleavable by a matriptase or MMP. In some embodiments, a prodomain comprises an EGFR MM and a CM that is cleavable by a matriptase and an MMP. In some embodiments, a prodomain comprises a CD3ε MM and a CM that is cleavable by a matriptase and an MMP. Provided herein are activatable antibodies (AAs) comprising a prodomain. Also provided herein are nucleotides encoding a prodomain of the invention.

Accordingly, provided herein is a CD3 AA comprising: (a) an antibody or antigen binding fragment thereof (AB) that specifically binds to the epsilon chain of CD3 (CD3ε), wherein the antibody comprises a heavy chain domain as set forth in SEQ ID NO: 2 or SEQ ID NO: 3 or comprises a light chain domain as set forth in SEQ ID NO: 1 or SEQ ID NO: 4; (b) a masking moiety (MM) coupled to the AB, wherein the MM reduces or inhibits the binding of the AB to the CD3ε when the AA is in an uncleaved state; and (c) a cleavable moiety (CM) coupled to the AB, wherein the CM is a polypeptide that functions as a substrate for a protease. As described above, (b) and (c) together are part of the prodomain.

In some embodiments, the AB of the CD3 AA is any one of the CD3 antibodies described in the preceding section.

In some embodiments, the AB of the CD3 AA comprises a heavy chain variable domain as set forth in SEQ ID NO: 2.

In some embodiments, the AB of the CD3 AA comprises a heavy chain variable domain as set forth in SEQ ID NO: 3.

In some embodiments, the AB of the CD3 AA comprises a light chain variable domain as set forth in SEQ ID NO: 1.

In some embodiments, the AB of the CD3 AA comprises a light chain variable domain as set forth in SEQ ID NO: 4.

In some embodiments, the AB of the CD3 AA comprises a heavy chain variable domain as set forth in SEQ ID NO: 2 and a light chain domain as set forth in SEQ ID NO: 1.

In some embodiments, the AB of the CD3 AA comprises a heavy chain variable domain as set forth in SEQ ID NO: 3 and a light chain domain as set forth in SEQ ID NO: 1.

In some embodiments, the AB of the CD3 AA comprises a heavy chain variable domain as set forth in SEQ ID NO: 3 and a light chain domain as set forth in SEQ ID NO: 4.

In some embodiments, the AB is a scFv comprising a heavy chain variable region (VH) linked to a light chain variable region (VL), wherein the VH is linked to the VL by a linker L3 comprising amino acid sequence SEQ ID NO: 98. Exemplary sequences with such a linker are provided in Table 1.

In some embodiments, the MM of the CD3 AA comprises any one of the sequences set forth in Table 3.

Exemplary CD3 masking moieties (MMs) of the invention are provided in Table 3.

In some embodiments, the MM of the CD3 AA comprises the sequence set forth in SEQ ID NO: 12. In some embodiments, the MM of the CD3 AA is the sequence set forth in SEQ ID NO: 10. In some embodiments, the MM of the CD3 AA is the sequence set forth in SEQ ID NO: 11.

TABLE 3

| MM | Name | AA sequence | SEQ ID NO: |
|---|---|---|---|
| CD3 MM | JF15865 | MMYCGGNEVLCGPRV | SEQ ID NO: 10 |
| CD3 MM | JF15003 | GYRWGCEWNCGGITT | SEQ ID NO: 11 |
| CD3 MM | h20GG | GYLWGCEWNCGGITT | SEQ ID NO: 12 |

In some embodiments, the CM of the CD3 AA comprises any one of the sequences set forth in Table 4. Exemplary cleavable moieties (CMs) of the invention are provided in Table 4.

In some embodiments, the CM of an AA of the disclosure comprises any one of the sequences set forth in Table 4-1.

TABLE 4

| CM Name | AA sequence | SEQ ID NO: |
|---|---|---|
| 0001 | LSGRSDNH | SEQ ID NO: 13 |
| 0011 | LSGRSDDH | SEQ ID NO: 14 |
| 2001 | ISSGLLSGRSDNH | SEQ ID NO: 15 |
| 2008 | ISSGLLSGRSDQH | SEQ ID NO: 16 |
| 2006 | ISSGLLSGRSDDH | SEQ ID NO: 17 |

TABLE 4-1

| CM Name | AA sequence | SEQ ID NO: |
|---|---|---|
| 0001 | LSGRSDNH | SEQ ID NO: 18 |
| 0002 | LSGRSGNH | SEQ ID NO: 19 |
| 0003 | TSTSGRSANPRG | SEQ ID NO: 20 |
| 1001 | ISSGLLSS | SEQ ID NO: 21 |
| 1002 | QNQALRMA | SEQ ID NO: 22 |
| 1003 | VHMPLGFLGP | SEQ ID NO: 23 |
| 1004 | AVGLLAPP | SEQ ID NO: 24 |
| 0011 | LSGRSDDH | SEQ ID NO: 25 |
| 0021 | LSGRSDIH | SEQ ID NO: 26 |
| 0031 | LSGRSDQH | SEQ ID NO: 27 |
| 0041 | LSGRSDTH | SEQ ID NO: 28 |
| 0051 | LSGRSDYH | SEQ ID NO: 29 |
| 0061 | LSGRSDNP | SEQ ID NO: 30 |
| 0071 | LSGRSANP | SEQ ID NO: 31 |
| 0081 | LSGRSANI | SEQ ID NO: 32 |
| 0091 | LSGRSDNI | SEQ ID NO: 33 |

TABLE 4-1-continued

| CM Name | AA sequence | SEQ ID NO: |
|---|---|---|
| 2001 | ISSGLLSGRSDNH | SEQ ID NO: 34 |
| 2002 | ISSGLLSGRSGNH | SEQ ID NO: 35 |
| 2003 | ISSGLLSGRSANPRG | SEQ ID NO: 36 |
| 2005 | AVGLLAPPSGRSANPRG | SEQ ID NO: 37 |
| 2006 | ISSGLLSGRSDDH | SEQ ID NO: 38 |
| 2007 | ISSGLLSGRSDIH | SEQ ID NO: 39 |
| 2008 | ISSGLLSGRSDQH | SEQ ID NO: 40 |
| 2009 | ISSGLLSGRSDTH | SEQ ID NO: 41 |
| 2010 | ISSGLLSGRSDYH | SEQ ID NO: 42 |
| 2011 | ISSGLLSGRSDNP | SEQ ID NO: 43 |
| 2012 | ISSGLLSGRSANP | SEQ ID NO: 44 |
| 2013 | ISSGLLSGRSANI | SEQ ID NO: 45 |
| 2014 | ISSGLLSGRSDNI | SEQ ID NO: 46 |
| 3001 | AVGLLAPPGGLSGRSDNH | SEQ ID NO: 47 |
| 3006 | AVGLLAPPGGLSGRSDDH | SEQ ID NO: 48 |
| 3007 | AVGLLAPPGGLSGRSDIH | SEQ ID NO: 49 |
| 3008 | AVGLLAPPGGLSGRSDQH | SEQ ID NO: 50 |
| 3009 | AVGLLAPPGGLSGRSDTH | SEQ ID NO: 51 |
| 3010 | AVGLLAPPGGLSGRSDYH | SEQ ID NO: 52 |
| 3011 | AVGLLAPPGGLSGRSDNP | SEQ ID NO: 53 |
| 3012 | AVGLLAPPGGLSGRSANP | SEQ ID NO: 54 |
| 3013 | AVGLLAPPGGLSGRSANI | SEQ ID NO: 55 |
| 3014 | AVGLLAPPGGLSGRSDNI | SEQ ID NO: 56 |

3. Antibodies with Fc Mutations

Provided herein are IgG1 antibodies that that have Fc mutations or antibody fragments containing antigen-binding domains (e.g. scFv, Fab, F(ab')2) linked to a Fc domain, wherein the Fc exhibits reduced effector function (referred to herein as Fc variants). Any of the BAAs, AAs, and antibodies described herein may comprise any Fc variants disclosed herein.

The antibodies that comprise these Fc mutations result in reduced effector function, while maintaining target binding affinity. Accordingly, provided herein are antibodies that bind to a target of interest, wherein the antibody is an IgG1 antibody or an antibody fragment linked to an Fc, wherein the Fc region comprises an amino acid substitution in at least one of amino acid positions L234, L235, and P331, as numbered by the EU index as set forth in Kabat, such that the antibody has reduced effector function. In some embodiments, the amino acid substitution is any one or more of L234F, L235E, and P331S. In some embodiments, there is an additional mutation in N297. In some embodiments, the amino acid substitution is N297Q or N297A.

In some embodiments, the Fc is selected from the Fc sequences presented in Table 4-2. In some embodiments, the Fc is selected from SEQ ID NO: 154, SEQ ID NO:156, SEQ ID NO: SEQ ID NO:158, and SEQ ID NO:160, wherein the X is selected from the group consisting of any naturally occurring amino acid (e.g. alanine, arginine, asparagine, aspartic acid, cysteine, glutamine, glutamic acid, glycine, histidine, isoleucine, leucine, lysine, methionine, phenylalanine, proline, pyrrolysine, selenocysteine, serine, threonine, tryptophan, tyrosine, valine) or any non-naturally occurring amino acid (e.g. trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine).

TABLE 4-2

| Name SEQ ID NO: | AA Sequence |
|---|---|
| Fc-N297X (SEQ ID NO: 154) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PELLGGPSVFLFPPKPKDTLMISRTPEVTCVVVDVSHE DPEVKFNWYVDGVEVHNAKTKPREEQYXSTYRVVSVLT VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| Fc-N297Q (SEQ ID NO: 155) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PELLGGPSVFLFPPKPKDTLMISRTPEVTCVVVDVSHE DPEVKFNWYVDGVEVHNAKTKPREEQYQSTYRVVSVLT VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| Fc-L234X (SEQ ID NO: 156) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PEXLGGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| Fc-L234F (SEQ ID NO: 157) | QVQLKQSGPGLVQPSQSLSITCTVSGFSLTNYGVHWVR QSPGKGLEWLGVIWSGGNTDYNTPFTSRLSINKDNSKS QVFFKMNSLQSQDTAIYYCARALTYYDYEFAYWGQGTL VTVS(S/A)ASTKGPSVFPLAPSSKSTSGGTAALGCLV KDYFPEPVTVSWNSGALTSGVHTFPAVLQSSGLYSLSS VVTVPSSSLGTQTYICNVNHKPSNTKVDKKVEPKSCDK THTCPPCPAPEFLGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPAPIEKTI SKAKGQPREPQVYTLPPSREEMTKNQVSLTCLVKGFYP SDIAVEWESNGQPENNYKTTPPVLDSDGSFFLYSKLTV DKSRWQQGNVFSCSVMHEALHNHYTQKSLSLSPGK |
| Fc-L235X (SEQ ID NO: 158) | QVQLKQSGPGLVQPSQSLSITCTVSGFSLTNYGVHWVR QSPGKGLEWLGVIWSGGNTDYNTPFTSRLSINKDNSKS QVFFKMNSLQSQDTAIYYCARALTYYDYEFAYWGQGTL VTVS(S/A)ASTKGPSVFPLAPSSKSTSGGTAALGCLV KDYFPEPVTVSWNSGALTSGVHTFPAVLQSSGLYSLSS VVTVPSSSLGTQTYICNVNHKPSNTKVDKKVEPKSCDK THTCPPCPAPELXGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPAPIEKTI SKAKGQPREPQVYTLPPSREEMTKNQVSLTCLVKGFYP SDIAVEWESNGQPENNYKTTPPVLDSDGSFFLYSKLTV DKSRWQQGNVFSCSVMHEALHNHYTQKSLSLSPGK |

TABLE 4-2-continued

| Name SEQ ID NO: | AA Sequence |
|---|---|
| Fc-L235E (SEQ ID NO: 159) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PELEGGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| Fc-P331X (SEQ ID NO: 160) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PELLGGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAXIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| Fc-P331S (SEQ ID NO: 161) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PELLGGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPASIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| Fc-Fcmt3 (SEQ ID NO: 162) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PEFEGGPSVFLEPPKPKDTLMISRTPEVTCVVVDVSHE DPEVKFNWYVDGVEVHNAKTKPREEQYNSTYRVVSVLT VLHQDWLNGKEYKCKVSNKALPASIEKTISKAKGQPRE PQVYTLPPSREEMTKNQVSLTCLVKGEYPSDIAVEWES NGQPENNYKTTPPVLDSDGSFFLYSKLTVDKSRWQQGN VFSCSVMHEALHNHYTQKSLSLSPGK |
| C225v5Fcmt4 HC (SEQ ID NO: 163) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PEFEGGPSVFLEPPKPKDTLMISRTPEVTCVVVDVSHE DPEVKFNWYVDGVEVHNAKTKPREEQYQSTYRVVSVLT VLHQDWLNGKEYKCKVSNKALPASIEKTISKAKGQPRE PQVYTLPPSREEMTKNQVSLTCLVKGEYPSDIAVEWES NGQPENNYKTTPPVLDSDGSFFLYSKLTVDKSRWQQGN VFSCSVMHEALHNHYTQKSLSLSPGK |

Antibodies, AAs, bispecific antibodies, and BAAs comprising these Fc mutations are provided herein.

In some embodiments, such Fc variant-containing AAs and BAAs can bind an immune effector cell. In some embodiments, they can bind a target selectively located on an immune effector cell. In some embodiments, they can bind CD3. In some embodiments, they can bind any target listed in Table 9. In some embodiments, they can bind EGFR.

Accordingly, in some embodiments, provided herein is an activatable antibody (AA) comprising:
 a) an antibody (AB) that specifically binds a target, wherein the antibody is an IgG1 antibody, and wherein the Fc region of the antibody comprises an amino acid substitution in at least one of amino acid positions L234, L235, and P331, as numbered by the EU index as set forth in Kabat, such that the AA has reduced effector function;
 b) a masking moiety (MM) coupled to the AB, wherein the MM reduces or inhibits the binding of the AB to the target when the AA is in an uncleaved state; and c) a cleavable moiety (CM) coupled to the AB, wherein the CM is a polypeptide that functions as a substrate for a protease.

In some embodiments, the Fc region comprises amino acid substitutions in at least amino acid positions L234, L235, N297 and P331, as numbered by the EU index as set forth in Kabat, such that the AA has reduced effector function. In some embodiments, the target is selected from the group consisting of the targets presented in Table 9.

In some embodiments, provided herein is a bispecific activatable antibody (BAA) comprising:
a) an IgG antibody (AB1) that specifically binds to a first target wherein the AB1 comprises:
  i. two heavy chains (AB1 HCs) and two light chains (AB1 LCs); and
  ii. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease,
b) two scFvs (AB2) that each specifically binds to a second target wherein each AB2 comprises:
  i. a heavy chain variable region linked to a light chain variable region, wherein the carboxyl terminus of each AB2 is linked to the amino terminus each of the AB1 heavy chains; and
  ii. a second masking moiety (MM2) linked to a second cleavable moiety (CM2) to form a MM2-CM2 construct, wherein the carboxyl terminus of a MM2-CM2 construct is linked to the amino terminus of each AB2 wherein
    the MM2 inhibits the binding of the AB2 to its target; and
    the CM2 is a polypeptide that functions as a substrate for a second protease,
and wherein the AB1 comprises an Fc region comprises an amino acid substitution in at least one of amino acid positions L234, L235, N297, and P331, as numbered by the EU index as set forth in Kabat, such that the BAA has reduced effector function.

In some embodiments provided herein, the BAAs provided herein comprise:
a) A bispecific activatable antibody (BAA) comprising:
  i) an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein
    the MM1 inhibits the binding of the AB1 to its target; and
    the CM1 is a polypeptide that functions as a substrate for a first protease,
  ii) two scFvs (each an AB2) that each specifically binds to a second target wherein each AB2 comprises a heavy chain variable region linked to a light chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein
    the MM2 inhibits the binding of the AB2 to its target; and
    the CM2 is a polypeptide that functions as a substrate for a second protease,
and wherein the AB1 comprises an Fc region comprises an amino acid substitution in at least one of amino acid positions L234, L235, N297, and P331, as numbered by the EU index as set forth in Kabat, such that the BAA has reduced effector function.

4. EGFR Antibodies

Provided herein are antibodies or antigen binding fragments thereof (AB) that specifically bind to EGFR. Exemplary CDR sequences of EGFR-binding antibodies are provided in Table 5.

Provided herein are EGFR antibodies, bispecific antibodies with one arm targeting EGFR, AAs capable of binding EGFR upon activation, and BAAs capable of binding EGFR upon activation. In some embodiments, the EGFR antibody comprises the CDRs of Table 5.

In some embodiments, e.g. in a BAA format, provided herein are IgG1 antibodies that specifically bind to the Epidermal Growth Factor Receptor (EGFR) and impart reduced effector function. The antibodies comprise Fc mutations that result in reduced effector function, while maintaining EGFR binding affinity. Accordingly, provided herein are antibodies that bind to EGFR, wherein the antibody is an IgG1 antibody, wherein the antibody comprises an Fc region comprising an amino acid substitution in at least one of amino acid positions L234, L235, and P331, as numbered by the EU index as set forth in Kabat, such that the antibody has reduced effector function. In some embodiments, the amino acid substitution is any one or more of L234F, L235E, and P331S.

In some embodiments, the antibody comprises amino acid substitutions in at least two of amino acid positions L234, L235, and P331.

In some embodiments, the antibody comprises amino acid substitutions at amino acid positions L234, L235, and P331.

In some embodiments, the antibody comprises L234F, L235E, and P331S amino acid substitutions.

In some embodiments, the antibody comprises an Fc region comprising an amino acid substitution at N297 along with an amino acid substitution in at least one of amino acid positions L234, L235, and/or P331. In some embodiments, the Fc region comprises an N297Q mutation. In some embodiments, the Fc region comprises an N297A mutation.

In some embodiments, the antibody comprises L234F, L235E, P331S and N297Q substitutions. In some embodiments, the antibody comprises L234F, L235E, P331S and N297A substitutions.

Exemplary CDR sequences of EGFR-binding antibodies are provided in Table 5, set forth in Kabat.

TABLE 5

| Name | Sequence | SEQ ID NO: |
| --- | --- | --- |
| C225L1 | RASQSIGTNIH | SEQ ID NO: 57 |
| C225L2 | YASESIS | SEQ ID NO: 58 |
| C225L3 | QQNNNWPTT | SEQ ID NO: 59 |
| C225H1 | NYGVH | SEQ ID NO: 60 |

TABLE 5-continued

| Name | Sequence | SEQ ID NO: |
|---|---|---|
| C225H2 | VIWSGGNTDYNTPFTS | SEQ ID NO: 61 |
| C225H3 | ALTYYDYEFAY | SEQ ID NO: 62 |

Exemplary amino acid sequences of EGFR-binding antibodies are provided in Table 6. (VL and VH denote the variable light and variable heavy chains, respectively; LC and HC denote the light and heavy chains, respectively).

In some embodiments, the EGFR antibodies comprise any one of the sequences provided in Table 6.

In some embodiments, the heavy chain of the EGFR antibody comprises any one of the sequences set forth in SEQ ID NO: 67, SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76, as set forth in Table 6. In some embodiments, the heavy chain EGFR antibody comprises any one of the sequences set forth in SEQ ID NO: 67, SEQ ID NO: 69, SEQ ID NO: 71, and SEQ ID NO: 73, wherein in X is selected from any naturally occurring amino acid (e.g. alanine, arginine, asparagine, aspartic acid, cysteine, glutamine, glutamic acid, glycine, histidine, isoleucine, leucine, lysine, methionine, phenylalanine, proline, pyrrolysine, selenocysteine, serine, threonine, tryptophan, tyrosine, valine) or any non-naturally occurring amino acid (e.g., trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine). The notation Fcmt3 comprises a triple point mutation, wherein the Fc region of the heavy chain of the EGFR antibody comprises the following three point mutations: L234F, L235E, and P331S. Accordingly, in some embodiments, the EGFR antibody comprises a heavy chain with an amino acid sequence set forth in SEQ ID NO: C225v5Fcmt3 HC. In some embodiments, the Fc region of the heavy chain of the EGFR antibody comprises a fourth point mutation, N297Q. The notation Fcmt4 comprises the Fcmt3 triple point mutation and the fourth point mutation, N297Q. Accordingly, in such embodiments, the EGFR antibody comprises a heavy chain with an amino acid sequence set forth in SEQ ID NO: 76.

TABLE 6

| Name SEQ ID NO: | AA Sequence |
|---|---|
| C225v5-VL (SEQ ID NO: 63) | QILLTQSPVILSVSPGERVSFSCRASQSIGTNIHWYQ QRTNGSPRLLIKYASESISGIPSRFSGSGSGTDFTLS INSVESEDIADYYCQQNNNWPTTFGAGTKLELK |
| C225v5-VH (SEQ ID NO: 64) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A) |
| C225v5 LC (SEQ ID NO: 65) | QILLTQSPVILSVSPGERVSFSCRASQSIGTNIHWYQ QRTNGSPRLLIKYASESISGIPSRFSGSGSGTDFTLS INSVESEDIADYYCQQNNNWPTTFGAGTKLELKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| C225v5 HC (SEQ ID NO: 66) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPELLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| C225v5N297X HC (SEQ ID NO: 67) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPELLGGPSVFLFPPKPKDTLMI SRTPEVTCVVVDVSHEDPEVKFNWYVDGVEVHNAKTK PREEQYXSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| C225v5N297Q HC (SEQ ID NO: 68) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPELLGGPSVFLFPPKPKDTLMI SRTPEVTCVVVDVSHEDPEVKFNWYVDGVEVHNAKTK PREEQYQSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| C225v5 L234X HC (SEQ ID NO: 69) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPEXLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| C225v5 L234F HC (SEQ ID NO: 70) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPEFLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| C225v5 L235X HC (SEQ ID NO: 71) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE |

TABLE 6-continued

| Name SEQ ID NO: | AA Sequence |
|---|---|
| | PKSCDKTHTCPPCPAPELXGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGEYPSDIAVEWESNGQPENNYKTTPPVLDSD GSFFLYSKLTVDKSRWQQGNVFSCSVMHEALHNHYTQ KSLSLSPGK |
| C225v5 L235E HC (SEQ ID NO: 72) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPELEGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGEYPSDIAVEWESNGQPENNYKTTPPVLDSD GSFFLYSKLTVDKSRWQQGNVFSCSVMHEALHNHYTQ KSLSLSPGK |
| C225v5 P331X HC (SEQ ID NO: 73) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPELLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAXIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| C225v5 P331S HC (SEQ ID NO: 74) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPELLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPASIEKTISKAKGQPREPQVYTLPPSREEMTKNQVS LTCLVKGEYPSDIAVEWESNGQPENNYKTTPPVLDSD GSFFLYSKLTVDKSRWQQGNVFSCSVMHEALHNHYTQ KSLSLSPGK |
| C225v5Fcmt3 HC (SEQ ID NO: 75) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPEFEGGPSVFLEPPKPKDTLMI SRTPEVTCVVVDVSHEDPEVKFNWYVDGVEVHNAKTK PREEQYNSTYRVVSVLTVLHQDWLNGKEYKCKVSNKA LPASIEKTISKAKGQPREPQVYTLPPSREEMTKNQVS LTCLVKGEYPSDIAVEWESNGQPENNYKTTPPVLDSD GSFFLYSKLTVDKSRWQQGNVFSCSVMHEALHNHYTQ KSLSLSPGK |
| C225v5Fcmt4 HC (SEQ ID NO: 76) | QVQLKQSGPGLVQPSQSLSITCTVSGFSLTNYGVHWV RQSPGKGLEWLGVIWSGGNTDYNTPFTSRLSINKDNS KSQVFFKMNSLQSQDTAIYYCARALTYYDYEFAYWGQ GTLVTVS(S/A)ASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPEFEGGPSVFLFPPKPKDTLMI SRTPEVTCVVVDVSHEDPEVKFNWYVDGVEVHNAKTK PREEQYQSTYRVVSVLTVLHQDWLNGKEYKCKVSNKA LPASIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| SynFcmt4 HC (SEQ ID NO: 77) | QVTLRESGPALVKPTQTLTLTCTFSGFSLSTSGMSVG WIRQPPGKALEWLADIWWDDKKDYNPSLKSRLTISKD TSKNQVVLKVTNMDPADTATYYCARSMITNWYFDVWG AGTTVTVS(S/A)ASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPEFEGGPSVFLFPPKPKDTLM ISRTPEVTCVVVDVSHEDPEVKFNWYVDGVEVHNAKT KPREEQYQSTYRVVSVLTVLHQDWLNGKEYKCKVSNK ALPASIEKTISKAKGQPREPQVYTLPPSREEMTKNQV SLTCLVKGFYPSDIAVEWESNGQPENNYKTTPPVLDS DGSFFLYSKLTVDKSRWQQGNVFSCSVMHEALHNHYT QKSLSLSPGK |

5. Activatable EGFR Antibodies

In some embodiments, any one of the EGFR antibodies provided herein are in an AA format (EGFR AAs). As described above for the CD3 AAs, the EGFR AAs also comprise a prodomain.

Accordingly provided herein are AAs comprising antibodies or antigen binding fragments thereof (AB) that specifically bind to EGFR. Exemplary CDR sequences of EGFR-binding antibodies are provided in Table 5.

In some embodiments, the AA comprises: (a) any antibody or an antigen binding fragment thereof (AB) that specifically binds to Epidermal Growth Factor Receptor (EGFR); (b) and a prodomain, wherein the prodomain comprises (i) a masking moiety (MM) coupled to the AB, wherein the MM reduces or inhibits the binding of the AB to the EGFR when the AA is in an uncleaved state, and wherein the MM comprises an amino acid sequence selected from the group consisting of sequences presented in Table 7; and (ii) a cleavable moiety (CM) coupled to the AB, wherein the CM is a polypeptide that functions as a substrate for a protease.

Exemplary EGFR masking moieties (MMs) of the invention are provided in Table 7 and Table 8.

TABLE 7

| MM | Name | AA sequence | SEQ ID NO: |
|---|---|---|---|
| EGFR MM | CF41 | LSCEGWAMNREQCRA | SEQ ID NO: 78 |
| EGFR MM | CF08 | PPLECNTKSMCSKHD | SEQ ID NO: 79 |
| EGFR MM | CF13 | DRDCRGRRARCQQEG | SEQ ID NO: 80 |
| EGFR MM | CF19 | FTCEGWAMNREQCRT | SEQ ID NO: 81 |
| EGFR MM | CF22 | GRCPPSRDIRFCTYM | SEQ ID NO: 82 |
| EGFR MM | CF46 | FSCEGWAMNRSQCRT | SEQ ID NO: 83 |
| EGFR MM | CF48 | FTCEGWAMNRDQCRT | SEQ ID NO: 84 |

TABLE 8

| MM | Name | AA sequence | SEQ ID NO: |
|---|---|---|---|
| EGFR MM | 3954 | CISPRGCPDGPYVMY | SEQ ID NO: 85 |
| EGFR MM | 3954a | CISPRGCPDGPYVM | SEQ ID NO: 86 |
| EGFR MM | 3960 | CISPRGC | SEQ ID NO: 87 |

In some embodiments, the MM of the EGFR AA comprises the amino acid sequence of SEQ ID NO: 78. In some embodiments, the MM of the EGFR AA comprises the amino acid sequence of SEQ ID NO: 85.

In some embodiments, the CM of the EGFR AA comprises an amino acid sequence selected from the group consisting of sequences presented in Table 4. In some embodiments, the CM comprises the amino acid sequence of SEQ ID NO: 14. In some embodiments, the CM comprises the amino acid sequence of SEQ ID NO: 16.

In some embodiments, provided herein is an activatable antibody (AA) comprising: (a) an antibody that specifically binds to Epidermal Growth Factor Receptor (EGFR), wherein the antibody is an IgG1 antibody, and wherein the Fc region of the antibody comprises an amino acid substitution in at least one of amino acid positions L234, L235, and P331, as numbered by the EU index as set forth in Kabat, such that the AA has reduced effector function; (b) a masking moiety (MM) coupled to the AB, wherein the MM reduces or inhibits the binding of the AB to the EGFR when the AA is in an uncleaved state; and (c) a cleavable moiety (CM) coupled to the AB, wherein the CM is a polypeptide that functions as a substrate for a protease. The EGFR IgG1 antibodies can be any of the IgG1 antibodies described in the immediately preceding section. In some embodiments, the MM comprises an amino acid sequence selected from the group consisting of sequences presented in Table 7.

In an exemplary embodiment, provided herein is an activatable antibody (AA) comprising: (a) an antibody (AB) that specifically binds to Epidermal Growth Factor Receptor (EGFR), wherein the AB is an IgG1 antibody, and wherein the Fc region of the AB comprises an amino acid substitution in at least one of amino acid positions L234, L235, and P331, as numbered by the EU index as set forth in Kabat, such that the AA has reduced effector function; (b) a masking moiety (MM) coupled to the AB, wherein the MM reduces or inhibits the binding of the AB to the EGFR when the AA is in an uncleaved state; and (c) a cleavable moiety (CM) coupled to the AB, wherein the CM is a polypeptide that functions as a substrate for a protease. In some embodiments, the amino acid substitution is any one or more of L234F, L235E, and P331S. In some embodiments, the AB comprises amino acid substitutions in at least two of amino acid positions L234, L235, and P331. In some embodiments, the AB comprises amino acid substitutions at amino acid positions L234, L235, and P331. In some embodiments, the AB comprises L234F, L235E, and P331S amino acid substitutions. In some embodiments, the AB comprises an Fc region comprising an amino acid substitution at N297. In some embodiments, the Fc region comprises an N297Q mutation. In some embodiments, the AB comprises L234F, L235E, P331S, and N297Q amino acid substitutions. In some embodiments, the MM comprises an amino acid sequence selected from the group consisting of sequences presented in Table 7 or Table 8. In some embodiments, the MM comprises the amino acid sequence of SEQ ID NO: 78. In some embodiments, the MM comprises the amino acid sequence of SEQ ID NO: 85. In some embodiments, the CM comprises an amino acid sequence selected from the group consisting of sequences presented in Table 4. In some embodiments, the CM comprises the amino acid sequence of SEQ ID NO: 14. In some embodiments, the CM comprises the amino acid sequence of SEQ ID NO: 16. In some embodiments, the AA is part of a BAA.

6. Bispecific Activatable Antibodies (BAAs)

Figure 17:
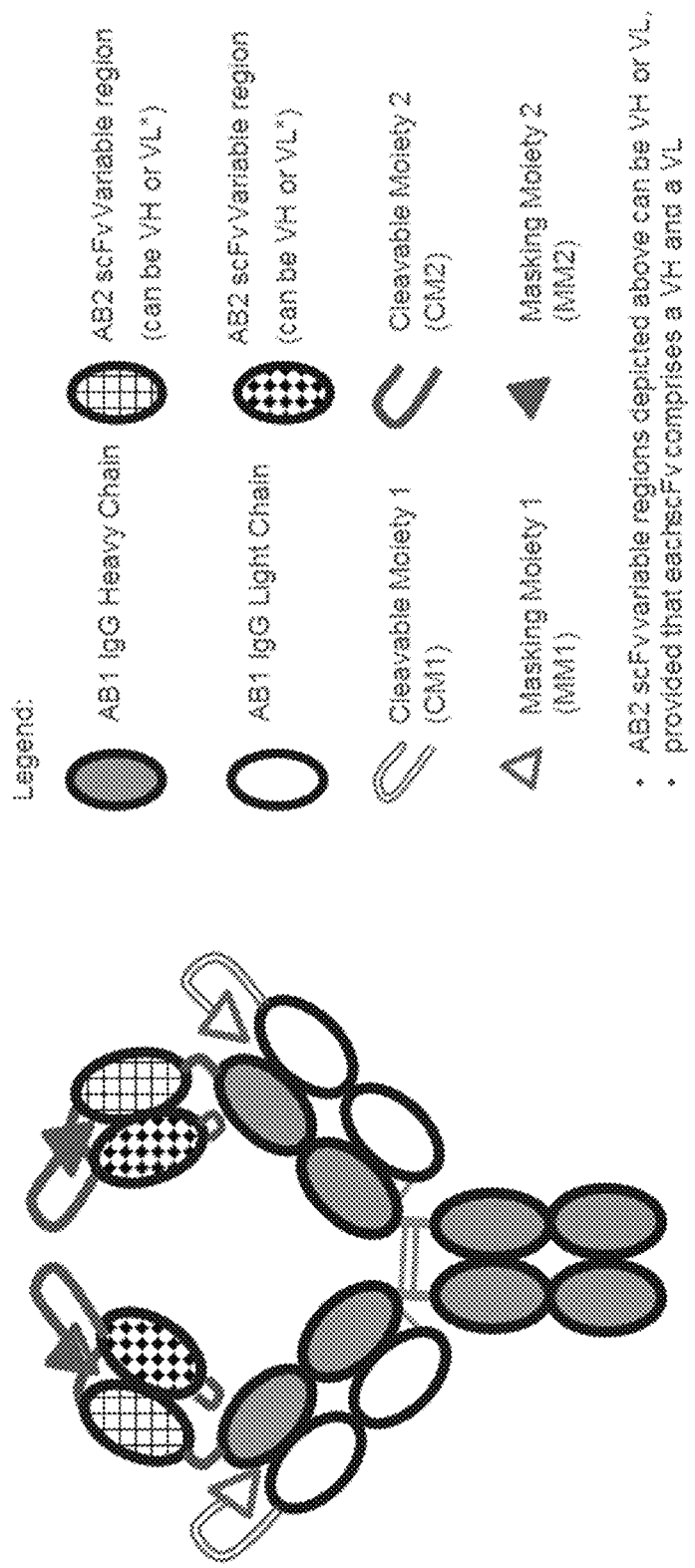
FIGS. 17-19 illustrate exemplary BAAs provided herein.
Figure 18:
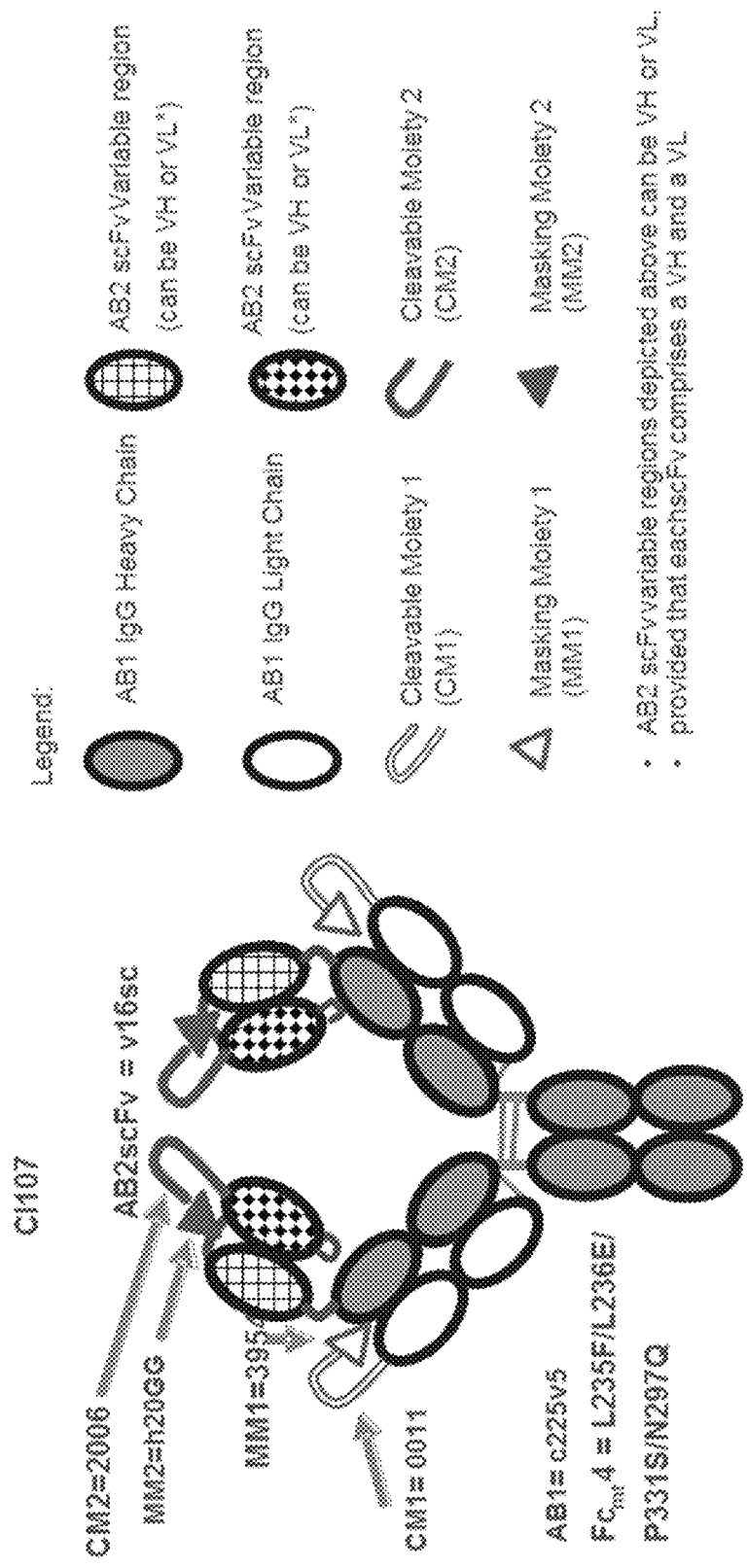
Figure 19:
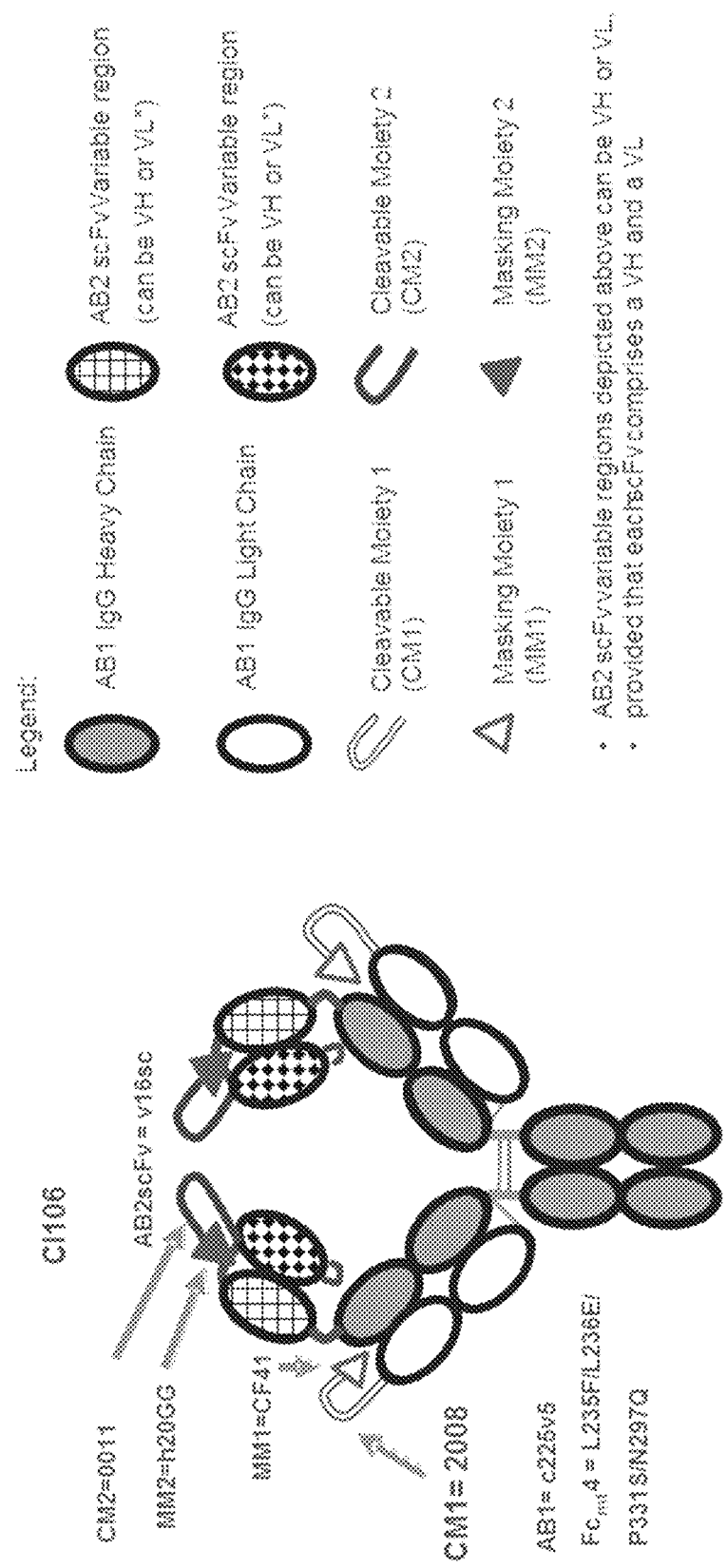
Figure 20:
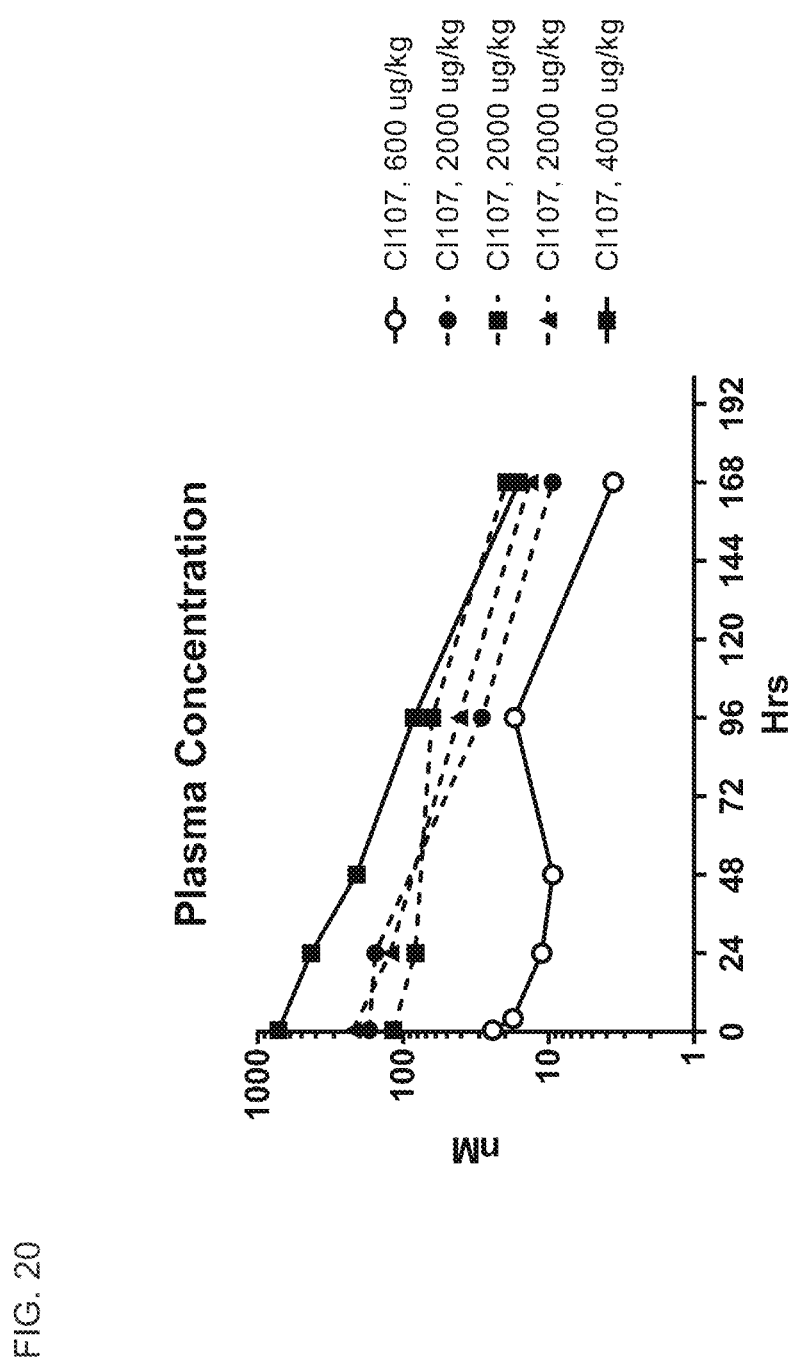
FIG. 20 depicts PK of the dually masked BAA CI107 following a single dose administration of 600, 2000, or 4000 ug/kg.
Figure 21:
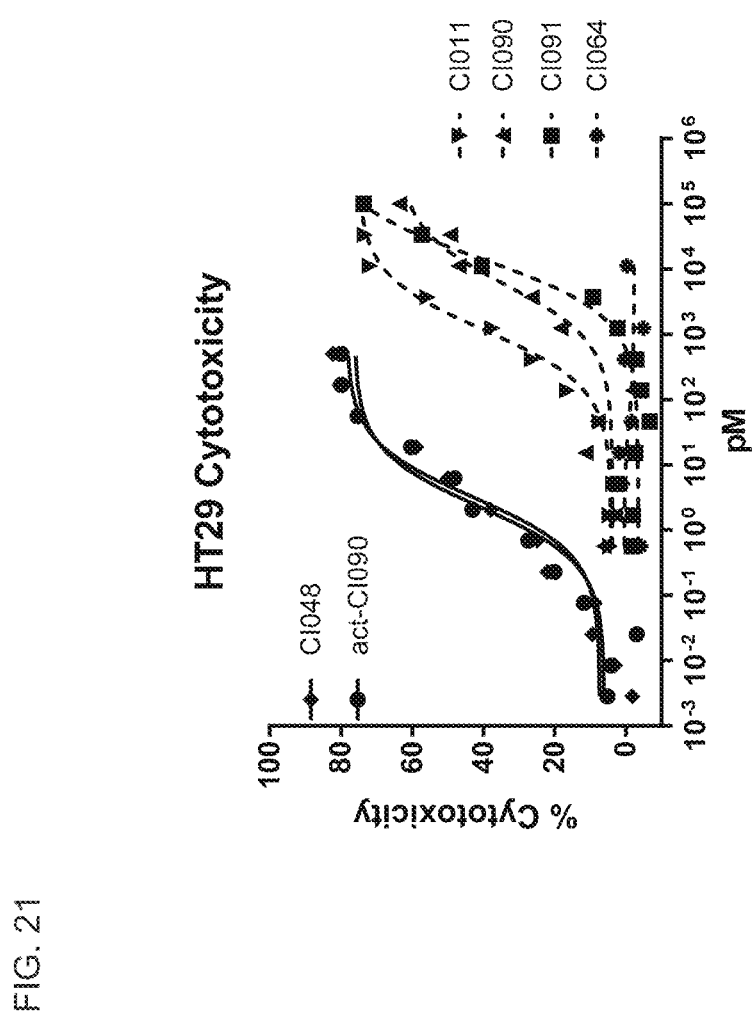
FIG. 21 demonstrates that the cytotoxicity of C1090 and CI091 was attenuated relative to CI011, on HT29-luc2 cells.
Figure 22:
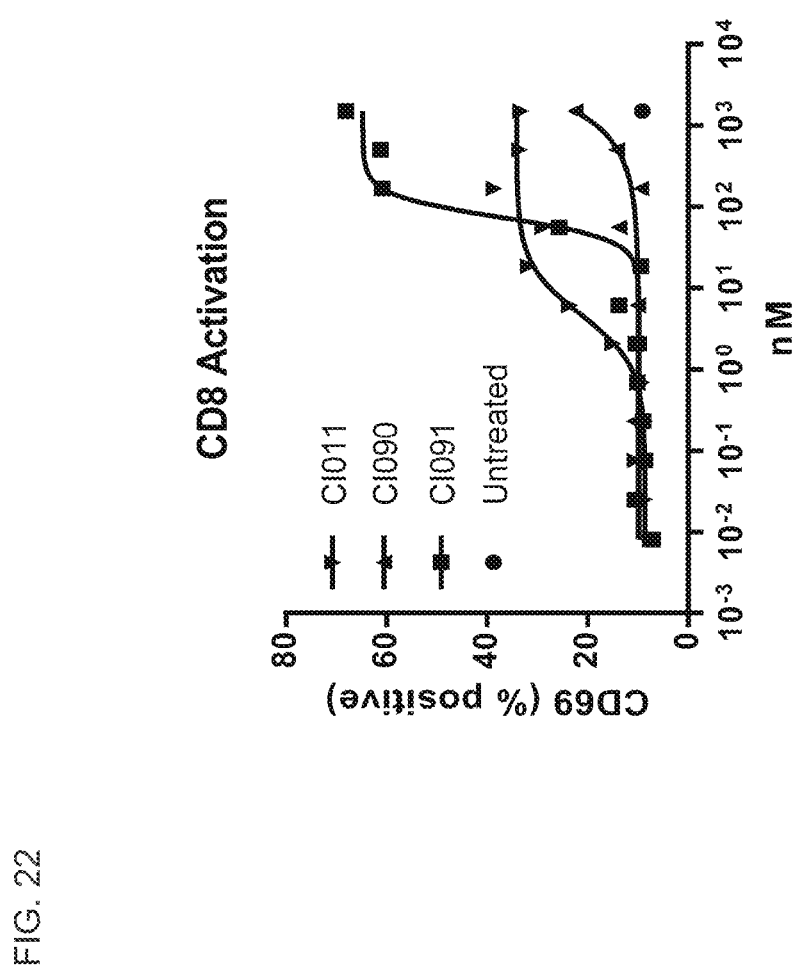
FIG. 22 demonstrates that activation of primary CD8+ T cells was attenuated by CI090 and CI091 relative to CI011.
Figure 23:
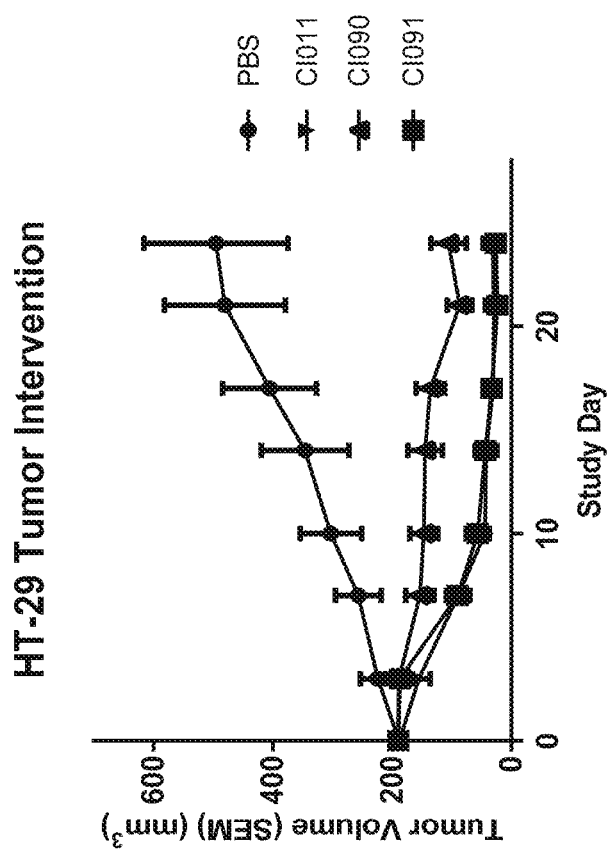
FIG. 23 depicts efficacy in a HT29-luc2 tumor intervention model in PBMC engrafted NSG mice. Showing anti-tumor potency of CI091, CI090 and CI011.

Provided herein are BAAs (bispecific AAs, BAAs), wherein said BAA, when activated, specifically binds to two targets (e.g. binds two different targets, or binds two different epitopes on the same target) and can comprise and can comprise one of the exemplary structures provided in FIGS. 17-19.

In some embodiments, the first target is selected from the group consisting of the targets presented in Table 9 and the second target is selected from the group consisting of the target presented in Table 9.

As generally provided herein, and as described above in the section describing AAs, the BAAs of the invention comprise MM-CM constructs, also referred to herein as a prodomain. Accordingly, as used herein, the term "prodomain" refers to a polypeptide comprising a masking moiety (MM) and a cleavable moiety (CM). In some embodiments, the MM and the CM are separated by a linker, referred to herein as L1. In some embodiments, the prodomain comprises a linker at the carboxyl terminus of the CM; this linker, referred to herein as L2, links the CM of the prodomain to the AB. In some embodiments, the prodomain comprises a linker between MM and CM and a linker after CM. In some embodiments, the MM and the CM are not separated by a linker. In certain embodiments a prodomain comprises one of the following formulae (where the formula below represents an amino acid sequence in either N- to C-terminal direction or C- to N-terminal direction): (MM)-L1-(CM), (MM)-(CM)-L2, (MM)-L1-(CM)-L2, or (MM)-(CM). In exemplary embodiments, a prodomain comprises an EGFR MM and a CM cleavable by a matriptase or MMP; or a CD3ε MM and a CM cleavable by a matriptase or MMP. In some embodiments, a prodomain comprises an EGFR MM and a CM that is cleavable by a matriptase and an MMP. In some embodiments, a prodomain comprises a CD3ε MM and a CM that is cleavable by a matriptase and an MMP. Provided herein are bispecific activatable antibodies (BAAs) comprising a prodomain. Also provided herein are nucleotides encoding a prodomain of the invention.

In some embodiments, provided herein is a BAA, wherein said BAA, when activated, specifically binds to two targets (e.g. two different targets; or two different epitopes on the same target), and wherein said BAA, when not activated, comprises the following structure:

a) an IgG antibody (AB1) that specifically binds to a first target wherein the AB1 comprises:
  i. two heavy chains (AB1 HCs) and two light chains (AB1 LCs); and
  ii. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein
    1. the MM1 inhibits the binding of the AB1 to its target; and
    2. the CM1 is a polypeptide that functions as a substrate for a first protease,
b) two scFvs (AB2) that each specifically bind to a second target wherein each AB2 comprises:
  i. a heavy chain variable region linked to a light chain variable region, wherein the carboxyl terminus of each AB2 is linked to the amino terminus each of the AB1 heavy chains; and ii. a second masking moiety (MM2) linked to a second cleavable moiety (CM2) to form a MM2-CM2 construct, wherein the carboxyl terminus of a MM2-CM2 construct is linked to the amino terminus of each AB2 wherein the MM2 inhibits the binding of the AB2 to its target; and the CM2 is a polypeptide that functions as a substrate for a second protease, and wherein the BAA has at least one of the following characteristics:

i. MM2 comprises amino acid sequence SEQ ID NO: 12;

ii. MM1 comprises an amino acid sequence selected from the group consisting of sequences presented in Table 7;

iii. AB2 comprises a heavy chain variable domain as set forth in SEQ ID NO: 2 or SEQ ID NO: 3 or a light chain variable domain as set forth in SEQ ID NO: 1 or SEQ ID NO: 4; and iv. AB1 comprises an Fc region comprising an amino acid substitution in at least one of amino acid positions L234, L235, N297, and P331 or L234, L235 and P331, as numbered by the EU index as set forth in Kabat, such that the BAA has reduced effector function.

In some embodiments, the BAAs provided herein comprise:

1. A bispecific activatable antibody (BAA), wherein said BAA, when activated, specifically binds to two targets and comprises the following structure:

a. an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, b. two scFvs (each an AB2) that each specifically binds to a second target wherein each AB2 comprises a light chain variable region linked to a heavy chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and the CM2 is a polypeptide that functions as a substrate for a second protease, and wherein the BAA has at least one of the following characteristics:

i. MM2 comprises amino acid sequence SEQ ID NO: 12;

ii. MM1 comprises an amino acid sequence selected from the group consisting of sequences presented in Table 7;

iii. AB2 comprises a heavy chain variable domain as set forth in SEQ ID NO: 2 or SEQ ID NO: 3 or a light chain variable domain as set forth in SEQ ID NO: 1 or SEQ ID NO: 4; and iv. AB1 comprises an Fc region comprising an amino acid substitution in at least one of amino acid positions L234, L235, N297, and P331, as numbered by the EU index as set forth in Kabat, such that the BAA has reduced effector function.

In some embodiments, the BAAs provided herein comprise:

a) an IgG antibody (AB1) that specifically binds to a first target wherein the AB1 comprises:

a. two heavy chains (AB1 HCs) and two light chains (AB1 LCs); and b. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein 1. the MM1 inhibits the binding of the AB1 to its target; and 2. the CM1 is a polypeptide that functions as a substrate for a first protease, b) two scFvs (AB2) that each specifically binds to a second target wherein each AB2 comprises:

a. a heavy chain variable region linked to a light chain variable region, wherein the carboxyl terminus of each AB2 is linked to the amino terminus each of the AB1 heavy chains; and b. a second masking moiety (MM2) linked to a second cleavable moiety (CM2) to form a MM2-CM2 construct, wherein the carboxyl terminus of a MM2-CM2 construct is linked to the amino terminus of each AB2 wherein 1. the MM2 inhibits the binding of the AB2 to its target; and 2. the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function. In some embodiments, the Fc region comprises amino acid substitutions in at least amino acid positions L234, L235, N297 and P331, as numbered by the EU index as set forth in Kabat, such that the BAA has reduced effector function.

In some embodiments, the BAAs provided herein comprise:

(1) A bispecific activatable antibody (BAA) comprising:

(a) an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, (b) two scFvs (each an AB2) that each specifically binds to a second target wherein each AB2 comprises a heavy chain variable region linked to a light chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function.

As provided above, the BAAs of the invention comprise two scFvs (AB2) that each specifically binds to a second target. The VL and VH of the scFvs can be in any order, either VL-VH or VH-VL.

In some embodiments, the Fc region of the AB1 comprises amino acid substitutions in at least amino acid positions L234, L235, and P331, as numbered by the EU index as set forth in Kabat, such that the BAA has reduced effector function. In some embodiments, the first target is selected from the group consisting of the targets presented in Table 9 and the second target is selected from the group consisting of the targets presented in Table 9.

In some embodiments, AB1 binds a target antigen, e.g. a tumor antigen, and the AB2 binds an immune effector target.

In some embodiments, AB2 binds a target antigen, e.g. a tumor antigen, and the AB1 binds an immune effector target.

In some embodiments, the AB1 binds EGFR and the AB2 binds CD3.

In some embodiments, the MM1 comprises SEQ ID NO: 78.

In some embodiments, the MM2 comprises the amino acid sequence SEQ ID NO: 12.

In some embodiments, the bispecific AA is CI106, as provided in Table 11, in Example 1.

In some embodiments, the BAA is CI107, as provided in Table 11, in Example 1.

In some embodiments, the BAA is CI011, as provided in Table 11, in Example 1.

In some embodiments, the BAA is CI020, as provided in Table 11, in Example 1.

In some embodiments, the BAA is CI040, as provided in Table 11, in Example 1.

In some embodiments, the BAA is CI079, as provided in Table 11, in Example 1.

In some embodiments, the BAA is CI090, as provided in Table 11, in Example 1.

In an exemplary embodiment, AB1 comprises the amino acid sequence of C225v5Fcmt3 HC or C225v5Fcmt4 HC.

In some embodiments, the first and second proteases are the same protease. In some embodiments, the first and second proteases are different proteases. In some embodiments, CM1 and CM2 comprise the same amino acid sequence. In some embodiments, CM1 and CM2 comprise different amino acid sequences. In some embodiments, CM1 and CM2 comprise different amino acid sequences that are cleavable by the same protease or proteases. In some embodiments, CM1 and CM2 are cleavable by more than one protease. In some embodiments, CM1 and/or CM2 is cleavable by a serine protease. In some embodiments, CM1 and/or CM2 is cleavable by a matrix metalloproteinase (MMP). In some embodiments, CM1 and/or CM2 is cleavable by a serine protease and an MMP.

Exemplary BAAs of the disclosure include, for example, those shown in the Examples provided herein, and variants thereof.

In some non-limiting embodiments, at least one of the AB in the BAA is specific for CD3 and at least one other AB is a binding partner for any target listed in Table 9.

In an exemplary embodiment, AB2 of the BAA is specific for CD3 and AB1 is a binding partner for any target listed in Table 9.

TABLE 9

Exemplary Targets

| | | | | | |
|---|---|---|---|---|---|
| 1-92-LFA-3 | CD52 | DL44 | HVEM | LAG-3 | STEAP1 |
| Alpha-4 integrin | CD56 | DLK1 | Hyaluronidase | LIF-R | STEAP2 |
| Alpha-V integrin | CD64 | DLL4 | ICOS | Lewis X | TAG-72 |
| alpha4beta1 integrin | CD70 | DPP-4 | IFNalpha | LIGHT | TAPA1 |
| alpha4beta7 integrin | CD71 | DSG1 | IFNbeta | LRP4 | TGFbeta |
| AGR2 | CD74 | EGFR | IFNgamma | LRRC26 | TIGIT |
| Anti-Lewis-Y | | EGFRviii | IgE | MCSP | TIM-3 |
| Apelin J receptor | CD80 | Endothelin B receptor (ETBR) | IgE Receptor (FceRI) | Mesothelin | TLR2 |
| APRIL | CD81 | ENPP3 | IGF | MRP4 | TLR4 |
| B7-H4 | CD86 | EpCAM | IGF1R | MUC1 | TLR6 |
| BAFF | CD95 | EPHA2 | IL1B | Mucin-16 (MUC16, CA-125) | TLR7 |
| BTLA | CD117 | EPHB2 | IL1R | Na/K ATPase | TLR8 |
| C5 complement | CD125 | ERBB3 | IL2 | Neutrophil elastase | TLR9 |
| C-242 | CD132 (IL-2RG) | F protein of RSV | IL11 | NGF | TMEM31 |
| CA9 | CD133 | FAP | IL12 | Nicastrin | TNFalpha |
| CA19-9 (Lewis a) | CD137 | FGF-2 | IL12p40 | Notch Receptors | TNFR |
| Carbonic anhydrase 9 | CD138 | FGF8 | IL-12R, IL-12Rbeta1 | Notch 1 | TNFRS12A |
| CD2 | CD166 | FGFR1 | IL13 | Notch 2 | TRAIL-R1 |
| CD3 | CD172A | FGFR2 | IL13R | Notch 3 | TRAIL-R2 |

TABLE 9-continued

| Exemplary Targets | | | | | |
|---|---|---|---|---|---|
| CD6 | CD248 | FGFR3 | IL15 | Notch 4 | Transferrin |
| CD9 | CDH6 | FGFR4 | IL17 | NOV | Transferrin receptor |
| CD11a | CEACAM5 (CEA) | Folate receptor | IL18 | OSM-R | TRK-A |
| CD19 | CEACAM6 (NCA-90) | GAL3ST1 | IL21 | OX-40 | TRK-B |
| CD20 | CLAUDIN-3 | G-CSF | IL23 | PAR2 | uPAR |
| CD22 | CLAUDIN-4 | G-CSFR | IL23R | PDGF-AA | VAP1 |
| CD24 | cMet | GD2 | IL27/IL27R (wsx1) | PDGF-BB | VCAM-1 |
| CD25 | Collagen | GITR | IL29 | PDGFRalpha | VEGF |
| CD27 | Cripto | GLUT1 | IL-31R | PDGFRbeta | VEGF-A |
| CD28 | CSFR | GLUT4 | IL31/IL31R | PD-1 | VEGF-B |
| CD30 | CSFR-1 | GM-CSF | IL2R | PD-L1 | VEGF-C |
| CD33 | CTLA-4 | GM-CSFR | IL4 | PD-L2 | VEGF-D |
| CD38 | CTGF | GP IIb/IIIa receptors | IL4R | Phosphatidyl-serine | VEGFR1 |
| CD40 | CXCL10 | Gp130 | IL6, IL6R | P1GF | VEGFR2 |
| CD40L | CXCL13 | GPIIB/IIIA | Insulin Receptor | PSCA | VEGFR3 |
| CD41 | CXCR1 | GPNMB | Jagged Ligands | PSMA | VISTA |
| CD44 | CXCR2 | GRP78 | Jagged 1 | RAAG12 | WISP-1 |
| CD44v6 | | HER2/neu | Jagged 2 | RAGE | WISP-2 |
| CD47 | CXCR4 | HGF | | SLC44A4 | WISP-3 |
| CD51 | CYR61 | hGH | | Sphingosine 1 Phosphate | |

In some embodiments, the unmasked EGFR-CD3 bispecific antibody exhibits EGFR-dependent tumor cell killing, while the doubly-masked EGFR-CD3 BAA reduces target-dependent cytotoxicity by more than 100,000-fold. In established tumor models where tumor-resident proteases are expected to be active, it is shown that BAAs potently induce tumor regressions. In non-human primates, the maximum tolerated dose (MTD) of the EGFR-CD3 BAA is more than 60-fold higher than the MTD of the unmasked bispecific antibody, and the tolerated exposure (AUC) is more than 10,000-fold higher. Despite the 60-fold dose differential at the MTDs, transient serum cytokine and AST/ALT increases observed in non-human primates treated with the BAA are still lower than those induced by the bispecific antibody. By localizing activity to the tumor microenvironment, BAAs have the potential to expand clinical opportunities for T cell-engaging bispecific therapies that are limited by on target toxicities, especially in solid tumors. Moreover, an EGFR-CD3 BAA has the potential to address EGFR-expressing tumors that are poorly responsive to existing EGFR-directed therapies.

7. Cleavable Moieties (CM)

Both the monospecific AAs and the BAAs of the disclosure comprise at least one CM, when masked and not activated.

In some embodiments, the cleavable moiety (CM) of the AA or BAA includes an amino acid sequence that can serve as a substrate for at least one protease, usually an extracellular protease. In the case of a BAA, the CM may be selected based on a protease that is co-localized in tissue with the desired target of at least one AB of the BAA or AA. A CM can serve as a substrate for multiple proteases, e.g. a substrate for a serine protease and a second different protease, e.g. an MMP. In some embodiments, a CM can serve as a substrate for more than one serine protease, e.g., a matriptase and uPA. In some embodiments, a CM can serve as a substrate for more than one MMP, e.g., an MMP9 and an MMP14.

A variety of different conditions are known in which a target of interest is co-localized with a protease, where the substrate of the protease is known in the art. In the example of cancer, the target tissue can be a cancerous tissue, particularly cancerous tissue of a solid tumor. There are reports in the literature of increased levels of proteases in a number of cancers, e.g., liquid tumors or solid tumors. See, e.g., La Rocca et al, (2004) British J. of Cancer 90(7): 1414-1421. Non-limiting examples of disease include: all types of cancers, (such as, but not limited to breast, lung, colorectal, gastric, glioblastoma, ovarian, endometrial, renal, sarcoma, skin cancer, cervical, liver, bladder, cholangiocarcinoma, prostate, melanomas, head and neck cancer (e.g. head and neck squamous cell cancer, pancreatic, etc.), rheumatoid arthritis, Crohn's disease, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as head and neck squamous cell cancer; esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of non-limiting example, renal cell carcinoma; and/or skin cancer, such as by way of non-limiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

The CM is specifically cleaved by an enzyme at a rate of about $0.001\text{-}1500\times10^4\ M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4\ M^{-1}S^{-1}$.

For specific cleavage by an enzyme, contact between the enzyme and CM is made. When the AA or BAA comprises at least a first AB coupled to a MM and a CM, e.g., the AA comprises an AB coupled to a MM via a CM, is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but is unable to cleave because of other cellular factors or protein modification of the enzyme.

Exemplary CMs of the disclosure are provided in Table 4 above. In some embodiments, the CM has a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length of up to 60 amino acids, a length in the range of 10-60 amino acids, a length in the range of 15-60 amino acids, a length in the range of 20-60 amino acids, a length in the range of 25-60 amino acids, a length in the range of 30-60 amino acids, a length in the range of 35-60 amino acids, a length in the range of 40-50 amino acids, a length in the range of 45-60 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, or a length in the range of 10-15 amino acids.

8. Masking Moieties (MMs)

In both the activatable monospecific CD3 and EGFR AAs and the BAAs described above, the AAs/BAAs contain a MM. As described herein, the AAs and BAAs of the invention comprise a prodomain, which comprises a MM.

In some embodiments, the MM is selected for use with a specific antibody or antibody fragment.

In certain embodiments, the MM is not a natural binding partner of the AB. In some embodiments, the MM contains no or substantially no homology to any natural binding partner of the AB. In other embodiments the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

Exemplary MMs of the disclosure can have a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length of up to 60 amino acids, a length in the range of 10-60 amino acids, a length in the range of 15-60 amino acids, a length in the range of 20-60 amino acids, a length in the range of 25-60 amino acids, a length in the range of 30-60 amino acids, a length in the range of 35-60 amino acids, a length in the range of 40-50 amino acids, a length in the range of 45-60 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, a length in the range of 10-15 amino acids, or a length of 10, 11, 12, 13, 14, 15, 16, 17, 18, 19, or 20 amino acids.

As provided herein, the MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified by or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified by or coupled to an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified with a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

Exemplary MMs of the disclosure are provided in Tables 3, 7, and 8, above.

In any of the AAs and BAAs provided herein, the masked AB has a lower binding affinity than unmasked AB.

9. Linkers

In many embodiments, it may be desirable to insert one or more linkers, e.g., flexible linkers, into the AA/BAA constructs so as to provide for flexibility at one or more of the MM-CM junction, the CM-AB/CM-scFv junction, or both. For example, the AB, MM, and/or CM may not contain a sufficient number of residues (e.g., Gly, Ser, Asp, Asn, especially Gly and Ser) to provide the desired flexibility. As such, the ability of such BAA constructs to remain intact (not activated) or be activated as disclosed herein may benefit from introduction of one or more amino acids to provide for a flexible linker.

For example, in certain embodiments an AA comprises one of the following formulae (where the formula below represents an amino acid sequence in either N- to C-terminal direction or C- to N-terminal direction):

(MM1)-L1-(CM1)-(AB1)
(MM1)-(CM1)-L2-(AB1)
(MM1)-L1-(CM1)-L2-(AB1)
(MM2)-L1-(CM2)-(AB2)
(MM2)-(CM2)-L2-(AB2)
(MM2)-L1-(CM2)-L2-(AB2)

wherein MM, CM, and AB are as defined above; wherein L1 and L2 are each independently and optionally present or absent, are the same or different flexible linkers that include at least 1 flexible amino acid (e.g., Gly, Ser).

In some embodiments, the BAA comprises 2 heavy chains, each comprising the structural arrangement from N-terminus to C-terminus of MM2-CM2-AB2-AB1 HC and two light chains each comprising the structural arrangement from N-terminus to C-terminus of MM1-CM1-AB1 LC.

In some embodiments, the structure including with linkers is provided in FIG. 17.

In some embodiments, (MM2)-L1-(CM2)-L2-(AB2) is linked to the heavy chain of AB1 and AB2 is a scFv.

Linkers suitable for use in compositions described herein are generally ones that provide flexibility of the modified AB or the AAs to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, 7, 8, 9, 10, 11, 12, 13, 14, 15, 16, 17, 18, 19, or 20 amino acids in length. In some embodiments, a suitable linker can be from 4 to 25 amino acids in length. In some embodiments, a suitable linker can be from 5 to 25 amino acids in length. In some embodiments, a suitable linker can be from 4 to 20 amino acids in length. In some embodiments, a suitable linker can be from 5 to 20 amino acids in length.

Exemplary linkers include glycine polymers (G)n, glycine-serine polymers (including, for example, (GS)n, (GSGGS)n (SEQ ID NO: 88) and (GGGS)n (SEQ ID NO: 89), where n is an integer of at least one), glycine-alanine polymers, alanine-serine polymers, and other flexible linkers known in the art. In some embodiments, n is from about 1 to about 10, or from about 1 to about 9, or from about 1 to about 8, or from about 1 to about 7, or from about 1 to about 6, or from about 1 to about 5, or from about 1 to about 4, or from about 1 to about 3, or from about 1 to about 2. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary linkers are provided in Table 9-1.

TABLE 9-1

Exemplary L1 and L2 Linkers

| SEQ ID NO: | Linker Amino Acid Sequence |
|---|---|
| SEQ ID NO: 88 | GSGGS |
| SEQ ID NO: 89 | GGGS |
| SEQ ID NO: 90 | GGSG |
| SEQ ID NO: 91 | GGSGG |
| SEQ ID NO: 92 | GSGSG |
| SEQ ID NO: 93 | GSGGG |
| SEQ ID NO: 94 | GGGSG |

TABLE 9-1-continued

Exemplary L1 and L2 Linkers

| SEQ ID NO: | Linker Amino Acid Sequence |
|---|---|
| SEQ ID NO: 95 | GSSSG |
| SEQ ID NO: 96 | GSSGGSGGSGG |
| SEQ ID NO: 97 | GGGS |
| SEQ ID NO: 99 | GGGGS |
| SEQ ID NO: 100 | GSSGGSGGSGGSG |
| SEQ ID NO: 101 | GSSGGSGGSGGGGGSGGGSGGGS |
| SEQ ID NO: 102 | GSSGGSGGSGGSGGGSGGGSGGS |
| SEQ ID NO: 103 | GSSGT |
| SEQ ID NO: 104 | GGGSSGGS |

The ordinarily skilled artisan will recognize that design of an AA can include linkers that are all or partially flexible, such that the linker can include a flexible linker as well as one or more portions that confer less flexible structure to provide for a desired AA structure.

10. Conjugation

In some embodiments, any of the antibodies, or ABs of the AAs, and BAAs disclosed herein may be conjugated to an agent. In some embodiments, the agent is a therapeutic agent. In some embodiments, the agent is a detectable moiety. In some embodiments, the agent is an antineoplastic agent. In some embodiments, the agent is a toxin or fragment thereof. In some embodiments, the agent is conjugated to the AB via a linker. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 10.

TABLE 10

Exemplary Pharmaceutical Agents for Conjugation

| CYTOTOXIC AGENTS |
|---|
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |

TABLE 10-continued

Exemplary Pharmaceutical Agents for Conjugation

Daunorubicin
Bryostatins
Camptothecin
Camptothecin derivatives
7-substituted Camptothecin
10,11-Difluoromethylenedioxycamptothecin
Combretastatins
Debromoaplysiatoxin
Kahalalide-F
Discodermolide
Ecteinascidins

ANTIVIRALS

Acyclovir
Vira A
Symmetrel

ANTIFUNGALS

Nystatin

ADDITIONAL ANTI-NEOPLASTICS

Adriamycin
Cerubidine
Bleomycin
Alkeran
Velban
Oncovin
Fluorouracil
Methotrexate
Thiotepa
Bisantrene
Novantrone
Thioguanine
Procarabizine
Cytarabine

ANTI-BACTERIALS

Aminoglycosides
Streptomycin
Neomycin
Kanamycin
Amikacin
Gentamicin
Tobramycin
Streptomycin B
Spectinomycin
Ampicillin
Sulfanilamide
Polymyxin
Chloramphenicol
Turbostatin
Phenstatins
Hydroxyphenstatin
Spongistatin 5
Spongistatin 7
Halistatin 1
Halistatin 2
Halistatin 3
Modified Bryostatins
Halocomstatins
Pyrrolobenzimidazoles
Cibrostatin6
Doxaliform
Anthracyclins analogues
Cemadotin analogue (CemCH2-SH)
*Pseudomonas toxin* A (PE38) variant
*Pseudomonas toxin* A (ZZ-PE38) variant
ZJ-101
OSW-1
4-Nitrobenzyloxycarbonyl Derivatives of O6-Benzylguanine
Topoisomerase inhibitors
Hemiasterlin
Cephalotaxine
Homoharringtonine
Pyrrolobenzodiazepine dimers (PBDs)
Functionalized pyrrolobenzodiazepenes

TABLE 10-continued

Exemplary Pharmaceutical Agents for Conjugation

Calicheamicins
Podophyllotoxins
Taxanes
Vinca alkaloids

CONJUGATABLE DETECTABLE MOIETIES

Fluorescein and derivatives thereof
Fluorescein isothiocyanate (FITC)

RADIOPHARMACEUTICALS $^{125}$I
$^{131}$I
$^{89}$Zr
$^{111}$In
$^{123}$I
$^{131}$I
$^{99m}$Tc
$^{201}$Tl
$^{133}$Xe
$^{11}$C
$^{62}$Cu
$^{18}$F
$^{68}$Ga
$^{13}$N
$^{15}$O
$^{38}$K
$^{82}$Rb
$^{99m}$Tc (Technetium)

HEAVY METALS

Barium
Gold
Platinum

ANTI-MYCOPLASMALS

Tylosine
Spectinomycin

Those of ordinary skill in the art will recognize that a large variety of possible moieties can be coupled to the resultant antibodies, AAs, and BAAs of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

In some embodiments, the antibody, AA or BAA comprises a detectable moiety. In some embodiments, the detectable moiety is a diagnostic agent.

In some embodiments, the antibody, AA or BAA contains one or more disulfide bonds. In some embodiments, the antibody, AA or BAA contains one or more lysines. In some embodiments, the antibody, AA or BAA can be engineered to include one or more disulfide bonds or can be otherwise engineered to enable site-specific conjugation.

11. Production

The disclosure also provides an isolated nucleic acid molecule encoding an antibody, AA or BAA described herein, as well as vectors that include these isolated nucleic acid sequences. The disclosure provides methods of producing an antibody, AA or BAA by culturing a cell under conditions that lead to expression of the antibody, AA or BAA, wherein the cell comprises such a nucleic acid molecule.

In some embodiments, the cell comprises such a vector. In some embodiments, the vector is pLW289. In some embodiments, the vector is pLW246. In some embodiments, the vector is pLW307. In some embodiments, the vector is pLW291. In some embodiments, the vector is pLW352. In some embodiments, the vector is pLW353. (these vectors and described and sequences provided below in Example 1)

12. Use of Antibodies, AAs, Bispecific Antibodies and BAAs

In some embodiments, the antibodies/bispecific antibodies/AAs/BAAs thereof may be used as therapeutic agents. Such agents will generally be employed to treat, alleviate, and/or prevent a disease or pathology in a subject. A therapeutic regimen is carried out by identifying a subject, e.g., a human patient or other mammal suffering from (or at risk of developing) a disorder using standard methods.

Administration of the antibodies/bispecific antibodies/AAs/BAAs thereof may abrogate or inhibit or interfere with the signaling function of one or more of the targets.

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semisolid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

A therapeutically effective amount of antibodies/bispecific antibodies/AAs/BAAs thereof of the disclosure relates generally to the amount needed to achieve a therapeutic objective.

Common ranges for therapeutically effective dosing of an antibodies/bispecific antibodies/AAs/BAAs thereof of the disclosure may be, by way of nonlimiting example, from about 0.1 mg/kg body weight to about 50 mg/kg body weight. Common dosing frequencies may range, for example, from twice daily to once a week.

Efficaciousness of treatment is determined in association with any known method for diagnosing or treating the particular disorder. Methods for the screening antibodies/bispecific antibodies/AAs/BAAs that possess the desired specificity include, but are not limited to, enzyme linked immunosorbent assay (ELISA) and other immunologically mediated techniques known within the art.

Other contemplated uses involve diagnostics, imaging, prognostics, and detection uses. In some embodiments, antibodies/bispecific antibodies/AAs/BAAs are used in methods known within the art relating to the localization and/or quantitation of the target (e.g., for use in measuring levels of one or more of the targets within appropriate physiological samples, for use in diagnostic methods, for use in imaging the protein, and the like).

In some embodiments, antibodies/bispecific antibodies/AAs/BAAs are used to isolate one or more of the targets by standard techniques, such as immunoaffinity, chromatography or immunoprecipitation. An antibody, an AA, a bispecific antibody or a BAA can be used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

In yet another embodiment, an antibody, bispecific antibody, AA, BAA directed two or more targets can be used as an agent for detecting the presence of one or more of the targets (or a fragment thereof) in a sample. In some embodiments, the antibody contains a detectable label. Antibodies are polyclonal, or in some embodiments, monoclonal. An intact antibody, or a fragment thereof (e.g., Fab, scFv, or F(ab')2) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of an antibody with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect a protein in a biological sample in vitro as well as in vivo. For example, in vitro techniques for detection of an analyte protein include enzyme linked immunosorbent assays (ELISAs), Western blots, immunoprecipitations, and immunofluorescence. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The antibodies, bispecific antibodies, AAs, and bispecific antibodies of the disclosure are also useful in a variety of diagnostic and prophylactic formulations. In one embodiment, an antibody, AA, bispecific antibody, BAA is administered to patients that are at risk of developing one or more of the aforementioned disorders. A patient's or organ's predisposition to one or more of the disorders can be determined using genotypic, serological or biochemical markers.

In another embodiment of the disclosure, an antibody, AA, bispecific antibody, BAA is administered to human individuals diagnosed with a clinical indication associated with one or more of the aforementioned disorders. Upon diagnosis, an antibody, AA, bispecific antibody, BAA is administered to mitigate or reverse the effects of the clinical indication.

Antibodies, bispecific antibodies, AAs, and bispecific antibodies are also useful in the detection of one or more targets in patient samples and accordingly are useful as diagnostics. For example, the antibodies, bispecific antibodies, AAs, and bispecific antibodies of the disclosure are used in in vitro assays, e.g., ELISA, to detect one or more target levels in a patient sample.

In one embodiment, an antibody, AA, bispecific antibody, BAA is immobilized on a solid support (e.g., the well(s) of a microtiter plate). The immobilized antibody and/or AA serves as a capture antibody for any target(s) that may be present in a test sample. Prior to contacting the immobilized antibody/AA with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen(s) in the test sample is determined by comparison with a standard curve developed from the standard samples.

It will be appreciated that based on the results obtained using the antibody, AA, bispecific antibody, BAA in an in vitro diagnostic assay, it is possible to stage a disease in a subject based on expression levels of the target antigen(s). For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Antibodies, bispecific antibodies, AAs, and BAAs can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, AAs, and bispecific antibodies having an enzymatically cleavable CM can be used to detect the presence or absence of an enzyme that is capable of cleaving the CM. Such AAs, and bispecific antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated or bispecific activated antibodies (i.e., antibodies or bispecific antibodies resulting from cleavage of an AA or a BAA) in a given cell or tissue of a given host organism. Such accumulation of activated bispecific antibodies indicates not only that the tissue expresses enzymatic activity (or an increased reduction potential depending on the nature of the CM) but also that the tissue expresses at least one target to which the activated bispecific antibody binds.

For example, the CM can be selected to be a protease substrate for a protease found at the site of a tumor, at the site of a viral or bacterial infection at a biologically confined site (e.g., such as in an abscess, in an organ, and the like), and the like. At least one of the AB can be one that binds a target antigen. Using methods familiar to one skilled in the art, a detectable label (e.g., a fluorescent label or radioactive label or radiotracer) can be conjugated to an AB or other region of an antibody, AA, bispecific antibody, BAA. Suitable detectable labels are discussed in the context of the above screening methods and additional specific examples are provided below. Using at least one AB specific to a protein or peptide of the disease state, along with a protease whose activity is elevated in the disease tissue of interest, AAs will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated bispecific antibodies in the disease tissue is enhanced relative to non-disease tissues.

In another example, antibodies, antibodies/bispecific antibodies/AAs/BAAs of the present disclosure can be used to detect the presence or absence of a cleaving agent in a sample. For example, where the antibodies/bispecific antibodies/AAs/BAAs contain a CM susceptible to cleavage by an enzyme, the BAAs can be used to detect (either qualitatively or quantitatively) the presence of an enzyme in the sample. In another example, where the antibodies/bispecific antibodies/AAs/BAAs contain a CM susceptible to cleavage by reducing agent, the antibodies/bispecific antibodies/AAs/BAAs can be used to detect (either qualitatively or quantitatively) the presence of reducing conditions in a sample. To facilitate analysis in these methods, the antibodies/bispecific antibodies/AAs/BAAs can be detectably labeled, and can be bound to a support (e.g., a solid support, such as a slide or bead). The detectable label can be positioned on a portion of the antibodies/bispecific antibodies/AAs/BAAs that is not released following cleavage, for example, the detectable label can be a quenched fluorescent label or other label that is not detectable until cleavage has occurred. The assay can be conducted by, for example, contacting the immobilized, detectably labeled antibodies/bispecific antibodies/AAs/BAAs with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the antibodies/bispecific antibodies/AAs/BAAs prior to contacting with the sample e.g., the presence of and/or an increase in detectable signal due to cleavage of the antibodies/bispecific antibodies/AAs/BAAs by the cleaving agent in the sample.

Such detection methods can be adapted to also provide for detection of the presence or absence of a target that is capable of binding at least one AB of the antibodies/bispecific antibodies/AAs/BAAs of the present disclosure. Thus, the assays can be adapted to assess the presence or absence of a cleaving agent and the presence or absence of a target of interest. The presence or absence of the cleaving agent can be detected by the presence of and/or an increase in detectable label of the antibodies/bispecific antibodies/AAs/BAAs as described above, and the presence or absence of the target can be detected by detection of a target-AB complex e.g., by use of a detectably labeled anti-target antibody.

AAs/BAAs of the present disclosure are also useful in in situ imaging for the validation of AA activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an AA/BAA is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, AA or BAA indicates that the sample contains the target and contains a protease that is specific for the CM of the AAs or BAAs of the present disclosure. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of MT-SP1; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the AAs or BAAs of the present disclosure. In some embodiments, the presence of the target can be confirmed using an agent that is specific for the target or the detectable label can be competed with unlabeled target. In some embodiments, unlabeled AA could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM of the AAs or BAAs of the present disclosure.

These techniques are also useful in kits and/or as reagents for the detection, identification or characterization of protease activity in a variety of cells, tissues, and organisms based on the protease-specific CM in the AAs or BAAs of the present disclosure.

13. Therapeutic Administration

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In some embodiments, the antibodies, bispecific antibodies, AAs, or BAAs (or conjugated compositions thereof) are administered in conjunction with one or more additional agents, or with a combination of additional agents. Suitable additional agents include current pharmaceutical and/or surgical therapies for an intended application. For example, they can be used in conjunction with an additional chemotherapeutic or anti-neoplastic agent.

In some embodiments, the antibodies, bispecific antibodies, AAs, or BAAs (or conjugated compositions thereof) of the present disclosure are administered in conjunction with one or more additional agents selected from the group consisting of antibodies, conjugated antibodies, AAs, conjugated AAs, bispecific antibodies, conjugated bispecific antibodies, BAAs, or conjugated BAAs. In some embodiments, the antibody portion of any of the above-referenced additional agents is directed against a target such as one or more of the targets disclosed in Table 9. It is appreciated that in some embodiments the antibody portion of antibodies, bispecific antibodies, AAs, or BAAs (or conjugated compositions thereof) of the present disclosure and the antibody portion of the additional agent is directed against the same target (e.g. both may target EGFR). In some embodiments, they are directed against the same target, but target different epitopes. In some embodiments, they are directed against different targets entirely (e.g., an activatable antibody of the present disclosure that targets EGFR may be administered in conjunction with an AA targeting a different target; likewise e.g. a BAA of the present disclosure that targets EGFR and CD3 may be administered in conjunction with an AA targeting a different target.

In some embodiments, antibodies, bispecific antibodies, AAs or BAAs (or conjugated compositions thereof) of the disclosure are administered in conjunction with an immunotherapeutic agent. In some embodiments, antibodies, bispecific antibodies, AAs or BAAs (or conjugated compositions thereof) of the disclosure are administered in conjunction with a chemotherapeutic agent. In some embodiments, antibodies, bispecific antibodies, AAs or BAAs (or conjugated compositions thereof) of the disclosure are administered in conjunction with both an immunotherapeutic agent and a chemotherapeutic agent. In some embodiments, one or more additional agents is administered with any of these combination embodiments.

In some embodiments, they are formulated into a single therapeutic composition, and the antibodies/bispecific antibodies/AAs/BAAs thereof and the additional agent are administered simultaneously. Alternatively, the antibodies/bispecific antibodies/AAs/BAAs thereof are administered separate from each other, e.g., each is formulated into a separate therapeutic composition, and the antibodies/bispecific antibodies/AAs/BAAs thereof and the additional agent are administered simultaneously, or the antibodies/bispecific antibodies/AAs/BAAs thereof and the additional agent are administered at different times during a treatment regimen. The antibodies/bispecific antibodies/AAs/BAAs thereof and the additional agent can be administered in multiple doses.

The antibodies/bispecific antibodies/AAs/BAAs thereof can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibodies/bispecific antibodies/AAs/BAAs thereof and a pharmaceutically acceptable carrier.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nano-capsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as autoimmune disorders and inflammatory diseases. The term "in combination" in this context means that the agents are given substantially contemporaneously, either simultaneously or sequentially. If given sequentially, at the onset of administration of the second compound, the first of the two compounds is still detectable at effective concentrations at the site of treatment.

For example, the combination therapy can include one or more antibodies/bispecific antibodies/AAs/BAAs thereof of the disclosure coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more antibodies/bispecific antibodies/AAs/BAAs thereof described herein may be used in combination with two or more of the therapeutic agents described herein (e.g. one BAA administered with another BAA or AA of the disclosure, and the like). Such combination therapies may advantageously utilize lower dosages of the administered therapeutic agents, thus avoiding possible toxicities or complications associated with the various monotherapies.

In other embodiments, one or more antibodies of the disclosure can be coformulated with, and/or coadministered with, one or more anti-inflammatory drugs, immunosuppressants, or metabolic or enzymatic inhibitors. Nonlimiting examples of the drugs or inhibitors that can be used in combination with the antibodies described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such, as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl)methyl] methylamino] benzoyl]-L-glutamic acid); and inhibitors of pyrimidine biosynthesis, e.g., dihydroorotate dehydrogenase (DHODH) inhibitors. Suitable therapeutic agents for use in combination with the antibodies of the disclosure include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppressants, e.g., cyclosporin, tacrolimus (FK-506); and mTOR inhibitors, e.g., sirolimus (rapamycin—RAPAMUNE™ or rapamycin derivatives, e.g., soluble rapamycin derivatives (e.g., ester rapamycin derivatives, e.g., CCI-779); agents that interfere with signaling by proinflammatory cytokines such as TNFα or IL-1 (e.g. IRAK, NIK, IKK, p38 or MAP kinase inhibitors); COX2 inhibitors, e.g., celecoxib, rofecoxib, and variants thereof; phosphodiesterase inhibitors, e.g., R973401 (phosphodiesterase Type IV inhibitor); phospholipase inhibitors, e.g., inhibitors of cytosolic phospholipase 2 (cPLA2) (e.g., trifluoromethyl ketone analogs); inhibitors of vascular endothelial cell growth factor or growth factor receptor, e.g., VEGF inhibitor and/or VEGF-R inhibitor; and inhibitors of angiogenesis. Suitable therapeutic agents for use in combination with the antibodies of the disclosure are immunosuppressants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs.

Additional examples of therapeutic agents that can be combined with an antibody of the disclosure include one or more of: 6-mercaptopurines (6-MP); azathioprine sulphasalazine; mesalazine; olsalazine; chloroquine/hydroxychloroquine (PLAQUENIL®); pencillamine; aurothiornalate (intramuscular and oral); azathioprine; coichicine; beta-2 adrenoreceptor agonists (salbutamol, terbutaline, salmeteral); xanthines (theophylline, arninophylline); cromoglycate; nedocromil; ketotifen; ipratropium and oxitropium; mycophenolate mofetil; adenosine agonists; antithrombotic agents; complement inhibitors; and adrenergic agents.

In some embodiments, antibodies/bispecific antibodies/AAs/BAAs thereof of the disclosure can be combined with one or more antibodies/bispecific antibodies/AAs/BAAs thereof.

14. Kits and Articles of Manufacture

Provided herein are kits and articles of manufacture comprising any one or more of the antibodies, AAs, bispecific antibodies, and BAAs provided herein The kits and articles of manufacture may comprise any one or more of the antibodies, AAs, bispecific antibodies, and BAAs provided herein in a format suitable for storage or shipping.

The kits and articles of manufacture may comprise at least a second component.

The kits and articles of manufacture may comprise a vessel, a diluent, a solvent, a second composition, or any component useful for converting a composition in a format for storage into a composition suitable for use in a method disclosed herein, if such a conversion is required. The method may be, for instance, a therapeutic method disclosed herein. The kit may comprise instructions for use.

The kits and articles of manufacture may comprise an agent as disclosed herein, for instance a cytotoxic agent or a detectable label, in a format suitable for conjugation to the antibodies, AAs, bispecific antibodies, and BAAs provided herein.

The following examples are included for illustrative purposes and are not intended to limit the scope of the invention.

Enumerated Embodiments

The invention may be defined by reference to the following enumerated, illustrative embodiments.

1. A bispecific activatable antibody (BAA), wherein said BAA, when activated, specifically binds to two targets and comprises the following structure:
   a. an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and
   the CM1 is a polypeptide that functions as a substrate for a first protease,
   b. two scFvs (each an AB2) that each specifically binds to a second target wherein each AB2 comprises a light chain variable region linked to a heavy chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and
   the CM2 is a polypeptide that functions as a substrate for a second protease, and wherein the BAA has at least one of the following characteristics:
      i. MM2 comprises amino acid sequence SEQ ID NO: 12;
      ii. MM1 comprises an amino acid sequence selected from the group consisting of sequences presented in Table 7;

iii. AB2 comprises a heavy chain variable domain as set forth in SEQ ID NO: 2 or SEQ ID NO: 3 or a light chain variable domain as set forth in SEQ ID NO: 1 or SEQ ID NO: 4; and iv. AB1 comprises an Fc region comprising an amino acid substitution in at least one of amino acid positions L234, L235, N297, and P331, as numbered by the EU index as set forth in Kabat, such that the BAA has reduced effector function.

2. The BAA of embodiment 1, wherein AB2 comprises a heavy chain variable domain as set forth in SEQ ID NO: 2 or SEQ ID NO: 3 and a light chain variable domain as set forth in SEQ ID NO: 1 or SEQ ID NO: 4.

3. The BAA of embodiment 1, wherein the AB1 binds a tumor target and the AB2 binds an immune effector target.

4. The BAA of any one of embodiments 1 to 3, wherein the BAA is a T cell-engaging bispecific (TCB) AA (TCBAA).

5. The BAA of any one of embodiments 1 to 4, wherein the AB1 binds EGFR and the AB2 binds CD3R.

6. The BAA of any one of embodiments 1 to 5, wherein the MM1 comprises an amino acid sequence selected from the group consisting of sequences presented in Table 7.

7. The BAA of any one of embodiments 1 to 5, wherein the MM1 comprises an amino acid sequence selected from the group consisting of SEQ ID NO: 85 and SEQ ID NO: 78.

8. The BAA of any one of embodiments 1 to 5, wherein the MM1 comprises SEQ ID NO: 78.

9. The BAA of any one of embodiments 1 to 8, wherein the MM2 comprises the amino acid sequence SEQ ID NO: 12.

10. The BAA of any one of embodiments 1 to 9, wherein the CM comprises the amino acid sequence of SEQ ID NO: 14.

11. The BAA of any one of embodiments 1 to 9, wherein the CM comprises the amino acid sequence of SEQ ID NO: 17.

12. The BAA of any one of embodiments 1 to 9, wherein the CM the CM comprises the amino acid sequence of SEQ ID NO: 16.

13. The BAA of any one of embodiments 1 to 9, wherein CM1 comprises an amino acid sequence selected from the group comprising SEQ ID NO: 14 and SEQ ID NO: 16.

14. The BAA of any one of embodiments 1 to 9, wherein CM2 comprises an amino acid sequence selected from the group comprising SEQ ID NO: 14 and SEQ ID NO: 17.

15. The BAA of any one of embodiments 1 to 14, wherein AB1 comprises amino acid substitutions in at least two of amino acid positions L234, L235, and P331.

16. The BAA of embodiment 15, wherein AB1 comprises amino acid substitutions at amino acid positions L234, L235, and P331.

17. The BAA of embodiment 15, wherein AB1 comprises L234F, L235E, and P331S amino acid substitutions.

18. The BAA of embodiment 15, wherein the AB1 comprises an Fc region comprising an amino acid substitution at N297.

19. The BAA of any one of embodiments 1 to 14, wherein AB1 comprises amino acid substitutions at amino acid positions L234F, L235E, P331S, and N297Q.

20. The BAA of embodiment 1, wherein the heavy chain of the AB1 comprises any one of SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76, as set forth in Table 6.

21. The BAA CI106, comprising the layout and sequence as provided in Table 11 and Example 1.

22. The BAA CI107, comprising the layout and sequence as provided in Table 11 and Example 1.

23. The BAA CI079, comprising the layout and sequence as provided in Table 11 and Example 1.

24. The BAA C1090, comprising the layout and sequence as provided in Table 11 and Example 1.

25. An activatable antibody (AA) comprising:
a) an antibody or antigen binding fragment thereof (AB) that specifically binds to the epsilon chain of CD3 (CD3ε);
b) a masking moiety (MM) coupled to the AB, wherein the MM reduces or inhibits the binding of the AB to the CD3ε when the AA is in an uncleaved state, wherein the MM comprises amino acid sequence SEQ ID NO: 12; and
c) a cleavable moiety (CM) coupled to the AB, wherein the CM is a polypeptide that functions as a substrate for a protease.

26. The AA of embodiment 25, wherein the CM comprises any one of the sequences set forth in Table 4.

27. The AA of embodiment 25, wherein the CM comprises a substrate cleavable by a serine protease or an MMP.

28. The AA of embodiment 25, wherein the CM comprises an amino acid sequence selected from the group consisting of SEQ ID NO: 18-56.

29. The AA of embodiment 25, wherein the protease is an MMP.

30. The AA of embodiment 25, wherein the protease is a serine protease.

31. The AA of embodiment 25, wherein the AB that specifically binds to CD3 is the antibody of any one of embodiments 38-47.

32. An activatable antibody (AA) comprising:
a. an antibody or an antigen binding fragment thereof (AB) that specifically binds to Epidermal Growth Factor Receptor (EGFR);
b. a masking moiety (MM) coupled to the AB, wherein the MM reduces or inhibits the binding of the AB to the EGFR when the AA is in an uncleaved state, and wherein the MM comprises an amino acid sequence selected from the group consisting of sequences presented in Table 7; and
c. a cleavable moiety (CM) coupled to the AB, wherein the CM is a polypeptide that functions as a substrate for a protease.

33. The AA of embodiment 32, wherein the MM comprises the amino acid sequence of SEQ ID NO: 78.

34. The AA of any one of embodiments 32 to 33, wherein the CM comprises a substrate cleavable by a serine protease or an MMP.

35. The AA of any one of embodiments 32 to 33, wherein the CM comprises an amino acid sequence selected from the group consisting of SEQ ID NO: 18-56.

36. The AA of embodiment 32, wherein the CM comprises the amino acid sequence of SEQ ID NO: 14.

37. The AA of embodiment 32, wherein the CM comprises the amino acid sequence of SEQ ID NO: 16.

38. An antibody or antigen binding fragment thereof (AB) that specifically binds to the epsilon chain of CD3 (CD3ε), wherein the antibody comprises a heavy chain variable domain as set forth in SEQ ID NO: 2 or SEQ ID NO: 3 or a light chain variable domain as set forth in SEQ ID NO: 1 or SEQ ID NO: 4.

39. The AB of embodiment 38, wherein, the antibody comprises a heavy chain variable domain as set forth in SEQ ID NO: 2 or SEQ ID NO: 3 and a light chain variable domain as set forth in SEQ ID NO: 1 or SEQ ID NO: 4.

40. The AB of embodiment 38, comprising a heavy chain variable domain as set forth in SEQ ID NO: 2.

41. The AB of embodiment 38, comprising a heavy chain variable domain as set forth in SEQ ID NO: 3.

42. The AB of embodiment 38, wherein the antibody comprises a light chain variable domain as set forth in SEQ ID NO: 1.

43. The AB of embodiment 38, comprising a light chain variable domain as set forth in SEQ ID NO: 4.

44. The AB of embodiment 38, comprising a heavy chain variable domain as set forth in SEQ ID NO: 2 and a light chain variable domain as set forth in SEQ ID NO: 1.

45. The AB of embodiment 38, comprising a heavy chain variable domain as set forth in SEQ ID NO: 3 and a light chain variable domain as set forth in SEQ ID NO: 1.

46. The AB of embodiment 38, comprising a heavy chain variable domain as set forth in SEQ ID NO: 3 and a light chain variable domain as set forth in SEQ ID NO: 4.

47. The AB of embodiment 38, comprising a heavy chain variable domain as set forth in SEQ ID NO: 2 and a light chain variable domain as set forth in SEQ ID NO: 4.

48. The AB of any one of embodiments 32 to 47, wherein the AB is a bispecific AB.

49. The AA of any one of embodiments 32 to 47, wherein the antibody is a scFv.

50. The AA of any one of embodiments 32 to 47, wherein the antibody is an IgG1 antibody.

51. An activatable antibody (AA) comprising:
  a) an antibody or antigen binding fragment thereof (AB) that specifically binds to the epsilon chain of CD3 (CD3ε), wherein the antibody comprises a heavy chain variable domain as set forth in SEQ ID NO: 2 or SEQ ID NO: 3 or comprises a light chain variable domain as set forth in SEQ ID NO: 1 or SEQ ID NO: 4;
  b) a masking moiety (MM) coupled to the AB, wherein the MM reduces or inhibits the binding of the AB to the CD3ε when the AA is in an uncleaved state; and
  c) a cleavable moiety (CM) coupled to the AB, wherein the CM is a polypeptide that functions as a substrate for a protease.

52. The AA of embodiment 51, wherein the AB comprises a heavy chain variable domain as set forth in SEQ ID NO: 2.

53. The AA of embodiment 51, wherein the AB comprises a heavy chain variable domain as set forth in SEQ ID NO: 3.

54. The AA of embodiment 51, wherein the AB comprises a light chain variable domain as set forth in SEQ ID NO: 1.

55. The AA of embodiment 51, wherein the AB comprises a light chain variable domain as set forth in SEQ ID NO: 4.

56. The AA of embodiment 51, wherein the AB comprises a heavy chain variable domain as set forth in SEQ ID NO: 2 and a light chain variable domain as set forth in SEQ ID NO: 1.

57. The AA of embodiment 51, wherein the AB comprises a heavy chain variable domain as set forth in SEQ ID NO: 3 and a light chain variable domain as set forth in SEQ ID NO: 1.

58. The AA of embodiment 51, wherein the AB comprises a heavy chain variable domain as set forth in SEQ ID NO: 2 and a light chain variable domain as set forth in SEQ ID NO: 4.

59. The AA of embodiment 51, wherein the AB comprises a heavy chain variable domain as set forth in SEQ ID NO: 3 and a light chain variable domain as set forth in SEQ ID NO: 4.

60. The AA of any one of embodiments 51 to 59, wherein the MM comprises any one of the sequences set forth in Table 3.

61. The AA of any one of embodiments 51 to 59, wherein the CM comprises any one of the sequences set forth in Table 4.

62. A bispecific activatable antibody (BAA) comprising any one of the AAs of embodiments 51 to 61.

63. An activatable antibody (AA) comprising:
  a. an antibody (AB) that specifically binds a target, wherein the antibody is an IgG1 antibody, and wherein the Fc region of the antibody comprises an amino acid substitution in amino acid positions L234, L235, and P331, as numbered by the EU index as set forth in Kabat, such that the AA has reduced effector function;
  b. a masking moiety (MM) coupled to the AB, wherein the MM reduces or inhibits the binding of the AB to the target when the AA is in an uncleaved state; and
  c. a cleavable moiety (CM) coupled to the AB, wherein the CM is a polypeptide that functions as a substrate for a protease.

64. The AA of embodiment 63, wherein the Fc region comprises amino acid substitutions in at least amino acid positions L234, L235, N297 and P331, as numbered by the EU index as set forth in Kabat, such that the AA has reduced effector function.

65. The AA of embodiment 63 or 64, wherein the target is selected from the group consisting of the targets presented in Table 9.

66. A bispecific activatable antibody (BAA) comprising:
  a. an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and
  the CM1 is a polypeptide that functions as a substrate for a first protease,
  b. two scFvs (each an AB2) that each specifically binds to a second target wherein each AB2 comprises a heavy chain variable region linked to a light chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and
  the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function.

67. The BAA of embodiment 66, wherein the Fc region comprises amino acid substitutions in at least amino acid positions L234, L235, N297 and P331, as numbered by the EU index as set forth in Kabat, such that the BAA has reduced effector function.

68. The BAA of embodiment 66, wherein the Fc region comprises amino acid substitutions in at least amino acid positions L234, L235, and P331, as numbered by the EU index as set forth in Kabat, such that the BAA has reduced effector function.

69. The BAA of any one of embodiments 66 to 68, wherein the first target is selected from the group consisting of the targets presented in Table 9 and the second target is selected from the group consisting of the targets presented in Table 9.

70. The AA or BAA of any one of the above embodiments, wherein the antigen binding fragment thereof is selected from the group consisting of a Fab fragment, a F(ab')2 fragment, a scFv, a scAb, a dAb, a single domain heavy chain antibody, and a single domain light chain antibody.

71. The AA or BAA of any one of the above embodiments wherein the antibody is a rodent antibody, a chimeric antibody, a humanized antibody, or a fully human monoclonal antibody.

72. The AA of any one of embodiments 32-37 and 51-71, wherein the AA is a BAA.

73. A pharmaceutical composition comprising the antibody, AA, or BAA of any one of embodiments 1-72 and optionally a carrier.

74. The pharmaceutical composition of embodiment 73 comprising an additional agent.

75. The pharmaceutical composition of embodiment 74, wherein the additional agent is a therapeutic agent.

76. An isolated nucleic acid molecule encoding the antibody, AA, or BAA of any one of embodiments 1-72.

77. A vector comprising the isolated nucleic acid molecule of embodiment 76.

78. A vector comprising the nucleic acid sequence of pLW289.

79. A vector comprising the nucleic acid sequence of pLW246.

80. A vector comprising the nucleic acid sequence of pLW307.

81. A vector comprising the nucleic acid sequence of pLW291.

82. A cell comprising any one of the vectors of embodiments 77-81.

83. A cell comprising pLW289 and pLW246.

84. A cell comprising pLW307 and pLW291.

85. A method of producing the antibody, AA, or BAA of any one of embodiments 1-72 by culturing a cell under conditions that lead to expression of the antibody, AA, or BAA, wherein the cell comprises the nucleic acid molecule of embodiment 76 or the vector of any one of embodiments 78-81.

86. A method of treating, alleviating a symptom of, or delaying the progression of a disorder or disease comprising administering a therapeutically effective amount of the antibody, AA, or BAA of any one of embodiments 1-72, or the pharmaceutical composition of any one of embodiments 73-75 to a subject in need thereof.

87. The method of embodiment 86, wherein the disorder or disease comprises disease cells expressing EGFR.

88. The method of embodiment 86 or 87, wherein the disorder or disease is cancer.

89. The method of embodiment 88, wherein the cancer is anal cancer, basal cell carcinoma, brain cancer, bladder cancer, breast cancer, bone cancer, cervical cancer, cholangiocarcinoma, colorectal cancer, endometrial cancer, esophageal cancer, gall bladder cancer, gastric cancer, glioblastoma, head and neck cancer, liver cancer, lung cancer, ovarian cancer, pancreatic cancer, prostate cancer, renal cancer, sarcoma, small bowel carcinoma, squamous cell cancer, skin cancer testicular cancer, thyroid cancer or uterine cancer.

90. A method of inhibiting angiogenesis in a subject comprising administering a therapeutically effective amount of the antibody, AA, or BAA of any one of embodiments 1-72, or the pharmaceutical composition of any one of embodiments 73-75 to a subject in need thereof.

91. The method of any one of embodiments 86-90, wherein the method comprises administering an additional agent.

92. The method of embodiment 91 wherein the additional agent is a therapeutic agent.

93. A method of reducing damage to healthy tissue caused by an antibody binding to its target on healthy tissue as well as on diseased tissue, the method comprising administering to a subject in need thereof an AA or BAA or a pharmaceutical composition comprising an AA or BAA, wherein said AA or BAA is an AA or BAA of any one of the embodiments provided herein.

94. A method to improve tolerability of an antibody treatment comprising administering to a subject in need thereof an AA or BAA or a pharmaceutical composition comprising an AA or BAA, wherein said AA or BAA is an AA or BAA of any one of the embodiments provided herein.

95. A method to recruit T cells to tumor tissue comprising administering to a subject in need thereof an AA or BAA or a pharmaceutical composition comprising an AA or BAA, wherein said AA or BAA is an AA or BAA of any one of the embodiments provided herein.

96. An antibody, AA, or BAA of any one of embodiments 1-72, or the pharmaceutical composition of any one of embodiments 73-75, for use as a medicament.

97. An antibody, AA, or BAA of any one of embodiments 1-72, or the pharmaceutical composition of any one of embodiments 73-75, for use in a method of treating, alleviating a symptom of, or delaying the progression of a disorder or disease, wherein the disorder or disease comprises disease cells expressing EGFR.

98. An antibody, AA, or BAA of any one of embodiments 1-72, or the pharmaceutical composition of any one of embodiments 73-75, for use in a method of treating cancer; optionally wherein the cancer is anal cancer, basal cell carcinoma, brain cancer, bladder cancer, breast cancer, bone cancer, cervical cancer, cholangiocarcinoma, colorectal cancer, endometrial cancer, esophageal cancer, gall bladder cancer, gastric cancer, glioblastoma, head and neck cancer, liver cancer, lung cancer, ovarian cancer, pancreatic cancer, prostate cancer, renal cancer, sarcoma, small bowel carcinoma, squamous cell cancer, skin cancer testicular cancer, thyroid cancer or uterine cancer.

99. An antibody, AA, or BAA of any one of embodiments 1-72, or the pharmaceutical composition of any one of embodiments 73-75, for use in a method of treatment, wherein the method comprises inhibiting angiogenesis.

100. The antibody, AA, or BAA, or the pharmaceutical composition, for use according to any one of embodiments 96 to 99, wherein the use comprises administering an additional agent, optionally wherein the additional agent is a therapeutic agent.

Examples

Example 1. Sequences, Vector Construction and Expression of Antibodies, BAAs and Activated BAAs

Antibodies of Interest

The molecules as provided in Table 11 below were constructed and tested. As indicated, activated molecules were produced as masked and proteolytically cleaved to produce the activated forms.

TABLE 11

| Molecule Name | Molecule Component Parts | Heavy Chain Vector | Light Chain Vector |
| --- | --- | --- | --- |
| CI011 | 3954-0001-C225v5N297Q-JF15865-0001-CD3LvHv-H-N | pLW023 | OPP022 |
| CI020 | 3954-Nsub-C225v5N297Q-JF15865-Nsub-hSP34LvHv-H-N | pLW073 | pLW071 |
| CI040 | 3954-2001-C225v5N297Q-JF15865-2001-hSP34LvHv-H-N | pLW101 | CTX122 |
| CI048 | Activated CI011: 3954-0001-C225v5N297Q-JF15865-0001-CD3LvHv-H-N | pLW023 | OPP022 |
| CI079 | 3954-0001-C225v5Fcmt3-h20GG-0001-v16sc-H-N | pLW225 | OPP022 |
| CI090 | 3954-0001-C225v5Fcmt4-h20GG-0001-v16sc-H-N | pLW233 | OPP022 |
| Activated CI090 | Activated 3954-0001-C225v5Fcmt4-h20GG-0001-v16sc-H-N | pLW233 | OPP022 |
| Activated CI104 | Activated 3954-0011-C225v5Fcmt4-h20GG-0011-v16sc-H-N | pLW289 | pLW291 |
| CI106 | CF41-2008-C225v5Fcmt4-h20GG-0011-v16sc-H-N | pLW289 | pLW246 |
| CI107 | 3954-0011-C225v5Fcmt4-h20GG-2006-v16sc-H-N | pLW307 | pLW291 |
| CI127 | SynFcmt4-h20GG-0011-v16sc-H-N | pLW334 | pLW139 |
| CI128 | SynFcmt4-h20GG-2006-v16sc-H-N | pLW335 | pLW139 |
| CI135 | CF41-2008-C225v5Fcmt4-h20GG-0011-v12sc-H-N | pLW352 | pLW246 |
| CI136 | CF41-2008-C225v5Fcmt4-h20GG-0011-v19sc-H-N | pLW353 | pLW246 |
| CI091 | 3954-1490DQH-C225v5Fcmt4-h20GG-2008-v16sc-H-N | pLW242 | CX320 |
| CI064 | SynN297Q-JF15865-0001-hSP34LvHv-H-N | pLW138 | pLW139 |
| v12 | Anti-CD3 variant | HV12 | LV12 |
| v16 | Anti-CD3 variant | HV20 | LV12 |
| v19 | Anti-CD3 variant | HV20 | LV19 |
| v26 | Anti-CD3 variant | HV12 | LV19 |

The sequences of the molecules and vectors are provided below. Brackets denote some of the component parts of the molecules presented. In some sequences, linkers are provided. Underlined amino acids denote predicted CDR sequences.

```
CI011: 3954-0001-C225v5N297Q-JF15865-0001-
CD3LvHv-H-N
pLW023: HC JF15865-0001-CD3LvHv-
C225v5N297Q (H-N)
Nucleotide Sequence
[spacer SEQ ID NO: 176]
[pLW023 without spacer SEQ ID NO: 177]
                             (SEQ ID NO: 105)
CAAGGCCAGTCTGGCCAAATGATGTATTGCGTGGGAATGAGGTGTTG

TGCGGGCCGCGGGTTGGCTCGAGCGGTGGCAGCGGTGGCTCTGGTGGT

CTGAGCGGCCGTTCCGATAATCATGGCGGCGGTTCTCAGACCGTGGTC

ACACAGGAGCCCTCACTGACAGTGAGCCCTGGCGGGACCGTCACACTG

ACTTGTCGCAGTTCAACTGGCGCCGTGACTACCAGCAATTACGCTAAC

TGGGTCCAGCAGAAACCAGGACAGGCACCACGAGGACTGATCGGAGGA

ACTAATAAGAGAGCACCAGGAACCCCTGCAAGGTTCTCCGGATCTCTG

CTGGGGGGAAAAGCCGCTCTGACACTGAGCGGCGTGCAGCCTGAGGAC

GAAGCTGAGTACTATTGCGCACTGTGGTACTCCAACCTGTGGGTGTTT

GGCGGGGGAACTAAGCTGACCGTCCTGGGAGGAGGAGGAAGCGGAGGA

GGAGGGAGCGGAGGAGGAGGATCCGAAGTGCAGCTGGTCGAGAGCGGA

GGAGGACTGGTGCAGCCAGGAGGATCCCTGAAGCTGTCTTGTGCAGCC

AGTGGCTTCACCTTCAACACTTACGCAATGAACTGGGTGCGGCAGGCA

CCTGGGAAGGGACTGGAATGGGTCGCCCGGATCAGATCTAAATACAAT

AACTATGCCACCTACTATGCTGACAGTGTGAAGGATAGGTTCACCATT

TCACGCGACGATAGCAAAAACACAGCTTATCTGCAGATGAATAACCTG

AAGACCGAGGATACAGCAGTGTACTATTGCGTCAGACACGGCAATTTC

GGGAACTCTTACGTGAGTTGGTTTGCCTATTGGGGACAGGGGACACTG

GTCACCGTCTCCTCAGGAGGTGGTGGATCCCAGGTGCAGCTGAAACAG

AGCGGCCCGGGCCTGGTGCAGCCGAGCCAGAGCCTGAGCATTACCTGC

ACCGTGAGCGGCTTTAGCCTGACCAACTATGGCGTGCATTGGGTGCGC

CAGAGCCCGGGCAAAGGCCTGGAATGGCTGGGCGTGATTTGGAGCGGC

GGCAACACCGATTATAACACCCCGTTTACCAGCCGCCTGAGCATTAAC

AAAGATAACAGCAAAAGCCAGGTGTTTTTTAAAATGAACAGCCTGCAA

AGCCAGGATACCGCGATTTATTATTGCGCGCGCGCGCTGACCTATTAT

GATTATGAATTTGCGTATTGGGGCCAGGGCACCCTGGTGACCGTGAGC

GCGGCTAGCACCAAGGGCCCATCGGTCTTCCCCCTGGCACCCTCCTCC

AAGAGCACCTCTGGGGGCACAGCGGCCCTGGGCTGCCTGGTCAAGGAC

TACTTCCCCGAACCGGTGACGGTGTCGTGGAACTCAGGCGCCCTGACC

AGCGGCGTGCACACCTTCCCGGCTGTCCTACAGTCCTCAGGACTCTAC

TCCCTCAGCAGCGTGGTGACCGTGCCCTCCAGCAGCTTGGGCACCCAG

ACCTACATCTGCAACGTGAATCACAAGCCCAGCAACACCAAGGTGGAC
```

-continued

AAGAAAGTTGAGCCCAAATCTTGTGACAAAACTCACACATGCCCACCG

TGCCCAGCACCTGAACTCCTGGGGGGACCGTCAGTCTTCCTCTTCCCC

CCAAAACCCAAGGACACCCTCATGATCTCCCGGACCCCTGAGGTCACA

TGCGTGGTGGTGGACGTGAGCCACGAAGACCCTGAGGTCAAGTTCAAC

TGGTACGTGGACGGCGTGGAGGTGCATAATGCCAAGACAAAGCCGCGG

GAGGAGCAGTACCAGAGCACGTACCGTGTGGTCAGCGTCCTCACCGTC

CTGCACCAGGACTGGCTGAATGGCAAGGAGTACAAGTGCAAGGTCTCC

AACAAAGCCCTCCCAGCCCCCATCGAGAAAACCATCTCCAAAGCCAAA

GGGCAGCCCCGAGAACCACAGGTGTACACCCTGCCCCCATCCCGGGAG

GAGATGACCAAGAACCAGGTCAGCCTGACCTGCCTGGTCAAAGGCTTC

TATCCCAGCGACATCGCCGTGGAGTGGGAGAGCAATGGGCAGCCGGAG

AACAACTACAAGACCACGCCTCCCGTGCTGGACTCCGACGGCTCCTTC

TTCCTCTACAGCAAGCTCACCGTGGACAAGAGCAGGTGGCAGCAGGGG

AACGTCTTCTCATGCTCCGTGATGCATGAGGCTCTGCACAACCACTAC

ACGCAGAAGAGCCTCTCCCTGTCTCCGGGTAAA

Amino Acid Sequence
[spacer SEQ ID NO: 178]
[pLW023 without spacer SEQ ID NO: 179]

(SEQ ID NO: 106)

QGQSGQ[MMYCGGNEVLCGPRV][GSSGGSGGSGG][LSGRSDNH][G

GGS]QTVVTQEPSLTVSPGGTVTLTCRSSTGAVTTSNYANWVQQKPGQ

APRGLIGGTNKRAPGTPARFSGSLLGGKAALTLSGVQPEDEAEYYCAL

WYSNLWVFGGGTKLTVL[GGGGSGGGGSGGGGS]EVQLVESGGGLVQP

GGSLKLSCAASGFTFNTYAMNWVRQAPGKGLEWVARIRSKYNNYATYY

ADSVKDRFTISRDDSKNTAYLQMNNLKTEDTAVYYCVRHGNFGNSYVS

WFAYWGQGTLVTVSS[GGGGS]QVQLKQSGPGLVQPSQSLSITCTVSG

FSLTNYGVHWVRQSPGKGLEWLGVIWSGGNTDYNTPFTSRLSINKDNS

KSQVFFKMNSLQSQDTAIYYCARALTYYDYEFAYWGQGTLVTVSAAST

KGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVV

DVSHEDPEVKFNWYVDGVEVHNAKTKPREEQYQSTYRVVSVLTVLHQD

WLNGKEYKCKVSNKALPAPIEKTISKAKGQPREPQVYTLPPSREEMTK

NQVSLTCLVKGFYPSDIAVEWESNGQPENNYKTTPPVLDSDGSFFLYS

KLTVDKSRWQQGNVFSCSVMHEALHNHYTQKSLSLSPGK

OPP022: LC 3954-0001-C225v5
Nucleotide Sequence
[spacer SEQ ID NO: 180]
[OPP022 without spacer SEQ ID NO: 181]

(SEQ ID NO: 107)

TCCGATAATCATGGCAGTAGCGGTACCCAGATCTTGCTGACCCAGAGC

CCGGTGATTCTGAGCGTGAGCCCGGGCGAACGTGTGAGCTTTAGCTGC

CGCGCGAGCCAGAGCATTGGCACCAACATTCATTGGTATCAGCAGCGC

ACCAACGGCAGCCCGCGCCTGCTGATTAAATATGCGAGCGAAAGCATT

AGCGGCATTCCGAGCCGCTTTAGCGGCAGCGGCAGCGGCACCGATTTT

-continued

ACCCTGAGCATTAACAGCGTGGAAAGCGAAGATATTGCGGATTATTAT

TGCCAGCAGAACAACAACTGGCCGACCACCTTTGGCGCGGGCACCAAA

CTGGAACTGAAACGTACGGTGGCTGCACCATCTGTCTTCATCTTCCCG

CCATCTGATGAGCAGTTGAAATCTGGAACTGCCTCTGTTGTGTGCCTG

CTGAATAACTTCTATCCCAGAGAGGCCAAAGTACAGTGGAAGGTGGAT

AACGCCCTCCAATCGGGTAACTCCCAGGAGAGTGTCACAGAGCAGGAC

AGCAAGGACAGCACCTACAGCCTCAGCAGCACCCTGACGCTGAGCAAA

GCAGACTACGAGAAACACAAAGTCTACGCCTGCGAAGTCACCCATCAG

GGCCTGAGCTCGCCCGTCACAAAGAGCTTCAACAGGGGAGAGTGT

Amino Acid Sequence
[spacer SEQ ID NO: 178]
[OPP022 without spacer SEQ ID NO: 182]

(SEQ ID NO: 108)

[SDNH][GSSGT][QILLTQSPVILSVSPGERVSFSCRASQSIGTNIH

WYQQRTNGSPRLLIKYASESISGIPSRFSGSGSGTDFTLSINSVESED

IADYYCQQNNNWPTTFGAGTKLELKRTVAAPSVFIFPPSDEQLKSGTA

SVVCLLNNFYPREAKVQWKVDNALQSGNSQESVTEQDSKDSTYSLSST

LTLSKADYEKHKVYACEVTHQGLSSPVTKSFNRGEC

CI020: 3954-Nsub-C225v5N297Q-JF15865-Nsub-hSP34LvHv-H-N
pLW073: HC C225v5N297Q-JF15865-Nsub-hSP34LvHv (H-N)
Nucleotide Sequence
[spacer SEQ ID NO: 176]
[pLW073 without spacer SEQ ID NO: 183]

(SEQ ID NO: 109)

CAAGGCCAGTCTGGCCAAATGATGTATTGCGGTGGGAATGAGGTGTTG

TGCGGGCCGCGGGTTGGCTCGAGCGGTGGCAGCGGTGGCTCTGGTGGT

GGTGGAGGCTCGGGCGGTGGGAGCGGCGGCGGTTCTCAGACCGTGGTC

ACACAGGAGCCCTCACTGACAGTGAGCCCTGGCGGGACCGTCACACTG

ACTTGTCGCAGTTCAACTGGCGCCGTGACTACCAGCAATTACGCTAAC

TGGGTCCAGCAGAAACCAGGACAGGCACCACGAGGACTGATCGGAGGA

ACTAATAAGAGAGCACCAGGAACCCCTGCAAGGTTCTCCGGATCTCTG

CTGGGGGGAAAAGCCGCTCTGACACTGAGCGGCGTGCAGCCTGAGGAC

GAAGCTGAGTACTATTGCGCACTGTGGTACTCCAACCTGTGGGTGTTT

GGCGGGGGAACTAAGCTGACCGTCCTGGGAGGAGGAGGAAGCGGAGGA

GGAGGGAGCGGAGGAGGAGGATCCGAAGTGCAGCTGGTCGAGAGCGGA

GGAGGACTGGTGCAGCCAGGAGGATCCCTGAAGCTGTCTTGTGCAGCC

AGTGGCTTCACCTTCAACACTTACGCAATGAACTGGGTGCGGCAGGCA

CCTGGGAAGGGACTGGAATGGGTCGCCCGGATCAGATCTAAATACAAT

AACTATGCCACCTACTATGCTGACAGTGTGAAGGATAGGTTCACCATT

TCACGCGACGATAGCAAAAACACAGCTTATCTGCAGATGAATAACCTG

AAGACCGAGGATACAGCAGTGTACTATTGCGTCAGACACGGCAATTTC

GGGAACTCTTACGTGAGTTGGTTTGCCTATTGGGGACAGGGGACACTG

GTCACCGTCTCCTCAGGAGGTGGTGGATCCCAGGTGCAGCTGAAACAG

AGCGGCCCGGGCCTGGTGCAGCCGAGCCAGAGCCTGAGCATTACCTGC

ACCGTGAGCGGCTTTAGCCTGACCAACTATGGCGTGCATTGGGTGCGC

```
CAGAGCCCGGGCAAAGGCCTGGAATGGCTGGGCGTGATTTGGAGCGGC

GGCAACACCGATTATAACACCCCGTTTACCAGCCGCCTGAGCATTAAC

AAAGATAACAGCAAAAGCCAGGTGTTTTTTAAAATGAACAGCCTGCAA

AGCCAGGATACCGCGATTTATTATTGCGCGCGCGCGCTGACCTATTAT

GATTATGAATTTGCGTATTGGGGCCAGGGCACCCTGGTGACCGTGAGC

GCGGCTAGCACCAAGGGCCCATCGGTCTTCCCCCTGGCACCCTCCTCC

AAGAGCACCTCTGGGGGCACAGCGGCCCTGGGCTGCCTGGTCAAGGAC

TACTTCCCCGAACCGGTGACGGTGTCGTGGAACTCAGGCGCCCTGACC

AGCGGCGTGCACACCTTCCCGGCTGTCCTACAGTCCTCAGGACTCTAC

TCCCTCAGCAGCGTGGTGACCGTGCCCTCCAGCAGCTTGGGCACCCAG

ACCTACATCTGCAACGTGAATCACAAGCCCAGCAACACCAAGGTGGAC

AAGAAAGTTGAGCCCAAATCTTGTGACAAAACTCACACATGCCCACCG

TGCCCAGCACCTGAACTCCTGGGGGGACCGTCAGTCTTCCTCTTCCCC

CCAAAACCCAAGGACACCCTCATGATCTCCCGGACCCCTGAGGTCACA

TGCGTGGTGGTGGACGTGAGCCACGAAGACCCTGAGGTCAAGTTCAAC

TGGTACGTGGACGGCGTGGAGGTGCATAATGCCAAGACAAAGCCGCGG

GAGGAGCAGTACCAGAGCACGTACCGTGTGGTCAGCGTCCTCACCGTC

CTGCACCAGGACTGGCTGAATGGCAAGGAGTACAAGTGCAAGGTCTCC

AACAAAGCCCTCCCAGCCCCCATCGAGAAAACCATCTCCAAAGCCAAA

GGGCAGCCCCGAGAACCACAGGTGTACACCCTGCCCCCATCCCGGGAG

GAGATGACCAAGAACCAGGTCAGCCTGACCTGCCTGGTCAAAGGCTTC

TATCCCAGCGACATCGCCGTGGAGTGGGAGAGCAATGGGCAGCCGGAG

AACAACTACAAGACCACGCCTCCCGTGCTGGACTCCGACGGCTCCTTC

TTCCTCTACAGCAAGCTCACCGTGGACAAGAGCAGGTGGCAGCAGGGG

AACGTCTTCTCATGCTCCGTGATGCATGAGGCTCTGCACAACCACTAC

ACGCAGAAGAGCCTCTCCCTGTCTCCGGGTAAA
```

Amino Acid Sequence
[spacer SEQ ID NO: 178]
[pLW073 without spacer SEQ ID NO: 184]
(SEQ ID NO: 110)
QGQSGQ[MMYCGGNEVLCGPRV][GSSGGSGGSGGGGGSGGGSGGGS]
QTVVTQEPSLTVSPGGTVTLTCRSSTGAVTTSNYANWVQQKPGQAPRG
LIGGTNKRAPGTPARFSGSLLGGKAALTLSGVQPEDEAEYYCALWYSN
LWVFGGGTKLTVL[GGGGSGGGGSGGGGS]EVQLVESGGGLVQPGGSL
KLSCAASGFTFNTYAMNWVRQAPGKGLEWVARIRSKYNNYATYYADSV
KDRFTISRDDSKNTAYLQMNNLKTEDTAVYYCVRHGNFGNSYVSWFAY
WGQGTLVTVSS[GGGGS]QVQLKQSGPGLVQPSQSLSITCTVSGFSLT
NYGVHWVRQSPGKGLEWLGVIWSGGNTDYNTPFTSRLSINKDNSKSQV
FFKMNSLQSDTAIYYCARALTYYDYEFAYWGQGTLVTVSAASTKGPS
VFPPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSH
EDPEVKFNWYVDGVEVHNAKTKPREEQYQSTYRVVSVLTVLHQDWLNG
KEYKCKVSNKALPAPIEKTISKAKGQPREPQVYTLPPSREEMTKNQVS
LTCLVKGFYPSDIAVEWESNGQPENNYKTTPPVLDSDGSFFLYSKLTV
DKSRWQQGNVFSCSVMHEALHNHYTQKSLSLSPGK pLW071: LC 3954-Nsub-C225v5
Nucleotide Sequence
[spacer SEQ ID NO: 180]
[pLW071 without spacer SEQ ID NO: 185]
(SEQ ID NO: 111)
```
CAAGGCCAGTCTGGCCAGTGCATCTCACCTCGTGGTTGTCCGGACGGC

CCATACGTCATGTACGGCTCGAGCGGTGGCAGCGGTGGCTCTGGTGGC

TCAGGTGGAGGCTCGGGCGGTGGGAGCGGCGGTTCTGATATCTTGCTG

ACCCAGAGCCCGGTGATTCTGAGCGTGAGCCCGGGCGAACGTGTGAGC

TTTAGCTGCCGCGCGAGCCAGAGCATTGGCACCAACATTCATTGGTAT

CAGCAGCGCACCAACGGCAGCCCGCGCCTGCTGATTAAATATGCGAGC

GAAAGCATTAGCGGCATTCCGAGCCGCTTTAGCGGCAGCGGCAGCGGC

ACCGATTTTACCCTGAGCATTAACAGCGTGGAAAGCGAAGATATTGCG

GATTATTATTGCCAGCAGAACAACAACTGGCCGACCACCTTTGGCGCG

GGCACCAAACTGGAACTGAAACGTACGGTGGCTGCACCATCTGTCTTC

ATCTTCCCGCCATCTGATGAGCAGTTGAAATCTGGAACTGCCTCTGTT

GTGTGCCTGCTGAATAACTTCTATCCCAGAGAGGCCAAAGTACAGTGG

AAGGTGGATAACGCCCTCCAATCGGGTAACTCCCAGGAGAGTGTCACA

GAGCAGGACAGCAAGGACAGCACCTACAGCCTCAGCAGCACCCTGACG

CTGAGCAAAGCAGACTACGAGAAACACAAAGTCTACGCCTGCGAAGTC

ACCCATCAGGGCCTGAGCTCGCCCGTCACAAAGAGCTTCAACAGGGGA

GAGTGT
```

Amino Acid Sequence
[spacer SEQ ID NO: 178]
[pLW071 without spacer SEQ ID NO: 186]
(SEQ ID NO: 112)
QGQSGQ[CISPRGCPDGPYVMY][GSSGGSGGSGGGGGSGGGSGGGS]
DILLTQSPVILSVSPGERVSFSCRASQSIGTNIHWYQQRTNGSPRLLI
KYASESISGIPSRFSGSGSGTDFTLSINSVESEDIADYYCQQNNNWPT
TFGAGTKLELKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC CI040: 3954-2001-C225v5N297Q-JF15865-2001-
hSP34LvHv-H-N
pLW101: HC JF15865-2001-CD3LvHv-
C225v5N297Q (H-N)
Nucleotide Sequence
[spacer SEQ ID NO: 176]
[pLW101 without spacer SEQ ID NO: 187]
(SEQ ID NO: 113)
```
CAAGGCCAGTCTGGCCAAATGATGTATTGCGGTGGGAATGAGGTGTTG

TGCGGGCCGCGGGTTGCTCGAGCGGTGGCAGCGGTGGCTCTGGTGGT

ATCTCTTCCGGACTGCTGTCCGGCAGATCCGACAATCACGGCGGCGGT

TCTCAGACCGTGGTCACACAGGAGCCCTCACTGACAGTGAGCCCTGGC

GGGACCGTCACACTGACTTGTCGCAGTTCAACTGGCGCCGTGACTACC
```

-continued
```
AGCAATTACGCTAACTGGGTCCAGCAGAAACCAGGACAGGCACCACGA
GGACTGATCGGAGGAACTAATAAGAGAGCACCAGGAACCCCTGCAAGG
TTCTCCGGATCTCTGCTGGGGGAAAAGCCGCTCTGACACTGAGCGGC
GTGCAGCCTGAGGACGAAGCTGAGTACTATTGCGCACTGTGGTACTCC
AACCTGTGGGTGTTTGGCGGGGGAACTAAGCTGACCGTCCTGGGAGGA
GGAGGAAGCGGAGGAGGAGGGAGCGGAGGAGGAGGATCCGAAGTGCAG
CTGGTCGAGAGCGGAGGAGGACTGGTGCAGCCAGGAGGATCCCTGAAG
CTGTCTTGTGCAGCCAGTGGCTTCACCTTCAACACTTACGCAATGAAC
TGGGTGCGGCAGGCACCTGGGAAGGGACTGGAATGGGTCGCCCGGATC
AGATCTAAATACAATAACTATGCCACCTACTATGCTGACAGTGTGAAG
GATAGGTTCACCATTTCACGCGACGATAGCAAAAACACAGCTTATCTG
CAGATGAATAACCTGAAGACCGAGGATACAGCAGTGTACTATTGCGTC
AGACACGGCAATTTCGGGAACTCTTACGTGAGTTGGTTTGCCTATTGG
GGACAGGGGACACTGGTCACCGTCTCCTCAGGAGGTGGTGGATCCCAG
GTGCAGCTGAAACAGAGCGGCCCGGGCCTGGTGCAGCCGAGCCAGAGC
CTGAGCATTACCTGCACCGTGAGCGGCTTTAGCCTGACCAACTATGGC
GTGCATTGGGTGCGCCAGAGCCCGGGCAAAGGCCTGGAATGGCTGGGC
GTGATTTGGAGCGGCGGCAACACCGATTATAACACCCCGTTTACCAGC
CGCCTGAGCATTAACAAAGATAACAGCAAAAGCCAGGTGTTTTTTAAA
ATGAACAGCCTGCAAAGCCAGGATACCGCGATTTATTATTGCGCGCGC
GCGCTGACCTATTATGATTATGAATTTGCGTATTGGGGCCAGGGCACC
CTGGTGACCGTGAGCGCGGCTAGCACCAAGGGCCCATCGGTCTTCCCC
CTGGCACCCTCCTCCAAGAGCACCTCTGGGGGCACAGCGGCCCTGGGC
TGCCTGGTCAAGGACTACTTCCCCGAACCGGTGACGGTGTCGTGGAAC
TCAGGCGCCCTGACCAGCGGCGTGCACACCTTCCCGGCTGTCCTACAG
TCCTCAGGACTCTACTCCCTCAGCAGCGTGGTGACCGTGCCCTCCAGC
AGCTTGGGCACCCAGACCTACATCTGCAACGTGAATCACAAGCCCAGC
AACACCAAGGTGGACAAGAAAGTTGAGCCCAAATCTTGTGACAAAACT
CACACATGCCCACCGTGCCCAGCACCTGAACTCCTGGGGGGACCGTCA
GTCTTCCTCTTCCCCCCAAAACCCAAGGACACCCTCATGATCTCCCGG
ACCCCTGAGGTCACATGCGTGGTGGTGGACGTGAGCCACGAAGACCCT
GAGGTCAAGTTCAACTGGTACGTGGACGGCGTGGAGGTGCATAATGCC
AAGACAAAGCCGCGGGAGGAGCAGTACCAGAGCACGTACCGTGTGGTC
AGCGTCCTCACCGTCCTGCACCAGGACTGGCTGAATGGCAAGGAGTAC
AAGTGCAAGGTCTCCAACAAAGCCCTCCCAGCCCCCATCGAGAAAACC
ATCTCCAAAGCCAAAGGGCAGCCCCGAGAACCACAGGTGTACACCCTG
CCCCCATCCCGGGAGGAGATGACCAAGAACCAGGTCAGCCTGACCTGC
CTGGTCAAAGGCTTCTATCCCAGCGACATCGCCGTGGAGTGGGAGAGC
AATGGGCAGCCGGAGAACAACTACAAGACCACGCCTCCCGTGCTGGAC
```

-continued
```
TCCGACGGCTCCTTCTTCCTCTACAGCAAGCTCACCGTGGACAAGAGC
AGGTGGCAGCAGGGGAACGTCTTCTCATGCTCCGTGATGCATGAGGCT
CTGCACAACCACTACACGCAGAAGAGCCTCTCCCTGTCTCCGGGTAAA
```

Amino Acid Sequence
[spacer SEQ ID NO: 178]
[pLW101 without spacer SEQ ID NO: 188]
(SEQ ID NO: 114)
```
QGQSGQ[MMYCGGNEVLCGPRV][GSSGGSGGSGG][ISSGLLSGRSD
NH][GGGS]QTVVTQEPSLTVSPGGTVTLTCRSSTGAVTTSNYANWVQ
QKPGQAPRGLIGGTNKRAPGTPARFSGSLLGGKAALTLSGVQPEDEAE
YYCALWYSNLWVFGGGTKLTVL[GGGGSGGGGSGGGGS]EVQLVESGG
GLVQPGGSLKLSCAASGFTFNTYAMNWVRQAPGKGLEWVARIRSKYNN
YATYYADSVKDRFTISRDDSKNTAYLQMNNLKTEDTAVYYCVRHGNFG
NSYVSWFAYWGQGTLVTVSS[GGGGS]QVQLKQSGPGLVQPSQSLSIT
CTVSGFSLTNYGVHWVRQSPGKGLEWLGVIWSGGNTDYNTPFTSRLSI
NKDNSKSQVFFKMNSLQSQDTAIYYCARALTYYDYEFAYWGQGTLVTV
SAASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKV
DKKVEPKSCDKTHTCPPCPAPELLGGPSVFLFPPKPKDTLMISRTPEV
TCVVVDVSHEDPEVKFNWYVDGVEVHNAKTKPREEQYQSTYRVVSVLT
VLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGS
FFLYSKLTVDKSRWQQGNVFSCSVMHEALHNHYTQKSLSLSPGK
```

CTX122: LC 3954-2001-C225v5
Nucleotide Sequence
[spacer SEQ ID NO: 180]
[CTX122 without spacer SEQ ID NO: 189]
(SEQ ID NO: 115)
```
CAAGGCCAGTCTGGCCAGTGCATCTCACCTCGTGGTTGTCCGGACGGC
CCATACGTCATGTACGGCTCGAGCGGTGGCAGCGGTGGCTCTGGTGGA
TCCGGTATTAGCAGTGGTCTGTTAAGCGGTCGTAGCGATAATCATGGC
AGTAGCGGTACCCAGATCTTGCTGACCCAGAGCCCGGTGATTCTGAGC
GTGAGCCCGGGCGAACGTGTGAGCTTTAGCTGCCGCGCGAGCCAGAGC
ATTGGCACCAACATTCATTGGTATCAGCAGCGCACCAACGGCAGCCCG
CGCCTGCTGATTAAATATGCGAGCGAAAGCATTAGCGGCATTCCGAGC
CGCTTTAGCGGCAGCGGCAGCGGCACCGATTTTACCCTGAGCATTAAC
AGCGTGGAAAGCGAAGATATTGCGGATTATTATTGCCAGCAGAACAAC
AACTGGCCGACCACCTTTGGCGCGGGCACCAAACTGGAACTGAAACGT
ACGGTGGCTGCACCATCTGTCTTCATCTTCCCGCCATCTGATGAGCAG
TTGAAATCTGGAACTGCCTCTGTTGTGTGCCTGCTGAATAACTTCTAT
CCCAGAGAGGCCAAAGTACAGTGGAAGGTGGATAACGCCCTCCAATCG
GGTAACTCCCAGGAGAGTGTCACAGAGCAGGACAGCAAGGACAGCACC
TACAGCCTCAGCAGCACCCTGACGCTGAGCAAAGCAGACTACGAGAAA
CACAAAGTCTACGCCTGCGAAGTCACCCATCAGGGCCTGAGCTCGCCC
GTCACAAAGAGCTTCAACAGGGGAGAGTGT
```

Amino Acid Sequence
[spacer SEQ ID NO: 178]
[CTX122 without spacer SEQ ID NO: 190]
(SEQ ID NO: 116)
QGQSGQ[CISPRGCPDGPYVMY][GSSGGSGGSGGS][ISSGLLSGR
SDNH][GSSGT]QILLTQSPVILSVSPGERVSFSCRASQSIGTNIHWY
QQRTNGSPRLLIKYASESISGIPSRFSGSGSGTDFTLSINSVESEDIA
DYYCQQNNNWPTTFGAGTKLELKRTVAAPSVFIFPPSDEQLKSGTASV
VCLLNNFYPREAKVQWKVDNALQSGNSQESVTEQDSKDSTYSLSSTLT
LSKADYEKHKVYACEVTHQGLSSPVTKSFNRGEC CI048: Activated CI011: 3954-0001-C225v5N297Q-
JF15865-0001-CD3LvHv-H-N
pLW023 and OPP022 sequences encoding
corresponding masked antibody components are
provided herein as "pLW023" and "OPP022,
respectively and are summarized in Table 11.
Activated pLW023: HC JF15865-0001-CD3LvHv-
C225v5N297Q (H-N)
Nucleotide Sequence
(SEQ ID NO: 117)
TCCGATAATCATGGCGGCGGTTCTCAGACCGTGGTCACACAGGAGCCC

TCACTGACAGTGAGCCCTGGCGGGACCGTCACACTGACTTGTCGCAGT

TCAACTGGCGCCGTGACTACCAGCAATTACGCTAACTGGGTCCAGCAG

AAACCAGGACAGGCACCACGAGGACTGATCGGAGGAACTAATAAGAGA

GCACCAGGAACCCCTGCAAGGTTCTCCGGATCTCTGCTGGGGGGAAAA

GCCGCTCTGACACTGAGCGGCGTGCAGCCTGAGGACGAAGCTGAGTAC

TATTGCGCACTGTGGTACTCCAACCTGTGGGTGTTTGGCGGGGGAACT

AAGCTGACCGTCCTGGGAGGAGGAGGAAGCGGAGGAGGAGGGAGCGGA

GGAGGAGGATCCGAAGTGCAGCTGGTCGAGAGCGGAGGAGGACTGGTG

CAGCCAGGAGGATCCCTGAAGCTGTCTTGTGCAGCCAGTGGCTTCACC

TTCAACACTTACGCAATGAACTGGGTGCGGCAGGCACCTGGGAAGGGA

CTGGAATGGGTCGCCCGGATCAGATCTAAATACAATAACTATGCCACC

TACTATGCTGACAGTGTGAAGGATAGGTTCACCATTTCACGCGACGAT

AGCAAAAACACAGCTTATCTGCAGATGAATAACCTGAAGACCGAGGAT

ACAGCAGTGTACTATTGCGTCAGACACGGCAATTTCGGGAACTCTTAC

GTGAGTTGGTTTGCCTATTGGGACAGGGGACACTGGTCACCGTCTCC

TCAGGAGGTGGTGGATCCCAGGTGCAGCTGAAACAGAGCGGCCCGGGC

CTGGTGCAGCCGAGCCAGAGCCTGAGCATTACCTGCACCGTGAGCGGC

TTTAGCCTGACCAACTATGGCGTGCATTGGGTGCGCCAGAGCCCGGGC

AAAGGCCTGGAATGGCTGGGCGTGATTTGGAGCGGCGGCAACACCGAT

TATAACACCCCGTTTACCAGCCGCCTGAGCATTAACAAAGATAACAGC

AAAAGCCAGGTGTTTTTTAAAATGAACAGCCTGCAAAGCCAGGATACC

GCGATTTATTATTGCGCGCGCGCGCTGACCTATTATGATTATGAATTT

GCGTATTGGGGCCAGGGCACCCTGGTGACCGTGAGCGCGGCTAGCACC

AAGGGCCCATCGGTCTTCCCCCTGGCACCCTCCTCCAAGAGCACCTCT

GGGGGCACAGCGGCCCTGGGCTGCCTGGTCAAGGACTACTTCCCCGAA

CCGGTGACGGTGTCGTGGAACTCAGGCGCCCTGACCAGCGGCGTGCAC

ACCTTCCCGGCTGTCCTACAGTCCTCAGGACTCTACTCCCTCAGCAGC

GTGGTGACCGTGCCCTCCAGCAGCTTGGGCACCCAGACCTACATCTGC

AACGTGAATCACAAGCCCAGCAACACCAAGGTGGACAAGAAAGTTGAG

CCCAAATCTTGTGACAAAACTCACACATGCCCACCGTGCCCAGCACCT

GAACTCCTGGGGGGACCGTCAGTCTTCCTCTTCCCCCCAAAACCCAAG

GACACCCTCATGATCTCCCGGACCCCTGAGGTCACATGCGTGGTGGTG

GACGTGAGCCACGAAGACCCTGAGGTCAAGTTCAACTGGTACGTGGAC

GGCGTGGAGGTGCATAATGCCAAGACAAAGCCGCGGGAGGAGCAGTAC

CAGAGCACGTACCGTGTGGTCAGCGTCCTCACCGTCCTGCACCAGGAC

TGGCTGAATGGCAAGGAGTACAAGTGCAAGGTCTCCAACAAAGCCCTC

CCAGCCCCCATCGAGAAAACCATCTCCAAAGCCAAAGGGCAGCCCCGA

GAACCACAGGTGTACACCCTGCCCCCATCCCGGGAGGAGATGACCAAG

AACCAGGTCAGCCTGACCTGCCTGGTCAAAGGCTTCTATCCCAGCGAC

ATCGCCGTGGAGTGGGAGAGCAATGGGCAGCCGGAGAACAACTACAAG

ACCACGCCTCCCGTGCTGGACTCCGACGGCTCCTTCTTCCTCTACAGC

AAGCTCACCGTGGACAAGAGCAGGTGGCAGCAGGGGAACGTCTTCTCA

TGCTCCGTGATGCATGAGGCTCTGCACAACCACTACACGCAGAAGAGC

CTCTCCCTGTCTCCGGGTAAA

Amino Acid Sequence
(SEQ ID NO: 118)
[SDNH][GGGS]QTVVTQEPSLTVSPGGTVTLTCRSSTGAVTTSNYAN

WVQQKPGQAPRGLIGGTNKRAPGTPARFSGSLLGGKAALTLSGVQPED

EAEYYCALWYSNLWVFGGGTKLTVL[GGGGSGGGGSGGGGS]EVQLVE

SGGGLVQPGGSLKLSCAASGFTFNTYAMNWVRQAPGKGLEWVARIRSK

YNNYATYYADSVKDRFTISRDDSKNTAYLQMNNLKTEDTAVYYCVRHG

NFGNSYVSWFAYWGQGTLVTVSS[GGGGS]QVQLKQSGPGLVQPSQSL

SITCTVSGFSLTNYGVHWVRQSPGKGLEWLGVIWSGGNTDYNTPFTSR

LSINKDNSKSQVFFKMNSLQSQDTAIYYCARALTYYDYEFAYWGQGTL

VTVSAASTKGPSVFPLAPSSKSTSGGTAALGCLVKDYFPEPVTVSWNS

GALTSGVHTFPAVLQSSGLYSLSSVVTVPSSSLGTQTYICNVNHKPSN

TKVDKKVEPKSCDKTHTCPPCPAPELLGGPSVFLFPPKPKDTLMISRT

PEVTCVVVDVSHEDPEVKFNWYVDGVEVHNAKTKPREEQYQSTYRVVS

VLTVLHQDWLNGKEYKCKVSNKALPAPIEKTISKAKGQPREPQVYTLP

PSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

Activated OPP022: LC 3954-0001-C225v5
Nucleotide Sequence
(SEQ ID NO: 119)
TCCGATAATCATGGCAGTAGCGGTACCCAGATCTTGCTGACCCAGAGC

CCGGTGATTCTGAGCGTGAGCCCGGGCGAACGTGTGAGCTTTAGCTGC

CGCGCGAGCCAGAGCATTGGCACCAACATTCATTGGTATCAGCAGCGC

ACCAACGGCAGCCCGCGCCTGCTGATTAAATATGCGAGCGAAAGCATT

AGCGGCATTCCGAGCCGCTTTAGCGGCAGCGGCAGCGGCACCGATTTT

-continued

```
ACCCTGAGCATTAACAGCGTGGAAAGCGAAGATATTGCGGATTATTAT

TGCCAGCAGAACAACAACTGGCCGACCACCTTTGGCGCGGGCACCAAA

CTGGAACTGAAACGTACGGTGGCTGCACCATCTGTCTTCATCTTCCCG

CCATCTGATGAGCAGTTGAAATCTGGAACTGCCTCTGTTGTGTGCCTG

CTGAATAACTTCTATCCCAGAGAGGCCAAAGTACAGTGGAAGGTGGAT

AACGCCCTCCAATCGGGTAACTCCCAGGAGAGTGTCACAGAGCAGGAC

AGCAAGGACAGCACCTACAGCCTCAGCAGCACCCTGACGCTGAGCAAA

GCAGACTACGAGAAACACAAAGTCTACGCCTGCGAAGTCACCCATCAG

GGCCTGAGCTCGCCCGTCACAAAGAGCTTCAACAGGGGAGAGTGT
```

Amino Acid Sequence
(SEQ ID NO: 120)

```
[SDNH][GSSGT]QILLTQSPVILSVSPGERVSFSCRASQSIGTNIHW

YQQRTNGSPRLLIKYASESISGIPSRFSGSGSGTDFTLSINSVESEDI

ADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTL

TLSKADYEKHKVYACEVTHQGLSSPVTKSFNRGEC
```

CI079: 3954-0001-C225v5Fcmt3-h20GG-0001-
v16sc-H-N
pLW225: HC h20GG-0001-v16sc-C225v5Fcmt3 (H-N)
Nucleotide Sequence
[spacer SEQ ID NO: 191]
[pLW225_without spacer SEQ ID NO: 192]
(SEQ ID NO: 121)

```
CAAGGCCAGTCTGGATCCGGTTATCTGTGGGGTTGCGAGTGGAATTGC

GGAGGGATCACTACAGGCTCGAGCGGTGGCAGCGGTGGCTCTGGTGGT

CTGAGCGGCCGTTCCGATAATCATGGCGGCGGTTCTCAAACTGTAGTA

ACTCAAGAACCAAGCTTCTCCGTCTCCCCTGGGGGAACAGTCACACTT

ACCTGCCGAAGTAGTACAGGTGCTGTTACGACCAGTAACTATGCCAAT

TGGGTACAACAAACGCCTGGTCAGGCTCCGCGCGGATTGATAGGAGGC

ACGAATAAACGGGCACCCGGTGTCCCGGACAGATTCAGCGGAAGCATA

CTCGGTAATAAGGCAGCTCTTACTATCACTGGGGCCCAAGCTGATGAT

GAAAGTGATTATTATTGTGCGCTCTGGTACAGCAACCTCTGGGTGTTT

GGGGGTGGCACGAAACTTACTGTCTTGGGCGGCGGCGGATCAGGGGGA

GGTGGCTCTGGAGGAGGAGGCTCAGAAGTCCAACTGGTCGAATCCGGG

GGAGGGCTCGTACAGCCGGTGGGTCCCTCAAACTCTCTTGTGCGGCC

TCAGGGTTTACCTTCAGTACATACGCGATGAATTGGGTCCGCAGGCC

AGTGGGAAAGGGCTCGAATGGGTAGGACGAATCCGATCAAAATACAAC

AACTACGCTACTTATTACGCTGATTCCGTGAAGGACAGATTCACAATA

TCCCGCGACGATAGCAAGAATACGGCATATCTTCAGATGAATTCTCTT

AAAACTGAGGATACCGCTGTGTATTACTGCACAAGACATGGTAATTTT

GGAAACTCATATGTCTCTTGGTTCGCTTATTGGGACAGGGCACGTTG

GTTACCGTGTCTAGCGGAGGTGGTGGATCCCAGGTGCAGCTGAAACAG

AGCGGCCCGGGCCTGGTGCAGCCGAGCCAGAGCCTGAGCATTACCTGC

ACCGTGAGCGGCTTTAGCCTGACCAACTATGCGTGCATTGGGTGCGC

CAGAGCCCGGGCAAAGGCCTGGAATGGCTGGGCGTGATTTGGAGCGGC
```

-continued

```
GGCAACACCGATTATAACACCCCGTTTACCAGCCGCCTGAGCATTAAC

AAAGATAACAGCAAAAGCCAGGTGTTTTTTAAAATGAACAGCCTGCAA

AGCCAGGATACCGCGATTTATTATTGCGCGCGCGCGCTGACCTATTAT

GATTATGAATTTGCGTATTGGGGCCAGGGCACCCTGGTGACCGTGAGC

GCGGCTAGCACCAAGGGCCCATCGGTCTTCCCCCTGGCACCCTCCTCC

AAGAGCACCTCTGGGGGCACAGCGGCCCTGGGCTGCCTGGTCAAGGAC

TACTTCCCCGAACCGGTGACGGTGTCGTGGAACTCAGGCGCCCTGACC

AGCGGCGTGCACACCTTCCCGGCTGTCCTACAGTCCTCAGGACTCTAC

TCCCTCAGCAGCGTGGTGACCGTGCCCTCCAGCAGCTTGGGCACCCAG

ACCTACATCTGCAACGTGAATCACAAGCCCAGCAACACCAAGGTGGAC

AAGAAAGTTGAGCCCAAATCTTGTGACAAAACTCACACATGCCCACCG

TGCCCAGCACCTGAATTTGAAGGGGGACCGTCAGTCTTCCTCTTCCCC

CCAAAACCCAAGGACACCCTCATGATCTCCCGGACCCCTGAGGTCACA

TGCGTGGTGGTGGACGTGAGCCACGAAGACCCTGAGGTCAAGTTCAAC

TGGTACGTGGACGGCGTGGAGGTGCATAATGCCAAGACAAAGCCGCGG

GAGGAGCAGTACAATAGCACGTACCGTGTGGTCAGCGTCCTCACCGTC

CTGCACCAGGACTGGCTGAATGGCAAGGAGTACAAGTGCAAGGTCTCC

AACAAAGCCCTCCCAGCCTCAATCGAGAAAACCATCTCCAAAGCCAAA

GGGCAGCCCCGAGAACCACAGGTGTACACCCTGCCCCCATCCCGGGAG

GAGATGACCAAGAACCAGGTCAGCCTGACCTGCCTGGTCAAAGGCTTC

TATCCCAGCGACATCGCCGTGGAGTGGGAGAGCAATGGGCAGCCGGAG

AACAACTACAAGACCACGCCTCCCGTGCTGGACTCCGACGGCTCCTTC

TTCCTCTACAGCAAGCTCACCGTGGACAAGAGCAGGTGGCAGCAGGGG

AACGTCTTCTCATGCTCCGTGATGCATGAGGCTCTGCACAACCACTAC

ACGCAGAAGAGCCTCTCCCTGTCTCCGGGTAAATGA
```

Amino Acid Sequence
[spacer SEQ ID NO: 178]
[pLW225_without spacer SEQ ID NO: 193]
(SEQ ID NO: 122)

```
QGQSGS[GYLWGCEWNCGGITT][GSSGGSGGSGG][LSGRSDNH][G

GGS]QTVVTQEPSFSVSPGGTVTLTCRSSTGAVTTSNYANWVQQTPGQ

APRGLIGGTNKRAPGVPDRFSGSILGNKAALTITGAQADDESDYYCAL

WYSNLWVFGGGTKLTVL[GGGGSGGGGSGGGGS]EVQLVESGGGLVQP

GGSLKLSCAASGFTFSTYAMNWVRQASGKGLEWVGRIRSKYNNYATYY

ADSVKDRFTISRDDSKNTAYLQMNSLKTEDTAVYYCTRHGNFGNSYVS

WFAYWGQGTLVTVSS[GGGGS]QVQLKQSGPGLVQPSQSLSITCTVSG

FSLTNYGVHWVRQSPGKGLEWLGVIWSGGNTDYNTPFTSRLSINKDNS

KSQVFFKMNSLQSQDTAIYYCARALTYYDYEFAYWGQGTLVTVSAAST

KGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVE

PKSCDKTHTCPPCPAPEFEGGPSVFLFPPKPKDTLMISRTPEVTCVVV

DVSHEDPEVKFNWYVDGVEVHNAKTKPREEQYNSTYRVVSVLTVLHQD

WLNGKEYKCKVSNKALPASIEKTISKAKGQPREPQVYTLPPSREEMTK
```

-continued

NQVSLTCLVKGFYPSDIAVEWESNGQPENNYKTTPPVLDSDGSFFLYS

KLTVDKSRWQQGNVFSCSVMHEALHNHYTQKSLSLSPGK

OPP022: LC 3954-0001-C225v5
Sequences provided above

CI090: 3954-0001-C225v5Fcmt4-h20GG-0001-
v16sc-H-N
pLW233: HC h20GG-0001-v16sc-C225v5Fcmt4 (H-N)
Nucleotide Sequence
[spacer SEQ ID NO: 191]
[pLW233_without spacer SEQ ID NO: 194]

(SEQ ID NO: 123)
CAAGGCCAGTCTGGATCCGGTTATCTGTGGGGTTGCGAGTGGAATTGC

GGAGGGATCACTACAGGCTCGAGCGGTGGCAGCGGTGGCTCTGGTGGT

CTGAGCGGCCGTTCCGATAATCATGGCGGCGGTTCTCAAACTGTAGTA

ACTCAAGAACCAAGCTTCTCCGTCTCCCTGGGGAACAGTCACACTT

ACCTGCCGAAGTAGTACAGGTGCTGTTACGACCAGTAACTATGCCAAT

TGGGTACAACAAACGCCTGGTCAGGCTCCGCGCGGATTGATAGGAGGC

ACGAATAAACGGGCACCCGGTGTCCCGGACAGATTCAGCGGAAGCATA

CTCGGTAATAAGGCAGCTCTTACTATCACTGGGGCCCAAGCTGATGAT

GAAAGTGATTATTATTGTGCGCTCTGGTACAGCAACCTCTGGGTGTTT

GGGGGTGGCACGAAACTTACTGTCTTGGGCGGCGGCGGATCAGGGGGA

GGTGGCTCTGGAGGAGGAGGCTCAGAAGTCCAACTGGTCGAATCCGGG

GGAGGGCTCGTACAGCCGGGTGGGTCCCTCAAACTCTCTTGTGCGGCC

TCAGGGTTTACCTTCAGTACATACGCGATGAATTGGGTCCGGCAGGCC

AGTGGGAAAGGGCTCGAATGGGTAGGACGAATCCGATCAAAATACAAC

AACTACGCTACTTATTACGCTGATTCCGTGAAGGACAGATTCACAATA

TCCCGCGACGATAGCAAGAATACGGCATATCTTCAGATGAATTCTCTT

AAAACTGAGGATACCGCTGTGTATTACTGCACAAGACATGGTAATTTT

GGAAACTCATATGTCTCTTGGTTCGCTTATTGGGACAGGGCACGTTG

GTTACCGTGTCTAGCGGAGGTGGTGGATCCCAGGTGCAGCTGAAACAG

AGCGGCCCGGGCCTGGTGCAGCCGAGCCAGAGCCTGAGCATTACCTGC

ACCGTGAGCGGCTTTAGCCTGACCAACTATGGCGTGCATTGGGTGCGC

CAGAGCCCGGGCAAAGGCCTGGAATGGCTGGGCGTGATTTGGAGCGGC

GGCAACACCGATTATAACACCCCGTTTACCAGCCGCCTGAGCATTAAC

AAAGATAACAGCAAAGCCAGGTGTTTTTAAAATGAACAGCCTGCAA

AGCCAGGATACCGCGATTTATTATTGCGCGCGCGCGCTGACCTATTAT

GATTATGAATTTGCGTATTGGGGCCAGGGCACCCTGGTGACCGTGAGC

GCGGCTAGCACCAAGGGCCCATCGGTCTTCCCCCTGGCACCCTCCTCC

AAGAGCACCTCTGGGGGCACAGCGGCCCTGGGCTGCCTGGTCAAGGAC

TACTTCCCCGAACCGGTGACGGTGTCGTGGAACTCAGGCGCCCTGACC

AGCGGCGTGCACACCTTCCCGGCTGTCCTACAGTCCTCAGGACTCTAC

TCCCTCAGCAGCGTGGTGACCGTGCCCTCCAGCAGCTTGGGCACCCAG

ACCTACATCTGCAACGTGAATCACAAGCCCAGCAACACCAAGGTGGAC

AAGAAAGTTGAGCCCAAATCTTGTGACAAAACTCACACATGCCCACCG

TGCCCAGCACCTGAATTTGAAGGGGGACCGTCAGTCTTCCTCTTCCCC

CCAAAACCCAAGGACACCCTCATGATCTCCCGGACCCCTGAGGTCACA

TGCGTGGTGGTGGACGTGAGCCACGAAGACCCTGAGGTCAAGTTCAAC

TGGTACGTGGACGGCGTGGAGGTGCATAATGCCAAGACAAAGCCGCGG

GAGGAGCAGTACCAGAGCACGTACCGTGTGGTCAGCGTCCTCACCGTC

CTGCACCAGGACTGGCTGAATGGCAAGGAGTACAAGTGCAAGGTCTCC

AACAAAGCCCTCCCAGCCTCAATCGAGAAAACCATCTCCAAAGCCAAA

GGGCAGCCCCGAGAACCACAGGTGTACACCCTGCCCCCATCCCGGGAG

GAGATGACCAAGAACCAGGTCAGCCTGACCTGCCTGGTCAAAGGCTTC

TATCCCAGCGACATCGCCGTGGAGTGGGAGAGCAATGGGCAGCCGGAG

AACAACTACAAGACCACGCCTCCCGTGCTGGACTCCGACGGCTCCTTC

TTCCTCTACAGCAAGCTCACCGTGGACAAGAGCAGGTGGCAGCAGGGG

AACGTCTTCTCATGCTCCGTGATGCATGAGGCTCTGCACAACCACTAC

ACGCAGAAGAGCCTCTCCCTGTCTCCGGGTAAATGA

Amino Acid Sequence
[spacer SEQ ID NO: 178]
[pLW233_without spacer SEQ ID NO: 195]

(SEQ ID NO: 124)
QGQSGS[GYLWGCEWNCGGITT][GSSGGSGGSGG][LSGRSDNH][G

GGS]QTVVTQEPSFSVSPGGTVTLTCRSSTGAVTTSNYANWVQQTPGQ

APRGLIGGTNKRAPGVPDRFSGSILGNKAALTITGAQADDESDYYCAL

WYSNLWVFGGGTKLTVL[GGGGSGGGGSGGGGS]EVQLVESGGGLVQP

GGSLKLSCAASGFTFSTYAMNWVRQASGKGLEWVGRIRSKYNNYATYY

ADSVKDRFTISRDDSKNTAYLQMNSLKTEDTAVYYCTRHGNFGNSYVS

WFAYWGQGTLVTVSS[GGGGS]QVQLKQSGPGLVQPSQSLSITCTVSG

FSLTNYGVHWVRQSPGKGLEWLGVIWSGGNTDYNTPFTSRLSINKDNS

KSQVFFKMNSLQSQDTAIYYCARALTYYDYEFAYWGQGTLVTVSAAST

KGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVE

PKSCDKTHTCPPCPAPEFEGGPSVFLFPPKPKDTLMISRTPEVTCVVV

DVSHEDPEVKFNWYVDGVEVHNAKTKPREEQYQSTYRVVSVLTVLHQD

WLNGKEYKCKVSNKALPASIEKTISKAKGQPREPQVYTLPPSREEMTK

NQVSLTCLVKGFYPSDIAVEWESNGQPENNYKTTPPVLDSDGSFFLYS

KLTVDKSRWQQGNVFSCSVMHEALHNHYTQKSLSLSPGK

OPP022: LC 3954-0001-C225v5
Sequences provided above

Activated CI090: Activated-3954-0001-
C225v5Fcmt4-h20GG--0001-v16sc-H-N
Activated pLW233: HC C225v5Fcmt4-h20GG-0001-
v16sc (H-N)
Nucleic Acid Sequence (SEQ ID NO: 164
TCCGATAATCATGGCGGCGGTTCTCAAACTGTAGTAACTCAAGAACCA

AGCTTCTCCGTCTCCCTGGGGAACAGTCACACTTACCTGCCGAAGT

AGTACAGGTGCTGTTACGACCAGTAACTATGCCAATTGGGTACAACAA

ACGCCTGGTCAGGCTCCGCGCGGATTGATAGGAGGCACGAATAAACGG

```
GCACCCGGTGTCCCGGACAGATTCAGCGGAAGCATACTCGGTAATAAG
GCAGCTCTTACTATCACTGGGGCCCAAGCTGATGATGAAAGTGATTAT
TATTGTGCGCTCTGGTACAGCAACCTCTGGGTGTTTGGGGGTGGCACG
AAACTTACTGTCTTGGGCGGCGGCGGATCAGGGGGAGGTGGCTCTGGA
GGAGGAGGCTCAGAAGTCCAACTGGTCGAATCCGGGGGAGGGCTCGTA
CAGCCGGGTGGGTCCCTCAAACTCTCTTGTGCGGCCTCAGGGTTTACC
TTCAGTACATACGCGATGAATTGGGTCCGGCAGGCCAGTGGGAAGGG
CTCGAATGGGTAGGACGAATCCGATCAAAATACAACAACTACGCTACT
TATTACGCTGATTCCGTGAAGGACAGATTCACAATATCCCGCGACGAT
AGCAAGAATACGGCATATCTTCAGATGAATTCTCTTAAAACTGAGGAT
ACCGCTGTGTATTACTGCACAAGACATGGTAATTTTGGAAACTCATAT
GTCTCTTGGTTCGCTTATTGGGGACAGGGCACGTTGGTTACCGTGTCT
AGCGGAGGTGGTGGATCCCAGGTGCAGCTGAAACAGAGCGGCCCGGGC
CTGGTGCAGCCGAGCCAGAGCCTGAGCATTACCTGCACCGTGAGCGGC
TTTAGCCTGACCAACTATGGCGTGCATTGGGTGCGCCAGAGCCCGGGC
AAAGGCCTGGAATGGCTGGGCGTGATTTGGAGCGGCGGCAACACCGAT
TATAACACCCCGTTTACCAGCCGCCTGAGCATTAACAAAGATAACAGC
AAAAGCCAGGTGTTTTTTAAAATGAACAGCCTGCAAAGCCAGGATACC
GCGATTTATTATTGCGCGCGCGCGCTGACCTATTATGATTATGAATTT
GCGTATTGGGGCCAGGGCACCCTGGTGACCGTGAGCGCGGCTAGCACC
AAGGGCCCATCGGTCTTCCCCCTGGCACCCTCCTCCAAGAGCACCTCT
GGGGGCACAGCGGCCCTGGGCTGCCTGGTCAAGGACTACTTCCCCGAA
CCGGTGACGGTGTCGTGGAACTCAGGCGCCCTGACCAGCGGCGTGCAC
ACCTTCCCGGCTGTCCTACAGTCCTCAGGACTCTACTCCCTCAGCAGC
GTGGTGACCGTGCCCTCCAGCAGCTTGGGCACCCAGACCTACATCTGC
AACGTGAATCACAAGCCCAGCAACACCAAGGTGGACAAGAAAGTTGAG
CCCAAATCTTGTGACAAAACTCACACATGCCCACCGTGCCCAGCACCT
GAATTTGAAGGGGACCGTCAGTCTTCCTCTTCCCCCCAAAACCCAAG
GACACCCTCATGATCTCCCGGACCCCTGAGGTCACATGCGTGGTGGTG
GACGTGAGCCACGAAGACCCTGAGGTCAAGTTCAACTGGTACGTGGAC
GGCGTGGAGGTGCATAATGCCAAGACAAAGCCGCGGGAGGAGCAGTAC
CAGAGCACGTACCGTGTGGTCAGCGTCCTCACCGTCCTGCACCAGGAC
TGGCTGAATGGCAAGGAGTACAAGTGCAAGGTCTCCAACAAAGCCCTC
CCAGCCTCAATCGAGAAAACCATCTCCAAAGCCAAAGGGCAGCCCCGA
GAACCACAGGTGTACACCCTGCCCCCATCCCGGGAGGAGATGACCAAG
AACCAGGTCAGCCTGACCTGCCTGGTCAAAGGCTTCTATCCCAGCGAC
ATCGCCGTGGAGTGGGAGAGCAATGGGCAGCCGGAGAACAACTACAAG
ACCACGCCTCCCGTGCTGGACTCCGACGGCTCCTTCTTCCTCTACAGC
AAGCTCACCGTGGACAAGAGCAGGTGGCAGCAGGGGAACGTCTTCTCA
TGCTCCGTGATGCATGAGGCTCTGCACAACCACTACACGCAGAAGAGC
CTCTCCCTGTCTCCGGGTAAA
```

Amino Acid Sequence
(SEQ ID NO: 165)
[SDNH]GGGSQTVVTQEPSFSVSPGGTVTLTCRSSTGAVTTSNYANWV
QQTPGQAPRGLIGGTNKRAPGVPDRFSGSILGNKAALTITGAQADDES
DYYCALWYSNLWVFGGGTKLTVLGGGSGGGGSGGGGSEVQLVESGGG
LVQPGGSLKLSCAASGFTFSTYAMNWVRQASGKGLEWVGRIRSKYNNY
ATYYADSVKDRFTISRDDSKNTAYLQMNSLKTEDTAVYYCTRHGNFGN
SYVSWFAYWGQGTLVTVSSGGGGSQVQLKQSGPGLVQPSQSLSITCTV
SGESLTNYGVHWVRQSPGKGLEWLGVIWSGGNTDYNTPFTSRLSINKD
NSKSQVFFKMNSLQSQDTAIYYCARALTYYDYEFAYWGQGTLVTVSAA
STKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKK
VEPKSCDKTHTCPPCPAPEFEGGPSVFLEPPKPKDTLMISRTPEVTCV
VVDVSHEDPEVKFNWYVDGVEVHNAKTKPREEQYQSTYRVVSVLTVLH
QDWLNGKEYKCKVSNKALPASIEKTISKAKGQPREPQVYTLPPSREEM
TKNQVSLTCLVKGFYPSDIAVEWESNGQPENNYKTTPPVLDSDGSFFL
YSKLTVDKSRWQQGNVFSCSVMHEALHNHYTQKSLSLSPGK Activated OPP022: 3954-0001-C225v5
Nucleic Acid Sequence
(SEQ ID NO: 166)
TCCGATAATCATGGCAGTAGCGGTACCCAGATCTTGCTGACCCAGAGC
CCGGTGATTCTGAGCGTGAGCCCGGGCGAACGTGTGAGCTTTAGCTGC
CGCGCGAGCCAGAGCATTGGCACCAACATTCATTGGTATCAGCAGCGC
ACCAACGGCAGCCCGCGCCTGCTGATTAAATATGCGAGCGAAAGCATT
AGCGGCATTCCGAGCCGCTTTAGCGGCAGCGGCAGCGGCACCGATTTT
ACCCTGAGCATTAACAGCGTGGAAAGCGAAGATATTGCGGATTATTAT
TGCCAGCAGAACAACAACTGGCCGACCACCTTTGGCGCGGGCACCAAA
CTGGAACTGAAACGTACGGTGGCTGCACCATCTGTCTTCATCTTCCCG
CCATCTGATGAGCAGTTGAAATCTGGAACTGCCTCTGTTGTGTGCCTG
CTGAATAACTTCTATCCCAGAGAGGCCAAAGTACAGTGGAAGGTGGAT
AACGCCCTCCAATCGGGTAACTCCCAGGAGAGTGTCACAGAGCAGGAC
AGCAAGGACAGCACCTACAGCCTCAGCAGCACCCTGACGCTGAGCAAA
GCAGACTACGAGAAACACAAAGTCTACGCCTGCGAAGTCACCCATCAG
GGCCTGAGCTCGCCCGTCACAAAGAGCTTCAACAGGGGAGAGTGT Amino Acid Sequence
(SEQ ID NO: 167)
[SDNH]GSSGTQILLTQSPVILSVSPGERVSFSCRASQSIGTNIHWYQ
QRTNGSPRLLIKYASESISGIPSRFSGSGSGTDFTLSINSVESEDIAD
YYCQQNNNWPTTFGAGTKLELKRTVAAPSVFIFPPSDEQLKSGTASVV
CLLNNFYPREAKVQWKVDNALQSGNSQESVTEQDSKDSTYSLSSTLTL
SKADYEKHKVYACEVTHQGLSSPVTKSFNRGEC CI104: 3954-0011-C225v5Fcmt4-h20GG-0011-v16sc-H-N
pLW289 and pLW291 sequences encoding corresponding masked antibody components are provided herein as "pLW289" and "pLW291", respectively and are summarized in Table 11.
Activated CI104: 3954-0011-C225v5Fcmt4-h20GG-0011-v16sc-H-N
Activated pLW289: HC h20GG-0011-v16sc-C225v5Fcmt4 (H-N)
Nucleotide Sequence (SEQ ID NO: 125)

TCCGATGATCATGGCGGCGGTTCTCAAACTGTAGTAACTCAAGAACCA

AGCTTCTCCGTCTCCCCTGGGGGAACAGTCACACTTACCTGCCGAAGT

AGTACAGGTGCTGTTACGACCAGTAACTATGCCAATTGGGTACAACAA

ACGCCTGGTCAGGCTCCGCGCGGATTGATAGGAGGCACGAATAAACGG

GCACCCGGTGTCCCGGACAGATTCAGCGGAAGCATACTCGGTAATAAG

GCAGCTCTTACTATCACTGGGGCCCAAGCTGATGATGAAAGTGATTAT

TATTGTGCGCTCTGGTACAGCAACCTCTGGGTGTTTGGGGGTGGCACG

AAACTTACTGTCTTGGGCGGCGGCGGATCAGGGGGAGGTGGCTCTGGA

GGAGGAGGCTCAGAAGTCCAACTGGTCGAATCCGGGGGAGGGCTCGTA

CAGCCGGGTGGGTCCCTCAAACTCTCTTGTGCGGCCTCAGGGTTTACC

TTCAGTACATACGCGATGAATTGGGTCCGGCAGGCCAGTGGGAAAGGG

CTCGAATGGGTAGGACGAATCCGATCAAAATACAACAACTACGCTACT

TATTACGCTGATTCCGTGAAGGACAGATTCACAATATCCCGCGACGAT

AGCAAGAATACGGCATATCTTCAGATGAATTCTCTTAAAACTGAGGAT

ACCGCTGTGTATTACTGCACAAGACATGGTAATTTTGGAAACTCATAT

GTCTCTTGGTTCGCTTATTGGGGACAGGGCACGTTGGTTACCGTGTCT

AGCGGAGGTGGTGGATCCCAGGTGCAGCTGAAACAGAGCGGCCCGGGC

CTGGTGCAGCCGAGCCAGAGCCTGAGCATTACCTGCACCGTGAGCGGC

TTTAGCCTGACCAACTATGGCGTGCATTGGGTGCGCCAGAGCCCGGGC

AAAGGCCTGGAATGGCTGGGCGTGATTTGGAGCGGCGGCAACACCGAT

TATAACACCCCGTTTACCAGCCGCCTGAGCATTAACAAAGATAACAGC

AAAAGCCAGGTGTTTTTTAAAATGAACAGCCTGCAAAGCCAGGATACC

GCGATTTATTATTGCGCGCGCGCGCTGACCTATTATGATTATGAATTT

GCGTATTGGGGCCAGGGCACCCTGGTGACCGTGAGCGCGGCTAGCACC

AAGGGCCCATCGGTCTTCCCCCTGGCACCCTCCTCCAAGAGCACCTCT

GGGGGCACAGCGGCCCTGGGCTGCCTGGTCAAGGACTACTTCCCCGAA

CCGGTGACGGTGTCGTGGAACTCAGGCGCCCTGACCAGCGGCGTGCAC

ACCTTCCCGGCTGTCCTACAGTCCTCAGGACTCTACTCCCTCAGCAGC

GTGGTGACCGTGCCCTCCAGCAGCTTGGGCACCCAGACCTACATCTGC

AACGTGAATCACAAGCCCAGCAACACCAAGGTGGACAAGAAAGTTGAG

CCCAAATCTTGTGACAAAACTCACACATGCCCACCGTGCCCAGCACCT

GAATTTGAAGGGGGACCGTCAGTCTTCCTCTTCCCCCCAAAACCCAAG

GACACCCTCATGATCTCCCGGACCCCTGAGGTCACATGCGTGGTGGTG

GACGTGAGCCACGAAGACCCTGAGGTCAAGTTCAACTGGTACGTGGAC

-continued

GGCGTGGAGGTGCATAATGCCAAGACAAAGCCGCGGGAGGAGCAGTAC

CAGAGCACGTACCGTGTGGTCAGCGTCCTCACCGTCCTGCACCAGGAC

TGGCTGAATGGCAAGGAGTACAAGTGCAAGGTCTCCAACAAAGCCCTC

CCAGCCTCAATCGAGAAAACCATCTCCAAAGCCAAAGGGCAGCCCCGA

GAACCACAGGTGTACACCCTGCCCCCATCCCGGGAGGAGATGACCAAG

AACCAGGTCAGCCTGACCTGCCTGGTCAAAGGCTTCTATCCCAGCGAC

ATCGCCGTGGAGTGGGAGAGCAATGGGCAGCCGGAGAACAACTACAAG

ACCACGCCTCCCGTGCTGGACTCCGACGGCTCCTTCTTCCTCTACAGC

AAGCTCACCGTGGACAAGAGCAGGTGGCAGCAGGGGAACGTCTTCTCA

TGCTCCGTGATGCATGAGGCTCTGCACAACCACTACACGCAGAAGAGC

CTCTCCCTGTCTCCGGGTAAA

Amino Acid Sequence (SEQ ID NO: 126)

[SDDH][GGGS]QTVVTQEPSFSVSPGGTVTLTCRSSTGAVTTSNYAN

WVQQTPGQAPRGLIGGTNKRAPGVPDRFSGSILGNKAALTITGAQADD

ESDYYCALWYSNLWVFGGGTKLTVL][GGGGSGGGGSGGGGS]EVQLV

ESGGGLVQPGGSLKLSCAASGFTFSTYAMNWVRQASGKGLEWVGRIRS

KYNNYATYYADSVKDRFTISRDDSKNTAYLQMNSLKTEDTAVYYCTRH

GNFGNSYVSWFAYWGQGTLVTVSS[GGGGS]QVQLKQSGPGLVQPSQS

LSITCTVSGFSLTNYGVHWVRQSPGKGLEWLGVIWSGGNTDYNTPFTS

RLSINKDNSKSQVFFKMNSLQSQDTAIYYCARALTYYDYEFAYWGQGT

LVTVSAASTKGPSVFPLAPSSKSTSGGTAALGCLVKDYFPEPVTVSWN

SGALTSGVHTFPAVLQSSGLYSLSSVVTVPSSSLGTQTYICNVNHKPS

NTKVDKKVEPKSCDKTHTCPPCPAPEFEGGPSVFLFPPKPKDTLMISR

TPEVTCVVVDVSHEDPEVKFNWYVDGVEVHNAKTKPREEQYQSTYRVV

SVLTVLHQDWLNGKEYKCKVSNKALPASIEKTISKAKGQPREPQVYTL

PPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

Activated pLW291: LC 3954-0011-C225v5
Nucleotide Sequence (SEQ ID NO: 127)

TCCGATGATCATGGCAGTAGCGGTACCCAGATCTTGCTGACCCAGAGC

CCGGTGATTCTGAGCGTGAGCCCGGGCGAACGTGTGAGCTTTAGCTGC

CGCGCGAGCCAGAGCATTGGCACCAACATTCATTGGTATCAGCAGCGC

ACCAACGGCAGCCCGCGCCTGCTGATTAAATATGCGAGCGAAAGCATT

AGCGGCATTCCGAGCCGCTTTAGCGGCAGCGGCAGCGGCACCGATTTT

ACCCTGAGCATTAACAGCGTGGAAAGCGAAGATATTGCGGATTATTAT

TGCCAGCAGAACAACAACTGGCCGACCACCTTTGGCGCGGGCACCAAA

CTGGAACTGAAACGTACGGTGGCTGCACCATCTGTCTTCATCTTCCCG

CCATCTGATGAGCAGTTGAAATCTGGAACTGCCTCTGTTGTGTGCCTG

CTGAATAACTTCTATCCCAGAGAGGCCAAAGTACAGTGGAAGGTGGAT

AACGCCCTCCAATCGGGTAACTCCCAGGAGAGTGTCACAGAGCAGGAC

AGCAAGGACAGCACCTACAGCCTCAGCAGCACCCTGACGCTGAGCAAA

```
GCAGACTACGAGAAACACAAAGTCTACGCCTGCGAAGTCACCCATCAG

GGCCTGAGCTCGCCCGTCACAAAGAGCTTCAACAGGGGAGAGTGT
```

Amino Acid Sequence
(SEQ ID NO: 128)
[SDDH][GSSGT]QILLTQSPVILSVSPGERVSFSCRASQSIGTNIHW

YQQRTNGSPRLLIKYASESISGIPSRFSGSGSGTDFTLSINSVESEDI

ADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTL

TLSKADYEKHKVYACEVTHQGLSSPVTKSFNRGEC

CI106: CF41-2008-C225v5Fcmt4-h20GG-0011-v16sc-H-N
pLW289: HC h20GG-0011-v16sc-C225v5Fcmt4 (H-N)
Nucleotide Sequence
[spacer SEQ ID NO: 191]
[pLW289 without spacer SEQ ID NO: 196]
(SEQ ID NO: 129)
```
CAAGGCCAGTCTGGATCCGGTTATCTGTGGGGTTGCGAGTGGAATTGC

GGAGGGATCACTACAGGCTCGAGCGGTGGCAGCGGTGGCTCTGGTGGT

CTGAGCGGCCGTTCCGATGATCATGGCGGCGGTTCTCAAACTGTAGTA

ACTCAAGAACCAAGCTTCTCCGTCTCCCTGGGGAACAGTCACACTT

ACCTGCCGAAGTAGTACAGGTGCTGTTACGACCAGTAACTATGCCAAT

TGGGTACAACAAACGCCTGGTCAGGCTCCGCGCGGATTGATAGGAGGC

ACGAATAAACGGGCACCCGGTGTCCCGGACAGATTCAGCGGAAGCATA

CTCGGTAATAAGGCAGCTCTTACTATCACTGGGGCCCAAGCTGATGAT

GAAAGTGATTATTATTGTGCGCTCTGGTACAGCAACCTCTGGGTGTTT

GGGGGTGGCACGAAACTTACTGTCTTGGGCGGCGGCGGATCAGGGGGA

GGTGGCTCTGGAGGAGGAGGCTCAGAAGTCCAACTGGTCGAATCCGGG

GGAGGGCTCGTACAGCCGGTGGGTCCCTCAAACTCTCTTGTGCGGCC

TCAGGGTTTACCTTCAGTACATACGCGATGAATTGGGTCCGGCAGGCC

AGTGGGAAAGGGCTCGAATGGGTAGGACGAATCCGATCAAAATACAAC

AACTACGCTACTTATTACGCTGATTCCGTGAAGGACAGATTCACAATA

TCCCGCGACGATAGCAAGAATACGGCATATCTTCAGATGAATTCTCTT

AAAACTGAGGATACCGCTGTGTATTACTGCACAAGACATGGTAATTTT

GGAAACTCATATGTCTCTTGGTTCGCTTATTGGGACAGGGCACGTTG

GTTACCGTGTCTAGCGGAGGTGGTGGATCCCAGGTGCAGCTGAAACAG

AGCGGCCCGGGCCTGGTGCAGCCGAGCCAGAGCCTGAGCATTACCTGC

ACCGTGAGCGGCTTTAGCCTGACCAACTATGGCGTGCATTGGGTGCGC

CAGAGCCCGGGCAAAGGCCTGGAATGGCTGGGCGTGATTTGGAGCGGC

GGCAACACCGATTATAACACCCCGTTTACCAGCCGCCTGAGCATTAAC

AAAGATAACAGCAAAGCCAGGTGTTTTTAAAATGAACAGCCTGCAA

AGCCAGGATACCGCGATTTATTATTGCGCGCGCGCTGACCTATTAT

GATTATGAATTTGCGTATTGGGGCCAGGGCACCCTGGTGACCGTGAGC

GCGGCTAGCACCAAGGGCCCATCGGTCTTCCCCCTGGCACCCTCCTCC

AAGAGCACCTCTGGGGGCACAGCGGCCCTGGGCTGCCTGGTCAAGGAC

TACTTCCCCGAACCGGTGACGGTGTCGTGGAACTCAGGCGCCCTGACC
```

```
AGCGGCGTGCACACCTTCCCGGCTGTCCTACAGTCCTCAGGACTCTAC

TCCCTCAGCAGCGTGGTGACCGTGCCCTCCAGCAGCTTGGGCACCCAG

ACCTACATCTGCAACGTGAATCACAAGCCCAGCAACACCAAGGTGGAC

AAGAAAGTTGAGCCCAAATCTTGTGACAAAACTCACACATGCCCACCG

TGCCCAGCACCTGAATTTGAAGGGGGACCGTCAGTCTTCCTCTTCCCC

CCAAAACCCAAGGACACCCTCATGATCTCCCGGACCCCTGAGGTCACA

TGCGTGGTGGTGGACGTGAGCCACGAAGACCCTGAGGTCAAGTTCAAC

TGGTACGTGGACGGCGTGGAGGTGCATAATGCCAAGACAAAGCCGCGG

GAGGAGCAGTACCAGAGCACGTACCGTGTGGTCAGCGTCCTCACCGTC

CTGCACCAGGACTGGCTGAATGGCAAGGAGTACAAGTGCAAGGTCTCC

AACAAAGCCCTCCCAGCCTCAATCGAGAAAACCATCTCCAAAGCCAAA

GGGCAGCCCCGAGAACCACAGGTGTACACCCTGCCCCCATCCCGGGAG

GAGATGACCAAGAACCAGGTCAGCCTGACCTGCCTGGTCAAAGGCTTC

TATCCCAGCGACATCGCCGTGGAGTGGGAGAGCAATGGGCAGCCGGAG

AACAACTACAAGACCACGCCTCCCGTGCTGGACTCCGACGGCTCCTTC

TTCCTCTACAGCAAGCTCACCGTGGACAAGAGCAGGTGGCAGCAGGGG

AACGTCTTCTCATGCTCCGTGATGCATGAGGCTCTGCACAACCACTAC

ACGCAGAAGAGCCTCTCCCTGTCTCCGGGTAAA
```

Amino Acid Sequence
[spacer SEQ ID NO: 178]
[pLW289 without spacer SEQ ID NO: 197]
(SEQ ID NO: 130)
QGQSGS[GYLWGCEWNCGGITT][GSSGGSGGSGG][LSGRSDDH][G

GGS]QTVVTQEPSFSVSPGGTVTLTCRSSTGAVTTSNYANWVQQTPGQ

APRGLIGGTNKRAPGVPDRFSGSILGNKAALTITGAQADDESDYYCAL

WYSNLWVFGGGTKLTVL[GGGGSGGGGSGGGGS]EVQLVESGGGLVQP

GGSLKLSCAASGFTFSTYAMNWVRQASGKGLEWVGRIRSKYNNYATYY

ADSVKDRFTISRDDSKNTAYLQMNSLKTEDTAVYYCTRHGNFGNSYVS

WFAYWGQGTLVTVSS[GGGGS]QVQLKQSGPGLVQPSQSLSITCTVSG

FSLTNYGVHWVRQSPGKGLEWLGVIWSGGNTDYNTPFTSRLSINKDNS

KSQVFFKMNSLQSQDTAIYYCARALTYYDYEFAYWGQGTLVTVSAAST

KGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVE

PKSCDKTHTCPPCPAPEFEGGPSVFLFPPKPKDTLMISRTPEVTCVVV

DVSHEDPEVKFNWYVDGVEVHNAKTKPREEQYQSTYRVVSVLTVLHQD

WLNGKEYKCKVSNKALPASIEKTISKAKGQPREPQVYTLPPSREEMTK

NQVSLTCLVKGFYPSDIAVEWESNGQPENNYKTTPPVLDSDGSFFLYS

KLTVDKSRWQQGNVFSCSVMHEALHNHYTQKSLSLSPGK pLW246: LC CF41-2008-C225v5
Nucleotide Sequence
[spacer SEQ ID NO: 176]
[pLW246 without spacer SEQ ID NO: 198]
(SEQ ID NO: 131)
```
CAAGGCCAGTCTGGCCAAGGTCTTAGTTGTGAAGGTTGGGCGATGAAT

AGAGAACAATGTCGAGCCGGAGGTGGCTCGAGCGGCGGCTCTATCTCT
```

-continued
TCCGGACTGCTGTCCGGCAGATCCGACCAGCACGGCGGAGGATCCCAA

ATCCTGCTGACACAGTCTCCTGTCATACTGAGTGTCTCCCCCGGCGAG

AGAGTCTCTTTCTCATGTCGGGCCAGTCAGTCTATTGGGACTAACATA

CACTGGTACCAGCAACGCACCAACGGAAGCCCGCGCCTGCTGATTAAA

TATGCGAGCGAAAGCATTAGCGGCATTCCGAGCCGCTTTAGCGGCAGC

GGCAGCGGCACCGATTTTACCCTGAGCATTAACAGCGTGGAAAGCGAA

GATATTGCGGATTATTATTGCCAGCAGAACAACAACTGGCCGACCACC

TTTGGCGCGGGCACCAAACTGGAACTGAAACGTACGGTGGCTGCACCA

TCTGTCTTCATCTTCCCGCCATCTGATGAGCAGTTGAAATCTGGAACT

GCCTCTGTTGTGTGCCTGCTGAATAACTTCTATCCCAGAGAGGCCAAA

GTACAGTGGAAGGTGGATAACGCCCTCCAATCGGGTAACTCCCAGGAG

AGTGTCACAGAGCAGGACAGCAAGGACAGCACCTACAGCCTCAGCAGC

ACCCTGACGCTGAGCAAAGCAGACTACGAGAAACACAAAGTCTACGCC

TGCGAAGTCACCCATCAGGGCCTGAGCTCGCCCGTCACAAAGAGCTTC

AACAGGGGAGAGTGT

Amino Acid Sequence
[spacer SEQ ID NO: 178]
[pLW246 without spacer SEQ ID NO: 199]
(SEQ ID NO: 132)
QGQSGQG[LSCEGWAMNREQCRA][GGGSSGGS][ISSGLLSGRSDQ

H][GGGS]QILLTQSPVILSVSPGERVSFSCRASQSIGTNIHWYQQRT

NGSPRLLIKYASESISGIPSRFSGSGSGTDFTLSINSVESEDIADYYC

QQNNNWPTTFGAGTKLELKRTVAAPSVFIFPPSDEQLKSGTASVVCLL

NNFYPREAKVQWKVDNALQSGNSQESVTEQDSKDSTYSLSSTLTLSKA

DYEKHKVYACEVTHQGLSSPVTKSFNRGEC

CI107: 3954-0011-C225v5Fcmt4-h20GG-2006-
v16sc-H-N
pLW307: HC h20GG-2006-v16sc-C225v5Fcmt4 (H-N)
Nucleotide Sequence
[spacer SEQ ID NO: 191]
[pLW307 without spacer SEQ ID NO: 200]
(SEQ ID NO: 133)
CAAGGCCAGTCTGGATCCGGTTATCTGTGGGGTTGCGAGTGGAATTGC

GGAGGGATCACTACAGGCTCGAGCGGTGGCAGCGGTGGCTCTGGTGGT

ATATCGAGTGGATTGCTGTCTGGCAGATCTGACGATCACGGCGGCGGT

TCTCAAACTGTAGTAACTCAAGAACCAAGCTTCTCCGTCTCCCCTGGG

GGAACAGTCACACTTACCTGCCGAAGTAGTACAGGTGCTGTTACGACC

AGTAACTATGCCAATTGGGTACAACAAACGCCTGGTCAGGCTCCGCGC

GGATTGATAGGAGGCACGAATAAACGGGCACCCGGTGTCCCGGACAGA

TTCAGCGGAAGCATACTCGGTAATAAGGCAGCTCTTACTATCACTGGG

GCCCAAGCTGATGATGAAAGTGATTATTATTGTGCGCTCTGGTACAGC

AACCTCTGGGTGTTTGGGGGTGGCACGAAACTTACTGTCTTGGGCGGC

GGCGGATCAGGGGGAGGTGGCTCTGGAGGAGGAGGCTCAGAAGTCCAA

CTGGTCGAATCCGGGGGAGGGCTCGTACAGCCGGGTGGGTCCCTCAAA

CTCTCTTGTGCGGCCTCAGGGTTTACCTTCAGTACATACGCGATGAAT

TGGGTCCGGCAGGCCAGTGGGAAAGGGCTCGAATGGGTAGGACGAATC

-continued
CGATCAAAATACAACAACTACGCTACTTATTACGCTGATTCCGTGAAG

GACAGATTCACAATATCCCGCGACGATAGCAAGAATACGGCATATCTT

CAGATGAATTCTCTTAAAACTGAGGATACCGCTGTGTATTACTGCACA

AGACATGGTAATTTTGGAAACTCATATGTCTCTTGGTTCGCTTATTGG

GGACAGGGCACGTTGGTTACCGTGTCTAGCGGAGGTGGTGGATCCCAG

GTGCAGCTGAAACAGAGCGGCCCGGGCCTGGTGCAGCCGAGCCAGAGC

CTGAGCATTACCTGCACCGTGAGCGGCTTTAGCCTGACCAACTATGGC

GTGCATTGGGTGCGCCAGAGCCCGGGCAAAGGCCTGGAATGGCTGGGC

GTGATTTGGAGCGGCGGCAACACCGATTATAACACCCCGTTTACCAGC

CGCCTGAGCATTAACAAAGATAACAGCAAAAGCCAGGTGTTTTTTAAA

ATGAACAGCCTGCAAAGCCAGGATACCGCGATTTATTATTGCGCGCGC

GCGCTGACCTATTATGATTATGAATTTGCGTATTGGGGCCAGGGCACC

CTGGTGACCGTGAGCGCGGCTAGCACCAAGGGCCCATCGGTCTTCCCC

CTGGCACCCTCCTCCAAGAGCACCTCTGGGGGCACAGCGGCCCTGGGC

TGCCTGGTCAAGGACTACTTCCCCGAACCGGTGACGGTGTCGTGGAAC

TCAGGCGCCCTGACCAGCGGCGTGCACACCTTCCCGGCTGTCCTACAG

TCCTCAGGACTCTACTCCCTCAGCAGCGTGGTGACCGTGCCCTCCAGC

AGCTTGGGCACCCAGACCTACATCTGCAACGTGAATCACAAGCCCAGC

AACACCAAGGTGGACAAGAAAGTTGAGCCCAAATCTTGTGACAAAACT

CACACATGCCCACCGTGCCCAGCACCTGAATTTGAAGGGGGACCGTCA

GTCTTCCTCTTCCCCCCAAAACCCAAGGACACCCTCATGATCTCCCGG

ACCCCTGAGGTCACATGCGTGGTGGTGGACGTGAGCCACGAAGACCCT

GAGGTCAAGTTCAACTGGTACGTGGACGGCGTGGAGGTGCATAATGCC

AAGACAAAGCCGCGGGAGGAGCAGTACCAGAGCACGTACCGTGTGGTC

AGCGTCCTCACCGTCCTGCACCAGGACTGGCTGAATGGCAAGGAGTAC

AAGTGCAAGGTCTCCAACAAAGCCCTCCCAGCCTCAATCGAGAAAACC

ATCTCCAAAGCCAAAGGGCAGCCCCGAGAACCACAGGTGTACACCCTG

CCCCCATCCCGGGAGGAGATGACCAAGAACCAGGTCAGCCTGACCTGC

CTGGTCAAAGGCTTCTATCCCAGCGACATCGCCGTGGAGTGGGAGAGC

AATGGGCAGCCGGAGAACAACTACAAGACCACGCCTCCCGTGCTGGAC

TCCGACGGCTCCTTCTTCCTCTACAGCAAGCTCACCGTGGACAAGAGC

AGGTGGCAGCAGGGGAACGTCTTCTCATGCTCCGTGATGCATGAGGCT

CTGCACAACCACTACACGCAGAAGAGCCTCTCCCTGTCTCCGGGTAAA

Amino Acid Sequence
[spacer SEQ ID NO: 178]
[pLW307 without spacer SEQ ID NO: 201]
(SEQ ID NO: 134)
QGQSGS[GYLWGCEWNCGGITT][GSSGGSGGSGG][ISSGLLSGRSD

DH][GGGS]QTVVTQEPSFSVSPGGTVTLTCRSSTGAVTTSNYANWVQ

QTPGQAPRGLIGGTNKRAPGVPDRFSGSILGNKAALTITGAQADDESD

YYCALWYSNLWVFGGGTKLTVL[GGGGSGGGGSGGGGS]EVQLVESGG

GLVQPGGSLKLSCAASGFTFSTYAMNWVRQASGKGLEWVGRIRSKYNN

YATYYADSVKDRFTISRDDSKNTAYLQMNSLKTEDTAVYYCTRHGNFG

NSYVSWFAYWGQGTLVTVSS[GGGGS]QVQLKQSGPGLVQPSQSLSIT

CTVSGFSLTNYGVHWVRQSPGKGLEWLGVIWSGGNTDYNTPFTSRLSI

NKDNSKSQVFFKMNSLQSQDTAIYYCARALTYYDYEFAYWGQGTLVTV

SAASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKV

DKKVEPKSCDKTHTCPPCPAPEFEGGPSVFLFPPKPKDTLMISRTPEV

TCVVVDVSHEDPEVKFNWYVDGVEVHNAKTKPREEQYQSTYRVVSVLT

VLHQDWLNGKEYKCKVSNKALPASIEKTISKAKGQPREPQVYTLPPSR

EEMTKNQVSLTCLVKGFYPSDIAVEWESNGQPENNYKTTPPVLDSDGS

FFLYSKLTVDKSRWQQGNVFSCSVMHEALHNHYTQKSLSLSPGK pLW291: LC 3954-0011-C225v5
Nucleotide Sequence
[spacer SEQ ID NO: 180]
[pLW291 without spacer SEQ ID NO: 202]
(SEQ ID NO: 135)
CAAGGCCAGTCTGGCCAGTGCATCTCACCTCGTGGTTGTCCGGACGGC

CCATACGTCATGTACGGCTCGAGCGGTGGCAGCGGTGGCTCTGGTGGA

TCCGGTCTGAGCGGCCGTTCCGATGATCATGGCAGTAGCGGTACCCAG

ATCTTGCTGACCCAGAGCCCGGTGATTCTGAGCGTGAGCCCGGGCGAA

CGTGTGAGCTTTAGCTGCCGCGCGAGCCAGAGCATTGGCACCAACATT

CATTGGTATCAGCAGCGCACCAACGGCAGCCCGCGCCTGCTGATTAAA

TATGCGAGCGAAAGCATTAGCGGCATTCCGAGCCGCTTTAGCGGCAGC

GGCAGCGGCACCGATTTTACCCTGAGCATTAACAGCGTGGAAAGCGAA

GATATTGCGGATTATTATTGCCAGCAGAACAACAACTGGCCGACCACC

TTTGGCGCGGGCACCAAACTGGAACTGAAACGTACGGTGGCTGCACCA

TCTGTCTTCATCTTCCCGCCATCTGATGAGCAGTTGAAATCTGGAACT

GCCTCTGTTGTGTGCCTGCTGAATAACTTCTATCCCAGAGAGGCCAAA

GTACAGTGGAAGGTGGATAACGCCCTCCAATCGGGTAACTCCCAGGAG

AGTGTCACAGAGCAGGACAGCAAGGACAGCACCTACAGCCTCAGCAGC

ACCCTGACGCTGAGCAAAGCAGACTACGAGAAACACAAAGTCTACGCC

TGCGAAGTCACCCATCAGGGCCTGAGCTCGCCCGTCACAAAGAGCTTC

AACAGGGGAGAGTGT

Amino Acid Sequence
[spacer SEQ ID NO: 178]
[pLW291 without spacer SEQ ID NO: 203]
(SEQ ID NO: 136)
QGQSGQ[CISPRGCPDGPYVMY][GSSGGSGGSGGSG][LSGRSDDH]

[GSSGT]QILLTQSPVILSVSPGERVSFSCRASQSIGTNIHWYQQRTN

GSPRLLIKYASESISGIPSRFSGSGSGTDFTLSINSVESEDIADYYCQ

QNNNWPTTFGAGTKLELKRTVAAPSVFIFPPSDEQLKSGTASVVCLLN

NFYPREAKVQWKVDNALQSGNSQESVTEQDSKDSTYSLSSTLTLSKAD

YEKHKVYACEVTHQGLSSPVTKSFNRGEC

CI127: SynFcmt4-h20GG-0011-v16sc-H-N
pLW334: HC h20GG-0011-v16sc-Synagis® Fcmt4 (H-N)
Nucleotide Sequence
[spacer SEQ ID NO: 191]
[pLW334 without spacer SEQ ID NO: 204]
(SEQ ID NO: 137)
CAAGGCCAGTCTGGATCCGGTTATCTGTGGGGTTGCGAGTGGAATTGC

GGAGGGATCACTACAGGCTCGAGCGGTGGCAGCGGTGGCTCTGGTGGT

CTGAGCGGCCGTTCCGATGATCATGGCGGCGGTTCTCAAACTGTAGTA

ACTCAAGAACCAAGCTTCTCCGTCTCCCCTGGGGAACAGTCACACTTT

ACCTGCCGAAGTAGTACAGGTGCTGTTACGACCAGTAACTATGCCAAT

TGGGTACAACAAACGCCTGGTCAGGCTCCGCGCGGATTGATAGGAGGC

ACGAATAAACGGGCACCCGGTGTCCCGGACAGATTCAGCGGAAGCATA

CTCGGTAATAAGGCAGCTCTTACTATCACTGGGGCCCAAGCTGATGAT

GAAAGTGATTATTATTGTGCGCTCTGGTACAGCAACCTCTGGGTGTTT

GGGGGTGGCACGAAACTTACTGTCTTGGGCGGCGGCGGATCAGGGGGA

GGTGGCTCTGGAGGAGGAGGCTCAGAAGTCCAACTGGTCGAATCCGGG

GGAGGGCTCGTACAGCCGGGTGGGTCCCTCAAACTCTCTTGTGCGGCC

TCAGGGTTTACCTTCAGTACATACGCGATGAATTGGGTCCGGCAGGCC

AGTGGGAAAGGGCTCGAATGGGTAGGACGAATCCGATCAAAATACAAC

AACTACGCTACTTATTACGCTGATTCCGTGAAGGACAGATTCACAATA

TCCCGCGACGATAGCAAGAATACGGCATATCTTCAGATGAATTCTCTT

AAAACTGAGGATACCGCTGTGTATTACTGCACAAGACATGGTAATTTT

GGAAACTCATATGTCTCTTGGTTCGCTTATTGGGGACAGGGCACGTTG

GTTACCGTGTCTAGCGGAGGTGGTGGATCCCAAGTGACCCTGAGAGAG

TCTGGCCCTGCCCTCGTGAAGCCTACCCAGACCCTGACACTGACCTGC

ACCTTCAGCGGCTTCAGCCTGAGCACCAGCGGCATGTCTGTGGGCTGG

ATCAGACAGCCTCCTGGCAAGGCCCTGGAATGGCTGGCCGACATTTGG

TGGGACGACAAGAAGGACTACAACCCCAGCCTGAAGTCCCGGCTGACC

ATCAGCAAGGACACCAGCAAGAACCAGGTGGTGCTGAAAGTGACCAAC

ATGGACCCCGCCGACACCGCCACCTACTACTGCGCCAGATCCATGATC

ACCAACTGGTACTTCGACGTGTGGGGAGCCGGCACCACCGTGACAGTG

TCATCTGCTAGCACCAAGGGCCCATCGGTCTTCCCCCTGGCACCCTCC

TCCAAGAGCACCTCTGGGGGCACAGCGGCCCTGGGCTGCCTGGTCAAG

GACTACTTCCCCGAACCGGTGACGGTGTCGTGGAACTCAGGCGCCCTG

ACCAGCGGCGTGCACACCTTCCCGGCTGTCCTACAGTCCTCAGGACTC

TACTCCCTCAGCAGCGTGGTGACCGTGCCCTCCAGCAGCTTGGGCACC

CAGACCTACATCTGCAACGTGAATCACAAGCCCAGCAACACCAAGGTG

GACAAGAAAGTTGAGCCCAAATCTTGTGACAAAACTCACACATGCCCA

CCGTGCCCAGCACCTGAATTTGAAGGGGGACCGTCAGTCTTCCTCTTC

CCCCCAAAACCCAAGGACACCCTCATGATCTCCCGGACCCCTGAGGTC

ACATGCGTGGTGGTGGACGTGAGCCACGAAGACCCTGAGGTCAAGTTC

AACTGGTACGTGGACGGCGTGGAGGTGCATAATGCCAAGACAAAGCCG

-continued
CGGGAGGAGCAGTACCAGAGCACGTACCGTGTGGTCAGCGTCCTCACC

GTCCTGCACCAGGACTGGCTGAATGGCAAGGAGTACAAGTGCAAGGTC

TCCAACAAAGCCCTCCCAGCCTCAATCGAGAAAACCATCTCCAAAGCC

AAAGGGCAGCCCCGAGAACCACAGGTGTACACCCTGCCCCCATCCCGG

GAGGAGATGACCAAGAACCAGGTCAGCCTGACCTGCCTGGTCAAAGGC

TTCTATCCCAGCGACATCGCCGTGGAGTGGGAGAGCAATGGGCAGCCG

GAGAACAACTACAAGACCACGCCTCCCGTGCTGGACTCCGACGGCTCC

TTCTTCCTCTACAGCAAGCTCACCGTGGACAAGAGCAGGTGGCAGCAG

GGGAACGTCTTCTCATGCTCCGTGATGCATGAGGCTCTGCACAACCAC

TACACGCAGAAGAGCCTCTCCCTGTCTCCGGGTAAA

Amino Acid Sequence
[spacer SEQ ID NO: 178]
[pLW334 without spacer SEQ ID NO: 205]
(SEQ ID NO: 138)
QGQSGS[GYLWGCEWNCGGITT][GSSGGSGGSGG][LSGRSDDH][G

GGS]QTVVTQEPSFSVSPGGTVTLTCRSSTGAVTTSNYANWVQQTPGQ

APRGLIGGTNKRAPGVPDRFSGSILGNKAALTITGAQADDESDYYCAL

WYSNLWVFGGGTKLTVL[GGGGSGGGGSGGGGS]EVQLVESGGGLVQP

GGSLKLSCAASGFTFSTYAMNWVRQASGKGLEWVGRIRSKYNNYATYY

ADSVKDRFTISRDDSKNTAYLQMNSLKTEDTAVYYCTRHGNFGNSYVS

WFAYWGQGTLVTVSS[GGGGS]QVTLRESGPALVKPTQTLTLTCTFSG

FSLSTSGMSVGWIRQPPGKALEWLADIWWDDKKDYNPSLKSRLTISKD

TSKNQVVLKVTNMDPADTATYYCARSMITNWYFDVWGAGTTVTVSSAS

TKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKV

EPKSCDKTHTCPPCPAPEFEGGPSVFLFPPKPKDTLMISRTPEVTCVV

VDVSHEDPEVKFNWYVDGVEVHNAKTKPREEQYQSTYRVVSVLTVLHQ

DWLNGKEYKCKVSNKALPASIEKTISKAKGQPREPQVYTLPPSREEMT

KNQVSLTCLVKGFYPSDIAVEWESNGQPENNYKTTPPVLDSDGSFFLY

SKLTVDKSRWQQGNVFSCSVMHEALHNHYTQKSLSLSPGK pLW139: LC Synagis®
Nucleotide Sequence
(SEQ ID NO: 139)
GACATCCAGATGACCCAGAGCCCCAGCACACTGAGCGCCAGCGTGGGC

GACAGAGTGACCATCACATGCAAGTGCCAGCTGAGCGTGGGCTACATG

CACTGGTATCAGCAGAAGCCCGGCAAGGCCCCCAAGCTGCTGATCTAC

GACACCAGCAAGCTGGCCTCCGGCGTGCCCAGCAGATTTTCTGGCAGC

GGCTCCGGCACCGAGTTCACCCTGACAATCAGCAGCCTGCAGCCCGAC

GACTTCGCCACCTACTACTGTTTTCAAGGCTCCGGCTACCCCTTCACC

TTCGGCGGAGGCACCAAGCTGGAAATCAAGCGGACGGTGGCTGCACCA

TCTGTCTTCATCTTCCCGCCATCTGATGAGCAGTTGAAATCTGGAACT

GCCTCTGTTGTGTGCCTGCTGAATAACTTCTATCCCAGAGAGGCCAAA

GTACAGTGGAAGGTGGATAACGCCCTCCAATCGGGTAACTCCCAGGAG

AGTGTCACAGAGCAGGACAGCAAGGACAGCACCTACAGCCTCAGCAGC

ACCCTGACGCTGAGCAAAGCAGACTACGAGAAACACAAAGTCTACGCC

TGCGAAGTCACCCATCAGGGCCTGAGCTCGCCCGTCACAAAGAGCTTC

AACAGGGGAGAGTGT

Amino Acid Sequence
(SEQ ID NO: 140)
DIQMTQSPSTLSASVGDRVTITCKCQLSVGYMHWYQQKPGKAPKWYDT

SKLASGVPSRFSGSGSGTEFTLTISSLQPDDFATYYCFQGSGYPFTFG

GGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACE

VTHQGLSSPVTKSFNRGEC

CI128: SynFcmt4-h20GG-2006-v16sc-H-N
pLW335: HC h20GG-2006-v16sc-Synagis® Fcmt4 (H-N)
Nucleotide Sequence
[spacer SEQ ID NO: 191]
[pLW335 without spacer SEQ ID NO: 206]
(SEQ ID NO: 141)
CAAGGCCAGTCTGGATCCGGTTATCTGTGGGGTTGCGAGTGGAATTGC

GGAGGGATCACTACAGGCTCGAGCGGTGGCAGCGGTGGCTCTGGTGGT

ATATCGAGTGGATTGCTGTCTGGCAGATCTGACGATCACGGCGGCGGT

TCTCAAACTGTAGTAACTCAAGAACCAAGCTTCTCCGTCTCCCCTGGG

GGAACAGTCACACTTACCTGCCGAAGTAGTACAGGTGCTGTTACGACC

AGTAACTATGCCAATTGGGTACAACAAACGCCTGGTCAGGCTCCGCGC

GGATTGATAGGAGGCACGAATAAACGGGCACCCGGTGTCCCGGACAGA

TTCAGCGGAAGCATACTCGGTAATAAGGCAGCTCTTACTATCACTGGG

GCCCAAGCTGATGATGAAAGTGATTATTATTGTGCGCTCTGGTACAGC

AACCTCTGGGTGTTTGGGGGTGGCACGAAACTTACTGTCTTGGGCGGC

GGCGGATCAGGGGAGGTGGCTCTGGAGGAGGAGGCTCAGAAGTCCAA

CTGGTCGAATCCGGGGGAGGGCTCGTACAGCCGGGTGGGTCCCTCAAA

CTCTCTTGTGCGGCCTCAGGGTTTACCTTCAGTACATACGCGATGAAT

TGGGTCCGGCAGGCCAGTGGGAAAGGGCTCGAATGGGTAGGACGAATC

CGATCAAAATACAACAACTACGCTACTTATTACGCTGATTCCGTGAAG

GACAGATTCACAATATCCCGCGACGATAGCAAGAATACGGCATATCTT

CAGATGAATTCTCTTAAAACTGAGGATACCGCTGTGTATTACTGCACA

AGACATGGTAATTTTGGAAACTCATATGTCTCTTGGTTCGCTTATTGG

GGACAGGGCACGTTGGTTACCGTGTCTAGCGGAGGTGGTGGATCCCAA

GTGACCCTGAGAGAGTCTGGCCCTGCCCTCGTGAAGCCTACCCAGACC

CTGACACTGACCTGCACCTTCAGCGGCTTCAGCCTGAGCACCAGCGGC

ATGTCTGTGGGCTGGATCAGACAGCCTCCTGGCAAGGCCCTGGAATGG

CTGGCCGACATTTGGTGGGACGACAAGAAGGACTACAACCCCAGCCTG

AAGTCCCGGCTGACCATCAGCAAGGACACCAGCAAGAACCAGGTGGTG

CTGAAAGTGACCAACATGGACCCCGCCGACACCGCCACCTACTACTGC

GCCAGATCCATGATCACCAACTGGTACTTCGACGTGTGGGGAGCCGGC

ACCACCGTGACAGTGTCATCTGCTAGCACCAAGGGCCCATCGGTCTTC

CCCCTGGCACCCTCCTCCAAGAGCACCTCTGGGGGCACAGCGGCCCTG

GGCTGCCTGGTCAAGGACTACTTCCCCGAACCGGTGACGGTGTCGTGG

```
AACTCAGGCGCCCTGACCAGCGGCGTGCACACCTTCCCGGCTGTCCTA

CAGTCCTCAGGACTCTACTCCCTCAGCAGCGTGGTGACCGTGCCCTCC

AGCAGCTTGGGCACCCAGACCTACATCTGCAACGTGAATCACAAGCCC

AGCAACACCAAGGTGGACAAGAAAGTTGAGCCCAAATCTTGTGACAAA

ACTCACACATGCCCACCGTGCCCAGCACCTGAATTTGAAGGGGGACCG

TCAGTCTTCCTCTTCCCCCCAAAACCCAAGGACACCCTCATGATCTCC

CGGACCCCTGAGGTCACATGCGTGGTGGTGGACGTGAGCCACGAAGAC

CCTGAGGTCAAGTTCAACTGGTACGTGGACGGCGTGGAGGTGCATAAT

GCCAAGACAAAGCCGCGGGAGGAGCAGTACCAGAGCACGTACCGTGTG

GTCAGCGTCCTCACCGTCCTGCACCAGGACTGGCTGAATGGCAAGGAG

TACAAGTGCAAGGTCTCCAACAAAGCCCTCCCAGCCTCAATCGAGAAA

ACCATCTCCAAAGCCAAAGGGCAGCCCCGAGAACCACAGGTGTACACC

CTGCCCCCATCCCGGGAGGAGATGACCAAGAACCAGGTCAGCCTGACC

TGCCTGGTCAAAGGCTTCTATCCCAGCGACATCGCCGTGGAGTGGGAG

AGCAATGGGCAGCCGGAGAACAACTACAAGACCACGCCTCCCGTGCTG

GACTCCGACGGCTCCTTCTTCCTCTACAGCAAGCTCACCGTGGACAAG

AGCAGGTGGCAGCAGGGGAACGTCTTCTCATGCTCCGTGATGCATGAG

GCTCTGCACAACCACTACACGCAGAAGAGCCTCTCCCTGTCTCCGGGT

AAA

Amino Acid Sequence
[spacer SEQ ID NO: 178]
[pLW335 without spacer SEQ ID NO: 207]
                                    (SEQ ID NO: 142)
QGQSGS[GYLWGCEWNCGGITT][GSSGGSGGSGG][ISSGLLSGRSD

DH][GGGS]QTVVTQEPSFSVSPGGTVTLTCRSSTGAVTTSNYANWVQ

QTPGQAPRGLIGGTNKRAPGVPDRFSGSILGNKAALTITGAQADDESD

YYCALWYSNLWVFGGGTKLTVL[GGGGSGGGGSGGGGS]EVQLVESGG

GLVQPGGSLKLSCAASGFTFSTYAMNWVRQASGKGLEWVGRIRSKYNN

YATYYADSVKDRFTISRDDSKNTAYLQMNSLKTEDTAVYYCTRHGNFG

NSYVSWFAYWGQGTLVTVSS[GGGGS]QVTLRESGPALVKPTQTLTLT

CTFSGFSLSTSGMSVGWIRQPPGKALEWLADIWWDDKKDYNPSLKSRL

TISKDTSKNQVVLKVTNMDPADTATYYCARSMITNWYFDVWGAGTTVT

VSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTK

VDKKVEPKSCDKTHTCPPCPAPEFEGGPSVFLFPPKPKDTLMISRTPE

VTCVVVDVSHEDPEVKFNWYVDGVEVHNAKTKPREEQYQSTYRVVSVL

TVLHQDWLNGKEYKCKVSNKALPASIEKTISKAKGQPREPQVYTLPPS

REEMTKNQVSLTCLVKGFYPSDIAVEWESNGQPENNYKTTPPVLDSDG

SFFLYSKLTVDKSRWQQGNVFSCSVMHEALHNHYTQKSLSLSPGK pLW139: LC Synagis®
Sequences provided above CI135: CF41-2008-C225v5Fcmt4-h20GG-0011-
v12sc-H-N
pLW352: HC h20GG-0011-v12sc-C225v5Fcmt4 (H-N)
Nucleotide Sequence
[spacer SEQ ID NO: 208]
[pLW352 without spacer SEQ ID NO: 209]
                                    (SEQ ID NO: 151)
CAAGGCCAGTCTGGTTCTGGTTATCTGTGGGGTTGCGAGTGGAATTGC

GGAGGGATCACTACAGGCTCGAGCGGTGGCAGCGGTGGCTCTGGTGGT

CTGAGCGGCCGTTCCGATGATCATGGCGGCGGATCCCAGACGGTAGTG

ACTCAGGAGCCATCATTTTCTGTCTCTCCTGGAGGTACTGTGACACTC

ACATGTAGAAGCTCAACTGGTGCAGTCACCACTTCAAATTACGCGAAT

TGGGTCCAGCAGACCCCTGGGCAGGCTCCGAGAGGGTTGATTGGAGGT

ACTAACAAACGGGCACCGGGAGTGCCTGATAGGTTTTCCGGTTCTATT

CTCGGAAACAAGGCGGCTCTCACGATCACGGGTGCGCAGGCCGACGAT

GAATCAGACTATTACTGCGCTTTGTGGTACTCAAACCTGTGGGTATTC

GGAGGGGGCACCAAGCTGACGGTGTTGGGTGGGGGGGGCTCTGGGGGA

GGGGGAAGCGGAGGTGGGGGCAGCGAGGTTCAGCTTGTTGAAAGTGGT

GGCGGACTCGTACAACGGGTGGAAGTCTTAGACTCTCATGTGCAGCA

TCTGGATTTACTTTTTCTACTTATGCTATGAACTGGGTAAGACAGGCA

CCGGGGAAAGGGCTGGAATGGGTTGCACGCATTCGATCTAAATACAAT

AACTATGCTACATACTACGCCGATAGTGTTAAGGATCGATTCACTATA

TCTCGGGACGACAGTAAGAACTCACTTTACCTGCAGATGAATTCCTTG

AAAACTGAGGACACGGCCGTTTATTATTGTACGCGGCACGGGAATTTC

GGCAATTCTTACGTTTCCTGGTTCGCCTATTGGGGGCAAGGTACGCTG

GTCACGGTGTCTAGCGGAGGTGGTGGATCCCAGGTGCAGCTGAAACAG

AGCGGCCCGGGCCTGGTGCAGCCGAGCCAGAGCCTGAGCATTACCTGC

ACCGTGAGCGGCTTTAGCCTGACCAACTATGGCGTGCATTGGGTGCGC

CAGAGCCCGGGCAAAGGCCTGGAATGGCTGGGCGTGATTTGGAGCGGC

GGCAACACCGATTATAACACCCCGTTTACCAGCCGCCTGAGCATTAAC

AAAGATAACAGCAAAAGCCAGGTGTTTTTTAAAATGAACAGCCTGCAA

AGCCAGGATACCGCGATTTATTATTGCGCGCGCGCGCTGACCTATTAT

GATTATGAATTTGCGTATTGGGGCCAGGGCACCCTGGTGACCGTGAGC

GCGGCTAGCACCAAGGGCCCATCGGTCTTCCCCCTGGCACCCTCCTCC

AAGAGCACCTCTGGGGGCACAGCGGCCCTGGGCTGCCTGGTCAAGGAC

TACTTCCCCGAACCGGTGACGGTGTCGTGGAACTCAGGCGCCCTGACC

AGCGGCGTGCACACCTTCCCGGCTGTCCTACAGTCCTCAGGACTCTAC

TCCCTCAGCAGCGTGGTGACCGTGCCCTCCAGCAGCTTGGGCACCCAG

ACCTACATCTGCAACGTGAATCACAAGCCCAGCAACACCAAGGTGGAC

AAGAAAGTTGAGCCCAAATCTTGTGACAAAACTCACACATGCCCACCG

TGCCCAGCACCTGAATTTGAAGGGGGACCGTCAGTCTTCCTCTTCCCC

CCAAAACCCAAGGACACCCTCATGATCTCCCGGACCCCTGAGGTCACA
```

```
TGCGTGGTGGTGGACGTGAGCCACGAAGACCCTGAGGTCAAGTTCAAC

TGGTACGTGGACGGCGTGGAGGTGCATAATGCCAAGACAAAGCCGCGG

GAGGAGCAGTACCAGAGCACGTACCGTGTGGTCAGCGTCCTCACCGTC

CTGCACCAGGACTGGCTGAATGGCAAGGAGTACAAGTGCAAGGTCTCC

AACAAAGCCCTCCCAGCCTCAATCGAGAAAACCATCTCCAAAGCCAAA

GGGCAGCCCCGAGAACCACAGGTGTACACCCTGCCCCCATCCCGGGAG

GAGATGACCAAGAACCAGGTCAGCCTGACCTGCCTGGTCAAAGGCTTC

TATCCCAGCGACATCGCCGTGGAGTGGGAGAGCAATGGGCAGCCGGAG

AACAACTACAAGACCACGCCTCCCGTGCTGGACTCCGACGGCTCCTTC

TTCCTCTACAGCAAGCTCACCGTGGACAAGAGCAGGTGGCAGCAGGGG

AACGTCTTCTCATGCTCCGTGATGCATGAGGCTCTGCACAACCACTAC

ACGCAGAAGAGCCTCTCCCTGTCTCCGGGTAAA

Amino Acid Sequence
[spacer SEQ ID NO: 176]
[pLW352 without spacer SEQ ID NO: 210]
                                  (SEQ ID NO: 146)
QGQSGS[GYLWGCEWNCGGITT][GSSGGSGGSGG][LSGRSDDH][G

GGS]QTVVTQEPSFSVSPGGTVTLTCRSSTGAVTTSNYANWVQQTPGQ

APRGLIGGTNKRAPGVPDRFSGSILGNKAALTITGAQADDESDYYCAL

WYSNLWVFGGGTKLTVL[GGGGSGGGGSGGGGS]EVQLVESGGGLVQP

GGSLRLSCAASGFTFSTYAMNWVRQAPGKGLEWVARIRSKYNNYATYY

ADSVKDRFTISRDDSKNSLYLQMNSLKTEDTAVYYCVRHGNFGNSYVS

WFAYWGQGTLVTVSS[GGGGS]QVQLKQSGPGLVQPSQSLSITCTVSG

FSLTNYGVHWVRQSPGKGLEWLGVIWSGGNTDYNTPFTSRLSINKDNS

KSQVFFKMNSLQSQDTAIYYCARALTYYDYEFAYWGQGTLVTVSAAST

KGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVE

PKSCDKTHTCPPCPAPEFEGGPSVFLFPPKPKDTLMISRTPEVTCVVV

DVSHEDPEVKFNWYVDGVEVHNAKTKPREEQYQSTYRVVSVLTVLHQD

WLNGKEYKCKVSNKALPASIEKTISKAKGQPREPQVYTLPPSREEMTK

NQVSLTCLVKGFYPSDIAVEWESNGQPENNYKTTPPVLDSDGSFFLYS

KLTVDKSRWQQGNVFSCSVMHEALHNHYTQKSLSLSPGK pLW246: LC CF41-2008-C225v5
Nucleotide Sequence
Sequences provided above Amino Acid Sequence
Sequences provided above CI136: CF41-2008-C225v5Fcmt4-h20GG-0011-
v19sc-H-N
pLW353: HC h20GG-0011-v19sc-C225v5Fcmt4 (H-N)
Nucleotide Sequence
[spacer SEQ ID NO: 191]
[pLW353 without spacer SEQ ID NO: 211]
                                  (SEQ ID NO: 152)
CAAGGCCAGTCTGGATCCGGTTATCTGTGGGGTTGCGAGTGGAATTGC

GGAGGGATCACTACAGGCTCGAGCGGTGGCAGCGGTGGCTCTGGTGGT

CTGAGCGGCCGTTCCGATGATCATGGCGGCGGTTCTCAGGCCGTTGTT

ACACAAGAGCCTTCACTTACTGTGTCTCCAGGAGGCACTGTGACACTT

ACGTGCCGATCCTCTACGGGTGCCGTGACCACAAGCAACTATGCCAAC

TGGGTCCAGCAGAAGCCAGGTCAAGCGCCTCGAGGTCTGATCGGGGGC

ACGAATAAACGAGCTCCTGGAACTCCGGCCAGATTTTCTGGGAGTCTT

ATTGGTGGCAAGGCGGCGTTGACCCTGAGTGGAGCCCAACCGGAAGAC

GAGGCCGAGTACTACTGCGCCTTGTGGTATTCCAATTTGTGGGTCTTC

GGAGGCGGAACAAAGCTCACAGTACTGGGAGGTGGAGGTAGCGGGGGC

GGAGGCTCCGGGGGAGGTGGTTCCGAAGTCCAGCTTGTTGAATCAGGT

GGGGGCTTGGTACAACCAGGTGGTTCACTGAAGTTGTCCTGTGCAGCG

TCCGGATTTACATTTAGTACGTATGCTATGAACTGGGTCAGGCAGGCC

AGTGGTAAAGGTCTCGAATGGGTTGGCCGGATAAGGTCAAAGTACAAT

AATTACGCAACCTACTACGCGGATTCCGTGAAAGACAGGTTCACTATT

TCACGAGATGATAGCAAAAATACTGCGTATCTCCAAATGAATAGTCTT

AAAACTGAAGACACTGCCGTATATTATTGCACTAGGCACGGCAACTTT

GGTAACTCTTATGTTTCTTGGTTCGCATACTGGGGACAAGGAACTTTG

GTCACTGTCTCATCTGGAGGTGGTGGATCCCAGGTGCAGCTGAAACAG

AGCGGCCCGGGCCTGGTGCAGCCGAGCCAGAGCCTGAGCATTACCTGC

ACCGTGAGCGGCTTTAGCCTGACCAACTATGGCGTGCATTGGGTGCGC

CAGAGCCCGGGCAAAGGCCTGGAATGGCTGGGCGTGATTTGGAGCGGC

GGCAACACCGATTATAACACCCCGTTTACCAGCCGCCTGAGCATTAAC

AAAGATAACAGCAAAAGCCAGGTGTTTTTTAAAATGAACAGCCTGCAA

AGCCAGGATACCGCGATTTATTATTGCGCGCGCGCGCTGACCTATTAT

GATTATGAATTTGCGTATTGGGGCCAGGGCACCCTGGTGACCGTGAGC

GCGGCTAGCACCAAGGGCCCATCGGTCTTCCCCCTGGCACCCTCCTCC

AAGAGCACCTCTGGGGGCACAGCGGCCCTGGGCTGCCTGGTCAAGGAC

TACTTCCCCGAACCGGTGACGGTGTCGTGGAACTCAGGCGCCCTGACC

AGCGGCGTGCACACCTTCCCGGCTGTCCTACAGTCCTCAGGACTCTAC

TCCCTCAGCAGCGTGGTGACCGTGCCCTCCAGCAGCTTGGGCACCCAG

ACCTACATCTGCAACGTGAATCACAAGCCCAGCAACACCAAGGTGGAC

AAGAAAGTTGAGCCCAAATCTTGTGACAAAACTCACACATGCCCACCG

TGCCCAGCACCTGAATTTGAAGGGGGACCGTCAGTCTTCCTCTTCCCC

CCAAAACCCAAGGACACCCTCATGATCTCCCGGACCCCTGAGGTCACA

TGCGTGGTGGTGGACGTGAGCCACGAAGACCCTGAGGTCAAGTTCAAC

TGGTACGTGGACGGCGTGGAGGTGCATAATGCCAAGACAAAGCCGCGG

GAGGAGCAGTACCAGAGCACGTACCGTGTGGTCAGCGTCCTCACCGTC

CTGCACCAGGACTGGCTGAATGGCAAGGAGTACAAGTGCAAGGTCTCC

AACAAAGCCCTCCCAGCCTCAATCGAGAAAACCATCTCCAAAGCCAAA

GGGCAGCCCCGAGAACCACAGGTGTACACCCTGCCCCCATCCCGGGAG

GAGATGACCAAGAACCAGGTCAGCCTGACCTGCCTGGTCAAAGGCTTC

TATCCCAGCGACATCGCCGTGGAGTGGGAGAGCAATGGGCAGCCGGAG

AACAACTACAAGACCACGCCTCCCGTGCTGGACTCCGACGGCTCCTTC
```

-continued
TTCCTCTACAGCAAGCTCACCGTGGACAAGAGCAGGTGGCAGCAGGGG

AACGTCTTCTCATGCTCCGTGATGCATGAGGCTCTGCACAACCACTAC

ACGCAGAAGAGCCTCTCCCTGTCTCCGGGTAAA

Amino Acid Sequence
[spacer SEQ ID NO: 178]
[pLW353 without spacer SEQ ID NO: 212]
(SEQ ID NO: 148)
QGQSGS[GYLWGCEWNCGGITT][GSSGGSGGSGG][LSGRSDDH][G

GGS]QAVVTQEPSLTVSPGGTVTLTCRSSTGAVTTSNYANWVQQKPGQ

APRGLIGGTNKRAPGTPARFSGSLIGGKAALTLSGAQPEDEAEYYCAL

WYSNLWVFGGGTKLTVL[GGGGSGGGGSGGGGS]EVQLVESGGGLVQP

GGSLKLSCAASGFTFSTYAMNWVRQASGKGLEWVGRIRSKYNNYATYY

ADSVKDRFTISRDDSKNTAYLQMNSLKTEDTAVYYCTRHGNFGNSYVS

WFAYWGQGTLVTVSS[GGGGS]QVQLKQSGPGLVQPSQSLSITCTVSG

FSLTNYGVHWVRQSPGKGLEWLGVIWSGGNTDYNTPFTSRLSINKDNS

KSQVFFKMNSLQSQDTAIYYCARALTYYDYEFAYWGQGTLVTVSAAST

KGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVE

PKSCDKTHTCPPCPAPEFEGGPSVFLFPPKPKDTLMISRTPEVTCVVV

DVSHEDPEVKFNWYVDGVEVHNAKTKPREEQYQSTYRVVSVLTVLHQD

WLNGKEYKCKVSNKALPASIEKTISKAKGQPREPQVYTLPPSREEMTK

NQVSLTCLVKGFYPSDIAVEWESNGQPENNYKTTPPVLDSDGSFFLYS

KLTVDKSRWQQGNVFSCSVMHEALHNHYTQKSLSLSPGK pLW246: LC CF41-2008-C225v5
Sequences provided above CI091: 3954-1490DQH-C225v5Fcmt4-h20GG-2008-
v16sc-H-N
pLW242: HC C225v5Fcmt4-h20GG-2008-v16sc (H-N)
Nucleic Acid Sequence
[spacer SEQ ID NO: 191]
[pLW242 without spacer SEQ ID NO: 213]
(SEQ ID NO: 168)
CAAGGCCAGTCTGGATCCGGTTATCTGTGGGGTTGCGAGTGGAATTGC

GGAGGGATCACTACAGGCTCGAGCGGTGGCAGCGGTGGCTCTGGTGGT

ATATCGAGTGGATTGCTGTCTGGCAGATCTGACCAACACGGCGGCGGT

TCTCAAACTGTAGTAACTCAAGAACCAAGCTTCTCCGTCTCCCTGGG

GGAACAGTCACACTTACCTGCCGAAGTAGTACAGGTGCTGTTACGACC

AGTAACTATGCCAATTGGGTACAACAAACGCCTGGTCAGGCTCCGCGC

GGATTGATAGGAGGCACGAATAAACGGGCACCCGGTGTCCCGGACAGA

TTCAGCGGAAGCATACTCGGTAATAAGGCAGCTCTTACTATCACTGGG

GCCCAAGCTGATGATGAAAGTGATTATTATTGTGCGCTCTGGTACAGC

AACCTCTGGGTGTTTGGGGGTGGCACGAAACTTACTGTCTTGGGCGGC

GGCGGATCAGGGGAGGTGGCTCTGGAGGAGGAGGCTCAGAAGTCCAA

CTGGTCGAATCCGGGGAGGGCTCGTACAGCCGGGTGGGTCCCTCAAA

CTCTCTTGTGCGGCCTCAGGGTTTACCTTCAGTACATACGCGATGAAT

TGGGTCCGGCAGGCCAGTGGGAAAGGGCTCGAATGGGTAGGACGAATC

CGATCAAAATACAACAACTACGCTACTTATTACGCTGATTCCGTGAAG

-continued
GACAGATTCACAATATCCCGCGACGATAGCAAGAATACGGCATATCTT

CAGATGAATTCTCTTAAAACTGAGGATACCGCTGTGTATTACTGCACA

AGACATGGTAATTTTGGAAACTCATATGTCTCTTGGTTCGCTTATTGG

GGACAGGGCACGTTGGTTACCGTGTCTAGCGGAGGTGGTGGATCCCAG

GTGCAGCTGAAACAGAGCGGCCCGGGCCTGGTGCAGCCGAGCCAGAGC

CTGAGCATTACCTGCACCGTGAGCGGCTTTAGCCTGACCAACTATGGC

GTGCATTGGGTGCGCCAGAGCCCGGGCAAAGGCCTGGAATGGCTGGGC

GTGATTTGGAGCGGCGGCAACACCGATTATAACACCCCGTTTACCAGC

CGCCTGAGCATTAACAAAGATAACAGCAAAAGCCAGGTGTTTTTTAAA

ATGAACAGCCTGCAAAGCCAGGATACCGCGATTTATTATTGCGCGCGC

GCGCTGACCTATTATGATTATGAATTTGCGTATTGGGGCCAGGGCACC

CTGGTGACCGTGAGCGCGGCTAGCACCAAGGGCCCATCGGTCTTCCCC

CTGGCACCCTCCTCCAAGAGCACCTCTGGGGGCACAGCGGCCCTGGGC

TGCCTGGTCAAGGACTACTTCCCCGAACCGGTGACGGTGTCGTGGAAC

TCAGGCGCCCTGACCAGCGGCGTGCACACCTTCCCGGCTGTCCTACAG

TCCTCAGGACTCTACTCCCTCAGCAGCGTGGTGACCGTGCCCTCCAGC

AGCTTGGGCACCCAGACCTACATCTGCAACGTGAATCACAAGCCCAGC

AACACCAAGGTGGACAAGAAAGTTGAGCCCAAATCTTGTGACAAAACT

CACACATGCCCACCGTGCCCAGCACCTGAATTTGAAGGGGGACCGTCA

GTCTTCCTCTTCCCCCCAAAACCCAAGGACACCCTCATGATCTCCCGG

ACCCCTGAGGTCACATGCGTGGTGGTGGACGTGAGCCACGAAGACCCT

GAGGTCAAGTTCAACTGGTACGTGGACGGCGTGGAGGTGCATAATGCC

AAGACAAAGCCGCGGGAGGAGCAGTACCAGAGCACGTACCGTGTGGTC

AGCGTCCTCACCGTCCTGCACCAGGACTGGCTGAATGGCAAGGAGTAC

AAGTGCAAGGTCTCCAACAAAGCCCTCCCAGCCTCAATCGAGAAAACC

ATCTCCAAAGCCAAAGGGCAGCCCCGAGAACCACAGGTGTACACCCTG

CCCCCATCCCGGGAGGAGATGACCAAGAACCAGGTCAGCCTGACCTGC

CTGGTCAAAGGCTTCTATCCCAGCGACATCGCCGTGGAGTGGGAGAGC

AATGGGCAGCCGGAGAACAACTACAAGACCACGCCTCCCGTGCTGGAC

TCCGACGGCTCCTTCTTCCTCTACAGCAAGCTCACCGTGGACAAGAGC

AGGTGGCAGCAGGGGAACGTCTTCTCATGCTCCGTGATGCATGAGGCT

CTGCACAACCACTACACGCAGAAGAGCCTCTCCCTGTCTCCGGGTAAA

Amino Acid Sequence
[spacer SEQ ID NO: 178]
[pLW242 without spacer SEQ ID NO: 214]
(SEQ ID NO: 169)
QGQSGS[GYLWGCEWNCGGITT]GSSGGSGGSGG[ISSGLLSGRSDQ

H]GGGSQTVVTQEPSFSVSPGGTVTLTCRSSTGAVTTSNYANWVQQTP

GQAPRGLIGGTNKRAPGVPDRFSGSILGNKAALTITGAQADDESDYYC

ALWYSNLWVFGGGTKLTVLGGGGSGGGGSGGGGSEVQLVESGGGLVQP

GGSLKLSCAASGFTFSTYAMNWVRQASGKGLEWVGRIRSKYNNYATYY

ADSVKDRFTISRDDSKNTAYLQMNSLKTEDTAVYYCTRHGNFGNSYVS

-continued

WFAYWGQGTLVTVSSGGGGSQVQLKQSGPGLVQPSQSLSITCTVSGFS

LTNYGVHWVRQSPGKGLEWLGVIWSGGNTDYNTPFTSRLSINKDNSKS

QVFFKMNSLQSQDTAIYYCARALTYYDYEFAYWGQGTLVTVSAASTKG

PSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPK

SCDKTHTCPPCPAPEFEGGPSVFLFPPKPKDTLMISRTPEVTCVVVDV

SHEDPEVKFNWYVDGVEVHNAKTKPREEQYQSTYRVVSVLTVLHQDWL

NGKEYKCKVSNKALPASIEKTISKAKGQPREPQVYTLPPSREEMTKNQ

VSLTCLVKGFYPSDIAVEWESNGQPENNYKTTPPVLDSDGSFFLYSKL

TVDKSRWQQGNVFSCSVMHEALHNHYTQKSLSLSPGK

CX320: 3954-C225v5-2008
Nucleic Acid Sequence
[spacer SEQ ID NO: 180]
[CX320 without spacer SEQ ID NO: 215]
(SEQ ID NO: 170)
CAAGGCCAGTCTGGCCAGTGCATCTCACCTCGTGGTTGTCCGGACGGC

CCATACGTCATGTACGGCTCGAGCGGTGGCAGCGGTGGCTCTGGTGGA

TCCGGTATATCGAGTGGATTGCTGTCTGGCAGATCTGACCAACACGGC

AGTAGCGGTACCCAGATCTTGCTGACCCAGAGCCCGGTGATTCTGAGC

GTGAGCCCGGGCGAACGTGTGAGCTTTAGCTGCCGCGCGAGCCAGAGC

ATTGGCACCAACATTCATTGGTATCAGCAGCGCACCAACGGCAGCCCG

CGCCTGCTGATTAAATATGCGAGCGAAAGCATTAGCGGCATTCCGAGC

CGCTTTAGCGGCAGCGGCAGCGGCACCGATTTTACCCTGAGCATTAAC

AGCGTGGAAAGCGAAGATATTGCGGATTATTATTGCCAGCAGAACAAC

AACTGGCCGACCACCTTTGGCGCGGGCACCAAACTGGAACTGAAACGT

ACGGTGGCTGCACCATCTGTCTTCATCTTCCCGCCATCTGATGAGCAG

TTGAAATCTGGAACTGCCTCTGTTGTGTGCCTGCTGAATAACTTCTAT

CCCAGAGAGGCCAAAGTACAGTGGAAGGTGGATAACGCCCTCCAATCG

GGTAACTCCCAGGAGAGTGTCACAGAGCAGGACAGCAAGGACAGCACC

TACAGCCTCAGCAGCACCCTGACGCTGAGCAAAGCAGACTACGAGAAA

CACAAAGTCTACGCCTGCGAAGTCACCCATCAGGGCCTGAGCTCGCCC

GTCACAAAGAGCTTCAACAGGGGAGAGTGT

Amino Acid Sequence
[spacer SEQ ID NO: 178]
[CX320 without spacer SEQ ID NO: 216]
(SEQ ID NO: 171)
QGQSGQ[CISPRGCPDGPYVMY]GSSGGSGGSGGSG[ISSGLLSGRSD

QH]GSSGTQILLTQSPVILSVSPGERVSFSCRASQSIGTNIHWYQQRT

NGSPRLLIKYASESISGIPSRFSGSGSGTDFTLSINSVESEDIADYYC

QQNNNWPTTFGAGTKLELKRTVAAPSVFIFPPSDEQLKSGTASVVCLL

NNFYPREAKVQWKVDNALQSGNSQESVTEQDSKDSTYSLSSTLTLSKA

DYEKHKVYACEVTHQGLSSPVTKSFNRGEC

CI064: SynN297Q-JF15865-0001-hSP34LvHv-H-N
pLW138: HC SynN297Q-JF15865-0001-hSP34LvHv-H-N
Nucleic Acid Sequence
[spacer SEQ ID NO: 176]
[pLW138 without spacer SEQ ID NO: 147]
(SEQ ID NO: 172)
CAAGGCCAGTCTGGCCAAATGATGTATTGCGGTGGGAATGAGGTGTTG

TGCGGGCCGCGGGTTGGCTCGAGCGGTGGCAGCGGTGGCTCTGGTGGT

CTGAGCGGCCGTTCCGATAATCATGGCGGCGGTTCTCAGACCGTGGTC

ACACAGGAGCCCTCACTGACAGTGAGCCCTGGCGGGACCGTCACACTG

ACTTGTCGCAGTTCAACTGGCGCCGTGACTACCAGCAATTACGCTAAC

TGGGTCCAGCAGAAACCAGGACAGGCACCACGAGGACTGATCGGAGGA

ACTAATAAGAGAGCACCAGGAACCCCTGCAAGGTTCTCCGGATCTCTG

CTGGGGGGAAAAGCCGCTCTGACACTGAGCGGCGTGCAGCCTGAGGAC

GAAGCTGAGTACTATTGCGCACTGTGGTACTCCAACCTGTGGGTGTTT

GGCGGGGGAACTAAGCTGACCGTCCTGGGAGGAGGAGGAAGCGGAGGA

GGAGGGAGCGGAGGAGGAGGATCCGAAGTGCAGCTGGTCGAGAGCGGA

GGAGGACTGGTGCAGCCAGGAGGATCCCTGAAGCTGTCTTGTGCAGCC

AGTGGCTTCACCTTCAACACTTACGCAATGAACTGGGTGCGGCAGGCA

CCTGGGAAGGGACTGGAATGGGTCGCCCGGATCAGATCTAAATACAAT

AACTATGCCACCTACTATGCTGACAGTGTGAAGGATAGGTTCACCATT

TCACGCGACGATAGCAAAAACACAGCTTATCTGCAGATGAATAACCTG

AAGACCGAGGATACAGCAGTGTACTATTGCGTCAGACACGGCAATTTC

GGGAACTCTTACGTGAGTTGGTTTGCCTATTGGGGACAGGGGACACTG

GTCACCGTCTCCTCAGGAGGTGGTGGATCCCAAGTGACCCTGAGAGAG

TCTGGCCCTGCCCTCGTGAAGCCTACCCAGACCCTGACACTGACCTGC

ACCTTCAGCGGCTTCAGCCTGAGCACCAGCGGCATGTCTGTGGGCTGG

ATCAGACAGCCTCCTGGCAAGGCCCTGGAATGGCTGGCCGACATTTGG

TGGGACGACAAGAAGGACTACAACCCCAGCCTGAAGTCCCGGCTGACC

ATCAGCAAGGACACCAGCAAGAACCAGGTGGTGCTGAAAGTGACCAAC

ATGGACCCCGCCGACACCGCCACCTACTACTGCGCCAGATCCATGATC

ACCAACTGGTACTTCGACGTGTGGGGAGCCGGCACCACCGTGACAGTG

TCATCTGCTAGCACCAAGGGCCCATCGGTCTTCCCCCTGGCACCCTCC

TCCAAGAGCACCTCTGGGGGCACAGCGGCCCTGGGCTGCCTGGTCAAG

GACTACTTCCCCGAACCGGTGACGGTGTCGTGGAACTCAGGCGCCCTG

ACCAGCGGCGTGCACACCTTCCCGGCTGTCCTACAGTCCTCAGGACTC

TACTCCCTCAGCAGCGTGGTGACCGTGCCCTCCAGCAGCTTGGGCACC

CAGACCTACATCTGCAACGTGAATCACAAGCCCAGCAACACCAAGGTG

GACAAGAAAGTTGAGCCCAAATCTTGTGACAAAACTCACACATGCCCA

CCGTGCCCAGCACCTGAACTCCTGGGGGGACCGTCAGTCTTCCTCTTC

CCCCCAAAACCCAAGGACACCCTCATGATCTCCCGGACCCCTGAGGTC

ACATGCGTGGTGGTGGACGTGAGCCACGAAGACCCTGAGGTCAAGTTC

AACTGGTACGTGGACGGCGTGGAGGTGCATAATGCCAAGACAAAGCCG

-continued
CGGGAGGAGCAGTACCAGAGCACGTACCGTGTGGTCAGCGTCCTCACC

GTCCTGCACCAGGACTGGCTGAATGGCAAGGAGTACAAGTGCAAGGTC

TCCAACAAAGCCCTCCCAGCCCCCATCGAGAAAACCATCTCCAAAGCC

AAAGGGCAGCCCCGAGAACCACAGGTGTACACCCTGCCCCCATCCCGG

GAGGAGATGACCAAGAACCAGGTCAGCCTGACCTGCCTGGTCAAAGGC

TTCTATCCCAGCGACATCGCCGTGGAGTGGGAGAGCAATGGGCAGCCG

GAGAACAACTACAAGACCACGCCTCCCGTGCTGGACTCCGACGGCTCC

TTCTTCCTCTACAGCAAGCTCACCGTGGACAAGAGCAGGTGGCAGCAG

GGGAACGTCTTCTCATGCTCCGTGATGCATGAGGCTCTGCACAACCAC

TACACGCAGAAGAGCCTCTCCCTGTCTCCGGGTAAA

Amino Acid Sequence
[spacer SEQ ID NO: 178]
[pLW138 without spacer SEQ ID NO: 153]
(SEQ ID NO: 173)
QGQSGQ[MMYCGGNEVLCGPRV]GSSGGSGGSGG[LSGRSDNH]GGGS

QTVVTQEPSLTVSPGGTVTLTCRSSTGAVTTSNYANWVQQKPGQAPRG

LIGGTNKRAPGTPARFSGSLLGGKAALTLSGVQPEDEAEYYCALWYSN

LWVFGGGTKLTVLGGGGSGGGGSGGGGSEVQLVESGGGLVQPGGSLKL

SCAASGFTFNTYAMNWVRQAPGKGLEWVARIRSKYNNYATYYADSVKD

RFTISRDDSKNTAYLQMNNLKTEDTAVYYCVRHGNFGNSYVSWFAYWG

QGTLVTVSSGGGGSQVTLRESGPALVKPTQTLTLTCTFSGFSLSTSGM

SVGWIRQPPGKALEWLADIWWDDKKDYNPSLKSRLTISKDTSKNQVVL

KVTNMDPADTATYYCARSMITNWYFDVWGAGTTVTVSSASTKGPSVFP

LAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDP

EVKFNWYVDGVEVHNAKTKPREEQYQSTYRVVSVLTVLHQDWLNGKEY

KCKVSNKALPAPIEKTISKAKGQPREPQVYTLPPSREEMTKNQVSLTC

LVKGFYPSDIAVEWESNGQPENNYKTTPPVLDSDGSFFLYSKLTVDKS

RWQQGNVFSCSVMHEALHNHYTQKSLSLSPGK pLW139: LC Syn kappa
Nucleic Acid Sequence
(SEQ ID NO: 174)
GACATCCAGATGACCCAGAGCCCCAGCACACTGAGCGCCAGCGTGGGC

GACAGAGTGACCATCACATGCAAGTGCCAGCTGAGCGTGGGCTACATG

CACTGGTATCAGCAGAAGCCCGGCAAGGCCCCCAAGCTGCTGATCTAC

GACACCAGCAAGCTGGCCTCCGGCGTGCCCAGCAGATTTTCTGGCAGC

GGCTCCGGCACCGAGTTCACCCTGACAATCAGCAGCCTGCAGCCCGAC

GACTTCGCCACCTACTACTGTTTTCAAGGCTCCGGCTACCCCTTCACC

TTCGGCGGAGGCACCAAGCTGGAAATCAAGCGGACGGTGGCTGCACCA

TCTGTCTTCATCTTCCCGCCATCTGATGAGCAGTTGAAATCTGGAACT

GCCTCTGTTGTGTGCCTGCTGAATAACTTCTATCCCAGAGAGGCCAAA

GTACAGTGGAAGGTGGATAACGCCCTCCAATCGGGTAACTCCCAGGAG

AGTGTCACAGAGCAGGACAGCAAGGACAGCACCTACAGCCTCAGCAGC

-continued
ACCCTGACGCTGAGCAAAGCAGACTACGAGAAACACAAAGTCTACGCC

TGCGAAGTCACCCATCAGGGCCTGAGCTCGCCCGTCACAAAGAGCTTC

AACAGGGGAGAGTGT

Amino Acid Sequence
(SEQ ID NO: 175)
DIQMTQSPSTLSASVGDRVTITCKCQLSVGYMHWYQQKPGKAPKLLIY

DTSKLASGVPSRFSGSGSGTEFTLTISSLQPDDFATYYCFQGSGYPFT

FGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC

Anti-CD3 scFv variant v12
Light chain LV12
Heavy chain HV12
Sequences provided above Anti-CD3 scFv variant v16
Light chain LV12
Heavy chain HV20
Sequences provided above Anti-CD3 scFv variant v19
Light chain LV19
Heavy chain HV20
Sequences provided above Anti-CD3 scFv variant v26
Light chain LV19
Heavy chain HV12
Sequences provided above Vector Construction The heavy and light chains were cloned separately into a mammalian expression vector using standard molecular biology techniques. Briefly, DNA fragments encoding the region of interest were amplified with primers binding to the terminal ends. Overlapping fragments were combined and amplified with flanking primers as needed to build the entire desired region. DNA fragments were subsequently cloned into the expression vector using a commercially available homologous recombination kit (MCLabs, South San Francisco, Calif.). The mammalian expression vector is a modified version of cDNA™3.1(+) from Invitrogen with selection marker of G418 or hygromycin. Mutations were introduced using the QuikChange Kit (Agilent, Santa Clara, Calif.).

Expression of AAs and Dually Masked BAAs (BAAs)

AAs and BAAs were expressed in mammalian cells using a standard transfection kit (Life Technologies, Grand Island, N.Y.). Briefly, 293 cells were transfected with nucleic acids using a lipid-based system, following the manufacturer's recommended protocol. AAs and dually masked BAAs were purified from cell-free supernatant using Protein A beads (GE, Piscataway, N.J.) and concentrated using standard buffer exchange columns (Millipore, Temecula, Calif.).

Example 2. Binding of Dually Masked, Bispecific, AAs to EGFR+HT-29 Cells and CD3ε+ Jurkat Cells To determine if the described EGFR and CD3ε masking peptides and protease substrates could inhibit binding in the context of a dually masked, bispecific, AA, a flow cytometry-based binding assay was performed.

HT-29-luc2 (Caliper) and Jurkat (Clone E6-1, ATCC, TIB-152) cells were cultured in RPMI-1640+glutamax (Life Technologies, Catalog 72400-047), 10% Heat Inactivated-Fetal Bovine Serum (HI-FBS, Life Technologies, Catalog 10438-026), 100 U/ml penicillin, and 100 µg/ml streptomycin (Life Technologies, Catalog 15140-122) according to manufacturer guidelines. The following bispecific, activated antibodies CI048 and CI104 (act-104), and dually masked, bispecific, AAs CI011, CI106, and CI107 were tested. Two versions of SP34 scFv were utilized, namely the scFv in CI011 and CI048 versus the scFv in CI104, CI106, and CI107. Two versions of the EGFR mask were utilized, namely the EGFR mask in CI011 and CI107 versus the EGFR mask in CI106. Two versions of the CD3 mask were utilized, namely the CD3 mask in CI011 versus the CD3 mask in CI106 and CI107.

HT29-luc2 cells were detached with Versene™ (Life Technologies, Catalog 15040-066), washed, plated in 96 well plates at 150,000 cells/well, and re-suspended in 50 µL of primary antibody. Titrations started at the concentrations indicated in FIGS. 1A-1B followed by 3-fold serial dilutions in FACS Stain Buffer+2% FBS (BD Pharmingen, Catalog 554656). Cells were incubated at 4° C. with shaking for about 1 hour, harvested, and washed with 2×200 µL of FACS Stain Buffer. Cells were resuspended in 50 µL of Alexa Fluor 647 conjugated anti-Human IgG Fc (10 µg/ml, Jackson ImmunoResearch, Product 109-606-008) and incubated at 4° C. with shaking for about 1 hour. HT29-luc2 were harvested, washed, and resuspended in a final volume of 60 µL of FACS Stain Buffer containing 2.5 µg/ml 7-AAD (BD Biosciences, Catalog 559925). Cells stained with secondary antibody alone were used as a negative control. Data was acquired on a MACSQuant® Analyzer 10 (Miltenyi) and the median fluorescence intensity (MFI) of viable cells was calculated using FlowJo® V10 (Treestar). Background subtracted MFI data was graphed in GraphPad Prism 6 using curve fit analysis.

Jurkats growing in suspension were harvested, washed, plated in 96 well plates at 150000 cells/well and resuspended in 50 µl of primary antibody. Staining and data acquisition were carried out as described for HT29-luc2 cells above.

Figure 1B:
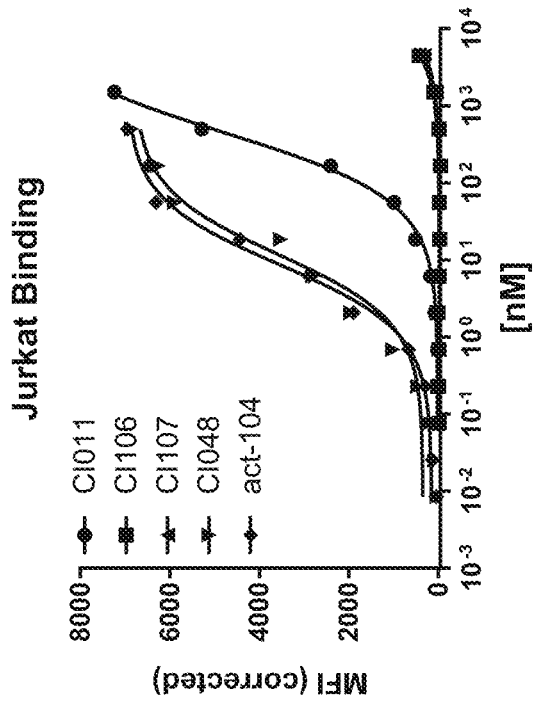

FIG. 1A demonstrates that incorporation of the h20GG CD38 masking peptide into the EGFR masked BAAs CI106 and CI107 significantly reduced binding to Jurkat cells relative to CI011. In some embodiments, the reduction in binding to Jurkat cells was more than 5,000-fold. In some embodiments, an scFv of the disclosure also led to reduced binding. A reduction in binding to EGFR+HT29-luc2 cells was also evident for CI106 and CI107 relative to CI011 (FIG. 1B). In some embodiments, the reduction in binding to EGFR+HT29-luc2 cells was more than 1,000-fold. In FIG. 1A and FIG. 1B, the dually masked, BAAs exhibit reduced binding relative to the activated bispecific antibodies.

Example 3. EGFR-Dependent Cytotoxicity of Dually Masked BAAs

To determine if the CD38 and EGFR masks and the protease substrates in CI106 and CI107 could further attenuate cell killing relative to CI011 and CI040, a cytotoxicity assay was performed. Human PBMCs were purchased in frozen aliquots (HemaCare) and co-cultured with EGFR expressing HT29-luc2 cells at a ratio of 10:1 in RPMI-1640+glutamax supplemented with 5% heat inactivated human serum (Sigma, Catalog H3667). Titrations of the following bispecific, activated antibodies and dually masked BAAs were tested: CI011, CI040, activated CI104, CI106, and CI107. In addition, non-EGFR binding, masked bispecific, AAs CI127 and CI128 were used to demonstrate the EGFR dependence of cytotoxicity. After 48 hours, cytotoxicity was evaluated using the ONE-Glo™ Luciferase Assay System (Promega, Catalog E6130). Luminescence was measured on the Infinite M200 Pro (Tecan). Percent cytotoxicity was calculated and plotted in GraphPad PRISM with curve fit analysis. EGFR receptor number on a panel of cell lines was quantified by flow cytometry using QIFIKIT (Dako).

Figure 2A:
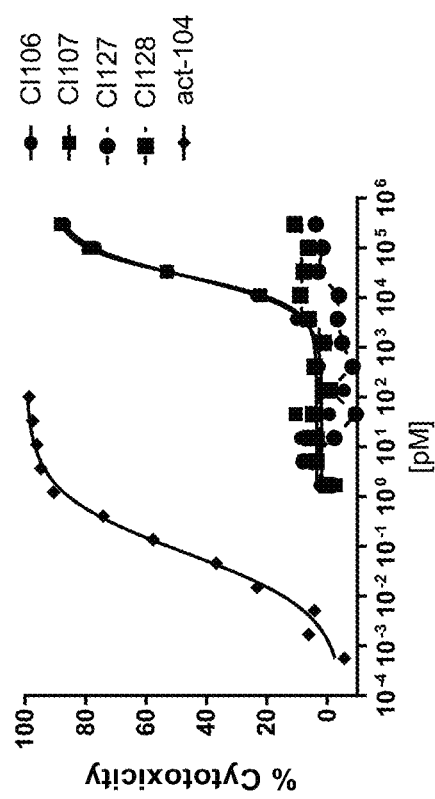
FIG. 2A demonstrates that killing of EGFR+HT29-luc2 cells was further attenuated by CI106 and CI107 relative to CI011 and CI040.
Figure 2B:
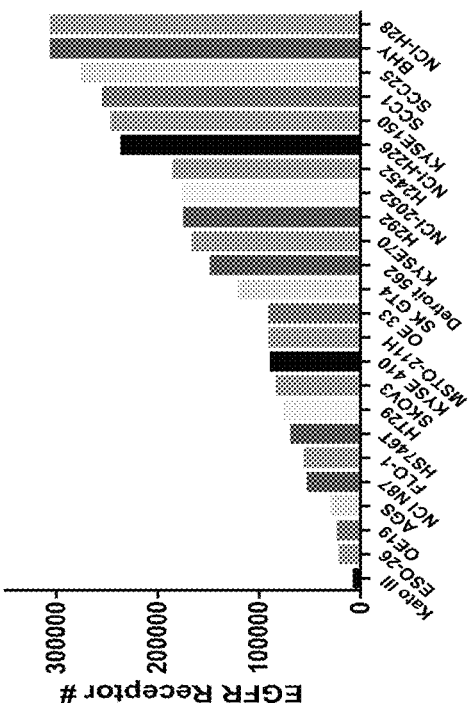
FIG. 2B shows that no detectable cytotoxicity was observed when cells were treated with CI127 and CI128 demonstrating the dependence of EGFR targeting for cell killing.
Figure 2C:
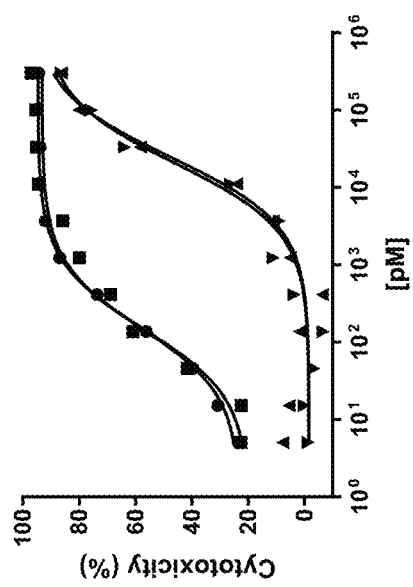
FIG. 2C depicts the EGFR receptor number on a panel of cell lines that includes HT29. The approximate EGFR receptor number on HT29 cells was 75,000, indicating that high antigen density was not required for potent cytotoxicity of the tested BAAs.

FIG. 2A demonstrates that killing of EGFR+HT29-luc2 cells was further attenuated by CI106 and CI106 relative to CI011 and CI040. FIG. 2B shows that no cytotoxicity was observed when cells were treated with CI1127 and CI1128 demonstrating the dependence of EGFR targeting for cell killing. Additionally, FIG. 2B depicts a more than 300,000 fold EC50 shift of the dually masked bispecific antibodies CI106 and CI107 relative to the protease activated bispecific antibody act-104. FIG. 2C depicts the EGFR receptor number on a panel of cell lines that includes HT29. The approximate EGFR receptor number on HT29 cells was 75,000, indicating that high antigen density was not required for potent cytotoxicity of the tested antibodies.

Example 4. Primary T Cell Activation by Dually Masked BAAs

To determine if the CD3ε and EGFR masks in CI106 and CI107 could attenuate primary T cell activation relative to CI011 and CI040, a flow cytometry assay was performed. Human PBMCs and U266 cells were co-cultured according to the conditions described in Example 3. After a 48 hour incubation, cells were pelleted, media was removed, and cells were resuspended in 50 µl of a cocktail containing anti-CD45 VioBlue® (Miltenyi, Catalog 130-002-880), anti-CD8 APC-Vio770 (Miltenyi, Catalog 130-096-561) and anti-CD69 PE (BD Pharmingen, Catalog 555531) in FACS Stain Buffer+2% FBS. Cells were stained for 1 h at 4° C. with shaking, harvested, washed, and re-suspended in a final volume of 60 µL FACS Buffer. Data was acquired on a MACSQuant® Analyzer 10 (Miltenyi) and activation was quantified in FlowJo® V10 (Treestar) as the percentage of CD8+ T cells with expression of CD69 above the PE isotype control. Data was plotted in GraphPad PRISM 6 with curve fit analysis.

FIG. 3A demonstrates that activation of primary CD8+ T cells was attenuated by CI106 and CI107, relative to CI011 and CI040. FIG. 3B demonstrates that dually masked antibodies display a shifted dose response curve for T cell activation relative to protease activated bispecific antibody act-104 indicating that masking attenuates T cell activation.

Example 5. Dually Masked, Bispecific, AAs of the Embodiments Induced Regression of Established HT29-Luc2 Tumors in Mice In this example, dually masked BAAs CI106 and CI107 targeting EGFR and CD3ε were analyzed for the ability to induce regression or reduce growth of established HT-29-Luc2 xenograft tumors in human T-cell engrafted NSG mice.

The human colon cancer cell line HT29-luc2 was obtained from Perkin Elmer, Inc., Waltham, Mass. (formerly Caliper Life Sciences, Inc.) and cultured according to established procedures. Purified, frozen human PBMCs were obtained from Hemacare, Inc., Van Nuys, Calif. NSG™ (NOD.Cg-Prkdcscid Il2rg$^{tm1Wjl}$/SzJ) mice were obtained from The Jackson Laboratories, Bar Harbor, Me.

On day 0, each mouse was inoculated subcutaneously at the right flank with 2×10⁶ HT29-luc2 cells in 100 μL RPMI+ Glutamax, serum-free medium. Previously frozen PBMCs from a single donor were administered (i.p.) on day 3 at a CD3+ T cell to tumor cell ratio of 1:1. When tumor volumes reached 200 mm³ (approximately day 12), mice were randomized, assigned to treatment groups and dosed i.v. according to Table 12. Tumor volume and body weights were measured twice weekly.

TABLE 12

Groups and doses for HT2-9luc2 xenograft study.

| Group | Count | Treatment | Dose (mg/kg) |
|---|---|---|---|
| 1 | 7 | PBS | N/A |
| 2 | 7 | CI106 | 0.5 |
| 3 | 7 | CI106 | 1.5 |
| 4 | 7 | CI107 | 0.5 |
| 5 | 7 | CI107 | 1.5 |

Figure 4:
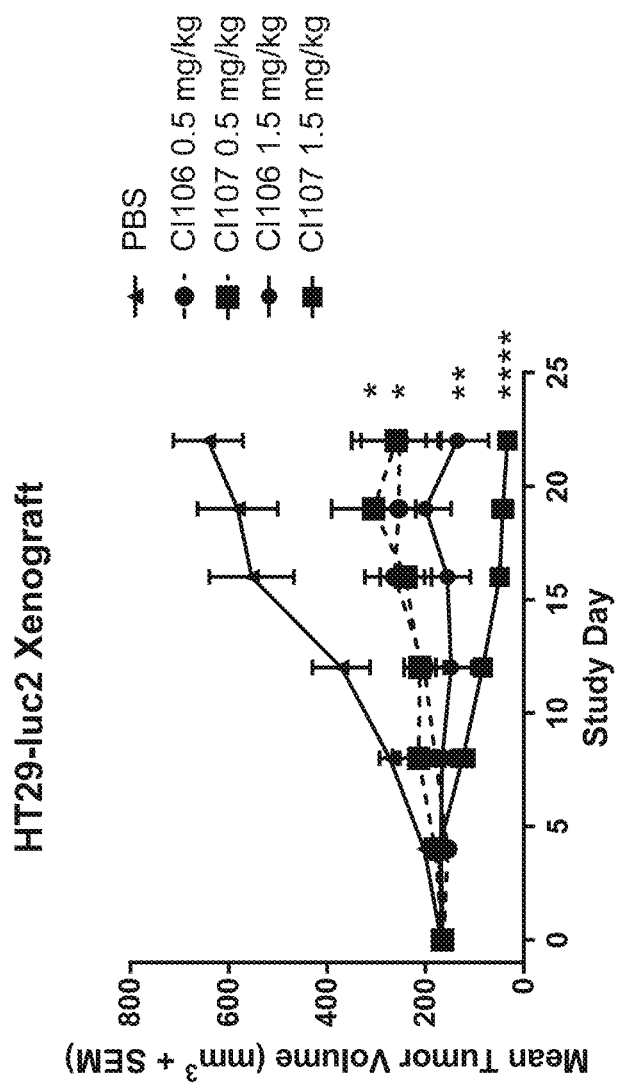
FIG. 4, which plots tumor volume versus days post initial treatment dose, demonstrates a dose-dependent effect of CI106 and CI107 dually masked, bispecific, AAs on the growth of HT29-luc2 xenograft tumors.

FIG. 4, which plots tumor volume versus days post initial treatment dose, demonstrates a dose-dependent effect of CI106 and CI107 dually masked, bispecific, AAs on the growth of HT29-luc2 xenograft tumors. The most efficacious dose tested was 1.5 mg/kg, resulting in tumor regression. Statistical analysis (RMANOVA with Dunnett's vs. PBS control) was carried out in GraphPad PRISM. $*=p<0.05$, $=p<0.01$, $**=p<0.0001$.

Example 6. Dually Masked, Bispecific, AAs and Bispecific Antibodies of the Embodiments Reduce Growth of Established HCT116 Tumors in Mice In this example, bispecific antibody, activated CI104, and dually masked BAAs CI106 and C1107 targeting EGFR and CD3ε were analyzed for the ability to induce regression or reduce growth of established HCT116 xenograft tumors in human T-cell engrafted NSG mice. The human colon cancer cell line HCT116 was obtained from ATCC and was cultured in RPMI+Glutamax+10% FBS according to established procedures. The tumor model was carried out as described in Example 5. Mice were dosed according to Table 13.

TABLE 13

Groups and doses for HCT116 xenograft study.

| Group | Count | Treatment | Dose (mg/kg) |
|---|---|---|---|
| 1 | 8 | PBS | N/A |
| 2 | 8 | CI106 | 0.3 |
| 3 | 8 | CI106 | 1.0 |
| 4 | 8 | CI107 | 0.3 |
| 5 | 8 | CI107 | 1.0 |
| 6 | 8 | act-104 | 0.3 |

Figure 5:
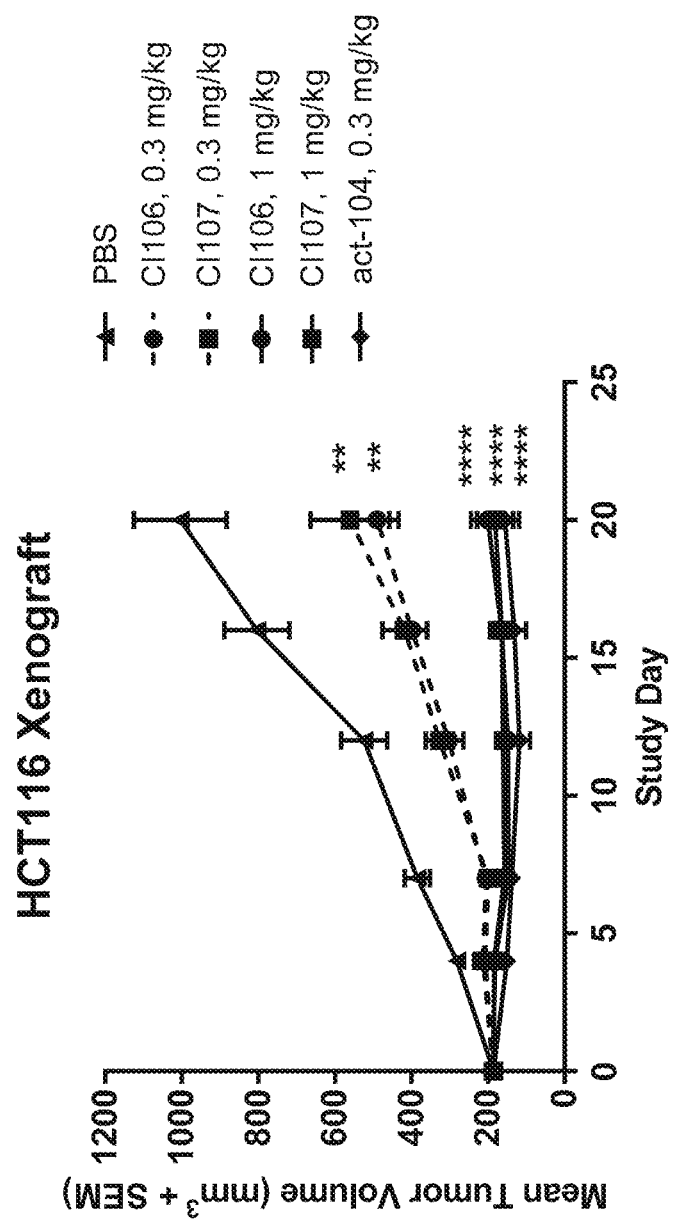
FIG. 5, which plots tumor volume versus days post initial treatment dose, demonstrated a dose-dependent effect of CI106 and CI107 dually masked, bispecific, AAs on the growth of HCT116 xenograft tumors.

FIG. 5 which plots tumor volume versus days post initial treatment dose, demonstrated a dose-dependent effect of CI106 and CI107 dually masked bispecific, AAs on the growth of HCT116 xenograft tumors. The most efficacious dose tested was 1.0 mg/kg, resulting in tumor stasis. Act-104 dosed at 0.3 mg/kg also resulted in tumor stasis, demonstrating a 3 fold difference in efficacy between dually masked and protease activated bispecific antibodies. Statistical analysis (RMANOVA with Dunnett's vs. PBS control) was carried out in GraphPad PRISM. $*=p<0.05$, $=p<0.01$, $**=p<0.0001$.

Example 7. Cross Reactivity of Dually Masked Bispecific, AAs to Cynomolgus Monkey T Cells To confirm that Cynomolgus monkey is a relevant toxicity species, protease activated CI104, CI106 and CI107 were used in a flow cytometry based cell binding assay and a HT29-luc2 cytotoxicity assay using Cynomolgus pan T cells (BioreclamationIVT) and the potency was compared to human PBMCs. Protocol was as described in Examples 2 and 3.

Figures 6A, 6B, 6C, 6D:
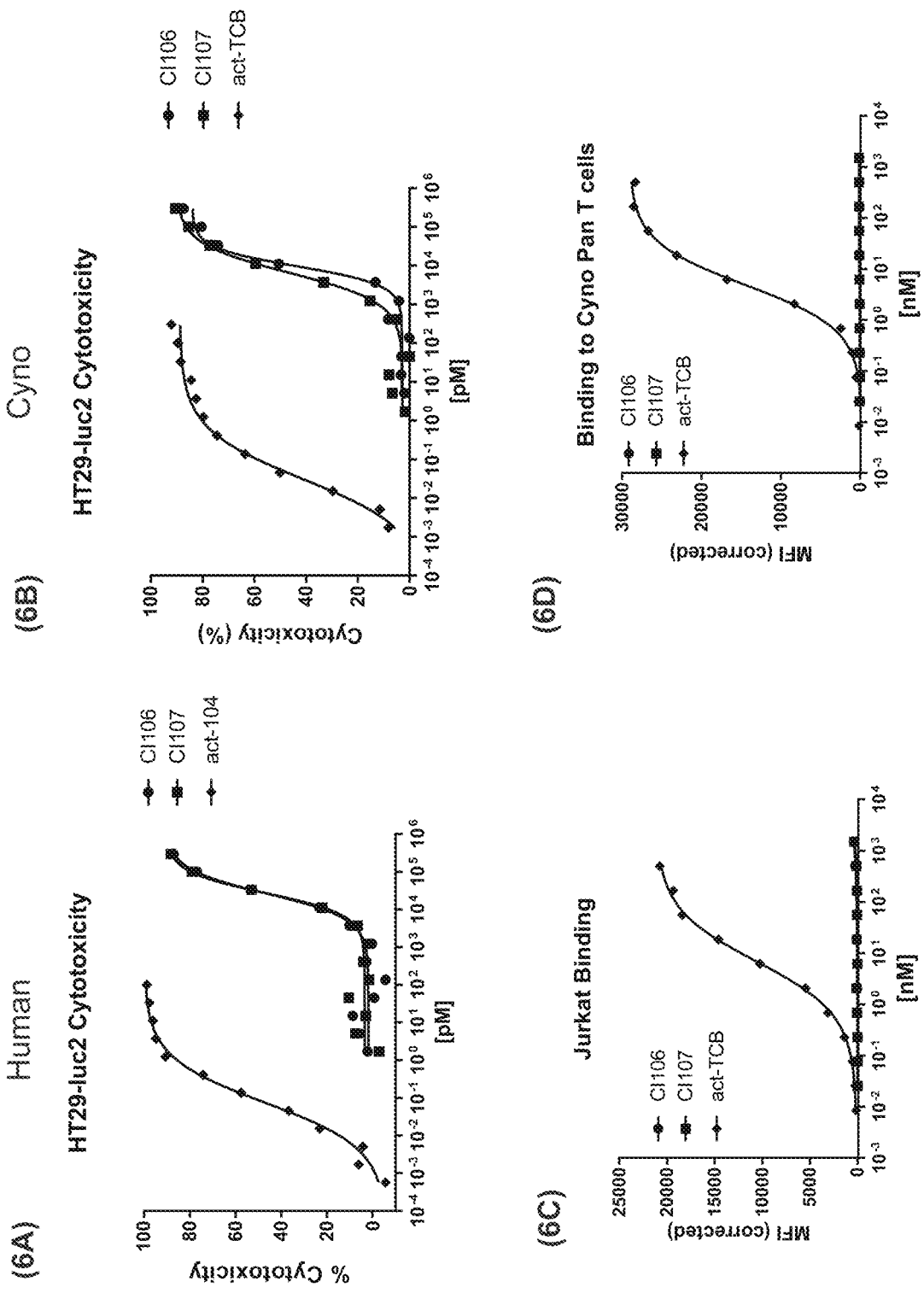

FIG. 6A and FIG. 6B demonstrate that the EC50s of the tested dually masked and protease activated bispecific antibodies in a cytotoxicity assay are similar when either human (6A) or cyno (6B) effector cells are used. FIG. 6C and FIG. 6D demonstrate that binding of the protease-activated and dually masked antibodies to human (6C) and cyno (6D) T cells is similar.

Therefore, cynomolgus monkey was determined to be a relevant species for tolerability studies.

Example 8. Mutations in the Fc Region Affect Tolerability of Dually Masked, Bispecific, AAs in Cynomolgus Monkeys In this example, CI079 and CI090 were dosed at 600, μg/kg in naïve cynomolgus monkeys (n=1) to assess tolerability. The starting dose of 600 μg/kg was chosen based on the MTD of CI011 as previously established. The monkeys were of Chinese origin and ranged in weight from 2.5 to 4 kg. Each study animal was monitored for a minimum of 7 days. Tolerability was evaluated based on clinical signs, body weight, and food consumption. This study was conducted in compliance with standard operating procedures at SNBL USA, Ltd. (Everett, Wash.).

Table 14 describes clinical observations following dosing of CI079 and CI090 dually masked, bispecific, AAs (BAAs) that differ only in their Fc regions (Table 15). CI079 contains Fc mutations L234F, L235E, and P331S. CI090 contains those Fc mutations and N297Q mutation. No clinical observations were noted following dosing of CI090 at 600 μg/kg, whereas, emesis was noted in the first 24 hours following dosing of CI079, demonstrating that mutations in the Fc region contribute to tolerability of these molecules.

TABLE 14

| BAA | Dose (μpk) | Observations |
|---|---|---|
| CI079 | 600 | emesis during 1ˢᵗ 24 hours |
| CI090 | 600 | no clinical observations |

TABLE 15

| BAA | EGFR Mask & Substrate | CD3 Mask &Substrate | Fc |
|---|---|---|---|
| CI079 | 3954 0001 | h20GG 0001 | Fcmt3 |
| CI090 | 3954 0001 | h20GG 0001 | Fcmt4 |

Example 9. Tolerability of Dually Masked BAAs in Cynomolgus Monkeys

In this example, CI106 and CI107 were dosed at 600, 2000, 4000 μg/kg (CI107 only), or 6000 μg/kg (CI107 only) to establish the maximum tolerated dose (MTD) following a single IV bolus administration to naïve cynomolgus monkeys (n=1). The starting dose of 600 µg/kg was chosen based on the MTD of CI011 as previously established. The monkeys were of Chinese origin and ranged in weight from 2.5 to 4 kg. Each study animal was monitored for a minimum of 7 days. Tolerability was evaluated based on clinical signs, body weight, food consumption and laboratory analyses that included serum chemistry, hematology, cytokine analysis, and flow cytometry to evaluate T cell activation. Blood was collected for standard serum chemistry and hematology analysis once during acclimation and at pre-dose, 48 h, 72 h (hematology only), and 7 days post dose. Blood was collected for cytokine analysis pre-dose and at 1 h, 4 h, 8 h, and 24 h post dose. Flow cytometry was performed on peripheral blood pre-dose, 72 h, and 7 days post dose. This study was conducted in compliance with standard operating procedures at SNBL USA, Ltd. (Everett, Wash.).

CI107 dosed at 6000 µg/kg was fatal within 24 hours post dose. In the other groups, abnormal clinical signs including emesis and reduced food intake were observed in cynos treated with CI106 and CI107 at doses of 2000 µg/kg and above. These findings, when present, were transient and generally confined to the 48 h post-dose period. Serum chemistry findings at these doses included mild elevations of alanine transaminase (ALT) and aspartate aminotransferase (AST) at 48 h that did not exceed normal ranges. In CI107 treated animals at 2000 and 4000 µg/kg, total bilirubin increased outside of normal range at 48 hours and was fully reversed by day 8. In both CI106 and C1107 treated animals, transient increases in serum cytokines IL-2, IL-6, and IFNg were observed after dosing and were resolved by 24 h post dose. An increase in the percentage of T cells expressing CD69, Ki67, and PD-1 was observed at 72 h post-dose and, generally, the percentage of positive cells was greater for CI107 treated animals.

Figures 7A, 7B, 7C:
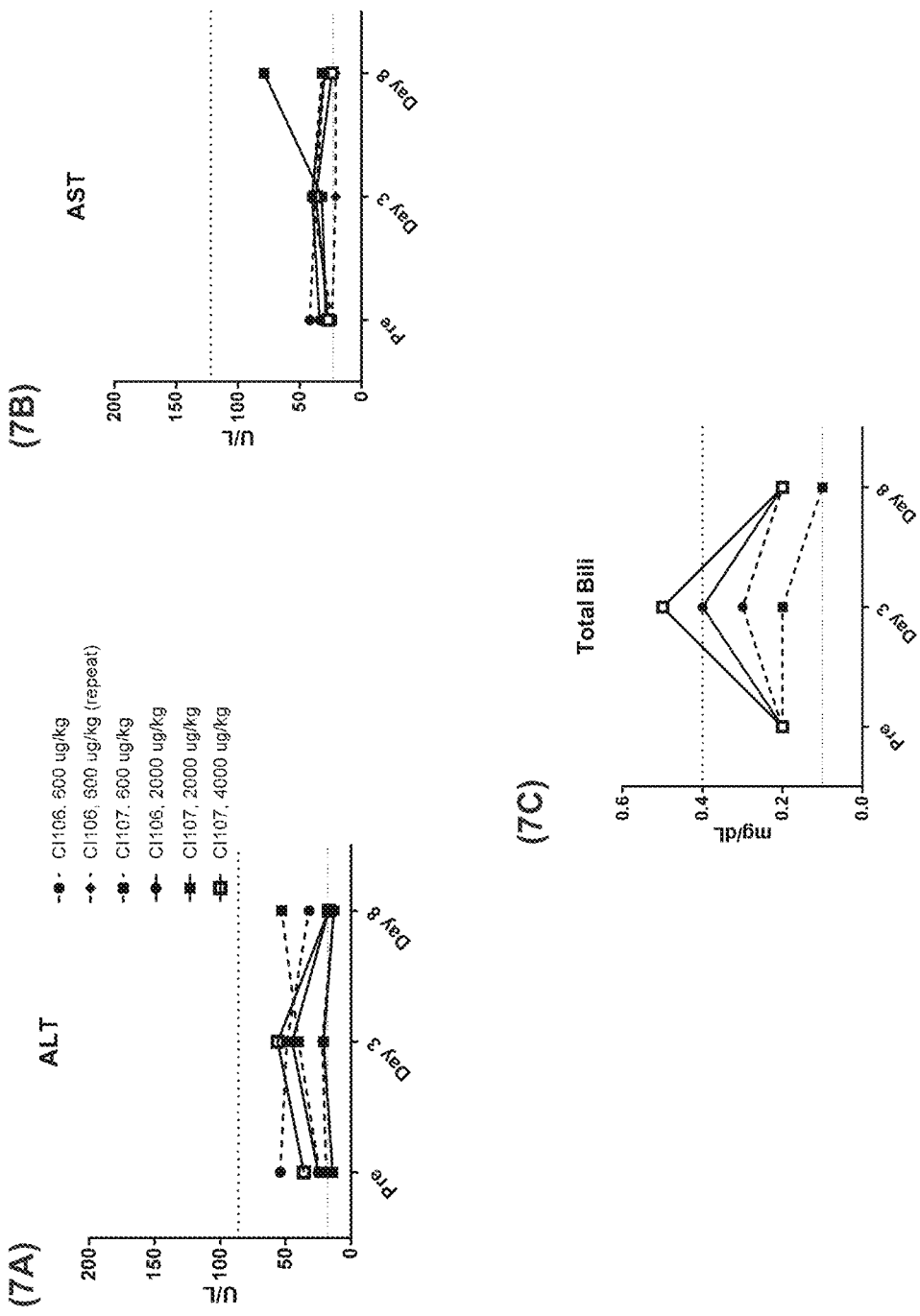
FIGS. 7A-7C depict pre-dose, 48 h, and 7 days post-dose serum concentrations of ALT (7A), AST (7B), and total bilirubin (7C) in cynomolgus monkeys treated with CI106 or CI107.

FIGS. 7A-7C depict pre-dose, 48 h, and 7 days post-dose serum concentration of ALT (7A), AST (7B), and total bilirubin (7C). With the exception of total bilirubin at 2000 and 4000 µg/kg, all values are within established normal ranges for cynomolgus monkeys. Only pre-dose data was available for CI107 at 6000 µg/kg, and was not included.

Figures 8A, 8B, 8C:
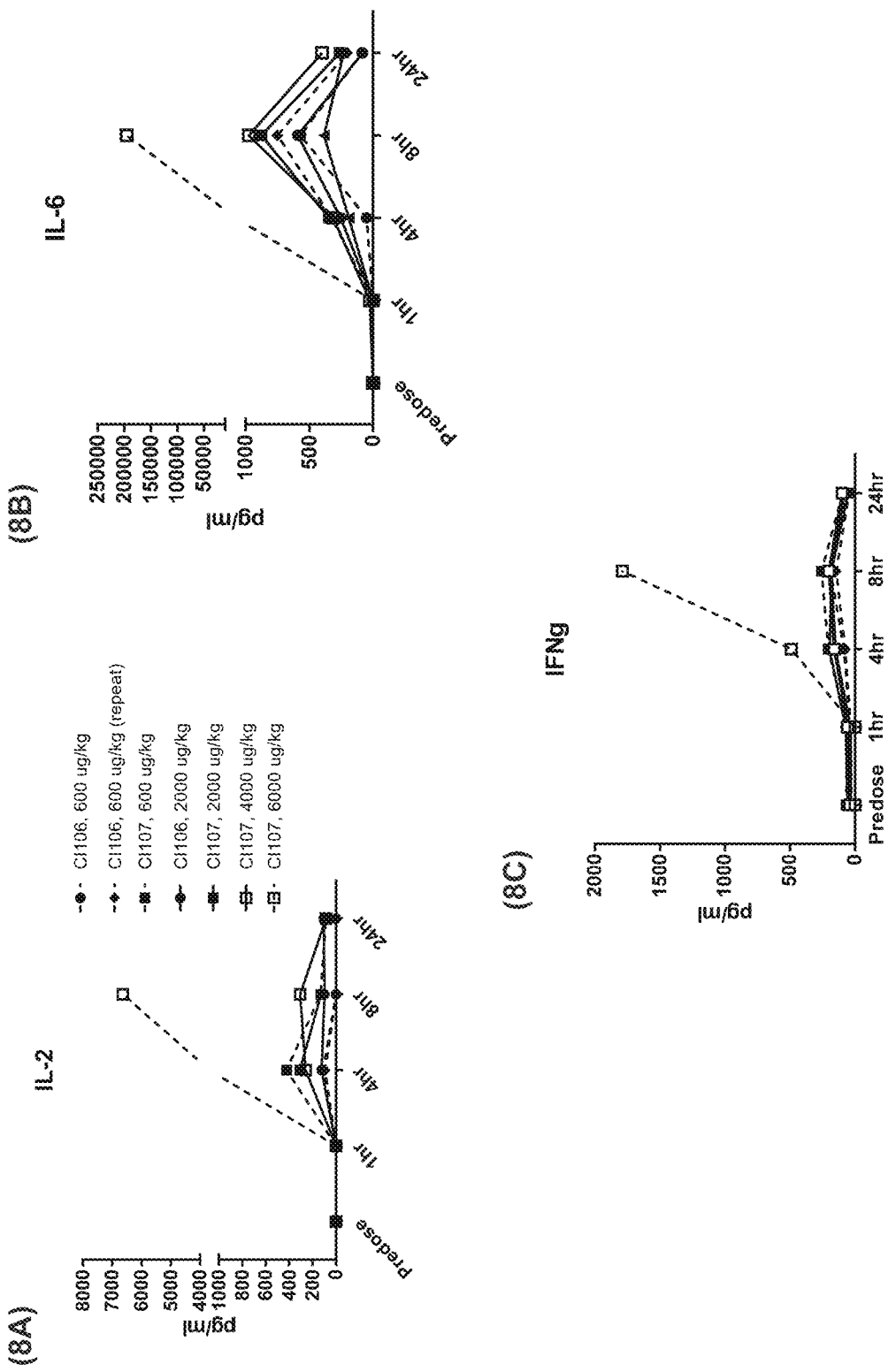
FIGS. 8A-8C plot the increase in serum cytokine levels for IL-2 (8A), IL-6 (8B), and IFN-g (8C) in cynomolgus monkeys treated with CI106 or CI107.

FIGS. 8A-8C plot the increase in serum cytokine levels for L-2 (8A), IL-6 (8B), and IFN-g (8C).

Figures 9A, 9B, 9C:
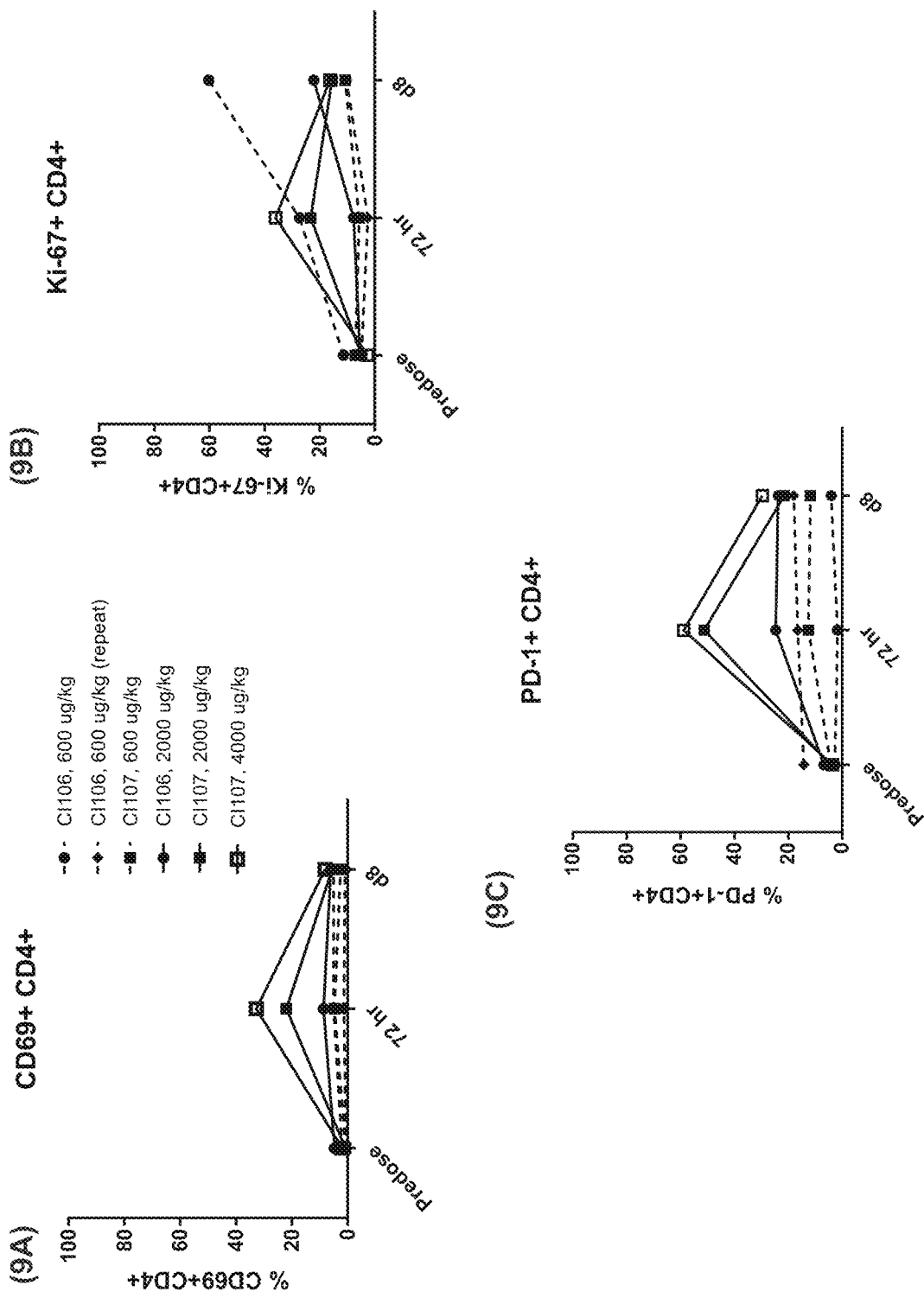
FIGS. 9A-9C depict T cell activation as measured by CD69 (9A), Ki67 (9B), and PD-1 (9B) expression on CD4+ T cells in cynomolgus monkeys treated with CI106 or CI107.

FIGS. 9A-9C depict T cell activation as measured by CD69 (9A), Ki67 (9B), and PD-1(9B) expression on CD4+ T cells.

Example 10. Dually Masked, Bispecific, AAs are Safer in Cynomolgus Monkeys than Activated Bispecific Antibodies In this example, protease activated CI104 and dually masked CI106 and CI107 were dosed in cynomolgus monkeys (n=1) at 60, 180 (activated CI104 only), 600, 2000, 4000 µg/kg (CI107 only), or 6000 µg/kg (CI107 only) to compare the tolerability of masked and unmasked antibodies following a single IV bolus. Tolerability evaluation and blood collections were as described in Example 9. Dually masked, BAAs CI106 and CI107 were tolerated at 30-60 fold higher dose level than the protease activated, bispecific antibody.

FIGS. 10A-E plot dose dependent increases in AST at 48 h post dose (10A), ALT at 48 h post dose (10B), L-6 at 8 h post dose (10C), IFNg at 8 h post dose (10D), and Ki67 at 72 h post dose (10E). The dose response curve for all parameters was shifted for the dually masked antibodies indicating improved tolerability and decreased pharmacodynamics effects relative to the protease activated bispecific antibody. In some embodiments, the L-6 dose response curve was shifted by more than 60-fold.

Example 11. Tolerability of EGFR Binding, Dually Masked, Bispecific, AAs is Dependent on EGFR In this example, dually masked bispecific antibody, CI107, targeting EGFR and CD38 and CI128, targeting RSV and CD38 were dosed at 2000 µg/kg in cynomolgus monkeys (n=1). Tolerability evaluation and blood collections were as described in Example 9 above. There was no effect of CI128 on measures of acute organ toxicity (total bilirubin) and T cell activation (IL-6, PD-1) demonstrating that the toxicity observed in cyno was dependent on EGFR binding. These data also demonstrate that CD38 binding alone was not sufficient to induce toxicity.

Figures 11A, 11B, 11C:
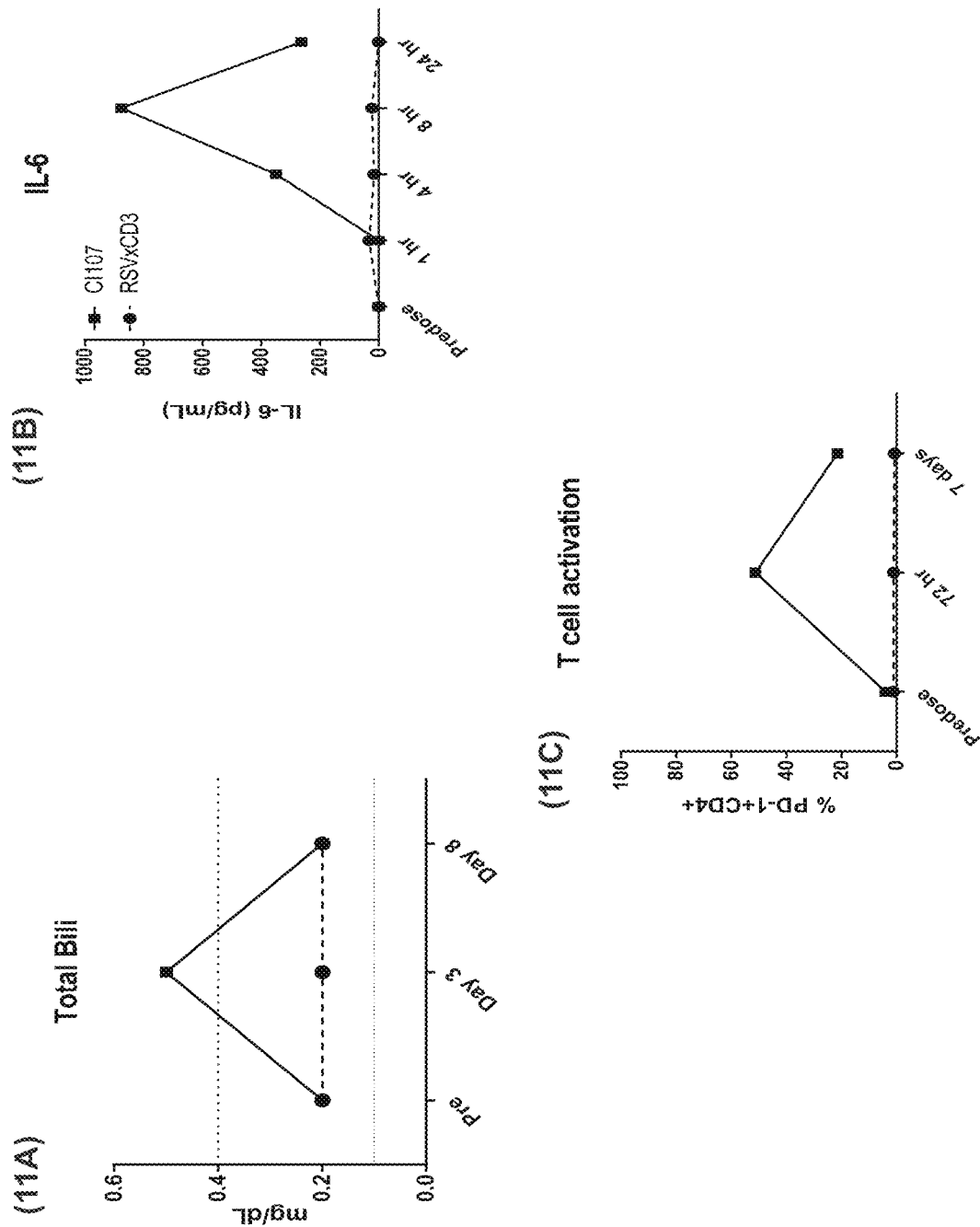
FIGS. 11A-11C compare the effects of EGFR-binding CI107 and non-EGFR-binding CI128 (RSV×CD3) on increases in total bilirubin (11A), IL-6 (11B), and PD-1 expressing CD4+ T cells (11C) in cynomolgus monkeys treated with CI107 or CI128.

FIGS. 11A-11C compares the effects of EGFR binding CI107 and non EGFR binding CI128 on increases in total bilirubin (11A), L-6 (11B), and PD-1 expressing CD4+ T cells (11C).

Example 12. Humanization of Anti-CD3 Variants v12, v16, and v19 which have Different Affinities and Potencies This example describes anti-CD3 antibody variants v12, v16, and v19. These three variants were derived from the parent antibody hSP34

Humanization of the anti-human CD3 single-chain variable fragment (scFv) was performed by selectively mutating the framework. Briefly, CDRs were grafted into a series of light chain (LC) and heavy chain (HC) human IgG scaffolds and a number of amino acids in the variable region framework was selectively mutated. Immunoglobulins were expressed in all possible combinations of LC and HC, and then evaluated for expression level, percent monomer, and CD3 affinity using ELISA and on-cell binding to Jurkat cells. The variable regions of desirable combinations were expressed as scFv in the bispecific antibody (TCB) format and then evaluated for expression levels, percent monomer, CD3 affinity and function in cell cytotoxicity assays.

The affinity of v12, v16, and v19 variant was measured using surface plasmon resonance (SPR). Surfaces were HC200m, carboylated hydrogel based on a linear, synthetic polycarboxylate. Surface channels were activated with a standard EDC/NHS amine coupling protocols. Channels 1 and 2 were blank, Channels 3 and 4 were various anti-human CD3 antibodies. Surfaces were generated by diluting v12, v16, v19 and MM194 antibodies to 5 µg/ml in 1.0 mL 10 mM Sodium Acetate pH 4.5.

Kinetic analysis was performed in PBST (10 mM Sodium Phosphates, pH 7.4, 150 mM Sodium Chloride, 0.05% TWEEN® 20) at 20° C. Regeneration was a series of three injections; a single 5 µl injection of 20 mM Sodium Hydroxide followed by two 5 µL injection of 10 mM Sodium Hydroxide freshly-made.

The configuration was run with an inverse 3-fold serial dilution alternating with buffer blanks. Human CD3egFc was from Sino Biological Inc., (Beijing, China, Catalog #CT041-H0305H) reconstituted with sterile water from a lyophilized formulation based on PBS and stabilizers. Serial dilutions with the analyte in solution from concentrations starting at 300 nM or 100 nM human CD3. Processing was done with Scrubber software.

These variants were also engineered using described methods into dually masked, bispecific, AAs targeting EGFR and CD3 and used in an in vitro cytotoxicity assay as described in example 3.

Figures 12A, 12B:
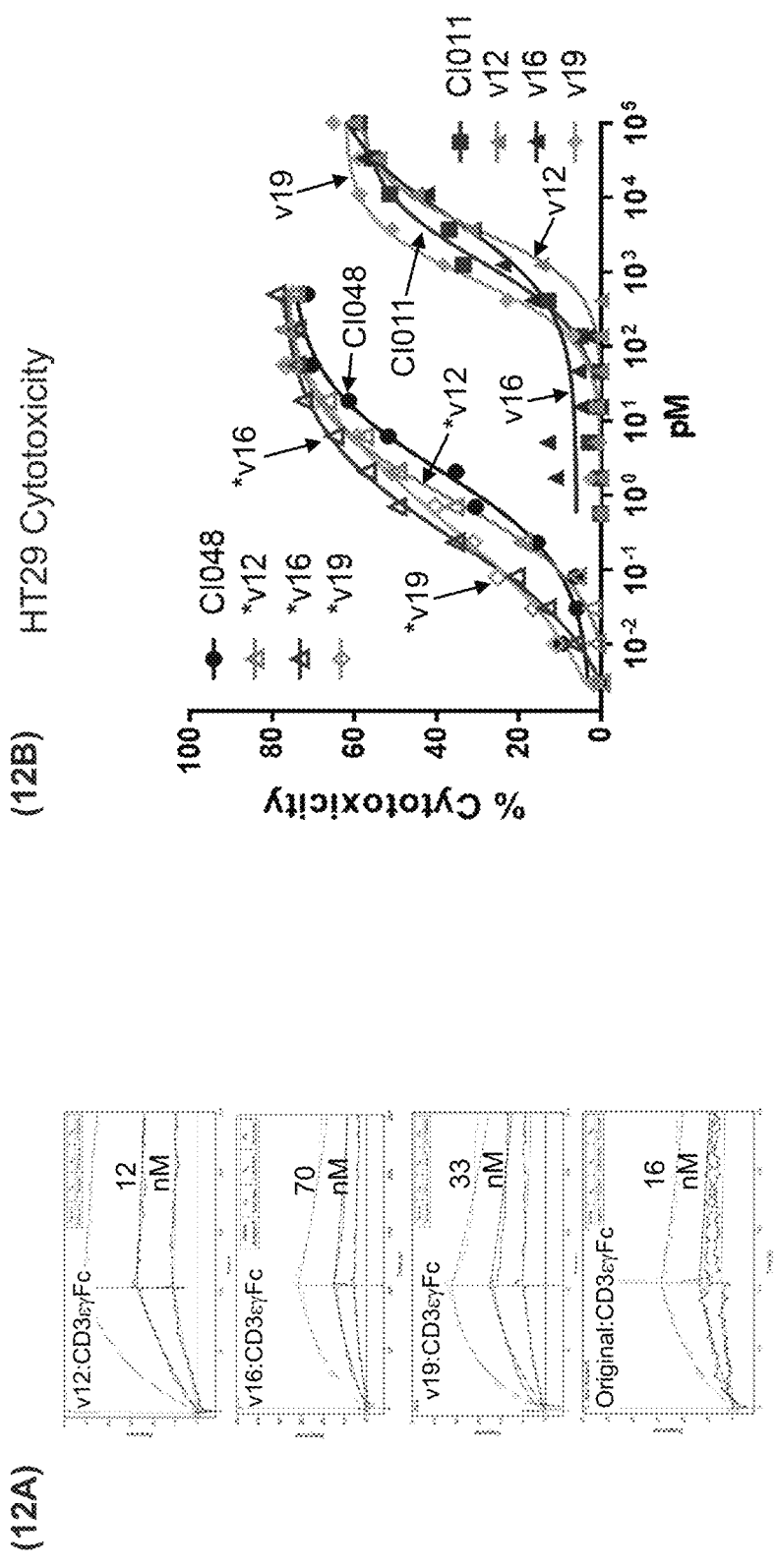
FIG. 12A depicts the affinity measurements of v12, v16, and v19 CD3 antibodies relative to hSP34.
FIG. 12B depicts the cytotoxicity of activated or dually masked, bispecific antibodies on HT29-luc2 cells.

FIG. 12A depicts the affinity measurements of v12, v16, and v19 relative to hSP34. V12 was the highest affinity at 12 nM while v16 was the lowest affinity at 70 nM.

FIG. 12B depicts the cytotoxicity of activated or dually masked, bispecific antibodies on HT29-luc2 cells. There were slight differences in the potency of cell killing of the activated molecules with v16 being the most potent. There are also slight differences in protection against cell killing for the dually masked molecules.

Example 13. Dually Masked BAAs Enable Extended PK in Cynomolgus Monkeys

In this example, protease activated, bispecific antibody act-104 and dually masked, bispecific antibody CI107 were dosed at 60 µg/kg, 180 µg/kg (act-104) or 2000 µg/kg (CI107) in cynomolgus monkey. Plasma samples were collected at 5 min (act-104 only), 30 min, 4 h (act-104 only), 24 h, 48 h (act-104 only), 96 h, and 168 h. Plasma concentration was measured by ELISA using an anti-idiotype antibody to capture, a horseradish peroxidase (HRP) labeled anti-human IgG (Fc) for detection, and visualized using 3,3',5,5'-tetramethylbenzidine (TMB). Plasma concentration values were interpolated from a standard curve and plotted using GraphPad PRISM. Area under the curve (AUC) analysis was also performed.

Figure 13:
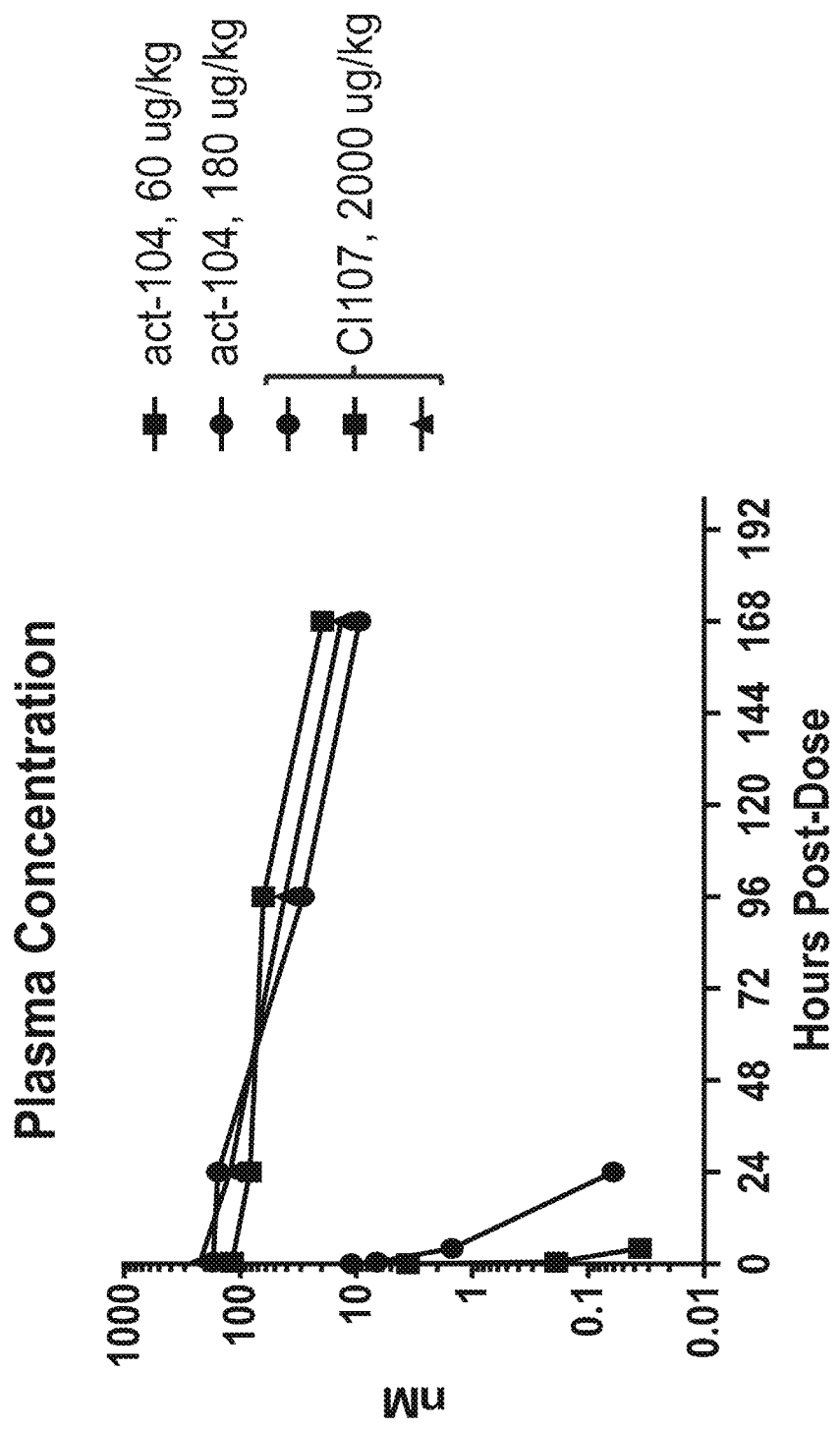
FIG. 13 depicts the extended PK of the dually masked antibody, CI107, relative to the protease activated bispecific antibody, act-104.

FIG. 13 depicts the extended PK of the dually masked molecule, C1107, relative to the protease activated molecule, act-104. Exposure (AUC) of C1107 was 448 day*nM and act-104 (60 µg/kg) was 0.04 day*nM representing a greater than 10,000 fold difference in plasma exposure.

Example 14. Sensitivity to Protease Cleavage of Dually Masked, Bispecific, AAs Correlates to Tumor Efficacy and Tumor T Cell Infiltration This example describes anti-tumor efficacy and tumor T cell infiltration in a HT29-luc2 xenograft model. The model was carried out as described in example 5. In the tumor T cell infiltration study, mice received a single dose of test article and tumors were harvested 7 days post dose. Formalin fixed paraffin embedded (FFPE) blocks were created to use for histology. Test articles used are CI011, C1020 (a dually masked bispecific antibody devoid of a cleavable substrate), C1040, and C1048. Protease sensitivity and substrate cleavability of the test articles is as follows: CI040>CI011>C1020. Mice were dosed according to Table 16.

TABLE 16

Groups and doses for HT29-luc2 xenograft study.

| Group | Count | Treatment | Dose (mg/kg) | Study |
|---|---|---|---|---|
| 1 | 8 | PBS | N/A | Efficacy |
| 2 | 8 | CI011 | 0.3 | Efficacy |
| 3 | 8 | CI020 | 0.3 | Efficacy |
| 4 | 8 | CI040 | 0.3 | Efficacy |
| 5 | 8 | CI048 | 0.3 | Efficacy |
| 6 | 5 | PBS | N/A | Infiltration |
| 7 | 5 | CI011 | 1.0 | Infiltration |
| 8 | 5 | CI020 | 1.0 | Infiltration |
| 9 | 5 | CI040 | 1.0 | Infiltration |
| 10 | 5 | CI048 | 1.0 | Infiltration |

Figure 14A:
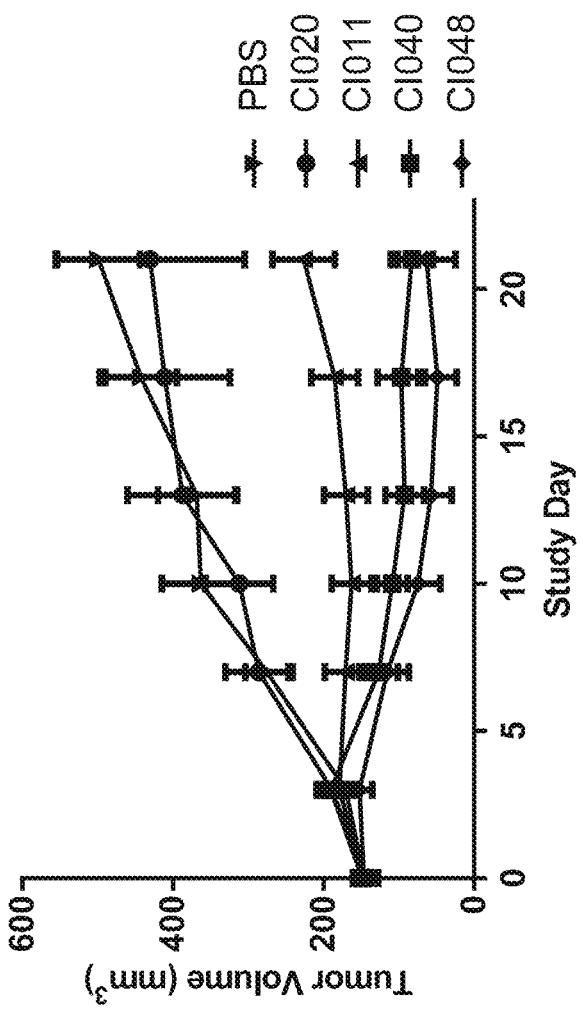
FIG. 14A depicts efficacy in a HT29-luc2 tumor intervention model in PBMC engrafted NSG mice. Anti-tumor potency in this example correlates to protease sensitivity and substrate cleavability of the test articles, with the most efficacious test article being the fully protease activated C1048.

FIG. 14A depicts efficacy in a HT29-luc2 tumor intervention model in PBMC engrafted NSG mice. Anti-tumor potency in this example correlates to protease sensitivity and substrate cleavability of the test articles, with the most efficacious test article being the fully protease activated CI048.

Figure 14B:
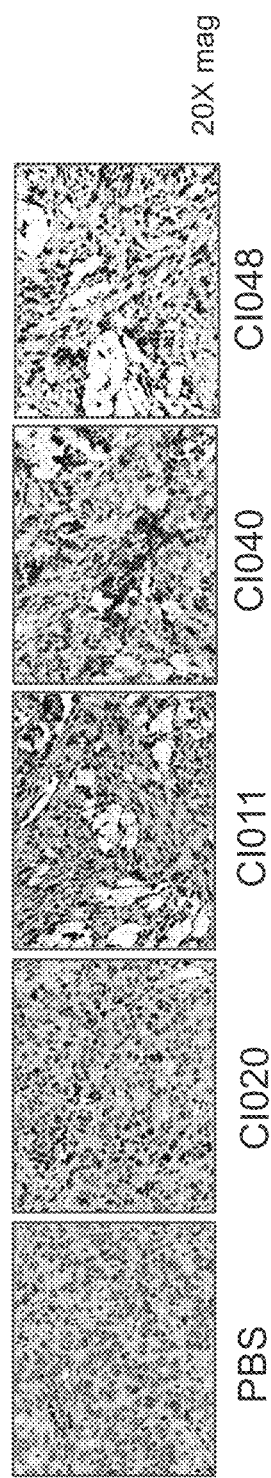
FIG. 14B depicts staining of tumor sections for CD3 (dark staining) as a measure of the degree of T cell infiltration into tumors. Tumor T cell infiltration correlates with protease sensitivity and substrate cleavability of the test articles.
Figure 15:
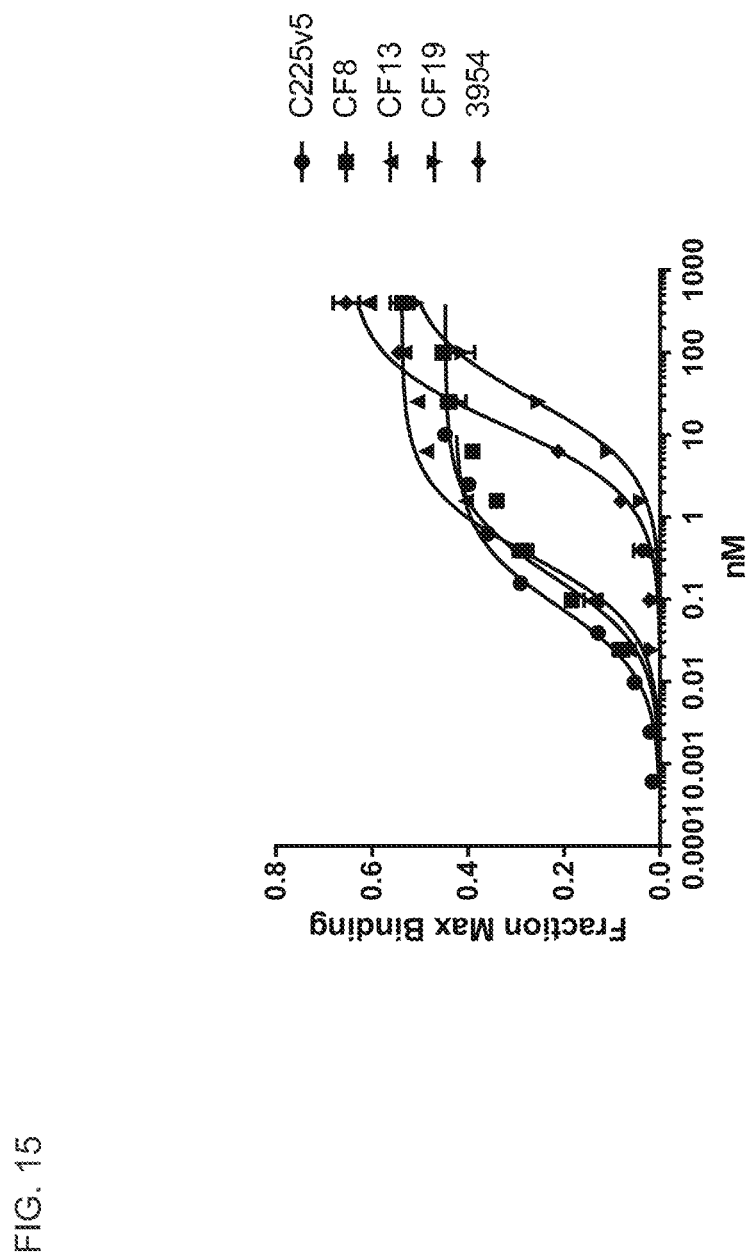
FIG. 15 and FIG. 16 are plots of binding isotherms for activatable anti-EGFR C225v5 antibodies of the disclosure, for activatable anti-EGFR antibody 3954-2001-C225v5 described herein, and for anti-EGFR antibody C225v5.
Figure 16:
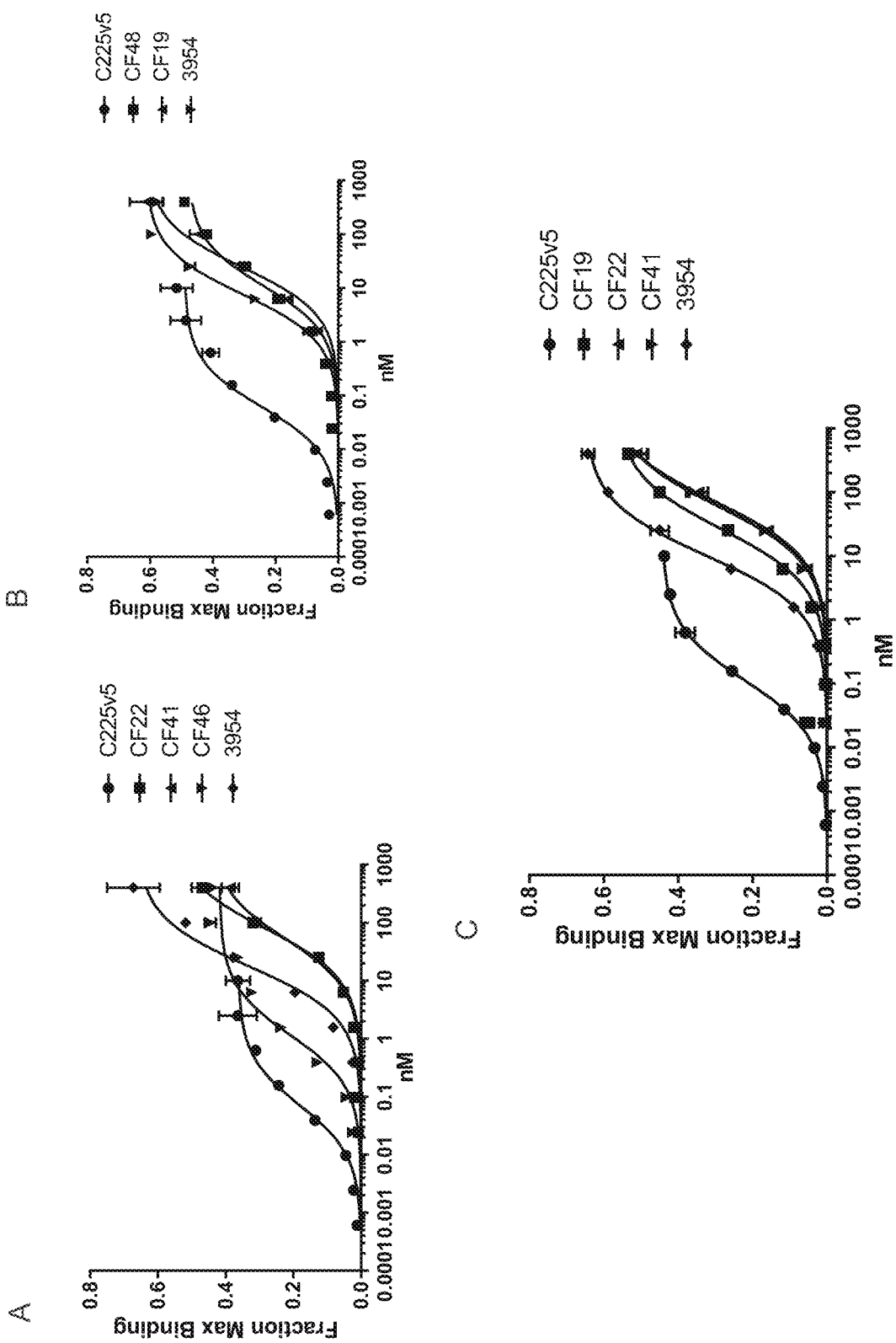

FIG. 14B depicts staining of tumor sections for CD3 (dark staining) as a measure of the degree of T cell infiltration into tumors. Tumor T cell infiltration correlates with protease sensitivity and substrate cleavability of the test articles.

Example 15. Second Generation Dually Masked, Bispecific, AAs are Safer in Cynomolgus Monkeys than First Generation Molecules In this example, cynomolgus tolerability data was compared for CI011, CI040, CI048 (first generation molecules), act-104, CI106, and CI107 (second generation molecules). Data presented in this example was compiled from two cyno tolerability studies. Protease activated CI104 and CI048 were dosed in cynomolgus monkeys at 20 (CI048 only), 60 or 180 µg/kg (act-104 only). Dually masked CI011, CI040, CI106 and CI107 were dosed at 600, 2000, 4000 (CI107 only), or 6000 (CI107 only) µg/kg to compare the tolerability of dually masked and activated bispecific antibodies following a single IV bolus. Tolerability evaluation was as described in Example 8.

Table 17 summarizes the clinical observations following a single dose of test article. Second generation, protease activated bispecific antibody act-104 was tolerated at 2-fold higher dose than first generation protease activated bispecific antibody CI048. CI106 and CI107 were tolerated at 30-60-fold higher dose than first generation antibodies CI011 and CI040.

TABLE 17

| BAA | Dose (µg/kg) | Clinical Observations |
|---|---|---|
| CI048 | 20 | 1. Emesis and hunching in $1^{st}$ 24 hrs |
| (n = 2) | | 2. None |
| | 60 | Emesis at 4 hr; hunching lasting 4 days and inappetence lasting 2 days; 10% weight loss |
| CI011 | 600 | 1. None |
| (n = 3) | | 2. Emesis at 4 hrs, inappetence on day 4 |
| | 2000 | 3. Hunching and inappetence through day 5. 5% weight loss Emesis days 1-2, inappetence days 2-4 |
| CI040 | 600 | 1. Emesis at 4 hr |
| (n = 2) | | 2. Emesis within 12 hrs, inappetence on day 4 |
| | 2000 | Emesis days 1-2, moribund and euthanized day 2 |
| act-104 | 60 | Emesis and hunching in $1^{st}$ 24 hrs |
| CI104 | 180 | Severe emesis; hunching, paleness, inappetence lasting 3 days |
| CI106 | 600 | none |
| | 2000 | none |
| CI107 | 600 | None |
| | 2000 | Emesis, once in $1^{st}$ 24 hrs |
| | 4000 | Emesis, multiple incidences in $1^{st}$ 24 hrs |
| | 6000 | Severe emesis; bloody diarrhea |

Example 16. Evaluation of Masking Efficiencies of Activatable Anti-EGFR Antibodies Masking the ability of an antibody to bind to its antigen is an example of inhibition of binding and is enumerated herein as masking efficiency (ME). Masking efficiency can be calculated as the $K_D$ for binding of the AA divided by the $K_D$ for binding of the antibody measured under the same conditions. The extent of inhibition is dependent on the affinity of the antibody for its antigen, the affinity of the inhibitor (i.e., the masking moiety) for the antibody and the concentration of all reactants. Local concentrations of the tethered masking moiety peptide (inhibitor) is very high in the AA context, on the order of 10 mM, therefore moderate affinity peptides would effectively mask AA antigen binding.

The general outline for this assay is as follows: Nunc, Maxisorp™ plates are coated overnight at 4° C. with 100 μl/well of a 1 μg/mL solution of human EGFR (R and D Systems) in PBS, pH 7.4. Plates are washed 3X PBST (PBS, pH 7.4, 0.05% TWEEN® 20), and wells are blocked with 200 μl/well, 10 mg/mL BSA in PBST for 2 hours at RT. Plates are washed 3X PBST (PBS, pH 7.4, 0.05% TWEEN® 20). Dilution curves can be prepared, in 10 mg/mL BSA in PBST, as illustrated below in Table 18. In this example the highest concentrations are 10 nM for the parental antibody and 400 nM for the AAs, however, the top concentrations can be increased or decreased to give full saturation binding curves for AAs with stronger or weaker masking.

TABLE 18

Plate layout for masking efficiency assay.

| | [Antibody] = nM Columns 1-3 | [AA 1] = nM Columns 4-6 | [AA 2] = nM Columns 7-9 | [AA 3] = nM Columns 10-12 |
|---|---|---|---|---|
| A | 10 | 400 | 400 | 400 |
| B | 2 | 100 | 100 | 100 |
| C | 0.625 | 25 | 25 | 25 |
| D | 0.156 | 6.25 | 6.25 | 6.25 |
| E | 0.039 | 1.56 | 1.56 | 1.56 |
| F | 0.0097 | 0.39 | 0.39 | 0.39 |
| G | 0.0024 | 0.098 | 0.098 | 0.098 |
| H | 0.0006 | 0.024 | 0.024 | 0.024 |

The binding solutions are added to the plates, which are then are incubated for 1 hour at room temperature, and then washed 3X PBST (PBS, pH 7.4, 0.05% TWEEN® 20). 100 μl/well 1:4000 dilution goat-anti-human IgG (Fab specific, Sigma cat #A0293) in 10 mg/mL BSA in PBST is added, and the plate is incubated for 1 hour at room temperature. The plate is developed with TMB and IN HCL. Shown in FIG. 15 and FIG. 16 are plots of binding isotherms for activatable anti-EGFR C225v5 antibodies of the disclosure, for activatable anti-EGFR antibody 3954-2001-C225v5 described above, and for anti-EGFR antibody C225v5. Plots are generated in GraphPad PRISM and the data are fit to a model of single site saturation and a $K_D$ is determined. The $K_D$ and ME values are provided in Table 19.

TABLE 19

$K_D$ and ME values calculated from the binding isotherms shown in FIG. 15 and FIG. 16

| | $K_D$ (nM) | ME |
|---|---|---|
| 3954-2001-C225v5 | 13 | 130 |
| CF08-2001-C225v5 | 0.2 | 2 |
| CF13-2001-C225v5 | 0.3 | 3 |
| CF19-2001-C225v5 | 27 | 270 |
| CF22-2001-C225v5 | 78 | 780 |
| CF41-2001-C225v5 | 52 | 520 |
| CF46-2001-C225v5 | 1 | 10 |

Example 17. Pharmacokinetics of Dually Masked BAAs in Cynomolgus Monkeys

In this example, dually masked bispecific antibody CI107 was dosed at 600 μg/kg, 2000 μg/kg, or 4000 μg/kg in cynomolgus monkey. Plasma samples were collected at 30 min, 4 h (600 μg/kg only), 24 h, 48 h (600 and 4000 μg/kg only), 96 h, and 168 h. Plasma concentration was measured by ELISA as in example 13.

FIG. 20 depicts the PK of the dually masked BAA CI107 following a single i.v. dose of either 600, 2000, or 4000 μg/kg.

Example 18. EGFR-Dependent Cytotoxicity of Dually Masked, Bispecific, Activatable Antibodies To determine whether the anti-CD3ε, CD3 mask, and protease substrates in CI090 and CI091 could further attenuate cell killing relative to CI011, a cytotoxicity assay was performed using the method described in Example 3. Titrations of the following bispecific, activated antibodies and dually masked, bispecific, activatable antibodies were tested: CI011, CI090, CI091, activated CI090, and CI048. In addition, non-EGFR binding, bispecific, activatable antibody CI064 was used to demonstrate the EGFR dependence of cytotoxicity.

FIG. 21 demonstrates that killing of EGFR+HT29-luc2 cells was further attenuated by CI090 and CI091 relative to CI011, however the potency of the activated CI090 is equivalent to CI048. The EC50 shift of CI090 and CI091 relative to activated bispecific antibody is increased representing increased masking efficiency of these molecules relative to CI011. No cytotoxicity was observed when cells were treated with CI064, demonstrating the dependence of EGFR targeting for cell killing.

Example 19. Primary T Cell Activation by Dually Masked, Bispecific, Activatable Antibodies To determine if the anti-CD3, CD3 mask, and protease substrates in CI090 and CI091 could attenuate primary T cell activation relative to CI011, a flow cytometry assay was performed as described in Example 4.

FIG. 22 demonstrates that activation of primary CD8+ T cells was further attenuated by CI090 and CI091, relative to CI011.

Example 20. Dually Masked, Bispecific, Activatable Antibodies of the Embodiments Induced Regression of Established HT29-Luc2 Tumors in Mice In this example, bispecific activatable antibodies CI011, CI090, and CI091 were analyzed for the ability to induce regression or reduce growth of established HT-29-Luc2 xenograft tumors in human PBMC engrafted NSG mice. The method is as described in Example 5.

TABLE 20

Groups and doses for HT-29-luc2 xenograft study.

| Group | Count | Treatment | Dose (mg/kg) |
|---|---|---|---|
| 1 | 7 | PBS | N/A |
| 2 | 7 | CI011 | 1.0 |
| 3 | 7 | CI090 | 1.0 |
| 4 | 7 | CI091 | 1.0 |

FIG. 23, which plots tumor volume versus days post initial treatment dose, demonstrates that a 1 mg/kg, weekly dose induced tumor regression for all bispecific activatable antibodies tested.

Example 21. Dually Masked, Bispecific, Activatable Antibodies Elicit Less Cytokine Release than Activated Bispecific Antibodies in Cynomolgus Monkey In this example, protease activated CI104, and dually masked CI011, CI090, and CI091 were dosed in cynomolgus monkeys (n=1) at 0.06, 0.18 (activated CI104), or 600 mg/kg (CI011, CI090, CI091). Blood was collected for cytokine analysis pre-dose and at 1 h, 4 h, 8 h, and 24 h post dose. Samples were analyzed using Life Technologies Monkey Magnetic 29-Plex Panel Kit (Product No. LCP0005M). Data was acquired on a BioRad BioPlex 200 instrument. This analysis was conducted in compliance with standard operating procedures at SNBL USA, Ltd. (Everett, Wash.).

Figure 24:
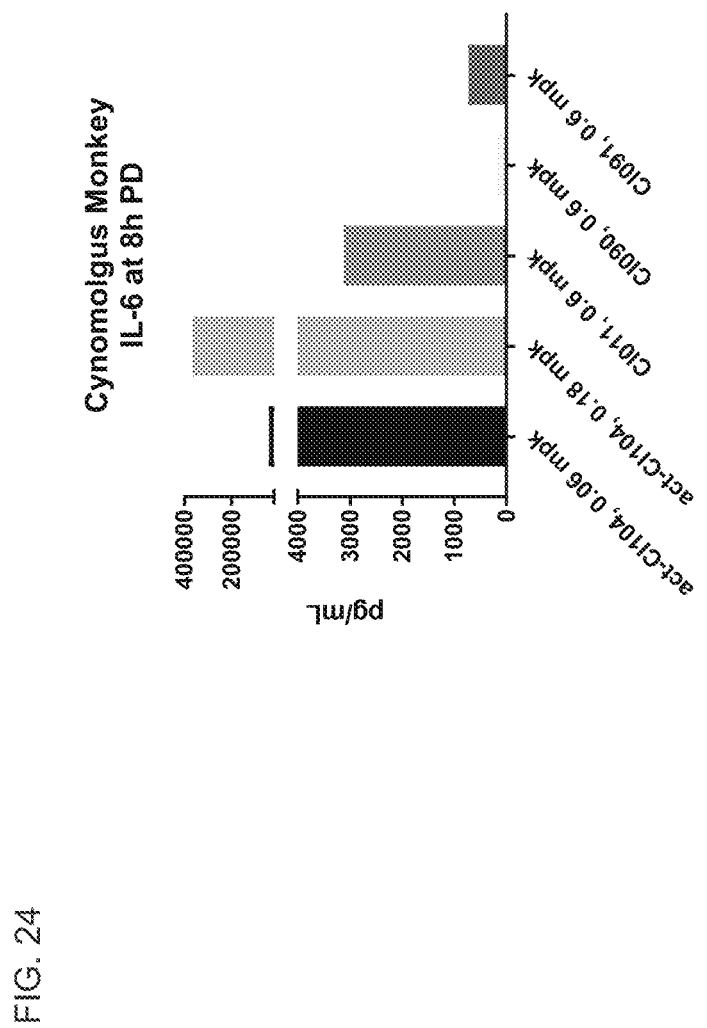
FIG. 24 plots IL-6 levels in cynomolgus monkeys in vivo study at 8 h post dose.

FIG. 24 plots IL-6 levels at 8 h post dose. The dually masked bispecific activatable antibody CI011 induces significantly less cytokine release than activated CI104 even when delivered at a higher dose, demonstrating the effect of masking on T cell activation. IL-6 is even further reduced in CI090 and CI091 treated animals reflecting the increased masking efficiency of these molecules relative to CI011.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A bispecific activatable antibody (BAA) comprising the following structure:
   a. an IgG antibody (AB1) that specifically binds to an EGFR wherein the AB1 comprises two heavy chains (AB1 HCs) and two light chains (AB1 LCs), wherein the AB1 comprises a VH CDR1 amino acid sequence comprising NYGVH (SEQ ID NO:60), a VH CDR2 amino acid sequence comprising VIWSGGNTDYN-TPFTS (SEQ ID NO:61), a VH CDR3 amino acid sequence comprising ALTYYDYEFAY (SEQ ID NO:62), a VL CDR1 amino acid sequence comprising RASQSIGTNIH (SEQ ID NO:57), a VL CDR2 amino acid sequence comprising YASESIS (SEQ ID NO:58), and a VL CDR3 amino acid sequence comprising QQNNNWPTT (SEQ ID NO:59);

wherein the AB1 comprises an Fc region comprising an amino acid substitution in at least one of amino acid positions L234, L235, N297, and P331 as numbered by the EU index as set forth in Kabat, such that the BAA has reduced effector function; and wherein the amino terminus of each of the two AB1 LCs is linked to the carboxyl terminus of a MM1-CM1 construct, wherein each MM1-CM1 construct comprises:

i. a first masking moiety (MM1), the MM1 comprising an amino acid sequence selected from the group consisting of SEQ ID NOs: 78-84; and ii. a first cleavable moiety (CM1), the CM1 being a substrate for a first protease;

wherein the MM1 is linked in an N- to C-terminal direction to the CM1, to form each MM1-CM1 construct; and b. two single chain variable antibody fragments (scFvs) (each an AB2), wherein each of the AB2s comprises a heavy chain variable domain as set forth in SEQ ID NO: 2 or SEQ ID NO: 3 and a light chain variable domain as set forth in SEQ ID NO: 1 or SEQ ID NO: 4; and wherein the carboxyl terminus of each AB2 is linked to the amino terminus of a AB1 heavy chain; and wherein each AB2 is linked to:

i. a second masking moiety (MM2), the MM2 comprising the amino acid sequence SEQ ID NO: 12; and ii. a second cleavable moiety (CM2), the CM2 being a substrate for a second protease;

wherein the MM2 is linked to the CM2 to form a MM2-CM2 construct, wherein the carboxyl terminus of each MM2-CM2 construct is linked to the amino terminus of a corresponding AB2.

2. The BAA of claim 1, wherein the MM1 comprises an amino acid sequence of SEQ ID NO: 78.

3. The BAA of claim 1, wherein the CM1 or CM2 comprises one of the following characteristics:

(a) amino acid sequence of SEQ ID NO: 14, (b) amino acid sequence of SEQ ID NO: 17, or (c) amino acid sequence of SEQ ID NO: 16.

4. The BAA of claim 1, wherein the CM1 comprises an amino acid sequence selected from the group consisting of SEQ ID NO: 14 and SEQ ID NO: 16.

5. The BAA of claim 1, wherein the CM2 comprises an amino acid sequence selected from the group consisting of SEQ ID NO: 14 and SEQ ID NO: 17.

6. The BAA of claim 1, wherein the AB1 comprises at least one of the following characteristics:

(a) amino acid substitutions in at least two of amino acid positions L234, L235, N297 and P331, (b) amino acid substitutions in at least three of amino acid positions L234, L235, N297 and P331, (c) amino acid substitutions at amino acid positions L234, L235, N297 and P331, (d) amino acid substitutions at amino acid positions L234F, L235E, and P331S, (e) amino acid substitutions at amino acid positions L234F, L235E, N297Q and P331S.

7. The BAA of claim 1, wherein the heavy chain of the AB1 comprises any one of SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76.

8. The BAA of claim 1, wherein the BAA is selected from the group consisting of:

a) comprising a heavy chain amino acid sequence of SEQ ID NO: 130 and a light chain amino acid sequence of SEQ ID NO: 132 or a heavy chain amino acid sequence of SEQ ID NO: 197 and a light chain amino acid sequence of SEQ ID NO:199, b) comprising a heavy chain amino acid sequence of SEQ ID NO: 134 and a light chain amino acid sequence of SEQ ID NO: 136 or a heavy chain amino acid sequence of SEQ ID NO: 201 and a light chain amino acid sequence of SEQ ID NO: 203, c) comprising a heavy chain amino acid sequence of SEQ ID NO: 121 and a light chain amino acid sequence of SEQ ID NO: 122 or a heavy chain amino acid sequence of SEQ ID NO: 192 and a light chain amino acid sequence of SEQ ID NO: 193, d) comprising a heavy chain amino acid sequence of SEQ ID NO: 124 and a light chain amino acid sequence of SEQ ID NO: 108 or a heavy chain amino acid sequence of SEQ ID NO: 195 and a light chain amino acid sequence of SEQ ID NO: 182.

9. The BAA of claim 1, comprising the sequence of a heavy chain amino acid sequence of SEQ ID NO: 130 and a light chain amino acid sequence of SEQ ID NO: 132.

10. The BAA of claim 1, comprising the sequence of a heavy chain amino acid sequence of SEQ ID NO: 134 and a light chain amino acid sequence of SEQ ID NO: 136.

11. The BAA of claim 1, comprising the sequence of a heavy chain amino acid sequence of SEQ ID NO: 121 and a light chain amino acid sequence of SEQ ID NO: 122.

12. The BAA of claim 1, comprising the sequence of a heavy chain amino acid sequence of SEQ ID NO: 124 and a light chain amino acid sequence of SEQ ID NO: 108.

13. The BAA of claim 1, wherein the antibody is a rodent antibody, a chimeric antibody, a humanized antibody, or a fully human monoclonal antibody.

14. A pharmaceutical composition comprising the BAA of claim 1 and a carrier.

15. The pharmaceutical composition of claim 14, comprising an additional agent.

16. The pharmaceutical composition of claim 15, wherein the additional agent is a therapeutic agent.

17. A method of producing the BAA of claim 1 by culturing a cell to express the BAA.

18. An activatable antibody (AA) comprising:

a) an antibody or antigen binding fragment thereof (AB) that specifically binds to the epsilon chain of CD3 (CD3ε);

b) a masking moiety (MM) coupled to the AB, wherein the MM reduces or inhibits the binding of the AB to the CD3ε when the AA is in an uncleaved state, wherein the MM comprises amino acid sequence SEQ ID NO: 12; and c) a cleavable moiety (CM) coupled to the AB, wherein the CM is a polypeptide that functions as a substrate for a protease.

* * * * *